US012491259B2

(12) United States Patent
Bamdad et al.

(10) Patent No.: US 12,491,259 B2
(45) Date of Patent: Dec. 9, 2025

(54) ANTI-VARIABLE MUC1* ANTIBODIES AND USES THEREOF

(71) Applicant: Minerva Biotechnologies Corporation, Waltham, MA (US)

(72) Inventors: Cynthia Bamdad, Boston, MA (US); Benoit Smagghe, Honolulu, HI (US); Scott Moe, Sudbury, MA (US); Thomas Jeon, Woburn, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 18/726,319

(22) PCT Filed: Apr. 11, 2023

(86) PCT No.: PCT/US2023/065637

§ 371 (c)(1),
(2) Date: Jul. 2, 2024

(87) PCT Pub. No.: WO2023/201234

PCT Pub. Date: Oct. 19, 2023

(65) Prior Publication Data

US 2025/0114471 A1 Apr. 10, 2025

Related U.S. Application Data

(60) Provisional application No. 63/330,277, filed on Apr. 12, 2022.

(51) Int. Cl.
*A61K 47/65* (2017.01)
*A61K 47/68* (2017.01)
*C07K 16/30* (2006.01)

(52) U.S. Cl.
CPC .......... *A61K 47/6851* (2017.08); *A61K 47/65* (2017.08); *A61K 47/68031* (2023.08); *C07K 16/3092* (2013.01); *C07K 2317/565* (2013.01)

(58) Field of Classification Search
CPC ................ A61K 47/6851; A61K 47/65; A61K 47/68031; A61K 47/6879; A61K 47/68037; A61K 47/68033; A61K 47/68035; C07K 16/3092; C07K 2317/565; C07K 2317/24; C07K 2317/31; C07K 2317/56; C07K 2317/77; C07K 16/2809; A61P 35/00
USPC ...................................................... 424/134.1
See application file for complete search history.

(56) References Cited

U.S. PATENT DOCUMENTS 4,496,542 A 1/1985 Skiles et al.
7,498,298 B2 3/2009 Doronina et al.
7,709,226 B2 5/2010 Foote
8,535,944 B2 9/2013 Bamdad
8,759,496 B2 6/2014 Govindan et al.
8,859,495 B2 10/2014 Bamdad
9,102,735 B2 8/2015 Govindan et al.
9,107,960 B2 8/2015 Govindan et al.
9,708,388 B2 7/2017 Beckmann
9,808,537 B2 11/2017 Masuda et al.
9,932,407 B2 4/2018 Bamdad
9,944,719 B2 4/2018 Beckmann et al.
10,195,288 B2 2/2019 Masuda et al.
10,421,819 B2 9/2019 Bamdad et al.
10,703,821 B2 7/2020 Bamdad
10,724,027 B2 7/2020 Bamdad
10,973,924 B2 4/2021 Masuda et al.
11,202,775 B2 12/2021 Bamdad
11,560,435 B2 1/2023 Bamdad et al.
11,591,565 B2 2/2023 Bamdad et al.
11,702,483 B2 7/2023 Bamdad et al.
11,746,159 B2 9/2023 Bamdad et al.
11,897,967 B2 2/2024 Bamdad et al.
11,898,160 B2 2/2024 Bamdad et al.
11,931,347 B2 3/2024 Bamdad et al.
11,932,690 B2 3/2024 Sadelain et al.
11,976,132 B2 5/2024 Bamdad
11,976,295 B2 5/2024 Bamdad et al.
12,006,371 B2 6/2024 Bamdad et al.
12,037,413 B2 7/2024 Bamdad et al.
12,049,514 B2 7/2024 Bamdad et al.
12,049,618 B2 7/2024 Bamdad
12,104,170 B2 10/2024 Bamdad et al.
12,115,192 B2 10/2024 Bamdad et al.
12,195,728 B2 1/2025 Bamdad
(Continued)

FOREIGN PATENT DOCUMENTS

CN 101652469 A 2/2010
EP 3604334 A2 2/2020
(Continued)

OTHER PUBLICATIONS

Abdollahpour-Alitappeh, Meghdad et al. Evaluation of factors influencing antibody reduction for development of antibody drug conjugates. Iranian biomedical journal 21(4):270-274 (2017).
(Continued)

*Primary Examiner* — Yan Xiao

(74) *Attorney, Agent, or Firm* — WILSON SONSINI GOODRICH & ROSATI

(57) ABSTRACT

Described herein are methods and compositions for the targeted delivery of therapeutic agents and multispecific antibodies or antibody fragments comprising a binding domain to MUC1* and a binding domain to CD3. The present disclosure also provides compositions comprising antibodies and methods for treating diseases and disorders such as cancer.

20 Claims, 93 Drawing Sheets

Specification includes a Sequence Listing.

(56) References Cited

U.S. PATENT DOCUMENTS

| | | | |
|---|---|---|---|
| 12,202,799 | B2 | 1/2025 | Bamdad et al. |
| 12,351,646 | B2 | 7/2025 | Bamdad |
| 2002/0164611 | A1 | 11/2002 | Bamdad et al. |
| 2005/0053964 | A1 | 3/2005 | Bamdad et al. |
| 2009/0075926 | A1 | 3/2009 | Bamdad |
| 2012/0156246 | A1 | 6/2012 | Bamdad |
| 2014/0044696 | A1 | 2/2014 | Bamdad |
| 2014/0065113 | A1 | 3/2014 | Bamdad et al. |
| 2015/0089677 | A1 | 3/2015 | Bamdad |
| 2015/0203823 | A1 | 7/2015 | Bamdad |
| 2015/0320840 | A1 | 11/2015 | Bamdad |
| 2016/0326263 | A1 | 11/2016 | Bamdad et al. |
| 2017/0106046 | A1 | 4/2017 | Bamdad et al. |
| 2017/0121406 | A1 | 5/2017 | Bamdad |
| 2017/0204191 | A1 | 7/2017 | Bamdad et al. |
| 2017/0204196 | A1 | 7/2017 | Bamdad et al. |
| 2018/0112007 | A1 | 4/2018 | Bamdad et al. |
| 2018/0235193 | A1 | 8/2018 | Bamdad et al. |
| 2018/0258186 | A1 | 9/2018 | Bamdad et al. |
| 2018/0312605 | A1 | 11/2018 | Kufe et al. |
| 2019/0031778 | A1 | 1/2019 | Bamdad et al. |
| 2019/0290692 | A1 | 9/2019 | Bamdad et al. |
| 2020/0062812 | A1 | 2/2020 | Bamdad et al. |
| 2020/0385485 | A1 | 12/2020 | Bamdad |
| 2020/0390870 | A1 | 12/2020 | Bamdad |
| 2020/0405832 | A1 | 12/2020 | Bamdad et al. |
| 2021/0077632 | A1 | 3/2021 | Smith et al. |
| 2021/0085799 | A1 | 3/2021 | Yu et al. |
| 2021/0087143 | A1 | 3/2021 | Bamdad et al. |
| 2021/0115153 | A1 | 4/2021 | Moon et al. |
| 2021/0187118 | A1 | 6/2021 | Gellert et al. |
| 2021/0221910 | A1 | 7/2021 | Gellert et al. |
| 2021/0299109 | A1 | 9/2021 | Bamdad et al. |
| 2021/0308213 | A1 | 10/2021 | Bamdad et al. |
| 2021/0353764 | A1 | 11/2021 | Xu et al. |
| 2022/0023436 | A1 | 1/2022 | Ogitani et al. |
| 2022/0089779 | A1 | 3/2022 | Bamdad et al. |
| 2022/0184120 | A1 | 6/2022 | Bamdad et al. |
| 2022/0193270 | A1 | 6/2022 | Bamdad |
| 2022/0202786 | A1 | 6/2022 | Bamdad |
| 2022/0218846 | A1 | 7/2022 | Bamdad et al. |
| 2022/0233708 | A1 | 7/2022 | Bao et al. |
| 2022/0242823 | A1 | 8/2022 | Bamdad et al. |
| 2022/0252604 | A1 | 8/2022 | Bamdad |
| 2022/0289865 | A1 | 9/2022 | Bamdad et al. |
| 2022/0339291 | A1 | 10/2022 | Park et al. |
| 2023/0049461 | A1 | 2/2023 | Bamdad |
| 2023/0242678 | A1 | 8/2023 | Bamdad et al. |
| 2023/0242874 | A1 | 8/2023 | Bamdad et al. |
| 2023/0295340 | A1 | 9/2023 | Bamdad et al. |
| 2024/0166743 | A1 | 5/2024 | Sadelain et al. |
| 2024/0247229 | A1 | 7/2024 | Bamdad et al. |
| 2024/0261331 | A1 | 8/2024 | Bamdad et al. |
| 2024/0261406 | A1 | 8/2024 | Bamdad et al. |
| 2024/0277803 | A1 | 8/2024 | Bamdad et al. |
| 2024/0294590 | A1 | 9/2024 | Bamdad et al. |
| 2024/0299507 | A1 | 9/2024 | Bamdad |
| 2024/0307359 | A1 | 9/2024 | Bamdad et al. |
| 2024/0390418 | A1 | 11/2024 | Bamdad et al. |
| 2024/0392038 | A1 | 11/2024 | Bamdad et al. |
| 2024/0409515 | A1 | 12/2024 | Bamdad et al. |
| 2024/0424025 | A1 | 12/2024 | Bamdad et al. |
| 2025/0019651 | A1 | 1/2025 | Bamdad et al. |
| 2025/0026853 | A1 | 1/2025 | Bamdad et al. |
| 2025/0066505 | A1 | 2/2025 | Bamdad |
| 2025/0067746 | A1 | 2/2025 | Bamdad |
| 2025/0121088 | A1 | 4/2025 | Bamdad et al. |

FOREIGN PATENT DOCUMENTS

| | | | | |
|---|---|---|---|---|
| WO | WO-0043783 | A2 | 7/2000 | |
| WO | WO-0043791 | A2 | 7/2000 | |
| WO | WO-0192277 | A1 | 12/2001 | |
| WO | WO-0201228 | A2 | 1/2002 | |
| WO | WO-0201230 | A2 | 1/2002 | |
| WO | WO-0228507 | A2 | 4/2002 | |
| WO | WO-0229411 | A2 | 4/2002 | |
| WO | WO-0237109 | A2 | 5/2002 | |
| WO | WO-02056022 | A2 | 7/2002 | |
| WO | WO-02061129 | A2 | 8/2002 | |
| WO | WO-03018846 | A1 | 3/2003 | |
| WO | WO-03020279 | A2 | 3/2003 | |
| WO | WO-03020280 | A2 | 3/2003 | |
| WO | WO-2004059347 | A2 | 7/2004 | |
| WO | WO-2005019269 | A2 | 3/2005 | |
| WO | WO-2006105448 | A2 | 10/2006 | |
| WO | WO-2007053135 | A1 | 5/2007 | |
| WO | WO-2008070171 | A2 | 6/2008 | |
| WO | WO-2009042814 | A1 | 4/2009 | |
| WO | WO-2009042815 | A1 | 4/2009 | |
| WO | WO-2010042562 | A2 | 4/2010 | |
| WO | WO-2010042891 | A2 | 4/2010 | |
| WO | WO-2010144887 | A1 | 12/2010 | |
| WO | WO-2011159960 | A2 | 12/2011 | |
| WO | WO-2012126013 | A2 | 9/2012 | |
| WO | WO-2012154759 | A2 | 11/2012 | |
| WO | WO-2013059373 | A2 | 4/2013 | |
| WO | WO-2013123084 | A1 | 8/2013 | |
| WO | WO-2014012115 | A2 | 1/2014 | |
| WO | WO-2014018679 | A2 | 1/2014 | |
| WO | WO-2014028668 | A2 | 2/2014 | |
| WO | WO-2014130741 | A2 | 8/2014 | |
| WO | WO-2015023694 | A2 | 2/2015 | |
| WO | WO-2015157322 | A2 | 10/2015 | |
| WO | WO-2016130726 | A1 | 8/2016 | |
| WO | WO-2017004601 | A1 | 1/2017 | |
| WO | WO-2017053886 | A2 | 3/2017 | |
| WO | WO-2017180834 | A1 | 10/2017 | |
| WO | WO-2018071583 | A2 | 4/2018 | |
| WO | WO-2018183654 | A1 | 10/2018 | |
| WO | WO-2019104306 | A1 | 5/2019 | |
| WO | WO-2019126357 | A1 | 6/2019 | |
| WO | WO-2019165421 | A1 | 8/2019 | |
| WO | WO-2019173815 | A2 | 9/2019 | |
| WO | WO-2019219889 | A1 * | 11/2019 | ......... A61K 31/4745 |
| WO | WO-2019236954 | A1 | 12/2019 | |
| WO | WO-2020146902 | A2 | 7/2020 | |
| WO | WO-2020163325 | A1 | 8/2020 | |
| WO | WO-2020233174 | A1 | 11/2020 | |
| WO | WO-2020259258 | A1 | 12/2020 | |
| WO | WO-2021151984 | A1 | 8/2021 | |
| WO | WO-2021242935 | A1 | 12/2021 | |
| WO | WO-2021252551 | A2 | 12/2021 | |
| WO | WO-2021263227 | A2 | 12/2021 | |
| WO | WO-2021263241 | A1 | 12/2021 | |
| WO | WO-2022015880 | A2 | 1/2022 | |
| WO | WO-2022027039 | A1 | 2/2022 | |
| WO | WO-2023201234 | A2 | 10/2023 | |
| WO | WO-2023220560 | A1 | 11/2023 | |
| WO | WO-2025049494 | A1 | 3/2025 | |
| WO | WO-2025080693 | A1 | 4/2025 | |

OTHER PUBLICATIONS

Barrios, Yvelise et al. Length of Antibody Heavy Chain Complementarity Determining Region 3 as a Specificity-determining Factor. Journal of Molecular Recognition 17:332-338 (2004).

Brassard, Julyanne et al. Antibody-drug conjugates targeting tumor-specific mucin glycoepitopes. Frontiers in Bioscience-Landmark 27(11):301, 1-13 (2022).

ClinicalTrials.gov Identifier: NCT00352131. Maytansinoid DM4-Conjugated Humanized Monoclonal Antibody huC242 in Treating Patients With Solid Tumors, Record Created Jul. 13, 2006; [retrieved on Mar. 21, 2025]. Available at URL: https://clinicaltrials.gov/study/NCT00352131?cond=NCT00352131&rank=1 pp. 1-10.

ClinicalTrials.gov Identifier: NCT02984683. Study Evaluating Efficacy and Safety of SAR566658 Treatment in Patients With CA6 Positive Metastatic Triple Negative Breast Cancer ClinicalTrials.gov ID NCT02984683, Record Created Dec. 4, 2016; [retrieved on Mar. 21, 2025]. Available at URL: https://clinicaltrials.gov/study/NCT02984683?cond=NCT02984683&limit=10&rank=1 pp. 1-15.

ClinicalTrials.gov Identifier: NCT04695847. M1231 in Participants With Solid Tumors, Record Created Jan. 4, 2021; [retrieved on Mar.

(56) References Cited

OTHER PUBLICATIONS 21, 2025]. Available at URL: https://clinicaltrials.gov/study/NCT04695847?term=NCT04695847&rank=1 pp. 1-27.
Epenetos, A. A. et al. Targeting of iodine-123-labelled tumour-associated monoclonal antibodies to ovarian, breast, and gastrointestinal tumours. The Lancet 320(8306):999-1004 (1982).
Gu, Yuheng et al. Clinical Progresses and Challenges of Bispecific Antibodies for the Treatment of Solid Tumors. Molecular Diagnosis & Therapy 28(6):669-702 (2024).
Knuehl, Christine et al. Abstract 5284: M1231 is a bispeci c anti-MUC1xEGFR antibody-drug conjugate designed to treat solid tumors with MUC1 and EGFR co-expression.Cancer Res 82(12_Supplement):5284, 1-4 (2022).
Li, Wei et al. Synthesis and Evaluation of Camptothecin Antibody-Drug Conjugates. ACS Medicinal Chemistry Letters 10(10):1386-1392 (2019).
Meyerholz, David K. et al., Principles and Approaches For Reproducible Scoring of Tissue Stains in Research. Laboratory Investigation 98(7):844-855 (2019).
Nakada, Takashi et al. Novel antibody drug conjugates containing exatecan derivative-based cytotoxic payloads. Bioorganic and medicinal chemistry letters 26(6):1542-1545 (2016).
Nejadmoghaddam, Mohammad-Reza et al. Antibody-Drug Conjugates: Possibilities and Challenges. Avicenna Journal of Medical Biotechnology 2(1):3-23 (2019).
Okamoto, Hiromi et al. Pharmacokinetics of Trastuzumab Deruxtecan (T-DXd), a Novel Anti-HER2 Antibody-drug Conjugate, in HER2-Positive Tumour-bearing Mice. Xenobiotica; The Fate of Foreign Compounds in Biological Systems 50(10):1242-1250 (2020).
PCT/US2024/050546 International Search Report and Written Opinion dated Jan. 29, 2025.
Q2 2018 Performance Positions Sanofi for New Growth Phase. Sanofi, Jul. 31, 2018; [retrieved on Mar. 21, 2025].Available at URL: https://www.news.sanofi.us/2018-07-31-Q2-2018-Performance-Positions-Sanofi-for-New-Growth-Phase pp. 1-6.
Ram, Sripad et al. Pixelwise H-score: A Novel Digital Image Analysis-based Metric to Quantify Membrane Biomarker Expression From Immunohistochemistry Images. PLOS One 16(9):e0245638, 1-20 (2021).
Riechmann, Lutz et al. Reshaping Human Antibodies for Therapy. Nature 332(6162):323-327 (1988).
Rudikoff, Stuart et al. Single amino acid substitution altering antigen-binding specificity. PNAS USA 79(6):1979-1983 (1982).
Strop, Pavel et al. Location Matters: Site of Conjugation Modulates Stability and Pharmacokinetics of Antibody Drug Conjugates. Chemistry and Biology 20(2):161-167 (2013).
Sun, Michael MC. et al. Reduction-Alkylation Strategies for the Modification of Specific Monoclonal Antibody Disulfides. Bioconjugate Chem. 16:1282-1290 (2005).
Syrkina, Marina S. MUC1 story: great expectations, disappointments and the renaissance. Current medicinal chemistry 26(3):554-563 (2019).
U.S. Appl. No. 18/910,445 Office Action dated Feb. 27, 2025.
U.S. Appl. No. 18/910,445 Office Action dated Mar. 6, 2025.
Waltham, Mass. ImmunoGen, Inc. Elects to Discontinue Further Internal Development of Its IMGN242 Compound. abbvie, Jun. 11, 2009; [retrieved on Mar. 26, 2025]. Available at URL: https://news.abbvie.com/2009-06-11-ImmunoGen,-Inc-Elects-to-Discontinue-Further-Internal-Development-of-Its-IMGN242-Compound pp. 1-3.
Wu, Herren et al. Humanization of a Murine Monoclonal Antibody By Simultaneous Optimization of Framework and CDR residues. Journal of Molecular Biology 294(1):151-162 (1999).
Al-Lazikani, Bissan et al. Standard Conformations for the Canonical Structures of Immunoglobulins. Journal of Molecular Biology 273(4):927-948 (1997).
Baeuerle, Patrick A. et al Bispecific T-cell engaging Antibodies for Cancer Therapy. Cancer Res 69(12):4941-4944 (2009).
Bird, Robert E. et al. Single-chain Antigen-binding Proteins. Science 242(4877):423-426 (1988).
Boerner, Paula et al. Production of Antigen-Specific Human Monoclonal Antibodies From In Vitro-primed Human Splenocytes. Journal of Immunology 147(1):86-95 (1991).
Brinkmann, Ulrich et al. The Making of Bispecific Antibodies. MAbs 9(2):182-212 (2017).
Bruggemann, Marianne et al. Designer mice: the Production of Human Antibody Repertoires in Transgenic Animals. The Year in immunology 7:33-40 (1993).
Carter, M. G. et al. A Primitive Growth Factor, NME7AB , is Sufficient to Induce Stable Naïve State Human Pluripotency; Reprogramming in This Novel Growth Factor Confers Superior Differentiation. Stem Cells 34(4):847-859 (2016).
Chothia, Cyrus et al. Canonical Structures for the Hypervariable Regions of Immunoglobulins. Journal of Molecular Biology 196(4):901-917 (1987).
Chothia, Cyrus et al. Structural Repertoire of the Human VH Segments. Journal of Molecular Biology 227(3):799-817 (1992).
Cole, S.P.C. et al. The EBV-Hybridoma Technique and its Application to Human Lung Cancer. Monoclonal Antibodies and Cancer Therapy 27:77-96 (1985).
Czajkowsky, Daniel M. et al. Fc-fusion proteins: New Developments and Future Perspectives. EMBO molecular medicine 4(10):1015-1028 (2012).
Dai, Hanren et al. Chimeric Antigen Receptors Modified T-Cells for Cancer Therapy. Journal of the National Cancer Institute 108(7):djv439, 1-14 (2016).
Dufour, Antoine et al. Small-molecule anticancer compounds selectively target the hemopexin domain of matrix metalloproteinase-9. Cancer Res 71(14):4911-88 (2011).
Fessler, Shawn P. et al. MUC1* is a determinant of Trastuzumab (Herceptin) Resistance in Breast Cancer Cells. Breast Cancer Research and Treatment 118:113-124 (2009).
Feucht, Judith et al. Calibration of CAR Activation Potential directs Alternative T Cell Fates and Therapeutic Potency. Nature medicine 25(1):82-88 (2019).
Hamblett, Kevin J. et al. Effects of Drug Loading on the Antitumor Activity of a Monoclonal Antibody Drug Conjugate. Clinical Cancer Research 10(20):7063-7070 (2004).
Holliger, Philipp et al. Engineered Antibody Fragments and the Rise of Single Domains. Nature Biotechnology 23(9):1126-1136 (2005).
Hombach, Andreas A. et al. 0X40 Costimulation by a Chimeric antigen Receptor Abrogates CD28 and IL-2 induced IL-10 Secretion by RedirectedCD4(+) T Cells. Oncolmmunology 1(4):458-466 (2012).
Hoogenboom, Hennie R. et al. By-passing Immunisation. Human Antibodies From Synthetic Repertoires of Germline VH Gene Segments Rearranged in Vitro. Journal of Molecular Biology 227(2):381-388 (1992).
Huston, James S. et al. Protein Engineering of Antibody Binding Sites: Recovery of Specific Activity in an Anti-digoxin Single-chain Fv Analogue Produced in *Escherichia coli*. PNAS USA 85(16):5879-5883 (1988).
Jakobovits, Aya et al. Analysis of Homozygous Mutant Chimeric Mice: Deletion of the Immunoglobulin Heavy-chain Joining Region Blocks B-cell Development and Antibody Production. PNAS USA 90(6):2551-2555 (1993).
Jakobovits, Aya et al. Germ-line Transmission and Expression of a Human-Derived Yeast Artificial Chromosome. Nature 362(6417):255-258 (1993).
Kabat, Elvin A, et al. Attempts to Locate Complementarity-Determining Residues in the Variable Positions of Light and Heavy Chains. Annals of the New York Academy of Sciences 190:382-393 (1971).
Kabat, Elvin A. et al. Sequences of Proteins of Immunological Interest. Fifth Edition, NIH Pub. No. 91-3242. Public Health Service, U.S. Department of Health and Human Services, National Institutes of Health (pp. 647-669) (1991).
Kaltenbronn, James S. et al. In: Proceedings 11th American Peptide Symposium. Netherlands: ESCOM Publishers 1990:969-970 (1990).
Kim, Min Jung et al. Novel Antibodies targeting MUC1-C showed Anti-metastasis and Growth-inhibitory Effects on Human Breast Cancer Cells. International Journal of Molecular Sciences 21(9):3258, 1-18 (2020).

(56) References Cited

OTHER PUBLICATIONS

Kowolik, Claudia M. et al. CD28 Costimulation provided through a CD19-specific Chimeric Antigen Receptor Enhances in Vivo Persistence and Antitumor Efficacy of Adoptively Transferred T Cells. Cancer Research 66(22):10995-11004 (2006).
Lefranc, Marie-Paule et al. IMGT, The International ImMunoGeneTics Database. Nucleic Acids Research 27(1):209-212 (1999).
Lefranc, Marie-Paule et al. The IMGT Unique Numbering for Immunoglobulins. T-Cell Receptors and Ig-Like Domains. The Immunologist 7(4):132-136 (1999).
Loskog, A. et al. Addition of the CD28 signaling domain to Chimeric T-cell Receptors Enhances Chimeric T-cell Resistance to T Regulatory Cells. Leukemia 20(10):1819-1828 (2006).
Lynn, Rachel C. et al. c-Jun Overexpression in CAR T Cells Induces Exhaustion Resistance. Nature 576(7786):293-300 (2019).
Maccallum, Robert M. et al. Antibody-Antigen Interactions: Contact Analysis and Binding Site Topography. Journal of Molecular Biology 262:732-745 (1996).
Madhavan, H N. Simple Laboratory Methods to Measure Cell Proliferation using DNA Synthesis Property . Journal of Stem Cells & Regenerative Medicine 3(1):12-14 (2007).
Mahanta, Sanjeev et al. A Minimal Fragment of MUCI Mediates Growth of Cancer Cells. PLoS One 3(4):e2054, 1-12 (2008).
Marks, James D. et al. By-passimg Immunization Human Antibodies from V-gene Libraries Displayed on Phage. Journal of Molecular Biology 222(3):581-597 (1991).
Martin, Andrew CR. Protein Sequence and Structure Analysis of Antibody Variable Domains. Antibody Engineering:422-439 (2001).
Milone, Michael C. et al. Chimeric Receptors Containing CD137 Signal Transduction Domains Mediate Enhanced Survival of T Cells and increased Antileukemic Efficacy in Vivo. Molecular Therapy 17(8):1453-1464 (2009).
Osbourn, Jane K. et al. Directed selection of MIP-alpha Neutralizing CCR5 Antibodies from a Phage Display Human Antibody Library. Nature Biotechnology 16(8):778-781 (1998).
Ouyang, Jun. Drug-to-antibody Ratio (DAR) and Drug Load Distribution by Hydrophobic Interaction Chromatography and Reversed Phase High-performance Liquid Chromatography. Methods in Molecular Biology 1045:275-283 (2013).
Owyong, Mark et al. MMP9 Modulates the Metastatic Cascade and Immune Landscape for Breast Cancer Anti-metastatic Therapy. Life Science Alliance 2(6):e201800226, 1-16 (2019).
Pan, Deng et al. An Antibody-drug Conjugate Targeting a GSTA Glycosite-signature Epitope of MUC1 Expressed by Non-small Cell Lung Cancer. Cancer Medicine 9(24):9529-9540 (2020).
PCT/US2023/065637 International Invitation to Pay Additional Fees dated Jul. 6, 2023.
PCT/US2023/065637 International Search Report and Written Opinion dated Sep. 26, 2023.
Pule, Martin A. et al. A Chimeric T Cell Antigen Receptor that Augments Cytokine Release and Supports Clonal Expansion of Primary Human T cells. Molecular Therapy 12(5):933-941 (2005).
Salter, Alexander I. et al. Phosphoproteomic Analysis of Chimeric Antigen Receptor Signaling Reveals Kinetic and Quantitative Differences That Affect Cell Function. Science Signaling 11(544):1-18 (2018).
Smagghe, Benoit J. et al. MUCI* ligand, NM23-H1, is a Novel Growth Factor that Maintains Human Stem Cells in a more Naive State. PLoS One 8(3):E58601, 1-15 (2013).
Song, De-Gang et al. In Vivo Persistence, Tumor Localization, and Antitumor Activity of CAR-Engineered T Cells is Enhanced by Costimulatory Signaling through CD137 (4-1BB). Cancer Research 71(13):4617-4627 (2011).
Spatola, Arno F. et al. Chemistry and Biochemistry of Amino Acids, Peptides and Proteins. B. Weinstein, ed. New York: Marcel Dekker. 7:267-357 (1983).
Spiess, Christoph et al. Alternative Molecular Formats and Therapeutic Applications for Bispecific Antibodies. Molecular Immunology 67(2):95-106 (2015).
Tramontano, Anna et al. Framework Residue 71 is a Major Determinant of the Position and Conformation of the Second Hypervariable Region in the VH Domains of Immunoglobulins. Journal of Molecular Biology 215(1):175-182 (1990).
Van Dijk, Marc A, et al. Human Antibodies as Next Generation Therapeutics. Current Opinion in Chemical Biology 5(4):368-374 (2001).
Van't Veer, Laura J. et al. Gene Expression Profiling Predicts Clinical outcome of Breast Cancer. Nature 415(6871):530-536 (2002).
Xu, Yang et al. Closely related T-memory Stem Cells Correlate with in Vivo Expansion of Car. CD19-T Cells and are Preserved by IL-7 and IL-15. Blood 123(24):3750-3759 (2014).
Co-pending U.S. Appl. No. 18/863,779, inventors Bamdada; Cynthia et al., filed Nov. 7, 2024.
Co-pending U.S. Appl. No. 18/891,801, inventors Bamdad; Cynthia et al., filed Sep. 20, 2024.
Co-pending U.S. Appl. No. 18/892,093, inventors Bamdad; Cynthia et al., filed Sep. 20, 2024.
Co-pending U.S. Appl. No. 19/098,785, inventors Cynthia; Bamdad et al., filed Apr. 2, 2025.
Co-pending U.S. Appl. No. 19/098,802, inventors Cynthia; Bamdad et al., filed Apr. 2, 2025.
Co-pending U.S. Appl. No. 19/117,740, inventors Cynthia; Bamdad et al., filed Apr. 2, 2025.

* cited by examiner

20A10-OKT3-BiTE

- KIH (knob in hole) 20A10 (anti MUC1*)/OKT3 (anti CD3)

T47D : T cells (1:10 - 10,000:100,000)

1000 ng/mL 333 ng/mL 111 ng/mL 37 ng/mL 12.3 ng/mL 4.1 ng/mL 1.3 ng/mL 0.4 ng/mL

20A10-OKT3-BiTE

- KIH (knob in hole) 20A10 (anti MUC1*)/OKT3 (anti CD3)

T47D : T cells (1:10 - 10,000:100,000)

0.15 ng/mL 0.05 ng/mL 0 ng/mL ctl

20A10-12F6-BiTE
- KIH (knob in hole) 20A10 (anti MUC1*)/OKT3 (anti CD3)
T47D : T cells (1:10 - 5,000:50,000)
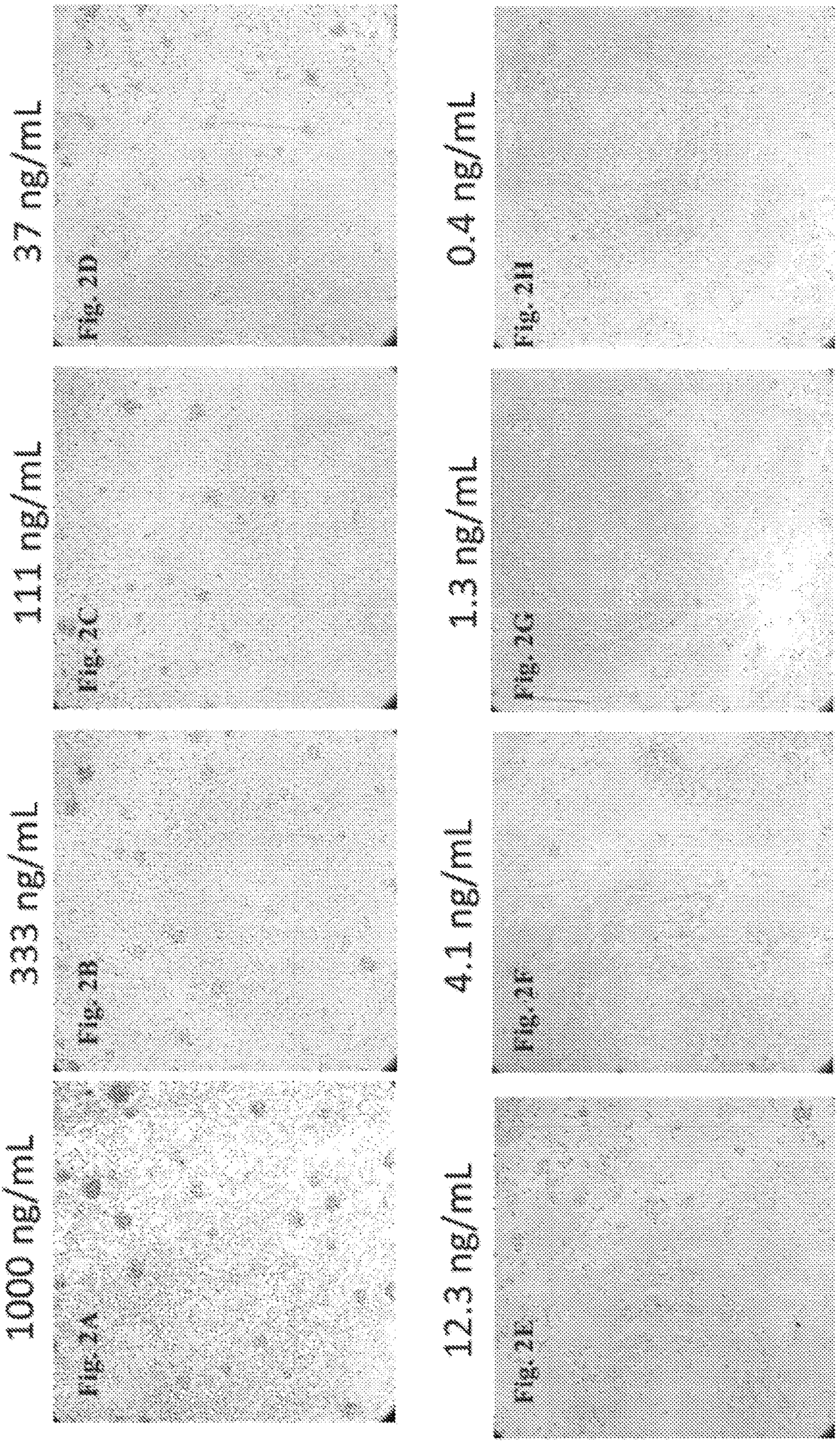

20A10-12F6-BiTE

- KIH (knob in hole) 20A10 (anti MUC1*)/OKT3 (anti CD3)

T47D : T cells (1:10 - 5,000:50,000)

0.15 ng/mL 0.05 ng/mL 0 ng/mL ctl

20A10-OKT3-BiTE

- KIH (knob in hole) 20A10 (anti MUC1*)/OKT3 (anti CD3)

**HCT-MUC1* : T cells (1:10 - 10,000:100,000)**

0.15 ng/mL 0.05 ng/mL 0 ng/mL ctl

20A10-12F6-BiTE
- KIH (knob in hole) 20A10 (anti MUC1*)/OKT3 (anti CD3)
**HCT-MUC1* : T cells (1:10 - 5,000:50,000)**
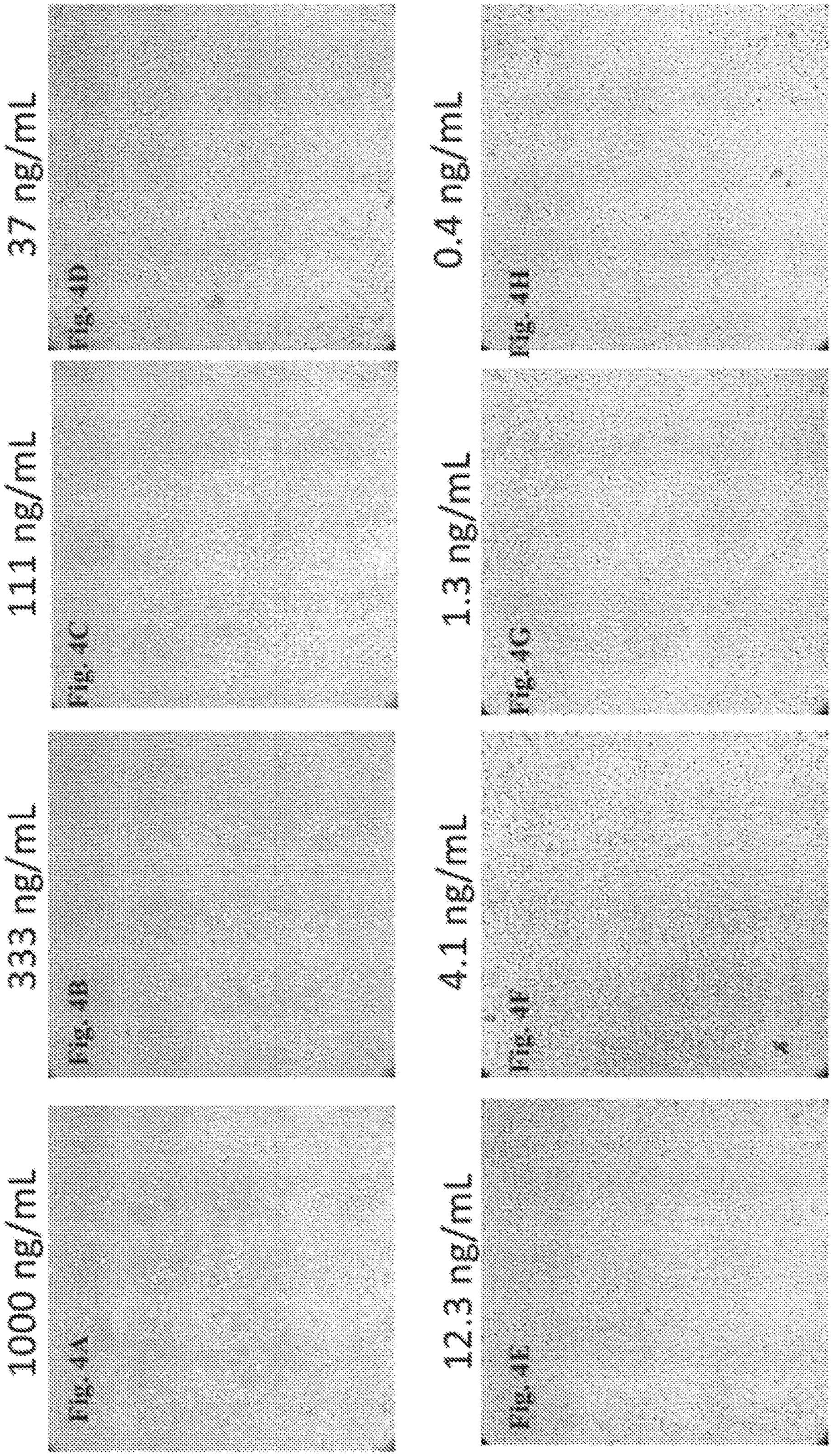

20A10-12F6-BiTE

- KIH (knob in hole) 20A10 (anti MUC1*)/OKT3 (anti CD3)

**HCT-MUC1* : T cells (1:10 - 5,000:50,000)**

0.15 ng/mL 0.05 ng/mL 0 ng/mL ctl

HCT-WT negative control

Cells (10,000/well) were mixed with MNC2-ADC and incubated for 72h 100 nM 10 nM 0.1 nM 0.01 nM 0.001 nM 0 nM

**HCT-MUC1* Positive**
Cells (10,000/well) were mixed with MNC2-ADC and incubated for 72h
Fig. 6A 100 nM
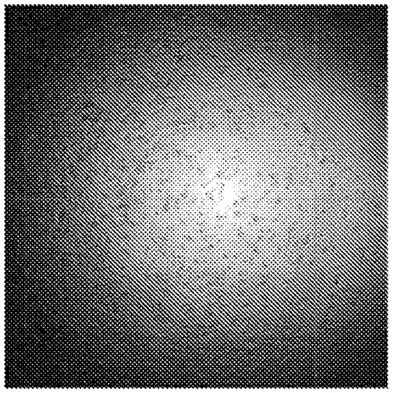
Fig. 6B 10 nM
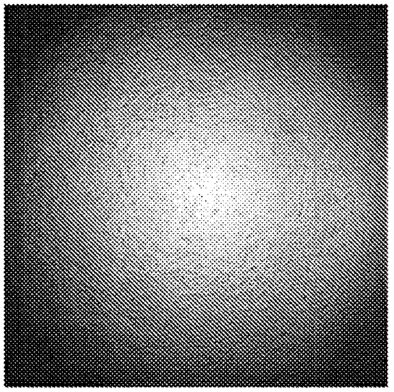
Fig. 6C 1 nM
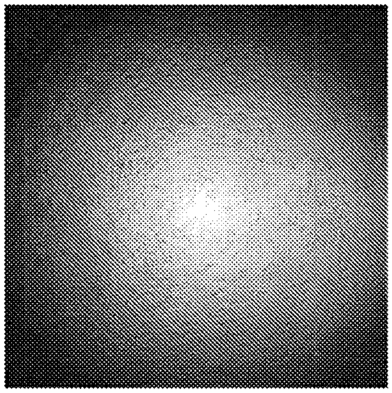
Fig. 6D 0.1 nM
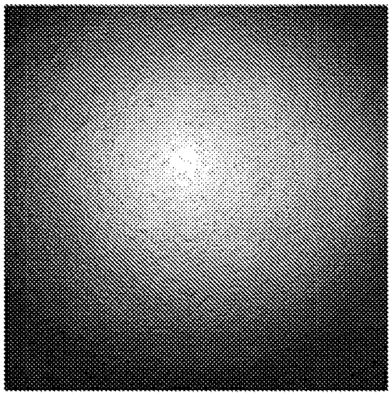
Fig. 6E 0.01 nM
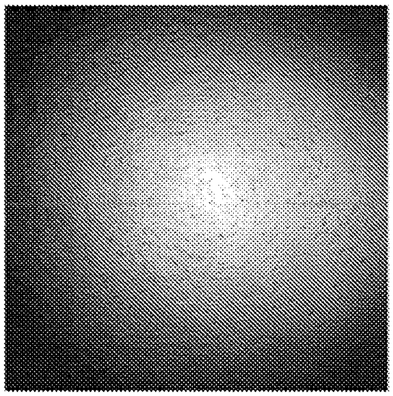
Fig. 6F 0.001 nM
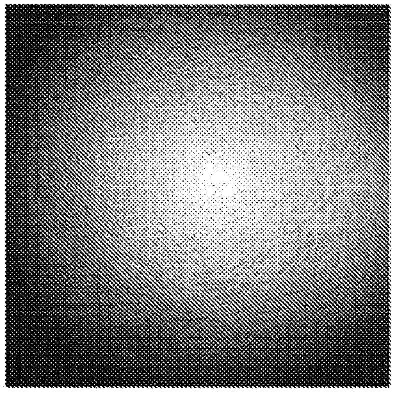
Fig. 6G 0 nM
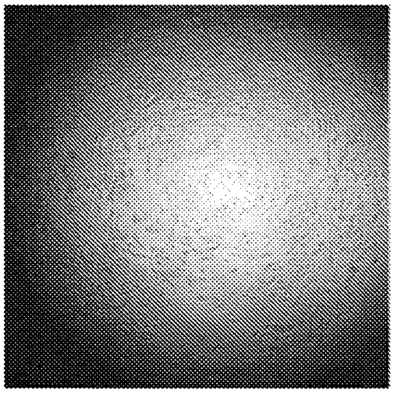

K562-WT negative control
Cells (10,000/well) were mixed with MNC2-ADC and incubated for 72h
Fig. 7A 100 nM
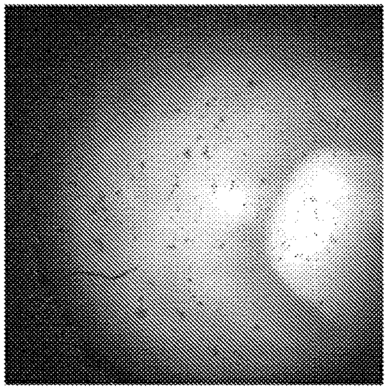
Fig. 7B 10 nM
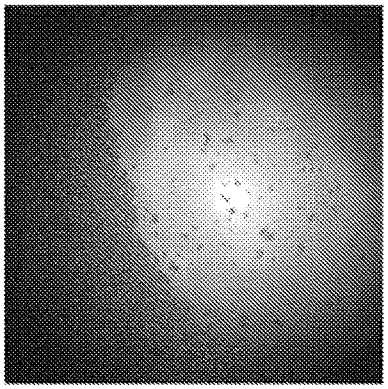
Fig. 7C 1 nM
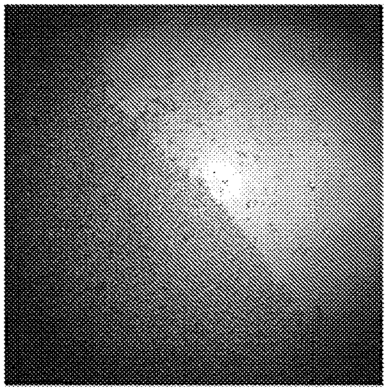
Fig. 7D 0.1 nM
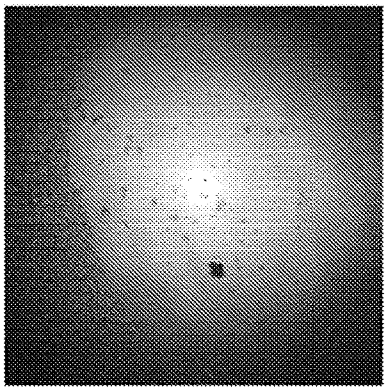
Fig. 7E 0.01 nM
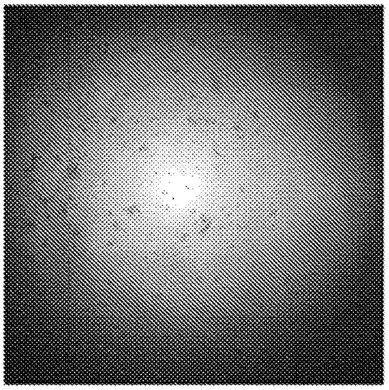
Fig. 7F 0.001 nM
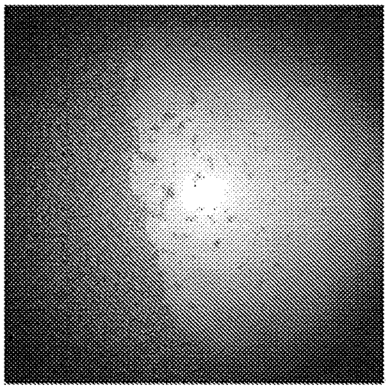
Fig. 7G 0 nM
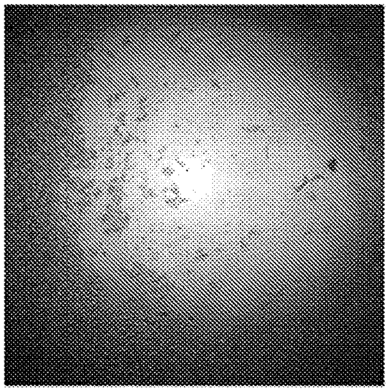

**K562-MUC1* Positive**

Cells (10,000/well) were mixed with MNC2-ADC and incubated for 72h 100 nM 10 nM 1 nM 0.1 nM 0.01 nM 0.001 nM 0 nM Cell viability after 72h Cell viability after 72h

**T47D-wt breast cancer cell line expresses both full-length MUC1 (not recognized by antibody) and MUC1* (target)**

Cells (10,000/well) were mixed with MNC2-ADC and incubated for 72h 100 nM 10 nM 1 nM 0.1 nM 0.01 nM 0.001 nM 0 nM

**T47D-MUC1* T47Ds transduced to express even more MUC1***
Cells (10,000/well) were mixed with MNC2-ADC and incubated for 72h
Fig. 11A 100 nM
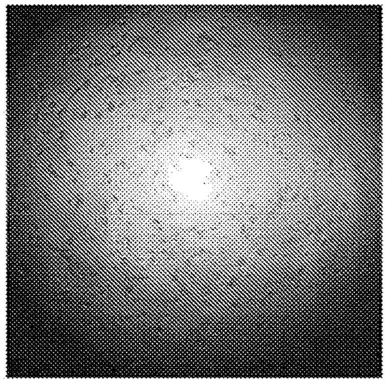
Fig. 11B 10 nM
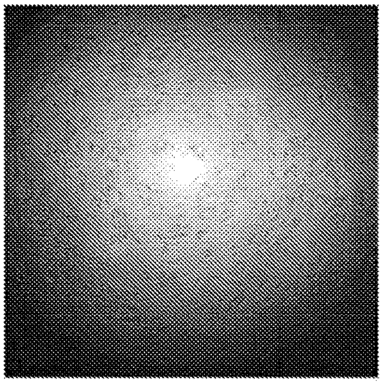
Fig. 11C 1 nM
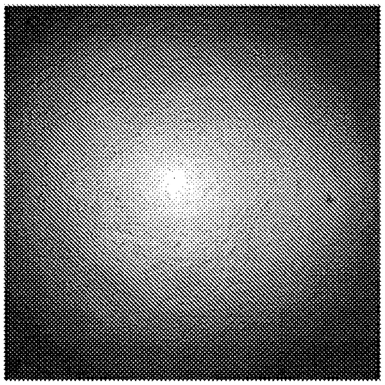
Fig. 11D 0.1 nM
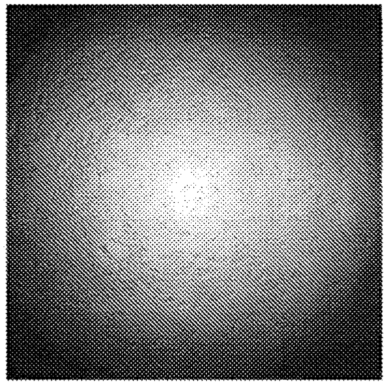
Fig. 11E 0.01 nM
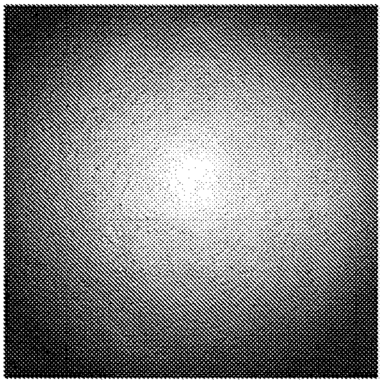
Fig. 11F 0.001 nM
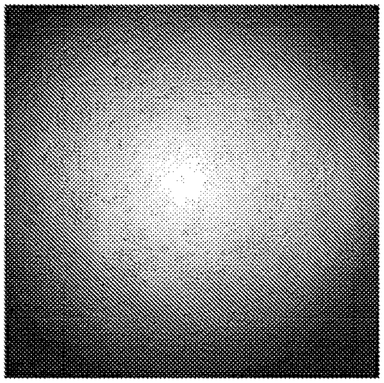
Fig. 11G 0 nM
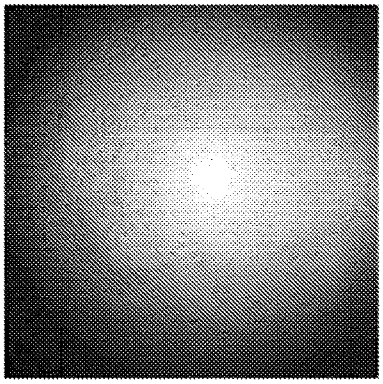

Cell viability after 72h

**T47D-wt breast cancer cell line expresses both full-length MUC1 (not recognized by antibody) and MUC1* (target)**

Cells (10,000/well) were mixed with MNC2-ADC and incubated for 72h 0 nM 0.1 nM 0.39 nM 1 nM 3.9 nM 10 nM 39 nM 100 nM 393 nM 1000 nM

**T47D-MUC1* T47Ds transduced to express even more MUC1***

Cells (10,000/well) were mixed with MNC2-ADC and incubated for 72h 0 nM 0.1 nM 0.39 nM 1 nM 3.9 nM 10 nM 39 nM 100 nM 393 nM 1000 nM

Cell viability after 72h

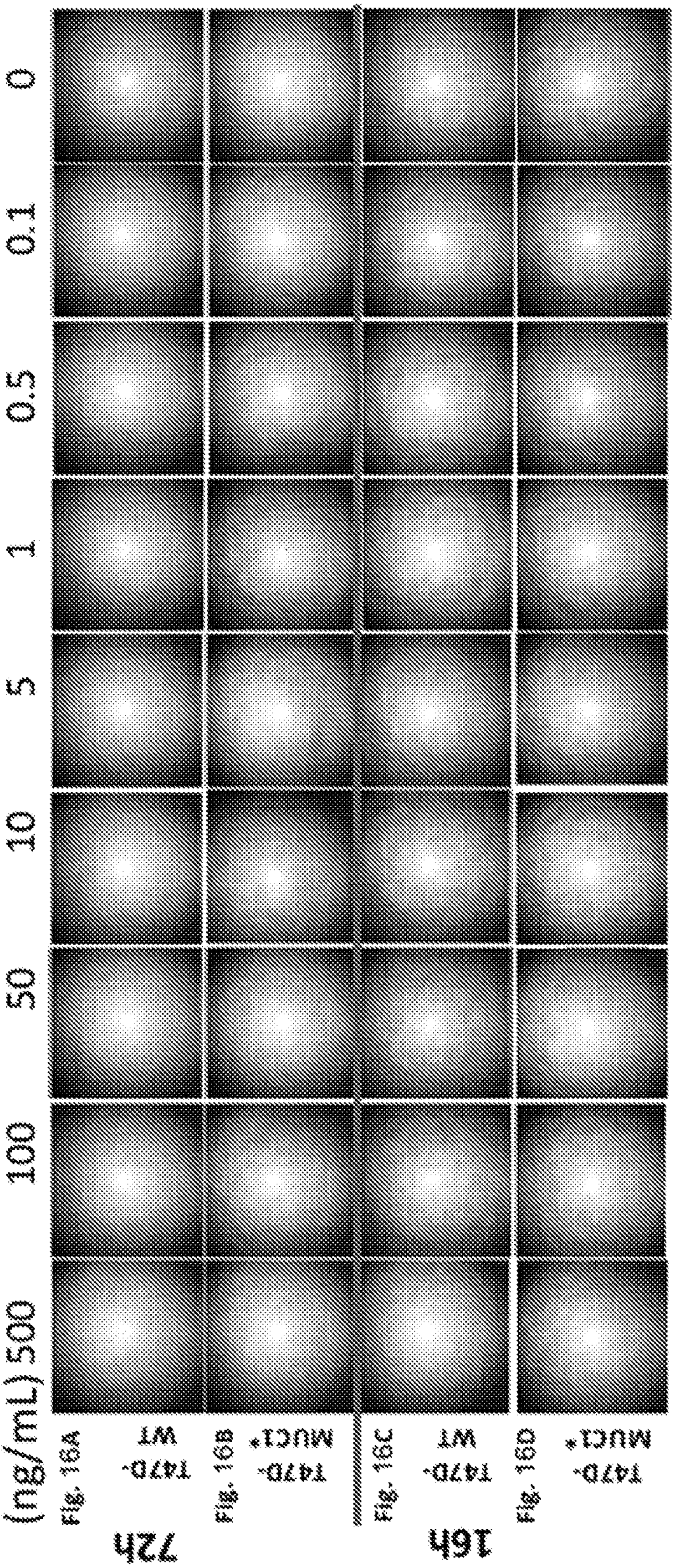
Fig. 16A T47D-WT
Fig. 16B T47D-MUC1*
Fig. 16C T47D-WT
Fig. 16D T47D-MUC1*
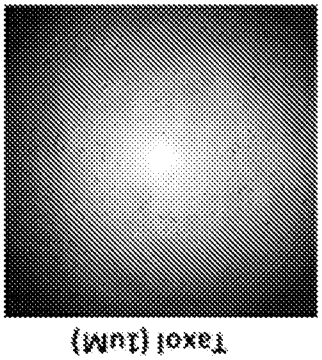
Fig. 16E T47D WT
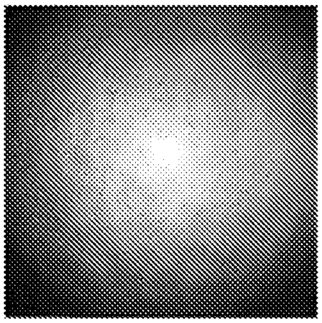
Fig. 16F T47D MUC1*

| 1h | mC2 T47D WT | mC2 T47D MUC1* | mC2 T47D WT 16h | mC2 T47D MUC1* 16h | m20A10 T47D WT | m20A10 T47D MUC1* | m20A10 T47D WT 16h | m20A10 T47D MUC1* 16h |
|---|---|---|---|---|---|---|---|---|
| IC50 (nM) | 599.8 | 20.54 | ND | 77.03 | 115.1 | 1.16 | 247.5 | 2.168 |
| R squared | 0.8993 | 0.9716 | -0.2981 | 0.9206 | 0.9384 | 0.86 | 0.7932 | 0.9611 |

MN20A10-OKT3 knob in hole format
FIG. 21A
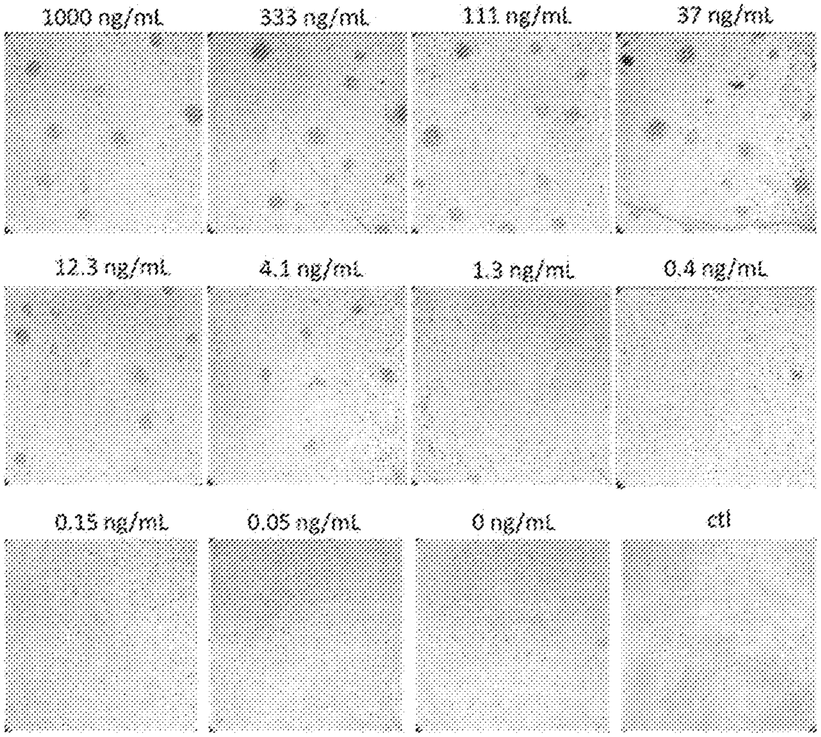
[conc bispecific 20A10-CD3]
FIG. 21B
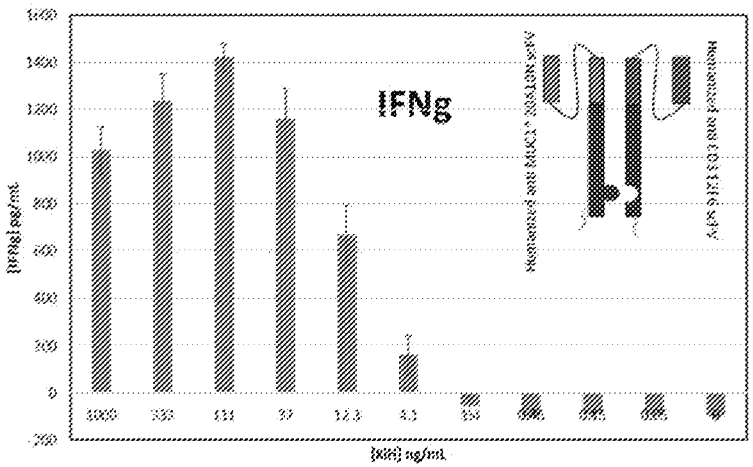
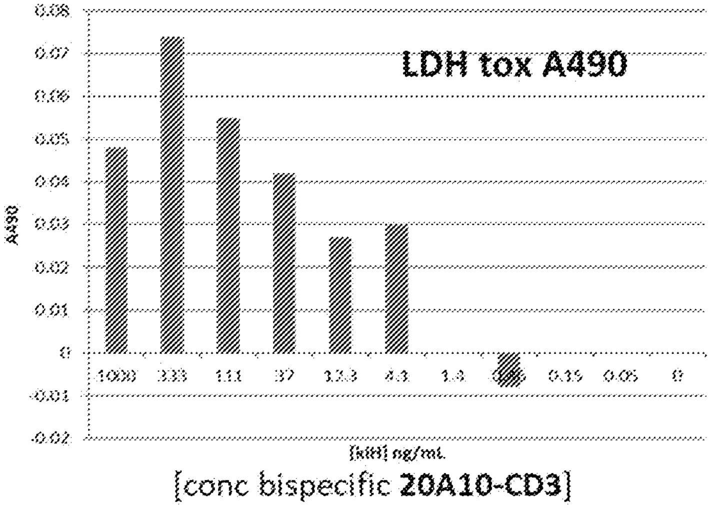
[conc bispecific 20A10-CD3]
FIG. 21C

IC50s MN20A10-OKT3 or MN20A10-12F6 in various bispecific formats

| T47D | IC50 pM | | T47D-MUC1* | IC50 pM |
|---|---|---|---|---|
| OKT3 IgG1 L1 MUC1* scFV | 3.7 | | OKT3 IgG1 L1 MUC1* scFV | 1.6 |
| 12F6 IgG1 L1 MUC1* scFV | 710 | | OKT3 scFV-Fc L1 MUC1* scFV | 5.4 |
| 12F6 scFV-Fc L1 MUC1* scFV | 773 | | MUC1* scFV-Fc/12F6 scFV-Fc SMCC | 8.3 |
| OKT3 scFV-Fc L1 MUC1* scFV | 873 | | 12F6 IgG1 L1 MUC1* scFV | 25.6 |
| MUC1* scFV-Fc/12F6 scFV-Fc SMCC | 1983 | | 12F6 scFV-Fc L1 MUC1* scFV | 76.5 |
| KiH MUC1* scFV-Fc knob-His/12F6 scFv-Fc Hole Strep | 4231 | | KiH MUC1* scFV-Fc knob-His/12F6 scFv-Fc Hole Strep | 678 |

IC50s MN20A10-OKT3 or MN20A10-12F6 in various bispecific formats

Anti-MUC1* Bispecific T Cell Engagers: Multiple Formats

MN20A10 kills MUC1* positive cancer cells; demonstrated with anti-CD3 antibodies OKT3 & 12F6

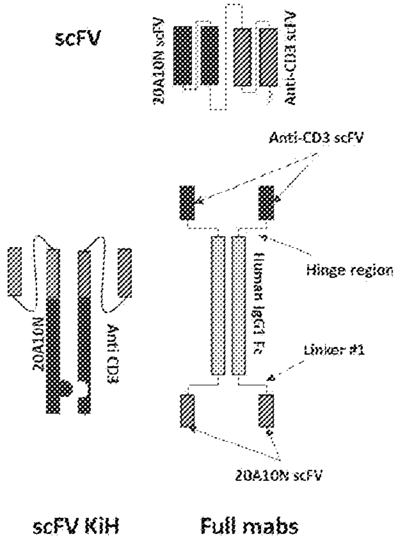

| | | T47D | T47D-MUC1* | HCT | HCT MUC1* |
|---|---|---|---|---|---|
| KiH 20A10N/12F6 | IC50 (pM) | 1636 | 583 | / | 769 |
| | R square | 0.95 | 0.96 | / | 0.94 |
| 20A10N/12F6 SMCC | IC50 (pM) | 1983 | 8.3 | / | 9.5 |
| | R square | 0.83 | 0.98 | / | 0.91 |
| 20A10N Full/12F6 SMCC | IC50 (pM) | / | 6.95 | / | 7.3 |
| | R square | / | 0.96 | / | 0.95 |
| KiH 20A10N-His/12F6 | IC50 (pM) | 4231 | 678 | / | 707 |
| | R square | 0.81 | 0.97 | / | 0.79 |
| OKT3-L1-20A10N | IC50 (pM) | 873 | 5.4 | / | 21.4 |
| | R square | 0.85 | 0.94 | / | 0.74 |
| 20A10N-L1-OKT3 | IC50 (pM) | 11307 | 30.8 | / | 127.5 |
| | R square | 0.65 | 0.98 | / | 0.86 |
| 20A10N-L2-OKT3 | IC50 (pM) | 17091 | 24 | / | 152.4 |
| | R square | 0.41 | 0.98 | / | 0.91 |

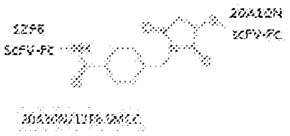

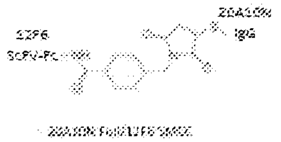

FIG. 24

Chemical structure of MC-VC-PAB-MMAE

Abbreviations:
MC-VC-PAB-MMAE
MC = maleimidocaproyl
VC = valine-citroline
PAB = para-aminobenzyl
MMAE = Monomethyl Auristatin E

Chemical structure of MC-VC-PAB-MMAF

MC VC

MMAF

Abbreviations:
MC-VC-PAB-MMAF
MC = maleimidocaproyl
VC = valine-citroline
PAB = para-aminobenzyl
MMAF = Monomethylauristatin F

Chemical structure of Deruxtecan
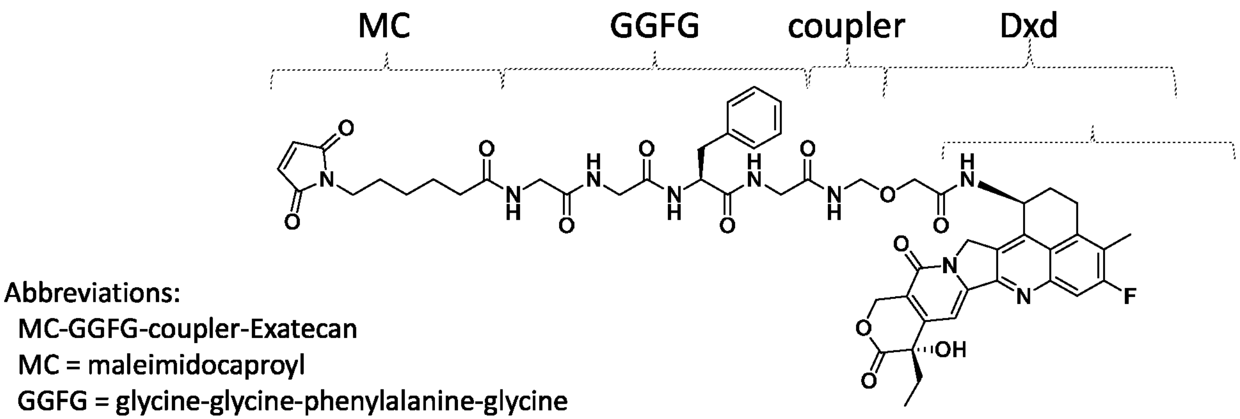
payload
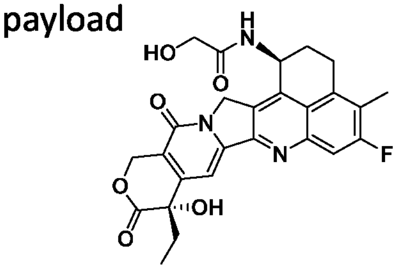
Abbreviations:
MC-GGFG-coupler-Exatecan
MC = maleimidocaproyl
GGFG = glycine-glycine-phenylalanine-glycine
Coupler = -HN-CH2-
Dxd = HO-CH2CO-Exatecan
Exatecan
FIG. 28

Chemical structure of an Exatecan
MC-VC-PAB-Exatecan
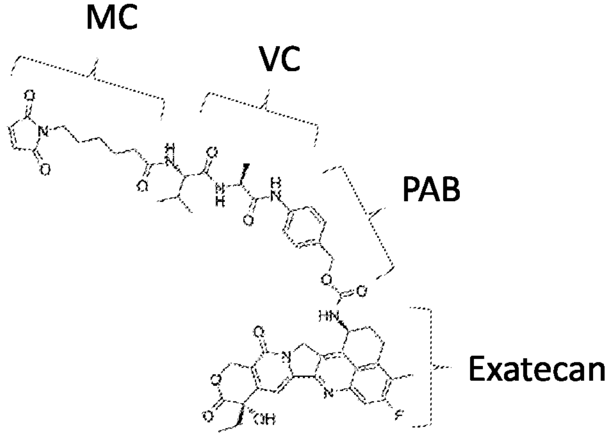
payload
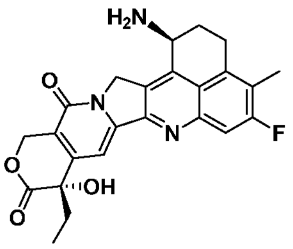
Abbreviations:
MC = maleimidocaproyl
VC = valine-citroline
PAB = para-aminobenzyl
Exactecan
FIG. 29

MNC2-MMAE: HIC chromatogram

MNC2-MMAF HIC chromatogram

MNC2-deruxtecan HIC chromatogram

MNC2-MC-VC-PAB-Exatecan HIC chromatogram

MN20A10-MMAE: HIC chromatogram

MN20A10-MMAF HIC chromatogram

MN20A10-deruxtecan HIC chromatogram

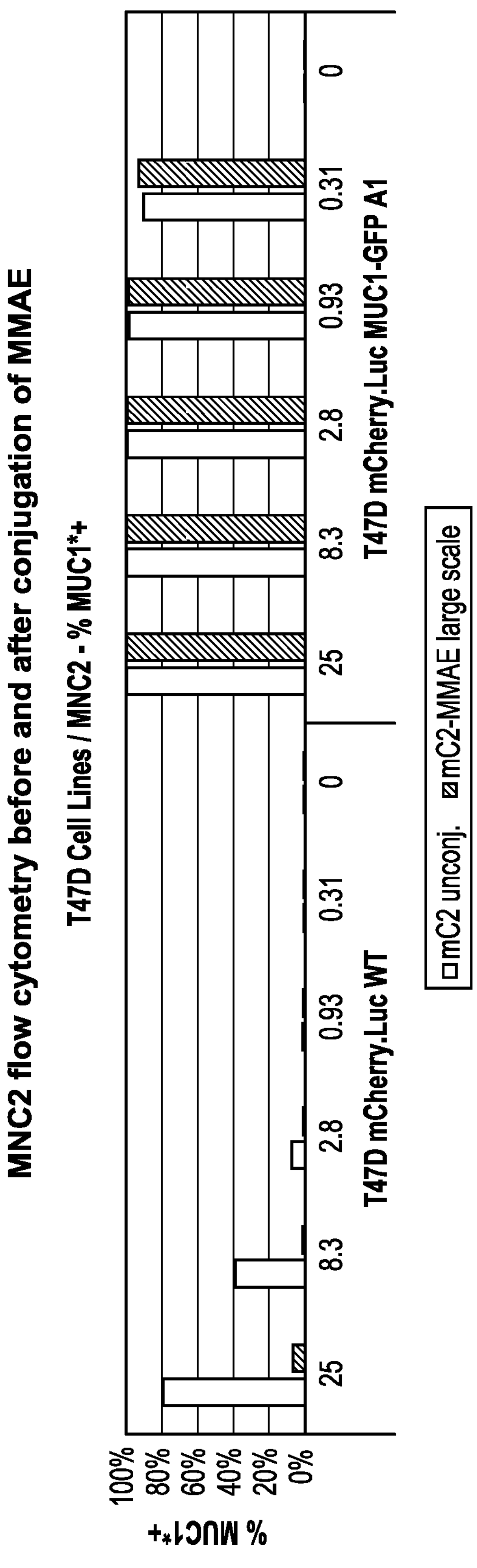
FIG. 36A
FIG. 36B
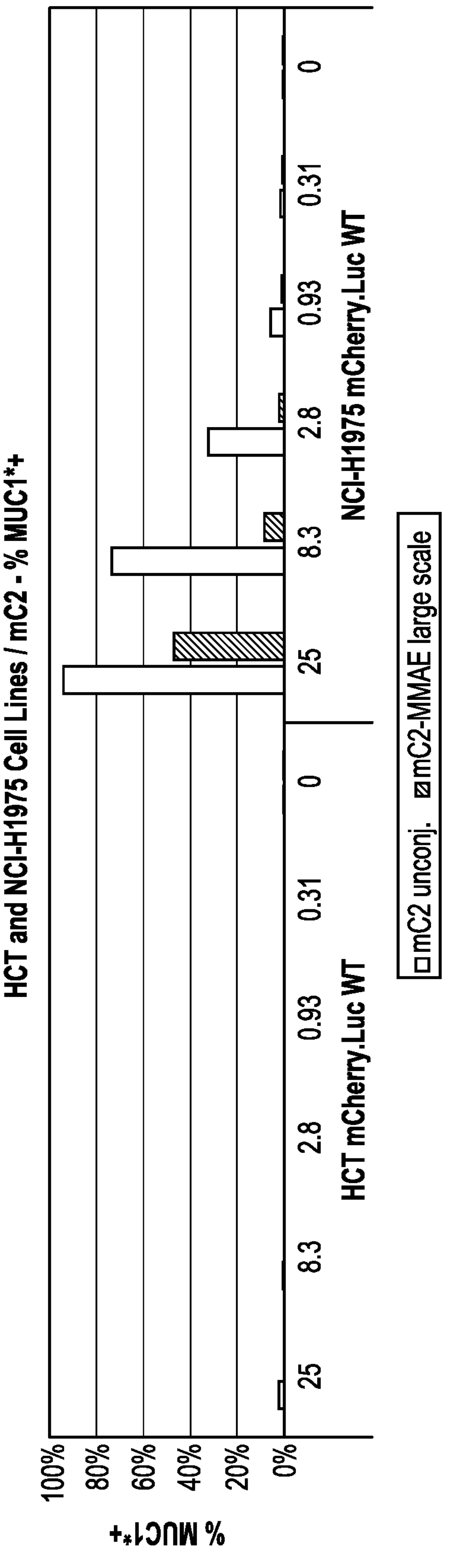
FIG. 36C
FIG. 36D

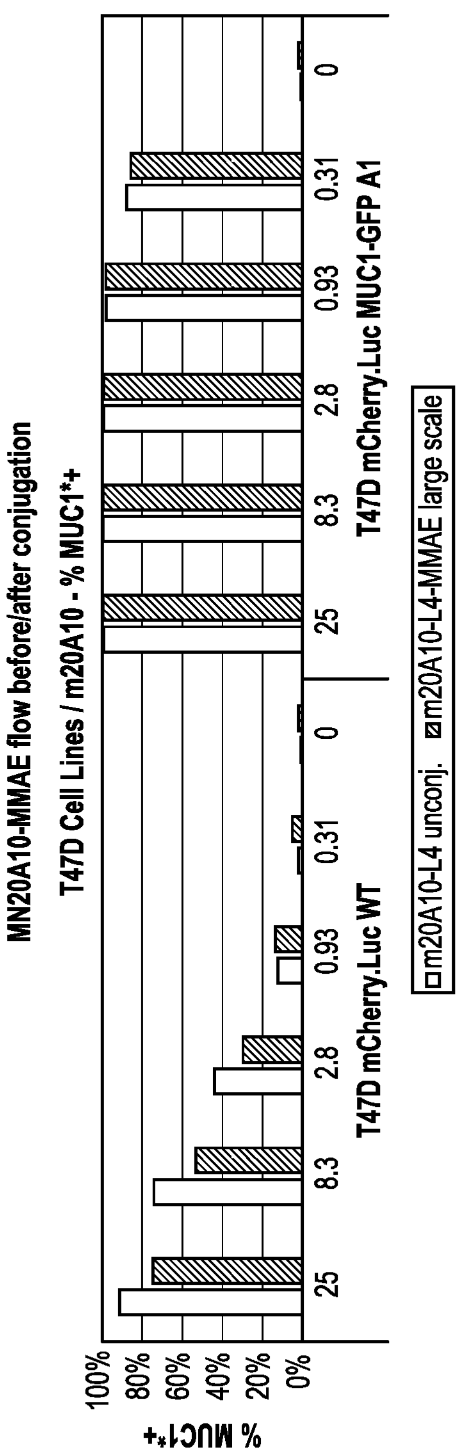
FIG. 37A
FIG. 37B
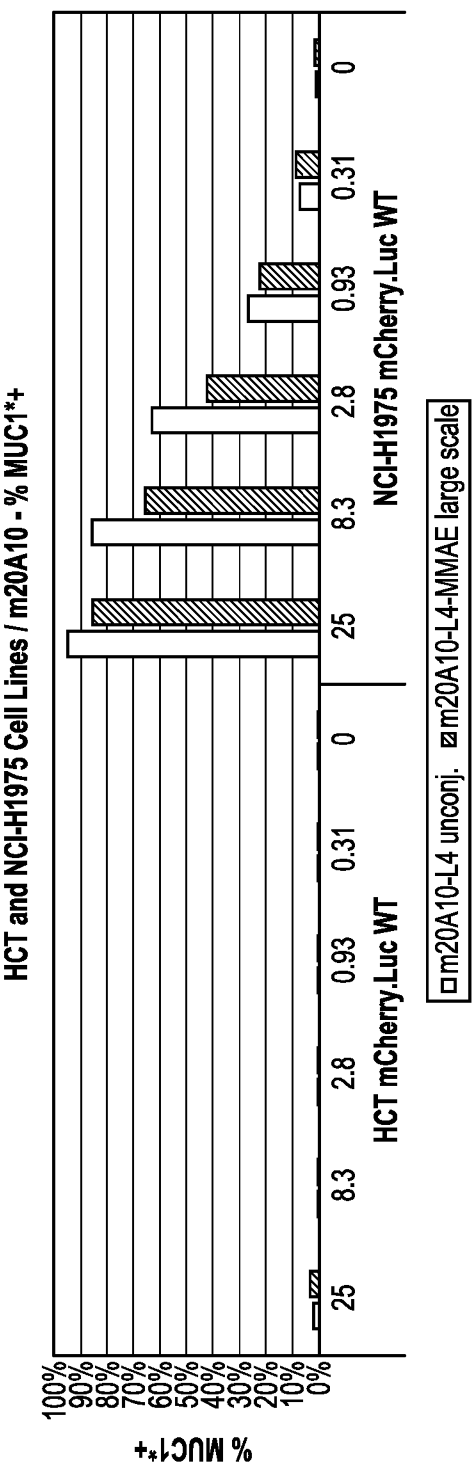
FIG. 37C
FIG. 37D

| | DAR | IC50 nM | $R^2$ |
|---|---|---|---|
| T47D WT_MNC2-MMAE | 4.1 | >150 | 0.93 |
| T47D WT_MNC2-MMAF | 3.7 | >150 | 0.99 |
| HPAF-II WT_MNC2-MMAE | 4.1 | 66.62 | 0.981 |
| HPAF-II WT_MNC2-MMAF | 3.7 | 100.31 | 0.980 |

FIG. 38E

| | DAR | IC50 nM | $R^2$ |
|---|---|---|---|
| T47D MUC1*_MNC2-MMAE | 4.1 | 3.62 | 0.999 |
| T47D MUC1*_MNC2-MMAF | 3.7 | 1.28 | 0.998 |
| HPAF-II MUC1*_MNC2-MMAE | 4.1 | 41.58 | 0.988 |
| HPAF-II MUC1*_MNC2-MMAF | 3.7 | 89.61 | 0.998 |

FIG. 38F

| | DAR | IC50 nM | $R^2$ |
|---|---|---|---|
| T47D WT_MN20A10-MMAE | 5.8 | 50.88 | 0.99 |
| T47D WT_MN20A10-MMAF | 3.8 | >150 | 0.99 |
| HPAF-II WT_MN20A10-MMAE | 5.8 | 17.32 | 0.997 |
| HPAF-II WT_MN20A10-MMAF | 3.8 | 93.49 | 0.976 |

FIG. 39E

| | DAR | IC50 nM | $R^2$ |
|---|---|---|---|
| T47D MUC1*_MN20A10-MMAE | 5.8 | 2.81 | 0.991 |
| T47D MUC1*_MN20A10-MMAF | 3.8 | 4.62 | 0.999 |
| HPAF-II MUC1*_MN20A10-MMAE | 5.8 | 25.25 | 0.99 |
| HPAF-II MUC1*_MN20A10-MMAF | 3.8 | 58.35 | 0.99 |

FIG. 39F

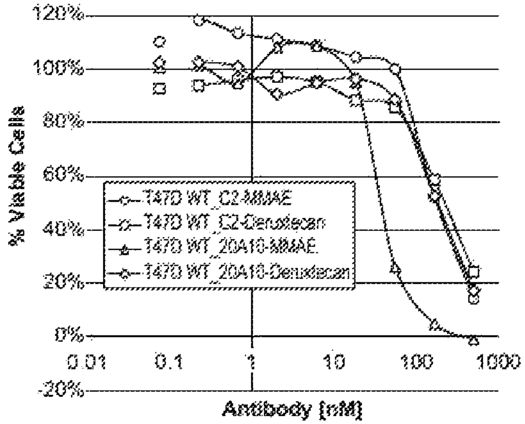
FIG. 40A
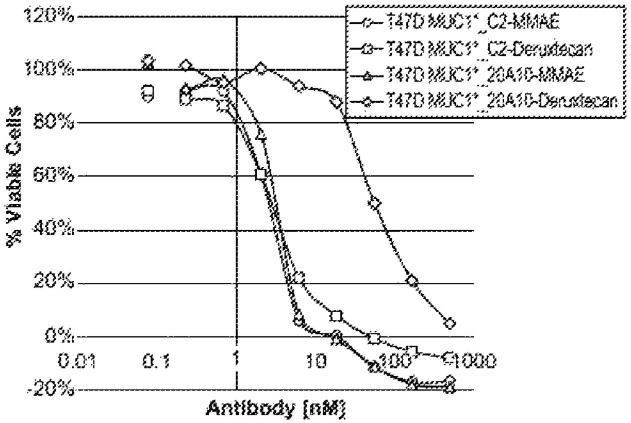
FIG. 40B
| | DAR | IC50 nM | $R^2$ |
|---|---|---|---|
| T47D WT_MNC2-MMAE | 4.1 | 149.17 | 0.9911 |
| T47D WT_MNC2-Deruxtecan | 7.2 | 239.12 | 0.9934 |
| T47D WT_MN20A10-MMAE | 5.8 | 39.52 | 0.9913 |
| T47D WT_MN20A10-Deruxtecan | 4.6 | 166.79 | 0.9834 |
| T47D MUC1*_MNC2-MMAE | 4.1 | 3.09 | 0.9915 |
| T47D MUC1*_MNC2-Deruxtecan | 7.2 | 5.27 | 0.9976 |
| T47D MUC1*_MN20A10-MMAE | 5.8 | 3.57 | 0.9909 |
| T47D MUC1*_MN20A10-Deruxtecan | 4.6 | 57.12 | 0.9943 |
FIG. 40C

| | DAR | IC50 nM | $R^2$ |
|---|---|---|---|
| DU-145 WT_C2-MMAE | 4.1 | 86.82 | 0.9930 |
| DU-145 WT_20A10-MMAE | 5.8 | 36.47 | 0.9975 |
| | | | |

| | DAR | IC50 nM | R² |
|---|---|---|---|
| NCI-H1975_C2-MMAE | 4.3 | 55.85 | 0.9898 |
| NCI-H1975_20A10-MMAE | 4.9 | 14.42 | 0.9974 |
| | | | |

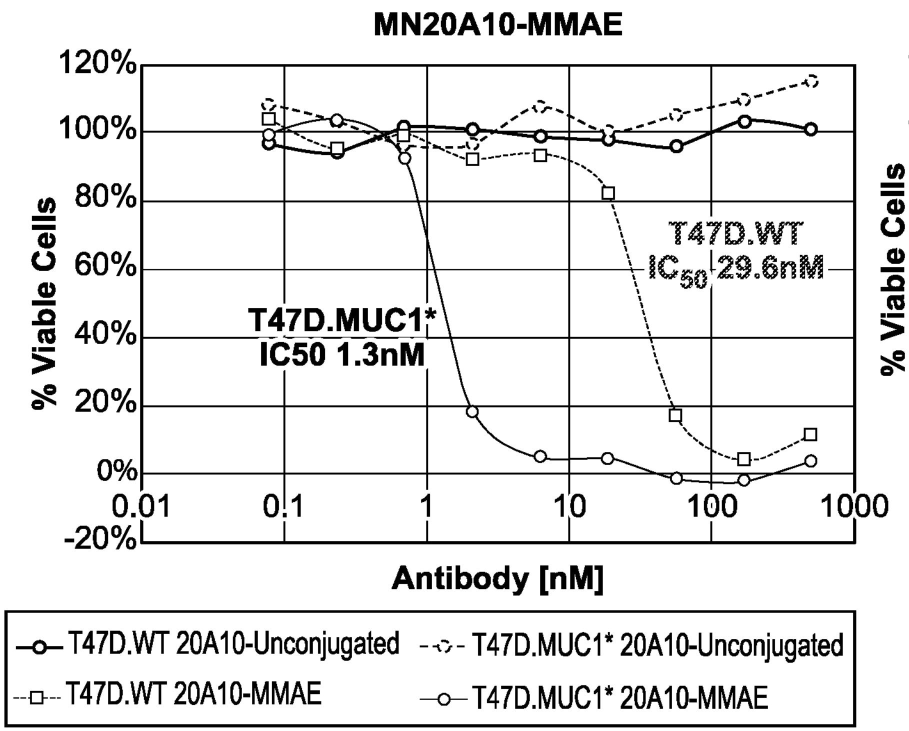
FIG. 43A
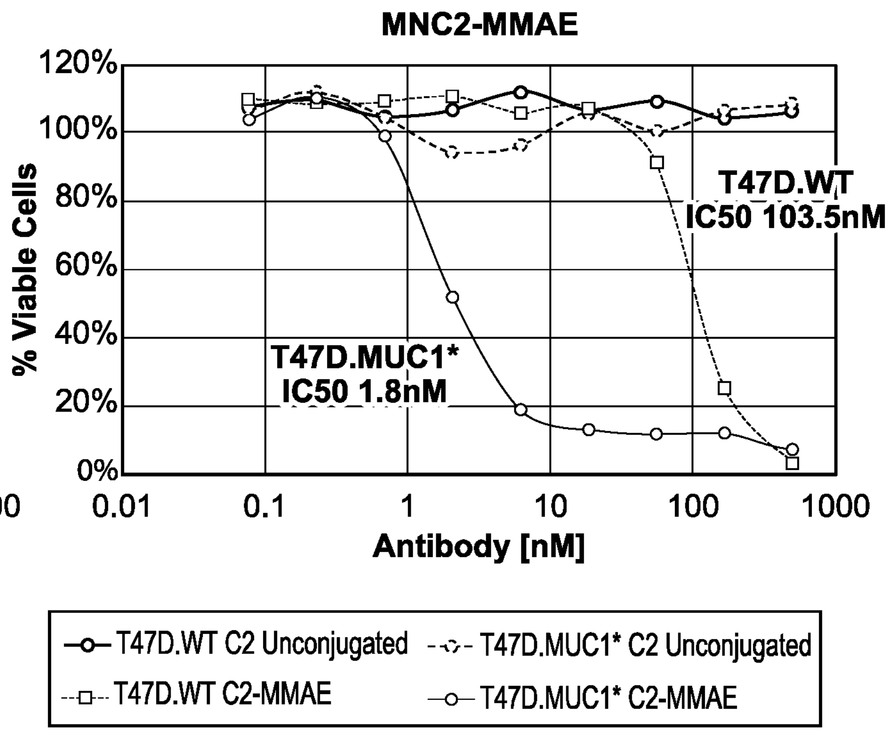
FIG. 43B
| | DAR | IC50 nM | $R^2$ |
|---|---|---|---|
| T47D WT_MN20A10-MMAE | 5.2 | 29.6 | |
| T47D-MUC1*_MN20A10-MMAE | 5.2 | 1.3 | |
| T47D WT_MNC2-MMAE | 4.3 | 103.5 | |
| T47D-MUC1* MNC2-MMAE | 4.3 | 1.8 | |
FIG. 43C

| | DAR |
|---|---|
| HCT-MUC1*_MN20A10-MMAE | 3.8 |
| HCT-MUC1*_IgG2b-MMAE | 4.8 |
| HCT-116_IgG2b-MMAE | 4.8 |

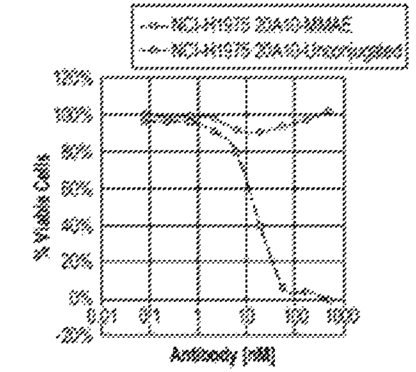
FIG. 45A
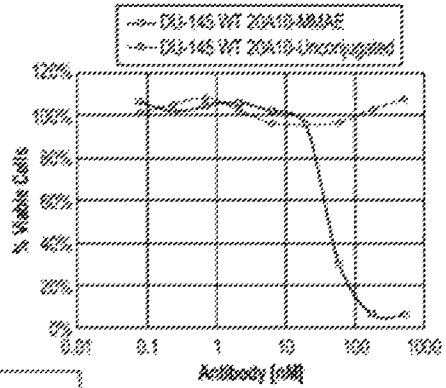
FIG. 45B
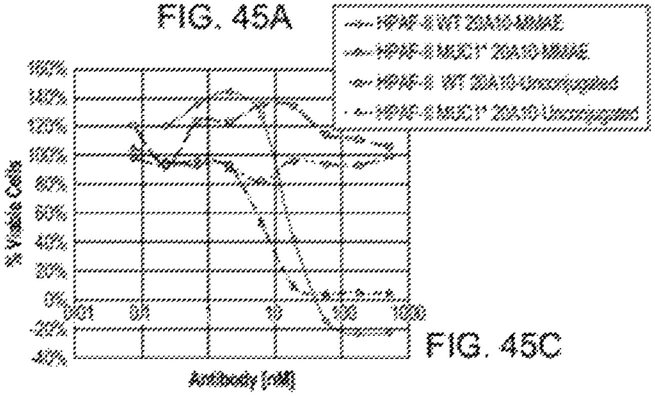
FIG. 45C
| | DAR | IC50 nM | $R^2$ |
|---|---|---|---|
| NCI-H1975_MN20A10-MMAE | 5.2 | 14.97 | 0.99 |
| NCI-H1975_MN20A10-unconjugated | NA | >150 | |
| DU-145 WT_MN20A10-MMAE | 5.2 | 39.23 | 0.99 |
| DU-145 WT_MN20A10-unconjugated | NA | >150 | |
| HPAF-II WT_MN20A10-MMAE | 4.3 | 14.97 | 0.99 |
| HPAF-II WT_MN20A10-unconjugated | NA | >150 | |
| HPAF-II MUC1*_MN20A10-MMAE | 5.2 | 6.4 | 0.99 |
| HPAF-II MUC1*_MN20A10-unconjugated | NA | >150 | |
FIG. 45D

MNC2-MMAE 500 nM 6.2 nM 0.0 nM

MNC2-Deruxtecan 500 nM 6.2 nM 0.0 nM

MNC2-MMAE and MNC2-deruxtecan incubated with T47D-MUC1* breast cancer cells photographed at 120 hrs at 4x magnification

MNC2-MMAE 6.2 nM 0.0 nM

MNC2-Deruxtecan 6.2 nM 0.0 nM

MNC2-MMAE and MNC2-deruxtecan incubated with T47D-MUC1* breast cancer cells, 120 hrs at 20X magnification

MNC2-MMAE 500 nM 0.0 nM

MNC2-Deruxtecan 500 nM 0.0 nM

MNC2-MMAE and MNC2-Deruxtecan incubated with DU145 prostate cancer cells

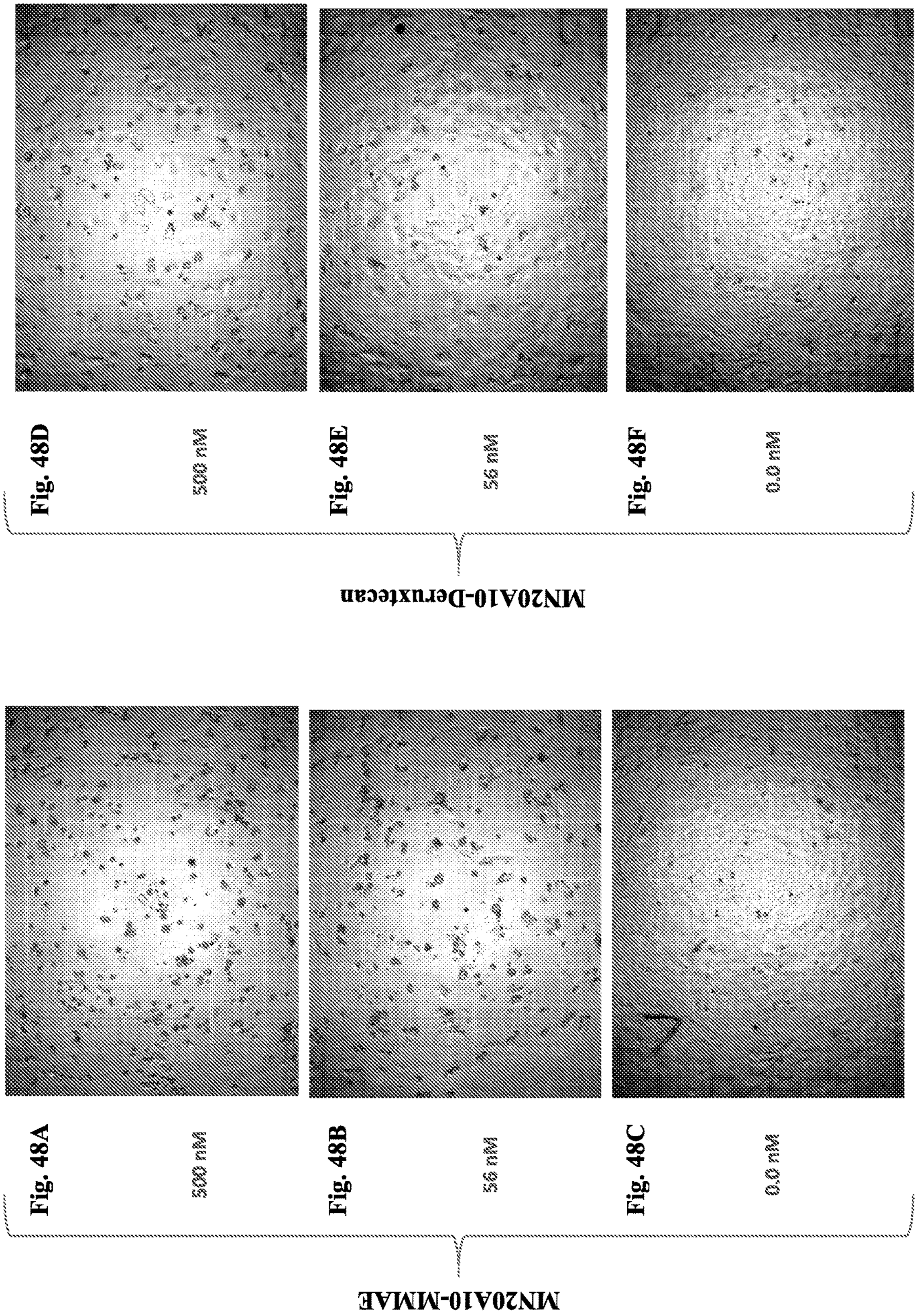
MN20A10-MMAE and MN20A10-deruxtecan incubated with T47D-MUC1* breast cancer cells

MN20A10-MMAE 56 nM 0.0 nM

MN20A10-Deruxtecan 56 nM 0.0 nM

MN20A10-MMAE and MN20A10-deruxtecan incubated with T47D-MUC1* breast cancer cells

MN20A10-MMAE 500 nM 0.0 nM 56 nM

MN20A10-Deruxtecan 500 nM 0.0 nM

MN20A10-MMAE and MN20A10-deruxtecan incubated with DU145 prostate cancer cells at 120 hrs 4x magnification MNC2/MN20A10-MMAE, -MMAF or Deruxtecan xCELLigence real-time killing assay; 120 hour analysis HPAF II-WT pancreatic cancer cells
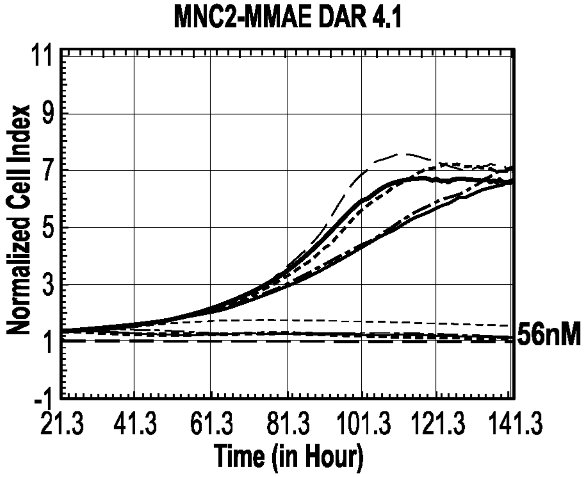
FIG. 52E
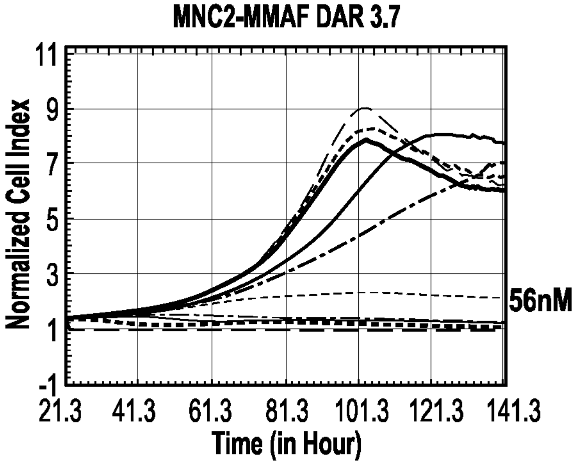
FIG. 52F
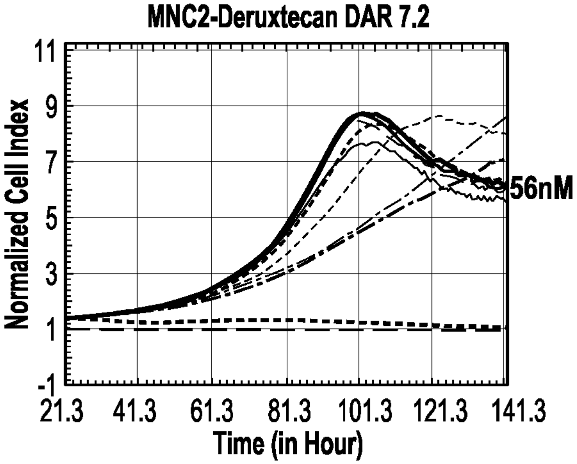
FIG. 52G
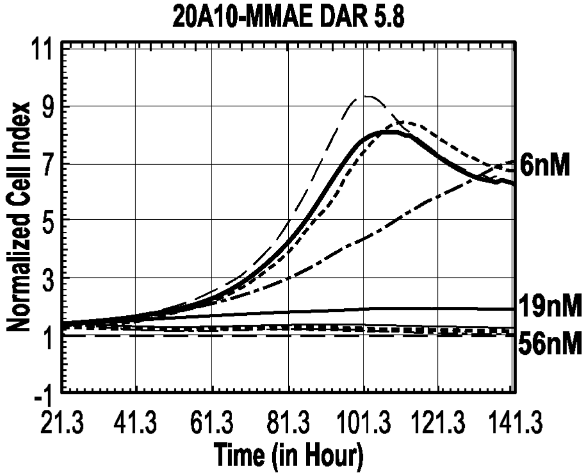
FIG. 52H
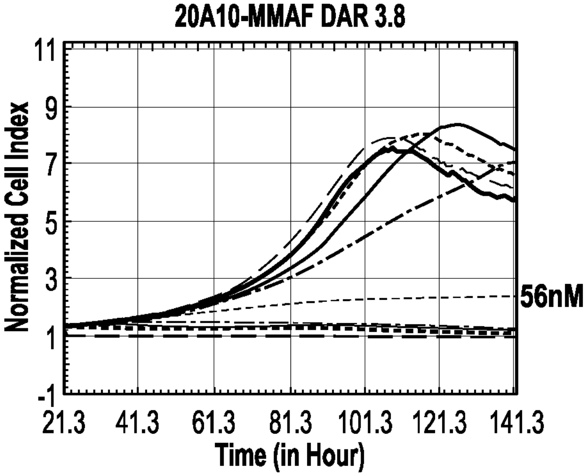
FIG. 52I
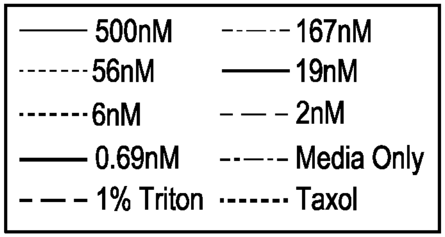

T47D-wt breast cancer cells treated with MNC2-MMAE, MNC2-Deruxtecan, or MNC2-Exatecan
xCELLigence real-time killing assay; 120 hour
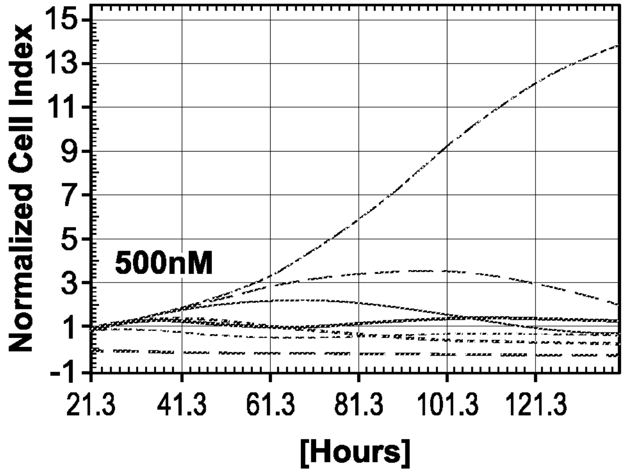
FIG. 54A
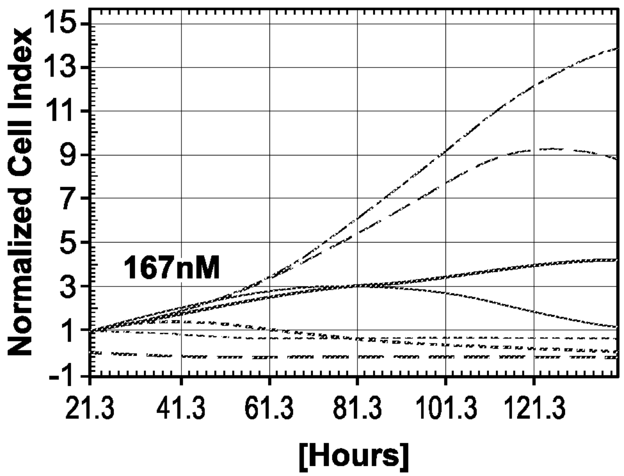
FIG. 54B
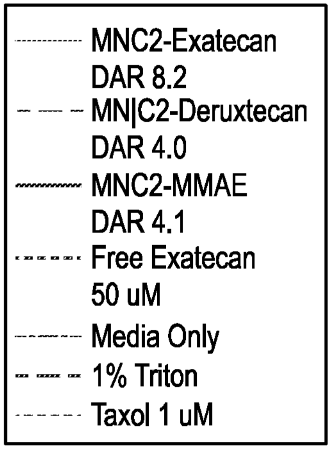
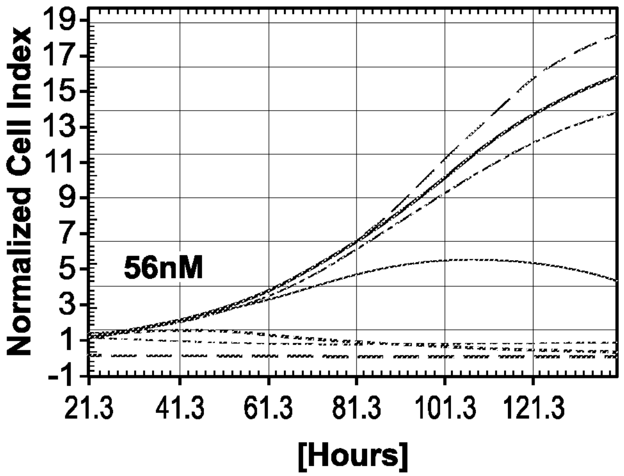
FIG. 54C
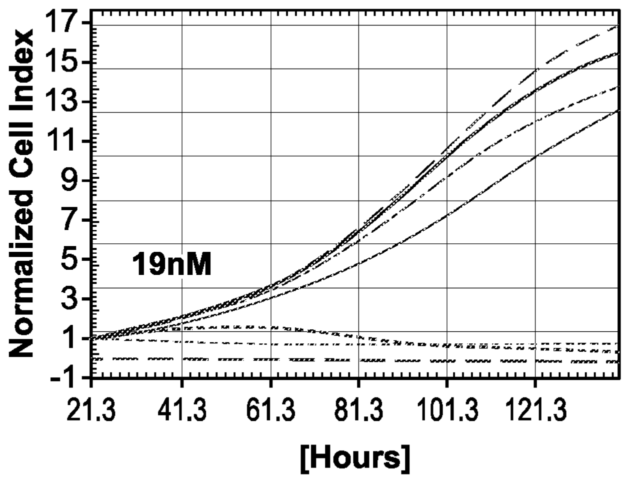
FIG. 54D NCI-H1975 lung cancer cells treated with MNC2-MMAE, MNC2-Deruxtecan, or MNC2-Exatecan xCELLigence real-time killing assay; 120 hour MNC2-MMAE T47D vs T47D-MUC1*

MN20A10-MMAE T47D vs T47D-MUC1*

MN20A10-MMAE animal data

HPAF II-WT Ctrl

HPAF II-WT MNC2-MMAE DAR 4.10

T47D wild type cell pellet, t<implantation; FFPE

Excised Day 62 from PBS mock treatment mouse; representative tissue shown

ANTI-VARIABLE MUC1* ANTIBODIES AND USES THEREOF

CROSS REFERENCE

This application is a National Stage Entry of International Application No. PCT/US2023/065637, filed on Apr. 11, 2023, which claims the benefit of U.S. provisional application 63/330,277, filed on Apr. 12, 2022, the entirety of each of which is hereby incorporated by reference herein.

SEQUENCE LISTING

The instant application contains a Sequence Listing which has been submitted electronically in ASCII format and is hereby incorporated by reference in its entirety. Said ASCII copy, created on Jul. 31, 2025, is named 56699-751_831_SL.xml and is 230 kilobytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

FIELD

Provided herein are multispecific antibodies comprising a MUC1* binding domain and a CD3 binding domain. Also provided herein are antibody conjugates of the formulas described herein comprising one or more moieties derived from therapeutic agents (e.g., topoisomerase I inhibitors, tubulin formation inhibitors), and wherein the conjugates further comprise a polypeptide, such as an antibody, that binds a target of interest (e.g., antibodies targeting MUC1*). Said multispecific antibodies and antibody-drug conjugates are useful for the treatment of diseases or disorder, for example, a proliferative disease such as a cancer. Also provided herein are uses and methods for treating diseases and disorders using these multispecific antibodies and antibody conjugates.

SUMMARY

Disclosed here in is a conjugate for Formula (I): [Ab]-[Z-L-R-X]$_y$, Formula (I), wherein: X is a moiety derived from a compound capable of inhibiting topoisomerase I or a compound capable of inhibiting tubulin formation; R is a coupling moiety; L is a di- or tri- or tetra-peptide linking moiety having Z bonded to N-terminus and R bonded to the C-terminus; [Ab] is an antibody comprising an anti-MUC1* binding domain comprising three heavy chain (HC) complementarity determining region (CDRs): MUC1* HC-CDR1, MUC1* HC-CDR2, and MUC1* HC-CDR3; wherein the MUC1* HC-CDR1, the MUC1* HC-CDR2, and the MUC1* HC-CDR3 of the MUC1* binding domain comprises amino acid sequences selected from those set forth in Table 1; wherein the MUC1* binding domain comprises three light chain (LC) complementarity determining region (CDRs): MUC1* LC-CDR1, MUC1* LC-CDR2, and MUC1* LC-CDR3; wherein the MUC1* LC-CDR1, the MUC1* LC-CDR2, and the MUC1* LC-CDR3 of the MUC1* binding domain comprises amino acid sequences selected from those set forth in Table 1; Z is a conjugation moiety capable of forming a covalent bond with a sulfur atom of a cysteine residue; and wherein y is an integer from 1 to 10.

L can comprise a valine and a citrulline. L can comprise a glycine and a phenylalanine. R can comprise a para-aminobenzyl. R can comprise a moiety comprising the structure of:

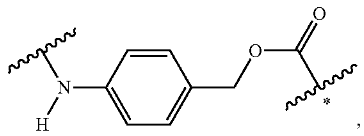 [SMILES: *Nc1ccc(COC(*)=O)cc1]
, wherein the * indicates the point of attachment for the X group. R can comprise a moiety comprising the structure of:

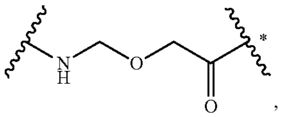 [SMILES: *NCOCC(*)=O]
, wherein the * indicates the point of attachment for the X group. R can comprise a moiety comprising the structure of:

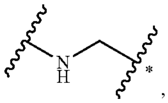 [SMILES: *CN*]
, wherein the * indicates the point of attachment for the X group

L can be a dipeptide linking moiety comprising the structure of:

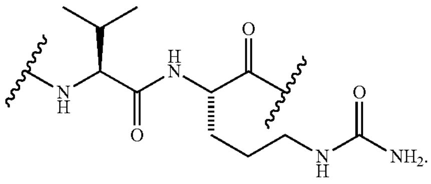 [SMILES: *N[C@H](C(=O)N[C@@H](CCCNC(N)=O)C(*)=O)C(C)C]
.

L can be a tetra-peptide linking moiety comprising the structure of:

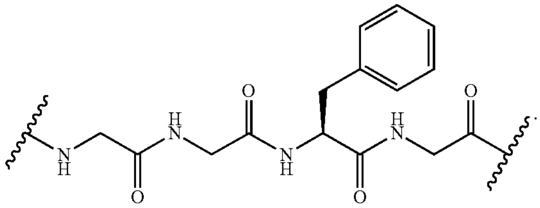 [SMILES: *NCC(=O)NCC(=O)N[C@@H](Cc1ccccc1)C(=O)NCC(*)=O]
.

X can be MMAE or MMAF. X can be exatecan or Dxd. R can comprise a moiety comprising the structure of:

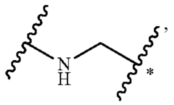

wherein the * indicates the point of attachment for the X group, and wherein X is Dxd. R can comprise a moiety comprising the structure of:

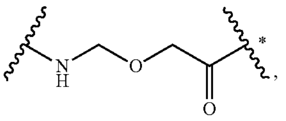 [SMILES: *NCOCC(*)=O]

wherein the * indicates the point of attachment for the X group, and wherein X is exatecan.

The antibody can be isotype IgG1 or IgG2. The antibody can be isotype IgG2b.

The anti-MUC1* binding domain can comprise a heavy chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 38 or 44. The anti-MUC1* binding domain can comprise a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 39 or 45.

The anti-MUC1* binding domain can comprise a light chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 41 or 47. The anti-MUC1* binding domain can comprise a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 42 or 48.

The anti-MUC1* binding domain can comprise a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 129 or 130.

Disclosed herein is an antibody conjugate comprising an antibody comprising an anti-MUC1* binding domain, wherein the antibody is conjugated to a payload via a maleimide-cysteine bond, wherein the payload comprises a linker and a cytotoxic compound, wherein the cytotoxic compound comprises a tubulin inhibitor or a topoisomerase I inhibitor. The linker can comprise a valine. The linker can comprise a citrulline. The linker can comprise a valine and a citrulline. The linker can be a dipeptide linking moiety comprising the structure of:

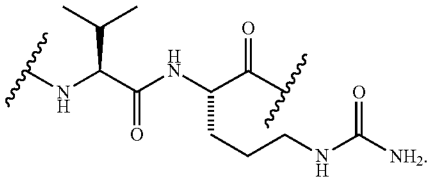 [SMILES: *N[C@H](C(=O)N[C@@H](CCCNC(N)=O)C(*)=O)C(C)C]

The linker can comprise at least one glycine. The linker can comprise at least one glycine and a phenylalanine. The linker can comprise a structure of:

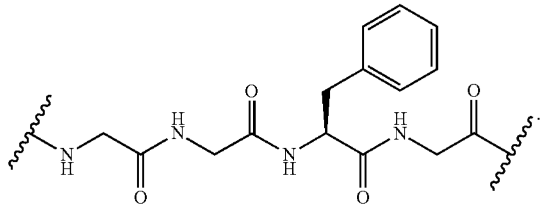 [SMILES: *NCC(=O)NCC(=O)N[C@@H](Cc1ccccc1)C(=O)NCC(*)=O]

The linker can comprise a para-aminobenzyl. The linker can comprise a group of structure

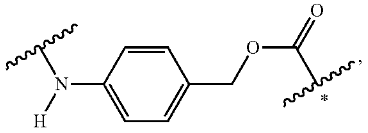 [SMILES: *Nc1ccc(COC(*)=O)cc1]

wherein the * indicates the point of attachment for the cytotoxic group. The linker can comprise a group of structure

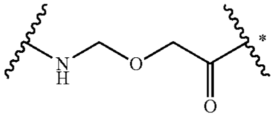

or

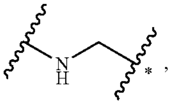

wherein the * indicates the point of attachment for the cytotoxic group. The tubulin inhibitor can be MMAE or MMAF. The topoisomerase I inhibitor can be exatecan or deruxtecan, or a derivative thereof. The linker can comprise a group comprising the structure of:

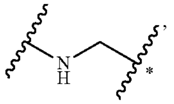 [SMILES: *CN*]

wherein the * indicates the point of attachment for the cytotoxic group, and wherein the topoisomerase I inhibitor is Dxd. The linker can comprise a group comprising the structure of:

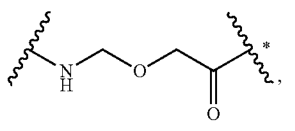 [SMILES: *NCOCC(*)=O]

wherein the * indicates the point of attachment for the cytotoxic group, and wherein the topoisomerase I inhibitor is exatecan.

The antibody conjugate can comprise the structure provided below wherein n is 1 to 10:

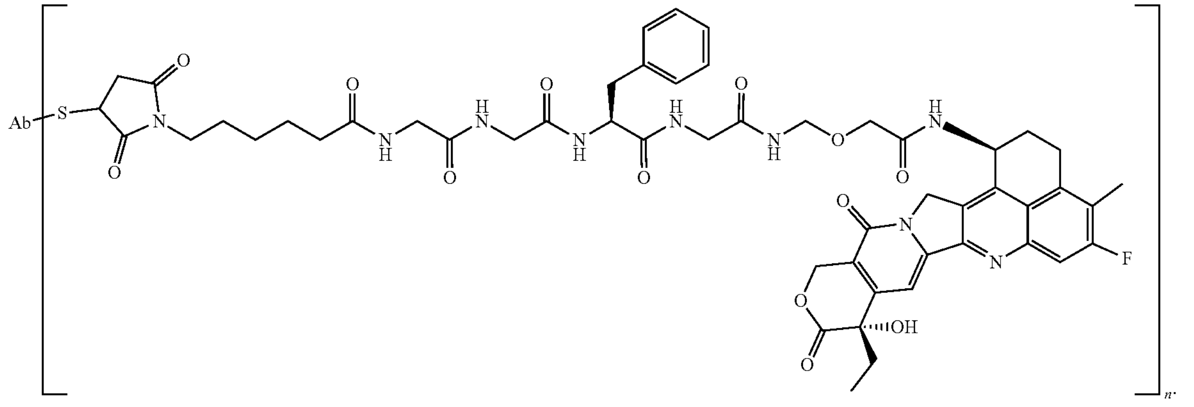

The antibody conjugate can comprise the structure provided below wherein n is 1 to 10:

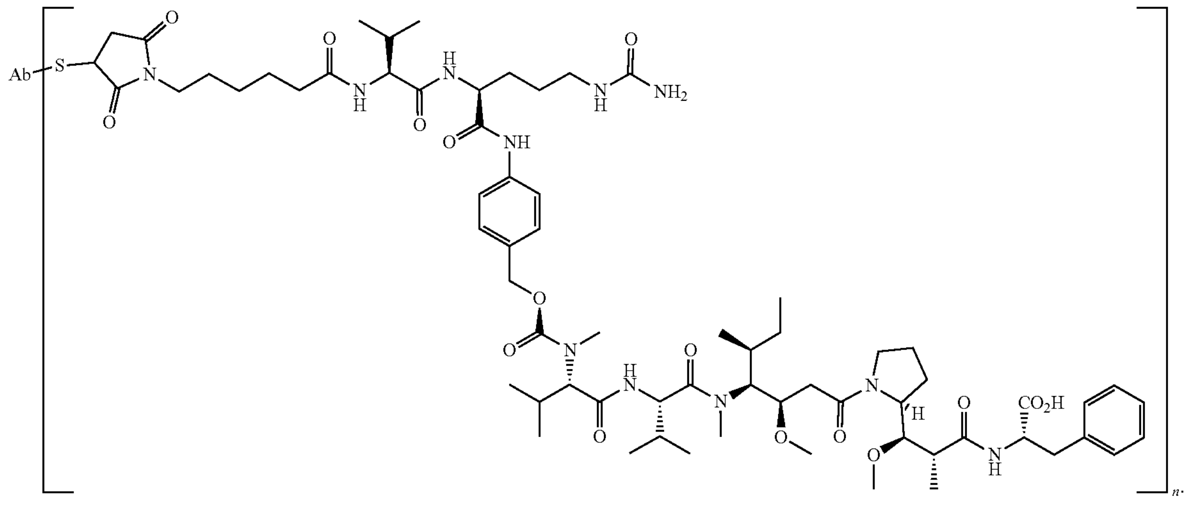

The antibody isotype can be IgG1 or IgG2. The antibody isotype can be IgG2b. The antibody can be conjugated to at least two payloads. The antibody can be conjugated to at least three payloads. The antibody can be conjugated to at least four payloads. The antibody can be conjugated to at least five payloads. The antibody can be conjugated to at least six payloads. The antibody can be conjugated to at least seven payloads. The antibody can be conjugated to at least eight payloads. The anti-MUC1* binding domain can comprise three light chain (LC) complementarity determining region (CDRs): LC-CDR1, LC-CDR2, and LC-CDR3; wherein the LC-CDR1, the LC-CDR2, and the LC-CDR3 of the MUC1* binding domain can comprise amino acid sequences selected from those set forth in Table 1; and wherein at least one of the LC-CDR1, LC-CDR2 and LC-CDR3 can comprise from 0-2 amino acid modification(s). The anti-MUC1* binding domain can comprise three heavy chain (HC) complementarity determining region (CDRs): HC-CDR1, HC-CDR2, and HC-CDR3; wherein the HC-CDR1, the HC-CDR2, and the HC-CDR3 of the MUC1* binding domain can comprise amino acid sequences selected from those set forth in Table 1; and wherein at least one of the HC-CDR1, HC-CDR2 and HC-CDR3 can comprise from 0-2 amino acid modification(s). The anti-MUC1* binding domain can comprise a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 2. The anti-MUC1* binding domain can comprise a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 2. The anti-MUC1* binding domain can comprise a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 3.

Disclosed herein is an antibody comprising a MUC1* binding domain and a CD3 binding domain, wherein the MUC1* binding domain can comprise three heavy chain (HC) complementarity determining region (CDRs): MUC1* HC-CDR1, MUC1* HC-CDR2, and MUC1* HC-CDR3; wherein the MUC1* HC-CDR1 can comprise an amino acid sequence of SEQ ID NO: 1, the MUC1* HC-CDR2 can comprise an amino acid sequence of SEQ ID NO: 2, and the MUC1* HC-CDR3 can comprise an amino acid sequence of SEQ ID NO: 3; wherein the MUC1* binding domain can comprise three light chain (LC) complementarity determining region (CDRs): MUC1* LC-CDR1, MUC1* LC-CDR2, and MUC1* LC-CDR3; wherein the MUC1* LC-CDR1 can comprise an amino acid sequence of SEQ ID NO: 13, the MUC1* LC-CDR2 can comprise an amino acid sequence of SEQ ID NO: 14, and the MUC1* LC-CDR3 can comprise an amino acid sequence of SEQ ID NO: 15; wherein the CD3 binding domain can comprise three heavy chain (HC) complementarity determining region (CDRs): CD3 HC-CDR1, CD3 HC-CDR2, and CD3 HC-CDR3; wherein the CD3 HC-CDR1, the CD3 HC-CDR2, and the CD3 HC-CDR3 of the CD3 binding domain can comprise amino acid sequences selected from those set forth in Table 2; and wherein the CD3 binding domain can comprise three light chain (LC) complementarity determining region (CDRs): CD3 LC-CDR1, CD3 LC-CDR2, and CD3 LC-CDR3; wherein the CD3 LC-CDR1, the CD3 LC-CDR2, and the CD3 LC-CDR3 of the CD3 binding domain can comprise amino acid sequences selected from those set forth in Table 4.

The antibody can comprise an Fc domain. The Fc domain can be a heterodimeric Fc domain. The heterodimeric Fc domain can comprise a knob chain and a hole chain, forming a knob-into-hole (KiH) structure. The knob chain can comprise a sequence having at least about 95% identity to a sequence selected from SEQ ID NOs: 121, 122, 123 or 124. The hole chain can comprise a sequence having at least about 95% identity to a sequence selected from SEQ ID NOs: 125, 126, 127, or 128. The MUC1* binding domain can comprise a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 2. The MUC1* binding domain a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 2. The MUC1* binding domain can comprise a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 3. The CD3 binding domain can comprise a heavy chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 26 or 31. The CD3 binding domain a light chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 29 or 35. The CD3 binding domain can comprise a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 131 or 132. The antibody can comprise a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 50, 52, 54, 58, 62, 66, 70, 74, 78, 82, 86, 90, 94, 98, 102, 106, 110, or 114.

Disclosed herein is a method of treating cancer comprising administering an antibody of any one of claims 1-64 to a subject in need thereof. In some embodiments, the cancer expresses MUC1*. The cancer can be breast cancer, colon cancer, prostate cancer, pancreatic cancer, or lung cancer.

BRIEF DESCRIPTION OF THE DRAWINGS

In FIG. 1A the concentration of the bispecific antibody is 1,000 ng/mL. FIG. 1O shows a graph of secreted interferon-gamma that is secreted by the T cells as a function of added anti-MUC1*/anti-CD3 bispecific antibody, wherein the anti-MUC1* antibody is 20A10 and the anti-CD3 antibody is OKT3. FIG. 1P shows a graph of secreted TNF-alpha that is secreted by the T cells as a function of added anti-MUC1*/anti-CD3 bispecific antibody, wherein the anti-MUC1* antibody is 20A10 and the anti-CD3 antibody is OKT3.

FIGS. 2A-2P show photographs of MUC1* positive breast cancer cells, T47D, in culture with human T cells to which have been added various concentrations of bispecific antibody 20A10-12F6-BiTE. 20A10 is a humanized anti-MUC1* antibody and 12F6 is an antibody that binds to CD3 that is present on human T cells. As can be seen in the figure, the addition of the bispecific antibody mediates the joining together of T cells and cancer cells, seen here as T cell clustering, a sign of activation directed by the bispecific bridge between T cell CD3 and cancer cell MUC1*. In FIG. 2A the concentration of the bispecific antibody is 1,000 ng/mL. In FIG. 2B concentration is 333 ng/mL. In FIG. 2C concentration is 111 ng/mL. In FIG. 2D concentration is 37 ng/mL. In FIG. 2E concentration is 12.3 ng/ml. In FIG. 2F concentration is 4.1 ng/ml. In FIG. 2G concentration is 1.3 ng/mL. In FIG. 2H concentration is 0.4 ng/mL. FIG. 2O shows a graph of secreted interferon-gamma that is secreted by the T cells as a function of added anti-MUC1*/anti-CD3 bispecific antibody, wherein the anti-MUC1* antibody is 20A10 and the anti-CD3 antibody is 12F6. FIG. 2P shows a graph of secreted TNF-alpha that is secreted by the T cells as a function of added anti-MUC1*/anti-CD3 bispecific antibody, wherein the anti-MUC1* antibody is 20A10 and the anti-CD3 antibody is 12F6.

In FIG. 3A the concentration of the bispecific antibody is 1,000 ng/mL. In FIG. 3B concentration is 333 ng/mL. In FIG. 3C concentration is 111 ng/mL. In FIG. 3D concentration is 37 ng/mL. In FIG. 3E concentration is 12.3 ng/mL. In FIG. 3F concentration is 4.1 ng/ml. In FIG. 3G concentration is 1.3 ng/mL. In FIG. 3H concentration is 0.4 ng/mL. In FIG. 3I concentration is 0.15 ng/mL. In FIG. 3J concentration is 0.05 ng/ml. FIG. 3K is a control well in which both T cells and cancer cells are present, but no bispecific antibody has been added. FIG. 3L is a control well in which only cancer cells are present.

FIGS. 4A-4L shows photographs of HCT-MUC1*-transduced cancer cells in culture with human T cells to which have been added various concentrations of bispecific antibody 20A10-12F6-BiTE. 20A10 is a humanized anti-MUC1* antibody and 12F6 is an antibody that binds to CD3 that is present on human T cells. As can be seen in the figure, the addition of the bispecific antibody mediates the joining together of T cells and cancer cells, seen here as cell clustering. In FIG. 4A the concentration of the bispecific antibody is 1,000 ng/mL. In FIG. 4B concentration is 333 ng/ml. In FIG. 4C concentration is 111 ng/mL. In FIG. 4D concentration is 37 ng/mL. In FIG. 4E concentration is 12.3 ng/mL. In FIG. 4F concentration is 4.1 ng/ml. In FIG. 4G concentration is 1.3 ng/mL. In FIG. 4H concentration is 0.4 ng/mL. In FIG. 4I concentration is 0.15 ng/mL. In FIG. 4J concentration is 0.05 ng/ml. FIG. 4K is a control well in which both T cells and cancer cells are present, but no bispecific antibody has been added. FIG. 4L is a control well in which bispecific antibody has been added to cancer cells, but no T cells are present.

In FIG. 5A the concentration of the MNC2-ADC is 100 nM. In FIG. 5B the concentration of the MNC2-ADC is 10 nM. In FIG. 5C the concentration of the MNC2-ADC is 0.1 nM. In FIG. 5D the concentration of the MNC2-ADC is 0.01 nM. In FIG. 5E the concentration of the MNC2-ADC is 0.001 nM. In FIG. 5F the concentration of the MNC2-ADC is 0 nM.

FIGS. 6A-6G show photographs of HCT-MUC1* cancer cells. These HCT cells were transduced to express the target of antibody MNC2, which is MUC1*. The cancer cells have been incubated with MNC2-ADC for 72 hours. In this specific case, the toxic MMAE (monomethyl auristatin) was covalently coupled to a deglycosylated MNC2, which binds to MUC1*. As can be seen in the figure, the addition of the MNC2-ADC at the highest concentration tested here, 100 nM, induced cell clumping which is an indicator of cell death. In FIG. 6A the concentration of the MNC2-ADC is 100 nM. In FIG. 6B the concentration of the MNC2-ADC is 10 nM. In FIG. 6C the concentration of the MNC2-ADC is 1.0 nM. In FIG. 6D the concentration of the MNC2-ADC is 0.1 nM. In FIG. 6E the concentration of the MNC2-ADC is 0.01 nM. In FIG. 6F the concentration of the MNC2-ADC is 0.001 nM. In FIG. 6G the concentration of the MNC2-ADC is 0 nM.

FIGS. 7A-7G show photographs of K562-WT cells, which are negative for MUC1 and MUC1*. The cells have been incubated with MNC2-ADC for 72 hours. In this specific case, the toxic MMAE (monomethyl auristatin) was covalently coupled to a deglycosylated MNC2, which binds to MUC1*. As can be seen in the figures, the addition of the MNC2-ADC did not affect the viability of these MUC1-negative cells. In FIG. 7A the concentration of the MNC2-ADC is 100 nM. In FIG. 7B the concentration of the MNC2-ADC is 10 nM. In FIG. 7C the concentration of the MNC2-ADC is 1.0 nM. In FIG. 7D the concentration of the MNC2-ADC is 0.1 nM. In FIG. 7E the concentration of the MNC2-ADC is 0.01 nM. In FIG. 7F the concentration of the MNC2-ADC is 0.001. In FIG. 7G the concentration of the MNC2-ADC is 0 nM.

In FIG. 8A the concentration of the MNC2-ADC is 100 nM. In FIG. 8B the concentration of the MNC2-ADC is 10 nM. In FIG. 8C the concentration of the MNC2-ADC is 1.0 nM. In FIG. 8D the concentration of the MNC2-ADC is 0.1 nM. In FIG. 8E the concentration of the MNC2-ADC is 0.01 nM. In FIG. 8F the concentration of the MNC2-ADC is 0.001 nM. In FIG. 8G the concentration of the MNC2-ADC is 0 nM.

FIG. 9B shows cell viability as a function of MNC2-ADC concentration, comparing the effect of MNC2-ADC on HCT-WT cells versus HCT-MUC1* cells. As can be seen, the MNC2-ADC antibody induced death only of the MUC1* expressing cells at the high concentrations.

In FIG. 10A the concentration of the MNC2-ADC is 100 nM. In FIG. 10B the concentration of the MNC2-ADC is 10 nM. In FIG. 10C the concentration of the MNC2-ADC is 1.0 nM. In FIG. 10D the concentration of the MNC2-ADC is 0.1 nM. In FIG. 10E the concentration of the MNC2-ADC is 0.01 nM. In FIG. 10F the concentration of the MNC2-ADC is 0.001. In FIG. 10G the concentration of the MNC2-ADC is 0 nM.

FIGS. 11A-11G show photographs of T47D-MUC1* cells, which have been transduced to express even more MUC1*. The cells have been incubated with MNC2-ADC for 72 hours. In this specific case, the toxic MMAE (monomethyl auristatin) was covalently coupled to a deglycosylated MNC2, which binds to MUC1*. As can be seen in the figure, the addition of the MNC2-ADC at the higher concentrations tested here, 10 nM and 100 nM, induced cell clumping which is an indicator of cell death. In FIG. 11A the concentration of the MNC2-ADC is 100 nM. In FIG. 11B the concentration of the MNC2-ADC is 10 nM. In FIG. 11C the concentration of the MNC2-ADC is 1.0 nM. In FIG. 11D the concentration of the MNC2-ADC is 0.1 nM. In FIG. 11E the concentration of the MNC2-ADC is 0.01 nM. In FIG. 11F the concentration of the MNC2-ADC is 0.001. In FIG. 11G the concentration of the MNC2-ADC is 0 nM.

FIG. 12 shows a graph of a cell viability assay, wherein PrestoBlue was used to measure cell death. The graph shows cell viability as a function of MNC2-ADC concentration, comparing the effect of MNC2-ADC on T47D-WT cells versus T47D-MUC1* cells. As can be seen, the MNC2-ADC antibody induced death of the MUC1* expressing cells at concentrations of 10 nM and 100 nM.

In FIG. 13A the concentration of the MNC2-ADC is 0 nM. In FIG. 13B the concentration of the MNC2-ADC is 0.1 nM. In FIG. 13C the concentration of the MNC2-ADC is 0.39 nM. In FIG. 13D the concentration of the MNC2-ADC is 1.0 nM. In FIG. 13E the concentration of the MNC2-ADC is 3.9 nM. In FIG. 13F the concentration of the MNC2-ADC is 10 nM. In FIG. 13G the concentration of the MNC2-ADC is 39 nM. In FIG. 13H the concentration of the MNC2-ADC is 100 nM. In FIG. 13I the concentration of the MNC2-ADC is 393 nM. In FIG. 13J the concentration of the MNC2-ADC is 1000 nM.

In FIG. 14A the concentration of the MNC2-ADC is 0 nM. In FIG. 14B the concentration of the MNC2-ADC is 0.1 nM. In FIG. 14C the concentration of the MNC2-ADC is 0.39 nM. In FIG. 14D the concentration of the MNC2-ADC is 1.0 nM. In FIG. 14E the concentration of the MNC2-ADC is 3.9 nM. In FIG. 14F the concentration of the MNC2-ADC is 10 nM. In FIG. 14G the concentration of the MNC2-ADC is 39 nM. In FIG. 14H the concentration of the MNC2-ADC is 100 nM. In FIG. 14I the concentration of the MNC2-ADC is 393 nM. In FIG. 14J the concentration of the MNC2-ADC is 1000 nM.

FIGS. 16A-16F show magnified photographs of cancer cells to which was added an MNC2-ADC over a range of concentrations. Here, the toxin that is conjugated to the antibody is MMAE. FIG. 16A shows photographs of breast cancer cells T47D wild-type to which MNC2-ADC was added at concentrations ranging from 500 ng/ml to 0.1 ng/mL. As a control, no MNC2-ADC was added. Photographs were taken 72 hours after MNC2-ADC was added to the cancer cells. FIG. 16B shows photographs of breast cancer cells T47D-MUC1*, meaning the cells were stably transfected with even more MUC1* than the naturally express, to which MNC2-ADC was added at concentrations ranging from 500 ng/ml to 0.1 ng/mL. As a control, no MNC2-ADC was added. Photographs were taken 72 hours after MNC2-ADC was added to the cancer cells. FIG. 16C shows photographs of breast cancer cells T47D wild-type to which MNC2-ADC was added at concentrations ranging from 500 ng/mL to 0.1 ng/mL. As a control, no MNC2-ADC was added. In this case, the MNC2-ADC was removed after 16 hours and media replaced. Photographs were taken 72 hours after MNC2-ADC was initially added to the cancer cells. FIG. 16D shows photographs of breast cancer cells T47D-MUC1*, meaning the cells were stably transfected with even more MUC1* than the naturally express, to which MNC2-ADC was added at concentrations ranging from 500 ng/mL to 0.1 ng/mL. As a control, no MNC2-ADC was added. In this case, the MNC2-ADC was removed after 16 hours and media replaced. Photographs were taken 72 hours after MNC2-ADC was initially added to the cancer cells. FIG. 16E shows magnified photograph of T47D-wt cells to which was added 1 μM Taxol for 72 hours. FIG. 16F shows magnified photograph of T47D-MUC1* cells to which was added 1 μM Taxol for 72 hours.

FIG. 18A shows photographs of breast cancer cells T47D wild-type to which 20A10-ADC was added at concentrations ranging from 500 ng/mL to 0.1 ng/mL. As a control, no 20A10-ADC was added. Photographs were taken 72 hours after 20A10-ADC was added to the cancer cells. FIG. 18B shows photographs of breast cancer cells T47D-MUC1*, meaning the cells were stably transfected with even more MUC1* than the naturally express, to which 20A10-ADC was added at concentrations ranging from 500 ng/ml to 0.1 ng/mL. As a control, no 20A10-ADC was added. Photographs were taken 72 hours after 20A10-ADC was added to the cancer cells. FIG. 18C shows photographs of breast cancer cells T47D wild-type to which 20A10-ADC was added at concentrations ranging from 500 ng/mL to 0.1 ng/mL. As a control, no 20A10-ADC was added. In this case, the 20A10-ADC was removed after 16 hours and media replaced. Photographs were taken 72 hours after 20A10-ADC was initially added to the cancer cells. FIG. 18D shows photographs of breast cancer cells T47D-MUC1*, meaning the cells were stably transfected with even more MUC1* than the naturally express, to which 20A10-ADC was added at concentrations ranging from 500 ng/mL to 0.1 ng/mL. As a control, no 20A10-ADC was added. In this case, the 20A10-ADC was removed after 16 hours and media replaced. Photographs were taken 72 hours after 20A10-ADC was initially added to the cancer cells. FIG. 18E shows magnified photograph of T47D-wt cells to which was added 1 μM Taxol for 72 hours. FIG. 18F shows magnified photograph of T47D-MUC1* cells to which was added 1 μM Taxol for 72 hours.

FIG. 20A shows a graph of the IC50 fitted data of cancer cell killing mediated by either MNC2-ADC or 20A10-ADC, wherein the cancer cells are either T47D-wt or T47D-MUC1*, and where the ADC is incubated with the target cancer cells for either 16 hours or 72 hours. FIG. 20B shows a table listed IC50 for each ADC for each cell type and incubation condition.

FIGS. 21A-21C show MN20A10-OKT3 knob in hole format. FIG. 21A shows photographs of shows photographs of MUC1* positive breast cancer cells, T47D, in culture with human T cells to which have been added various concentrations of bispecific antibody 20A10-OKT3-BiTE. 20A10 is a humanized anti-MUC1* antibody and OKT3 is an antibody that binds to CD3 that is present on human T cells. As can be seen in the figure, the addition of the bispecific antibody mediates the joining together of T cells and cancer cells, seen here as T cell clustering, which is a sign of activation directed by the bispecific bridge between T cell CD3 and cancer cell MUC1*. FIG. 21B shows a graph of secreted interferon-gamma that is secreted by the T cells as a function of added anti-MUC1*/anti-CD3 bispecific antibody, wherein the anti-MUC1* antibody is 20A10 and the anti-CD3 antibody is OKT3. FIG. 21C shows the graph of cell killing as a function of the concentration of 20A10-OKT3, anti-MUC1*/anti-CD3 bispecific antibody.

FIG. 22B shows graph of T-cell mediated cancer cell killing in presence of 12F6-MN20A10 bispecific. FIG. 22A is a cartoon of 12F6-MN20A10N bispecific format used in FIG. 22B. FIG. 22D shows graph of T-cell mediated cancer cell killing in presence of MN20A10-12F6 KiH bispecific. FIG. 22C is a cartoon of KiH bispecific format used in FIG. 22D. FIG. 22F shows graph of T-cell mediated cancer cell killing in presence of OKT3-MN20A10 bispecific.

FIG. 22E is a cartoon of OKT3-MN20A10 bispecific format used in FIG. 22F. FIG. 22H shows graph of T-cell mediated cancer cell killing in presence of MN20A10-12F6 chemically coupled bispecific. FIG. 22G is a cartoon of MN20A10-12F6 bispecific format used in FIG. 22H.

FIG. 24 shows IC50s MN20A10-OKT3 or MN20A10-12F6 in various bispecific formats FIG. 25A shows that at time zero, the antibody is attached to the surface of the cells. FIG. 25B shows that at after 45 minutes, the antibody has been internalized and is seen throughout the cytoplasm. Antibody internalization is required for an ADC to work.

FIG. 28 shows the chemical structure of an Exatecan derivative, Dxd, incorporated into a reactive configuration called Deruxtecan that is ready to be conjugated to an antibody. MC indicates the maleimidocaproyl (MC) portion that facilitates coupling to a Cysteine on the antibody.

GGFG indicates the glycine-glycine-phenylalanine-glycine (GGFG) portion that provides a flexible linker. Coupler indicates the coupler (HN—CH2-O—CH2-CO) portion that bridges the linker and the payload via an ether-diamide coupler. Exatecan indicates the Dxd portion that is the toxic payload, after cellular internalization and/or cleavage of non-toxic portions.

FIG. 29 shows the chemical structure of an Exatecan derivative incorporated into a different chemical entity that facilitates conjugation to an antibody. MC indicates the maleimidocaproyl (MC) portion that facilitates coupling to a Cysteine on the antibody. VC indicates the valine-citrulline (VC) portion and PAB indicates the para-aminobenzyl (PAB), both of which facilitate enzymatic cleavage of the toxic payload inside the cancer cells by the lysosomal enzyme, cathepsin B. Exatecan indicates the Exatecan portion, the toxic payload after cellular internalization and/or cleavage of non-toxic portions.

Figure 30:
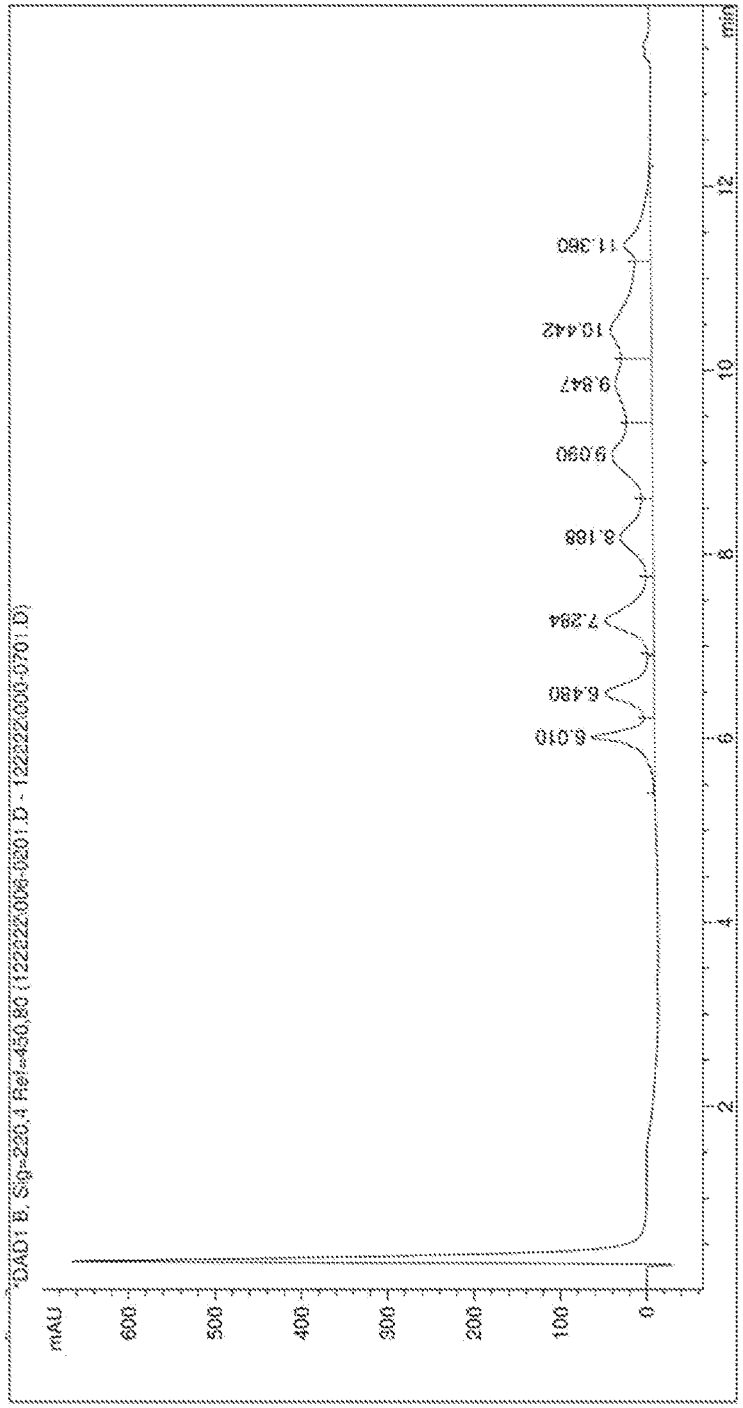

FIG. 30 shows the Hydrophobic interaction chromatography (HIC) chromatogram of MNC2 coupled to MMAE. An IgG1 antibody, like MNC2, has a maximum of eight (8) Cysteines with free thiols that can be conjugated through the free thiol to a toxin or pro-toxin. Therefore, a maximum of eight (8) toxins or payloads can be attached to each antibody. Analysis of the HIC chromatogram of MNC2 gave an average drug-antibody-ratio (DAR) of 4.10

Figure 31:
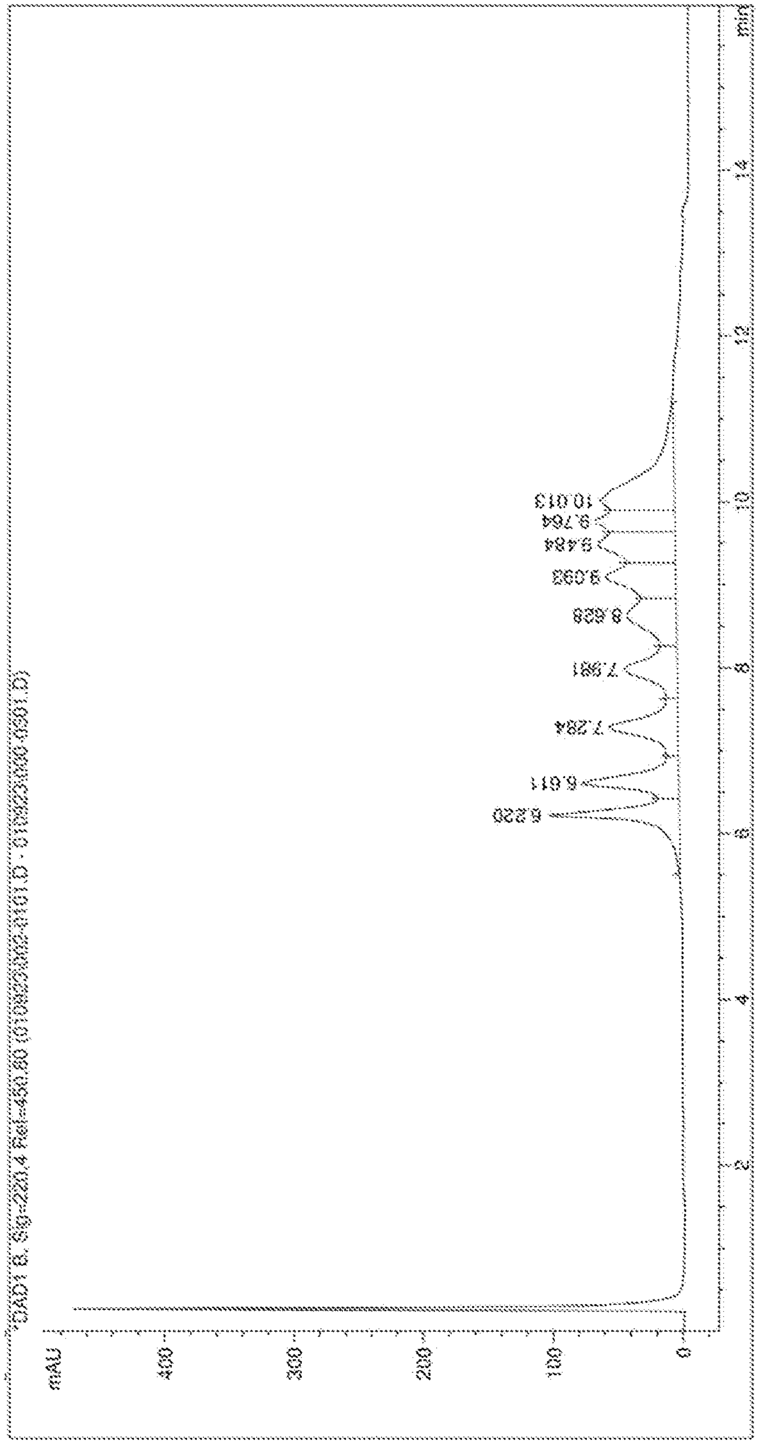

FIG. 31 shows the hydrophobic interaction chromatography (HIC) chromatogram of MNC2 coupled to MMAF. The average DAR for MNC2-MMAF was determined to be 3.65.

Figure 32A:
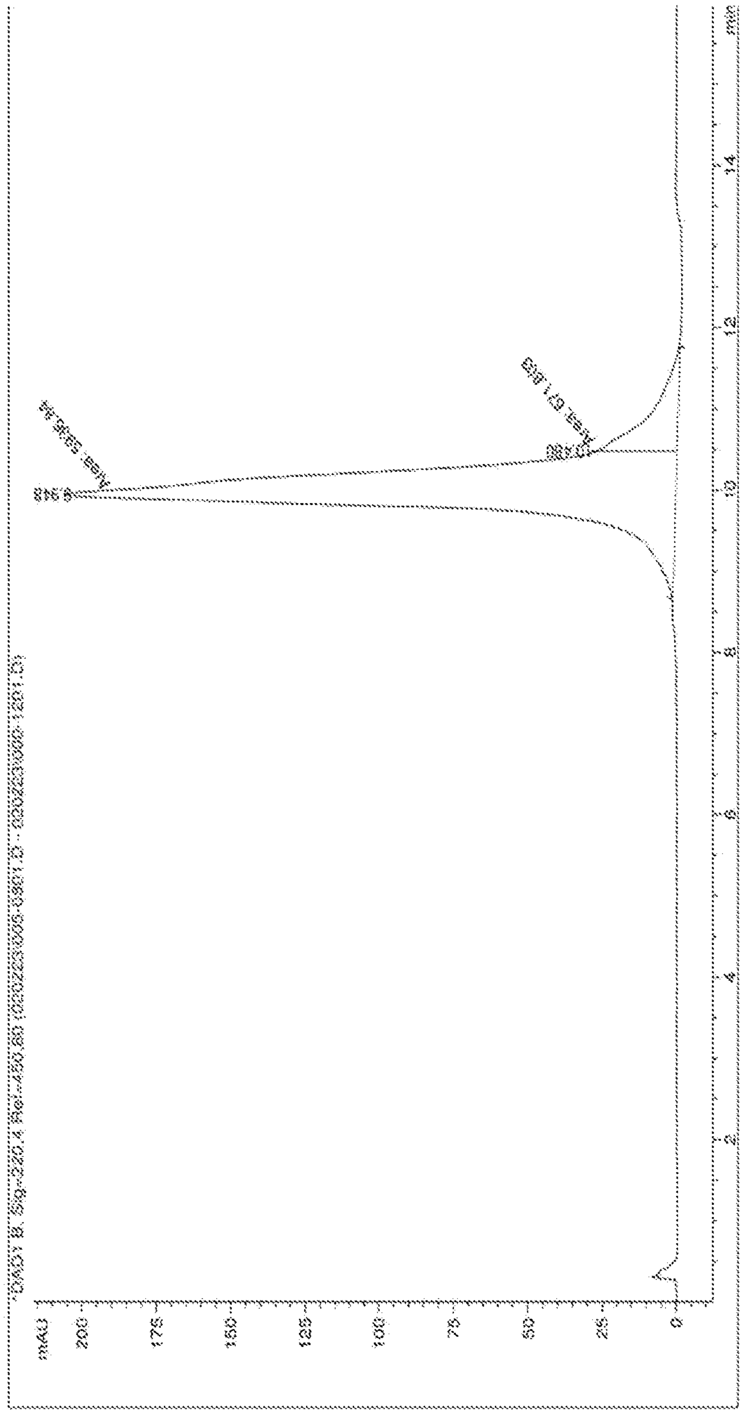
Figure 32B:
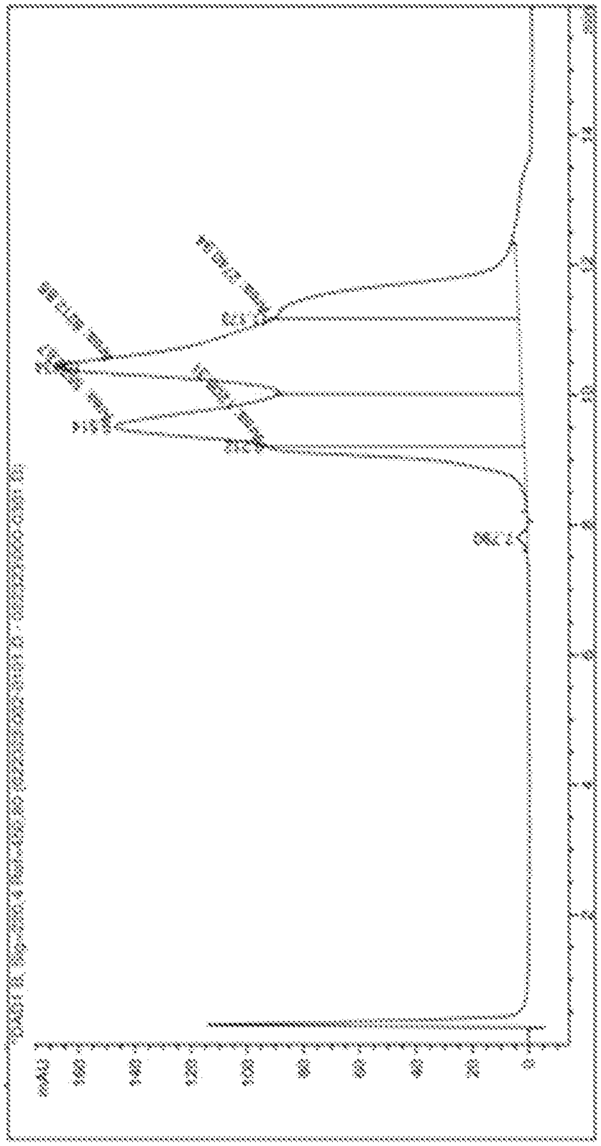

FIG. 32A-32B show the hydrophobic interaction chromatography (HIC) chromatograms of MNC2 coupled to deruxtecan or exatecan. FIG. 32A 32B shows the hydrophobic interaction chromatography (HIC) chromatograms of MNC2 coupled to deruxtecan. The DAR for MNC2-deruxtecan was determined to be 7.7. FIG. 32B shows the hydrophobic interaction chromatography (HIC) chromatograms of MNC2 coupled to exatecan. The DAR for MNC2-exatecan was determined to be 8.2.

Figure 33:
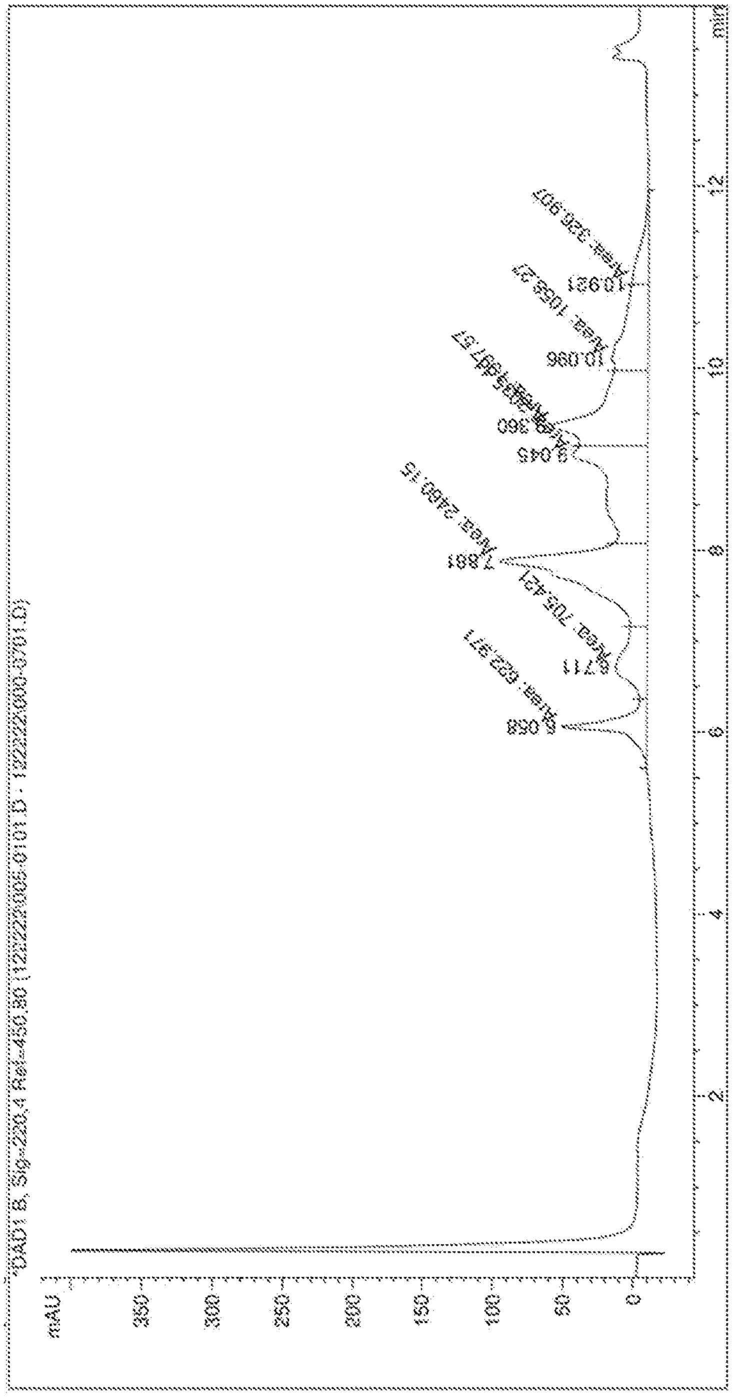

FIG. 33 shows the Hydrophobic interaction chromatography (HIC) chromatogram of MN20A10 coupled to MMAE. The average DAR for MN20A10-MMAE was 2.96

Figure 34:
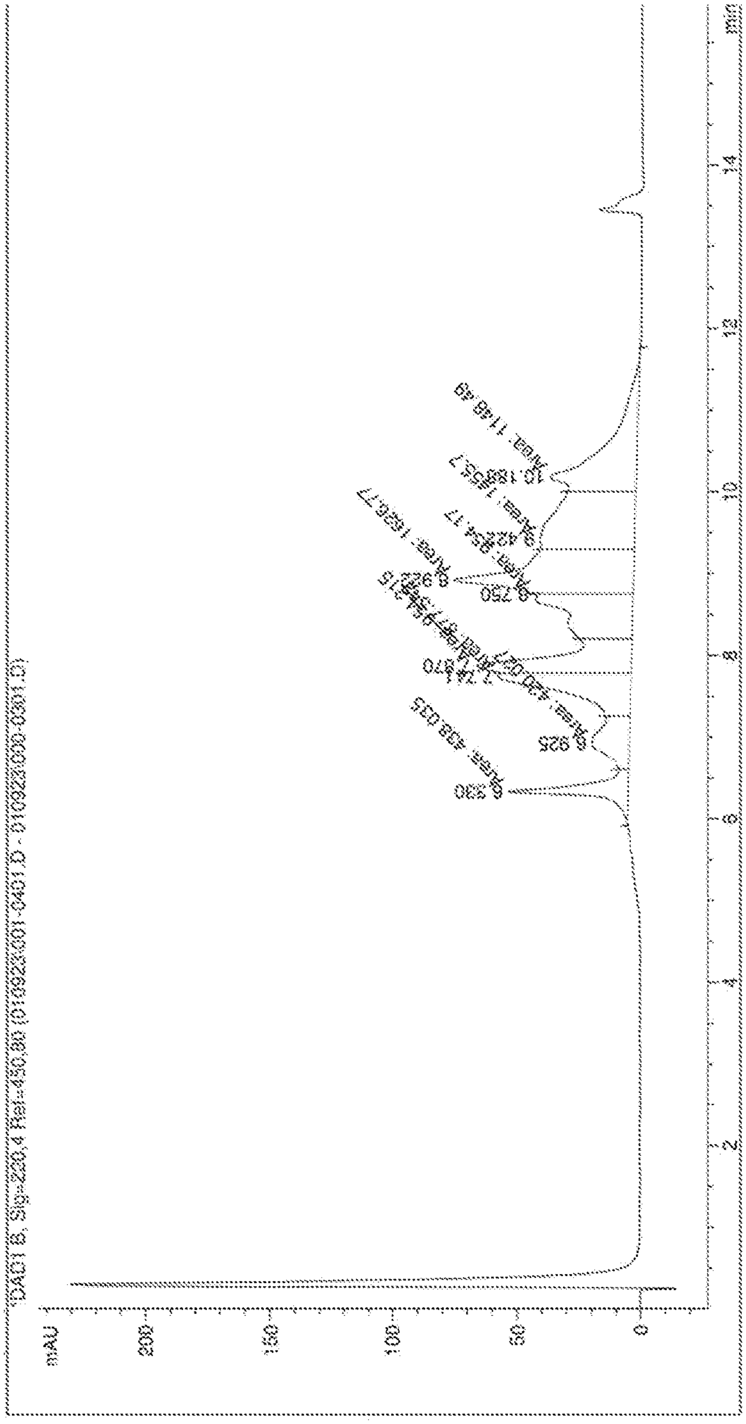

FIG. 34 shows the Hydrophobic interaction chromatography (HIC) chromatogram of MN20A10 coupled to MMAF. The average DAR for MN20A10-MMAF was 3.79

Figure 35:
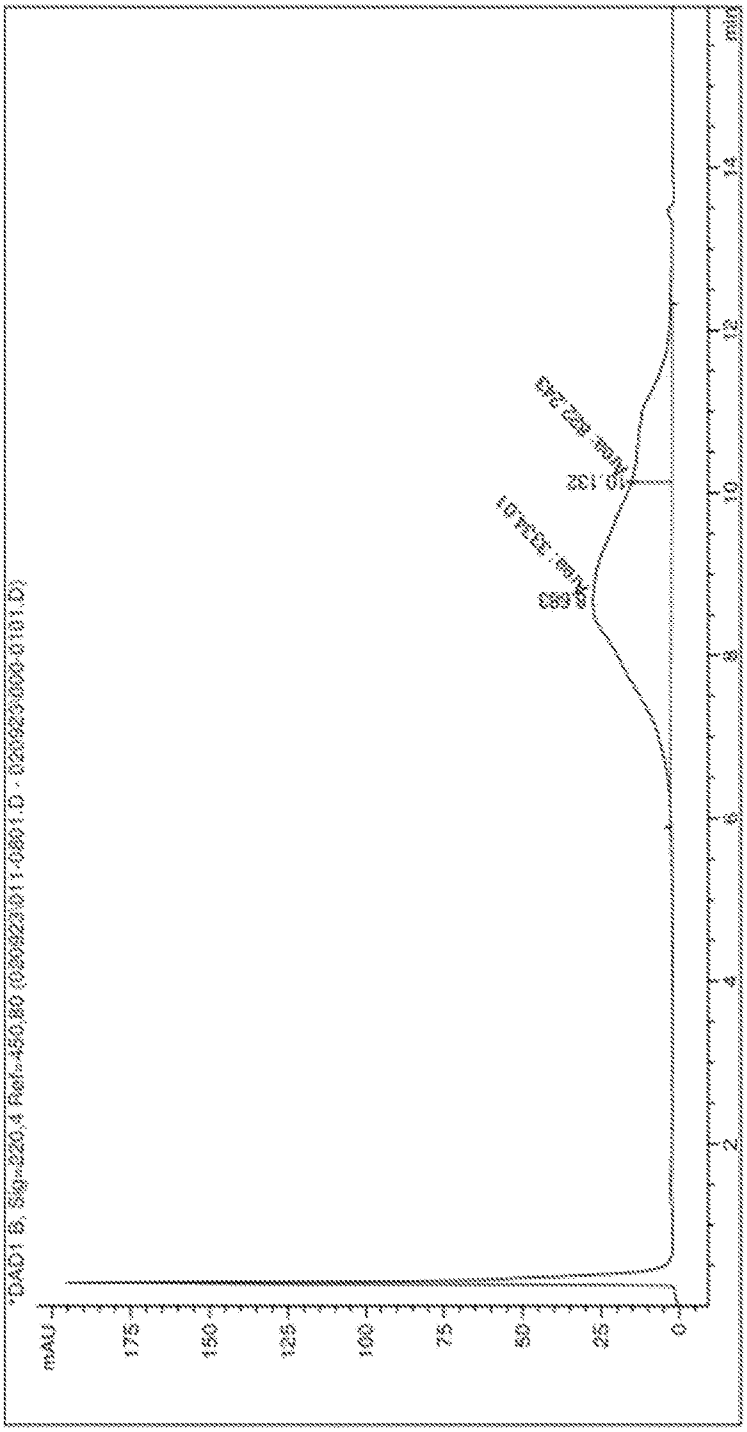

FIG. 35 shows the Hydrophobic interaction chromatography (HIC) chromatogram of MN20A10 coupled to deruxtecan. The average DAR for MN20A10-deruxtecan is 4.6

FIGS. 36A-36D shows graphs of flow cytometry measuring the ability of MNC2 to recognize cancer cells before then after coupling of MMAE. FIG. 36A shows the percentage of T47D breast cancer cells that are recognized by MNC2 before conjugation and after conjugation to MMAE. FIG. 36B shows the percentage of T47D breast cancer cells that are recognized by MNC2 after conjugation to MMAE. FIG. 36C shows the percentage of HCT-116, MUC1 negative cells that are recognized by MNC2 before or after conjugation to MMAE. FIG. 36D shows the percentage of NCI-H1975 lung cancer cells that are recognized by MNC2 after conjugation to MMAE.

FIGS. 37A-37D show graphs of flow cytometry measuring the ability of MN20A10 to recognize cancer cells before then after coupling of MMAE. FIG. 37A shows the percentage of T47D breast cancer cells that are recognized by MN20A10 before and after conjugation to MMAE. FIG. 37B shows the percentage of T47D breast cancer cells that are recognized by MN20A10 after conjugation to MMAE. FIG. 37C shows the percentage of HCT-116, MUC1 negative cancer cells that are recognized by MN20A10 before conjugation to MMAE. FIG. 37D shows the percentage of NCI-H1975 lung cancer cells that are recognized by MN20A10 after conjugation to MMAE.

Figure 38A:
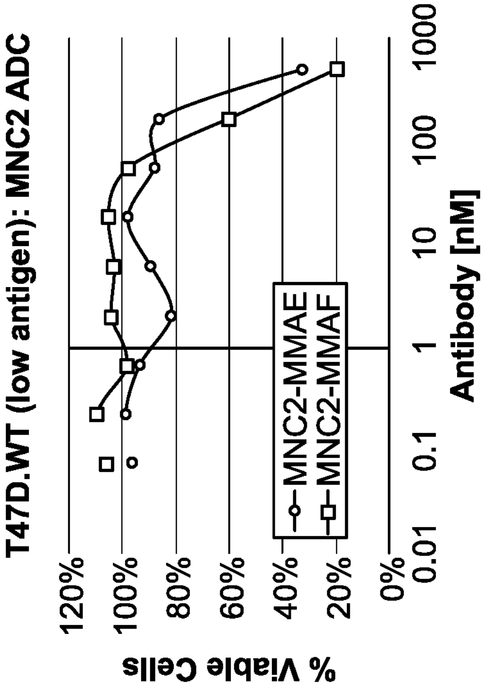
Figure 38B:
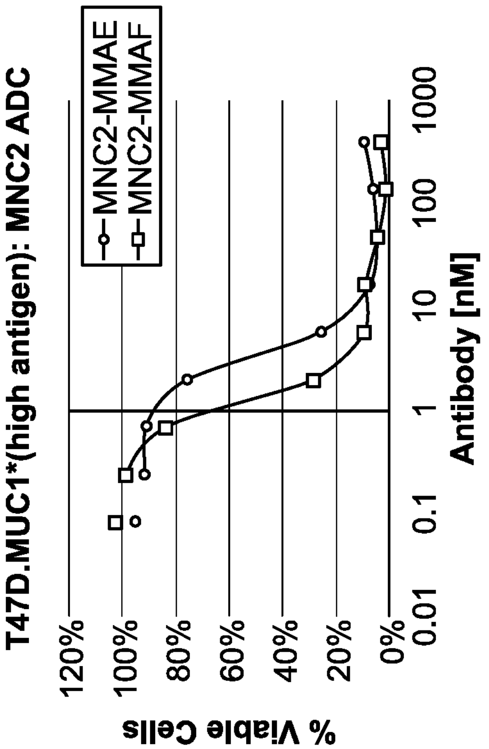
Figure 38C:
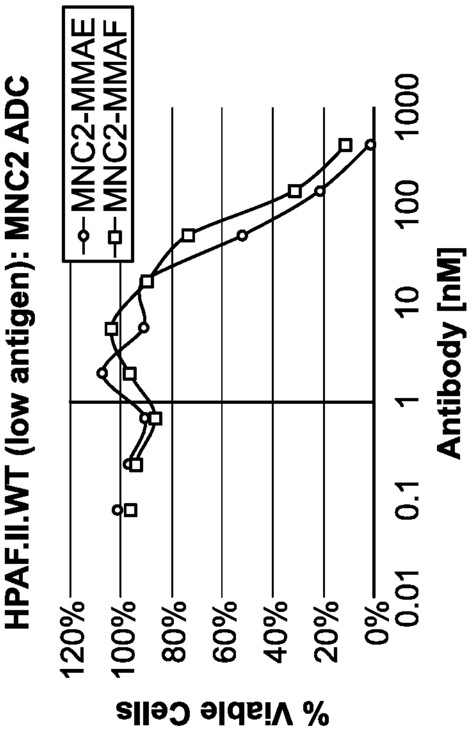
Figure 38D:
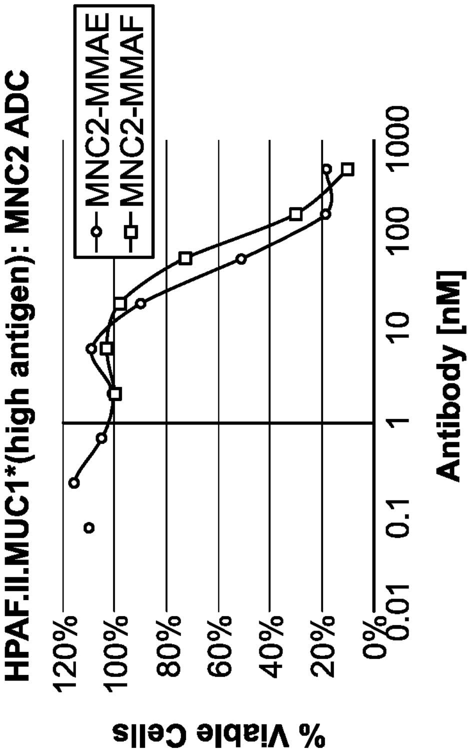

FIGS. 38A-38F show graphs of a plate reader assay wherein the viability of target cancer cells is measured as a function of the concentration of the MNC2-ADC added, wherein the viability is determined using PrestoBlue. The experiment was allowed to proceed for 72 hours before the measurements were taken. FIG. 38A shows the viability of T47D wild-type breast cancer cells after the addition of either MNC2-MMAE or MNC2-MMAF. FIG. 38B shows the viability of T47D breast cancer cells that have been engineered to express more MUC1*, called T47D-MUC1*, after the addition of either MNC2-MMAE or MNC2-MMAF. FIG. 38C shows the viability of HPAF II wild-type pancreatic cancer cells after the addition of either MNC2-MMAE or MNC2-MMAF. FIG. 38D shows the viability of HPAF II pancreatic cancer cells that have been engineered to express more MUC1*, called HPAF II-MUC1*, after the addition of either MNC2-MMAE or MNC2-MMAF. FIG. 38E shows a table of the calculated IC50s for the killing ability of MNC2-MMAE or MNC2-MMAF added to either breast cancer cells or pancreatic cells that express low levels of the target antigen, MUC1*. FIG. 38F shows a table of the calculated IC50s for the killing ability of MNC2-MMAE or MNC2-MMAF added to either breast cancer cells or pancreatic cells that express high levels of the target antigen, MUC1*.

Figure 39A:
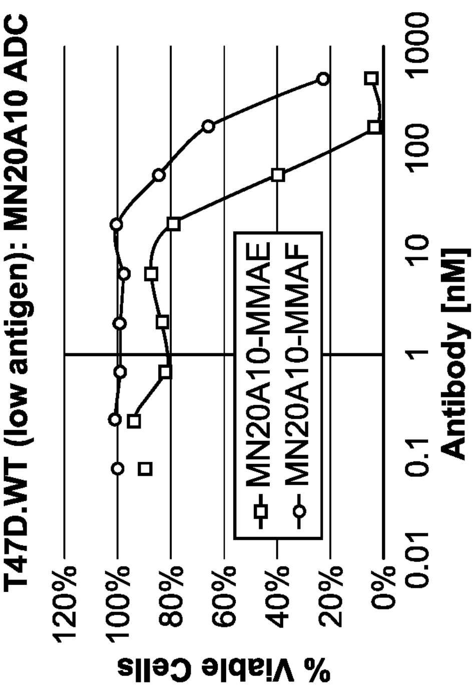
Figure 39B:
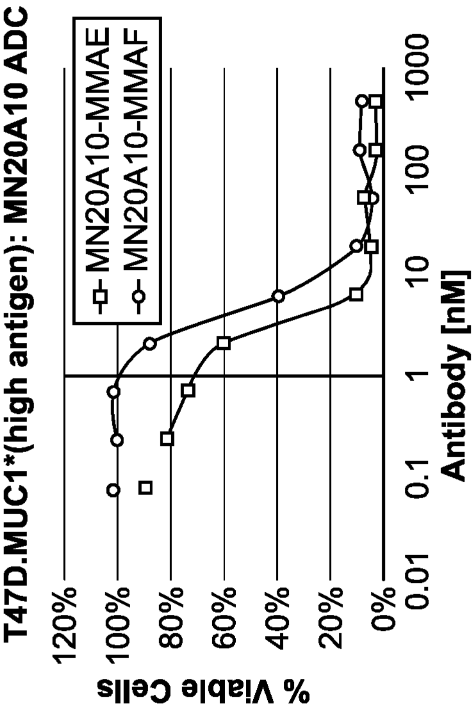
Figure 39C:
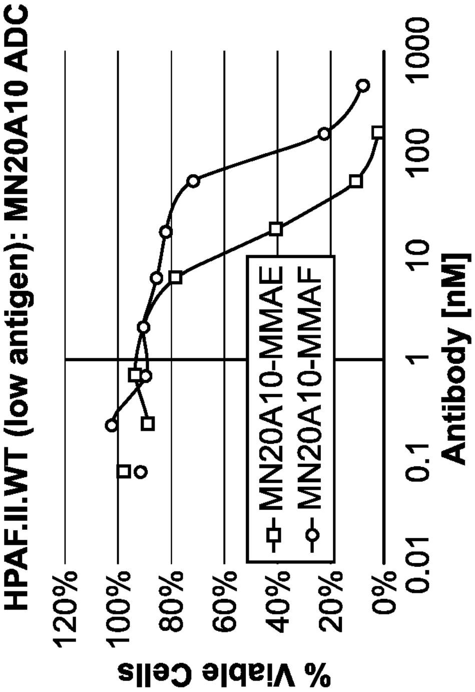
Figure 39D:
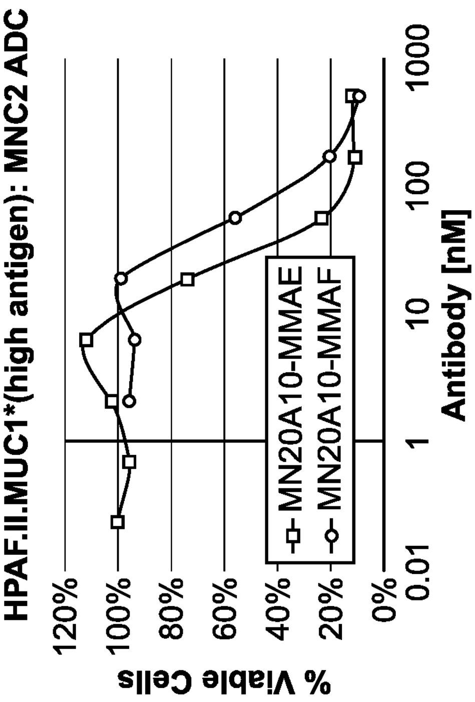

FIGS. 39A-39F show graphs of a plate reader assay wherein the viability of target cancer cells is measured as a function of the concentration of the MN20A10-ADC added, wherein the viability is determined using PrestoBlue. The experiment was allowed to proceed for 72 hours before the measurements were taken. FIG. 39A shows the viability of T47D wild-type breast cancer cells after the addition of either MN20A10-MMAE or MN20A10-MMAF. FIG. 39B shows the viability of T47D breast cancer cells that have been engineered to express more MUC1*, called T47D-MUC1*, after the addition of either MN20A10-MMAE or MN20A10-MMAF. FIG. 39C shows the viability of HPAF II wild-type pancreatic cancer cells after the addition of either MN20A10-MMAE or MN20A10-MMAF. FIG. 39D shows the viability of HPAF II pancreatic cancer cells that have been engineered to express more MUC1*, called HPAF II-MUC1*, after the addition of either MN20A10-MMAE or MN20A10-MMAF. FIG. 39E shows a table of the calculated IC50s for the killing ability of MN20A10-MMAE or MN20A10-MMAF added to either breast cancer cells or pancreatic cells that express low to medium levels of the target antigen, MUC1*. FIG. 39F shows a table of the calculated IC50s for the killing ability of MN20A10-MMAE or MN20A10-MMAF added to either breast cancer cells or pancreatic cells that express high levels of the target antigen, MUC1*.

FIGS. 40A-40C show graphs of a plate reader assay wherein the viability of target cancer cells is measured as a function of the concentration of the MNC2-ADC or the MN20A10-ADC added, wherein the viability is determined using PrestoBlue. The experiment was allowed to proceed for 72 or 120 hours for MMAE or Deruxtecan conjugates, respectively, before the measurements were taken. FIG. 40A shows the viability of T47D wild-type breast cancer cells after the addition of either MNC2-MMAE, MNC2-Deruxtecan, MN20A10-MMAE or MN20A10-Deruxtecan. FIG. 40B shows the viability of T47D breast cancer cells that have been engineered to express more MUC1*, called T47D-MUC1*, after the addition of either MNC2-MMAE, MNC2-Deruxtecan, MN20A10-MMAE or MN20A10-Deruxtecan. FIG. 40C shows a table of the calculated IC50s for the killing ability of MNC2-MMAE, MNC2-Deruxtecan, MN20A10-MMAE or MN20A10-Deruxtecan added to either medium to low MUC1* expressing T47D breast cancer cells or high MUC1* T47D-MUC1* breast cancer cells.

Figures 41A, 41B:
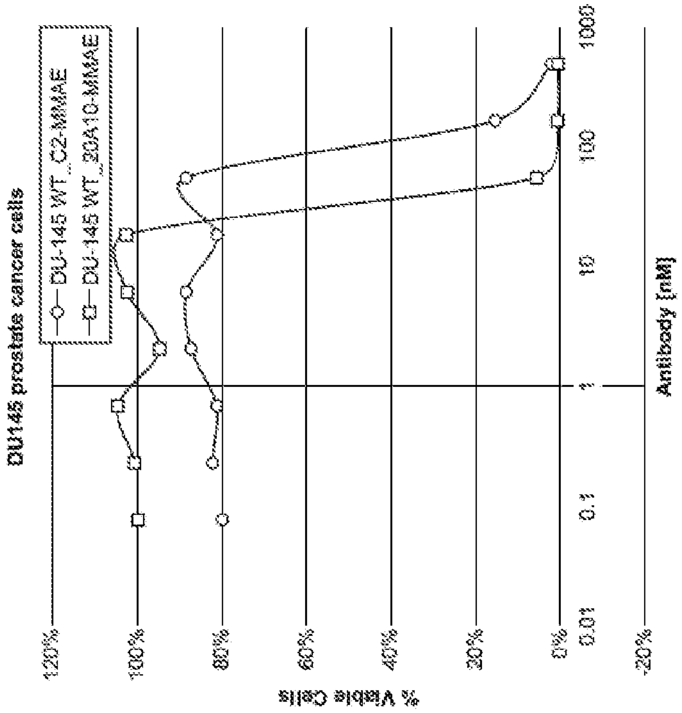

FIGS. 41A-41B show graphs of a plate reader assay wherein the viability of target cancer cells is measured as a function of the concentration of the MNC2-ADC or the MN20A10-ADC added, using PrestoBlue. The experiment was allowed to proceed for 72 before the measurements were taken. FIG. 41A shows the viability of DU145 wild-type hormone refractory prostate cancer cells after the addition of either MNC2-MMAE or MN20A10-MMAE. FIG. 41B shows a Table of the calculated IC50s for the killing ability of MNC2-MMAE and MN20A10-MMAE for these prostate cancer cells.

Figures 42A, 42B:
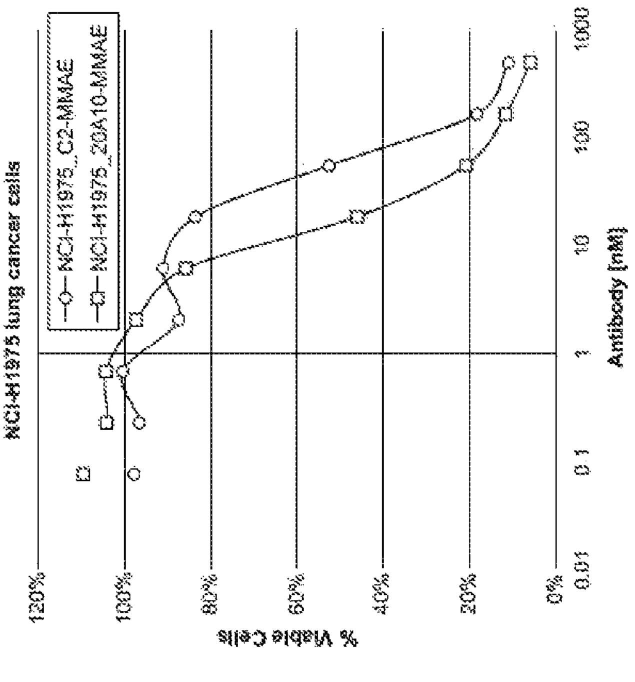

FIGS. 42A-42B show graphs of a plate reader assay wherein the viability of target cancer cells is measured as a function of the concentration of the MNC2-ADC or the MN20A10-ADC added, using PrestoBlue. The experiment was allowed to proceed for 72 before the measurements were taken. FIG. 42A shows the viability of NCI-H1975 non-small cell lung cancer cells after the addition of either MNC2-MMAE or MN20A10-MMAE. FIG. 42B shows a Table of the calculated IC50s for the killing ability of MNC2-MMAE and MN20A10-MMAE for these lung cancer cells.

FIGS. 43A-43C show graphs of a plate reader assay wherein the viability of target cancer cells is measured after the addition of MNC2-MMAE or MN20A10-MMAE. The experiment was allowed to proceed for 72, before the measurements were taken. FIG. 43A shows the viability of T47D wild-type breast cancer cells after the addition of either MNC2-MMAE or MN20A10-MMAE. FIG. 43B shows the viability of T47D breast cancer cells that were engineered to express more MUC1*, called T47D-MUC1*, after the addition of either MNC2-MMAE or MN20A10-MMAE.

Figures 44A, 44B:
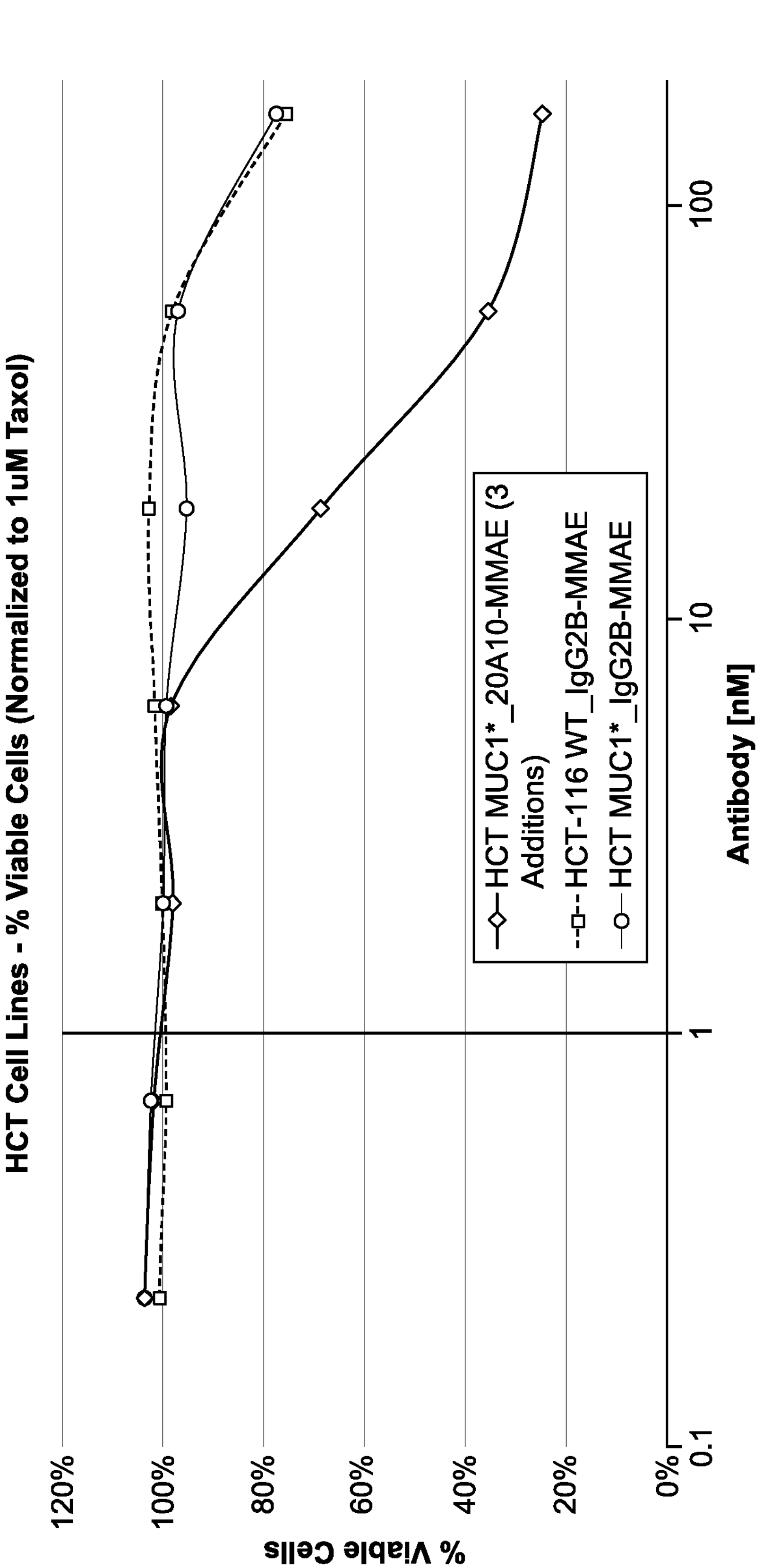

FIG. 44A-44B show graphs of a plate reader assay wherein the viability of MUC1* expressing cancer cells, HCT-MUC1*, is compared to MUC1* negative cancer cells, HCT-116-wt, after treatment with either MN20A10-MMAE or IgG2b-MMAE, an isotype control antibody. The experiment was allowed to proceed for 72 before the flow cytometry measurements were taken.

FIGS. 45A-45D show graphs of a plate reader assay wherein the viability of MUC1* expressing cancer cells is measured after the addition of either MN20A10, unconjugated, or MN20A10-MMAE. FIG. 45A shows the killing effect of MN20A10-MMAE on NCI H1975 non-small cell lung cancer cells. FIG. 45B shows the killing effect of MN20A10-MMAE on DU145 hormone refractory prostate cancer cells. FIG. 45C shows the killing effect of MN20A10-MMAE on wild-type HPAF II pancreatic cancer cells or HPAF II-MUC1* cancer cells that were engineered to express more MUC1*. FIG. 45D shows a table of IC50s.

Figure 46A:
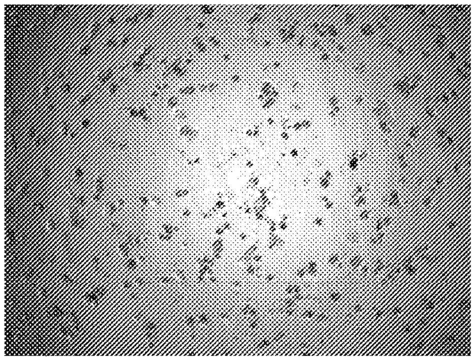
Figure 46B:
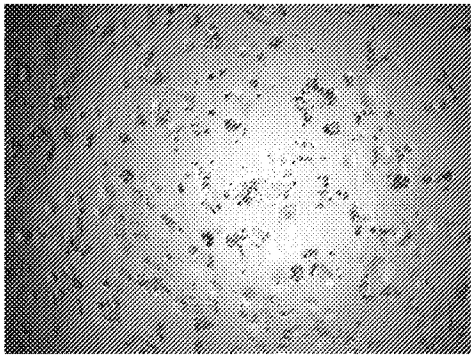
Figure 46C:
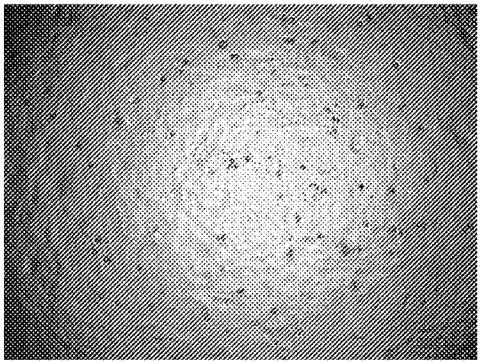
Figure 46D:
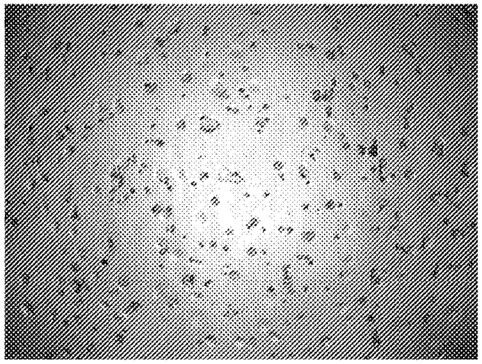
Figure 46E:
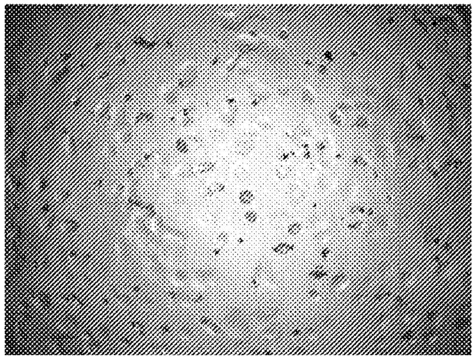
Figure 46F:
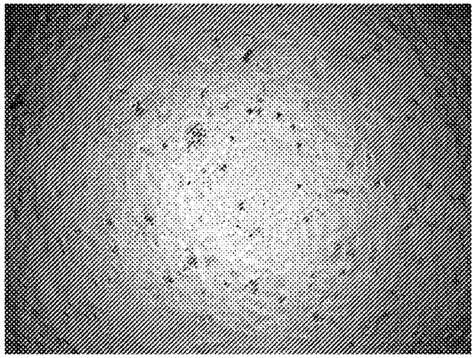
Figure 46G:
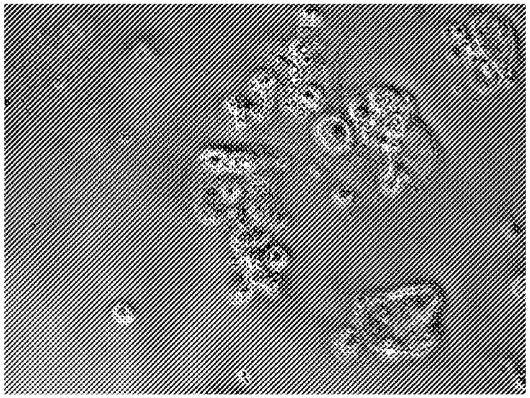
Figure 46H:
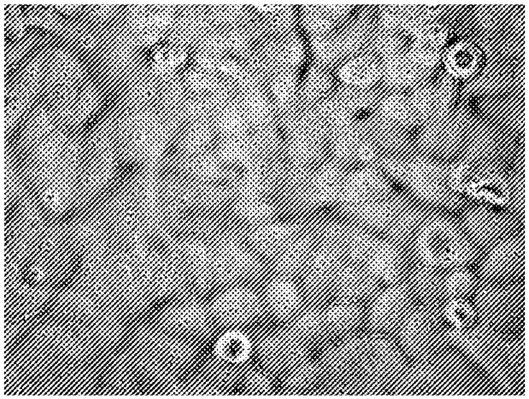
Figure 46I:
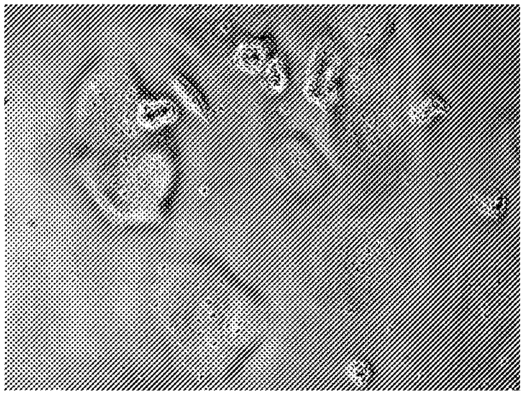
Figure 46J:
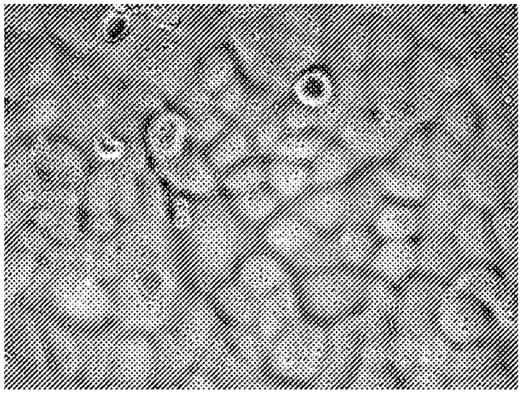

FIGS. 46A-46J show photographs taken at magnification of T47D-MUC1* breast cancer cells incubated with either MNC2-MMAE or MNC2-Deruxtecan. FIG. 46A photographs taken at 4× magnification show the killing effect of MNC2-MMAE at 500 nM on the breast cancer cells after 120 hours. FIG. 46B photographs taken at 4× magnification show the killing effect of MNC2-MMAE at 6.2 nM on the breast cancer cells after 120 hours. FIG. 46C photographs taken at 4× magnification show untreated T47D breast cancer cells as a control. FIG. 46D shows the killing effect of MNC2-Deruxtecan at 500 nM on the breast cancer cells after 120 hours. FIG. 46E shows the killing effect of MNC2-Deruxtecan at 6.2 nM on the breast cancer cells after 120 hours. FIG. 46F shows untreated T47D breast cancer cells as a control. FIG. 46G photographs taken at 20× magnification show the killing effect of MNC2-MMAE at 6.2 nM on the breast cancer cells after 120 hours. FIG. 46H photographs taken at 20× magnification show the untreated breast cancer cells as a control. FIG. 46I photographs taken at 20× magnification show the killing effect of MNC2-Deruxtecan at 6.2 nM on the breast cancer cells after 120 hours. FIG. 46J photographs taken at 20× magnification show the untreated breast cancer cells as a control. The killing effect can be readily seen as the significant decrease in cell number, the change in cell morphology to rounding up and lifting off of the cells. In contrast, the control wells show confluent monolayer of compact cells with the flat spreading morphology and without dead floating cells.

Figure 47A:
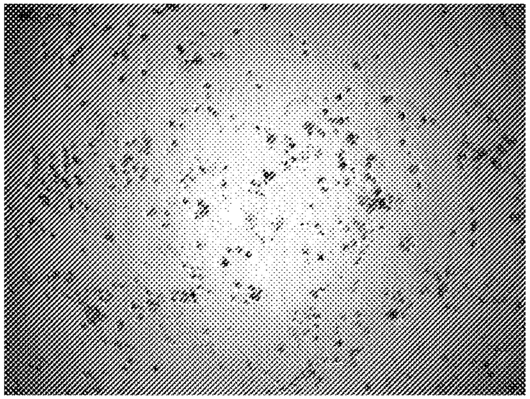
Figure 47B:
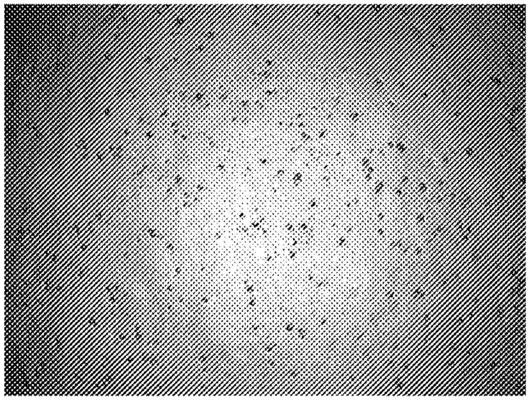
Figure 47C:
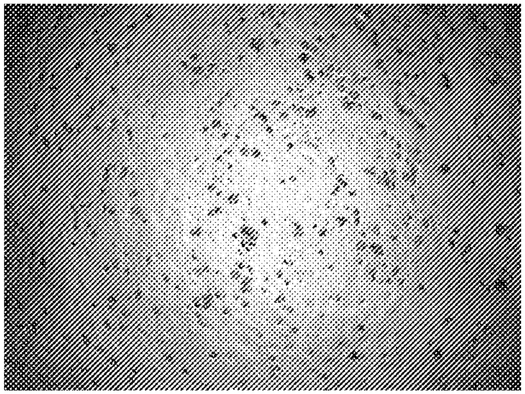
Figure 47D:
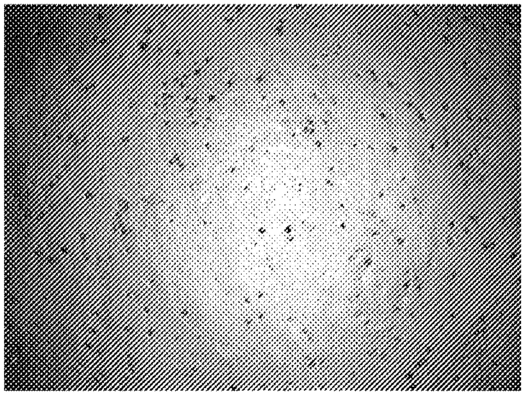

FIGS. 47A-47D show photographs taken at 4× magnification of DU145 prostate cancer cells incubated with either MNC2-MMAE or MNC2-Deruxtecan, after 120 hours. FIG. 47A magnified photograph shows the killing effect of MNC2-MMAE at 500 nM. FIG. 47B magnified photograph shows untreated cells with normal morphology and confluency. FIG. 47C magnified photograph shows the killing effect of MNC2-Deruxtecan at 500 nM. FIG. 47D magnified photograph shows untreated cells with normal morphology and confluency.

Figure 48G:
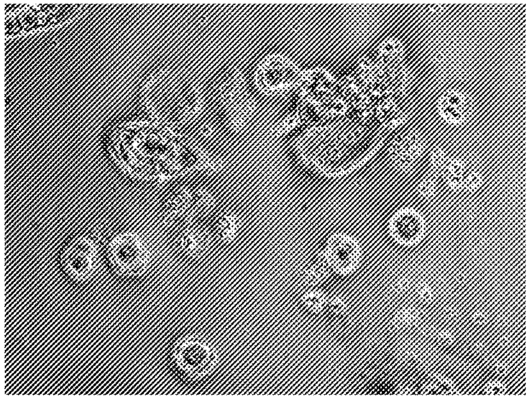
Figure 48H:
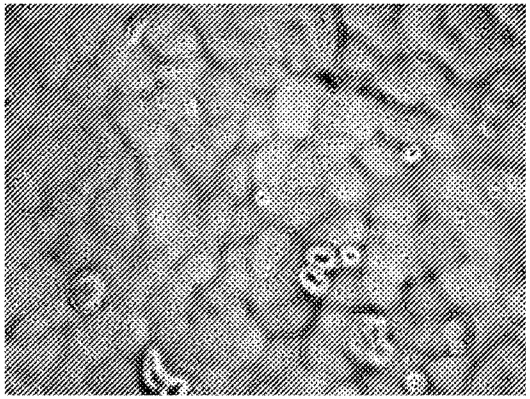
Figure 48I:
Figure 48J:
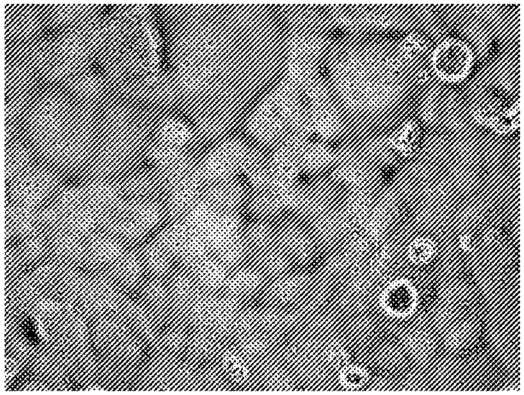
Figure 48K:
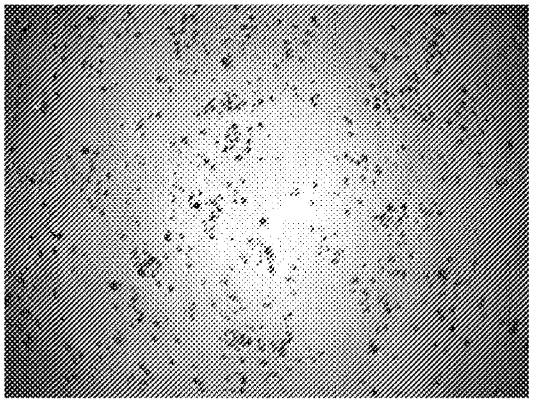
Figure 48L:
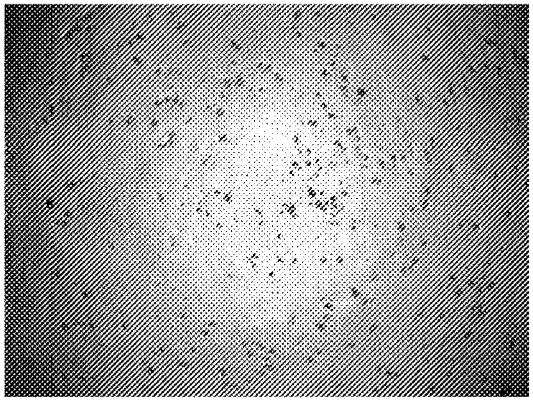
Figure 48M:
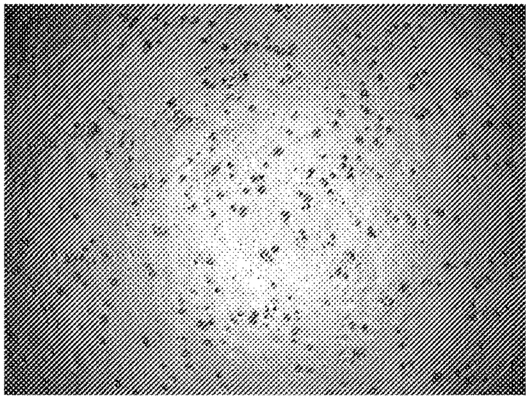
Figure 48N:
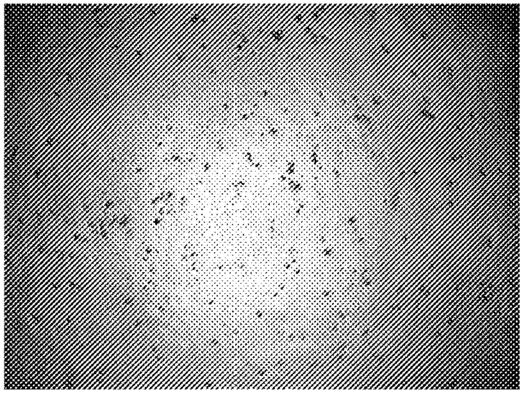

FIGS. 48A-48N show photographs taken at magnification of T47D-MUC1* breast cancer cells incubated with either MN20A10-MMAE or MN20A10-Deruxtecan. FIG. 48A photographs taken at 4× magnification show the killing effect of MN20A10-MMAE at 500 nM on the breast cancer cells after 120 hours. FIG. 48B photographs taken at 4× magnification show the killing effect of MN20A10-MMAE at 56 nM on the breast cancer cells after 120 hours. FIG. 48C photographs taken at 4× magnification show untreated T47D breast cancer cells as a control. FIG. 48D shows the killing effect of MN20A10-Deruxtecan at 500 nM on the breast cancer cells after 120 hours.

FIG. 48E shows the killing effect of MN20A10-Deruxtecan at 56 nM on the breast cancer cells after 120 hours. FIG. 48F shows untreated T47D breast cancer cells as a control. FIG. 48G photographs taken at 20× magnification show the killing effect of MN20A10-MMAE at 56 nM on the breast cancer cells after 120 hours. FIG. 48H photographs taken at 20× magnification show the untreated breast cancer cells as a control. FIG. 48I photographs taken at 20× magnification show the killing effect of MN20A10-Deruxtecan at 56 nM on the breast cancer cells after 120 hours. FIG. 48J photographs taken at 20× magnification show the untreated breast cancer cells as a control. FIG. 48K photographs taken at 20× magnification show DU145 prostate cancer cells treated with 500 nM MN20A10-MMAE, DAR 5.8. The treated cells show rounding up and dead cells. FIG. 48L photographs taken at 20× magnification show the untreated control DU145 prostate cancer cells. FIG. 48M photographs taken at 20× magnification show DU145 prostate cancer cells treated with 500 nM MN20A10-deruxtecan, DAR 4.6. The treated cells show rounding up and dead cells. FIG. 48N photographs taken at 20× magnification show the untreated control DU145 prostate cancer cells.

Figures 49A, 49B, 49C, 49D:
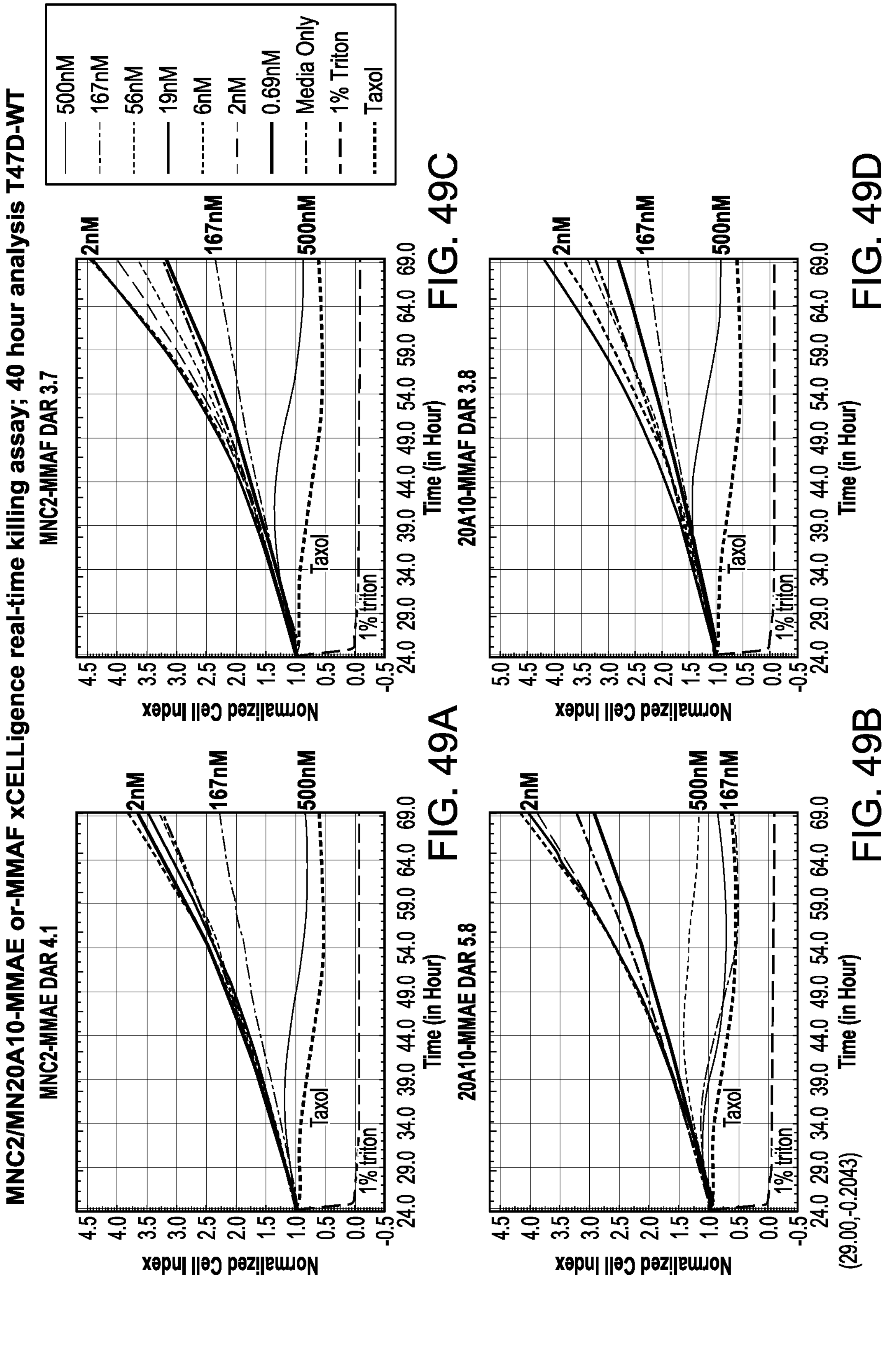
Figures 49E, 49F, 49G, 49H, 49I, 49J:
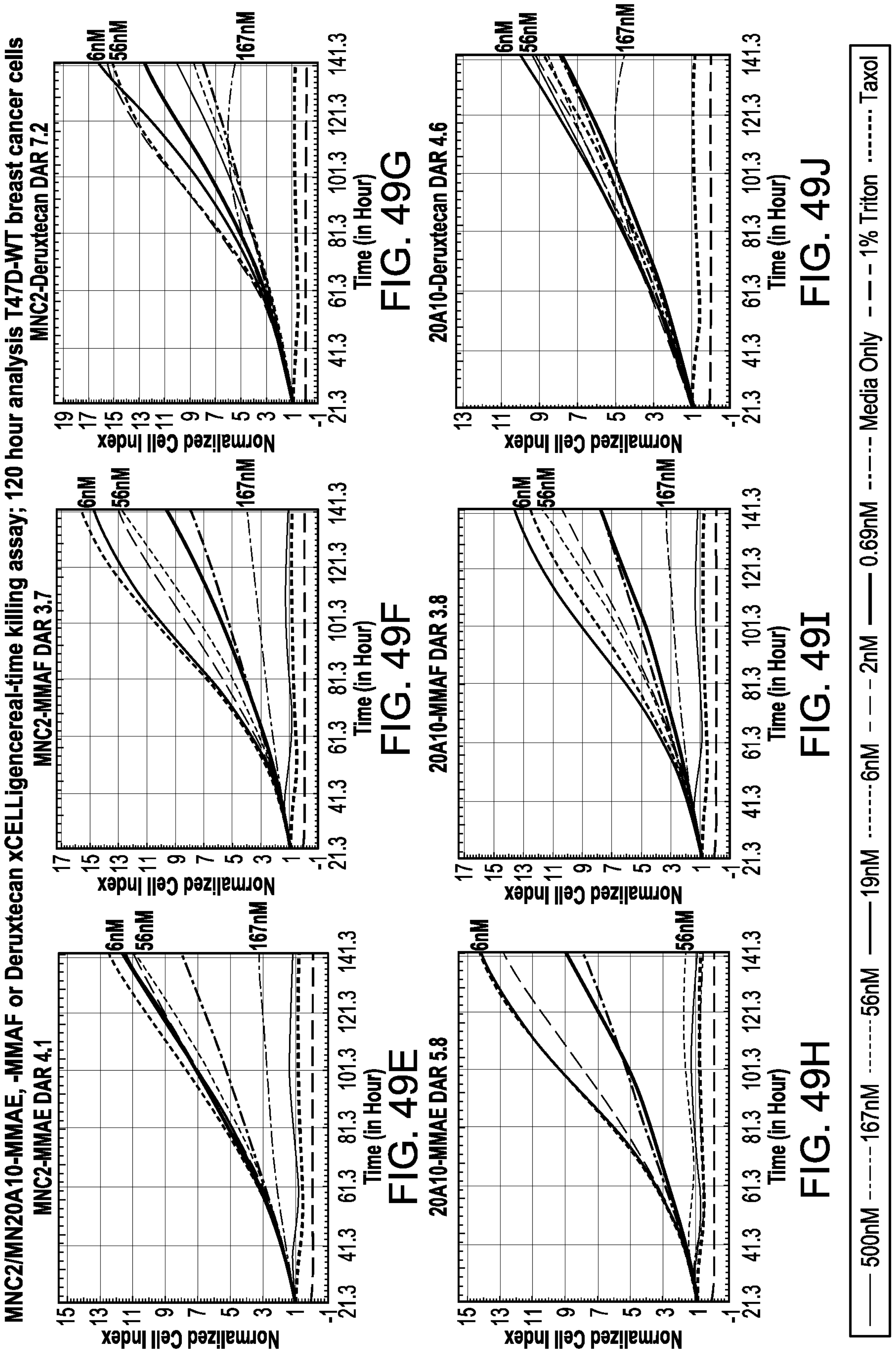

FIGS. 49A-49J show traces from the real-time killing assays performed on an xCELLigence instrument. In this assay, impedance is measured in real-time. When the adherent cancer cells are killed and come off of the electrode surface, impedance (insulation) decreases. T47D wild-type breast cancer cells were plated onto multi-electrode-well plates at 5,000 cells per well and allowed to adhere and grow for 24 hours before the addition of ADCs. Either MNC2-MMAE, DAR 4.1, MN20A10-MMAE, DAR 5.8, MNC2-MMAF, DAR 3.7, MN20A10-MMAF, DAR 3.8, MNC2-Deruxtecan, DAR 7.2, or MN20A10-Deruxtecan, DAR 4.6, was then added to the cancer cells. FIG. 49A shows MNC2-MMAE added to final concentrations of 500 nM, 167 nM or 2 nM and experimental readout is at 40 hours post ADC addition. Taxol and Triton are added as the positive killing control. FIG. 49B shows MN20A10-MMAE added to final concentrations of 167 nM, 56 nM or 2 nM and experimental readout is at 40 hours post ADC addition. FIG. 49C shows MNC2-MMAF added to final concentrations of 500 nM, 167 nM or 2 nM and experimental readout is at 40 hours post ADC addition. Taxol and Triton are added as the positive killing control. FIG. 49D shows MN20A10-MMAF added to final concentrations of 500 nM, 167 nM or 2 nM and experimental readout is at 40 hours post ADC addition. FIG. 49E shows MNC2-MMAE added to final concentrations of 500 nM, 167 nM or 2 nM and experimental readout is at 120 hours post ADC addition. As indicated, essentially all the tumor cells were killed at an MNC2-MMAE concentration of 167 nM. FIG. 49F shows MNC2-MMAF added to final concentrations of 500 nM, 167 nM or 2 nM and experimental readout is at 120 hours post ADC addition. As indicated, essentially all the tumor cells were killed at an MNC2-MMAF concentration of 167 nM. 49G shows MNC2-Deruxtecan added to final concentrations of 500 nM, 167 nM or 2 nM and experimental readout is at 120 hours post ADC addition. As indicated, significant tumor cell killing occurs later than MNC2-MMAE or -MMAF, but by 100 hours reaches approximately the same level of killing at an MNC2-Deruxtecan concentration of 167 nM. FIG. 49H shows MN20A10-MMAE added over a range of concentrations and experimental readout is at 120 hours post ADC addition. As indicated, essentially all the tumor cells were killed at an MN20A10-MMAE concentration of 56 nM. FIG. 49I shows MN20A10-MMAF added over a range of concentrations and experimental readout is at 120 hours post ADC addition. As indicated, essentially all the tumor cells were killed at an MN20A10-MMAF concentration of 167 nM. 49J shows MN20A10-Deruxtecan added over a range of concentrations and experimental readout is at 120 hours post ADC addition. As indicated, tumor cell killing occurs later than MN20A10-MMAE or -MMAF, but by 120 hours there is significant killing at an MN20A10-Deruxtecan concentration of 167 nM.

Figures 50A, 50B, 50C, 50D:
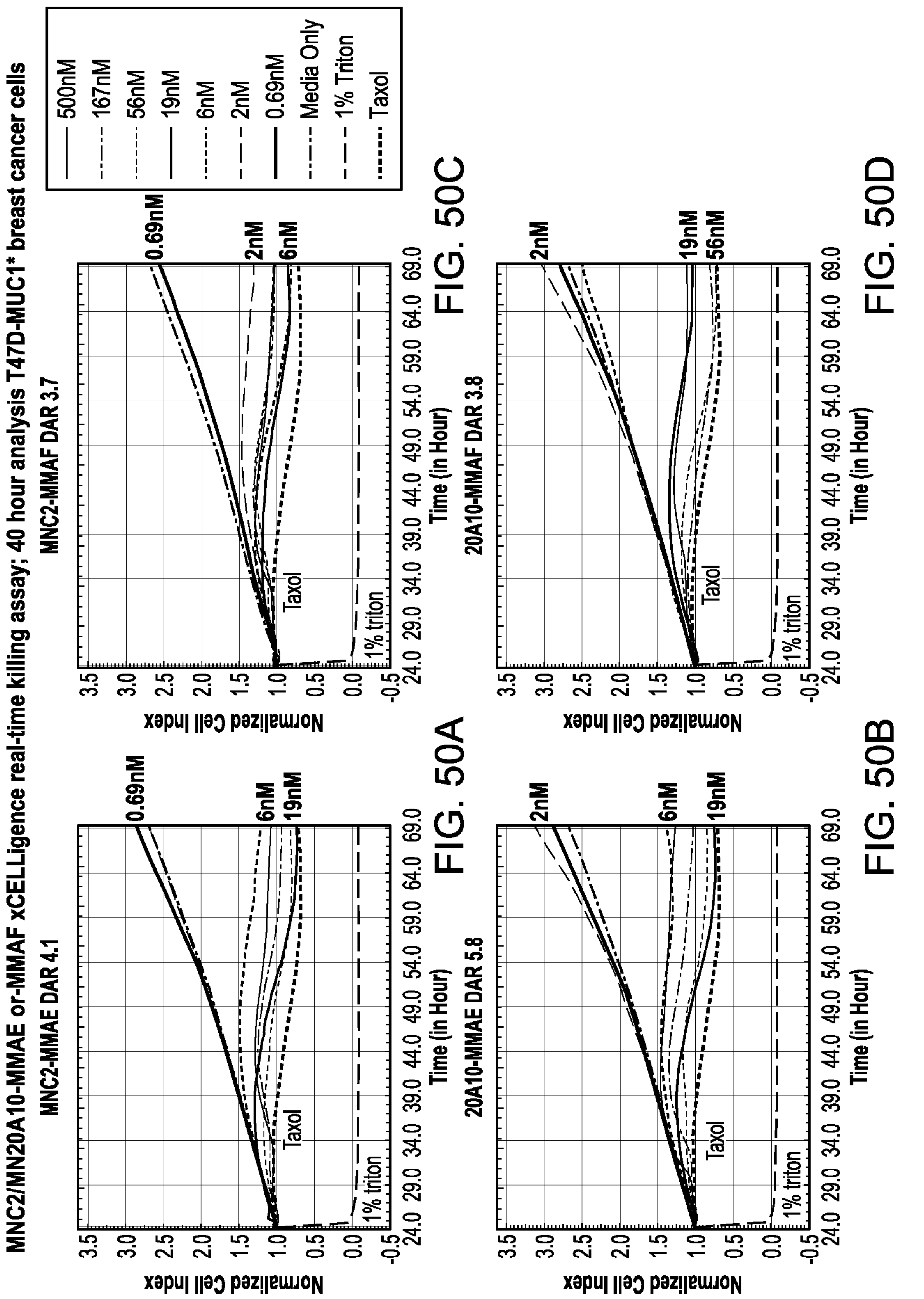
Figures 50E, 50F, 50G, 50H, 50I, 50J:
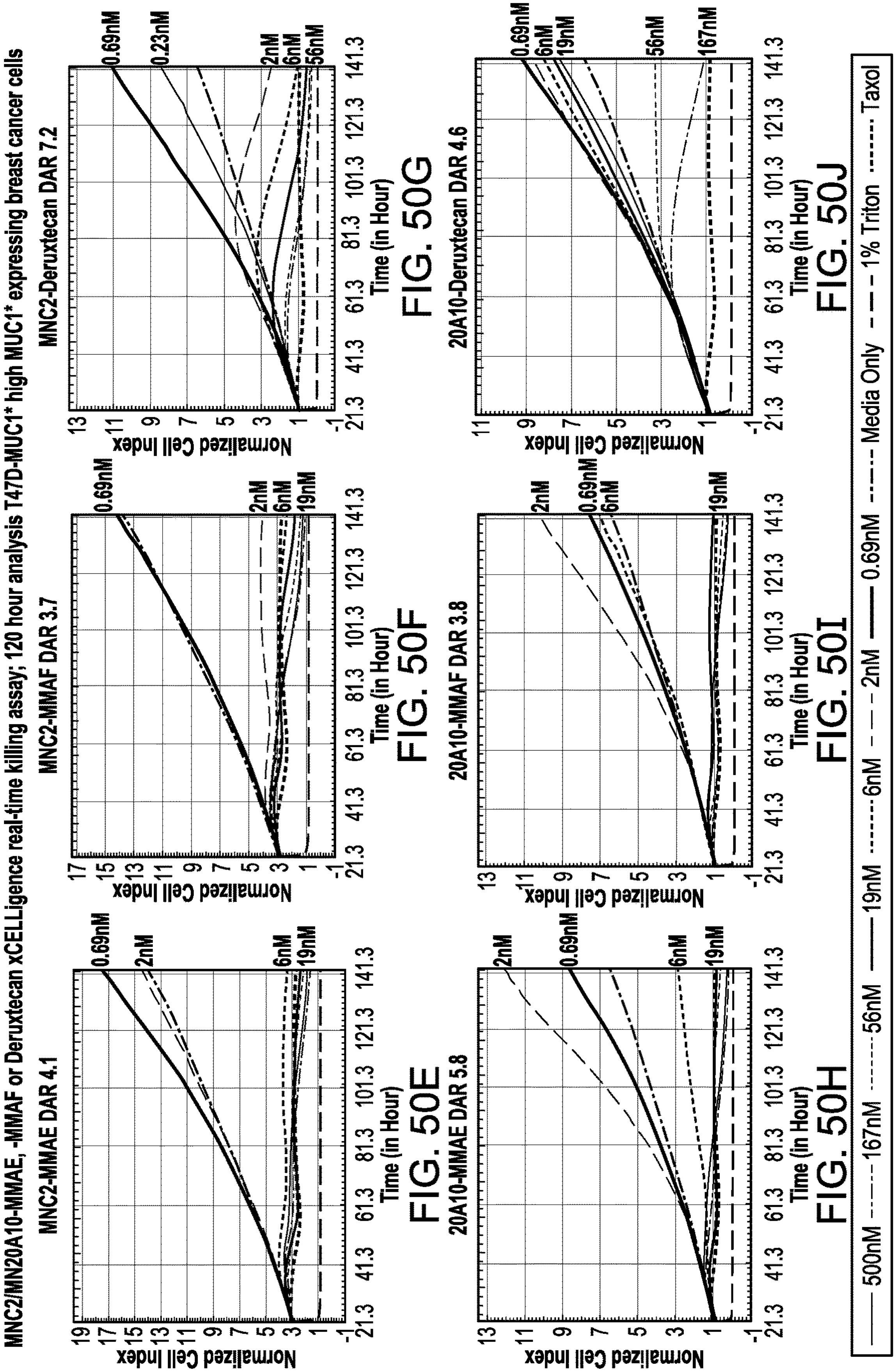

FIGS. 50A-50J show traces from the real-time killing assays performed on an xCELLigence instrument. In this assay, impedance is measured in real-time. When the adherent cancer cells are killed and come off of the electrode surface, impedance (insulation) decreases. T47D-MUC1* breast cancer cells, engineered to express more MUC1*, were plated onto multi-electrode-well plates at 5,000 cells per well and allowed to adhere and grow for 24 hours before the addition of ADCs. Either MNC2-MMAE, DAR 4.1, MN20A10-MMAE, DAR 5.8, MNC2-MMAF, DAR 3.7, MN20A10-MMAF, DAR 3.8, MNC2-Deruxtecan, DAR 7.2, or MN20A10-Deruxtecan, DAR 4.6, was then added to the cancer cells. FIG. 50A shows MNC2-MMAE added to final concentrations of 19 nM, 6 nM or 0.69 nM and experimental readout is at 40 hours post ADC addition. As can be seen essentially all the tumor cells are killed at 19 nM. Taxol and Triton are added as the positive killing control. FIG. 50B shows MN20A10-MMAE added to final concentrations of 19 nM, 6 nM or 2 nM and experimental readout is at 40 hours post ADC addition. As can be seen essentially all the tumor cells are killed at 19 nM. FIG. 50C shows MNC2-MMAF added to final concentrations of 6 nM, 2 nM or 0.69 nM and experimental readout is at 40 hours post ADC addition. As can be seen essentially all the tumor cells are killed at 6 nM. Taxol and Triton are added as the positive killing control. FIG. 50D shows MN20A10-MMAF added to final concentrations of 56 nM, 19 nM or 2 nM and experimental readout is at 40 hours post ADC addition. As can be seen essentially all the tumor cells are killed at 56 nM. FIG. 50E shows MNC2-MMAE added over a range of concentrations and experimental readout is at 120 hours post ADC addition. As indicated, essentially all the T47D-MUC1* tumor cells were killed at an MNC2-MMAE concentration of 6 nM. FIG. 50F shows MNC2-MMAF added over a range of concentrations and experimental readout is at 120 hours post ADC addition. As indicated, essentially all the T47D-MUC1* tumor cells were killed at an MNC2-MMAF concentration of 2 nM. 50G shows MNC2-Deruxtecan added over a range of concentrations and experimental readout is at 120 hours post ADC addition. As indicated, significant T47D-MUC1* tumor cell killing occurs later than MNC2-MMAE or -MMAF, but by 120 hours reaches approximately the same level of killing at an MNC2-Deruxtecan concentration of 6 nM. FIG. 50H shows MN20A10-MMAE added over a range of concentrations and experimental readout is at 120 hours post ADC addition. As indicated, essentially all the tumor cells were killed at an MN20A10-MMAE concentration of 19 nM. FIG. 50I shows MN20A10-MMAF added over a range of concentrations and experimental readout is at 120 hours post ADC addition. As indicated, essentially all the tumor cells were killed at an MN20A10-MMAF concentration of 19 nM. 50J shows MN20A10-Deruxtecan added over a range of concentrations and experimental readout is at 120 hours post ADC addition. As indicated, T47D-MUC1* tumor cell killing occurs later than MN20A10-MMAE or -MMAF, but by 120 hours essentially all the tumor cells have been killed at an MN20A10-Deruxtecan concentration of 167 nM.

Figures 51A, 51B, 51C, 51D:
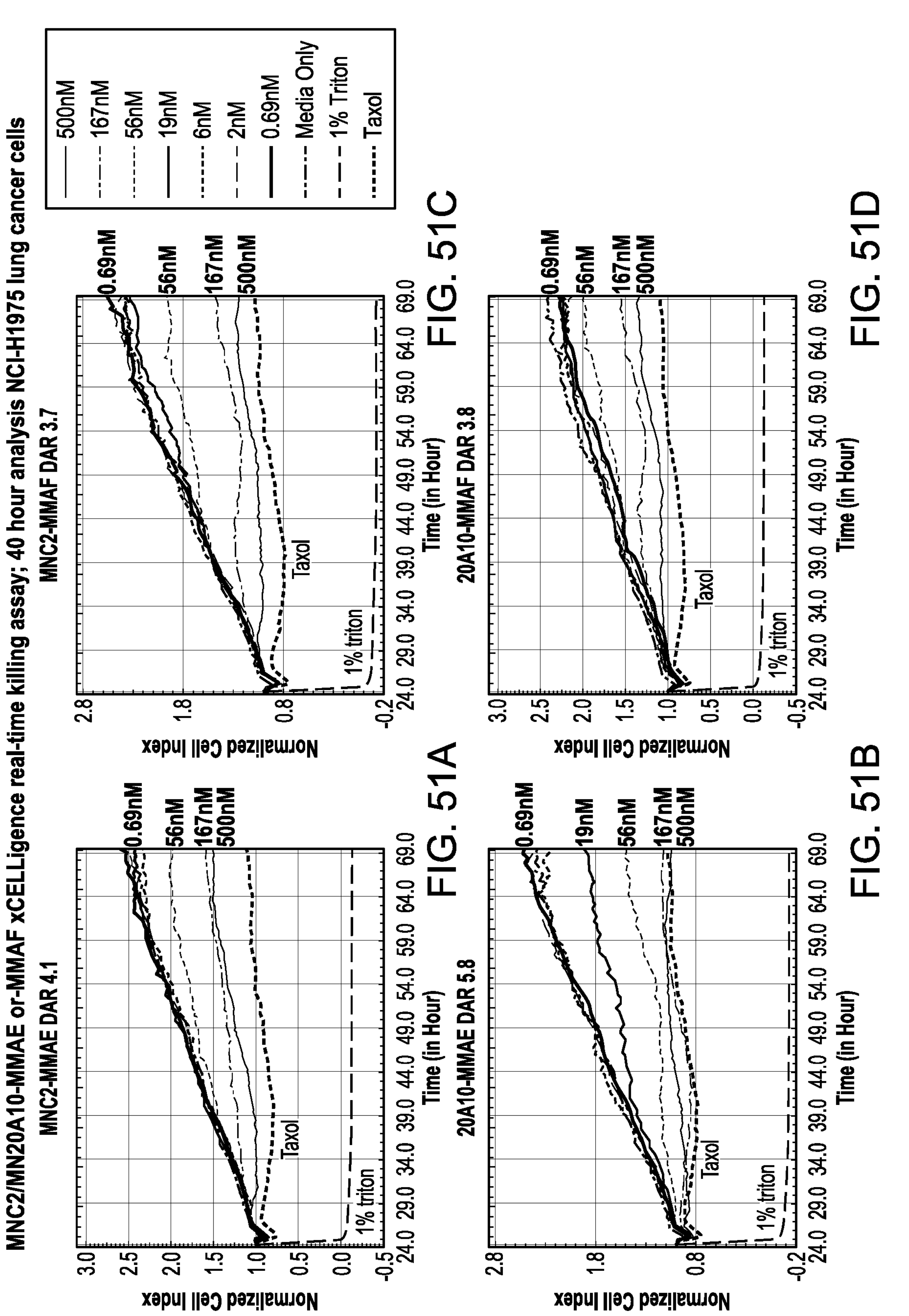
Figures 51E, 51F, 51G, 51H, 51I:
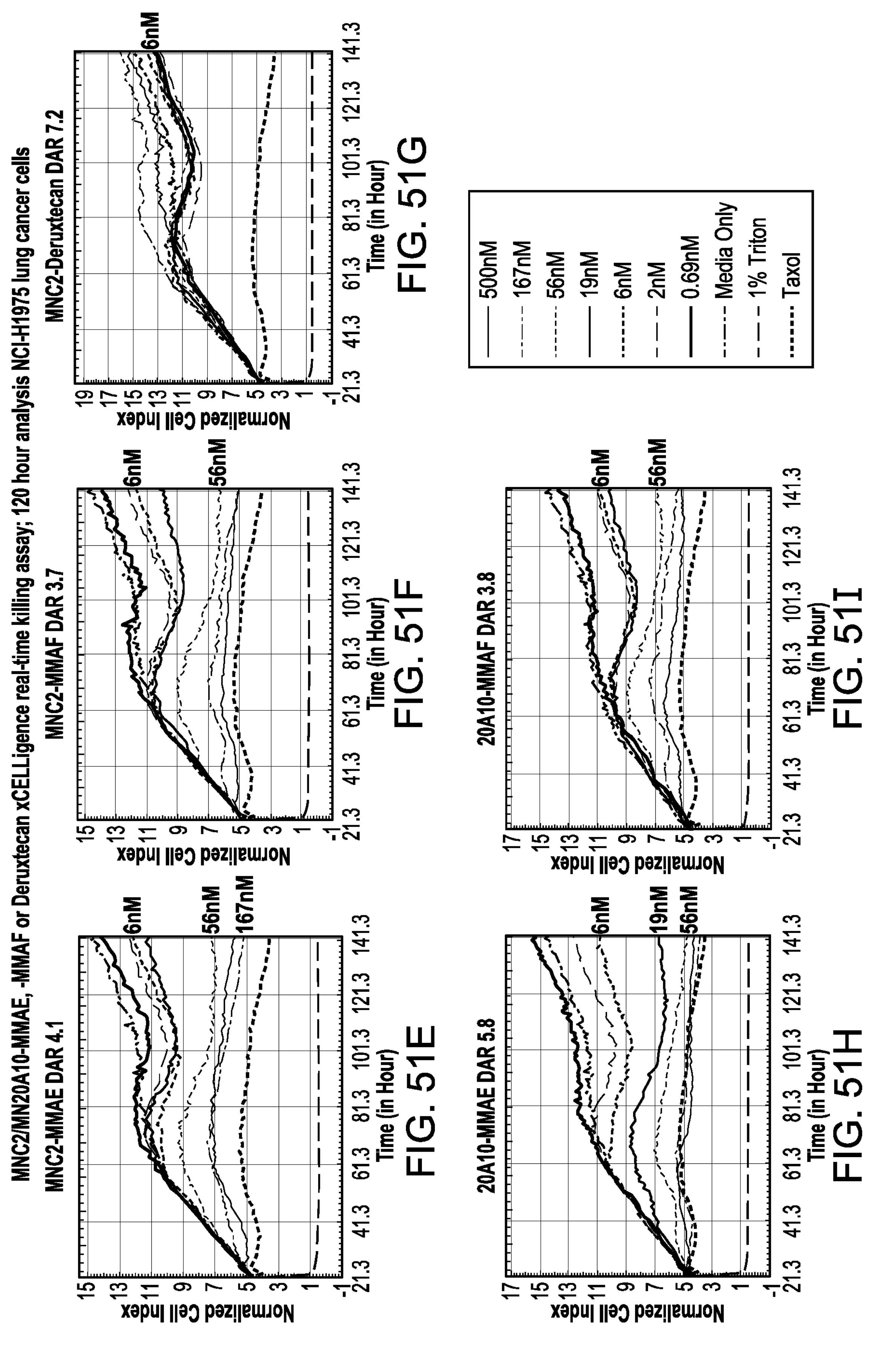

FIG. 51A-51I show traces from the real-time killing assays performed on an xCELLigence instrument. In this assay, impedance is measured in real-time. When the adherent cancer cells are killed and come off of the electrode surface, impedance (insulation) decreases. NCI-H1975 lung cancer cells were plated onto multi-electrode-well plates at 5,000 cells per well and allowed to adhere and grow for 24 hours before the addition of ADCs. Either MNC2-MMAE, DAR 4.1, MN20A10-MMAE, DAR 5.8, MNC2-MMAF, DAR 3.7, MN20A10-MMAF, DAR 3.8, MNC2-Deruxtecan, DAR 7.2, or MN20A10-Deruxtecan, DAR 4.6, was then added to the cancer cells. FIG. 51A shows MNC2-MMAE added over a range of concentrations and the experimental readout is at 40 hours. As indicated, essentially all the lung tumor cells were killed at a concentration of 167 nM. Taxol and Triton are added as the positive killing control. FIG. 51B shows MN20A10-MMAE added over a range of concentrations and the experimental readout is at 40 hours. As indicated, essentially all the lung tumor cells were killed at a concentration of 167 nM. FIG. 51C shows MNC2-MMAF added over a range of concentrations and the experimental readout is at 40 hours. As indicated, essentially all the lung tumor cells were killed at a concentration of 167 nM. Taxol and Triton are added as the positive killing control. FIG. 51D shows MN20A10-MMAF added over a range of concentrations and the experimental readout is at 40 hours. As indicated, essentially all the lung tumor cells were killed at a concentration of 167 nM. FIG. 51E shows MNC2-MMAE added over a range of concentrations and experimental readout is at 120 hours post ADC addition. As indicated, essentially all the lung tumor cells were killed at an MNC2-MMAE concentration of 167 nM. FIG. 51F shows MNC2-MMAF added over a range of concentrations and experimental readout is at 120 hours post ADC addition. As indicated, essentially all the tumor cells were killed at an MNC2-MMAF concentration of 56 nM. 51G shows MNC2-Deruxtecan added over a range of concentrations and experimental readout is at 120 hours post ADC addition. FIG. 51H shows MN20A10-MMAE added over a range of concentrations and experimental readout is at 120 hours post ADC addition. As indicated, essentially all the tumor cells were killed at an MN20A10-MMAE concentration of 56 nM-19 nM. FIG. 51I shows MN20A10-MMAF added over a range of concentrations and experimental readout is at 120 hours post ADC addition. As indicated, essentially all the tumor cells were killed at an MN20A10-MMAF concentration of 56 nM.

Figures 52A, 52B, 52C, 52D:
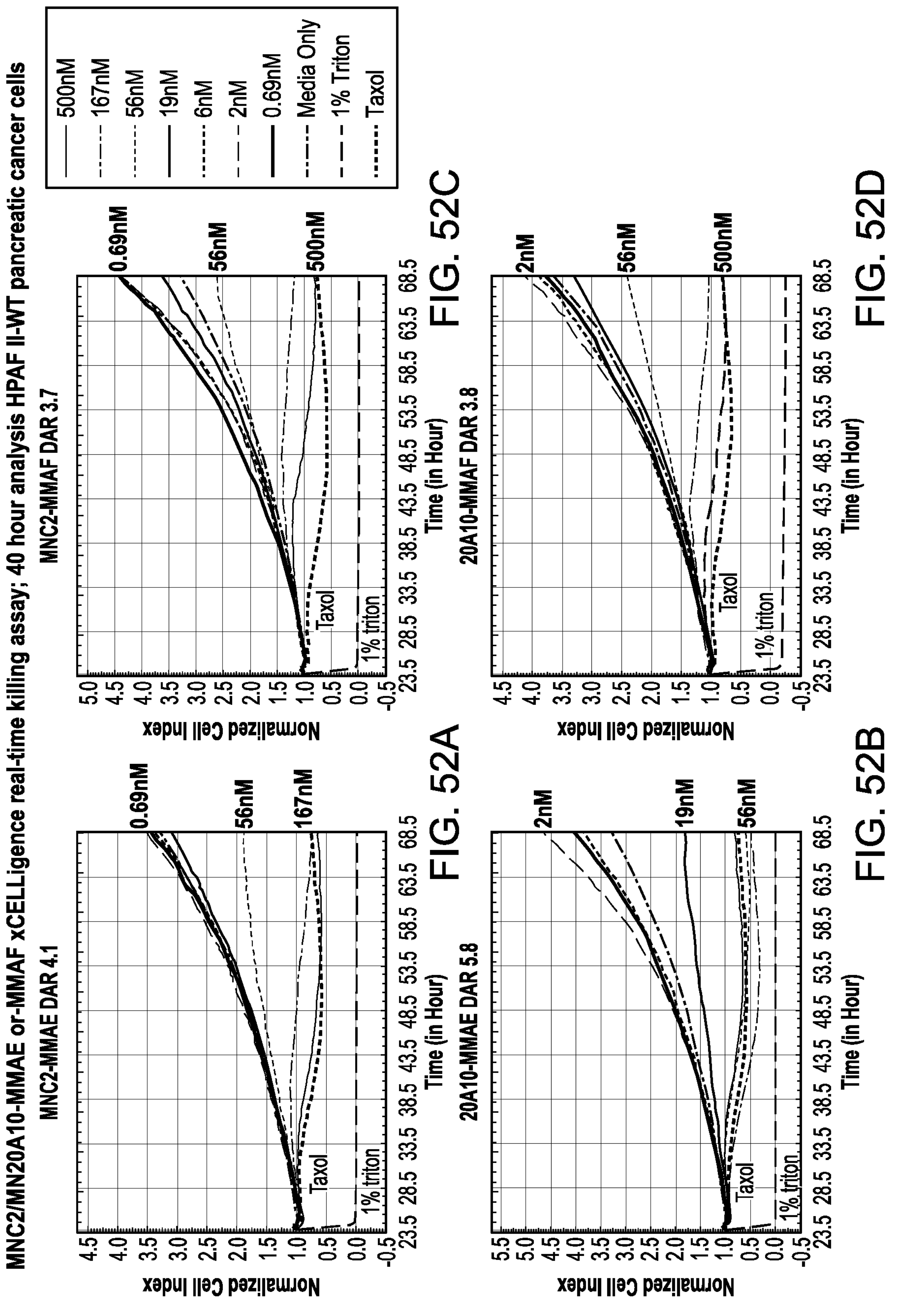

FIGS. 52A-52I shows traces from the real-time killing assays performed on an xCELLigence instrument. In this assay, impedance is measured in real-time. When the adherent cancer cells are killed and come off of the electrode surface, impedance (insulation) decreases. HPAF II wild-type (WT) pancreatic cancer cells were plated onto multi-electrode-well plates at 5,000 cells per well and allowed to adhere and grow for 24 hours before the addition of ADCs. Either MNC2-MMAE, DAR 4.1, MN20A10-MMAE, DAR 5.8, MNC2-MMAF, DAR 3.7, MN20A10-MMAF, DAR 3.8, MNC2-Deruxtecan, DAR 7.2, or MN20A10-Deruxtecan, DAR 4.6, was then added to the cancer cells. FIG. 52A shows MNC2-MMAE added over a range of concentrations and the experimental readout is at 40 hours. Taxol and Triton are added as the positive killing control. FIG. 52B shows MN20A10-MMAE added over a range of concentrations and the experimental readout is at 40 hours. FIG. 52C shows MNC2-MMAF added over a range of concentrations and the experimental readout is at 40 hours. Taxol and Triton are added as the positive killing control. FIG. 52D shows MN20A10-MMAF added over a range of concentrations and the experimental readout is at 40 hours. FIG. 52E shows MNC2-MMAE added over a range of concentrations and experimental readout is at 120 hours post ADC addition. As indicated, essentially all the pancreatic tumor cells were killed at an MNC2-MMAE concentration of 56 nM. FIG. 52F shows MNC2-MMAF added over a range of concentrations and experimental readout is at 120 hours post ADC addition. As indicated, essentially all the tumor cells were killed at an MNC2-MMAF concentration of 56 nM. 52G shows MNC2-Deruxtecan added over a range of concentrations and experimental readout is at 120 hours post ADC addition. Significant killing is measured at 120 hours at a concentration of about 56 nM. FIG. 52H shows MN20A10-MMAE added over a range of concentrations and experimental readout is at 120 hours post ADC addition. As indicated, essentially all the tumor cells were killed at an MN20A10-MMAE concentration of 56 nM-19 nM. FIG. 52I shows MN20A10-MMAF added over a range of concentrations and experimental readout is at 120 hours post ADC addition. As indicated, essentially all the tumor cells were killed at an MN20A10-MMAF concentration of 56 nM.

Figures 53A, 53B, 53C, 53D:
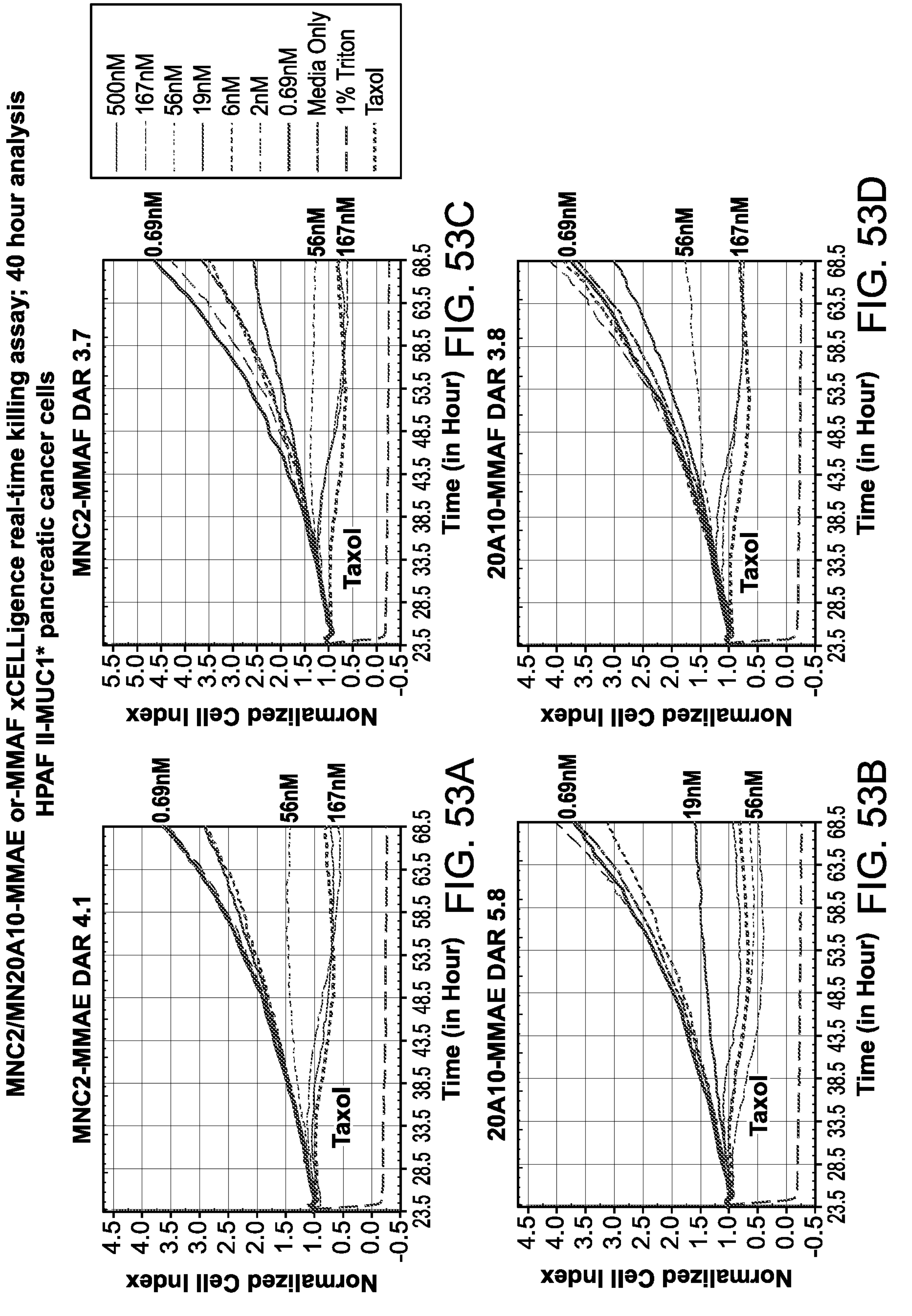
Figures 53E, 53F, 53G, 53H, 53I:
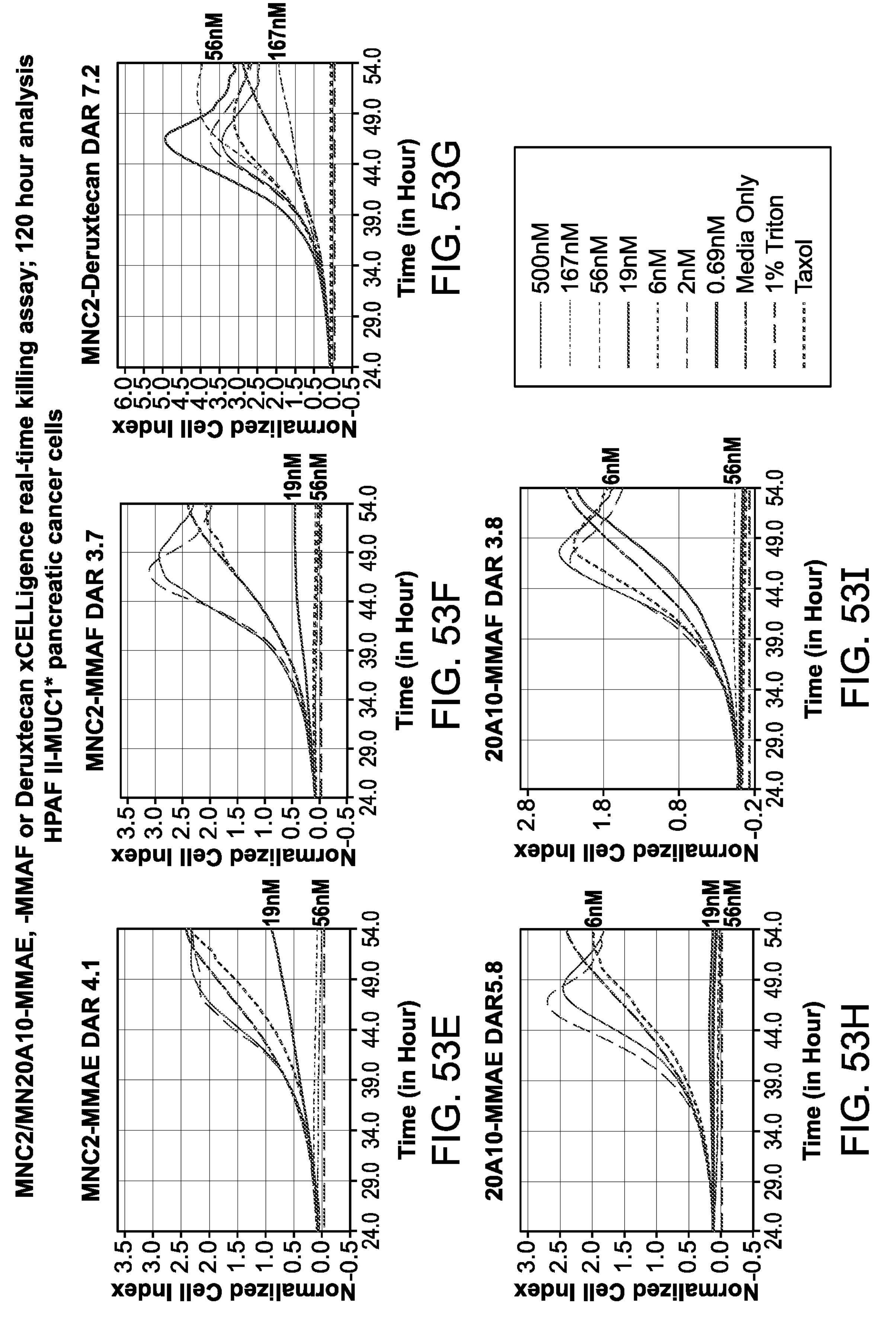

FIGS. 53A-53I show traces from the real-time killing assays performed on an xCELLigence instrument. In this assay, impedance is measured in real-time. When the adherent cancer cells are killed and come off of the electrode surface, impedance (insulation) decreases. HPAF II-MUC1* pancreatic cancer cells, engineered to express more MUC1*, were plated onto multi-electrode-well plates at 5,000 cells per well and allowed to adhere and grow for 24 hours before the addition of ADCs. Either MNC2-MMAE, DAR 4.1, MN20A10-MMAE, DAR 5.8, MNC2-MMAF, DAR 3.7, MN20A10-MMAF, DAR 3.8, MNC2-Deruxtecan, DAR 7.2, or MN20A10-Deruxtecan, DAR 4.6, was then added to the cancer cells. FIG. 53A shows MNC2-MMAE added over a range of concentrations and the experimental readout is at 40 hours. Taxol and Triton are added as the positive killing control. FIG. 53B shows MN20A10-MMAE added over a range of concentrations and the experimental readout is at 40 hours. FIG. 53C shows MNC2-MMAF added over a range of concentrations and the experimental readout is at 40 hours. Taxol and Triton are added as the positive killing control. FIG. 53D shows MN20A10-MMAF added over a range of concentrations and the experimental readout is at 40 hours. FIG. 53E shows MNC2-MMAE added over a range of concentrations and experimental readout is at 120 hours post ADC addition. As indicated, essentially all the pancreatic tumor cells were killed at an MNC2-MMAE concentration of 56 nM. FIG. 53F shows MNC2-MMAF added over a range of concentrations and experimental readout is at 120 hours post ADC addition. As indicated, essentially all the tumor cells were killed at an MNC2-MMAF concentration of 56 nM. 53G shows MNC2-Deruxtecan added over a range of concentrations and experimental readout is at 120 hours post ADC addition. As can be seen in the figure by 120 hours, nearly all the pancreatic cancer cells are killed at a concentration of 167 nM. FIG. 53H shows MN20A10-MMAE added over a range of concentrations and experimental readout is at 120 hours post ADC addition. As indicated, essentially all the tumor cells were killed at an MN20A10-MMAE concentration of 56 nM-19 nM. FIG. 53I shows MN20A10-MMAF added over a range of concentrations and experimental readout is at 120 hours post ADC addition. As indicated, essentially all the tumor cells were killed at an MN20A10-MMAF concentration of 56 nM.

FIGS. 54A-54D show traces from the real-time killing assays performed on an xCELLigence instrument. In this assay, impedance is measured in real-time. When the adherent cancer cells are killed and come off of the electrode surface, impedance (insulation) decreases. Here T47D-wt breast cancer cells that express low to medium levels of MUC1*, were plated onto multi-electrode 96-well plates at 5,000 cells per well and allowed to adhere and grow for 24 hours before the addition of ADCs. Either MNC2-Exatecan, DAR 8.2, MNC2-Deruxtecan, DAR 4.0, MNC2-MMAE, DAR 4.1, or free Exatecan at 50 μM, was then added to the cancer cells. The xCELLigence readout is from 0 to 120 hours FIG. 54A shows the various ADCs added at a concentration of 500 nM. FIG. 54B shows the various ADCs added at a concentration of 167 nM.

FIG. 54C shows the various ADCs added at a concentration of 56 nM. FIG. 54D shows the various ADCs added at a concentration of 19 nM. FIG. 54E shows the Key listing the color of the trace for each ADC as well as the DAR for each. As can be seen in the figure, MNC2-Exatecan is potently killing the target cancer cells at a concentration as low as 56 nM.

Figures 55A, 55B, 55C, 55D:
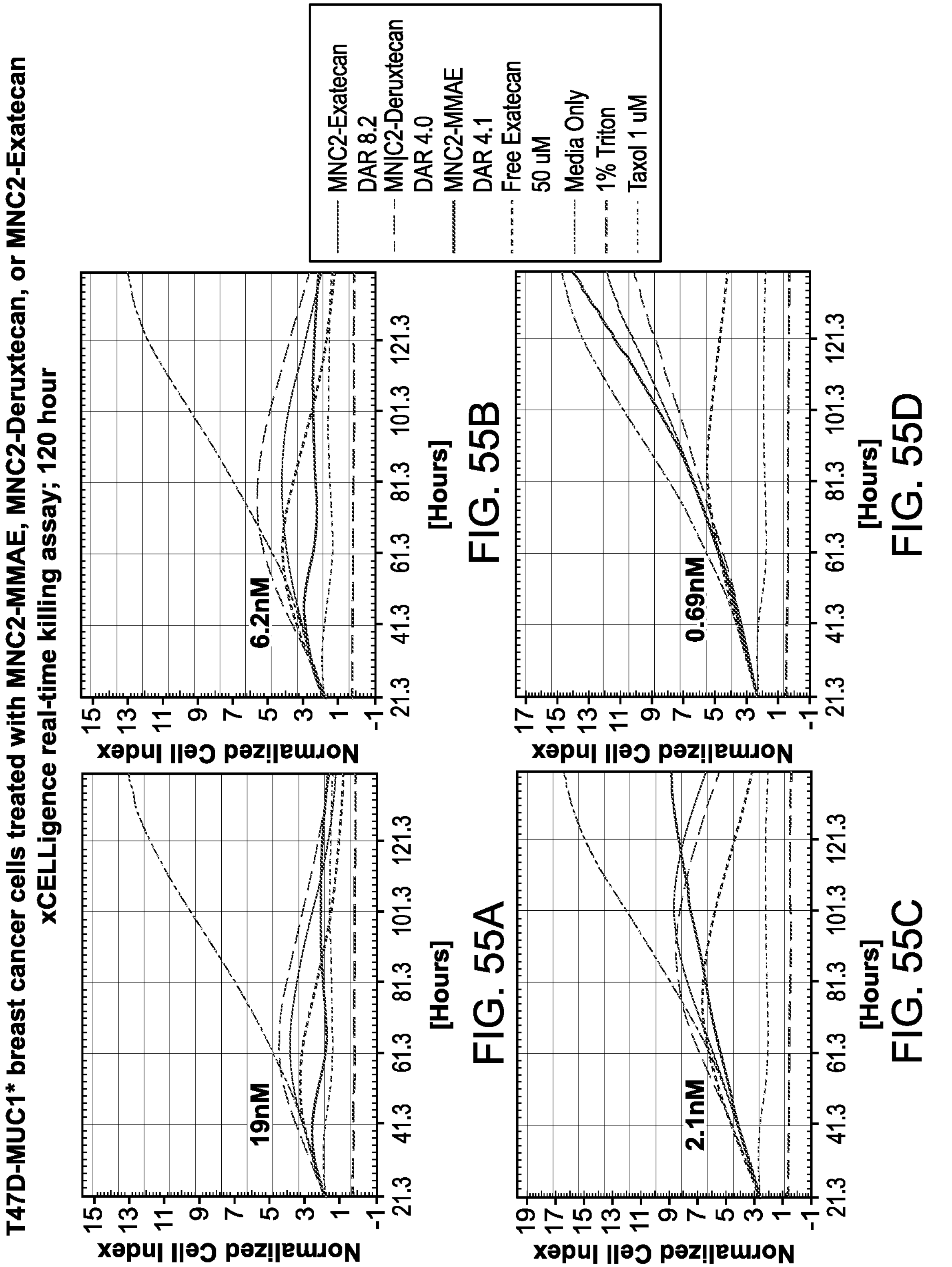

FIGS. 55A-55D show traces from the real-time killing assays performed on an xCELLigence instrument. In this assay, impedance is measured in real-time. When the adherent cancer cells are killed and come off of the electrode surface, impedance (insulation) decreases. Here T47D-MUC1* breast cancer cells, that were engineered to express high levels of MUC1*, were plated onto multi-electrode 96-well plates at 5,000 cells per well and allowed to adhere and grow for 24 hours before the addition of ADCs. Either MNC2-Exatecan, DAR 8.2, MNC2-Deruxtecan, DAR 4.0, MNC2-MMAE, DAR 4.1, or free Exatecan at 50 μM, was then added to the cancer cells. The xCELLigence readout is from 0 to 120 hours FIG. 55A shows the various ADCs added at a concentration of 19 nM. FIG. 55B shows the various ADCs added at a concentration of 6.2 nM. FIG. 55C shows the various ADCs added at a concentration of 2.1 nM. FIG. 55D shows the various ADCs added at a concentration of 0.69 nM. FIG. 55E shows the Key listing the color of the trace for each ADC as well as the DAR for each. As can be seen in the figure, MNC2-Exatecan and MNC2-Deruxtecan are potently killing cancer cells that express high levels of the target antigen at a concentration as low as 6.2 nM and even as low as 2.1 nM.

Figures 56A, 56B, 56C, 56D:
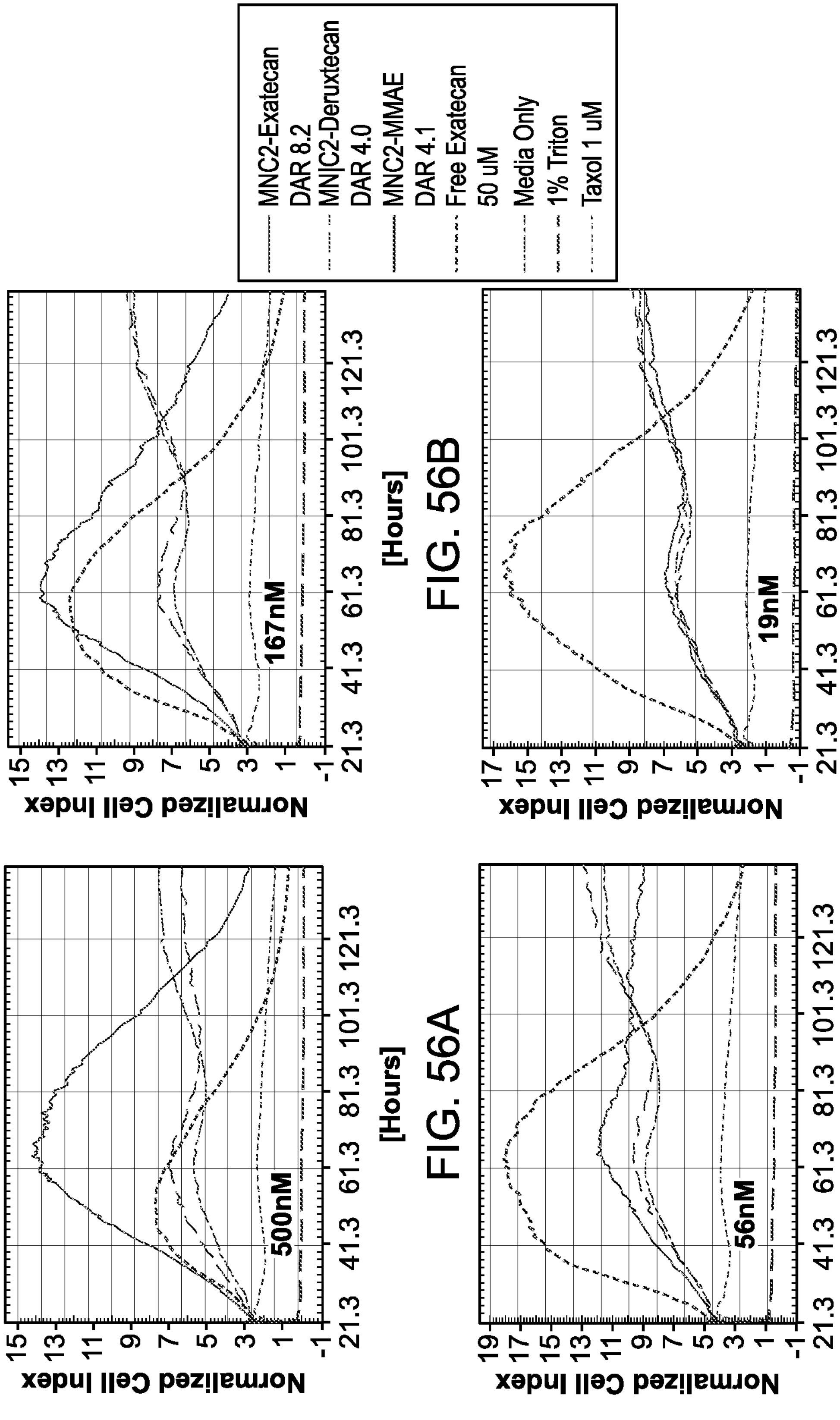

FIGS. 56A-56D show traces from the real-time killing assays performed on an xCELLigence instrument. In this assay, impedance is measured in real-time. When the adherent cancer cells are killed and come off of the electrode surface, impedance (insulation) decreases. Here NCI-H1975 non-small cell lung cancer cells that express very low levels of MUC1*, were plated onto multi-electrode 96-well plates at 5,000 cells per well and allowed to adhere and grow for 24 hours before the addition of ADCs. Either MNC2-Exatecan, DAR 8.2, MNC2-Deruxtecan, DAR 4.0, MNC2-MMAE, DAR 4.1, or free Exatecan at 50 μM, was then added to the cancer cells. The xCELLigence readout is from 0 to 120 hours FIG. 56A shows the various ADCs added at a concentration of 500 nM. FIG. 56B shows the various ADCs added at a concentration of 167 nM. FIG. 56C shows the various ADCs added at a concentration of 56 nM. FIG. 56D shows the various ADCs added at a concentration of 19 nM. FIG. 56E shows the Key listing the color of the trace for each ADC as well as the DAR for each. As can be seen in the figure, MNC2-Exatecan is potently killing cancer cells that express very low levels of the target antigen at a concentration as low as 167 nM.

Figures 57A, 57B, 57C, 57D:
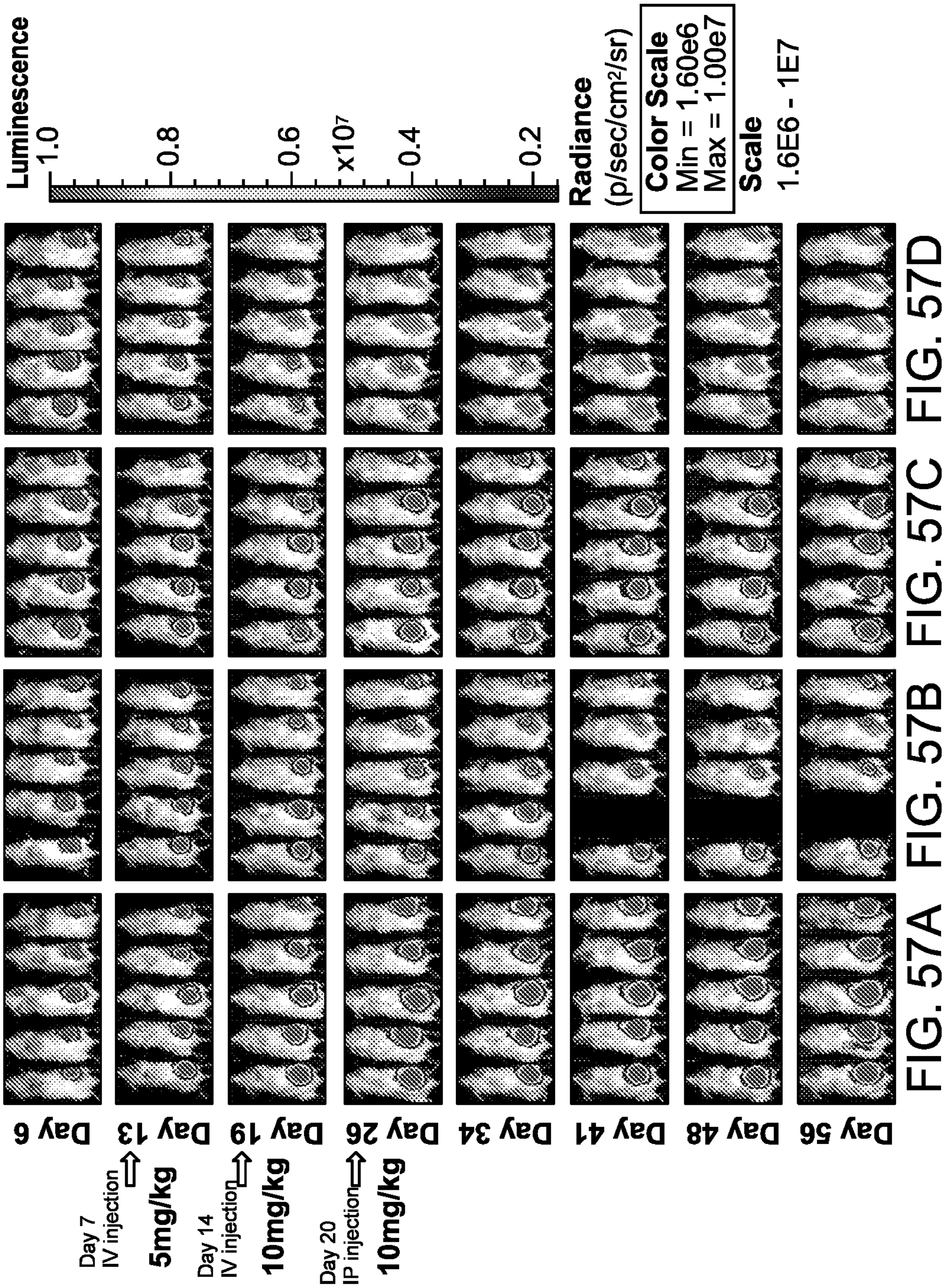
Figure 57E:
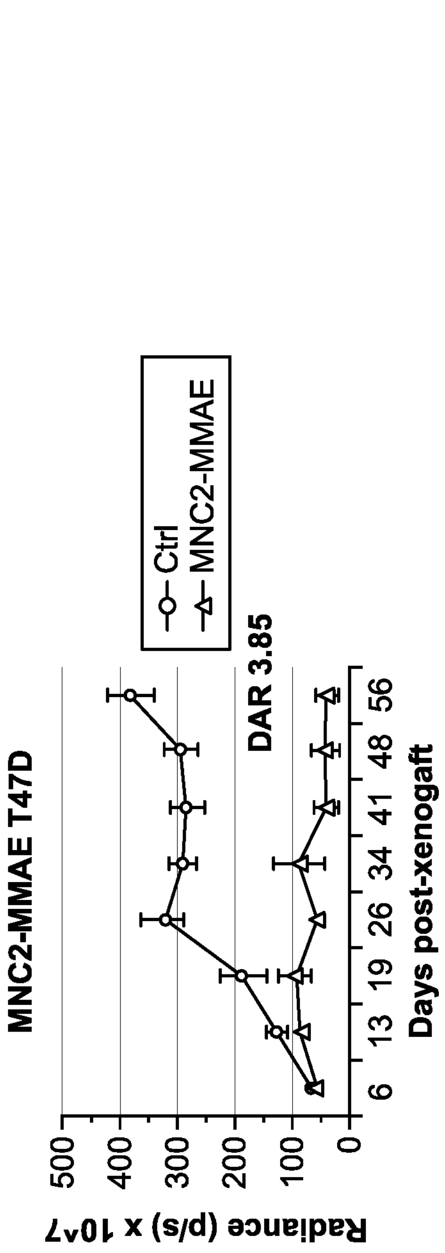
Figure 57F:
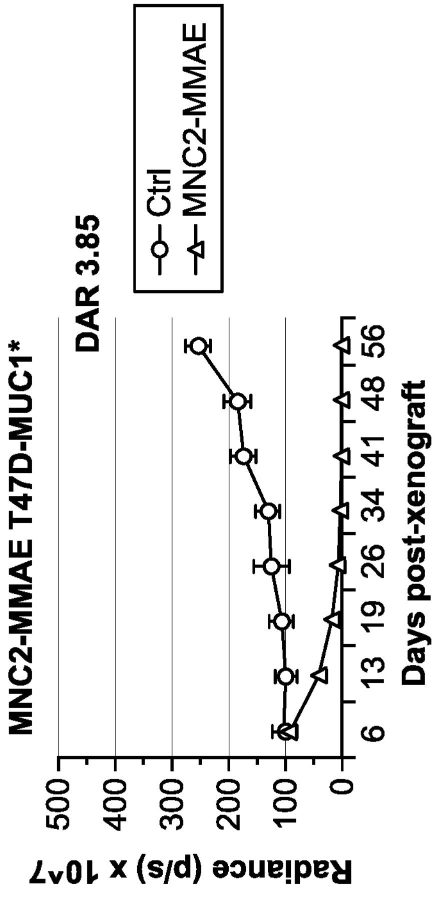

FIGS. 57A-57F show bioluminescence photographs of female NOD/SCID/GAMMA (NSG) mice, implanted with 90-day estrogen pellets and then implanted on the right flank with 1M human breast cancer cells that were either T47D wild-type cells that express low to medium levels of MUC1* or T47D-MUC1* cells that had been engineered to express more MUC1*. Day 7 post tumor implantation, the animals were injected with MNC2-MMAE, DAR 3.9, at 5 mg/kg, but was increased to 10 mg/kg for the Day 14 and Day 20 injections. FIG. 57A shows control animals that were implanted with T47D-wt tumor cells but were mock injected with PBS. FIG. 57B shows animals that were implanted with T47D-wt cells and then injected with MNC2-MMAE. FIG. 57C shows control animals that were implanted with T47D-MUC1* tumor cells but were mock injected with PBS. FIG. 57D shows animals that were implanted with T47D-MUC1* cells and then injected with MNC2-MMAE. FIG. 57E shows a graph of the IVIS measurements of bioluminescence (radiance photons/$cm^2$) as a function of days post tumor implantation for mice implanted with T47D wild-type breast cancer cells. FIG. 57F shows a graph of the IVIS measurements of bioluminescence (radiance photons/$cm^2$) as a function of days post tumor implantation for mice implanted with T47D-MUC1* breast cancer cells.

Figures 58A, 58B, 58C, 58D:
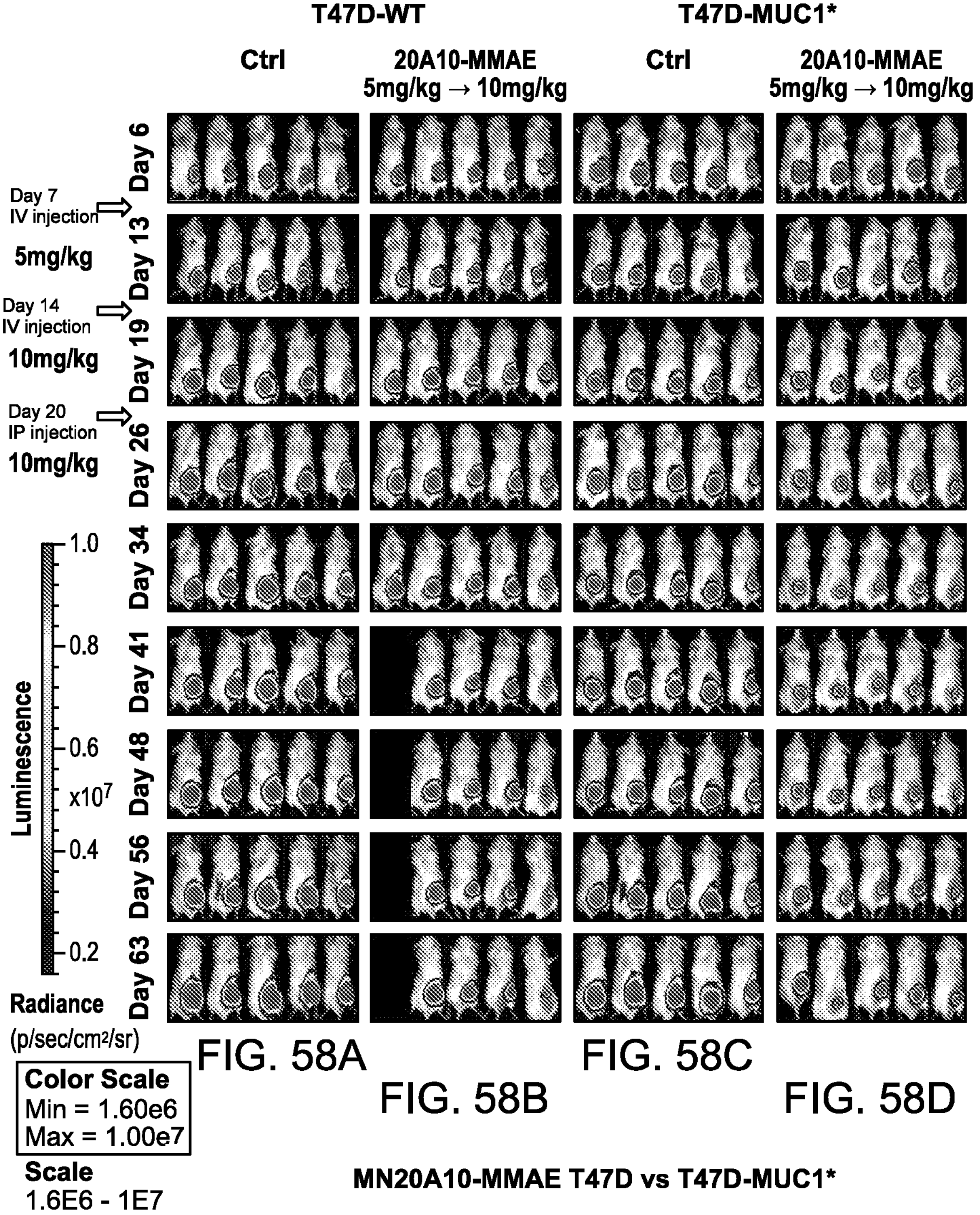
Figure 58E:
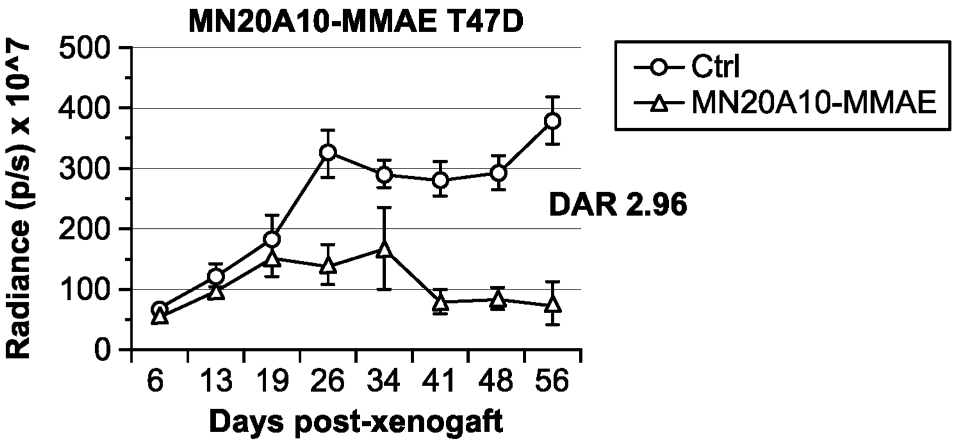
Figure 58F:
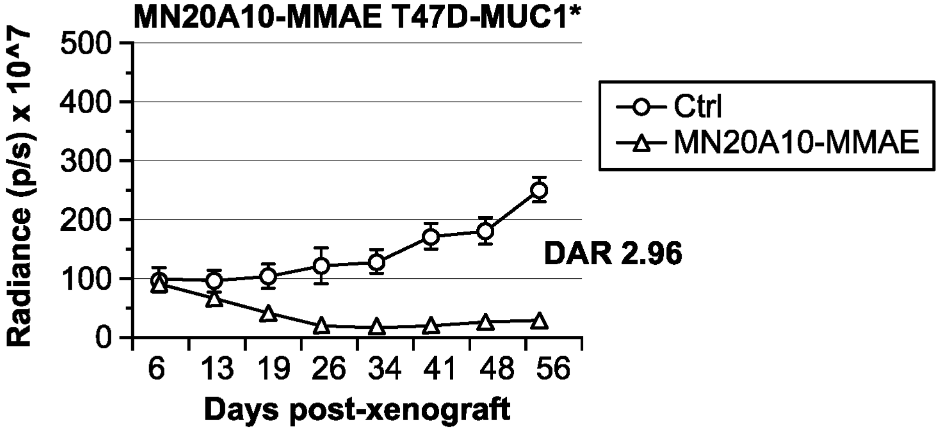

FIGS. 58A-58F show bioluminescence photographs of female NOD/SCID/GAMMA (NSG) mice, implanted with 90-day estrogen pellets and then implanted on the right flank with 1M human breast cancer cells that were either T47D wild-type cells that express low to medium levels of MUC1* or T47D-MUC1* cells that had been engineered to express more MUC1*. Day 7 post tumor implantation, the animals were injected with MN20A10-MMAE, DAR 3.0, at 5 mg/kg, but was increased to 10 mg/kg for the Day 14 and Day 20 injections. FIG. 58A shows control animals that were implanted with T47D-wt tumor cells but were mock injected with PBS. FIG. 58B shows animals that were implanted with T47D-wt cells and then injected with MN20A10-MMAE. FIG. 58C shows control animals that were implanted with T47D-MUC1* tumor cells but were mock injected with PBS. FIG. 58D shows animals that were implanted with T47D-MUC1* cells and then injected with MN20A10-MMAE. FIG. 58E shows a graph of the IVIS measurements of bioluminescence (radiance photons/$cm^2$) as a function of days post tumor implantation for mice implanted with T47D wild-type breast cancer cells. FIG. 58F shows a graph of the IVIS measurements of bioluminescence (radiance photons/sec/$cm^2$) as a function of days post tumor implantation for mice implanted with T47D-MUC1* breast cancer cells.

Figure 59A:
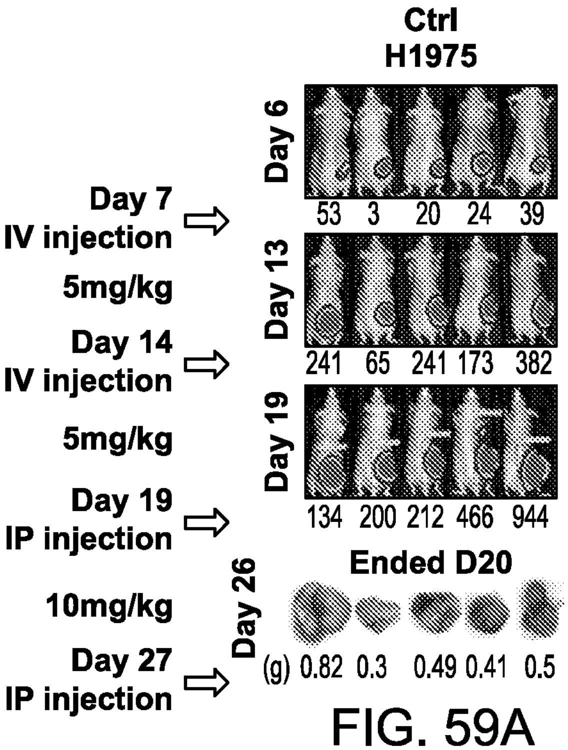
Figure 59B:
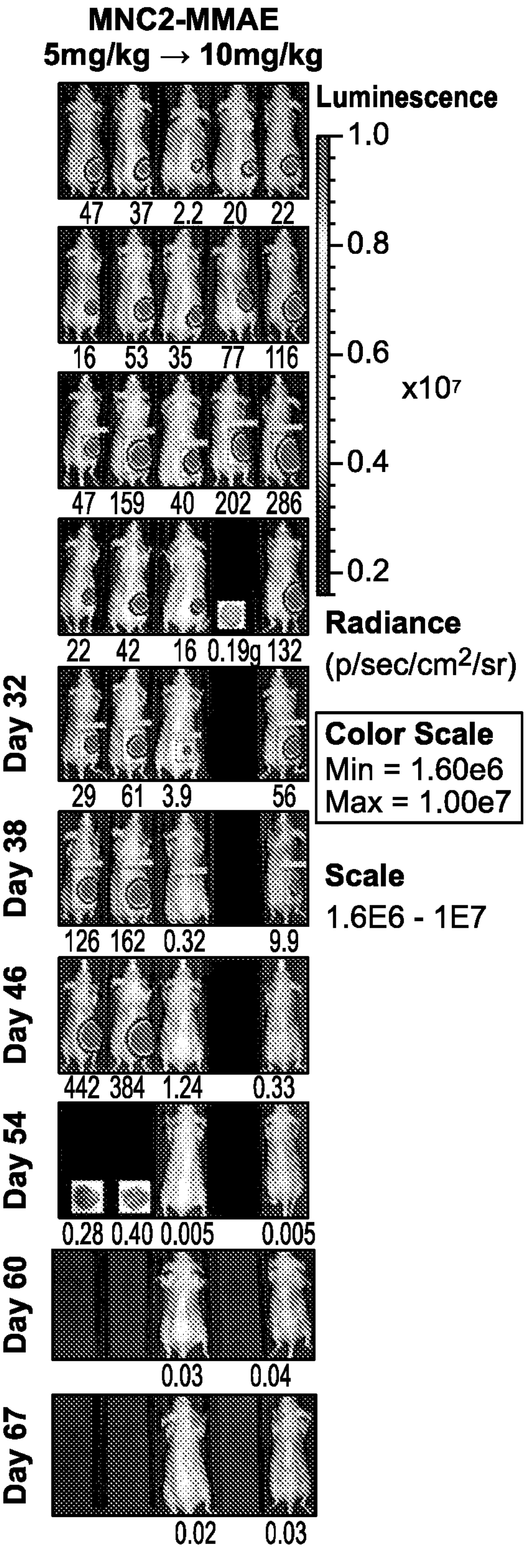
Figure 59C:
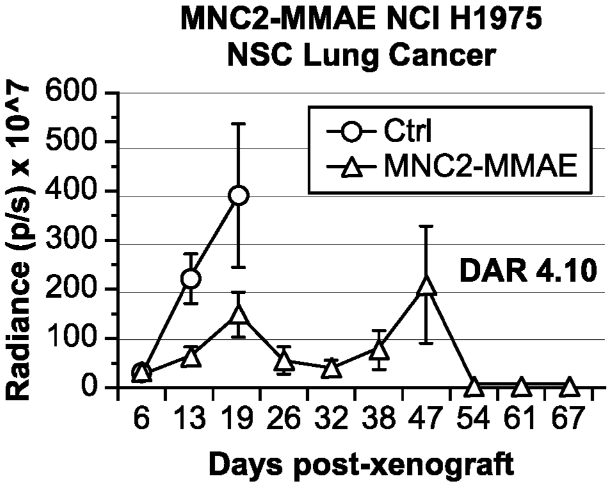

FIGS. 59A-59C show bioluminescence photographs of female nu/nu mice, implanted on the right flank with 1M human NCI-H1975 non-small cell lung cancer cells that express low to medium levels of MUC1*. Day 7 post tumor implantation, the animals were injected with MNC2-MMAE at either 5 mg/kg or 10 mg/kg as indicated. As can be seen in the bioluminescent photographs, increasing the dose of MNC2-MMAE, DAR 3.9, to 10 mg/kg on Day 19 and Day 27 increased the killing of the tumor cells. FIG. 59A shows control animals that were implanted with NCI-H1975 non-small cell lung cancer cells but were mock injected with PBS. FIG. 59B shows animals that were implanted with NCI-H1975 non-small cell lung cancer cells and then injected with MNC2-MMAE. FIG. 59C shows a graph of the IVIS measurement of bioluminescence (radiance photons/sec/$cm^2$) as a function of days post tumor implantation.

Figures 60A, 60B:
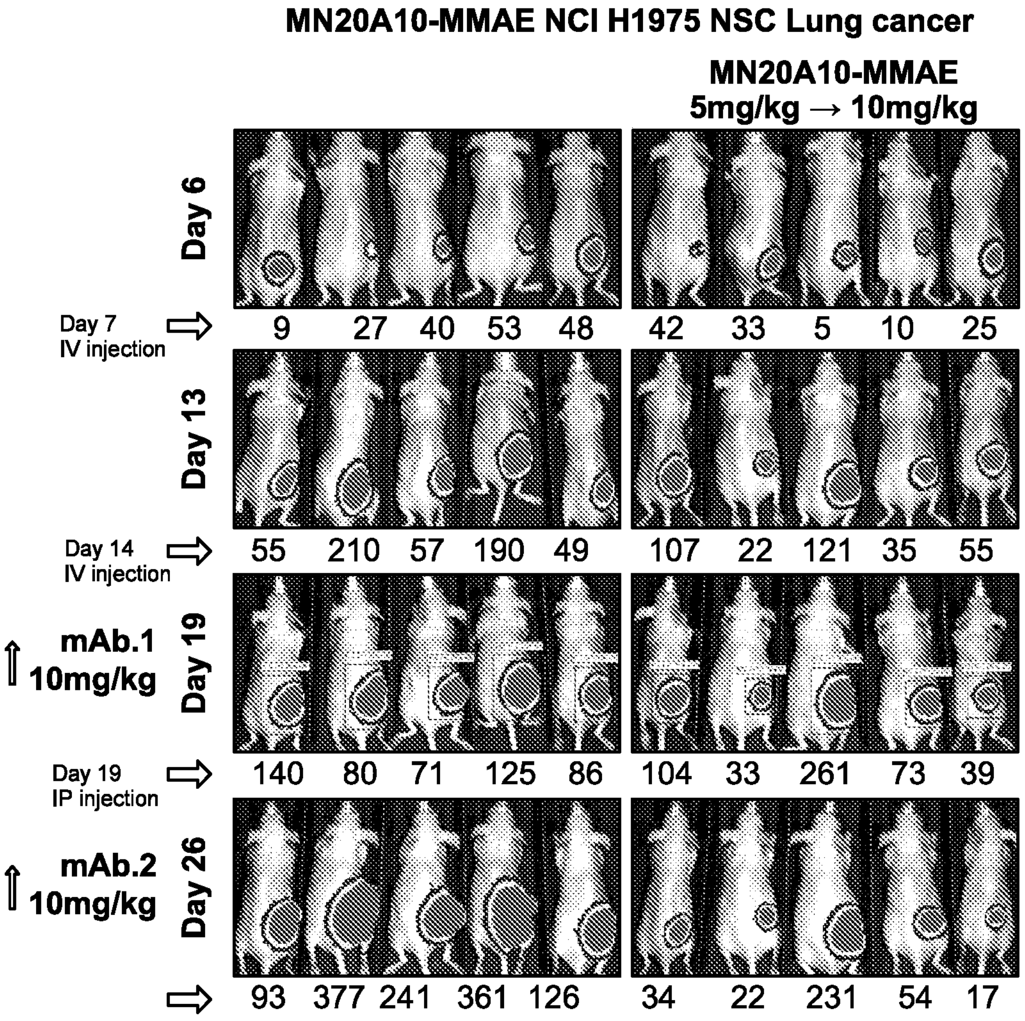
Figure 60C:
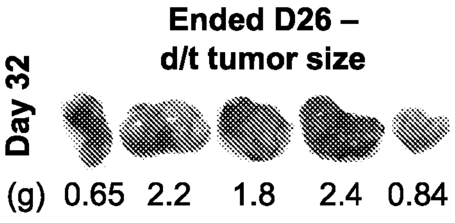
Figure 60D:
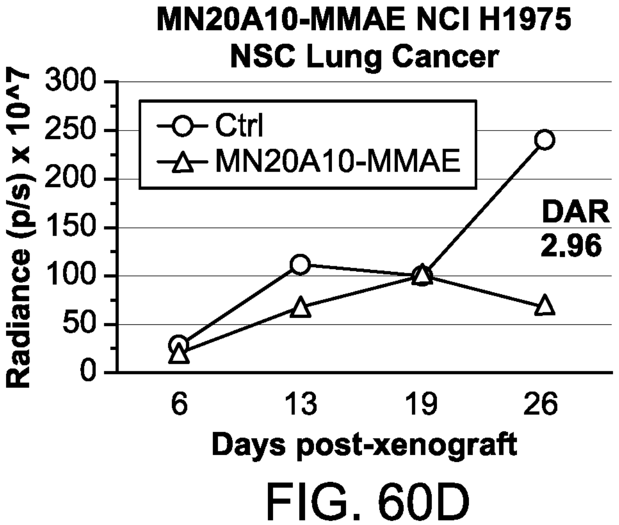

FIGS. 60A-60D show bioluminescence photographs, taken on an IVIS instrument, of female nu/nu mice, implanted on the right flank with 1M human NCI-H1975 non-small cell lung cancer cells that express low to medium levels of MUC1*. On Day 7 and Day 14, post tumor implantation, the animals were injected with MN20A10-MMAE, DAR 3.0, at 5 mg/kg. On Day 19, the dose was increased to 10 mg/kg and administered by intraperitoneal (ip) injection. As can be seen in the photographs and the graph, the increased dose dramatically increased the killing of the tumor cells. FIG. 60A shows control animals that were implanted with NCI-H1975 non-small cell lung cancer cells but were mock injected with PBS. FIG. 60B shows animals that were implanted with NCI-H1975 non-small cell lung cancer cells and then injected with MN20A10-MMAE. FIG. 60C shows photographs and weights of the tumors that were excised from the control animals at Day 26. FIG. 60D shows a graph of the IVIS measurement of bioluminescence (radiance photons/sec/$cm^2$) as a function of days post tumor implantation.

Figures 61A, 61B, 61C, 61D:
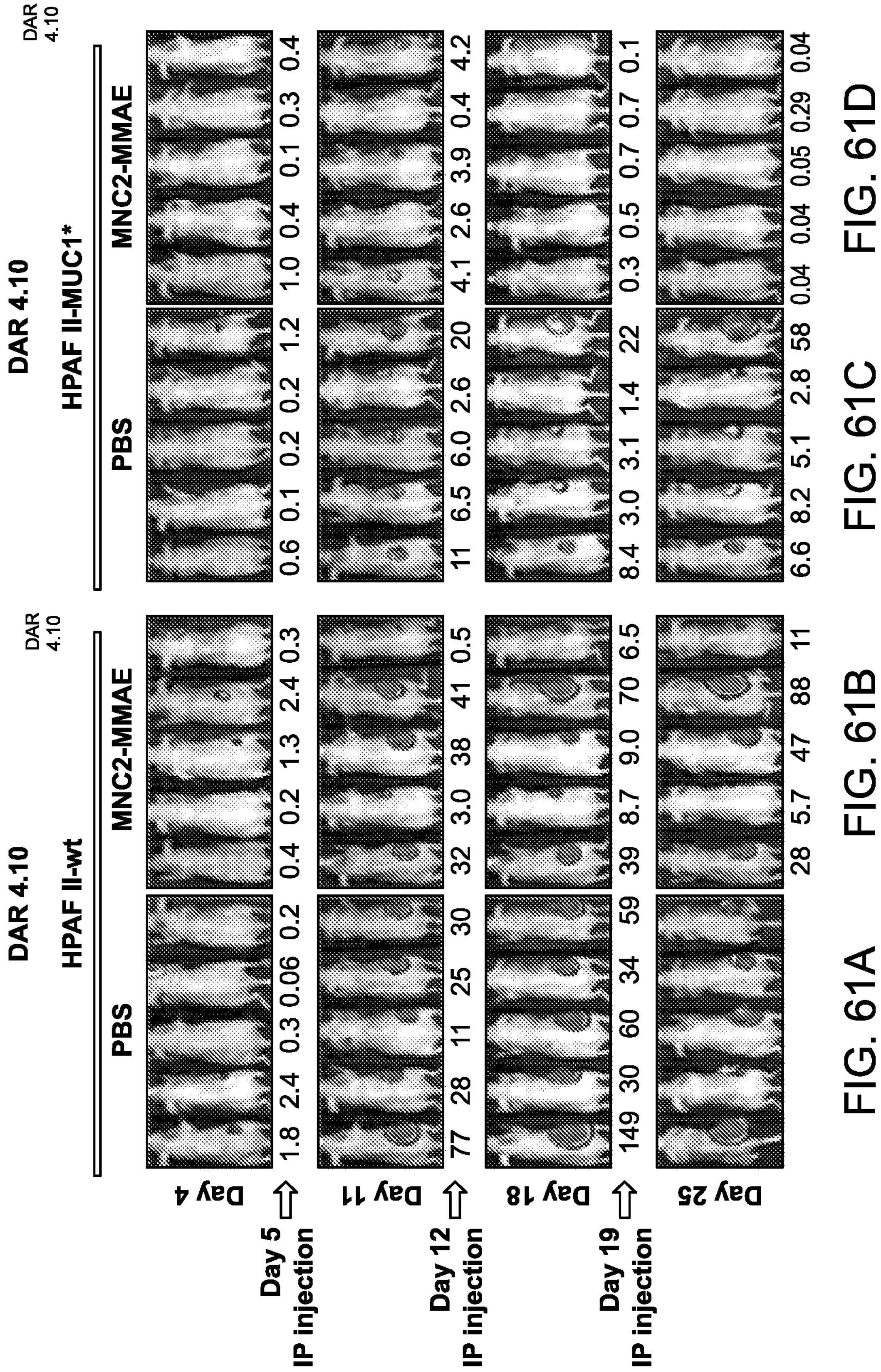
Figure 61E:
Figure 61F:
Figure 61G:
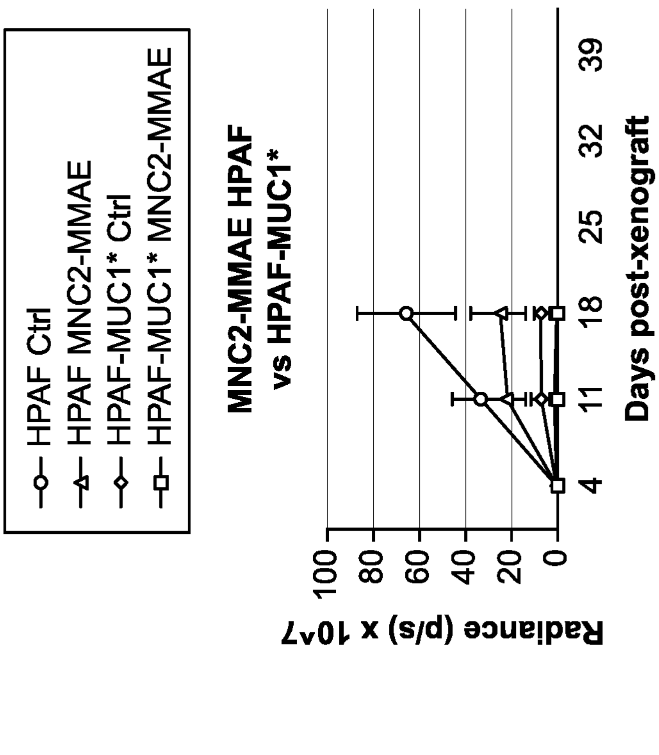
Figure 61H:
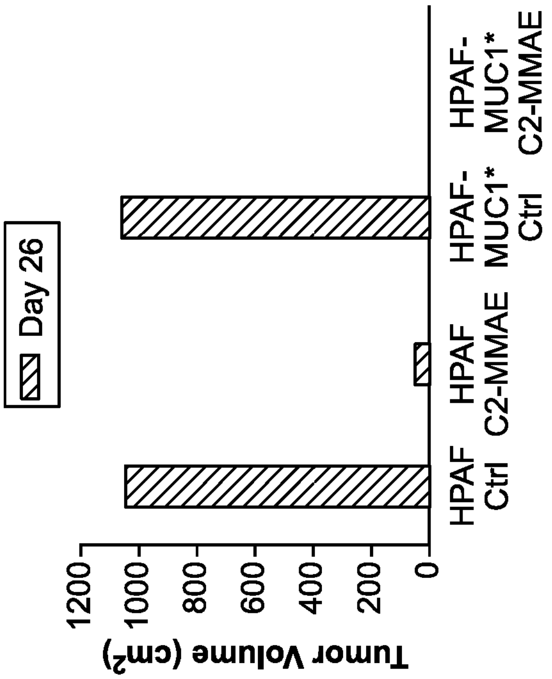
Figure 61I:
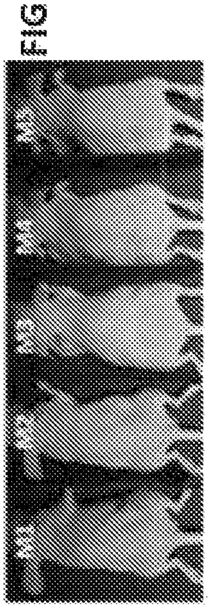
Figure 61J:
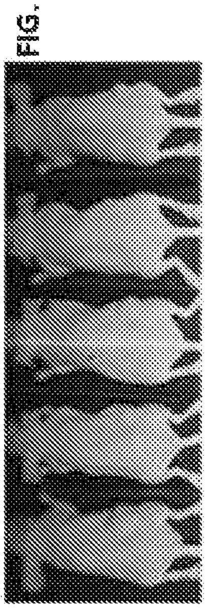
Figure 61K:
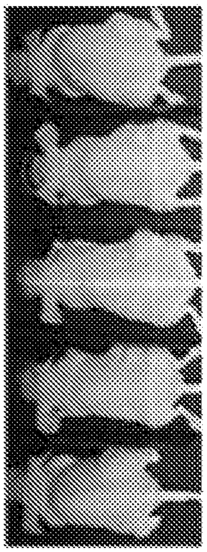
Figure 61L:
Figure 61M:
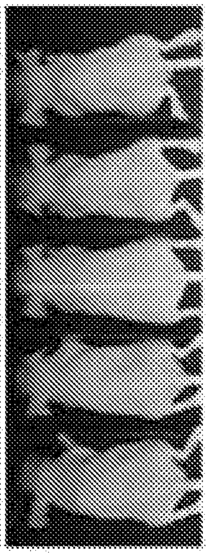
Figure 61N:
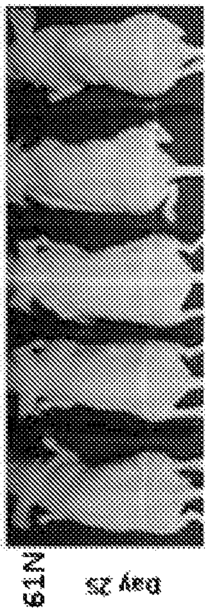
Figures 61O, 61P, 61Q, 61R, 61S, 61T, 61U, 61V:
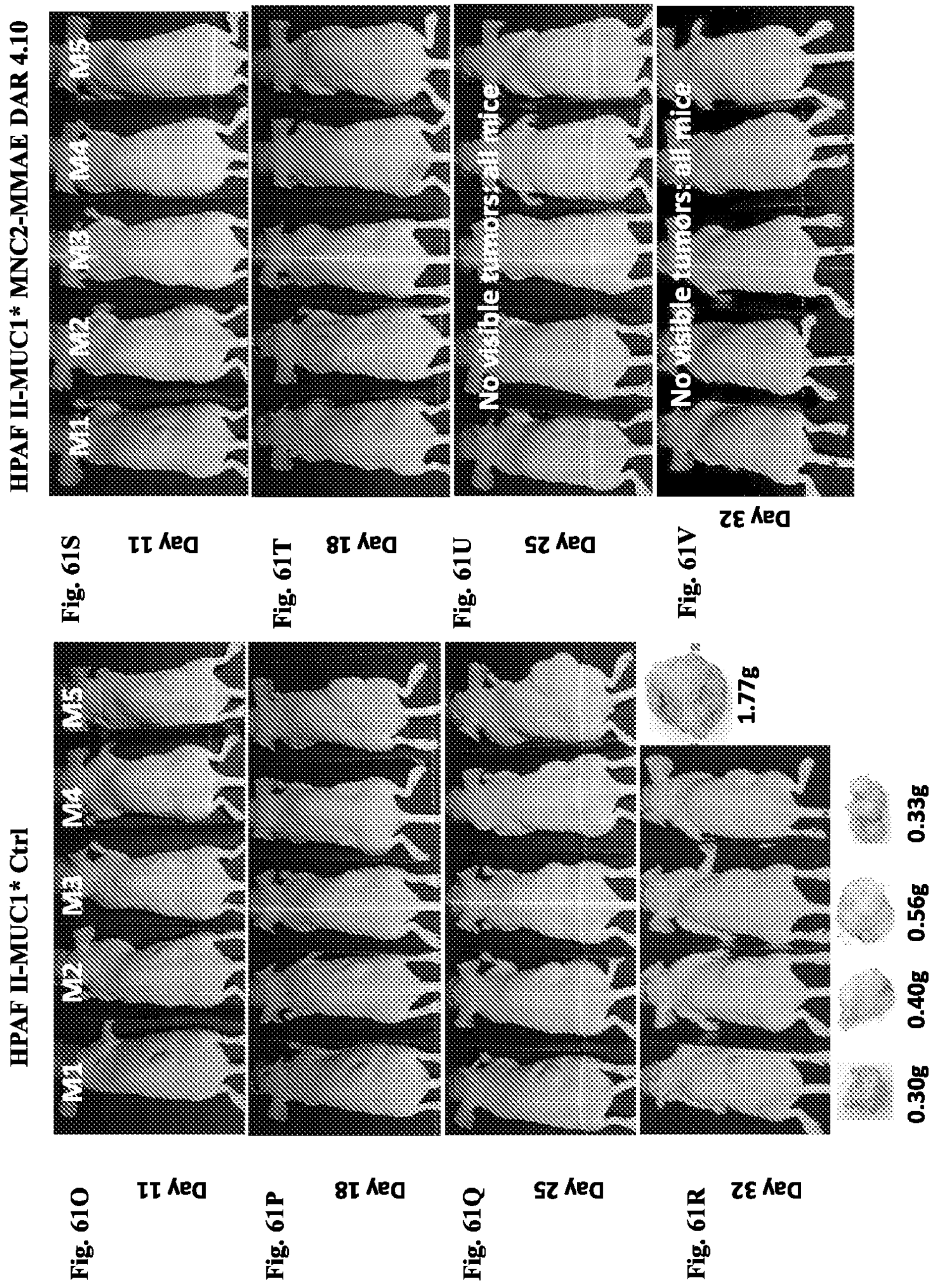

FIGS. 61A-61V show bioluminescence photographs, taken on an IVIS instrument, of female nu/nu mice, implanted on the right flank with 0.5M human pancreatic cancer cells that were either HPAF II wild-type (wt) cells that express low to medium levels of MUC1* or HP AF II-MUC1* cells that had been engineered to express more MUC1*. Day 7 post tumor implantation, the animals were injected with either PBS as a control or MNC2-MMAE, DAR 4.1, at 10 mg/kg. FIG. 61A shows IVIS bioluminescent photographs of control animals that were implanted with HPAF II-wt pancreatic cancer cells but were mock injected with PBS. FIG. 61B shows IVIS bioluminescent photographs of animals that were implanted with HPAF II-wt pancreatic cancer cells then injected with MNC2-MMAE. FIG. 61C shows IVIS bioluminescent photographs of control animals that were implanted with HPAF II-MUC1* pancreatic cancer cells but were mock injected with PBS. FIG. 61D shows IVIS bioluminescent photographs of animals that were implanted with HPAF II-MUC1* pancreatic cancer cells and then injected with MNC2-MMAE. FIG. 61E shows photographs of tumors excised from HPAF II-wt control animals that had to be sacrificed because of excess tumor burden. FIG. 61F shows photograph of tumor excised from HPAF II-MUC1* control animal that had to be sacrificed because of excess tumor burden. FIG. 61G shows an overlay graph of the IVIS measurements of bioluminescence (radiance photons/sec/$cm^2$) as a function of days post tumor implantation for both control and MNC2-MMAE treated mice. Day 25 IVIS data point omitted because of instrument malfunction. FIG. 61H shows a bar graph of caliper measurements of the tumors at Day 25. Caliper measurement eliminates the differences in the expression levels of luciferase in the HPAF II-wt cell line versus the HPAF II-MUC1* cell line. FIG. 61I shows Day 11 photographs of the control animals that were implanted with HPAF II-wt pancreatic cancer cells but were mock injected with PBS. FIG. 61J shows Day 18 photographs of the control animals that were implanted with HPAF II-wt pancreatic cancer cells but were mock injected with PBS. FIG. 61K shows Day 25 photographs of the control animals that were implanted with HPAF II-wt pancreatic cancer cells but were mock injected with PBS, showing increasingly large tumors on the right flank. FIG. 61L shows Day 11 photographs of animals that were implanted with HPAF II-wt pancreatic cancer cells then injected with MNC2-MMAE. FIG. 61M shows Day 18 photographs of animals that were implanted with HPAF II-wt pancreatic cancer cells then injected with MNC2-MMAE. FIG. 61N shows Day 25 photographs of animals that were implanted with HPAF II-wt pancreatic cancer cells then injected with MNC2-MMAE, where 3 of the mice have small tumors that are barely visible. FIG. 61O shows Day 11 photographs of control animals that were implanted with HPAF II-MUC1* pancreatic cancer cells but were mock injected with PBS. FIG. 61P shows Day 18 photographs of control animals that were implanted with HPAF II-MUC1* pancreatic cancer cells but were mock injected with PBS. FIG. 61Q shows Day 25 photographs of control animals that were implanted with HPAF II-MUC1* pancreatic cancer cells but were mock injected with PBS, showing large tumors on the right flank. FIG. 61R shows Day 11 photographs of animals that were implanted with HP AF II-MUC1* pancreatic cancer cells and then injected with MNC2-MMAE. FIG. 61S shows Day 18 photographs of animals that were implanted with HPAF II-MUC1* pancreatic cancer cells and then injected with MNC2-MMAE. FIG. 61T shows Day 25 photographs of animals that were implanted with HPAF II-MUC1* pancreatic cancer cells and then injected with MNC2-MMAE, where no tumors are visible nor palpable.

Figures 62A, 62B:
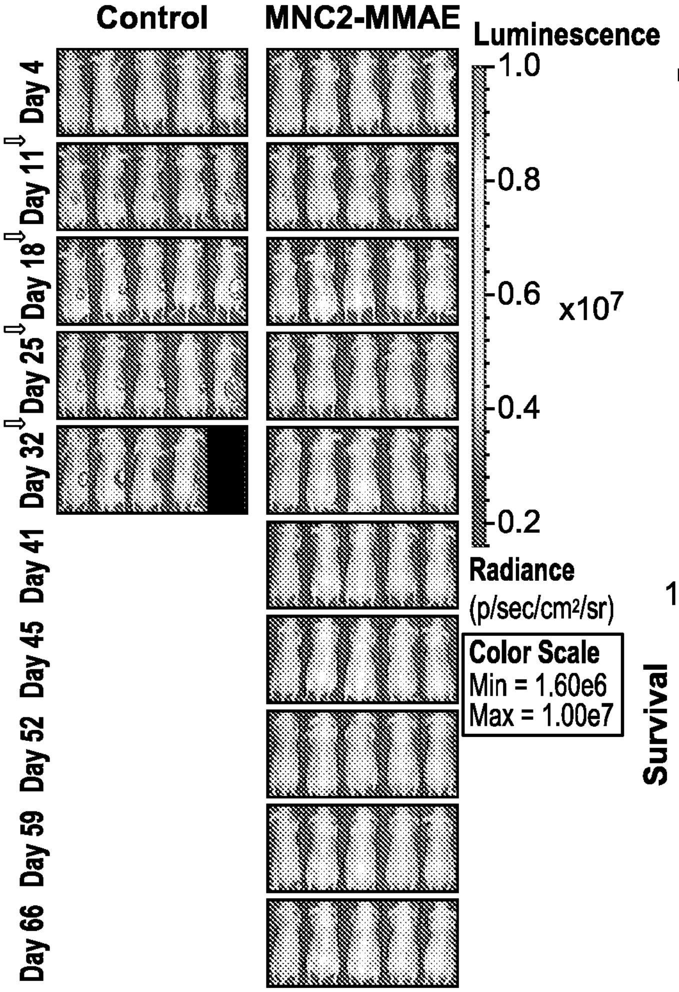
Figure 62D:
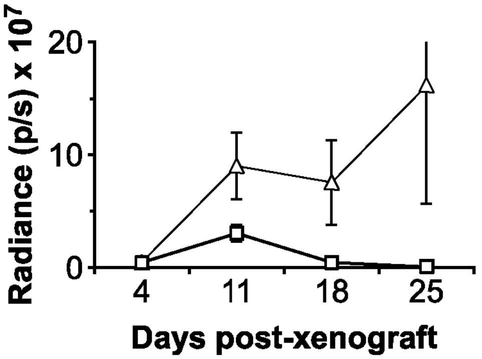
Figure 62E:
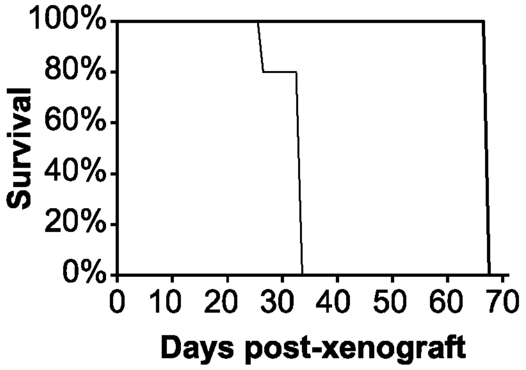
Figure 62C:
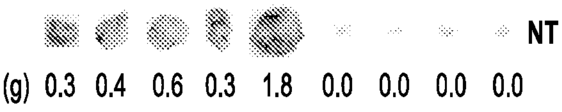
Figure 62F:
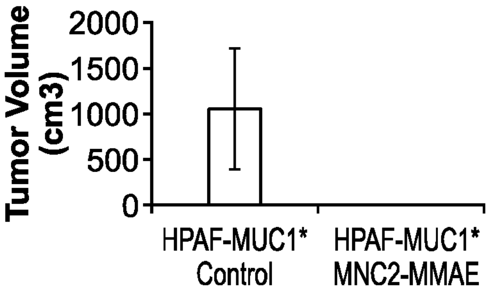

FIGS. 62A-62F show bioluminescence photographs, taken on an IVIS instrument, of female nu/nu mice, implanted on the right flank with 0.5M human pancreatic cancer cells, HPAF II-MUC1* cells that had been engineered to express more MUC1*. Day 7 post tumor implantation, the animals were injected with either PBS as a control or MNC2-MMAE, DAR 4.1, at 10 mg/kg. As can be seen in the figure by Day 66, the treated mice have no tumor or a speck of a residual tumor. Because the HPAF II cell line doesn't express Luciferase well, the Bioluminescence is weak. For that reason, we also performed caliper measurements, which document that actual size of the tumors. FIG. 62A shows IVIS bioluminescent photographs of control animals that were implanted with HPAF II-MUC1* pancreatic cancer cells but were mock injected with PBS. FIG. 61B shows IVIS bioluminescent photographs of animals that were implanted with HPAF II-MUC1* pancreatic cancer cells then injected with MNC2-MMAE at 10 mg/kg. FIG. 62C shows photographs of tumors excised from HPAF II-MUC1* control animals that had to be sacrificed because of excess tumor burden compared to specks of tumor or no tumor that remained in the MNC2-MMAE treated group. FIG. 62D shows an overlay graph of the IVIS measurements of bioluminescence (radiance photons/sec/$cm^2$) as a function of days post tumor implantation for both control and MNC2-MMAE treated mice. FIG. 62E shows a Kaplan-Meier survival plot of control versus treated mice. FIG. 62F shows a bar graph of caliper measurements of the control animals versus the treated animals.

Figures 63A, 63B, 63C, 63D:
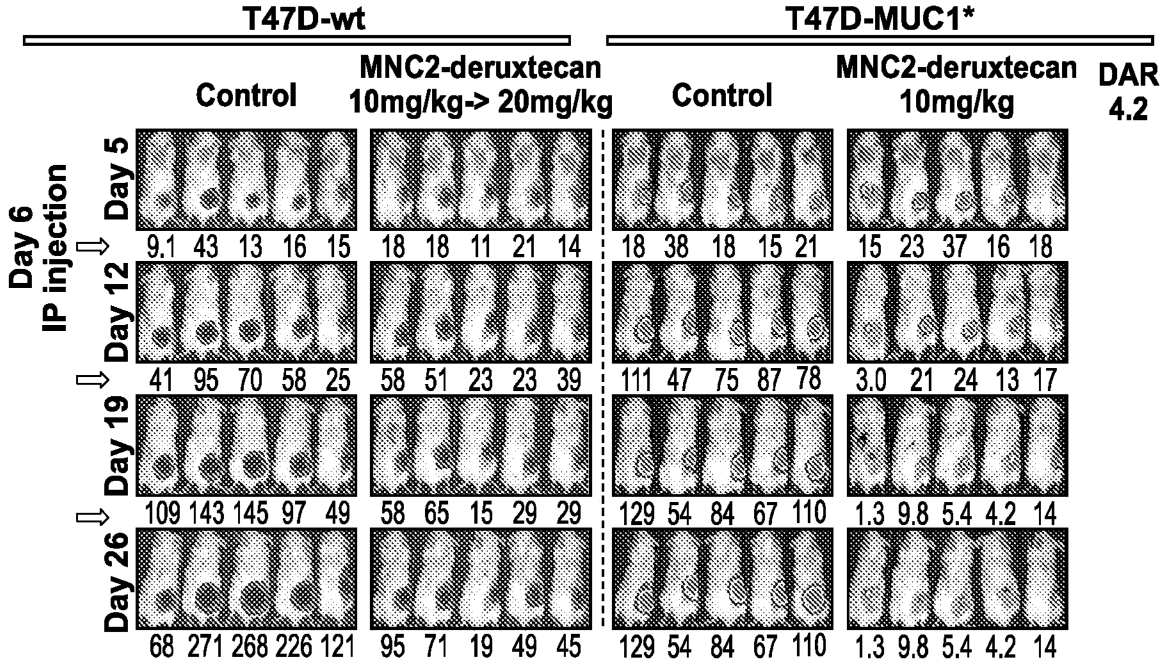
Figure 63E:
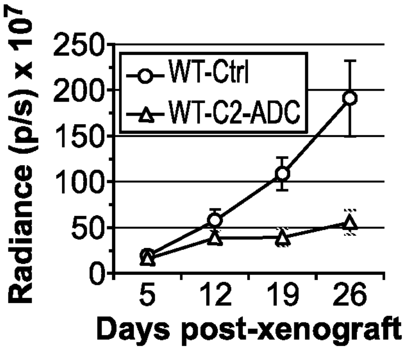
Figure 63F:
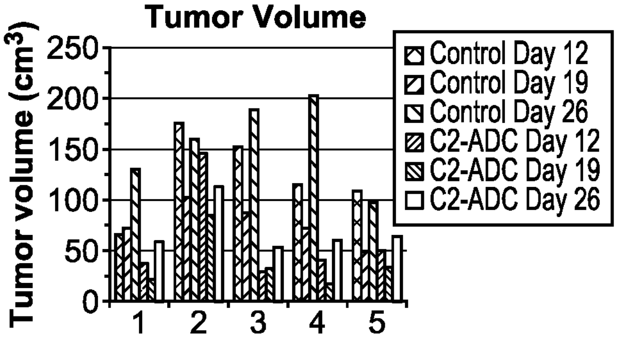
Figure 63G:
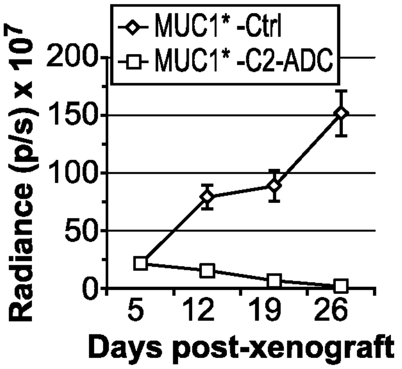
Figure 63H:
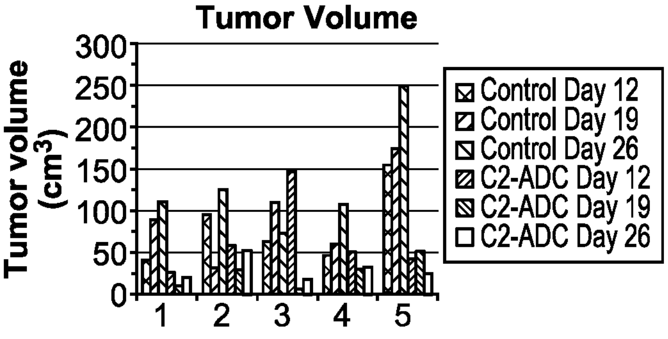

FIGS. 63A-63H show bioluminescence photographs of female NOD/SCID/GAMMA (NSG) mice, implanted with 90-day estrogen pellets and then implanted on the right flank with 1M human breast cancer cells that were either T47D wild-type cells that express low to medium levels of MUC1* or T47D-MUC1* cells that had been engineered to express more MUC1*. Day 6 post tumor implantation, the animals were injected with MNC2-deruxtecan, DAR 4.2, at 10 mg/kg, but was increased to 20 mg/kg for the T47D-wt treated mice. Treatment of the T47D-MUC1* treated mice remained constant at 10 mg/kg. FIG. 63A shows control animals that were implanted with T47D-wt tumor cells but were mock injected with PBS. FIG. 63B shows animals that were implanted with T47D-wt cells and then injected with MNC2-deruxtecan. FIG. 63C shows control animals that were implanted with T47D-MUC1* tumor cells but were mock injected with PBS. FIG. 63D shows animals that were implanted with T47D-MUC1* cells and then injected with MNC2-deruxtecan. FIG. 63E shows a graph of the IVIS measurements of bioluminescence (radiance photons/$cm^2$) as a function of days post tumor implantation for mice implanted with T47D wild-type breast cancer cells. FIG. 63F shows a bar graph of the bioluminescent measurement of each mouse by day for the animals implanted with T47D-wt breast cancer cells. FIG. 63G shows a graph of the IVIS measurements of bioluminescence (radiance photons/sec/$cm^2$) as a function of days post tumor implantation for mice implanted with T47D-MUC1* breast cancer cells. FIG. 63H shows a bar graph of the bioluminescent measurement of each mouse by day for the animals implanted with T47D-MUC1* breast cancer cells.

Figures 64A, 64B, 64C, 64D, 64E, 64F, 64G, 64H, 64I, 64J:
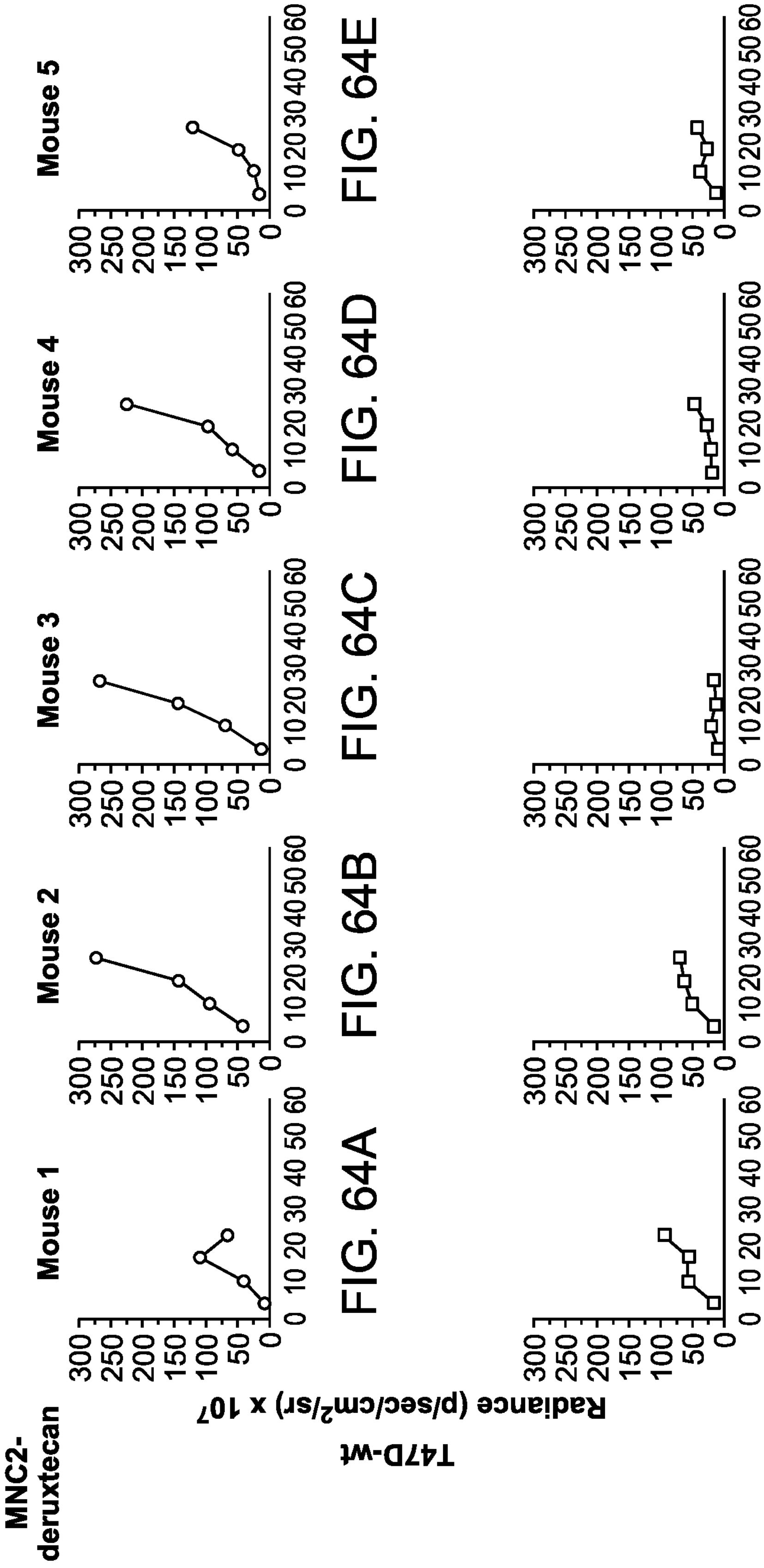
Figures 64K, 64L, 64M, 64N, 64O, 64P, 64Q, 64R, 64S, 64T:
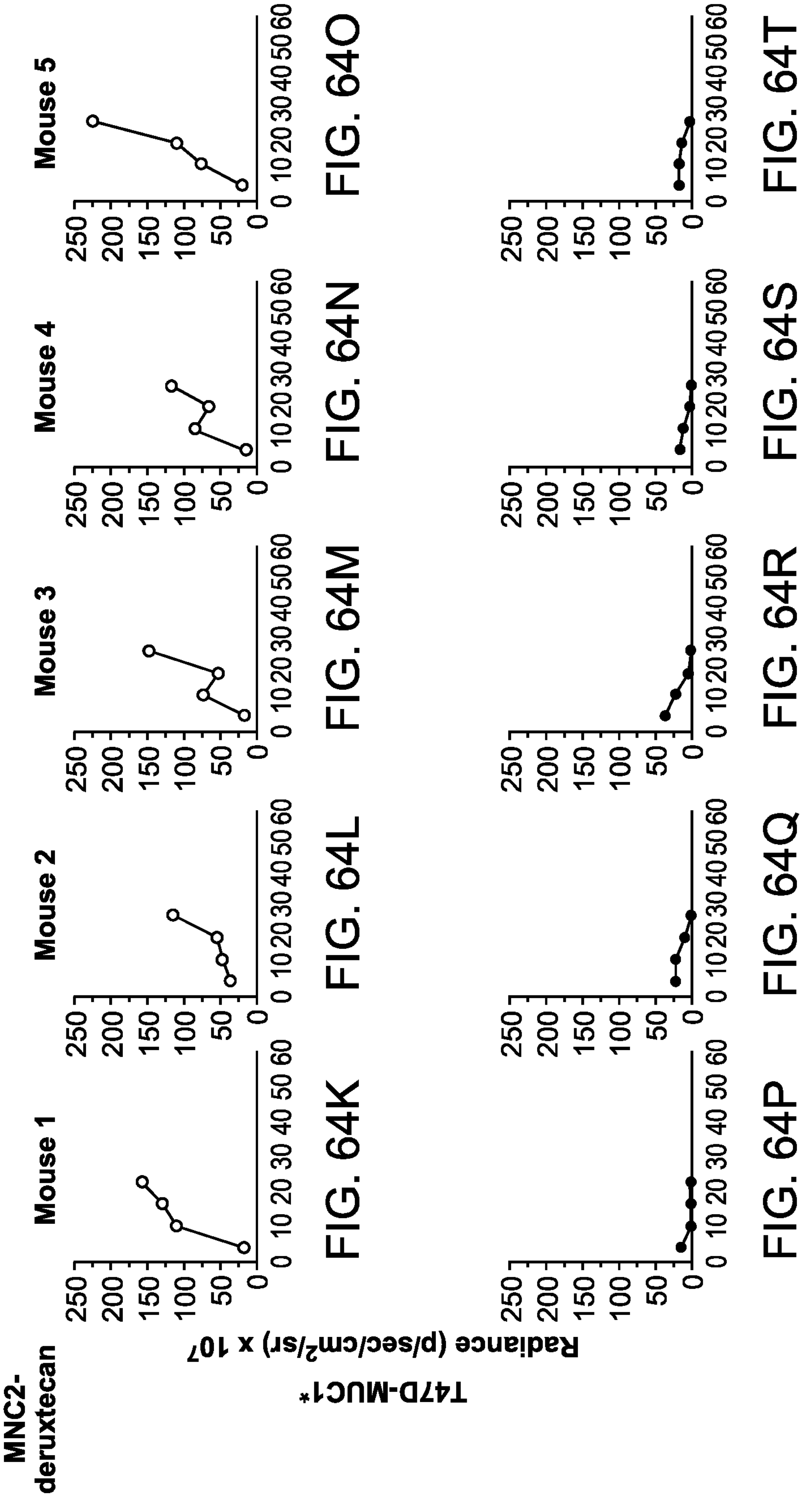
Figure 65A:
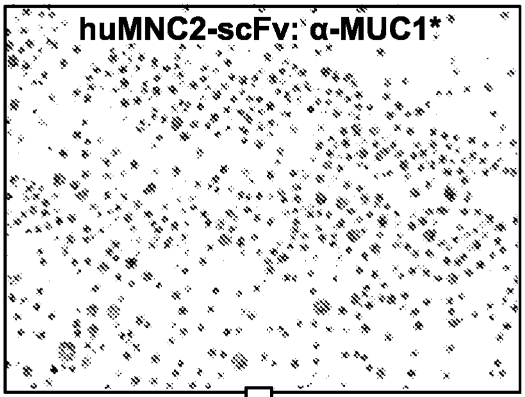
Figure 65B:
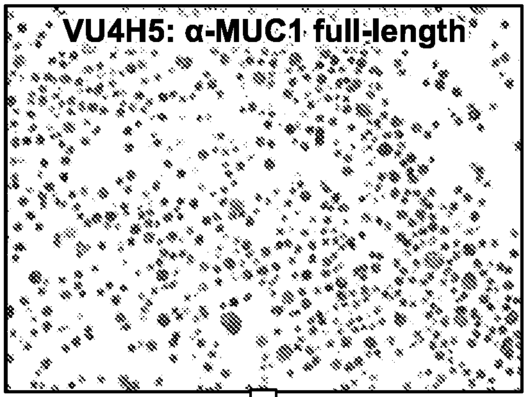
Figure 65C:
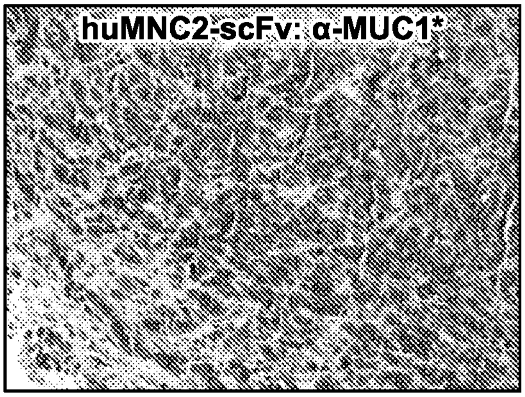
Figure 65D:
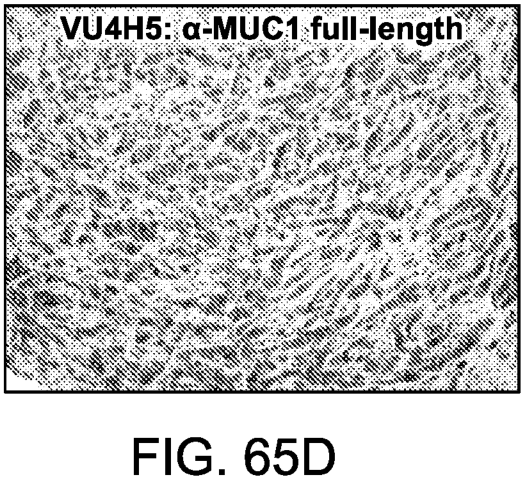

FIGS. 64A-64T show line graphs of IVIS luminescent measurement of the individual mice from Day 4 to Day 30. NOD/SCOD/GAMMA mice were implanted with either T47D-wt breast cancer cells or T47D-MUC1* cells that express more MUC1*. Both groups of mice were either mock treated with PBS or treated with MNC2-deruxtecan. Day 6 post tumor implantation, the animals were injected with MNC2-deruxtecan, DAR 4.2, at 10 mg/kg, but was increased to 20 mg/kg for the T47D-wt treated mice. Treatment of the T47D-MUC1* treated mice remained constant at 10 mg/kg. FIG. 64A shows growth of T47D-wt tumors in Mouse #1 in the control group. FIG. 64B shows growth of T47D-wt tumors in Mouse #2 in the control group. FIG. 64C shows growth of T47D-wt tumors in Mouse #3 in the control group. FIG. 64D shows growth of T47D-wt tumors in Mouse #4 in the control group. FIG. 64E shows growth of T47D-wt tumors in Mouse #5 in the control group. FIG. 64F shows growth of T47D-wt tumors in Mouse #1 of the group treated with MNC2-deruxtecan. FIG. 64G shows growth of T47D-wt tumors in Mouse #2 of the group treated with MNC2-deruxtecan. FIG. 64H shows growth of T47D-wt tumors in Mouse #3 of the group treated with MNC2-deruxtecan. FIG. 64I shows growth of T47D-wt tumors in Mouse #4 of the group treated with MNC2-deruxtecan. FIG. 64J shows growth of T47D-wt tumors in Mouse #5 of the group treated with MNC2-deruxtecan. FIG. 64K shows growth of T47D-MUC1* tumors in Mouse #1 in the control group. FIG. 64L shows growth of T47D-MUC1* tumors in Mouse #2 in the control group. FIG. 64M shows growth of T47D-MUC1* tumors in Mouse #3 in the control group. FIG. 64N shows growth of T47D-MUC1* tumors in Mouse #4 in the control group. FIG. 64O shows growth of T47D-MUC1* tumors in Mouse #5 in the control group. FIG. 64P shows growth of T47D-MUC1* tumors in Mouse #1 of the group treated with MNC2-deruxtecan. FIG. 64Q shows growth of T47D-MUC1* tumors in Mouse #2 of the group treated with MNC2-deruxtecan. FIG. 64R shows growth of T47D-MUC1* tumors in Mouse #3 of the group treated with MNC2-deruxtecan. FIG. 64S shows growth of T47D-MUC1* tumors in Mouse #4 of the group treated with MNC2-deruxtecan. FIG. 64T shows growth of T47D-MUC1* tumors in Mouse #5 of the group treated with MNC2-deruxtecan.

FIGS. 65A-65D show images of tumor cells. Staining of the Day 0 cells shows the cells express more full-length MUC1 than MUC1* and the staining intensity is light, indicating low numbers of MUC1* receptors, which is indicative of early cancers. Sixty-two (62) days post tumor implantation, which equates to approximately 7 years in human time, one can readily see that MUC1* expression, in terms of extent of expression as well as intensity of expression, has dramatically shifted from low expression to high expression in the late stage tumor. In contrast, the staining of a serial section of the tumor shows full-length MUC1 is expressed, as expected because it is cleaved to MUC1* after surface expression. However, the intensity of the staining has not increased, indicating that the vast majority of the expressed MUC1 has been cleaved to the growth factor receptor form, MUC1*, in the late-stage tumor.

DETAILED DESCRIPTION OF THE INVENTION

The present application relates to anti-MUC1* multispecific antibodies and anti-MUC1* antibody conjugates and methods of making and using them. A cleaved form of the MUC1 transmembrane protein is a growth factor receptor that drives the growth of over 75% of all human cancers. The cleaved form of MUC1, MUC1* (pronounced muk 1 star), is a growth factor receptor. Cleavage and release of the bulk of the extracellular domain of MUC1 unmasks a binding site for activating ligands dimeric NME1, NME6, NME7, NME7AB, NME7-X1 or NME8. It is an ideal target for cancer drugs as it is aberrantly expressed on over 75% of all cancers and is likely overexpressed on an even higher percentage of metastatic cancers (Mahanta et al. (2008) A Minimal Fragment of MUC1 Mediates Growth of Cancer Cells. PLOS ONE 3 (4): e2054. doi: 10.1371/journal.pone.0002054; Fessler et al. (2009), "MUC1* is a determinant of trastuzumab (Herceptin) resistance in breast cancer cells," Breast Cancer Res Treat. 118 (1): 113-124). After MUC1 cleavage most of its extracellular domain is shed from the cell surface. The remaining portion, MUC1*, has a truncated extracellular domain that comprises most or all of the primary growth factor receptor sequence, PSMGFR (SEQ ID NO: 133).

Many agents currently administered to a patient parenterally are not targeted, resulting in systemic delivery of the agent to cells and tissues of the body where it is unnecessary, and often undesirable. This may result in adverse drug side effects, and often limits the dose of a drug (e.g., chemotherapeutic (anti-cancer), cytotoxic, enzyme inhibitor agents and antiviral or antimicrobial drugs) that can be administered.

A major goal has been to develop methods for specifically targeting therapeutic agents to cells and tissues. The benefits of such treatment include avoiding the general physiological effects of inappropriate delivery of such agents to other cells and tissues. These and other limitations and problems of the past are addressed by the disclosure herein.

Certain Terminology

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention.

As used herein, ranges and amounts can be expressed as "about" a particular value or range. About also includes the exact amount. For example "about 1 mg" means "about 1 mg" and also "1 mg." The terms "about" and "approximately" generally include an amount that would be expected to be within experimental error.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds.

Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) Chem. Biochem. Amino Acids and Proteins 7:267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acids are grouped as hydrophobic amino acids, polar amino acids, non-polar amino acids, and charged amino acids. Hydrophobic amino acids include small hydrophobic amino acids and large hydrophobic amino acids. Small hydrophobic amino acid can be glycine, alanine, proline, and analogs thereof. Large hydrophobic amino acids can be valine, leucine, isoleucine, phenylalanine, methionine, tryptophan, and analogs thereof. Polar amino acids can be serine, threonine, asparagine, glutamine, cysteine, tyrosine, and analogs thereof. Non-polar amino acids can be glycine, alanine, valine, leucine, isoleucine, methionine, phenylalanine, tryptophan, proline, and analogs thereof. Charged amino acids can be lysine, arginine, histidine, aspartate, glutamate, and analogs thereof. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are either D amino acids or L amino acids.

As used in the specification and appended claims, unless specified to the contrary, the following terms have the meaning indicated below.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Thus, the compounds provided herein may be enantiomerically pure, or be stereoisomeric or diastereomeric mixtures. The compounds provided herein may contain chiral centers. Such chiral centers may be of either the (R) or(S) configurations, or may be a mixture thereof. The chiral centers of the compounds provided herein may undergo epimerization in vivo. As such, one of skill in the art will recognize that administration of a compound in its (R) form is equivalent, for compounds that undergo epimerization in vivo, to administration of the compound in its(S) form. Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

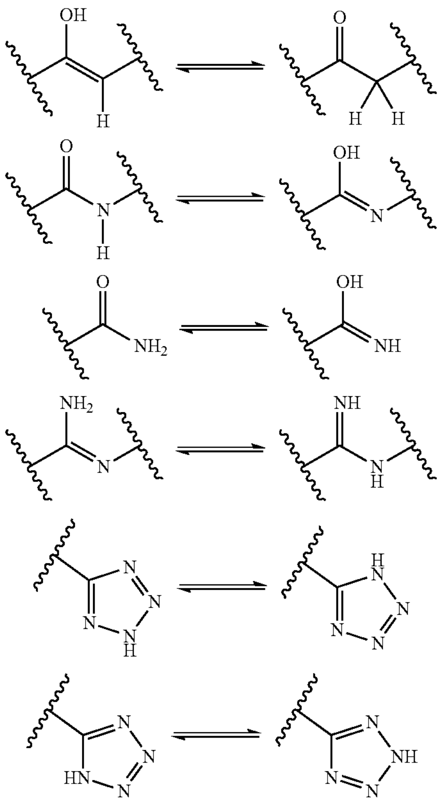

-continued

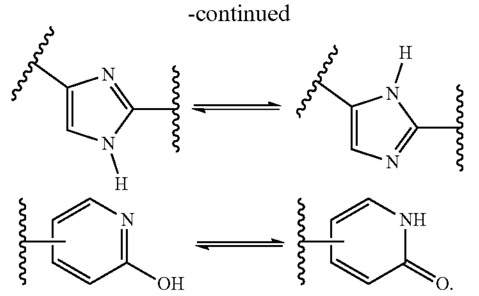

"Pharmaceutically acceptable salt" includes both acid and base addition salts. A pharmaceutically acceptable salt of any one of the compounds or conjugates described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

As used herein, the terms "antibody" and "immunoglobulin" are terms of art and can be used interchangeably herein, and refer to a molecule with an antigen binding site that specifically binds an antigen. In certain embodiments, an isolated antibody (e.g., monoclonal antibody) described herein, or an antigen-binding fragment thereof, which specifically binds to a protein of interest.

Antibodies can include, for example, monoclonal antibodies, recombinantly produced antibodies, monospecific antibodies, multispecific antibodies (including bispecific antibodies), human antibodies, humanized antibodies, chimeric antibodies, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain/antibody heavy chain pair, an antibody with two light chain/heavy chain pairs (e.g., identical pairs), intrabodies, heteroconjugate antibodies, single domain antibodies, monovalent antibodies, bivalent antibodies (including monospecific or bispecific bivalent antibodies), single chain antibodies, or single-chain variable fragments (scFv), camelized antibodies, affybodies, Fab fragments, F(ab') fragments, $F(ab')_2$ fragments, disulfide-linked Fvs (sdFv), anti-idiotypic (anti-Id) antibodies (including, e.g., anti-anti-Id antibodies), and epitope-binding fragments of any of the above.

Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies (e.g., human IgG), or a class (e.g., human IgG1, IgG2, IgG3 or IgG4) or subclass thereof.

The CDR sequence(s) for the antibodies disclosed herein, or the anti-MUC1* or anti-CD3 binding domain sequences disclosed herein, may be defined or determined according to (i) the Kabat numbering system (Kabat et al. (197) Ann. NY Acad. Sci. 190:382-391 and, Kabat et al. (1991) Sequences of Proteins of Immunological Interest Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215 (1): 175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al, 1999, Nucleic Acids Res., 27:209-212 ("IMGT CDRs"); or (iv) MacCallum et al, 1996, J. Mol. Biol., 262:732-745. See also, e.g., Martin, A., "Protein Sequence and Structure Analysis of Antibody Variable Domains," in Antibody Engineering, Kontermann and Diibel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35 A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The term "chimeric" antibody refers to an antibody in which a portion of the heavy and/or light chain is derived from a particular source or species, while the remainder of the heavy and/or light chain is derived from a different source or species.

The term "multispecific" means that the antibody is able to specifically bind to two or more distinct antigenic determinants for example two binding sites each formed by a pair of an antibody heavy chain variable domain (VH) and an antibody light chain variable domain (VL) binding to different antigens.

The term "human antibody" or "humanized antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). In some instances, human antibodies are also produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al, Proc. Natl. Acad. Sci. USA 90 (1993) 2551-2555; Jakobovits, A., et al, Nature 362 (1993) 255-258; Bruggemann, M., et al, Year Immunol. 7 (1993) 33-40). In additional instances, human antibodies are also produced in phage display libraries (Hoogenboom, H. R., and Winter, G., J. Mol. Biol. 227 (1992) 381-388; Marks, J. D., et al, J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al, J. Immunol. 147 (1991) 86-95).

As used herein, an "antigen" is a moiety or molecule that contains an epitope to which an antibody can specifically bind. As such, an antigen is specifically bound by an antibody. In a specific embodiment, the antigen, to which an antibody described herein binds, is a protein of interest, for example, MUC1*, CD3, or a fragment thereof.

As used herein, the term "heavy chain" when used in reference to an antibody can refer to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct types, e.g., kappa (κ) of lambda (λ) based on the amino acid sequence of the constant domains. Light chain amino acid sequences are well known in the art. In specific embodiments, the light chain is a human light chain.

As used herein, the term "percent (%) amino acid sequence identity" or "sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS ALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "full length antibody," "intact antibody" and "whole antibody" are used herein interchangeably to refer to an antibody in its substantially intact form, and are not antibody fragments as defined below. The terms particularly refer to an antibody with heavy chains that contain the Fc region.

"Antibody fragments" comprise only a portion of an intact antibody, wherein the portion retains at least one, two, three and as many as most or all of the functions normally associated with that portion when present in an intact antibody. In one aspect, an antibody fragment comprises an antigen binding site of the intact antibody and thus retains the ability to bind antigen.

As used herein, an "epitope" is a term known in the art and refers to a localized region of an antigen to which an antibody can specifically bind. An epitope can be a linear epitope of contiguous amino acids or can comprise amino acids from two or more non-contiguous regions of the antigen.

As used herein, the terms "binds," "binds to," "specifically binds" or "specifically binds to" in the context of antibody binding refer to antibody binding to an antigen (e.g., epitope) as such binding is understood by one skilled in the art. In a specific embodiment, molecules that specifically bind to an antigen bind to the antigen with an affinity ($K_d$) that is at least 2 logs, 2.5 logs, 3 logs, 4 logs lower (higher affinity) than the $K_d$ when the molecules bind to another antigen. In another specific embodiment, molecules that specifically bind to an antigen do not cross react with other proteins.

A "linking moiety" or "linker" (e.g., noted as L) is a molecule with two reactive termini, one for conjugation to a polypeptide (e.g., an antibody) through conjugation moiety Y and the other for conjugation to a linking moiety (noted as SP) or a moiety of T when SP is absent. The polypeptide conjugation reactive terminus of the linker is typically a site that is capable of conjugation to the polypeptide (e.g., an antibody) through a cysteine thiol group on the polypeptide (e.g., an antibody), and so is typically a thiol-reactive group such as a maleimide or a dibromomaleimide, or as defined herein.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

MUC1* Binding Domains

In some embodiments, disclosed herein is an antibody that comprises an anti-MUC1* binding domain. In some embodiments, the MUC1* binding domain comprises an antibody or antigen binding fragment or variant thereof. In some embodiments, the antibody or antigen binding fragment or variant thereof is a monoclonal antibody. In some embodiments, the antibody or antigen binding fragment or variant thereof is a human antibody, a murine antibody, a humanized antibody, or a chimeric antibody. In some embodiments, the MUC1* binding domain comprises a monovalent Fab, a bivalent Fab'2, a single-chain variable fragment (scFv), or functional fragment or variant thereof. In some embodiments, the MUC1* binding domain comprises an IgG1, IgG2, IgG3, or IgG4 domain. In some embodiments, the MUC1* binding domain comprises an IgG1 domain. In some embodiments, the MUC1* binding domain comprises an IgG2 domain. In some embodiments, the MUC1* binding domain comprises an IgG3 domain. In some embodiments, the MUC1* binding domain comprises an IgG4 domain.

In some embodiments, the antibody, or functional fragment or functional variant thereof that binds specifically to MUC1* comprises an anti-MUC1* heavy chain and an anti-MUC1* light chain.

In some embodiments, the anti-MUC1* heavy chain comprises an anti-MUC1* heavy chain variable domain. In some embodiments, the anti-MUC1* heavy chain variable domain comprises a variable domain of an IgG1, IgG2, IgG3, or IgG4 heavy chain. In some embodiments, the anti-MUC1* light chain comprises an anti-MUC1* light chain variable domain. In some embodiments, the anti-MUC1* light chain variable domain comprises a variable domain of a Kappa or Lambda light chain.

In some embodiments, the anti-MUC1* heavy chain variable domain comprises the variable domain of an IgG1 heavy chain and the anti-MUC1* light chain variable domain comprises the variable domain of a Kappa or Lambda light chain. In some embodiments, the anti-MUC1* heavy chain variable domain comprises the variable domain of an IgG2 heavy chain and the anti-MUC1* light chain variable domain comprises the variable domain of a Kappa or Lambda light chain. In some embodiments, the anti-MUC1* heavy chain variable domain comprises the variable domain of an IgG3 heavy chain and the anti-MUC1* light chain variable domain comprises the variable domain of a Kappa or Lambda light chain. In some embodiments, the anti-MUC1* heavy chain variable domain comprises the variable domain of an IgG4 heavy chain and the anti-MUC1* light chain variable domain comprises the variable domain of a Kappa or Lambda light chain.

In some embodiments, the anti-MUC1* heavy chain variable domain comprises the variable domain of an IgG1 heavy chain and the anti-MUC1* light chain variable domain comprises the variable domain of a Kappa light chain. In some embodiments, the anti-MUC1* heavy chain variable domain comprises the variable domain of an IgG2 heavy chain and the anti-MUC1* light chain variable domain comprises the variable domain of a Kappa light chain. In some embodiments, the anti-MUC1* heavy chain variable domain comprises the variable domain of an IgG3 heavy chain and the anti-MUC1* light chain variable domain comprises the variable domain of a Kappa light chain. In some embodiments, the anti-MUC1* heavy chain variable domain comprises the variable domain of an IgG4 heavy chain and the anti-MUC1* light chain variable domain comprises the variable domain of a Kappa light chain.

In some embodiments, the anti-MUC1* heavy chain variable domain comprises the variable domain of an IgG1 heavy chain and the anti-MUC1* light chain variable domain comprises the variable domain of a Lambda light chain. In some embodiments, the anti-MUC1* heavy chain variable domain comprises the variable domain of an IgG2 heavy chain and the anti-MUC1* light chain variable domain comprises the variable domain of a Lambda light chain. In some embodiments, the anti-MUC1* heavy chain variable domain comprises the variable domain of an IgG3 heavy chain and the anti-MUC1* light chain variable domain comprises the variable domain of a Lambda light chain. In some embodiments, the anti-MUC1* heavy chain variable domain comprises the variable domain of an IgG4 heavy chain and the anti-MUC1* light chain variable domain comprises the variable domain of a Lambda light chain.

In some embodiments, the antibody, or functional fragment or functional variant thereof, that binds specifically to MUC1* comprises a single-chain variable fragment (scFv) or an antigen-binding fragment (Fab). In some embodiments, the antibody, or functional fragment or functional variant thereof, that binds specifically to MUC1* comprises a single-chain variable fragment. In some embodiments, the antibody, or functional fragment or functional variant thereof, that binds specifically to MUC1* comprises an antigen-binding fragment (Fab).

In some embodiments, the anti-MUC1* heavy chain variable domain comprises complementarity determining regions (CDRs): HC-CDR1, HC-CDR2, and HC-CDR3, and wherein the HC-CDR1, the HC-CDR2, and the HC-CDR3 of the anti-MUC1* heavy chain variable domain comprise amino acid sequences according to HC-CDR1: SEQ ID NO:1 or 4; HC-CDR2: SEQ ID NO: 2 or 5; HC-CDR3: SEQ ID NO: 3 or 6; and wherein the CDRs comprise from 0-2 amino acid modification(s) (e.g., 0 or 1 amino acid modification(s)) in at least one of the HC-CDR1, HC-CDR2, or HC-CDR3.

In some embodiments, the anti-MUC1* light chain variable domain comprises complementarity determining regions (CDRs): LC-CDR1, LC-CDR2, and LC-CDR3, and wherein the LC-CDR1, the LC-CDR2, and the LC-CDR3 of the anti-MUC1* light chain variable domain comprises amino acid sequences according to LC-CDR1: SEQ ID NO: 13 or 16; LC-CDR2: SEQ ID NO: 14 or 17; LC-CDR3: SEQ ID NO: 15 or 18; and wherein the CDRs comprise from 0-2 amino acid modification(s) (e.g., 0 or 1 amino acid modification(s)) in at least one of the LC-CDR1, LC-CDR2, or LC-CDR3.

In some embodiments, the anti-MUC1* heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOS: 38 or 44. In some embodiments, the anti-MUC1* light chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 41 or 47.

TABLE 1

MUC1* Binding Domain CDR sequences

| Construct | SEQ ID NO | MUC1* HC-CDR1 | SEQ ID NO | MUC1* HC-CDR2 | SEQ ID NO | MUC1* HC-CDR3 |
|---|---|---|---|---|---|---|
| Anti-MUC1* 20A10 | 1 | TYAMS | 2 | SIGRAGSTYYSDSVKG | 3 | GPIYNDYDEFAY |
| Anti-MUC1* MNC2 | 4 | GYAMS | 5 | TISSGGTYIYYPDSVKG | 6 | LGGDNYYEYFDV |

TABLE 1-continued

| MUC1* Binding Domain CDR sequences | | | | | | |
|---|---|---|---|---|---|---|
| Construct | SEQ ID NO | MUC1* LC-CDR1 | SEQ ID NO | MUC1* LC-CDR2 | SEQ ID NO | MUC1* LC-CDR3 |
| Anti-MUC1* 20A10 | 13 | KSSQSVLYSSNQKNYLA | 14 | WASTRES | 15 | HQYLSSLT |
| Anti-MUC1* MNC2 | 16 | RASKSVSTSGYSYMH | 17 | LASNLES | 18 | QHSRELPFT |

TABLE 2

Example heavy chain sequences, heavy chain variable domain sequences, light chain sequences, and light chain variable domain sequences of the anti-MUC1* binding domains

| Construct | SEQ ID NO | Sequence |
|---|---|---|
| Anti-MUC1* MNC2 HC DNA | 37 | gaggtgcagctggtggagtctgggggaggcctggtcaagcctgggggtccctgagac<br>tc<br>tcctgtgcagcctctggattcaccttcagtggctatgccatgagctgggtccgccaggct<br>ccagggaaggggctggagtgggtctcaaccattagtagtggcggaacctacatatactac<br>cccgactcagtgaagggccgattcaccatctccagagacaacgccaagaactcactgtat<br>ctgcaaatgaacagcctgagagccgaggacacggccgtgtattactgtgcgagacttgg<br>g<br>ggggataattactacgaatacttcgatgtctggggcaaagggaccacggtcaccgtctcc<br>tccgcctccaccaagggcccatcggtcttccccctggcgccctgctccaggagcacctcc<br>gagagcacagccgccctgggctgcctggtcaaggactacttccccgaaccggtgacggt<br>g<br>tcgtggaactcaggcgctctgaccagcggcgtgcacaccttcccagctgtcctacagtcc<br>tcaggactctactccctcagcagcgtggtgaccgtgccctccagcaacttcggcacccag<br>acctacacctgcaacgtagatcacaagcccagcaacaccaaggtggacaagacagttga<br>g<br>cgcaaatgttgtgtcgagtgcccaccgtgcccagcaccacctgtggcaggaccgtcagtc<br>ttcctcttccccccaaaacccaaggacaccctcatgatctcccggacccctgaggtcacg<br>tgcgtggtggtggacgtgagccacgaagaccccgaggtccagttcaactggtacgtgga<br>c<br>ggcgtggaggtgcataatgccaagacaaagccacgggaggagcagttcaacagcacgt<br>tc<br>cgtgtggtcagcgtcctcaccgttgtgcaccaggactggctgaacggcaaggagtacaa<br>g<br>tgcaaggtctccaacaaaggcctcccagcccccatcgagaaaaccatctccaaaaccaa<br>a<br>gggcagccccgagaaccacaggtgtacaccctgcccccatcccgggaggagatgacca<br>ag<br>aaccaggtcagcctgacctgcctggtcaaaggcttctaccccagcgacatcgccgtggag<br>tgggagagcaatgggcagccggagaacaactacaagaccacacctcccatgctggact<br>cc<br>gacggctccttcttcctctacagcaagctcaccgtggacaagagcaggtggcagcaggg<br>aacgtcttctcatgctccgtgatgcatgaggctctgcacaaccactacacgcagaagagc<br>ctctccctgtctccgggtaaatagtaa |
| Anti-MUC1* MNC2 HC amino acid | 38 | EVQLVESGGGLVKPGGSLRLSCAASGFTFSGYAMSWVR<br>QAPGKGLEWVSTISSGGTYIYYPDSVKGRFTISRDNAKNS<br>LYLQMNSLRAEDTAVYYCARLGGDNYYEYFDVWGKGT<br>TVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRVVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| Anti-MUC1* MNC2 HC Variable domain | 39 | EVQLVESGGGLVKPGGSLRLSCAASGFTFSGYAMSWVR<br>QAPGKGLEWVSTISSGGTYIYYPDSVKGRFTISRDNAKNS<br>LYLQMNSLRAEDTAVYYCARLGGDNYYEYFDVWGKGT<br>TVTVSS |
| Anti-MUC1* MNC2 LC DNA | 40 | gacattgtgctgacccagtctccagcctccttggccgtgtctccaggacagagggccacc<br>atcacctgcagagccagtaagagtgtcagtaccagcggatactcctacatgcactggtatc<br>agcagaaaccaggacaacctcctaaactcctgatttacctggcatccaatctggagagcg<br>ggtcccagccaggttcagcggcagtgggtctgggaccgatttcaccctcacaattaatcc<br>tgtggaagctaatgatactgcaaattattactgtcagcacagtagggagctgcctttcacatt |

TABLE 2-continued

Example heavy chain sequences, heavy chain variable domain sequences, light chain sequences, and light chain variable domain sequences of the anti-MUC1* binding domains

| Construct | SEQ ID NO | Sequence |
|---|---|---|
| | | cggcggagggaccaaggtggagatcaaacgaactcgtacggtggctgcaccatctgtct<br>tcatcttcccgccatctgatgagcagttgaaatctggaactgcctctgttgtgtgcctgctga<br>ataacttctatcccagagaggccaaagtacagtggtgcgtggataacgccctccaatcgg<br>gtaactcccaggagagtgtcacagagcaggacagcaaggacagcacctacagcctcag<br>cagcaccctgacgctgagcaaagcagactacgagaaacacaaagtctacgcctgcgaa<br>gtcacccatcagggcctgagctcgcccgtcacaaagagcttcaacaggggagagtgtta<br>g |
| Anti-MUC1* MNC2 LC amino acid | 41 | DIVLTQSPASLAVSPGQRATITCRASKSVSTSGYSYMHW<br>YQQKPGQPPKLLIYLASNLESGVPARFSGSGSGTDFTLTI<br>NPVEANDTANYYCQHSRELPFTFGGGTKVEIKRTRTVAA<br>PSVFIFPPSDEQLKSGTASVVCLLNNFYPREAKVQWKVD<br>NALQSGNSQESVTEQDSKDSTYSLSSTLTLSKADYEKHK<br>VYACEVTHQGLSSPVTKSFNRGEC |
| Anti-MUC1* MNC2 LC Variable domain | 42 | DIVLTQSPASLAVSPGQRATITCRASKSVSTSGYSYMHW<br>YQQKPGQPPKLLIYLASNLESGVPARFSGSGSGTDFTLTI<br>NPVEANDTANYYCQHSRELPFTFGGGTKVEIKRT |
| Anti-MUC1* 20A10 HC DNA | 43 | CAGGTGCAGCTGGTTGAATCTGGCGGCGGACTTGTGA<br>AGCCTGGCGGATCTCTGAGACTGAGCTGTGCCGCCAG<br>CGGCTTCACCTTTAGCACATACGCCATGAGCTGGATCA<br>GACAGGCCCCTGGCAAAGGCCTGGAATGGGTGgcgTCT<br>ATTGGCAGAGCCGGCAGCACCTACTACAGCGACTCTG<br>TGAAGGGCAGATTCACCATCAGCCGGGACAACGCCAA<br>GAACAGCCTGTACCTGCAGATGAACTCCCTGAGAGCC<br>GAGGACACCGCCGTGTACTATTGTGCCAGAGGACCCA<br>TCTACAACGACTACGACGAGTTCGCCTATTGGGGCCA<br>GGGCACACTGGTCACAGTTTCTAGCGCTAGCACCAAG<br>GGCCCATCGGTCTTCCCCCTGGCACCCTCCTCCAAGAG<br>CACCTCTGGGGGCACAGCGGCCCTGGGCTGCCTGGTC<br>AAGGACTACTTCCCCGAGCCGGTGACGGTGTCGTGGA<br>ACTCAGGCGCCCTGACCAGCGGCGTGCACACCTTCCC<br>GGCTGTCCTACAGTCCTCAGGACTCTACTCCCTCAGCA<br>GCGTGGTGACCGTGCCCTCCAGCAGCTTGGGCACCCA<br>GACCTACATCTGCAACGTGAATCACAAGCCCAGCAAC<br>ACCAAGGTGGACAAGAAAGTTGAGCCCAAATCTTGTG<br>ACAAAACTCACACATGCCCACCGTGCCCAGCACCTGA<br>ACTCCTGGGGGGACCGTCAGTCTTCCTCTTCCCCCCAA<br>AACCCAAGGACACCCTCATGATCTCCCGGACCCCTGA<br>GGTCACATGCGTGGTGGTGGACGTGAGCCACGAAGAC<br>CCTGAGGTCAAGTTCAACTGGTACGTGGACGGCGTGG<br>AGGTGCATAATGCCAAGACAAAGCCGCGGGAGGAGC<br>AGTACAACAGCACGTACCGTGTGGTCAGCGTCCTCAC<br>CGTCCTGCACCAGGACTGGCTGAATGGCAAGGAGTAC<br>AAGTGCAAGGTCTCCAACAAAGCCCTCCCAGCCCCCA<br>TCGAGAAAACCATCTCCAAAGCCAAAGGGCAGCCCCG<br>AGAACCACAGGTGTACACCCTGCCCCCATCCCGGGAG<br>GAGATGACCAAGAACCAGGTCAGCCTGACCTGCCTGG<br>TCAAAGGCTTCTATCCCAGCGACATCGCCGTGGAGTG<br>GGAGAGCAATGGGCAGCCGGAGAACAACTACAAGAC<br>CACGCCTCCCGTGCTGGACTCCGACGGCTCCTTCTTCC<br>TCTACAGCAAGCTCACCGTGGACAAGAGCAGGTGGCA<br>GCAGGGGAACGTCTTCTCATGCTCCGTGATGCATGAG<br>GCTCTGCACAACCACTACACGCAGAAGAGCCTCTCCC<br>TGTCTCCGGGTAAA |
| Anti-MUC1* 20A10 HC amino acid | 44 | QVQLVESGGGLVKPGGSLRLSCAASGFTFSTYAMSWIRQ<br>APGKGLEWVASIGRAGSTYYSDSVKGRFTISRDNAKNSL<br>YLQMNSLRAEDTAVYYCARGPIYNDYDEFAYWGQGTL<br>VTVSSASTKGPSVFPLAPSSKSTSGGTAALGCLVKDYFPE<br>PVTVSWNSGALTSGVHTFPAVLQSSGLYSLSSVVTVPSSS<br>LGTQTYICNVNHKPSNTKVDKKVEPKSCDKTHTCPPCPA<br>PELLGGPSVFLFPPKPKDTLMISRTPEVTCVVVDVSHEDP<br>EVKFNWYVDGVEVHNAKTKPREEQYNSTYRVVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| Anti-MUC1* 20A10 HC Variable domain | 45 | QVQLVESGGGLVKPGGSLRLSCAASGFTESTYAMSWIRQ<br>APGKGLEWVASIGRAGSTYYSDSVKGRFTISRDNAKNSL |

TABLE 2-continued

Example heavy chain sequences, heavy chain variable domain sequences, light chain sequences, and light chain variable domain sequences of the anti-MUC1* binding domains

| Construct | SEQ ID NO | Sequence |
|---|---|---|
| | | YLQMNSLRAEDTAVYYCARGPIYNDYDEFAYWGQGTL VTVSS |
| Anti-MUC1* 20A10 LC DNA | 46 | Gaaattgtgctgacacagagccccgccacactgtcactttctccaggcgaaagagccac actgagctgcaagagcagccagagcgtgctgtactccagcaaccagaagaactacctgg cctggtatcagcagaagcccggccaagctcctcggctgctgatctattgggccagcacaa gagagagcggcatccctgccagattttctggcagcggctctggcaccgatttcaccctgac cataagcagcctggaacctgaggacttcgccgtgtattactgccaccagtacctgagcag cctgacctttggcggaggcaccaaggtggaaatcaagcggcgtacggtggctgcaccat ctgtcttcatcttcccgccatctgatgagcagttgaaatctggaactgcctctgttgtgtgcc tgctgaataacttctatcccagagaggccaaagtacagtggtgcgtggataacgccctcca atcgggtaactcccaggagagtgtcacagagcaggacagcaaggacagcacctacagc ctcagcagcaccctgacgctgagcaaagcagactacgagaaacacaaagtctacgcctg cgaagtcacccatcagggcctgagctcgcccgtcacaaagagcttcaacaggggagagt gttag |
| Anti-MUC1* 20A10 LC amino acid | 47 | EIVLTQSPATLSLSPGERATLSCKSSQSVLYSSNQKNYLA WYQQKPGQAPRLLIYWASTRESGIPARFSGSGSGTDFTLT ISSLEPEDFAVYYCHQYLSSLTFGGGTKVEIKRRTVAAPS VFIFPPSDEQLKSGTASVVCLLNNFYPREAKVQWKVDNA LQSGNSQESVTEQDSKDSTYSLSSTLTLSKADYEKHKVY ACEVTHQGLSSPVTKSFNRGEC |
| Anti-MUC1* 20A10 LC Variable domain | 48 | EIVLTQSPATLSLSPGERATLSCKSSQSVLYSSNQKNYLA WYQQKPGQAPRLLIYWASTRESGIPARFSGSGSGTDFTLT ISSLEPEDFAVYYCHQYLSSLTFGGGTKVEIKR |

TABLE 3 anti-MUC1* single chain variable fragment (scFv) sequences

| Construct | SEQ ID NO | Sequence |
|---|---|---|
| Anti-MUC1* 20A10 scFv | 129 | QVQLVESGGGLVKPGGSLRLSCAASGFTFSTYAMSWIRQ APGKGLEWVASIGRAGSTYYSDSVKGRFTISRDNAKNSL YLQMNSLRAEDTAVYYCARGPIYNDYDEFAYWGQGTL VTVSSGGGGSGGGGGGGGSEIVLTQSPATLSLSPGERAT LSCKSSQSVLYSSNQKNYLAWYQQKPGQAPRLLIYWAS TRESGIPARFSGSGSGTDFTLTISSLEPEDFAVYYCHQYLS SLTFGGGTKVEIKR |
| Anti-MUC1* MNC2 scFv | 130 | EVQLVESGGGLVKPGGSLRLSCAASGFTFSGYAMSWVR QAPGKGLEWVSTISSGGTYIYYPDSVKGRFTISRDNAKNS LYLQMNSLRAEDTAVYYCARLGGDNYYEYFDVWGKGT TVTVSSGGGGSGGGGSGGGGSDIVLTQSPASLAVSPGQR ATITCRASKSVSTSGYSYMHWYQQKPGQPPKLLIYLASN LESGVPARFSGSGSGTDFTLTINPVEANDTANYYCQHSRE LPFTFGGGTKVEIKRT |

CD3 Binding Domains

In some embodiments, disclosed herein is an antibody that comprises an anti-CD3 binding domain. In some embodiments, the CD3 binding domain comprises an antibody or antigen binding fragment or variant thereof. In some embodiments, the antibody or antigen binding fragment or variant thereof is a monoclonal antibody. In some embodiments, the antibody or antigen binding fragment or variant thereof is a human antibody, a murine antibody, a humanized antibody, or a chimeric antibody. In some embodiments, the CD3 binding domain comprises a monovalent Fab, a bivalent Fab'2, a single-chain variable fragment (scFv), or functional fragment or variant thereof.

In some embodiments, the CD3 binding domain comprises an IgG1, IgG2, IgG3, or IgG4 domain. In some embodiments, the CD3 binding domain comprises an IgG1 domain. In some embodiments, the CD3 binding domain comprises an IgG2 domain. In some embodiments, the CD3 binding domain comprises an IgG3 domain. In some embodiments, the CD3 binding domain comprises an IgG4 domain.

In some embodiments, the antibody, or functional fragment or functional variant thereof that binds specifically to CD3 comprises an anti-CD3 heavy chain and an anti-CD3 light chain.

In some embodiments, the anti-CD3 heavy chain comprises an anti-CD3 heavy chain variable domain. In some embodiments, the anti-CD3 heavy chain variable domain comprises a variable domain of an IgG1, IgG2, IgG3, or IgG4 heavy chain. In some embodiments, the anti-CD3 light chain comprises an anti-CD3 light chain variable domain. In some embodiments, the anti-CD3 light chain variable domain comprises a variable domain of a Kappa or Lambda light chain. In some embodiments, the anti-CD3 heavy chain variable domain comprises the variable domain of an IgG1 heavy chain and the anti-CD3 light chain variable domain comprises the variable domain of a Kappa or Lambda light chain. In some embodiments, the anti-CD3 heavy chain variable domain comprises the variable domain of an IgG2 heavy chain and the anti-CD3 light chain variable domain comprises the variable domain of a Kappa or Lambda light chain. In some embodiments, the anti-CD3 heavy chain variable domain comprises the variable domain of an IgG3 heavy chain and the anti-CD3 light chain variable domain comprises the variable domain of a Kappa or Lambda light chain. In some embodiments, the anti-CD3 heavy chain variable domain comprises the variable domain of an IgG4 heavy chain and the anti-CD3 light chain variable domain comprises the variable domain of a Kappa or Lambda light chain.

In some embodiments, the antibody, or functional fragment or functional variant thereof, that binds specifically to CD3 comprises a single-chain variable fragment (scFv) or an antigen-binding fragment (Fab). In some embodiments, the antibody, or functional fragment or functional variant thereof, that binds specifically to CD3 comprises a single-chain variable fragment (scFv). In some embodiments, the antibody, or functional fragment or functional variant thereof, that binds specifically to CD3 comprises an antigen-binding fragment (Fab).

In some embodiments, the anti-CD3 heavy chain variable domain comprises complementarity determining regions (CDRs): HC-CDR1, HC-CDR2, and HC-CDR3, and wherein the HC-CDR1, the HC-CDR2, and the HC-CDR3 of the anti-CD3 heavy chain variable domain comprise amino acid sequences according to HC-CDR1: SEQ ID NOs: 7 or 10; HC-CDR2: SEQ ID NOs: 8 or 11; HC-CDR3: SEQ ID NOs: 9 or 12; and wherein the CDRs comprise from 0-2 amino acid modification(s) (e.g., 0 or 1 amino acid modification(s)) in at least one of the HC-CDR1, HC-CDR2, or HC-CDR3.

In some embodiments, the anti-CD3 light chain variable domain comprises complementarity determining regions (CDRs): LC-CDR1, LC-CDR2, and LC-CDR3, and wherein the LC-CDR1, the LC-CDR2, and the LC-CDR3 of the anti-CD3 light chain variable domain comprises amino acid sequences according to LC-CDR1: SEQ ID NOs: 19 or 22; LC-CDR2: SEQ ID NOs: 20 or 23; LC-CDR3: SEQ ID NOs: 21 or 24; and wherein the CDRs comprise from 0-2 amino acid modification(s) (e.g., 0 or 1 amino acid modification(s)) in at least one of the LC-CDR1, LC-CDR2, or LC-CDR3.

In some embodiments, the anti-CD3 heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 26 or 32.

In some embodiments, the anti-CD3 heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to of SEQ ID NOs: 30 or 33.

In some embodiments, the anti-CD3 heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any amino acid sequence of Table 5.

In some embodiments, the anti-CD3 light chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any amino acid sequence of Table 5.

TABLE 4 anti-CD3 CDRs

| Construct | SEQ ID NO | CD3 HC-CDR1 | SEQ ID NO | CD3 HC-CDR2 | SEQ ID NO | CD3 HC-CDR3 |
|---|---|---|---|---|---|---|
| Anti-CD3 OKT3 | 7 | RYTMH | 8 | YINPSRGYTNYNQKVKD | 9 | YYDDHY |
| Anti-CD3 12F6 | 10 | SYTMH | 11 | YINPSSGYTKYNQKFKD | 12 | WQDYDVYFDY |
| **Construct** | **SEQ ID NO** | **CD3 LC-CDR1** | **SEQ ID NO** | **CD3 LC-CDR2** | **SEQ ID NO** | **CD3 LC-CDR3** |
| Anti-CD3 OKT3 | 19 | SASSSVSYMN | 20 | DTSKLAS | 21 | QQWSSNPFT |
| Anti-CD3 12F6 | 22 | RASSSVSYMH | 23 | YATSNLAS | 24 | QQWSSNPPT |

TABLE 5

Example heavy chain sequences, heavy chain variable domain sequences, light chain sequences, and light chain variable domain sequences of the anti-CD3 binding domains

| Construct | SEQ ID NO | Sequence |
|---|---|---|
| Anti-CD3 OKT3 HC DNA | 25 | caggttcaactggttcagagcggtggaggtgtggttcagcctggtcgtagcctgagact gagctgcaaggcctccggctacacctttacaagatacactatgcactgggtcagacagg cccctggcaagggcctggaatggattggctacatcaaccctagccggggatataccaa ctacaaccagaaagtgaaggacagattcaccatcagcacagataagtccaagtccacc |

TABLE 5-continued

Example heavy chain sequences, heavy chain variable domain sequences, light chain sequences, and light chain variable domain sequences of the anti-CD3 binding domains

| Construct | SEQ ID NO | Sequence |
|---|---|---|
| | | gctttcctgcagatggactccctgcgtccagaggacacagctgtgtactactgcgcccg<br>gtactacgacgaccattactgtctggattactggggtcagggaaccaccctgaccgttag<br>cagtgctagcaccaagggcccatcggtcttccccctggcaccctcctccaagagcacct<br>ctgggggcacagcggccctgggctgcctggtcaaggactacttccccgagccggtga<br>cggtgtcgtggaactcaggcgccctgaccagcggcgtgcacaccttcccggctgtccta<br>cagtcctcaggactctactccctcagcagcgtggtgaccgtgccctccagcagcttggg<br>cacccagacctacatctgcaacgtgaatcacaagcccagcaacaccaaggtggacaag<br>aaagttgagcccaaatcttgtgacaaaactcacacatgcccaccgtgcccagcacctga<br>actcctggggggaccgtcagtcttcctcttccccccaaaacccaaggacaccctcatgat<br>ctcccggacccctgaggtcacatgcgtggtggtggacgtgagccacgaagaccctgag<br>gtcaagttcaactggtacgtggacggcgtggaggtgcataatgccaagacaaagccgc<br>gggaggagcagtacaacagcacgtaccgtgtggtcagcgtcctcaccgtcctgcacca<br>ggactggctgaatggcaaggagtacaagtgcaaggtctccaacaaagccctcccagcc<br>cccatcgagaaaaccatctccaaagccaaagggcagccccgagaaccacaggtgtac<br>accctgcccccatcccgggacgagctgaccaagaaccaggtcagcctgacctgcctg<br>gtcaaaggcttctatcccagcgacatcgccgtggagtgggagagcaatgggcagccg<br>gagaacaactacaagaccacgcctcccgtgctggactccgacggctccttcttcctctac<br>agcaagctcaccgtggacaagagcaggtggcagcaggggaacgtcttctcatgctccg<br>tgatgcatgaggctctgcacaaccactacacgcagaagagcctctccctgtctccgggt<br>aaatga |
| Anti-CD3 OKT3 HC Amino Acid | 26 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSRDELTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGK |
| Anti-CD3 OKT3 HC variable domain | 27 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSS |
| Anti-CD3 OKT3 LC DNA | 28 | Cagatgacccagagcccttcttccttatctgccagcgtgggcgatagagtgaccatcac<br>atgcagcgccagctcttctgttagctacatgaactggtaccagcaaacacctggaaagg<br>cccctaaaagatggatctacgacaccagcaagctggcctctggcgtgccctctagattca<br>gcggctctggctccggcaccgactacacctttacaattagctccctgcagcccgaggat<br>atcgccacctactactgccagcagtggagcagcaaccccttcacattcggccagggca<br>caaagctgcaaatcaccagacgtacggtggctgcaccatctgtcttcatcttcccgccatc<br>tgatgagcagttgaaatctggaactgcctctgttgtgtgcctgctgaataacttctatccca<br>gagaggccaaagtacagtggtgcgtggataacgccctccaatcgggtaactcccagga<br>gagtgtcacagagcaggacagcaaggacagcacctacagcctcagcagcaccctgac<br>gctgagcaaagcagactacgagaaacacaaagtctacgcctgcgaagtcacccatcag<br>ggcctgagctcgcccgtcacaaagagcttcaacaggggagagtgttag |
| Anti-CD3 OKT3 LC amino acid | 29 | QMTQSPSSLSASVGDRVTITCSASSSVSYMNWYQQTPG<br>KAPKRWIYDTSKLASGVPSRFSGSGSGTDYTFTISSLQPE<br>DIATYYCQQWSSNPFTFGQGTKLQITRRTVAAPSVFIFPP<br>SDEQLKSGTASVVCLLNNFYPREAKVQWCVDNALQSG<br>NSQESVTEQDSKDSTYSLSSTLTLSKADYEKHKVYACE<br>VTHQGLSSPVTKSFNRGEC- |
| Anti-CD3 OKT3 LC variable domain | 30 | QMTQSPSSLSASVGDRVTITCSASSSVSYMNWYQQTPG<br>KAPKRWIYDTSKLASGVPSRFSGSGSGTDYTFTISSLQPE<br>DIATYYCQQWSSNPFTFGQGTKLQITRR |
| Anti-CD3 12F6 HC DNA | 31 | caagtgcagctggtgcagtccggaggaggcgtcgtgcagcctggaagaagcctccggc<br>tgagctgcaaggccagcggctatacattcaccagctacaccatgcactgggtgcggcag<br>gcccctggcaaaggcctggaatggatcggctacatcaacccttccagcggctacaccaa<br>gtacaaccagaaattcaaggaccggtttaccattagcgccgataagagcaagagcacag<br>cctttctgcagatggacagcctgagaccagaggacaccggcgtgtacttctgcgcccgct<br>ggcaggactacgacgtttatttcgactactggggccagggcaccccctgtgacagtgagca<br>gcgctagcaccaagggcccatcggtcttccccctggcaccctcctccaagagcacctctg<br>gggcacagcggccctgggctgcctggtcaaggactacttccccgagccggtgacggt<br>gtcgtggaactcaggcgccctgaccagcggcgtgcacaccttcccggctgtcctacagtc<br>ctcaggactctactccctcagcagcgtggtgaccgtgccctccagcagcttgggcaccca<br>gacctacatctgcaacgtgaatcacaagcccagcaacaccaaggtggacaagaaagttg |

TABLE 5-continued

Example heavy chain sequences, heavy chain variable domain sequences, light chain sequences, and light chain variable domain sequences of the anti-CD3 binding domains

| Construct | SEQ ID NO | Sequence |
|---|---|---|
| | | agcccaaatcttgtgacaaaactcacacatgcccaccgtgcccagcacctgaactcctgg<br>ggggaccgtcagtcttcctcttccccccaaaacccaaggacaccctcatgatctcccggac<br>ccctgaggtcacatgcgtggtggtggacgtgagccacgaagaccctgaggtcaagttca<br>actggtacgtggacggcgtggaggtgcataatgccaagacaaagccgcgggaggagca<br>gtacaacagcacgtaccgtgtggtcagcgtcctcaccgtcctgcaccaggactggctgaa<br>tggcaaggagtacaagtgcaaggtctccaacaaagccctcccagcccccatcgagaaaa<br>ccatctccaaagccaaagggcagccccgagaaccacaggtgtacaccctgcccccatcc<br>cgggacgagctgaccaagaaccaggtcagcctgacctgcctggtcaaaggcttctatccc<br>agcgacatcgccgtggagtgggagagcaatgggcagccggagaacaactacaagacc<br>acgcctcccgtgctggactccgacggctccttcttcctctacagcaagctcaccgtggaca<br>agagcaggtggcagcaggggaacgtcttctcatgctccgtgatgcatgaggctctgcaca<br>accactacacgcagaagagcctctccctgtctccgggtaaatga |
| Anti-CD3<br>12F6 HC amino acid | 32 | QVQLVQSGGGVVQPGRSLRLSCKASGYTFTSYTMHWVR<br>QAPGKGLEWIGYINPSSGYTKYNQKFKDRFTISADKSKST<br>AFLQMDSLRPEDIGVYFCARWQDYDVYFDYWGQGTPV<br>TVSSASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAP<br>ELLGGPSVFLFPPKPKDTLMISRTPEVTCVVVDVSHEDPE<br>VKFNWYVDGVEVHNAKTKPREEQYNSTYRVVSVLTVL<br>HQDWLNGKEYKCKVSNKALPAPIEKTISKAKGQPREPQV<br>YTLPPSRDELTKNQVSLTCLVKGFYPSDIAVEWESNGQP<br>ENNYKTTPPVLDSDGSFFLYSKLTVDKSRWQQGNVFSCS<br>VMHEALHNHYTQKSLSLSPGK |
| Anti-CD3<br>12F6 HC variable domain | 33 | QVQLVQSGGGVVQPGRSLRLSCKASGYTFTSYTMHWVR<br>QAPGKGLEWIGYINPSSGYTKYNQKFKDRFTISADKSKST<br>AFLQMDSLRPEDTGVYFCARWQDYDVYFDYWGQGTPV<br>TVSS |
| Anti-CD3<br>12F6 LC DNA | 34 | gatatccagatgacacagagccccagctctctgtctgcttctgtgggcgacagagtgacca<br>tgacctgtagagcctcctcaagcgtgtcctacatgcactggtaccagcaaacacctggcaa<br>ggccccaaagccttggatctacgccacctctaatctggccagcggcgtgccttctagattc<br>agcggcagcggatctggcaccgattacaccctgaccatcagcagcctgcagcccgagg<br>atatcgccacatactactgccagcagtggagctccaatcctcctaccttcggccagggcac<br>caagctgcagatcacaagacgtacggtggctgcaccatctgtcttcatcttcccgccatctg<br>atgagcagttgaaatctggaactgcctctgttgtgtgcctgctgaataacttctatcccaga<br>gaggccaaagtacagtggtgcgtggataacgccctccaatcgggtaactcccaggagagt<br>gtcacagagcaggacagcaaggacagcacctacagcctcagcagcaccctgacgctga<br>gcaaagcagactacgagaaacacaaagtctacgcctgcgaagtcacccatcagggcctg<br>agctcgcccgtcacaaagagcttcaacaggggagagtgttag |
| Anti-CD3<br>12F6 LC amino acid | 35 | DIQMTQSPSSLSASVGDRVTMTCRASSSVSYMHWYQQT<br>PGKAPKPWIYATSNLASGVPSRFSGSGSGTDYTLTISSLQ<br>PEDIATYYCQQWSSNPPTFGQGTKLQITRRTVAAPSVFIF<br>PPSDEQLKSGTASVVCLLNNFYPREAKVQWCVDNALQS<br>GNSQESVTEQDSKDSTYSLSSTLTLSKADYEKHKVYACE<br>VTHQGLSSPVTKSFNRGEC- |
| Anti-CD3<br>12F6 LC variable domain | 36 | DIQMTQSPSSLSASVGDRVTMTCRASSSVSYMHWYQQT<br>PGKAPKPWIYATSNLASGVPSRFSGSGSGTDYTLTISSLQ<br>PEDIATYYCQQWSSNPPTFGQGTKLQITRR |

TABLE 6 anti-CD3 single chain variable fragment (scFv) sequences

| Construct | SEQ ID NO | Sequence |
|---|---|---|
| Anti-CD3 12F6 scFv | 131 | QVQLVQSGGGVVQPGRSLRLSCKASGYTFTSYTMH<br>WVRQAPGKGLEWIGYINPSSGYTKYNQKFKDRFTIS<br>ADKSKSTAFLQMDSLRPEDTGVYFCARWQDYDVYF<br>DYWGQGTPVTVSSGGGGSGGGGSGGGGSDIQMTQS<br>PSSLSASVGDRVTMTCRASSSVSYMHWYQQTPGKA<br>PKPWIYATSNLASGVPSRFSGSGSGTDYTLTISSLQPE<br>DIATYYCQQWSSNPPTFGQGTKLQITR |

TABLE 6-continued anti-CD3 single chain variable fragment (scFv) sequences

| Construct | SEQ ID NO | Sequence |
|---|---|---|
| Anti-CD3 OKT3 scFv | 132 | QVQLVQSGGGVVQPGRSLRLSCKASGYTFTRYTMH WVRQAPGKGLEWIGYINPSRGYTNYNQKVKDRFTI STDKSKSTAFLQMDSLRPEDTAVYYCARYYDDHYC LDYWGQGTTLTVSSGGGGSGGGGSGGGGSDIQMTQ SPSSLSASVGDRVTITCSASSSVSYMNWYQQTPGKA PKRWIYDTSKLASGVPSRFSGSGSGTDYTFTISSLQP EDIATYYCQQWSSNPFTFGQGTKLQITR |

Antibodies that Bind to MUC1* and CD3

In some embodiments, the antibody, or functional fragment or functional variant thereof, that binds specifically to MUC1* comprises the Fab, and the antibody, or functional fragment or functional variant thereof, that binds specifically to CD3 comprises the scFv.

In some embodiments, the anti-MUC1* heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 38 or 44 and the anti-MUC1* light chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 41 or 47; and the scFv comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 131 or 132.

In some embodiments, the antibody, or functional fragment or functional variant thereof, that binds specifically to MUC1* comprises the scFv, and the antibody, or functional fragment or functional variant thereof, that binds specifically to CD3 comprises the Fab.

In some embodiments, the anti-CD3 heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 26, 27, 32, or 33 and the anti-CD3 light chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 29, 30, 35, or 36; and the scFv comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 129 or 130.

In some embodiments, the antibody comprises at least 3 CDRs of an anti-MUC1* binding domain selected from any one of SEQ ID NOs: 1, 2, 3, 4, 5, 6, 13, 14, 15, 16, 17, or 18 and from 0-2 amino acid modification(s) (e.g., 0-1 amino acid modification(s)) thereof; and at least 3 CDRs of an anti-CD3 binding domain selected from any one of SEQ ID NO: 7, 8, 9, 10, 11, 12, 19, 20, 21, 22, 23, or 24 and from 0-2 amino acid modification(s) (e.g., 0-1 amino acid modification(s)) thereof.

In some embodiments, the antibody or functional fragment or functional variant thereof, that binds specifically to MUC1* comprises a scFv, and the antibody, or functional fragment or functional variant thereof, that binds to CD3 comprises a scFv.

In some embodiments the anti-MUC1* scFv comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 129 or 130. In some embodiments the anti-CD3 scFv comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 131 or 132.

TABLE 7

Exemplary Sequences of Antibodies that bind to MUC1* and CD3

| Construct | SEQ ID NO | Sequence |
|---|---|---|
| Anti-CD3 12F6 scFV-Fc DNA | 49 | caagtgcagctggtgcagtccggaggaggcgtcgtgcagcctggaagaagcctccgg ctgagctgcaaggccagcggctatacattcaccagctacaccatgcactgggtgcggc aggcccctggcaaaggcctggaatggatcggctacatcaacccttccagcggctacac caagtacaaccagaaattcaaggaccggtttaccattagcgccgataagagcaagagc acagcctttctgcagatggacagcctgagaccagaggacaccggcgtgtacttctgcgc ccgctggcaggactacgacgtttatttcgactactggggccagggcaccccctgtgacag tgagcagcggcggcggaggctccggcggaggtggcagcggcggcggcggctctga tatccagatgacacagagccccagctctctgtctgcttctgtgggcgacagagtgaccat gacctgtagagcctcctcaagcgtgtcctacatgcactggtaccagcaaacacctggca aggccccaaagccttggatctacgccacctctaatctggccagcggcgtgccttctagat tcagcggcagcggatctggcaccgattacaccctgaccatcagcagcctgcagcccga ggatatcgccacatactactgccagcagtggagctccaatcctcctaccttcggccagg gcaccaagctgcagatcacaagagagcccaaatcttgtgacaaaactcacacatgccc accgtgcccagcacctgaactcctggggggaccgtcagtcttcctcttccccccaaaac ccaaggacaccctcatgatctcccggacccctgaggtcacatgcgtggtggtggacgtg agccacgaagaccctgaggtcaagttcaactggtacgtggacggcgtggaggtgcata atgccaagacaaagccgcgggaggagcagtacaacagcacgtaccgtgtggtcagcg tcctcaccgtcctgcaccaggactggctgaatggcaaggagtacaagtgcaaggtctcc aacaaagccctcccagcccccatcgagaaaaccatctccaaagccaaagggcagccc |

TABLE 7-continued

| Exemplary Sequences of Antibodies that bind to MUC1* and CD3 | | |
|---|---|---|
| Construct | SEQ ID NO | Sequence |
| | | cgagaaccacaggtgtacaccctgcccccatcccgggaggagatgaccaagaaccag gtcagcctgacctgcctggtcaaaggcttctatcccagcgacatcgccgtggagtggga gagcaatgggcagccggagaacaactacaagaccacgcctcccgtgctggactccga cggctccttcttcctctacagcaagctcaccgtggacaagagcaggtggcagcagggg aacgtcttctcatgctccgtgatgcatgaggctctgcacaaccactacacgcagaagagc ctctccctgtctccgggtaaa |
| Anti-CD3 12F6 scFV-Fc Amino acid | 50 | QVQLVQSGGGVVQPGRSLRLSCKASGYTFTSYTMHWV RQAPGKGLEWIGYINPSSGYTKYNQKFKDRFTISADKSK STAFLQMDSLRPEDTGVYFCARWQDYDVYFDYWGQG TPVTVSSGGGGSGGGGSGGGGSDIQMTQSPSSLSASVG DRVTMTCRASSSVSYMHWYQQTPGKAPKPWIYATSNL ASGVPSRFSGSGSGTDYTLTISSLQPEDIATYYCQQWSS NPPTFGQGTKLQITREPKSCDKTHTCPPCPAPELLGGPSV FLFPPKPKDTLMISRTPEVTCVVVDVSHEDPEVKFNWY VDGVEVHNAKTKPREEQYNSTYRVVSVLTVLHQDWLN GKEYKCKVSNKALPAPIEKTISKAKGQPREPQVYTLPPS REEMTKNQVSLTCLVKGFYPSDIAVEWESNGQPENNYK TTPPVLDSDGSFFLYSKLTVDKSRWQQGNVFSCSVMHE ALHNHYTQKSLSLSPGK |
| Anti-CD3 OKT3 scFV Fc DNA | 51 | caggtgcaactggtgcagtccggcggaggcgtggtgcagcctggccggagcctgaga ctgagctgcaaggcctccggctacacctttacaagatacactatgcactgggtcagaca ggcccctggcaagggcctggaatggattggctacatcaaccctagccggggatatacc aactacaaccagaaagtgaaggacagattcaccatcagcacagataagtccaagtcca ccgctttcctgcagatggactccctgcgtccagaggacacagctgtgtactactgcgccc ggtactacgacgaccactactgtctggactactggggacagggaaccaccctgaccgt cagctctggcggcggaggctccggcggaggtggcagcggcggcggcggctctgata tccagatgacccagagcccttcttccttatctgccagcgtgggcgatagagtgaccatca catgcagcgccagctcttctgttagctacatgaactggtaccagcaaacacctggaaag gcccctaaaagatggatctacgacaccagcaagctggcctctggcgtgccctctagatt cagcggctctggctccggcaccgactacacctttacaattagctccctgcagcccgagg atatcgccacctactactgccagcagtggagcagcaaccccttcacattcggccagggc acaaagctgcaaatcaccagagagcccaaatcttgtgacaaaactcacacatgcccacc gtgcccagcacctgaactcctggggggaccgtcagtcttcctcttccccccaaaaccca aggacaccctcatgatctcccggacccctgaggtcacatgcgtggtggtggacgtgag ccacgaagaccctgaggtcaagttcaactggtacgtggacggcgtggaggtgcataat gccaagacaaagccgcgggaggagcagtacaacagcacgtaccgtgtggtcagcgtc ctcaccgtcctgcaccaggactggctgaatggcaaggagtacaagtgcaaggtctcca acaaagccctcccagcccccatcgagaaaaccatctccaaagccaaagggcagcccc gagaaccacaggtgtacaccctgcccccatcccgggaggagatgaccaagaaccagg tcagcctgacctgcctggtcaaaggcttctatcccagcgacatcgccgtggagtgggag agcaatgggcagccggagaacaactacaagaccacgcctcccgtgctggactccgac ggctccttcttcctctacagcaagctcaccgtggacaagagcaggtggcagcaggggga acgtcttctcatgctccgtgatgcatgaggctctgcacaaccactacacgcagaagagcc tctccctgtctccgggtaaa |
| Anti-CD3 OKT3 scFV Fc Amino acid | 52 | QVQLVQSGGGVVQPGRSLRLSCKASGYTFTRYTMHWV RQAPGKGLEWIGYINPSRGYTNYNQKVKDRFTISTDKS KSTAFLQMDSLRPEDTAVYYCARYYDDHYCLDYWGQ GTTLTVSSGGGGSGGGGSGGGGSDIQMTQSPSSLSASV GDRVTITCSASSSVSYMNWYQQTPGKAPKRWIYDTSKL ASGVPSRFSGSGSGTDYTFTISSLQPEDIATYYCQQWSSN PFTFGQGTKLQITREPKSCDKTHTCPPCPAPELLGGPSVF LFPPKPKDTLMISRTPEVTCVVVDVSHEDPEVKFNWYV DGVEVHNAKTKPREEQYNSTYRVVSVLTVLHQDWLNG KEYKCKVSNKALPAPIEKTISKAKGQPREPQVYTLPPSR EEMTKNQVSLTCLVKGFYPSDIAVEWESNGQPENNYKT TPPVLDSDGSFFLYSKLTVDKSRWQQGNVFSCSVMHEA LHNHYTQKSLSLSPGK |
| OKT3 scFV-Fc L1 hMN20A10N scFV DNA | 53 | caggtgcaactggtgcagtccggcggaggcgtggtgcagcctggccggagcctgaga ctgagctgcaaggcctccggctacacctttacaagatacactatgcactgggtcagaca ggcccctggcaagggcctggaatggattggctacatcaaccctagccggggatatacc aactacaaccagaaagtgaaggacagattcaccatcagcacagataagtccaagtcca ccgctttcctgcagatggactccctgcgtccagaggacacagctgtgtactactgcgccc ggtactacgacgaccactactgtctggactactggggacagggaaccaccctgaccgt cagctctggcggcggaggctccggcggaggtggcagcggcggcggcggctctgata tccagatgacccagagcccttcttccttatctgccagcgtgggcgatagagtgaccatca catgcagcgccagctcttctgttagctacatgaactggtaccagcaaacacctggaaag gcccctaaaagatggatctacgacaccagcaagctggcctctggcgtgccctctagatt cagcggctctggctccggcaccgactacacctttacaattagctccctgcagcccgagg atatcgccacctactactgccagcagtggagcagcaaccccttcacattcggccagggc acaaagctgcaaatcaccagagagcccaaatcttgtgacaaaactcacacatgcccacc gtgcccagcacctgaactcctggggggaccgtcagtcttcctcttccccccaaaaccca |

TABLE 7-continued

Exemplary Sequences of Antibodies that bind to MUC1* and CD3

| Construct | SEQ ID NO | Sequence |
|---|---|---|
| | | aggacaccctcatgatctcccggacccctgaggtcacatgcgtggtggtggacgtgag<br>ccacgaagaccctgaggtcaagttcaactggtacgtggacggcgtggaggtgcataat<br>gccaagacaaagccgcgggaggagcagtacaacagcacgtaccgtgtggtcagcgtc<br>ctcaccgtcctgcaccaggactggctgaatggcaaggagtacaagtgcaaggtctcca<br>acaaagccctcccagcccccatcgagaaaaccatctccaaagccaaagggcagcccc<br>gagaaccacaggtgtacaccctgcccccatcccgggaggagatgaccaagaaccagg<br>tcagcctgacctgcctggtcaaaggcttctatcccagcgacatcgccgtggagtgggag<br>agcaatgggcagccggagaacaactacaagaccacgcctcccgtgctggactccgac<br>ggctccttcttcctctacagcaagctcaccgtggacaagagcaggtggcagcagggga<br>acgtcttctcatgctccgtgatgcatgaggctctgcacaaccactacacgcagaagagcc<br>tctccctgtctccgggtaaaggcggggggcggttctggtggtggtggctctggagga<br>ggaaccggtcaggtgcagctggttgaatctggcggcggacttgtgaagcctggcggat<br>ctctgagactgagctgtgccgccagcggcttcacctttagcacatacgccatgagctgga<br>tcagacaggcccctggcaaaggcctggaatgggtggcgtctattggcagagccggca<br>gcacctactacagcgactctgtgaagggcagattcaccatcagccgggacaacgccaa<br>gaacagcctgtacctgcagatgaactccctgagagccgaggacaccgccgtgtactatt<br>gtgccagaggacccatctacaacgactacgacgagttcgcctattggggccagggcac<br>actggtcacagtttctagcggcggtggcggaagcggaggcggtggctccggtggcgg<br>aggcagcgaaattgtgctgacacagagccccgccacactgtcactttctccaggcgaaa<br>gagccacactgagctgcaagagcagccagagcgtgctgtactccagcaaccagaaga<br>actacctggcctggtatcagcagaagcccggccaagctcctcggctgctgatctattgg<br>gccagcacaagagagagcggcatccctgccagattttctggcagcggctctggcaccg<br>atttcaccctgaccataagcagcctggaacctgaggacttcgccgtgtattactgccacc<br>agtacctgagcagcctgacctttggcggaggcaccaaggtggaaatcaagcggtgata<br>a |
| OKT3 scFV-Fc L1<br>hMN20A10N scFV<br>amino acid | 54 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV<br>GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITREPKSCDKTHTCPPCPAPELLGGPSVF<br>LFPPKPKDTLMISRTPEVTCVVVDVSHEDPEVKFNWYV<br>DGVEVHNAKTKPREEQYNSTYRVVSVLTVLHQDWLNG<br>KEYKCKVSNKALPAPIEKTISKAKGQPREPQVYTLPPSR<br>EEMTKNQVSLTCLVKGFYPSDIAVEWESNGQPENNYKT<br>TPPVLDSDGSFFLYSKLTVDKSRWQQGNVFSCSVMHEA<br>LHNHYTQKSLSLSPGKGGGGGSGGGGSGGGTGQVQLV<br>ESGGGLVKPGGSLRLSCAASGFTFSTYAMSWIRQAPGK<br>GLEWVASIGRAGSTYYSDSVKGRFTISRDNAKNSLYLQ<br>MNSLRAEDTAVYYCARGPIYNDYDEFAYWGQGTLVTV<br>SSGGGGSGGGGSGGGGSEIVLTQSPATLSLSPGERATLS<br>CKSSQSVLYSSNQKNYLAWYQQKPGQAPRLLIYWAST<br>RESGIPARFSGSGSGTDFTLTISSLEPEDFAVYYCHQYLS<br>SLTFGGGTKVEIKR |
| OKT3 scFV-Fc L1<br>hMNC2 scFV<br>DNA | 55 | caggtgcaactggtgcagtccggcggaggcgtggtgcagcctggccggagcctgaga<br>ctgagctgcaaggcctccggctacacctttacaagatacactatgcactgggtcagaca<br>ggccccctggcaagggcctggaatggattggctacatcaaccctagccggggatatacc<br>aactacaaccagaaagtgaaggacagattcaccatcagcacagataagtccaagtcca<br>ccgctttcctgcagatggactccctgcgtccagaggacacagctgtgtactactgcgccc<br>ggtactacgacgaccactactgtctggactactggggacagggaaccaccctgaccgt<br>cagctctggcggcggaggctccggcggaggtggcagcggcggcggcggctctgata<br>tccagatgacccagagcccttcttccttatctgccagcgtgggcgatagagtgaccatca<br>catgcagcgccagctcttctgttagctacatgaactggtaccagcaaacacctggaaag<br>gcccctaaaagatggatctacgacaccagcaagctggcctctggcgtgccctctagatt<br>cagcggctctggctccggcaccgactacacctttacaattagctccctgcagcccgagg<br>atatcgccacctactactgccagcagtggagcagcaaccccttcacattcggccagggc<br>acaaagctgcaaatcaccagagagcccaaatcttgtgacaaaactcacacatgcccacc<br>gtgcccagcacctgaactcctggggggaccgtcagtcttcctcttccccccaaaaccca<br>aggacaccctcatgatctcccggacccctgaggtcacatgcgtggtggtggacgtgag<br>ccacgaagaccctgaggtcaagttcaactggtacgtggacggcgtggaggtgcataat<br>gccaagacaaagccgcgggaggagcagtacaacagcacgtaccgtgtggtcagcgtc<br>ctcaccgtcctgcaccaggactggctgaatggcaaggagtacaagtgcaaggtctcca<br>acaaagccctcccagcccccatcgagaaaaccatctccaaagccaaagggcagcccc<br>gagaaccacaggtgtacaccctgcccccatcccgggaggagatgaccaagaaccagg<br>tcagcctgacctgcctggtcaaaggcttctatcccagcgacatcgccgtggagtgggag<br>agcaatgggcagccggagaacaactacaagaccacgcctcccgtgctggactccgac<br>ggctccttcttcctctacagcaagctcaccgtggacaagagcaggtggcagcagggga<br>acgtcttctcatgctccgtgatgcatgaggctctgcacaaccactacacgcagaagagcc<br>tctccctgtctccgggtaaaggcgggggtggcggttctggtggtggtggctctggagga<br>ggaaccggtgaggtgcagctggtggagtctgggggaggcctggtcaagcctggggg<br>gtccctgagactctcctgtgcagcctctggattcaccttcagtggctatgccatgagctgg<br>gtccgccaggctccagggaaggggctggagtgggtctcaaccattagtagtggcggaa |

TABLE 7-continued

| Exemplary Sequences of Antibodies that bind to MUC1* and CD3 | | |
|---|---|---|
| Construct | SEQ ID NO | Sequence |
| | | cctacatatactaccccgactcagtgaagggccgattcaccatctccagagacaacgcc<br>aagaactcactgtatctgcaaatgaacagcctgagagccgaggacacggccgtgtatta<br>ctgtgcgagacttgggggggataattactacgaatacttcgatgtctggggcaaaggga<br>ccacggtcaccgtctcctccggcggtggcggatccggcggtggcggatccggcggtg<br>gcggatccgacattgtgctgacccagtctccagcctccttggccgtgtctccaggacaga<br>gggccaccatcacctgcagagccagtaagagtgtcagtaccagcggatactcctacatg<br>cactggtatcagcagaaaccaggacaacctcctaaactcctgatttacctggcatccaat<br>ctggagagcggggtcccagccaggttcagcggcagtgggtctgggaccgatttcaccc<br>tcacaattaatcctgtggaagctaatgatactgcaaattattactgtcagcacagtaggga<br>gctgcctttcacattcggcggagggaccaaggtggagatcaaacgaacttgataa |
| OKT3 scFV-Fc L1<br>hMNC2 scFV<br>Amino acid | 56 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV<br>GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITREPKSCDKTHTCPPCPAPELLGGPSVF<br>LFPPKPKDTLMISRTPEVTCVVVDVSHEDPEVKFNWYV<br>DGVEVHNAKTKPREEQYNSTYRVVSVLTVLHQDWLNG<br>KEYKCKVSNKALPAPIEKTISKAKGQPREPQVYTLPPSR<br>EEMTKNQVSLTCLVKGFYPSDIAVEWESNGQPENNYKT<br>TPPVLDSDGSFFLYSKLTVDKSRWQQGNVFSCSVMHEA<br>LHNHYTQKSLSLSPGKGGGGGSGGGGSGGGTGEVQLV<br>ESGGGLVKPGGSLRLSCAASGFTFSGYAMSWVRQAPG<br>KGLEWVSTISSGGTYIYYPDSVKGRFTISRDNAKNSLYL<br>QMNSLRAEDTAVYYCARLGGDNYYEYFDVWGKGTTV<br>TVSSGGGGSGGGGSGGGGSDIVLTQSPASLAVSPGQRA<br>TITCRASKSVSTSGYSYMHWYQQKPGQPPKLLIYLASNL<br>ESGVPARFSGSGSGTDFTLTINPVEANDTANYYCQHSRE<br>LPFTFGGGTKVEIKRT** |
| OKT3 scFV-Fc L2<br>hMN20A10N scFV<br>DNA | 57 | caggtgcaactggtgcagtccggcggaggcgtggtgcagcctggccggagcctgaga<br>ctgagctgcaaggcctccggctacacctttacaagatacactatgcactgggtcagaca<br>ggcccctggcaagggcctggaatggattggctacatcaaccctagccggggatatacc<br>aactacaaccagaaagtgaaggacagattcaccatcagcacagataagtccaagtcca<br>ccgctttcctgcagatggactccctgcgtccagaggacacagctgtgtactactgcgccc<br>ggtactacgacgaccactactgtctggactactggggacagggaaccaccctgaccgt<br>cagctctggcggcggaggctccggcggaggtggcagcggcggcggcggctctgata<br>tccagatgacccagagcccttcttccttatctgccagcgtgggcgatagagtgaccatca<br>catgcagcgccagctcttctgttagctacatgaactggtaccagcaaacacctggaaag<br>gcccctaaaagatggatctacgacaccagcaagctggcctctggcgtgccctctagatt<br>cagcggctctggctccggcaccgactacacctttacaattagctccctgcagcccgagg<br>atatcgccacctactactgccagcagtggagcagcaaccccttcacattcggccagggc<br>acaaagctgcaaatcaccagagagcccaaatcttgtgacaaaactcacacatgcccacc<br>gtgcccagcacctgaactcctggggggaccgtcagtcttcctcttccccccaaaaccca<br>aggacaccctcatgatctcccggacccctgaggtcacatgcgtggtggtggacgtgag<br>ccacgaagaccctgaggtcaagttcaactggtacgtggacggcgtggaggtgcataat<br>gccaagacaaagccgcgggaggagcagtacaacagcacgtaccgtgtggtcagcgtc<br>ctcaccgtcctgcaccaggactggctgaatggcaaggagtacaagtgcaaggtctcca<br>acaaagccctcccagcccccatcgagaaaaccatctccaaagccaaagggcagcccc<br>gagaaccacaggtgtacaccctgcccccatcccgggaggagatgaccaagaaccagg<br>tcagcctgacctgcctggtcaaaggcttctatcccagcgacatcgccgtggagtgggag<br>agcaatgggcagccggagaacaactacaagaccacgcctcccgtgctggactccgac<br>ggctccttcttcctctacagcaagctcaccgtggacaagagcaggtggcagcagggga<br>acgtcttctcatgctccgtgatgcatgaggctctgcacaaccactacacgcagaagagcc<br>tctccctgtctccgggtaaaggcggcgggggagcggtggtggcggtagcaccggtc<br>aggtgcagctggttgaatctggcggcggacttgtgaagcctggcggatctctgagactg<br>agctgtgccgccagcggcttcacctttagcacatacgccatgagctggatcagacaggc<br>ccctggcaaaggcctggaatgggtggcgtctattggcagagccggcagcacctactac<br>agcgactctgtgaagggcagattcaccatcagccgggacaacgccaagaacagcctgt<br>acctgcagatgaactccctgagagccgaggacaccgccgtgtactattgtgccagagg<br>acccatctacaacgactacgacgagttcgcctattggggccagggcacactggtcacag<br>tttctagcggcggtggcggaagcggaggcggtggctccggtggcggaggcagcgaa<br>attgtgctgacacagagccccgccacactgtcactttctccaggcgaaagagccacact<br>gagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcggtgataa |
| OKT3 scFV-Fc L2<br>hMN20A10N scFV<br>Amino acid | 58 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV |

TABLE 7-continued

Exemplary Sequences of Antibodies that bind to MUC1* and CD3

| Construct | SEQ ID NO | Sequence |
|---|---|---|
| | | GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITREPKSCDKTHTCPPCPAPELLGGPSVF<br>LFPPKPKDTLMISRTPEVTCVVVDVSHEDPEVKFNWYV<br>DGVEVHNAKTKPREEQYNSTYRVVSVLTVLHQDWLNG<br>KEYKCKVSNKALPAPIEKTISKAKGQPREPQVYTLPPSR<br>EEMTKNQVSLTCLVKGFYPSDIAVEWESNGQPENNYKT<br>TPPVLDSDGSFFLYSKLTVDKSRWQQGNVFSCSVMHEA<br>LHNHYTQKSLSLSPGKGGGGSGGGGSTGQVQLVESGG<br>GLVKPGGSLRLSCAASGFTFSTYAMSWIRQAPGKGLEW<br>VASIGRAGSTYYSDSVKGRFTISRDNAKNSLYLQMNSL<br>RAEDTAVYYCARGPIYNDYDEFAYWGQGTLVTVSSGG<br>GGSGGGGSGGGGSEIVLTQSPATLSLSPGERATLSCKSS<br>QSVLYSSNQKNYLAWYQQKPGQAPRLLIYWASTRESGI<br>PARFSGSGSGTDFTLTISSLEPEDFAVYYCHQYLSSLTFG<br>GGTKVEIKR-- |
| OKT3 scFV-Fc L2<br>hMNC2 scFV<br>DNA | 59 | caggtgcaactggtgcagtccggcggaggcgtggtgcagcctggccggagcctgaga<br>ctgagctgcaaggcctccggctacacctttacaagatacactatgcactgggtcagaca<br>ggcccctggcaagggcctggaatggattggctacatcaaccctagccggggatatacc<br>aactacaaccagaaagtgaaggacagattcaccatcagcacagataagtccaagtcca<br>ccgctttcctgcagatggactccctgcgtccagaggacacagctgtgtactactgcgccc<br>ggtactacgacgaccactactgtctggactactggggacagggaaccaccctgaccgt<br>cagctctggcggcggaggctccggcggaggtggcagcggcggcggcggctctgata<br>tccagatgacccagagcccttcttccttatctgccagcgtgggcgatagagtgaccatca<br>catgcagcgccagctcttctgttagctacatgaactggtaccagcaaacacctggaaag<br>gcccctaaaagatggatctacgacaccagcaagctggcctctggcgtgccctctagatt<br>cagcggctctggctccggcaccgactacacctttacaattagctccctgcagcccgagg<br>atatcgccacctactactgccagcagtggagcagcaaccccttcacattcggccagggc<br>acaaagctgcaaatcaccagagagcccaaatcttgtgacaaaactcacacatgcccacc<br>gtgcccagcacctgaactcctggggggaccgtcagtcttcctcttccccccaaaaccca<br>aggacaccctcatgatctcccggacccctgaggtcacatgcgtggtggtggacgtgag<br>ccacgaagaccctgaggtcaagttcaactggtacgtggacggcgtggaggtgcataat<br>gccaagacaaagccgcgggaggagcagtacaacagcacgtaccgtgtggtcagcgtc<br>ctcaccgtcctgcaccaggactggctgaatggcaaggagtacaagtgcaaggtctcca<br>acaaagccctcccagcccccatcgagaaaaccatctccaaagccaaagggcagcccc<br>gagaaccacaggtgtacaccctgcccccatcccgggaggagatgaccaagaaccagg<br>tcagcctgacctgcctggtcaaaggcttctatcccagcgacatcgccgtggagtgggag<br>agcaatgggcagccggagaacaactacaagaccacgcctcccgtgctggactccgac<br>ggctccttcttcctctacagcaagctcaccgtggacaagagcaggtggcagcagggga<br>acgtcttctcatgctccgtgatgcatgaggctctgcacaaccactacacgcagaagagcc<br>tctccctgtctccgggtaaaggcggcgggggagcggtggtggcggtagcaccggtg<br>aggtgcagctggtggagtctgggggaggcctggtcaagcctggggggtccctgagac<br>tctcctgtgcagcctctggattcaccttcagtggctatgccatgagctgggtccgccaggc<br>tccagggaaggggctggagtgggtctcaaccattagtagtggcggaacctacatatact<br>accccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>ggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaacttgataa |
| OKT3 scFV-Fc L2<br>hMNC2 scFV<br>Amino acid | 60 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV<br>GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITREPKSCDKTHTCPPCPAPELLGGPSVF<br>LFPPKPKDTLMISRTPEVTCVVVDVSHEDPEVKFNWYV<br>DGVEVHNAKTKPREEQYNSTYRVVSVLTVLHQDWLNG<br>KEYKCKVSNKALPAPIEKTISKAKGQPREPQVYTLPPSR<br>EEMTKNQVSLTCLVKGFYPSDIAVEWESNGQPENNYKT<br>TPPVLDSDGSFFLYSKLTVDKSRWQQGNVFSCSVMHEA<br>LHNHYTQKSLSLSPGKGGGGSGGGGSTGEVQLVESGGG<br>LVKPGGSLRLSCAASGFTFSGYAMSWVRQAPGKGLEW<br>VSTISSGGTYIYYPDSVKGRFTISRDNAKNSLYLQMNSL<br>RAEDTAVYYCARLGGDNYYEYFDVWGKGTTVTVSSG<br>GGGSGGGGSGGGGSDIVLTQSPASLAVSPGQRATITCRA<br>SKSVSTSGYSYMHWYQQKPGQPPKLLIYLASNLESGVP |

TABLE 7-continued

Exemplary Sequences of Antibodies that bind to MUC1* and CD3

| Construct | SEQ ID NO | Sequence |
|---|---|---|
| | | ARFSGSGSGTDFTLTINPVEANDTANYYCQHSRELPFTF<br>GGGTKVEIKRT** |
| hMN20A10N scFV-Fc L1 OKT3 scFV DNA | 61 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagatttctggcagcggctctggcaccgatttcaccctg<br>accataagcagcctggaacctgaggacttcgccgtgtattactgccaccagtacctgag<br>cagcctgacctttggcggaggcaccaaggtggaaatcaaggggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgacctgcctggtcaaaggcttctatcccagc<br>gacatcgccgtggagtgggagagcaatgggcagccggagaacaactacaagaccac<br>gcctcccgtgctggactccgacggctccttcttcctctacagcaagctcaccgtggacaa<br>gagcaggtggcagcaggggaacgtcttctcatgctccgtgatgcatgaggctctgcaca<br>accactacacgcagaagagcctctccctgtctccgggtaaaggcgggggggcggttc<br>tggtggtggtggctctggaggaggaaccggtcaggtgcaactggtgcagtccggcgg<br>aggcgtggtgcagcctggccggagcctgagactgagctgcaaggcctccggctacac<br>ctttacaagatacactatgcactgggtcagacaggcccctggcaagggcctggaatgga<br>ttggctacatcaaccctagccggggatataccaactacaaccagaaagtgaaggacag<br>attcaccatcagcacagataagtccaagtccaccgctttcctgcagatggactccctgcgt<br>ccagaggacacagctgtgtactactgcgcccggtactacgacgaccactactgtctgga<br>ctactggggacagggaaccaccctgaccgtcagctctggcggcggaggctccggcgg<br>aggtggcagcggcggcggcggctctgatatccagatgacccagagcccttcttccttat<br>ctgccagcgtgggcgatagagtgaccatcacatgcagcgccagctcttctgttagctaca<br>tgaactggtaccagcaaacacctggaaaggcccctaaaagatggatctacgacaccag<br>caagctggcctctggcgtgccctctagattcagcggctctggctccggcaccgactaca<br>cctttacaattagctccctgcagcccgaggatatcgccacctactactgccagcagtgga<br>gcagcaaccccttcacattcggccagggcacaaagctgcaaatcaccagatgataa |
| hMN20A10N scFV-Fc L1 OKT3 scFV amino acid | 62 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFAVYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCS<br>VMHEALHNHYTQKSLSLSPGKGGGGGSGGGGSGGGTG<br>QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV<br>GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITR- |
| hMNC2 scFV-Fc L1 OKT3 scFV DNA | 63 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca |

TABLE 7-continued

Exemplary Sequences of Antibodies that bind to MUC1* and CD3

| Construct | SEQ ID NO | Sequence |
|---|---|---|
| | | cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgacctgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaaggcgggggtggcggttctggt<br>ggtggtggctctggaggaggaaccggtcaggtgcaactggtgcagtccggcggaggc<br>gtggtgcagcctggccggagcctgagactgagctgcaaggcctccggctacaccttta<br>caagatacactatgcactgggtcagacaggcccctggcaagggcctggaatggattgg<br>ctacatcaaccctagccggggatataccaactacaaccagaaagtgaaggacagattca<br>ccatcagcacagataagtccaagtccaccgctttcctgcagatggactccctgcgtccag<br>aggacacagctgtgtactactgcgcccggtactacgacgaccactactgtctggactact<br>ggggacagggaaccaccctgaccgtcagctctggcggcggaggctccggcggaggt<br>ggcagcggcggcggcggctctgatatccagatgacccagagcccttcttccttatctgc<br>cagcgtgggcgatagagtgaccatcacatgcagcgccagctcttctgttagctacatgaa<br>ctggtaccagcaaacacctggaaaggcccctaaaagatggatctacgacaccagcaag<br>ctggcctctggcgtgccctctagattcagcggctctggctccggcaccgactacacctttt<br>acaattagctccctgcagcccgaggatatcgccacctactactgccagcagtggagcag<br>caaccccttcacattcggccagggcacaaagctgcaaatcaccagatgataa |
| hMNC2 scFV-Fc L1<br>OKT3 scFV<br>amino acid | 64 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSGGGGSGGGGSGGGGSDIVLTQSPASLAVSP<br>GQRATITCRASKSVSTSGYSYMHWYQQKPGQPPKLLIY<br>LASNLESGVPARFSGSGSGTDFTLTINPVEANDTANYYC<br>QHSRELPFTFGGGTKVEIKRTEPKSCDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLH<br>QDWLNGKEYKCKVSNKALPAPIEKTISKAKGQPREPQV<br>YTLPPSREEMTKNQVSLTCLVKGFYPSDIAVEWESNGQ<br>PENNYKTTPPVLDSDGSFFLYSKLTVDKSRWQQGNVFS<br>CSVMHEALHNHYTQKSLSLSPGKGGGGGSGGGGSGGG<br>TGQVQLVQSGGGVVQPGRSLRLSCKASGYTFTRYTMH<br>WVRQAPGKGLEWIGYINPSRGYTNYNQKVKDRFTISTD<br>KSKSTAFLQMDSLRPEDTAVYYCARYYDDHYCLDYWG<br>QGTTLTVSSGGGGSGGGGSGGGGSDIQMTQSPSSLSAS<br>VGDRVTITCSASSSVSYMNWYQQTPGKAPKRWIYDTSK<br>LASGVPSRFSGSGSGTDYTFTISSLQPEDIATYYCQQWSS<br>NPFTFGQGTKLQITR** |
| hMN20A10N scFv-Fc<br>L2 OKT3 scFv<br>DNA | 65 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcgggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgacctgcctggtcaaaggcttctatcccagc<br>gacatcgccgtggagtgggagagcaatgggcagccggagaacaactacaagaccac<br>gcctcccgtgctggactccgacggctccttcttcctctacagcaagctcaccgtggacaa<br>gagcaggtggcagcaggggaacgtcttctcatgctccgtgatgcatgaggctctgcaca<br>accactacacgcagaagagcctctccctgtctccgggtaaaggcggcgggggagcg<br>gtggtggcggtagcaccggtcaggtgcaactggtgcagtccggcggaggcgtggtgc<br>agcctggccggagcctgagactgagctgcaaggcctccggctacacctttacaagata |

TABLE 7-continued

| Construct | SEQ ID NO | Sequence |
|---|---|---|
| Exemplary Sequences of Antibodies that bind to MUC1* and CD3 | | |
| | | cactatgcactgggtcagacaggcccctggcaagggcctggaatggattggctacatca<br>accctagccggggatataccaactacaaccagaaagtgaaggacagattcaccatcag<br>cacagataagtccaagtccaccgctttcctgcagatggactccctgcgtccagaggaca<br>cagctgtgtactactgcgcccggtactacgacgaccactactgtctggactactggggac<br>agggaaccaccctgaccgtcagctctggcggcggaggctccggcggaggtggcagc<br>ggcggcggcggctctgatatccagatgacccagagcccttcttccttatctgccagcgtg<br>ggcgatagagtgaccatcacatgcagcgccagctcttctgttagctacatgaactggtac<br>cagcaaacacctggaaaggcccctaaaagatggatctacgacaccagcaagctggcct<br>ctggcgtgccctctagattcagcggctctggctccggcaccgactacacctttacaattag<br>ctccctgcagcccgaggatatcgccacctactactgccagcagtggagcagcaacccc<br>ttcacattcggccagggcacaaagctgcaaatcaccagatgataa |
| hMN20A10N scFv-Fc L2 OKT3 scFv amino acid | 66 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFA VYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCS<br>VMHEALHNHYTQKSLSLSPGKGGGGSGGGGSTGQVQL<br>VQSGGGVVQPGRSLRLSCKASGYTFTRYTMHWVRQAP<br>GKGLEWIGYINPSRGYTNYNQKVKDRFTISTDKSKSTAF<br>LQMDSLRPEDTAVYYCARYYDDHYCLDYWGQGTTLT<br>VSSGGGGSGGGGSGGGGSDIQMTQSPSSLSASVGDRVTI<br>TCSASSSVSYMNWYQQTPGKAPKRWIYDTSKLASGVPS<br>RFSGSGSGTDYTFTISSLQPEDIATYYCQQWSSNPFTFGQ<br>GTKLQITR-- |
| hMNC2 scFv-Fc L2 OKT3 scFv DNA | 67 | gaggtgcagctggtggagtctgggggaggcctggtcaagcctgggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttggggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgacctgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaaggcggcgggggagcggtgg<br>tggcggtagcaccggtcaggtgcaactggtgcagtccggcggaggcgtggtgcagcc<br>tggccggagcctgagactgagctgcaaggcctccggctacacctttacaagatacacta<br>tgcactgggtcagacaggcccctggcaagggcctggaatggattggctacatcaaccct<br>agccggggatataccaactacaaccagaaagtgaaggacagattcaccatcagcacag<br>ataagtccaagtccaccgctttcctgcagatggactccctgcgtccagaggacacagct<br>gtgtactactgcgcccggtactacgacgaccactactgtctggactactggggacaggg<br>aaccaccctgaccgtcagctctggcggcggaggctccggcggaggtggcagcggcg<br>gcggcggctctgatatccagatgacccagagcccttcttccttatctgccagcgtgggcg<br>atagagtgaccatcacatgcagcgccagctcttctgttagctacatgaactggtaccagc<br>aaacacctggaaaggcccctaaaagatggatctacgacaccagcaagctggcctctgg<br>cgtgccctctagattcagcggctctggctccggcaccgactacacctttacaattagctcc<br>ctgcagcccgaggatatcgccacctactactgccagcagtggagcagcaaccccttca<br>cattcggccagggcacaaagctgcaaatcaccagatgataa |
| hMNC2 scFv-Fc L2 OKT3 scFv amino acid | 68 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK |

TABLE 7-continued

| Exemplary Sequences of Antibodies that bind to MUC1* and CD3 | | |
|---|---|---|
| Construct | SEQ ID NO | Sequence |
| | | GTTVTVSSGGGGSGGGGSGGGGSDIVLTQSPASLAVSP<br>GQRATITCRASKSVSTSGYSYMHWYQQKPGQPPKLLIY<br>LASNLESGVPARFSGSGSGTDFTLTINPVEANDTANYYC<br>QHSRELPFTFGGGTKVEIKRTEPKSCDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLH<br>QDWLNGKEYKCKVSNKALPAPIEKTISKAKGQPREPQV<br>YTLPPSREEMTKNQVSLTCLVKGFYPSDIAVEWESNGQ<br>PENNYKTTPPVLDSDGSFFLYSKLTVDKSRWQQGNVFS<br>CSVMHEALHNHYTQKSLSLSPGKGGGGSGGGGSTGQV<br>QLVQSGGGVVQPGRSLRLSCKASGYTFTRYTMHWVRQ<br>APGKGLEWIGYINPSRGYTNYNQKVKDRFTISTDKSKST<br>AFLQMDSLRPEDTAVYYCARYYDDHYCLDYWGQGTT<br>LTVSSGGGGSGGGGSGGGGSDIQMTQSPSSLSASVGDR<br>VTITCSASSSVSYMNWYQQTPGKAPKRWIYDTSKLASG<br>VPSRFSGSGSGTDYTFTISSLQPEDIATYYCQQWSSNPFT<br>FGQGTKLQITR** |
| hMN20A10N scFv-Fc L1 12F6 scFv DNA | 69 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcgggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgacctgcctggtcaaaggcttctatcccagc<br>gacatcgccgtggagtgggagagcaatgggcagccggagaacaactacaagaccac<br>gcctcccgtgctggactccgacggctccttcttcctctacagcaagctcaccgtggacaa<br>gagcaggtggcagcaggggaacgtcttctcatgctccgtgatgcatgaggctctgcaca<br>accactacacgcagaagagcctctccctgtctccgggtaaaggcgggggtggcggttc<br>tggtggtggtggctctggaggaggaaccggtcaagtgcagctggtgcagtccggagg<br>aggcgtcgtgcagcctggaagaagcctccggctgagctgcaaggccagcggctatac<br>attcaccagctacaccatgcactgggtgcggcaggcccctggcaaaggcctggaatgg<br>atcggctacatcaacccttccagcggctacaccaagtacaaccagaaattcaaggaccg<br>gtttaccattagcgccgataagagcaagagcacagcctttctgcagatggacagcctga<br>gaccagaggacaccggcgtgtacttctgcgcccgctggcaggactacgacgtttatttc<br>gactactggggccagggcacccctgtgacagtgagcagcggcggcggaggctccgg<br>cggaggtggcagcggcggcggcggctctgatatccagatgacacagagccccagctc<br>tctgtctgcttctgtgggcgacagagtgaccatgacctgtagagcctcctcaagcgtgtcc<br>tacatgcactggtaccagcaaacacctggcaaggccccaaagccttggatctacgccac<br>ctctaatctggccagcggcgtgccttctagattcagcggcagcggatctggcaccgatta<br>caccctgaccatcagcagcctgcagcccgaggatatcgccacatactactgccagcagt<br>ggagctccaatcctcctaccttcggccagggcaccaagctgcagatcacaagatgataa |
| hMN20A10N scFv-Fc L1 12F6 scFv amino acid | 70 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFAVYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCS<br>VMHEALHNHYTQKSLSLSPGKGGGGGSGGGGSGGGTG<br>QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSGGGGSGGGGSGGGGSDIQMTQSPSSLSASVG<br>DRVTMTCRASSSVSYMHWYQQTPGKAPKPWIYATSNL |

TABLE 7-continued

Exemplary Sequences of Antibodies that bind to MUC1* and CD3

| Construct | SEQ ID NO | Sequence |
|---|---|---|
| | | ASGVPSRFSGSGSGTDYTLTISSLQPEDIATYYCQQWSS<br>NPPTFGQGTKLQITR- |
| hMNC2 scFv-Fc L1<br>12F6 scFv<br>DNA | 71 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttggggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgacctgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaaggcgggggtggcggttctggt<br>ggtggtggctctggaggaggaaccggtcaagtgcagctggtgcagtccggaggaggc<br>gtcgtgcagcctggaagaagcctccggctgagctgcaaggccagcggctatacattca<br>ccagctacaccatgcactgggtgcggcaggcccctggcaaaggcctggaatggatcg<br>gctacatcaacccttccagcggctacaccaagtacaaccagaaattcaaggaccggttta<br>ccattagcgccgataagagcaagagcacagcctttctgcagatggacagcctgagacc<br>agaggacaccggcgtgtacttctgcgcccgctggcaggactacgacgtttatttcgacta<br>ctggggccagggcacccctgtgacagtgagcagcggcggcggaggctccggcgga<br>ggtggcagcggcggcggcggctctgatatccagatgacacagagccccagctctctgt<br>ctgcttctgtgggcgacagagtgaccatgacctgtagagcctcctcaagcgtgtcctaca<br>tgcactggtaccagcaaacacctggcaaggccccaaagccttggatctacgccacctct<br>aatctggccagcggcgtgccttctagattcagcggcagcggatctggcaccgattacac<br>cctgaccatcagcagcctgcagcccgaggatatcgccacatactactgccagcagtgg<br>agctccaatcctcctaccttcggccagggcaccaagctgcagatcacaagatgataa |
| hMNC2 scFv-Fc L1<br>12F6 scFv<br>amino acid | 72 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSGGGGSGGGGSGGGGSDIVLTQSPASLAVSP<br>GQRATITCRASKSVSTSGYSYMHWYQQKPGQPPKLLIY<br>LASNLESGVPARFSGSGSGTDFTLTINPVEANDTANYYC<br>QHSRELPFTFGGGTKVEIKRTEPKSCDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLH<br>QDWLNGKEYKCKVSNKALPAPIEKTISKAKGQPREPQV<br>YTLPPSREEMTKNQVSLTCLVKGFYPSDIAVEWESNGQ<br>PENNYKTTPPVLDSDGSFFLYSKLTVDKSRWQQGNVFS<br>CSVMHEALHNHYTQKSLSLSPGKGGGGGSGGGGSGGG<br>TGQVQLVQSGGGVVQPGRSLRLSCKASGYTFTSYTMH<br>WVRQAPGKGLEWIGYINPSSGYTKYNQKFKDRFTISAD<br>KSKSTAFLQMDSLRPEDTGVYFCARWQDYDVYFDYW<br>GQGTPVTVSSGGGGSGGGGSGGGGSDIQMTQSPSSLSA<br>SVGDRVTMTCRASSSVSYMHWYQQTPGKAPKPWIYAT<br>SNLASGVPSRFSGSGSGTDYTLTISSLQPEDIATYYCQQ<br>WSSNPPTFGQGTKLQITR** |
| hMN20A10N scFv-Fc<br>L2 12F6 scFv DNA | 73 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag |

TABLE 7-continued

Exemplary Sequences of Antibodies that bind to MUC1* and CD3

| Construct | SEQ ID NO | Sequence |
|---|---|---|
| | | cagcctgacctttggcggaggcaccaaggtggaaatcaagcgggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgacctgcctggtcaaaggcttctatcccagc<br>gacatcgccgtggagtgggagagcaatgggcagccggagaacaactacaagaccac<br>gcctcccgtgctggactccgacggctccttcttcctctacagcaagctcaccgtggacaa<br>gagcaggtggcagcaggggaacgtcttctcatgctccgtgatgcatgaggctctgcaca<br>accactacacgcagaagagcctctccctgtctccgggtaaaggcggcgggggagcg<br>gtggtggcggtagcaccggtcaagtgcagctggtgcagtccggaggaggcgtcgtgc<br>agcctggaagaagcctccggctgagctgcaaggccagcggctatacattcaccagcta<br>caccatgcactgggtgcggcaggcccctggcaaaggcctggaatggatcggctacatc<br>aacccttccagcggctacaccaagtacaaccagaaattcaaggaccggtttaccattagc<br>gccgataagagcaagagcacagcctttctgcagatggacagcctgagaccagaggac<br>accggcgtgtacttctgcgcccgctggcaggactacgacgtttatttcgactactggggc<br>cagggcacccctgtgacagtgagcagcggcggcggaggctccggcggaggtggca<br>gcggcggcggcggctctgatatccagatgacacagagccccagctctctgtctgcttct<br>gtgggcgacagagtgaccatgacctgtagagcctcctcaagcgtgtcctacatgcactg<br>gtaccagcaaacacctggcaaggccccaaagccttggatctacgccacctctaatctgg<br>ccagcggcgtgccttctagattcagcggcagcggatctggcaccgattacaccctgacc<br>atcagcagcctgcagcccgaggatatcgccacatactactgccagcagtggagctcca<br>atcctcctaccttcggccagggcaccaagctgcagatcacaagatgataa |
| hMN20A10N scFv-Fc L2 12F6 scFv amino acid | 74 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFAVYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCS<br>VMHEALHNHYTQKSLSLSPGKGGGGSGGGGSTGQVQL<br>VQSGGGVVQPGRSLRLSCKASGYTFTSYTMHWVRQAP<br>GKGLEWIGYINPSSGYTKYNQKFKDRFTISADKSKSTAF<br>LQMDSLRPEDTGVYFCARWQDYDVYFDYWGQGTPVT<br>VSSGGGGSGGGGSGGGGSDIQMTQSPSSLSASVGDRVT<br>MTCRASSSVSYMHWYQQTPGKAPKPWIYATSNLASGV<br>PSRFSGSGSGTDYTLTISSLQPEDIATYYCQQWSSNPPTF<br>GQGTKLQITR-- |
| hMNC2 scFv-Fc L2 12F6 scFV DNA | 75 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgacctgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaaggcggcgggggagcggtgg<br>tggcggtagcaccggtcaagtgcagctggtgcagtccggaggaggcgtcgtgcagcc<br>tggaagaagcctccggctgagctgcaaggccagcggctatacattcaccagctacacc |

TABLE 7-continued

Exemplary Sequences of Antibodies that bind to MUC1* and CD3

| Construct | SEQ ID NO | Sequence |
|---|---|---|
| | | atgcactgggtgcggcaggcccctggcaaaggcctggaatggatcggctacatcaacc cttccagcggctacaccaagtacaaccagaaattcaaggaccggtttaccattagcgcc gataagagcaagagcacagcctttctgcagatggacagcctgagaccagaggacacc ggcgtgtacttctgcgcccgctggcaggactacgacgtttatttcgactactggggccag ggcacccctgtgacagtgagcagcggcggcggaggctccggcggaggtggcagcg gcggcggcggctctgatatccagatgacacagagccccagctctctgtctgcttctgtgg gcgacagagtgaccatgacctgtagagcctcctcaagcgtgtcctacatgcactggtac cagcaaacacctggcaaggccccaaagccttggatctacgccacctctaatctggccag cggcgtgccttctagattcagcggcagcggatctggcaccgattacaccctgaccatca gcagcctgcagcccgaggatatcgccacatactactgccagcagtggagctccaatcct cctaccttcggccagggcaccaagctgcagatcacaagatgataa |
| hMNC2 scFv-Fc L2<br>12F6 scFV amino acid | 76 | EVQLVESGGGLVKPGGSLRLSCAASGFTFSGYAMSWVR QAPGKGLEWVSTISSGGTYIYYPDSVKGRFTISRDNAKN SLYLQMNSLRAEDTAVYYCARLGGDNYYEYFDVWGK GTTVTVSSGGGGSGGGGSGGGGSDIVLTQSPASLAVSP GQRATITCRASKSVSTSGYSYMHWYQQKPGQPPKLLIY LASNLESGVPARFSGSGSGTDFTLTINPVEANDTANYYC QHSRELPFTFGGGTKVEIKRTEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLH QDWLNGKEYKCKVSNKALPAPIEKTISKAKGQPREPQV YTLPPSREEMTKNQVSLTCLVKGFYPSDIAVEWESNGQ PENNYKTTPPVLDSDGSFFLYSKLTVDKSRWQQGNVFS CSVMHEALHNHYTQKSLSLSPGKGGGGSGGGGSTGQV QLVQSGGGVVQPGRSLRLSCKASGYTFTSYTMHWVRQ APGKGLEWIGYINPSSGYTKYNQKFKDRFTISADKSKST AFLQMDSLRPEDTGVYFCARWQDYDVYFDYWGQGTP VTVSSGGGGSGGGGSGGGGSDIQMTQSPSSLSASVGDR VTMTCRASSSVSYMHWYQQTPGKAPKPWIYATSNLAS GVPSRFSGSGSGTDYTLTISSLQPEDIATYYCQQWSSNPP TFGQGTKLQITR** |
| 12F6 scFv-Fc L1<br>hMN20A10N scFv DNA | 77 | Caagtgcagctggtgcagtccggaggaggcgtcgtgcagcctggaagaagcctccg gctgagctgcaaggccagcggctatacattcaccagctacaccatgcactgggtgcgg caggcccctggcaaaggcctggaatggatcggctacatcaacccttccagcggctaca ccaagtacaaccagaaattcaaggaccggtttaccattagcgccgataagagcaagag cacagcctttctgcagatggacagcctgagaccagaggacaccggcgtgtacttctgcg cccgctggcaggactacgacgtttatttcgactactggggccagggcacccctgtgaca gtgagcagcggcggcggaggctccggcggaggtggcagcggcggcggcggctctg atatccagatgacacagagccccagctctctgtctgcttctgtgggcgacagagtgacca tgacctgtagagcctcctcaagcgtgtcctacatgcactggtaccagcaaacacctggca aggccccaaagccttggatctacgccacctctaatctggccagcggcgtgccttctagat tcagcggcagcggatctggcaccgattacaccctgaccatcagcagcctgcagcccga ggatatcgccacatactactgccagcagtggagctccaatcctcctaccttcggccagg gcaccaagctgcagatcacaagagagcccaaatcttgtgacaaaactcacacatgccc accgtgcccagcacctgaactcctggggggaccgtcagtcttcctcttccccccaaaac ccaaggacaccctcatgatctcccggacccctgaggtcacatgcgtggtggtggacgtg agccacgaagaccctgaggtcaagttcaactggtacgtggacggcgtggaggtgcata atgccaagacaaagccgcgggaggagcagtacaacagcacgtaccgtgtggtcagcg tcctcaccgtcctgcaccaggactggctgaatggcaaggagtacaagtgcaaggtctcc aacaaagccctcccagcccccatcgagaaaaccatctccaaagccaaagggcagccc cgagaaccacaggtgtacaccctgcccccatcccgggaggagatgaccaagaaccag gtcagcctgacctgcctggtcaaaggcttctatcccagcgacatcgccgtggagtggga gagcaatgggcagccggagaacaactacaagaccacgcctcccgtgctggactccga cggctccttcttcctctacagcaagctcaccgtggacaagagcaggtggcagcagggg aacgtcttctcatgctccgtgatgcatgaggctctgcacaaccactacacgcagaagagc ctctccctgtctccgggtaaaggcggggggggcggttctggtggtggtggctctggagg aggaaccggtcaggtgcagctggttgaatctggcggcggacttgtgaagcctggcgga tctctgagactgagctgtgccgccagcggcttcacctttagcacatacgccatgagctgg atcagacaggcccctggcaaaggcctggaatgggtggcgtctattggcagagccggc agcacctactacagcgactctgtgaagggcagattcaccatcagccgggacaacgcca agaacagcctgtacctgcagatgaactccctgagagccgaggacaccgccgtgtactat tgtgccagaggacccatctacaacgactacgacgagttcgcctattggggccagggca cactggtcacagtttctagcggcggtggcggaagcggaggcggtggctccggtggcg gaggcagcgaaattgtgctgacacagagccccgccacactgtcactttctccaggcgaa agagccacactgagctgcaagagcagccagagcgtgctgtactccagcaaccagaag aactacctggcctggtatcagcagaagcccggccaagctcctcggctgctgatctattgg gccagcacaagagagagcggcatccctgccagattttctggcagcggctctggcaccg atttcaccctgaccataagcagcctggaacctgaggacttcgccgtgtattactgccacc agtacctgagcagcctgacctttggcggaggcaccaaggtggaaatcaagcggtgata a |
| 12F6 scFv-Fc L1<br>hMN20A10N scFv | 78 | QVQLVQSGGGVVQPGRSLRLSCKASGYTFTSYTMHWV RQAPGKGLEWIGYINPSSGYTKYNQKFKDRFTISADKSK |

TABLE 7-continued

Exemplary Sequences of Antibodies that bind to MUC1* and CD3

| Construct | SEQ ID NO | Sequence |
|---|---|---|
| amino acid | | STAFLQMDSLRPEDTGVYFCARWQDYDVYFDYWGQG<br>TPVTVSSGGGGSGGGGSGGGGSDIQMTQSPSSLSASVG<br>DRVTMTCRASSSVSYMHWYQQTPGKAPKPWIYATSNL<br>ASGVPSRFSGSGSGTDYTLTISSLQPEDIATYYCQQWSS<br>NPPTFGQGTKLQITREPKSCDKTHTCPPCPAPELLGGPSV<br>FLFPPKPKDTLMISRTPEVTCVVVDVSHEDPEVKFNWY<br>VDGVEVHNAKTKPREEQYNSTYRVVSVLTVLHQDWLN<br>GKEYKCKVSNKALPAPIEKTISKAKGQPREPQVYTLPPS<br>REEMTKNQVSLTCLVKGFYPSDIAVEWESNGQPENNYK<br>TTPPVLDSDGSFFLYSKLTVDKSRWQQGNVFSCSVMHE<br>ALHNHYTQKSLSLSPGKGGGGGSGGGGSGGGTGQVQL<br>VESGGGLVKPGGSLRLSCAASGFTFSTYAMSWIRQAPG<br>KGLEWVASIGRAGSTYYSDSVKGRFTISRDNAKNSLYL<br>QMNSLRAEDTAVYYCARGPIYNDYDEFAYWGQGTLVT<br>VSSGGGGSGGGGSGGGGSEIVLTQSPATLSLSPGERATL<br>SCKSSQSVLYSSNQKNYLAWYQQKPGQAPRLLIYWAST<br>RESGIPARFSGSGSGTDFTLTISSLEPEDFAVYYCHQYLS<br>SLTFGGGTKVEIKR-- |
| 12F6 scFV-Fc L1<br>hMNC2 scFV<br>DNA | 79 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcacccctgtgacag<br>tgagcagcggcggcggaggctccggcggaggtggcagcggcggcggcggctctga<br>tatccagatgacacagagccccagctctctgtctgcttctgtgggcgacagagtgaccat<br>gacctgtagagcctcctcaagcgtgtcctacatgcactggtaccagcaaacacctggca<br>aggccccaaagccttggatctacgccacctctaatctggccagcggcgtgccttctagat<br>tcagcggcagcggatctggcaccgattacaccctgaccatcagcagcctgcagcccga<br>ggatatcgccacatactactgccagcagtggagctccaatcctcctaccttcggccagg<br>gcaccaagctgcagatcacaagagagcccaaatcttgtgacaaaactcacacatgccc<br>accgtgcccagcacctgaactcctggggggaccgtcagtcttcctcttccccccaaaac<br>ccaaggacaccctcatgatctcccggacccctgaggtcacatgcgtggtggtggacgtg<br>agccacgaagaccctgaggtcaagttcaactggtacgtggacggcgtggaggtgcata<br>atgccaagacaaagccgcgggaggagcagtacaacagcacgtaccgtgtggtcagcg<br>tcctcaccgtcctgcaccaggactggctgaatggcaaggagtacaagtgcaaggtctcc<br>aacaaagccctcccagcccccatcgagaaaaccatctccaaagccaaagggcagccc<br>cgagaaccacaggtgtacaccctgcccccatcccgggaggagatgaccaagaaccag<br>gtcagcctgacctgcctggtcaaaggcttctatcccagcgacatcgccgtggagtgga<br>gagcaatgggcagccggagaacaactacaagaccacgcctcccgtgctggactccga<br>cggctccttcttcctctacagcaagctcaccgtggacaagagcaggtggcagcagggg<br>aacgtcttctcatgctccgtgatgcatgaggctctgcacaaccactacacgcagaagagc<br>ctctccctgtctccgggtaaaggcgggggtggcggttctggtggtggtggctctggagg<br>aggaaccggtgaggtgcagctggtggagtctgggggaggcctggtcaagcctgggg<br>ggtccctgagactctcctgtgcagcctctggattcaccttcagtggctatgccatgagctg<br>ggtccgccaggctccagggaaggggctggagtgggtctcaaccattagtagtggcgg<br>aacctacatatactaccccgactcagtgaagggccgattcaccatctccagagacaacg<br>ccaagaactcactgtatctgcaaatgaacagcctgagagccgaggacacggccgtgtat<br>tactgtgcgagacttgggggggataattactacgaatacttcgatgtctggggcaaaggg<br>accacggtcaccgtctcctccggcggtggcggatccggcggtggcggatccggcggt<br>ggcggatccgacattgtgctgacccagtctccagcctccttggccgtgtctccaggaca<br>gagggccaccatcacctgcagagccagtaagagtgtcagtaccagcggatactcctac<br>atgcactggtatcagcagaaaccaggacaacctcctaaactcctgatttacctggcatcc<br>aatctggagagcggggtcccagccaggttcagcggcagtgggtctgggaccgatttca<br>ccctcacaattaatcctgtggaagctaatgatactgcaaattattactgtcagcacagtag<br>ggagctgcctttcacattcggcggagggaccaaggtggagatcaaacgaacttgataa |
| 12F6 scFV-Fc L1<br>hMNC2 scFV<br>Amino acid | 80 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSGGGGSGGGGSGGGGSDIQMTQSPSSLSASVG<br>DRVTMTCRASSSVSYMHWYQQTPGKAPKPWIYATSNL<br>ASGVPSRFSGSGSGTDYTLTISSLQPEDIATYYCQQWSS<br>NPPTFGQGTKLQITREPKSCDKTHTCPPCPAPELLGGPSV<br>FLFPPKPKDTLMISRTPEVTCVVVDVSHEDPEVKFNWY<br>VDGVEVHNAKTKPREEQYNSTYRVVSVLTVLHQDWLN<br>GKEYKCKVSNKALPAPIEKTISKAKGQPREPQVYTLPPS<br>REEMTKNQVSLTCLVKGFYPSDIAVEWESNGQPENNYK<br>TTPPVLDSDGSFFLYSKLTVDKSRWQQGNVFSCSVMHE<br>ALHNHYTQKSLSLSPGKGGGGGSGGGGSGGGTGEVQL<br>VESGGGLVKPGGSLRLSCAASGFTFSGYAMSWVRQAP<br>GKGLEWVSTISSGGTYIYYPDSVKGRFTISRDNAKNSLY<br>LQMNSLRAEDTAVYYCARLGGDNYYEYFDVWGKGTT<br>VTVSSGGGGSGGGGSGGGGSDIVLTQSPASLAVSPGQR |

TABLE 7-continued

| Exemplary Sequences of Antibodies that bind to MUC1* and CD3 | | |
|---|---|---|
| Construct | SEQ ID NO | Sequence |
| | | ATITCRASKSVSTSGYSYMHWYQQKPGQPPKLLIYLAS<br>NLESGVPARFSGSGSGTDFTLTINPVEANDTANYYCQHS<br>RELPFTFGGGTKVEIKRT** |
| 12F6 scFv-Fc L2 hMN20A10N scFv DNA | 81 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcaccccctgtgacag<br>tgagcagcggcggcggaggctccggcggaggtggcagcggcggcggcggctctga<br>tatccagatgacacagagccccagctctctgtctgcttctgtgggcgacagagtgaccat<br>gacctgtagagcctcctcaagcgtgtcctacatgcactggtaccagcaaacacctggca<br>aggccccaaagccttggatctacgccacctctaatctggccagcggcgtgccttctagat<br>tcagcggcagcggatctggcaccgattacaccctgaccatcagcagcctgcagcccga<br>ggatatcgccacatactactgccagcagtggagctccaatcctcctaccttcggccagg<br>gcaccaagctgcagatcacaagagagcccaaatcttgtgacaaaactcacacatgccc<br>accgtgcccagcacctgaactcctggggggaccgtcagtcttcctcttccccccaaaac<br>ccaaggacaccctcatgatctcccggacccctgaggtcacatgcgtggtggtggacgtg<br>agccacgaagaccctgaggtcaagttcaactggtacgtggacggcgtggaggtgcata<br>atgccaagacaaagccgcgggaggagcagtacaacagcacgtaccgtgtggtcagcg<br>tcctcaccgtcctgcaccaggactggctgaatggcaaggagtacaagtgcaaggtctcc<br>aacaaagccctcccagcccccatcgagaaaaccatctccaaagccaaagggcagccc<br>cgagaaccacaggtgtacaccctgcccccatcccgggaggagatgaccaagaaccag<br>gtcagcctgacctgcctggtcaaaggcttctatcccagcgacatcgccgtggagtggga<br>gagcaatgggcagccggagaacaactacaagaccacgcctcccgtgctggactccga<br>cggctccttcttcctctacagcaagctcaccgtggacaagagcaggtggcagcagggg<br>aacgtcttctcatgctccgtgatgcatgaggctctgcacaaccactacacgcagaagagc<br>ctctccctgtctccgggtaaaggcggcgggggagcggtggtggcggtagcaccggt<br>caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcggtgataa |
| 12F6 scFv-Fc L2 hMN20A10N scFv amino acid | 82 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSGGGGSGGGGSGGGGSDIQMTQSPSSLSASVG<br>DRVTMTCRASSSVSYMHWYQQTPGKAPKPWIYATSNL<br>ASGVPSRFSGSGSGTDYTLTISSLQPEDIATYYCQQWSS<br>NPPTFGQGTKLQITREPKSCDKTHTCPPCPAPELLGGPSV<br>FLFPPKPKDTLMISRTPEVTCVVVDVSHEDPEVKFNWY<br>VDGVEVHNAKTKPREEQYNSTYRVVSVLTVLHQDWLN<br>GKEYKCKVSNKALPAPIEKTISKAKGQPREPQVYTLPPS<br>REEMTKNQVSLTCLVKGFYPSDIAVEWESNGQPENNYK<br>TTPPVLDSDGSFFLYSKLTVDKSRWQQGNVFSCSVMHE<br>ALHNHYTQKSLSLSPGKGGGGSGGGGSTGQVQLVESG<br>GGLVKPGGSLRLSCAASGFTFSTYAMSWIRQAPGKGLE<br>WVASIGRAGSTYYSDSVKGRFTISRDNAKNSLYLQMNS<br>LRAEDTAVYYCARGPIYNDYDEFAYWGQGTLVTVSSG<br>GGGSGGGGSGGGGSEIVLTQSPATLSLSPGERATLSCKS<br>SQSVLYSSNQKNYLAWYQQKPGQAPRLLIYWASTRESG<br>IPARFSGSGSGTDFTLTISSLEPEDFAVYYCHQYLSSLTF<br>GGGTKVEIKR-- |
| 12F6 scFv-Fc L2 hMNC2 scFv DNA | 83 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcaccccctgtgacag<br>tgagcagcggcggcggaggctccggcggaggtggcagcggcggcggcggctctga<br>tatccagatgacacagagccccagctctctgtctgcttctgtgggcgacagagtgaccat<br>gacctgtagagcctcctcaagcgtgtcctacatgcactggtaccagcaaacacctggca<br>aggccccaaagccttggatctacgccacctctaatctggccagcggcgtgccttctagat<br>tcagcggcagcggatctggcaccgattacaccctgaccatcagcagcctgcagcccga |

TABLE 7-continued

| Exemplary Sequences of Antibodies that bind to MUC1* and CD3 | | |
|---|---|---|
| Construct | SEQ ID NO | Sequence |
| | | ggatatcgccacatactactgccagcagtggagctccaatcctcctaccttcggccagg<br>gcaccaagctgcagatcacaagagagcccaaatcttgtgacaaaactcacacatgccc<br>accgtgcccagcacctgaactcctggggggaccgtcagtcttcctcttccccccaaaac<br>ccaaggacaccctcatgatctcccggacccctgaggtcacatgcgtggtggtggacgtg<br>agccacgaagaccctgaggtcaagttcaactggtacgtggacggcgtggaggtgcata<br>atgccaagacaaagccgcgggaggagcagtacaacagcacgtaccgtgtggtcagcg<br>tcctcaccgtcctgcaccaggactggctgaatggcaaggagtacaagtgcaaggtctcc<br>aacaaagccctcccagcccccatcgagaaaaccatctccaaagccaaagggcagccc<br>cgagaaccacaggtgtacaccctgcccccatcccgggaggagatgaccaagaaccag<br>gtcagcctgacctgcctggtcaaaggcttctatcccagcgacatcgccgtggagtggga<br>gagcaatgggcagccggagaacaactacaagaccacgcctcccgtgctggactccga<br>cggctccttcttcctctacagcaagctcaccgtggacaagagcaggtggcagcagggg<br>aacgtcttctcatgctccgtgatgcatgaggctctgcacaaccactacacgcagaagagc<br>ctctccctgtctccgggtaaaggcggcgggggagcggtggtggcggtagcaccggt<br>gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaacttgataa |
| 12F6 scFv-Fc L2<br>hMNC2 scFv<br>Amino acid | 84 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSGGGGSGGGGSGGGGSDIQMTQSPSSLSASVG<br>DRVTMTCRASSSVSYMHWYQQTPGKAPKPWIYATSNL<br>ASGVPSRFSGSGSGTDYTLTISSLQPEDIATYYCQQWSS<br>NPPTFGQGTKLQITREPKSCDKTHTCPPCPAPELLGGPSV<br>FLFPPKPKDTLMISRTPEVTCVVVDVSHEDPEVKFNWY<br>VDGVEVHNAKTKPREEQYNSTYRVVSVLTVLHQDWLN<br>GKEYKCKVSNKALPAPIEKTISKAKGQPREPQVYTLPPS<br>REEMTKNQVSLTCLVKGFYPSDIAVEWESNGQPENNYK<br>TTPPVLDSDGSFFLYSKLTVDKSRWQQGNVFSCSVMHE<br>ALHNHYTQKSLSLSPGKGGGGSGGGGSTGEVQLVESGG<br>GLVKPGGSLRLSCAASGFTFSGYAMSWVRQAPGKGLE<br>WVSTISSGGTYIYYPDSVKGRFTISRDNAKNSLYLQMNS<br>LRAEDTAVYYCARLGGDNYYEYFDVWGKGTTVTVSSG<br>GGGSGGGGSGGGGSDIVLTQSPASLAVSPGQRATITCRA<br>SKSVSTSGYSYMHWYQQKPGQPPKLLIYLASNLESGVP<br>ARFSGSGSGTDFTLTINPVEANDTANYYCQHSRELPFTF<br>GGGTKVEIKRT** |
| Human IgG1 HEAVY<br>CHAIN OKT3 L1<br>hMN20A10N scFv<br>DNA | 85 | caggttcaactggttcagagcggtggaggtgtggttcagcctggtcgtagcctgagact<br>gagctgcaaggcctccggctacacctttacaagatacactatgcactgggtcagacagg<br>cccctggcaagggcctggaatggattggctacatcaaccctagccggggatataccaa<br>ctacaaccagaaagtgaaggacagattcaccatcagcacagataagtccaagtccacc<br>gctttcctgcagatggactccctgcgtccagaggacacagctgtgtactactgcgcccg<br>gtactacgacgaccattactgtctggattactggggtcagggaaccaccctgaccgttag<br>cagtgctagcaccaagggcccatcggtcttccccctggcaccctcctccaagagcacct<br>ctgggggcacagcggccctgggctgcctggtcaaggactacttccccgagccggtga<br>cggtgtcgtggaactcaggcgccctgaccagcggcgtgcacaccttcccggctgtccta<br>cagtcctcaggactctactccctcagcagcgtggtgaccgtgccctccagcagcttggg<br>cacccagacctacatctgcaacgtgaatcacaagcccagcaacaccaaggtggacaag<br>aaagttgagcccaaatcttgtgacaaaactcacacatgcccaccgtgcccagcacctga<br>actcctggggggaccgtcagtcttcctcttccccccaaaacccaaggacaccctcatgat<br>ctcccggacccctgaggtcacatgcgtggtggtggacgtgagccacgaagaccctgag<br>gtcaagttcaactggtacgtggacggcgtggaggtgcataatgccaagacaaagccgc<br>gggaggagcagtacaacagcacgtaccgtgtggtcagcgtcctcaccgtcctgcacca<br>ggactggctgaatggcaaggagtacaagtgcaaggtctccaacaaagccctcccagcc<br>cccatcgagaaaaccatctccaaagccaaagggcagccccgagaaccacaggtgtac<br>accctgcccccatcccgggaggagatgaccaagaaccaggtcagcctgacctgcctg<br>gtcaaaggcttctatcccagcgacatcgccgtggagtgggagagcaatgggcagccg<br>gagaacaactacaagaccacgcctcccgtgctggactccgacggctccttcttcctctac<br>agcaagctcaccgtggacaagagcaggtggcagcaggggaacgtcttctcatgctccg<br>tgatgcatgaggctctgcacaaccactacacgcagaagagcctctccctgtctccgggt<br>aaaggcgggggtggcggttctggtggtggtggctctggaggaggaaccggtcaggtg<br>cagctggttgaatctggcggcggacttgtgaagcctggcggatctctgagactgagctgt<br>gccgccagcggcttcacctttagcacatacgccatgagctggatcagacaggcccctg |

TABLE 7-continued

| Exemplary Sequences of Antibodies that bind to MUC1* and CD3 | | |
|---|---|---|
| Construct | SEQ ID NO | Sequence |
| | | gcaaaggcctggaatgggtggcgtctattggcagagccggcagcacctactacagcga<br>ctctgtgaagggcagattcaccatcagccgggacaacgccaagaacagcctgtacctg<br>cagatgaactccctgagagccgaggacaccgccgtgtactattgtgccagaggaccca<br>tctacaacgactacgacgagttcgcctattggggccagggcacactggtcacagtttcta<br>gcggcggtggcggaagcggaggcggtggctccggtggcggaggcagcgaaattgtg<br>ctgacacagagccccgccacactgtcactttctccaggcgaaagagccacactgagct<br>gcaagagcagccagagcgtgctgtactccagcaaccagaagaactacctggcctggta<br>tcagcagaagcccggccaagctcctcggctgctgatctattgggccagcacaagagag<br>agcggcatccctgccagatttctggcagcggctctggcaccgatttcaccctgaccata<br>agcagcctggaacctgaggacttcgccgtgtattactgccaccagtacctgagcagcct<br>gacctttggcggaggcaccaaggtggaaatcaagcggtgataa |
| Human IgG1 HEAVY CHAIN OKT3 L1 hMN20A10N scFv Amino acid | 86 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGGSG<br>GGGSGGGTGQVQLVESGGGLVKPGGSLRLSCAASGFTF<br>STYAMSWIRQAPGKGLEWVASIGRAGSTYYSDSVKGRF<br>TISRDNAKNSLYLQMNSLRAEDTAVYYCARGPIYNDYD<br>EFAYWGQGTLVTVSSGGGGSGGGGSGGGGSEIVLTQSP<br>ATLSLSPGERATLSCKSSQSVLYSSNQKNYLAWYQQKP<br>GQAPRLLIYWASTRESGIPARFSGSGSGTDFTLTISSLEPE<br>DFAVYYCHQYLSSLTFGGGTKVEIKR-- |
| Human IgG1 HEAVY CHAIN OKT3 L1 hMNC2 scFv | 87 | caggttcaactggttcagagcggtggaggtgtggttcagcctggtcgtagcctgagact<br>gagctgcaaggcctccggctacacctttacaagatacactatgcactgggtcagacagg<br>cccctggcaagggcctggaatggattggctacatcaaccctagccggggatataccaa<br>ctacaaccagaaagtgaaggacagattcaccatcagcacagataagtccaagtccacc<br>gctttcctgcagatggactccctgcgtccagaggacacagctgtgtactactgcgcccg<br>gtactacgacgaccattactgtctggattactggggtcagggaaccaccctgaccgttag<br>cagtgctagcaccaagggcccatcggtcttccccctggcaccctcctccaagagcacct<br>ctgggggcacagcggccctgggctgcctggtcaaggactacttccccgagccggtga<br>cggtgtcgtggaactcaggcgccctgaccagcggcgtgcacaccttcccggctgtccta<br>cagtcctcaggactctactccctcagcagcgtggtgaccgtgccctccagcagcttggg<br>cacccagacctacatctgcaacgtgaatcacaagcccagcaacaccaaggtggacaag<br>aaagttgagcccaaatcttgtgacaaaactcacacatgcccaccgtgcccagcacctga<br>actcctggggggaccgtcagtcttcctcttccccccaaaacccaaggacaccctcatgat<br>ctcccggacccctgaggtcacatgcgtggtggtggacgtgagccacgaagaccctgag<br>gtcaagttcaactggtacgtggacggcgtggaggtgcataatgccaagacaaagccgc<br>gggaggagcagtacaacagcacgtaccgtgtggtcagcgtcctcaccgtcctgcacca<br>ggactggctgaatggcaaggagtacaagtgcaaggtctccaacaaagccctcccagcc<br>cccatcgagaaaaccatctccaaagccaaagggcagccccgagaaccacaggtgtac<br>accctgcccccatcccgggaggagatgaccaagaaccaggtcagcctgacctgcctg<br>gtcaaaggcttctatcccagcgacatcgccgtggagtgggagagcaatgggcagccg<br>gagaacaactacaagaccacgcctcccgtgctggactccgacggctccttcttcctctac<br>agcaagctcaccgtggacaagagcaggtggcagcaggggaacgtcttctcatgctccg<br>tgatgcatgaggctctgcacaaccactacacgcagaagagcctctccctgtctccgggt<br>aaaggcgggggtggcggttctggtggtggtggctctggaggaggaaccggtgaggtg<br>cagctggtggagtctgggggaggcctggtcaagcctggggggtccctgagactctcct<br>gtgcagcctctggattcaccttcagtggctatgccatgagctgggtccgccaggctccag<br>ggaaggggctggagtgggtctcaaccattagtagtggcggaacctacatatactacccc<br>gactcagtgaagggccgattcaccatctccagagacaacgccaagaactcactgtatct<br>gcaaatgaacagcctgagagccgaggacacggccgtgtattactgtgcgagacttggg<br>gggataattactacgaatacttcgatgtctggggcaaagggaccacggtcaccgtctc<br>ctccggcggtggcggatccggcggtggcggatccggcggtggcggatccgacattgt<br>gctgacccagtctccagcctccttggccgtgtctccaggacagagggccaccatcacct<br>gcagagccagtaagagtgtcagtaccagcggatactcctacatgcactggtatcagcag<br>aaaccaggacaacctcctaaactcctgatttacctggcatccaatctggagagcggggtc<br>ccagccaggttcagcggcagtgggtctgggaccgatttcaccctcacaattaatcctgtg<br>gaagctaatgatactgcaaattattactgtcagcacagtagggagctgcctttcacattcg<br>gcggagggaccaaggtggagatcaaacgaacttgataa |
| Human IgG1 HEAVY CHAIN OKT3 L1 hMNC2 scFv | 88 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSASTKGPSVFPLAPSSKSTSGGTAALGCLVKD<br>YFPEPVTVSWNSGALTSGVHTFPAVLQSSGLYSLSSVVT |

TABLE 7-continued

Exemplary Sequences of Antibodies that bind to MUC1* and CD3

| Construct | SEQ ID NO | Sequence |
| --- | --- | --- |
| | | VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGGSG<br>GGGSGGGTGEVQLVESGGGLVKPGGSLRLSCAASGFTF<br>SGYAMSWVRQAPGKGLEWVSTISSGGTYIYYPDSVKGR<br>FTISRDNAKNSLYLQMNSLRAEDTAVYYCARLGGDNY<br>YEYFDVWGKGTTVTVSSGGGGSGGGGSGGGGSDIVLT<br>QSPASLAVSPGQRATITCRASKSVSTSGYSYMHWYQQK<br>PGQPPKLLIYLASNLESGVPARFSGSGSGTDFTLTINPVE<br>ANDTANYYCQHSRELPFTFGGGTKVEIKRT** |
| Human IgG1 HEAVY CHAIN OKT3 L2 hMN20A10N scFv | 89 | caggttcaactggttcagagcggtggaggtgtggttcagcctggtcgtagcctgagact<br>gagctgcaaggcctccggctacacctttacaagatacactatgcactgggtcagacagg<br>cccctggcaagggcctggaatggattggctacatcaaccctagccggggatataccaa<br>ctacaaccagaaagtgaaggacagattcaccatcagcacagataagtccaagtccacc<br>gctttcctgcagatggactccctgcgtccagaggacacagctgtgtactactgcgcccg<br>gtactacgacgaccattactgtctggattactggggtcagggaaccaccctgaccgttag<br>cagtgctagcaccaagggcccatcggtcttccccctggcaccctcctccaagagcacct<br>ctgggggcacagcggccctgggctgcctggtcaaggactacttccccgagccggtga<br>cggtgtcgtggaactcaggcgccctgaccagcggcgtgcacaccttcccggctgtccta<br>cagtcctcaggactctactccctcagcagcgtggtgaccgtgccctccagcagcttggg<br>cacccagacctacatctgcaacgtgaatcacaagcccagcaacaccaaggggacaag<br>aaagttgagcccaaatcttgtgacaaaactcacacatgcccaccgtgcccagcacctga<br>actcctggggggaccgtcagtcttcctcttccccccaaaacccaaggacaccctcatgat<br>ctcccggacccctgaggtcacatgcgtggtggtggacgtgagccacgaagaccctgag<br>gtcaagttcaactggtacgtggacggcgtggaggtgcataatgccaagacaaagccgc<br>gggaggagcagtacaacagcacgtaccgtgtggtcagcgtcctcaccgtcctgcacca<br>ggactggctgaatggcaaggagtacaagtgcaaggtctccaacaaagccctcccagcc<br>cccatcgagaaaaccatctccaaagccaaagggcagccccgagaaccacaggtgtac<br>accctgcccccatcccgggaggagatgaccaagaaccaggtcagcctgacctgcctg<br>gtcaaaggcttctatcccagcgacatcgccgtggagtgggagagcaatgggcagccg<br>gagaacaactacaagaccacgcctcccgtgctggactccgacggctccttcttcctctac<br>agcaagctcaccgtggacaagagcaggtggcagcaggggaacgtcttctcatgctccg<br>tgatgcatgaggctctgcacaaccactacacgcagaagagcctctccctgtctccgggt<br>aaaggcggcgggggggagcggtggtggcggtagcaccggtcaggtgcagctggttga<br>atctggcggcggacttgtgaagcctggcggatctctgagactgagctgtgccgccagc<br>ggcttcacctttagcacatacgccatgagctggatcagacaggcccctggcaaaggcct<br>ggaatgggtggcgtctattggcagagccggcagcacctactacagcgactctgtgaag<br>ggcagattcaccatcagccgggacaacgccaagaacagcctgtacctgcagatgaact<br>ccctgagagccgaggacaccgccgtgtactattgtgccagaggacccatctacaacga<br>ctacgacgagttcgcctattggggccagggcacactggtcacagtttctagcggcggtg<br>gcggaagcggaggcggtggctccggtggcggaggcagcgaaattgtgctgacacag<br>agccccgccacactgtcactttctccaggcgaaagagccacactgagctgcaagagca<br>gccagagcgtgctgtactccagcaaccagaagaactacctggcctggtatcagcagaa<br>gcccggccaagctcctcggctgctgatctattgggccagcacaagagagagcggcatc<br>cctgccagattttctggcagcggctctggcaccgatttcaccctgaccataagcagcctg<br>gaacctgaggacttcgccgtgtattactgccaccagtacctgagcagcctgacctttggc<br>ggaggcaccaaggtggaaatcaagcggtgataa |
| Human IgG1 HEAVY CHAIN OKT3 L2 hMN20A10N scFv | 90 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGSGG<br>GGSTGQVQLVESGGGLVKPGGSLRLSCAASGFTFSTYA<br>MSWIRQAPGKGLEWVASIGRAGSTYYSDSVKGRFTISR<br>DNAKNSLYLQMNSLRAEDTAVYYCARGPIYNDYDEFA<br>YWGQGTLVTVSSGGGGSGGGGSGGGGSEIVLTQSPATL<br>SLSPGERATLSCKSSQSVLYSSNQKNYLAWYQQKPGQA<br>PRLLIYWASTRESGIPARFSGSGSGTDFTLTISSLEPEDFA<br>VYYCHQYLSSLTFGGGTKVEIKR-- |
| Human IgG1 HEAVY CHAIN OKT3 L2 | 91 | caggttcaactggttcagagcggtggaggtgtggttcagcctggtcgtagcctgagact<br>gagctgcaaggcctccggctacacctttacaagatacactatgcactgggtcagacagg |

TABLE 7-continued

Exemplary Sequences of Antibodies that bind to MUC1* and CD3

| Construct | SEQ ID NO | Sequence |
|---|---|---|
| hMNC2 scFv | | cccctggcaagggcctggaatggattggctacatcaaccctagccggggatataccaa ctacaaccagaaagtgaaggacagattcaccatcagcacagataagtccaagtccacc gctttcctgcagatggactccctgcgtccagaggacacagctgtgtactactgcgcccg gtactacgacgaccattactgtctggattactggggtcagggaaccaccctgaccgttag cagtgctagcaccaagggcccatcggtcttcccctggcaccctcctccaagagcacct ctgggggcacagcggccctgggctgcctggtcaaggactacttccccgagccggtga cggtgtcgtggaactcaggcgccctgaccagcggcgtgcacaccttcccggctgtccta cagtcctcaggactctactccctcagcagcgtggtgaccgtgccctccagcagcttggg cacccagacctacatctgcaacgtgaatcacaagcccagcaacaccaaggtggacaag aaagttgagcccaaatcttgtgacaaaactcacacatgcccaccgtgcccagcacctga actcctggggggaccgtcagtcttcctcttccccccaaaacccaaggacaccctcatgat ctcccggacccctgaggtcacatgcgtggtggtggacgtgagccacgaagaccctgag gtcaagttcaactggtacgtggacggcgtggaggtgcataatgccaagacaaagccgc gggaggagcagtacaacagcacgtaccgtgtggtcagcgtcctcaccgtcctgcacca ggactggctgaatggcaaggagtacaagtgcaaggtctccaacaaagccctcccagcc cccatcgagaaaaccatctccaaagccaaagggcagccccgagaaccacaggtgtac accctgcccccatcccgggaggagatgaccaagaaccaggtcagcctgacctgcctg gtcaaaggcttctatcccagcgacatcgccgtggagtgggagagcaatgggcagccg gagaacaactacaagaccacgcctcccgtgctggactccgacggctccttcttcctctac agcaagctcaccgtggacaagagcaggtggcagcaggggaacgtcttctcatgctccg tgatgcatgaggctctgcacaaccactacacgcagaagagcctctccctgtctccgggt aaaggcggcgggggggagcggtggtggcggtagcaccggtgaggtgcagctggtgg agtctgggggaggcctggtcaagcctggggggtccctgagactctcctgtgcagcctct ggattcaccttcagtggctatgccatgagctgggtccgccaggctccagggaaggggct ggagtgggtctcaaccattagtagtggcggaacctacatatactaccccgactcagtgaa gggccgattcaccatctccagagacaacgccaagaactcactgtatctgcaaatgaaca gcctgagagccgaggacacggccgtgtattactgtgcgagacttggggggggataatta ctacgaatacttcgatgtctggggcaaagggaccacggtcaccgtctcctccggcggtg gcggatccggcggtggcggatccggcggtggcggatccgacattgtgctgacccagt ctccagcctccttggccgtgtctccaggacagagggccaccatcacctgcagagccagt aagagtgtcagtaccagcggatactcctacatgcactggtatcagcagaaaccaggaca acctcctaaactcctgatttacctggcatccaatctggagagcggggtcccagccaggtt cagcggcagtgggtctgggaccgatttcaccctcacaattaatcctgtggaagctaatga tactgcaaattattactgtcagcacagtagggagctgcctttcacattcggcggagggac caaggtggagatcaaacgaacttgataa |
| Human IgG1 HEAVY CHAIN OKT3 L2 hMNC2 scFv | 92 | QVQLVQSGGGVVQPGRSLRLSCKASGYTFTRYTMHWV RQAPGKGLEWIGYINPSRGYTNYNQKVKDRFTISTDKS KSTAFLQMDSLRPEDTAVYYCARYYDDHYCLDYWGQ GTTLTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKAK GQPREPQVYTLPPSREEMTKNQVSLTCLVKGFYPSDIAV EWESNGQPENNYKTTPPVLDSDGSFFLYSKLTVDKSRW QQGNVFSCSVMHEALHNHYTQKSLSLSPGKGGGGSGG GGSTGEVQLVESGGGLVKPGGSLRLSCAASGFTFSGYA MSWVRQAPGKGLEWVSTISSGGTYIYYPDSVKGRFTISR DNAKNSLYLQMNSLRAEDTAVYYCARLGGDNYYEYF DVWGKGTTVTVSSGGGGSGGGGSGGGGSDIVLTQSPAS LAVSPGQRATITCRASKSVSTSGYSYMHWYQQKPGQPP KLLIYLASNLESGVPARFSGSGSGTDFTLTINPVEANDTA NYYCQHSRELPFTFGGGTKVEIKRT** |
| Human IgG1 HEAVY CHAIN 12F6 L1 hMN20A10N scFv | 93 | caagtgcagctggtgcagtccggaggaggcgtcgtgcagcctggaagaagcctccgg ctgagctgcaaggccagcggctatacattcaccagctacaccatgcactgggtgcggc aggcccctggcaaaggcctggaatggatcggctacatcaacccttccagcggctacac caagtacaaccagaaattcaaggaccggtttaccattagcgccgataagagcaagagc acagcctttctgcagatggacagcctgagaccagaggacaccggcgtgtacttctgcgc ccgctggcaggactacgacgtttatttcgactactggggccagggcaccccctgtgacag tgagcagcgctagcaccaagggcccatcggtcttcccctggcaccctcctccaagag cacctctgggggcacagcggccctgggctgcctggtcaaggactacttccccgagccg gtgacggtgtcgtggaactcaggcgccctgaccagcggcgtgcacaccttcccggctg tcctacagtcctcaggactctactccctcagcagcgtggtgaccgtgccctccagcagct tgggcacccagacctacatctgcaacgtgaatcacaagcccagcaacaccaaggtgga caagaaagttgagcccaaatcttgtgacaaaactcacacatgcccaccgtgcccagcac ctgaactcctggggggaccgtcagtcttcctcttccccccaaaacccaaggacaccctc atgatctcccggacccctgaggtcacatgcgtggtggtggacgtgagccacgaagacc ctgaggtcaagttcaactggtacgtggacggcgtggaggtgcataatgccaagacaaa gccgcgggaggagcagtacaacagcacgtaccgtgtggtcagcgtcctcaccgtcctg caccaggactggctgaatggcaaggagtacaagtgcaaggtctccaacaaagccctcc cagcccccatcgagaaaaccatctccaaagccaaagggcagccccgagaaccacag gtgtacaccctgcccccatcccgggaggagatgaccaagaaccaggtcagcctgacct |

TABLE 7-continued

Exemplary Sequences of Antibodies that bind to MUC1* and CD3

| Construct | SEQ ID NO | Sequence |
|---|---|---|
| | | gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcgggggtggcggttctggtggtggtggctctggaggaggaaccggtca<br>ggtgcagctggttgaatctggcggcggacttgtgaagcctggcggatctctgagactga<br>gctgtgccgccagcggcttcacctttagcacatacgccatgagctggatcagacaggcc<br>cctggcaaaggcctggaatgggtggcgtctattggcagagccggcagcacctactaca<br>gcgactctgtgaagggcagattcaccatcagccgggacaacgccaagaacagcctgta<br>cctgcagatgaactccctgagagccgaggacaccgccgtgtactattgtgccagagga<br>cccatctacaacgactacgacgagttcgcctattggggccagggcacactggtcacagt<br>ttctagcggcggtggcggaagcggaggcggtggctccggtggcggaggcagcgaaa<br>ttgtgctgacacagagccccgccacactgtcactttctccaggcgaaagagccacactg<br>agctgcaagagcagccagagcgtgctgtactccagcaaccagaagaactacctggcct<br>ggtatcagcagaagcccggccaagctcctcggctgctgatctattgggccagcacaag<br>agagagcggcatccctgccagattttctggcagcggctctggcaccgatttcaccctgac<br>cataagcagcctggaacctgaggacttcgccgtgtattactgccaccagtacctgagca<br>gcctgacctttggcggaggcaccaaggtggaaatcaagcggtgataa |
| Human IgG1 HEAVY<br>CHAIN 12F6 L1<br>hMN20A10N scFv | 94 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGGSGGG<br>GSGGGTGQVQLVESGGGLVKPGGSLRLSCAASGFTFST<br>YAMSWIRQAPGKGLEWVASIGRAGSTYYSDSVKGRFTI<br>SRDNAKNSLYLQMNSLRAEDTAVYYCARGPIYNDYDE<br>FAYWGQGTLVTVSSGGGGSGGGGSGGGGSEIVLTQSPA<br>TLSLSPGERATLSCKSSQSVLYSSNQKNYLAWYQQKPG<br>QAPRLLIYWASTRESGIPARFSGSGSGTDFTLTISSLEPED<br>FAVYYCHQYLSSLTFGGGTKVEIKR-- |
| Human IgG1 HEAVY<br>CHAIN 12F6 L1<br>hMNC2 scFv | 95 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcacccctgtgacag<br>tgagcagcgctagcaccaagggcccatcggtcttccccctggcaccctcctccaagag<br>cacctctgggggcacagcggccctgggctgcctggtcaaggactacttccccgagccg<br>gtgacggtgtcgtggaactcaggcgccctgaccagcggcgtgcacaccttcccggctg<br>tcctacagtcctcaggactctactccctcagcagcgtggtgaccgtgccctccagcagct<br>tgggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggaggagatgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcgggggtggcggttctggtggtggtggctctggaggaggaaccggtga<br>ggtgcagctggtggagtctgggggaggcctggtcaagcctggggggtccctgagact<br>ctcctgtgcagcctctggattcaccttcagtggctatgccatgagctgggtccgccaggct<br>ccagggaaggggctggagtgggtctcaaccattagtagtggcggaacctacatatacta<br>ccccgactcagtgaagggccgattcaccatctccagagacaacgccaagaactcactgt<br>atctgcaaatgaacagcctgagagccgaggacacggccgtgtattactgtgcgagactt<br>ggggggggataattactacgaatacttcgatgtctggggcaaagggaccacggtcaccgt<br>ctcctccggcggtggaggatctggcggaggtggatccggcggtggcggatctgacatt<br>gtgctgacccagtctccagcctccttggccgtgtctccaggacagagggccaccatcac<br>ctgcagagccagtaagagtgtcagtaccagcggatactcctacatgcactggtatcagc<br>agaaaccaggacaacctcctaaactcctgatttacctggcatccaatctggagagcggg<br>gtcccagccaggttcagcggcagtgggtctgggaccgatttcaccctcacaattaatcct |

TABLE 7-continued

Exemplary Sequences of Antibodies that bind to MUC1* and CD3

| Construct | SEQ ID NO | Sequence |
|---|---|---|
| | | gtggaagctaatgatactgcaaattattactgtcagcacagtagggagctgcctttcacat<br>tcggcggagggaccaaggtggagatcaaacgaacttgataa |
| Human IgG1 HEAVY<br>CHAIN 12F6 L1<br>hMNC2 scFv | 96 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGGSGGG<br>GSGGGTGEVQLVESGGGLVKPGGSLRLSCAASGFTFSG<br>YAMSWVRQAPGKGLEWVSTISSGGTYIYYPDSVKGRFT<br>ISRDNAKNSLYLQMNSLRAEDTAVYYCARLGGDNYYE<br>YFDVWGKGTTVTVSSGGGGSGGGGSGGGGSDIVLTQSP<br>ASLAVSPGQRATITCRASKSVSTSGYSYMHWYQQKPGQ<br>PPKLLIYLASNLESGVPARFSGSGSGTDFTLTINPVEAND<br>TANYYCQHSRELPFTFGGGTKVEIKRT** |
| Human IgG1 HEAVY<br>CHAIN 12F6 L2<br>hMN20A10N scFv | 97 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcaccccctgtgacag<br>tgagcagcgctagcaccaagggcccatcggtcttccccctggcaccctcctccaagag<br>cacctctgggggcacagcggccctgggctgcctggtcaaggactacttccccgagccg<br>gtgacggtgtcgtggaactcaggcgccctgaccagcggcgtgcacaccttcccggctg<br>tcctacagtcctcaggactctactccctcagcagcgtggtgaccgtgccctccagcagct<br>tgggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggaggagatgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcggcgggggagcggtggtggcggtagcaccggtcaggtgcagctg<br>gttgaatctggcggcggacttgtgaagcctggcggatctctgagactgagctgtgccgc<br>cagcggcttcacctttagcacatacgccatgagctggatcagacaggcccctggcaaag<br>gcctggaatgggtggcgtctattggcagagccggcagcacctactacagcgactctgtg<br>aagggcagattcaccatcagccgggacaacgccaagaacagcctgtacctgcagatg<br>aactccctgagagccgaggacaccgccgtgtactattgtgccagaggacccatctacaa<br>cgactacgacgagttcgcctattggggccagggcacactggtcacagtttctagcggcg<br>gtggcggaagcggaggcggtggctccggtggcggaggcagcgaaattgtgctgaca<br>cagagccccgccacactgtcactttctccaggcgaaagagccacactgagctgcaaga<br>gcagccagagcgtgctgtactccagcaaccagaagaactacctggcctggtatcagca<br>gaagcccggccaagctcctcggctgctgatctattgggccagcacaagagagagcgg<br>catccctgccagatttctggcagcggctctggcaccgatttcaccctgaccataagcag<br>cctggaacctgaggacttcgccgtgtattactgccaccagtacctgagcagcctgacctttt<br>ggcggaggcaccaaggtggaaatcaagcggtgataa |
| Human IgG1 HEAVY<br>CHAIN 12F6 L2<br>hMN20A10N scFv | 98 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGSGGGG<br>STGQVQLVESGGGLVKPGGSLRLSCAASGFTFSTYAMS<br>WIRQAPGKGLEWVASIGRAGSTYYSDSVKGRFTISRDN |

TABLE 7-continued

Exemplary Sequences of Antibodies that bind to MUC1* and CD3

| Construct | SEQ ID NO | Sequence |
|---|---|---|
| | | AKNSLYLQMNSLRAEDTAVYYCARGPIYNDYDEFAYW<br>GQGTLVTVSSGGGGSGGGGSGGGGSEIVLTQSPATLSLS<br>PGERATLSCKSSQSVLYSSNQKNYLAWYQQKPGQAPRL<br>LIYWASTRESGIPARFSGSGSGTDFTLTISSLEPEDFAVY<br>YCHQYLSSLTFGGGTKVEIKR-- |
| Human IgG1 HEAVY CHAIN 12F6 L2 hMNC2 scFv | 99 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcacccctgtgacag<br>tgagcagcgctagcaccaagggcccatcggtcttccccctggcaccctcctccaagag<br>cacctctgggggcacagcggccctgggctgcctggtcaaggactacttccccgagccg<br>gtgacggtgtcgtggaactcaggcgccctgaccagcggcgtgcacaccttcccggctg<br>tcctacagtcctcaggactctactccctcagcagcgtggtgaccgtgccctccagcagct<br>tgggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggaggagatgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcggcgggggagcggtggtggcggtagcaccggtgaggtgcagctg<br>gtggagtctgggggaggcctggtcaagcctggggggtccctgagactctcctgtgcag<br>cctctggattcaccttcagtggctatgccatgagctgggtccgccaggctccagggaag<br>gggctggagtgggtctcaaccattagtagtggcggaacctacatatactaccccgactca<br>gtgaagggccgattcaccatctccagagacaacgccaagaactcactgtatctgcaaat<br>gaacagcctgagagccgaggacacggccgtgtattactgtgcgagacttggggggat<br>aattactacgaatacttcgatgtctggggcaaagggaccacggtcaccgtctcctccggc<br>ggtggaggatctggcggaggtggatccggcggtggcggatctgacattgtgctgaccc<br>agtctccagcctccttggccgtgtctccaggacagagggccaccatcacctgcagagcc<br>agtaagagtgtcagtaccagcggatactcctacatgcactggtatcagcagaaaccagg<br>acaacctcctaaactcctgatttacctggcatccaatctggagagcggggtcccagccag<br>gttcagcggcagtgggtctgggaccgatttcaccctcacaattaatcctgtggaagctaat<br>gatactgcaaattattactgtcagcacagtagggagctgcctttcacattcggcggaggg<br>accaaggtggagatcaaacgaacttgataa |
| Human IgG1 HEAVY CHAIN 12F6 L2 hMNC2 scFv | 100 | QVQLVQSGGGVVQPGRSLRLSCKASGYTFTSYTMHWV<br>RQAPGKGLEWIGYINPSSGYTKYNQKFKDRFTISADKSK<br>STAFLQMDSLRPEDTGVYFCARWQDYDVYFDYWGQG<br>TPVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGSGGGG<br>STGEVQLVESGGGLVKPGGSLRLSCAASGFTFSGYAMS<br>WVRQAPGKGLEWVSTISSGGTYIYYPDSVKGRFTISRDN<br>AKNSLYLQMNSLRAEDTAVYYCARLGGDNYYEYFDV<br>WGKGTTVTVSSGGGGSGGGGSGGGGSDIVLTQSPASLA<br>VSPGQRATITCRASKSVSTSGYSYMHWYQQKPGQPPKL<br>LIYLASNLESGVPARFSGSGSGTDFTLTINPVEANDTAN<br>YYCQHSRELPFTFGGGTKVEIKRT** |
| Human IgG1 HEAVY CHAIN hMN20A10N L1 OKT3 scFv | 101 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcgctagcaccaagggcccatcggtcttccccctggcaccctcctccaagagc<br>acctctgggggcacagcggccctgggctgcctggtcaaggactacttccccgagccgg<br>tgacggtgtcgtggaactcaggcgccctgaccagcggcgtgcacaccttcccggctgt<br>cctacagtcctcaggactctactccctcagcagcgtggtgaccgtgccctccagcagctt<br>gggcacccagacctacatctgcaacgtgaatcacaagcccagcaacaccaaggtgga |

TABLE 7-continued

| Exemplary Sequences of Antibodies that bind to MUC1* and CD3 | | |
|---|---|---|
| Construct | SEQ ID NO | Sequence |
| | | caagaaagttgagcccaaatcttgtgacaaaactcacacatgcccaccgtgcccagcac ctgaactcctggggggaccgtcagtcttcctcttccccccaaaacccaaggacaccctc atgatctcccggacccctgaggtcacatgcgtggtggtggacgtgagccacgaagacc ctgaggtcaagttcaactggtacgtggacggcgtggaggtgcataatgccaagacaaa gccgcgggaggagcagtacaacagcacgtaccgtgtggtcagcgtcctcaccgtcctg caccaggactggctgaatggcaaggagtacaagtgcaaggtctccaacaaagccctcc cagcccccatcgagaaaaccatctccaaagccaaagggcagccccgagaaccacag gtgtacaccctgcccccatcccgggacgagctgaccaagaaccaggtcagcctgacct gcctggtcaaaggcttctatcccagcgacatcgccgtggagtgggagagcaatgggca gccggagaacaactacaagaccacgcctcccgtgctggactccgacggctccttcttcc tctacagcaagctcaccgtggacaagagcaggtggcagcaggggaacgtcttctcatg ctccgtgatgcatgaggctctgcacaaccactacacgcagaagagcctctccctgtctcc gggtaaaggcgggggtggcggttctggtggtggtggctctggaggaggaaccggtca ggtgcaactggtgcagtccggcggaggcgtggtgcagcctggccggagcctgagact gagctgcaaggcctccggctacacctttacaagatacactatgcactgggtcagacagg cccctggcaagggcctggaatggattggctacatcaaccctagccggggatataccaa ctacaaccagaaagtgaaggacagattcaccatcagcacagataagtccaagtccacc gctttcctgcagatggactccctgcgtccagaggacacagctgtgtactactgcgcccg gtactacgacgaccactactgtctggactactggggacagggaaccaccctgaccgtca gctctggcggcggaggctccggcggaggtggcagcggcggcggcggctctgatatc cagatgacccagagcccttcttccttatctgccagcgtgggcgatagagtgaccatcaca tgcagcgccagctcttctgttagctacatgaactggtaccagcaaacacctggaaaggc cctaaaagatggatctacgacaccagcaagctggcctctggcgtgccctctagattca gcggctctggctccggcaccgactacacctttacaattagctccctgcagcccgaggat atcgccacctactactgccagcagtggagcagcaaccccttcacattcggccagggca caaagctgcaaatcaccagatgataa |
| Human IgG1 HEAVY CHAIN hMN20A10N L1 OKT3 scFv | 102 | QVQLVESGGGLVKPGGSLRLSCAASGFTFSTYAMSWIR QAPGKGLEWVASIGRAGSTYYSDSVKGRFTISRDNAKN SLYLQMNSLRAEDTAVYYCARGPIYNDYDEFAYWGQG TLVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKKVEPKSCDKTHTCP PCPAPELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKGQ PREPQVYTLPPSRDELTKNQVSLTCLVKGFYPSDIAVEW ESNGQPENNYKTTPPVLDSDGSFFLYSKLTVDKSRWQQ GNVFSCSVMHEALHNHYTQKSLSLSPGKGGGGGSGGG GSGGGTGQVQLVQSGGGVVQPGRSLRLSCKASGYTFTR YTMHWVRQAPGKGLEWIGYINPSRGYTNYNQKVKDRF TISTDKSKSTAFLQMDSLRPEDTAVYYCARYYDDHYCL DYWGQGTTLTVSSGGGGSGGGGSGGGGSDIQMTQSPSS LSASVGDRVTITCSASSSVSYMNWYQQTPGKAPKRWIY DTSKLASGVPSRFSGSGSGTDYTFTISSLQPEDIATYYCQ QWSSNPFTFGQGTKLQITR-- |
| Human IgG1 HEAVY CHAIN hMNC2 L1 OKT3 scFv | 103 | gaggtgcagctggtggagtctgggggaggcctggtcaagcctggggggtccctgaga ctctcctgtgcagcctctggattcaccttcagtggctatgccatgagctgggtccgccagg ctccagggaaggggctggagtgggtctcaaccattagtagtggcggaacctacatatac taccccgactcagtgaagggccgattcaccatctccagagacaacgccaagaactcact gtatctgcaaatgaacagcctgagagccgaggacacggccgtgtattactgtgcgagac ttggggggggataattactacgaatacttcgatgtctggggcaaagggaccacggtcacc gtctcctccgctagcaccaagggcccatcggtcttccccctggcaccctcctccaagag cacctctgggggcacagcggccctgggctgcctggtcaaggactacttccccgagccg gtgacggtgtcgtggaactcaggcgccctgaccagcggcgtgcacaccttcccggctg tcctacagtcctcaggactctactccctcagcagcgtggtgaccgtgccctccagcagct tgggcacccagacctacatctgcaacgtgaatcacaagcccagcaacaccaaggtgga caagaaagttgagcccaaatcttgtgacaaaactcacacatgcccaccgtgcccagcac ctgaactcctggggggaccgtcagtcttcctcttccccccaaaacccaaggacaccctc atgatctcccggacccctgaggtcacatgcgtggtggtggacgtgagccacgaagacc ctgaggtcaagttcaactggtacgtggacggcgtggaggtgcataatgccaagacaaa gccgcgggaggagcagtacaacagcacgtaccgtgtggtcagcgtcctcaccgtcctg caccaggactggctgaatggcaaggagtacaagtgcaaggtctccaacaaagccctcc cagcccccatcgagaaaaccatctccaaagccaaagggcagccccgagaaccacag gtgtacaccctgcccccatcccgggaggagatgaccaagaaccaggtcagcctgacct gcctggtcaaaggcttctatcccagcgacatcgccgtggagtgggagagcaatgggca gccggagaacaactacaagaccacgcctcccgtgctggactccgacggctccttcttcc tctacagcaagctcaccgtggacaagagcaggtggcagcaggggaacgtcttctcatg ctccgtgatgcatgaggctctgcacaaccactacacgcagaagagcctctccctgtctcc gggtaaaggcgggggtggcggttctggtggtggtggctctggaggaggaaccggtca ggtgcaactggtgcagtccggcggaggcgtggtgcagcctggccggagcctgagact gagctgcaaggcctccggctacacctttacaagatacactatgcactgggtcagacagg cccctggcaagggcctggaatggattggctacatcaaccctagccggggatataccaa ctacaaccagaaagtgaaggacagattcaccatcagcacagataagtccaagtccacc |

TABLE 7-continued

Exemplary Sequences of Antibodies that bind to MUC1* and CD3

| Construct | SEQ ID NO | Sequence |
|---|---|---|
| | | gctttcctgcagatggactccctgcgtccagaggacacagctgtgtactactgcgcccg<br>gtactacgacgaccactactgtctggactactggggacagggaaccaccctgaccgtca<br>gctctggcggcggaggctccggcggaggtggcagcggcggcggcggctctgatatc<br>cagatgacccagagcccttcttccttatctgccagcgtgggcgatagagtgaccatcaca<br>tgcagcgccagctcttctgttagctacatgaactggtaccagcaaacacctggaaaggc<br>ccctaaaagatggatctacgacaccagcaagctggcctctggcgtgccctctagattca<br>gcggctctggctccggcaccgactacacctttacaattagctccctgcagcccgaggat<br>atcgccacctactactgccagcagtggagcagcaaccccttcacattcggccagggca<br>caaagctgcaaatcaccagatgataa |
| Human IgG1 HEAVY CHAIN hMNC2 L1 OKT3 scFv | 104 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGGSG<br>GGGSGGGTGQVQLVQSGGGVVQPGRSLRLSCKASGYT<br>FTRYTMHWVRQAPGKGLEWIGYINPSRGYTNYNQKVK<br>DRFTISTDKSKSTAFLQMDSLRPEDTAVYYCARYYDDH<br>YCLDYWGQGTTLTVSSGGGGSGGGGSGGGGSDIQMTQ<br>SPSSLSASVGDRVTITCSASSSVSYMNWYQQTPGKAPKR<br>WIYDTSKLASGVPSRFSGSGSGTDYTFTISSLQPEDIATY<br>YCQQWSSNPFTFGQGTKLQITR** |
| Human IgG1 HEAVY CHAIN hMN20A10N L2 OKT3 scFv | 105 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcgctagcaccaagggcccatcggtcttccccctggcaccctcctccaagagc<br>acctctgggggcacagcggccctgggctgcctggtcaaggactacttccccgagccgg<br>tgacggtgtcgtggaactcaggcgccctgaccagcggcgtgcacaccttcccggctgt<br>cctacagtcctcaggactctactccctcagcagcgtggtgaccgtgccctccagcagctt<br>gggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggacgagctgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcggcgggggagcggtggtggcggtagcaccggtcaggtgcaactgg<br>tgcagtccggcggaggcgtggtgcagcctggccggagcctgagactgagctgcaagg<br>cctccggctacacctttacaagatacactatgcactgggtcagacaggcccctggcaag<br>ggcctggaatggattggctacatcaaccctagccggggatataccaactacaaccagaa<br>agtgaaggacagattcaccatcagcacagataagtccaagtccaccgctttcctgcagat<br>ggactccctgcgtccagaggacacagctgtgtactactgcgcccggtactacgacgac<br>cactactgtctggactactggggacagggaaccaccctgaccgtcagctctggcggcg<br>gaggctccggcggaggtggcagcggcggcggcggctctgatatccagatgacccag<br>agcccttcttccttatctgccagcgtgggcgatagagtgaccatcacatgcagcgccagc<br>tcttctgttagctacatgaactggtaccagcaaacacctggaaaggcccctaaaagatgg<br>atctacgacaccagcaagctggcctctggcgtgccctctagattcagcggctctggctcc<br>ggcaccgactacacctttacaattagctccctgcagcccgaggatatcgccacctactac<br>tgccagcagtggagcagcaaccccttcacattcggccagggcacaaagctgcaaatca<br>ccagatgataa |
| Human IgG1 HEAVY CHAIN hMN20A10N L2 OKT3 scFv | 106 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS |

TABLE 7-continued

| Exemplary Sequences of Antibodies that bind to MUC1* and CD3 | | |
|---|---|---|
| Construct | SEQ ID NO | Sequence |
| | | HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSRDELTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGSGGGG<br>STGQVQLVQSGGGVVQPGRSLRLSCKASGYTFTRYTM<br>HWVRQAPGKGLEWIGYINPSRGYTNYNQKVKDRFTIST<br>DKSKSTAFLQMDSLRPEDTAVYYCARYYDDHYCLDYW<br>GQGTTLTVSSGGGGSGGGGSGGGGSDIQMTQSPSSLSA<br>SVGDRVTITCSASSSVSYMNWYQQTPGKAPKRWIYDTS<br>KLASGVPSRFSGSGSGTDYTFTISSLQPEDIATYYCQQW<br>SSNPFTFGQGTKLQITR-- |
| Human IgG1 HEAVY CHAIN hMNC2 L2 OKT3 scFv | 107 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttggggggataattactacgaatacttcgatgtctggggcaaagggaccacggtcacc<br>gtctcctccgctagcaccaagggcccatcggtcttccccctggcaccctcctccaagag<br>cacctctgggggcacagcggccctgggctgcctggtcaaggactacttccccgagccg<br>gtgacggtgtcgtggaactcaggcgccctgaccagcggcgtgcacaccttcccggctg<br>tcctacagtcctcaggactctactccctcagcagcgtggtgaccgtgccctccagcagct<br>tgggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggaggagatgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcggcgggggagcggtggtggcggtagcaccggtcaggtgcaactgg<br>tgcagtccggcggaggcgtggtgcagcctggccggagcctgagactgagctgcaagg<br>cctccggctacacctttacaagatacactatgcactgggtcagacaggcccctggcaag<br>ggcctggaatggattggctacatcaaccctagccggggatataccaactacaaccagaa<br>agtgaaggacagattcaccatcagcacagataagtccaagtccaccgctttcctgcagat<br>ggactccctgcgtccagaggacacagctgtgtactactgcgcccggtactacgacgac<br>cactactgtctggactactggggacagggaaccaccctgaccgtcagctctggcggcg<br>gaggctccggcggaggtggcagcggcggcggcggctctgatatccagatgacccag<br>agcccttcttccttatctgccagcgtgggcgatagagtgaccatcacatgcagcgccagc<br>tcttctgttagctacatgaactggtaccagcaaacacctggaaaggcccctaaaagatgg<br>atctacgacaccagcaagctggcctctggcgtgccctctagattcagcggctctggctcc<br>ggcaccgactacacctttacaattagctccctgcagcccgaggatatcgccacctactac<br>tgccagcagtggagcagcaaccccttcacattcggccagggcacaaagctgcaaatca<br>ccagatgataa |
| Human IgG1 HEAVY CHAIN hMNC2 L2 OKT3 scFv | 108 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGSGG<br>GGSTGQVQLVQSGGGVVQPGRSLRLSCKASGYTFTRYT<br>MHWVRQAPGKGLEWIGYINPSRGYTNYNQKVKDRFTI<br>STDKSKSTAFLQMDSLRPEDTAVYYCARYYDDHYCLD<br>YWGQGTTLTVSSGGGGSGGGGSGGGGSDIQMTQSPSSL<br>SASVGDRVTITCSASSSVSYMNWYQQTPGKAPKRWIYD<br>TSKLASGVPSRFSGSGSGTDYTFTISSLQPEDIATYYCQQ<br>WSSNPFTFGQGTKLQITR** |
| Human IgG1 HEAVY CHAIN hMN20A10N L1 12F6 scFv | 109 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct |

TABLE 7-continued

Exemplary Sequences of Antibodies that bind to MUC1* and CD3

| Construct | SEQ ID NO | Sequence |
|---|---|---|
| | | gtacctgcagatgaactccctgagagccgaggacaccgccgtgtactattgtgccagag<br>gacccatctacaacgactacgacgagttcgcctattggggccagggcacactggtcaca<br>gtttctagcgctagcaccaagggcccatcggtcttccccctggcaccctcctccaagagc<br>acctctgggggcacagcggccctgggctgcctggtcaaggactacttccccgagccgg<br>tgacggtgtcgtggaactcaggcgccctgaccagcggcgtgcacaccttcccggctgt<br>cctacagtcctcaggactctactccctcagcagcgtggtgaccgtgccctccagcagctt<br>gggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggacgagctgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcgggggtggcggttctggtggtggtggctctggaggaggaaccggtca<br>agtgcagctggtgcagtccggaggaggcgtcgtgcagcctggaagaagcctccggct<br>gagctgcaaggccagcggctatacattcaccagctacaccatgcactgggtgcggcag<br>gcccctggcaaaggcctggaatggatcggctacatcaacccttccagcggctacacca<br>agtacaaccagaaattcaaggaccggtttaccattagcgccgataagagcaagagcac<br>agcctttctgcagatggacagcctgagaccagaggacaccggcgtgtacttctgcgccc<br>gctggcaggactacgacgtttatttcgactactggggccagggcacccctgtgacagtg<br>agcagcggcggcggaggctccggcggaggtggcagcggcggcggcggctctgata<br>tccagatgacacagagccccagctctctgtctgcttctgtgggcgacagagtgaccatga<br>cctgtagagcctcctcaagcgtgtcctacatgcactggtaccagcaaacacctggcaag<br>gccccaaagccttggatctacgccacctctaatctggccagcggcgtgccttctagattc<br>agcggcagcggatctggcaccgattacaccctgaccatcagcagcctgcagcccgag<br>gatatcgccacatactactgccagcagtggagctccaatcctcctaccttcggccagggc<br>accaagctgcagatcacaagatgataa |
| Human IgG1 HEAVY CHAIN hMN20A10N L1 12F6 scFv | 110 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCP<br>PCPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSRDELTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGKGGGGGSGGG<br>GSGGGTGQVQLVQSGGGVVQPGRSLRLSCKASGYTFTS<br>YTMHWVRQAPGKGLEWIGYINPSSGYTKYNQKFKDRF<br>TISADKSKSTAFLQMDSLRPEDTGVYFCARWQDYDVYF<br>DYWGQGTPVTVSSGGGGSGGGGSGGGGSDIQMTQSPS<br>SLSASVGDRVTMTCRASSSVSYMHWYQQTPGKAPKPW<br>IYATSNLASGVPSRFSGSGSGTDYTLTISSLQPEDIATYY<br>CQQWSSNPPTFGQGTKLQITR-- |
| Human IgG1 HEAVY CHAIN hMNC2 L1 12F6 scFv | 111 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttggggggggataattactacgaatacttcgatgtctggggcaaagggaccacggtcacc<br>gtctcctccgctagcaccaagggcccatcggtcttccccctggcaccctcctccaagag<br>cacctctgggggcacagcggccctgggctgcctggtcaaggactacttccccgagccg<br>gtgacggtgtcgtggaactcaggcgccctgaccagcggcgtgcacaccttcccggctg<br>tcctacagtcctcaggactctactccctcagcagcgtggtgaccgtgccctccagcagct<br>tgggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggaggagatgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc |

TABLE 7-continued

| Construct | SEQ ID NO | Sequence |
|---|---|---|
| | | Exemplary Sequences of Antibodies that bind to MUC1* and CD3 |
| | | tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcgggggtggcggttctggtggtggctctggaggaggaaccggtca<br>agtgcagctggtgcagtccggaggaggcgtcgtgcagcctggaagaagcctccggct<br>gagctgcaaggccagcggctatacattcaccagctacaccatgcactgggtgcggcag<br>gcccctggcaaaggcctggaatggatcggctacatcaacccttccagcggctacacca<br>agtacaaccagaaattcaaggaccggtttaccattagcgccgataagagcaagagcac<br>agcctttctgcagatggacagcctgagaccagaggacaccggcgtgtacttctgcgccc<br>gctggcaggactacgacgtttatttcgactactggggccagggcacccctgtgacagtg<br>agcagcggcggcggaggctccggcggaggtggcagcggcggcggcggctctgata<br>tccagatgacacagagccccagctctctgtctgcttctgtgggcgacagagtgaccatga<br>cctgtagagcctcctcaagcgtgtcctacatgcactggtaccagcaaacacctggcaag<br>gccccaaagccttggatctacgccacctctaatctggccagcggcgtgccttctagattc<br>agcggcagcggatctggcaccgattacaccctgaccatcagcagcctgcagcccgag<br>gatatcgccacatactactgccagcagtggagctccaatcctcctaccttcggccagggc<br>accaagctgcagatcacaagatgataa |
| Human IgG1 HEAVY CHAIN hMNC2 L1 12F6 scFv | 112 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPAPIEKTISKAK<br>GQPREPQVYTLPPSREEMTKNQVSLTCLVKGFYPSDIAV<br>EWESNGQPENNYKTTPPVLDSDGSFFLYSKLTVDKSRW<br>QQGNVFSCSVMHEALHNHYTQKSLSLSPGKGGGGGSG<br>GGGSGGGTGQVQLVQSGGGVVQPGRSLRLSCKASGYT<br>FTSYTMHWVRQAPGKGLEWIGYINPSSGYTKYNQKFK<br>DRFTISADKSKSTAFLQMDSLRPEDTGVYFCARWQDYD<br>VYFDYWGQGTPVTVSSGGGGSGGGGSGGGGSDIQMTQ<br>SPSSLSASVGDRVTMTCRASSSVSYMHWYQQTPGKAPK<br>PWIYATSNLASGVPSRFSGSGSGTDYTLTISSLQPEDIAT<br>YYCQQWSSNPPTFGQGTKLQITR** |
| Human IgG1 HEAVY CHAIN hMN20A10N L2 12F6 scFv | 113 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcgctagcaccaagggcccatcggtcttccccctggcaccctcctccaagagc<br>acctctgggggcacagcggccctgggctgcctggtcaaggactacttccccgagccgg<br>tgacggtgtcgtggaactcaggcgccctgaccagcggcgtgcacaccttcccggctgt<br>cctacagtcctcaggactctactccctcagcagcgtggtgaccgtgccctccagcagctt<br>gggcacccagacctacatctgcaacgtgaatcacaagcccagcaacaccaaggtgga<br>caagaaagttgagcccaaatcttgtgacaaaactcacacatgcccaccgtgcccagcac<br>ctgaactcctggggggaccgtcagtcttcctcttccccccaaaacccaaggacaccctc<br>atgatctcccggacccctgaggtcacatgcgtggtggtggacgtgagccacgaagacc<br>ctgaggtcaagttcaactggtacgtggacggcgtggaggtgcataatgccaagacaaa<br>gccgcgggaggagcagtacaacagcacgtaccgtgtggtcagcgtcctcaccgtcctg<br>caccaggactggctgaatggcaaggagtacaagtgcaaggtctccaacaaagccctcc<br>cagcccccatcgagaaaaccatctccaaagccaaagggcagccccgagaaccacag<br>gtgtacaccctgcccccatcccgggacgagctgaccaagaaccaggtcagcctgacct<br>gcctggtcaaaggcttctatcccagcgacatcgccgtggagtgggagagcaatgggca<br>gccggagaacaactacaagaccacgcctcccgtgctggactccgacggctccttcttcc<br>tctacagcaagctcaccgtggacaagagcaggtggcagcaggggaacgtcttctcatg<br>ctccgtgatgcatgaggctctgcacaaccactacacgcagaagagcctctccctgtctcc<br>gggtaaaggcggcgggggagcggtggtggcggtagcaccggtcaagtgcagctgg<br>tgcagtccggaggaggcgtcgtgcagcctggaagaagcctccggctgagctgcaagg<br>ccagcggctatacattcaccagctacaccatgcactgggtgcggcaggcccctggcaa<br>aggcctggaatggatcggctacatcaacccttccagcggctacaccaagtacaaccag<br>aaattcaaggaccggtttaccattagcgccgataagagcaagagcacagcctttctgca<br>gatggacagcctgagaccagaggacaccggcgtgtacttctgcgcccgctggcagga<br>ctacgacgtttatttcgactactggggccagggcacccctgtgacagtgagcagcggcg<br>gcggaggctccggcggaggtggcagcggcggcggcggctctgatatccagatgaca<br>cagagccccagctctctgtctgcttctgtgggcgacagagtgaccatgacctgtagagc<br>ctcctcaagcgtgtcctacatgcactggtaccagcaaacacctggcaaggccccaaagc<br>cttggatctacgccacctctaatctggccagcggcgtgccttctagattcagcggcagcg<br>gatctggcaccgattacaccctgaccatcagcagcctgcagcccgaggatatcgccac<br>atactactgccagcagtggagctccaatcctcctaccttcggccagggcaccaagctgc<br>agatcacaagatgataa |

TABLE 7-continued

Exemplary Sequences of Antibodies that bind to MUC1* and CD3

| Construct | SEQ ID NO | Sequence |
|---|---|---|
| Human IgG1 HEAVY CHAIN hMN20A10N L2 12F6 scFv | 114 | QVQLVESGGGLVKPGGSLRLSCAASGFTFSTYAMSWIR QAPGKGLEWVASIGRAGSTYYSDSVKGRFTISRDNAKN SLYLQMNSLRAEDTAVYYCARGPIYNDYDEFAYWGQG TLVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKKVEPKSCDKTHTCP PCPAPELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKGQ PREPQVYTLPPSRDELTKNQVSLTCLVKGFYPSDIAVEW ESNGQPENNYKTTPPVLDSDGSFFLYSKLTVDKSRWQQ GNVFSCSVMHEALHNHYTQKSLSLSPGKGGGGSGGGG STGQVQLVQSGGGVVQPGRSLRLSCKASGYTFTSYTMH WVRQAPGKGLEWIGYINPSSGYTKYNQKFKDRFTISAD KSKSTAFLQMDSLRPEDTGVYFCARWQDYDVYFDYW GQGTPVTVSSGGGGSGGGGSGGGGSDIQMTQSPSSLSA SVGDRVTMTCRASSSVSYMHWYQQTPGKAPKPWIYAT SNLASGVPSRFSGSGSGTDYTLTISSLQPEDIATYYCQQ WSSNPPTFGQGTKLQITR-- |
| Human IgG1 HEAVY CHAIN hMNC2 L2 12F6 scFv | 115 | gaggtgcagctggtggagtctgggggaggcctggtcaagcctggggggtccctgaga ctctcctgtgcagcctctggattcaccttcagtggctatgccatgagctgggtccgccagg ctccagggaaggggctggagtgggtctcaaccattagtagtggggaacctacatatac taccccgactcagtgaagggccgattcaccatctccagagacaacgccaagaactcact gtatctgcaaatgaacagcctgagagccgaggacacggccgtgtattactgtgcgagac ttggggggggataattactacgaatacttcgatgtctggggcaaagggaccacggtcacc gtctcctccgctagcaccaagggcccatcggtcttccccctggcaccctcctccaagag cacctctgggggcacagcggccctgggctgcctggtcaaggactacttccccgagccg gtgacggtgtcgtggaactcaggcgccctgaccagcggcgtgcacaccttcccggctg tcctacagtcctcaggactctactccctcagcagcgtggtgaccgtgccctccagcagct tgggcacccagacctacatctgcaacgtgaatcacaagcccagcaacaccaaggtgga caagaaagttgagcccaaatcttgtgacaaaactcacacatgcccaccgtgcccagcac ctgaactcctggggggaccgtcagtcttcctcttccccccaaaacccaaggacaccctc atgatctcccggacccctgaggtcacatgcgtggtggtggacgtgagccacgaagacc ctgaggtcaagttcaactggtacgtggacggcgtggaggtgcataatgccaagacaaa gccgcgggaggagcagtacaacagcacgtaccgtgtggtcagcgtcctcaccgtcctg caccaggactggctgaatggcaaggagtacaagtgcaaggtctccaacaaagccctcc cagcccccatcgagaaaaccatctccaaagccaaagggcagccccgagaaccacag gtgtacaccctgcccccatcccgggaggagatgaccaagaaccaggtcagcctgacct gcctggtcaaaggcttctatcccagcgacatcgccgtggagtgggagagcaatgggca gccggagaacaactacaagaccacgcctcccgtgctggactccgacggctccttcttcc tctacagcaagctcaccgtggacaagagcaggtggcagcaggggaacgtcttctcatg ctccgtgatgcatgaggctctgcacaaccactacacgcagaagagcctctccctgtctcc gggtaaaggcggcgggggggagcggtggtggcggtagcaccggtcaagtgcagctgg tgcagtccggaggaggcgtcgtgcagcctggaagaagcctccggctgagctgcaagg ccagcggctatacattcaccagctacaccatgcactgggtgcggcaggcccctggcaa aggcctggaatggatcggctacatcaaccccttccagcggctacaccaagtacaaccag aaattcaaggaccggtttaccattagcgccgataagagcaagagcacagcctttctgca gatggacagcctgagaccagaggacaccggcgtgtacttctgcgcccgctggcagga ctacgacgtttatttcgactactggggccagggcacccctgtgacagtgagcagcggcg gcggaggctccggcggaggtggcagcggcggcggcggctctgatatccagatgaca cagagccccagctctctgtctgcttctgtgggcgacagagtgaccatgacctgtagagc ctcctcaagcgtgtcctacatgcactggtaccagcaaacacctggcaaggccccaaagc cttggatctacgccacctctaatctggccagcggcgtgccttctagattcagcggcagcg gatctggcaccgattacaccctgaccatcagcagcctgcagcccgaggatatcgccac atactactgccagcagtggagctccaatcctcctaccttcggccagggcaccaagctgc agatcacaagatgataa |
| Human IgG1 HEAVY CHAIN hMNC2 L2 12F6 scFv | 116 | EVQLVESGGGLVKPGGSLRLSCAASGFTFSGYAMSWVR QAPGKGLEWVSTISSGGTYIYYPDSVKGRFTISRDNAKN SLYLQMNSLRAEDTAVYYCARLGGDNYYEYFDVWGK GTTVTVSSASTKGPSVFPLAPSSKSTSGGTAALGCLVKD YFPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKAK GQPREPQVYTLPPSREEMTKNQVSLTCLVKGFYPSDIAV EWESNGQPENNYKTTPPVLDSDGSFFLYSKLTVDKSRW QQGNVFSCSVMHEALHNHYTQKSLSLSPGKGGGGSGG GGSTGQVQLVQSGGGVVQPGRSLRLSCKASGYTFTSYT MHWVRQAPGKGLEWIGYINPSSGYTKYNQKFKDRFTIS ADKSKSTAFLQMDSLRPEDTGVYFCARWQDYDVYFDY WGQGTPVTVSSGGGGSGGGGSGGGGSDIQMTQSPSSLS ASVGDRVTMTCRASSSVSYMHWYQQTPGKAPKPWIYA |

TABLE 7-continued

Exemplary Sequences of Antibodies that bind to MUC1* and CD3

| Construct | SEQ ID NO | Sequence |
| --- | --- | --- |
| | | TSNLASGVPSRFSGSGSGTDYTLTISSLQPEDIATYYCQQ<br>WSSNPPTFGQGTKLQITR** |
| hMNC2 scFv-Fc KNOB | 117 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgtggtgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaatgataa |
| hMNC2 scFv-Fc KNOB | 118 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSGGGGSGGGGSGGGGSDIVLTQSPASLAVSP<br>GQRATITCRASKSVSTSGYSYMHWYQQKPGQPPKLLIY<br>LASNLESGVPARFSGSGSGTDFTLTINPVEANDTANYYC<br>QHSRELPFTFGGGTKVEIKRTEPKSCDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLH<br>QDWLNGKEYKCKVSNKALPAPIEKTISKAKGQPREPQV<br>YTLPPSREEMTKNQVSLWCLVKGFYPSDIAVEWESNGQ<br>PENNYKTTPPVLDSDGSFFLYSKLTVDKSRWQQGNVFS<br>CSVMHEALHNHYTQKSLSLSPGK-- |
| hMNC2 scFv-Fc KNOB-HIS | 119 | gaggtgcagctggtggagtctgggggaggcctggtcaagcctggggggtccctgaga<br>ctctcctgtgcagcctctggattcaccttcagtggctatgccatgagctgggtccgccagg<br>ctccagggaaggggctggagtgggtctcaaccattagtagtggcggaacctacatatac<br>taccccgactcagtgaagggccgattcaccatctccagagacaacgccaagaactcact<br>gtatctgcaaatgaacagcctgagagccgaggacacggccgtgtattactgtgcgagac<br>ttgggggggataattactacgaatacttcgatgtctggggcaaagggaccacggtcacc<br>gtctcctccggcggtggcggatccggcggtggcggatccggcggtggcggatccgac<br>attgtgctgacccagtctccagcctccttggccgtgtctccaggacagagggccaccatc<br>acctgcagagccagtaagagtgtcagtaccagcggatactcctacatgcactggtatca<br>gcagaaaccaggacaacctcctaaactcctgatttacctggcatccaatctggagagcg<br>gggtcccagccaggttcagcggcagtgggtctgggaccgatttcaccctcacaattaat<br>cctgtggaagctaatgatactgcaaattattactgtcagcacagtagggagctgcctttca<br>cattcggcggagggaccaaggtggagatcaaacgaactgagcccaaatcttgtgacaa<br>aactcacacatgcccaccgtgcccagcacctgaactcctggggggaccgtcagtcttcc<br>tcttccccccaaaacccaaggacaccctcatgatctcccggacccctgaggtcacatgc<br>gtggtggtggacgtgagccacgaagaccctgaggtcaagttcaactggtacgtggacg<br>gcgtggaggtgcataatgccaagacaaagccgcgggaggagcagtacaacagcacg<br>taccgtgtggtcagcgtcctcaccgtcctgcaccaggactggctgaatggcaaggagta<br>caagtgcaaggtctccaacaaagccctcccagcccccatcgagaaaaccatctccaaa<br>gccaaagggcagccccgagaaccacaggtgtacaccctgcccccatcccgggagga<br>gatgaccaagaaccaggtcagcctgtggtgcctggtcaaaggcttctatcccagcgaca<br>tcgccgtggagtgggagagcaatgggcagccggagaacaactacaagaccacgcctc<br>ccgtgctggactccgacggctccttcttcctctacagcaagctcaccgtggacaagagc<br>aggtggcagcaggggaacgtcttctcatgctccgtgatgcatgaggctctgcacaacca<br>ctacacgcagaagagcctctccctgtctccgggtaaaaccggtcatcatcaccatcacca<br>ttgataa |
| hMNC2 scFv-Fc KNOB-HIS | 120 | EVQLVESGGGLVKPGGSLRLSCAASGFTFSGYAMSWVR<br>QAPGKGLEWVSTISSGGTYIYYPDSVKGRFTISRDNAKN<br>SLYLQMNSLRAEDTAVYYCARLGGDNYYEYFDVWGK<br>GTTVTVSSGGGGSGGGGSGGGGSDIVLTQSPASLAVSP<br>GQRATITCRASKSVSTSGYSYMHWYQQKPGQPPKLLIY |

TABLE 7-continued

Exemplary Sequences of Antibodies that bind to MUC1* and CD3

| Construct | SEQ ID NO | Sequence |
| --- | --- | --- |
| | | LASNLESGVPARFSGSGSGTDFTLTINPVEANDTANYYC<br>QHSRELPFTFGGGTKVEIKRTEPKSCDKTHTCPPCPAPEL<br>LGGPSVFLFPPKPKDTLMISRTPEVTCVVVDVSHEDPEV<br>KFNWYVDGVEVHNAKTKPREEQYNSTYRVVSVLTVLH<br>QDWLNGKEYKCKVSNKALPAPIEKTISKAKGQPREPQV<br>YTLPPSREEMTKNQVSLWCLVKGFYPSDIAVEWESNGQ<br>PENNYKTTPPVLDSDGSFFLYSKLTVDKSRWQQGNVFS<br>CSVMHEALHNHYTQKSLSLSPGKTGHHHHHH-- |
| hMN20A10N scFv-Fc KNOB | 121 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcgggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgtggtgcctggtcaaaggcttctatcccagcg<br>acatcgccgtggagtgggagagcaatgggcagccggagaacaactacaagaccacg<br>cctcccgtgctggactccgacggctccttcttcctctacagcaagctcaccgtggacaag<br>agcaggtggcagcaggggaacgtcttctcatgctccgtgatgcatgaggctctgcacaa<br>ccactacacgcagaagagcctctccctgtctccgggtaaatgataa |
| hMN20A10N scFv-Fc KNOB | 122 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFAVYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLWCLVKGFYPSDIAVEWESNGQP<br>ENNYKTTPPVLDSDGSFFLYSKLTVDKSRWQQGNVFSC<br>SVMHEALHNHYTQKSLSLSPGK-- |
| hMN20A10N scFv-Fc KNOB-HIS | 123 | caggtgcagctggttgaatctggcggcggacttgtgaagcctggcggatctctgagact<br>gagctgtgccgccagcggcttcacctttagcacatacgccatgagctggatcagacagg<br>cccctggcaaaggcctggaatgggtggcgtctattggcagagccggcagcacctacta<br>cagcgactctgtgaagggcagattcaccatcagccgggacaacgccaagaacagcct<br>gtacctgcagatgaactccctgagagccgaggacaccgccgtgtactattgtgccagag<br>gacccatctacaacgactacgacgagttcgcctattggggccagggcacactggtcaca<br>gtttctagcggcggtggcggaagcggaggcggtggctccggtggcggaggcagcga<br>aattgtgctgacacagagccccgccacactgtcactttctccaggcgaaagagccacac<br>tgagctgcaagagcagccagagcgtgctgtactccagcaaccagaagaactacctggc<br>ctggtatcagcagaagcccggccaagctcctcggctgctgatctattgggccagcacaa<br>gagagagcggcatccctgccagattttctggcagcggctctggcaccgatttcaccctg<br>accataagcagcctggaacctgaggacttcgccgtgtattactgccaccagtacctgag<br>cagcctgacctttggcggaggcaccaaggtggaaatcaagcgggagcccaaatcttgt<br>gacaaaactcacacatgcccaccgtgcccagcacctgaactcctggggggaccgtcag<br>tcttcctcttccccccaaaacccaaggacaccctcatgatctcccggacccctgaggtca<br>catgcgtggtggtggacgtgagccacgaagaccctgaggtcaagttcaactggtacgtg<br>gacggcgtggaggtgcataatgccaagacaaagccgcgggaggagcagtacaacag<br>cacgtaccgtgtggtcagcgtcctcaccgtcctgcaccaggactggctgaatggcaagg<br>agtacaagtgcaaggtctccaacaaagccctcccagcccccatcgagaaaaccatctcc<br>aaagccaaagggcagccccgagaaccacaggtgtacaccctgcccccatcccggga<br>ggagatgaccaagaaccaggtcagcctgtggtgcctggtcaaaggcttctatcccagcg<br>acatcgccgtggagtgggagagcaatgggcagccggagaacaactacaagaccacg<br>cctcccgtgctggactccgacggctccttcttcctctacagcaagctcaccgtggacaag<br>agcaggtggcagcaggggaacgtcttctcatgctccgtgatgcatgaggctctgcacaa<br>ccactacacgcagaagagcctctccctgtctccgggtaaaaccggtcatcatcaccatca<br>ccattgataa |

TABLE 7-continued

| Exemplary Sequences of Antibodies that bind to MUC1* and CD3 | | |
|---|---|---|
| Construct | SEQ ID NO | Sequence |
| hMN20A10N scFv-Fc KNOB-HIS | 124 | QVQLVESGGGLVKPGGSLRLSCAASGFTFSTYAMSWIR<br>QAPGKGLEWVASIGRAGSTYYSDSVKGRFTISRDNAKN<br>SLYLQMNSLRAEDTAVYYCARGPIYNDYDEFAYWGQG<br>TLVTVSSGGGGSGGGGSGGGGSEIVLTQSPATLSLSPGE<br>RATLSCKSSQSVLYSSNQKNYLAWYQQKPGQAPRLLIY<br>WASTRESGIPARFSGSGSGTDFTLTISSLEPEDFAVYYCH<br>QYLSSLTFGGGTKVEIKREPKSCDKTHTCPPCPAPELLG<br>GPSVFLFPPKPKDTLMISRTPEVTCVVVDVSHEDPEVKF<br>NWYVDGVEVHNAKTKPREEQYNSTYRVVSVLTVLHQ<br>DWLNGKEYKCKVSNKALPAPIEKTISKAKGQPREPQVY<br>TLPPSREEMTKNQVSLWCLVKGFYPSDIAVEWESNGQP<br>ENNYKTTPPVLDSDGSFFLYSKLTVDKSRWQQGNVFSC<br>SVMHEALHNHYTQKSLSLSPGKTGHHHHHH-- |
| OKT3 scFv-Fc HOLE-STREPTAG | 125 | caggtgcaactggtgcagtccggcggaggcgtggtgcagcctggccggagcctgaga<br>ctgagctgcaaggcctccggctacacctttacaagatacactatgcactgggtcagaca<br>ggcccctggcaagggcctggaatggattggctacatcaaccctagccggggatatacc<br>aactacaaccagaaagtgaaggacagattcaccatcagcacagataagtccaagtcca<br>ccgctttcctgcagatggactccctgcgtccagaggacacagctgtgtactactgcgccc<br>ggtactacgacgaccactactgtctggactactggggacagggaaccaccctgaccgt<br>cagctctggcggcggaggctccggcggaggtggcagcggcggcggcggctctgata<br>tccagatgacccagagcccttcttccttatctgccagcgtgggcgatagagtgaccatca<br>catgcagcgccagctcttctgttagctacatgaactggtaccagcaaacacctggaaag<br>gccccctaaaagatggatctacgacaccagcaagctggcctctggcgtgccctctagatt<br>cagcggctctggctccggcaccgactacacctttacaattagctccctgcagcccgagg<br>atatcgccacctactactgccagcagtggagcagcaaccccttcacattcggccagggc<br>acaaagctgcaaatcaccagagagcccaaatcttgtgacaaaactcacacatgcccacc<br>gtgcccagcacctgaactcctggggggaccgtcagtcttcctcttccccccaaaaccca<br>aggacaccctcatgatctcccggacccctgaggtcacatgcgtggtggtggacgtgag<br>ccacgaagaccctgaggtcaagttcaactggtacgtggacggcgtggaggtgcataat<br>gccaagacaaagccgcgggaggagcagtacaacagcacgtaccgtgtggtcagcgtc<br>ctcaccgtcctgcaccaggactggctgaatggcaaggagtacaagtgcaaggtctcca<br>acaaagccctcccagcccccatcgagaaaaccatctccaaagccaaagggcagcccc<br>gagaaccacaggtgtacaccctgcccccatcccgggaggagatgaccaagaaccagg<br>tcagcctgagctgcgccgtcaaaggcttctatcccagcgacatcgccgtggagtggga<br>gagcaatgggcagccggagaacaactacaagaccacgcctcccgtgctggactccga<br>cggctccttcttcctcgtgagcaagctcaccgtggacaagagcaggtggcagcagggg<br>aacgtcttctcatgctccgtgatgcatgaggctctgcacaaccactacacgcagaagagc<br>ctctccctgtctccgggtaaaaccggttggagccatcctcagttcgaaaagtgataa |
| OKT3 scFv-Fc HOLE-STREPTAG | 126 | QVQLVQSGGGVVQPGRSLRLSCKASGYTFTRYTMHWV<br>RQAPGKGLEWIGYINPSRGYTNYNQKVKDRFTISTDKS<br>KSTAFLQMDSLRPEDTAVYYCARYYDDHYCLDYWGQ<br>GTTLTVSSGGGGSGGGGSGGGGSDIQMTQSPSSLSASV<br>GDRVTITCSASSSVSYMNWYQQTPGKAPKRWIYDTSKL<br>ASGVPSRFSGSGSGTDYTFTISSLQPEDIATYYCQQWSSN<br>PFTFGQGTKLQITREPKSCDKTHTCPPCPAPELLGGPSVF<br>LFPPKPKDTLMISRTPEVTCVVVDVSHEDPEVKFNWYV<br>DGVEVHNAKTKPREEQYNSTYRVVSVLTVLHQDWLNG<br>KEYKCKVSNKALPAPIEKTISKAKGQPREPQVYTLPPSR<br>EEMTKNQVSLSCAVKGFYPSDIAVEWESNGQPENNYKT<br>TPPVLDSDGSFFLVSKLTVDKSRWQQGNVFSCSVMHEA<br>LHNHYTQKSLSLSPGKTGWSHPQFEK-- |
| 12F6 scFv-Fc HOLE-STREPTAG | 127 | caagtgcagctggtgcagtccggaggaggcgtcgtgcagcctggaagaagcctccgg<br>ctgagctgcaaggccagcggctatacattcaccagctacaccatgcactgggtgcggc<br>aggcccctggcaaaggcctggaatggatcggctacatcaacccttccagcggctacac<br>caagtacaaccagaaattcaaggaccggtttaccattagcgccgataagagcaagagc<br>acagcctttctgcagatggacagcctgagaccagaggacaccggcgtgtacttctgcgc<br>ccgctggcaggactacgacgtttatttcgactactggggccagggcaccccctgtgacag<br>tgagcagcggcggcggaggctccggcggaggtggcagcggcggcggcggctctga<br>tatccagatgacacagagccccagctctctgtctgcttctgtgggcgacagagtgaccat<br>gacctgtagagcctcctcaagcgtgtcctacatgcactggtaccagcaaacacctggca<br>aggccccaaagccttggatctacgccacctctaatctggccagcggcgtgccttctagat<br>tcagcggcagcggatctggcaccgattacaccctgaccatcagcagcctgcagcccga<br>ggatatcgccacatactactgccagcagtggagctccaatcctcctaccttcggccagg<br>gcaccaagctgcagatcacaagagagcccaaatcttgtgacaaaactcacacatgccc<br>accgtgcccagcacctgaactcctggggggaccgtcagtcttcctcttccccccaaaac<br>ccaaggacaccctcatgatctcccggacccctgaggtcacatgcgtggtggtggacgtg<br>agccacgaagaccctgaggtcaagttcaactggtacgtggacggcgtggaggtgcata<br>atgccaagacaaagccgcgggaggagcagtacaacagcacgtaccgtgtggtcagcg<br>tcctcaccgtcctgcaccaggactggctgaatggcaaggagtacaagtgcaaggtctcc<br>aacaaagccctcccagcccccatcgagaaaaccatctccaaagccaaagggcagccc<br>cgagaaccacaggtgtacaccctgcccccatcccgggaggagatgaccaagaaccag |

TABLE 7-continued

Exemplary Sequences of Antibodies that bind to MUC1* and CD3

| Construct | SEQ ID NO | Sequence |
|---|---|---|
| | | gtcagcctgagctgcgccgtcaaaggcttctatcccagcgacatcgccgtggagtggg agagcaatgggcagccggagaacaactacaagaccacgcctcccgtgctggactccg acggctccttcttcctcgtgagcaagctcaccgtggacaagagcaggtggcagcaggg gaacgtcttctcatgctccgtgatgcatgaggctctgcacaaccactacacgcagaaga gcctctccctgtctccgggtaaaaccggttggagccatcctcagttcgaaaagtgataa |
| 12F6 scFv-Fc HOLE-STREPTAG | 128 | QVQLVQSGGGVVQPGRSLRLSCKASGYTFTSYTMHWV RQAPGKGLEWIGYINPSSGYTKYNQKFKDRFTISADKSK STAFLQMDSLRPEDTGVYFCARWQDYDVYFDYWGQG TPVTVSSGGGGSGGGGSGGGGSDIQMTQSPSSLSASVG DRVTMTCRASSSVSYMHWYQQTPGKAPKPWIYATSNL ASGVPSRFSGSGSGTDYTLTISSLQPEDIATYYCQQWSS NPPTFGQGTKLQITREPKSCDKTHTCPPCPAPELLGGPSV FLFPPKPKDTLMISRTPEVTCVVVDVSHEDPEVKFNWY VDGVEVHNAKTKPREEQYNSTYRVVSVLTVLHQDWLN GKEYKCKVSNKALPAPIEKTISKAKGQPREPQVYTLPPS REEMTKNQVSLSCAVKGFYPSDIAVEWESNGQPENNYK TTPPVLDSDGSFFLVSKLTVDKSRWQQGNVFSCSVMHE ALHNHYTQKSLSLSPGKTGWSHPQFEK-- |

In some embodiments, the antibody further comprises a fragment crystallizable (Fc) region. In some embodiments, the Fc region comprises an IgG CH2 domain and an IgG CH3 domain. In some embodiments, the Fc region comprises a heterodimeric Fc region. In some embodiments, the heterodimeric Fc region comprises a(n) (e.g., human) IgG1, IgG2, IgG3, or IgG4 domain. In some embodiments, the heterodimeric Fc region comprises a(n) (e.g., human) IgG1 domain. In some embodiments, the heterodimeric Fc region comprises a(n) (e.g., human) IgG2 domain. In some embodiments, the heterodimeric Fc region comprises a(n) (e.g., human) IgG3 domain. In some embodiments, the heterodimeric Fc region comprises a(n) (e.g., human) IgG4 domain.

In some embodiments, the heterodimeric Fc region, wherein the heterodimeric Fc region comprises a knob chain and a hole chain, forming a knob-into-hole (KIH) structure (Spiess et al. Molecular Immunology 67, 95-106 (2015)), format. In some embodiments, the knob chain comprises a(n) (e.g., human) IgG1, IgG2, IgG3, or IgG4 domain. In some embodiments, the knob chain comprises a(n) (e.g., human) IgG1 domain. In some embodiments, the knob chain comprises a(n) (e.g., human) IgG2 domain. In some embodiments, the knob chain comprises a(n) (e.g., human) IgG3 domain. In some embodiments, the knob chain comprises a(n) (e.g., human) IgG4 domain. In some embodiments, the hole chain comprises a(n) (e.g., human) IgG1, IgG2, IgG3, or IgG4 domain. In some embodiments, the hole chain comprises a(n) (e.g., human) IgG1 domain. In some embodiments, the hole chain comprises a(n) (e.g., human) IgG2 domain. In some embodiments, the hole chain comprises a(n) (e.g., human) IgG3 domain. In some embodiments, the hole chain comprises a(n) (e.g., human) IgG4 domain.

In some embodiments, the target cell is a cancer cell. In some embodiments the cancer is breast cancer, colon cancer, prostate cancer, pancreatic cancer, or lung cancer.

In some embodiments, the antibody binds to a cancer cell that expresses MUC1* on the surface.

Figure 1A:
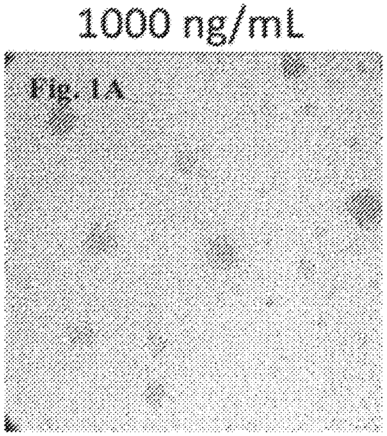
FIGS. 1A-1P shows photographs of MUC1* positive breast cancer cells, T47D, in culture with human T cells to which have been added various concentrations of bispecific antibody 20A10-OKT3-BiTE. 20A10 is a humanized anti-MUC1* antibody and OKT3 is an antibody that binds to CD3 that is present on human T cells. As can be seen in the figure, the addition of the bispecific antibody mediates the joining together of T cells and cancer cells, seen here as T cell clustering, which is a sign of activation directed by the bispecific bridge between T cell CD3 and cancer cell MUC1*.
Figure 1B:
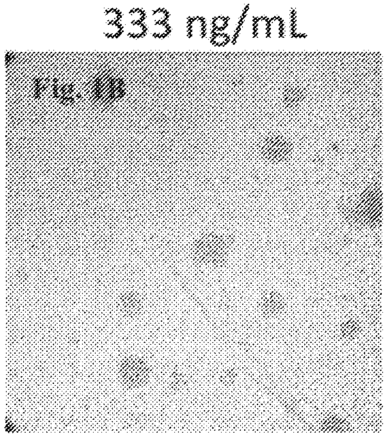
In FIG. 1B concentration is 333 ng/mL.
Figure 1C:
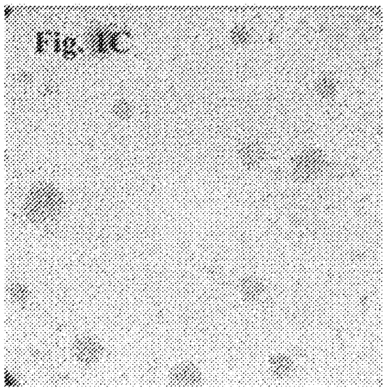
In FIG. 1C concentration is 111 ng/mL.
Figure 1D:
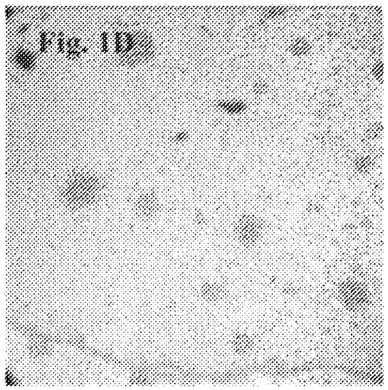
In FIG. 1D concentration is 37 ng/ml.
Figure 1E:
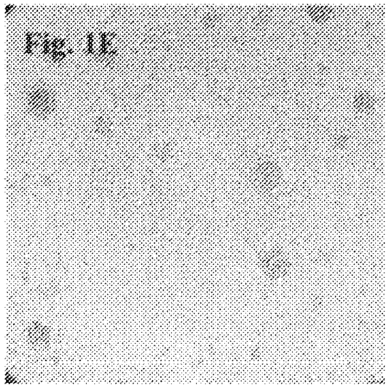
In FIG. 1E concentration is 12.3 ng/mL.
Figure 1F:
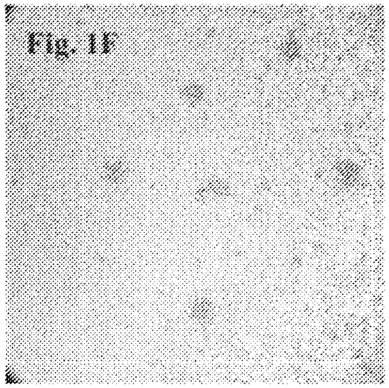
In FIG. 1F concentration is 4.1 ng/mL.
Figure 1G:
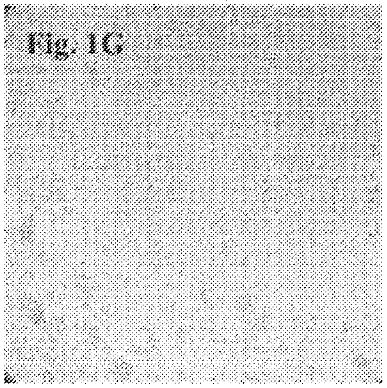
In FIG. 1G concentration is 1.3 ng/ml.
Figure 1H:
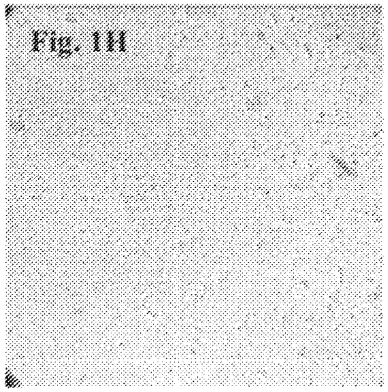
In FIG. 1H concentration is 0.4 ng/mL.
Figure 1I:
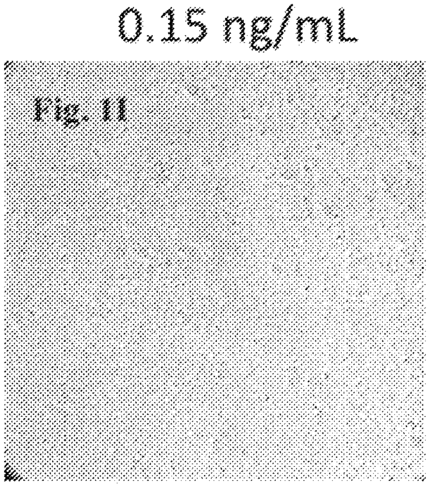
In FIG. 1I concentration is 0.15 ng/mL.
Figure 1J:
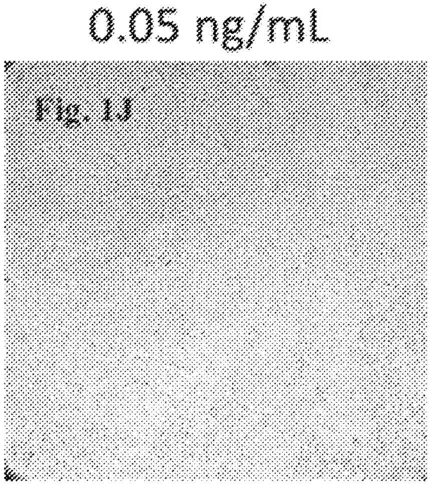
In FIG. 1J concentration is 0.05 ng/ml.
Figure 1K:
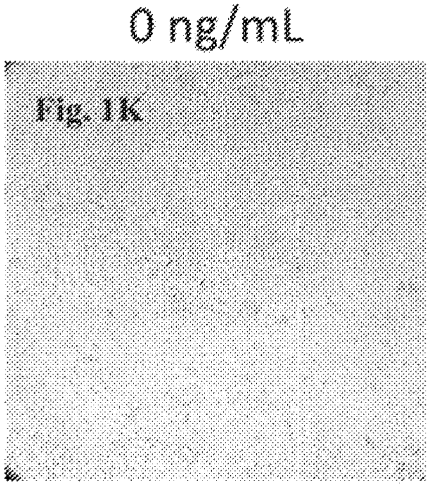
FIG. 1K is a control well in which both T cells and cancer cells are present, but no bispecific antibody has been added.
Figure 1L:
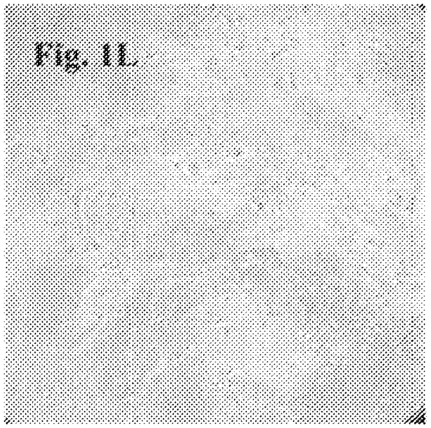
FIG. 1L is a control well in which only cancer cells are present.
Figure 1M:
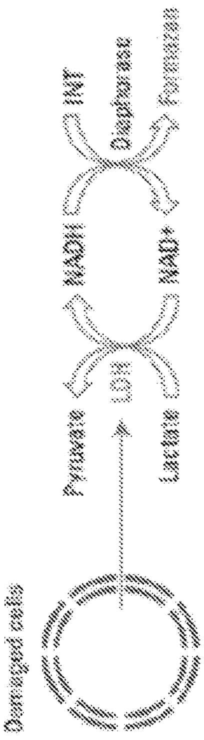
FIG. 1M shows a cartoon depicting how the LDH cytotoxicity assay works, wherein a higher measurement at A490 indicates higher cell killing.
Figure 1N:
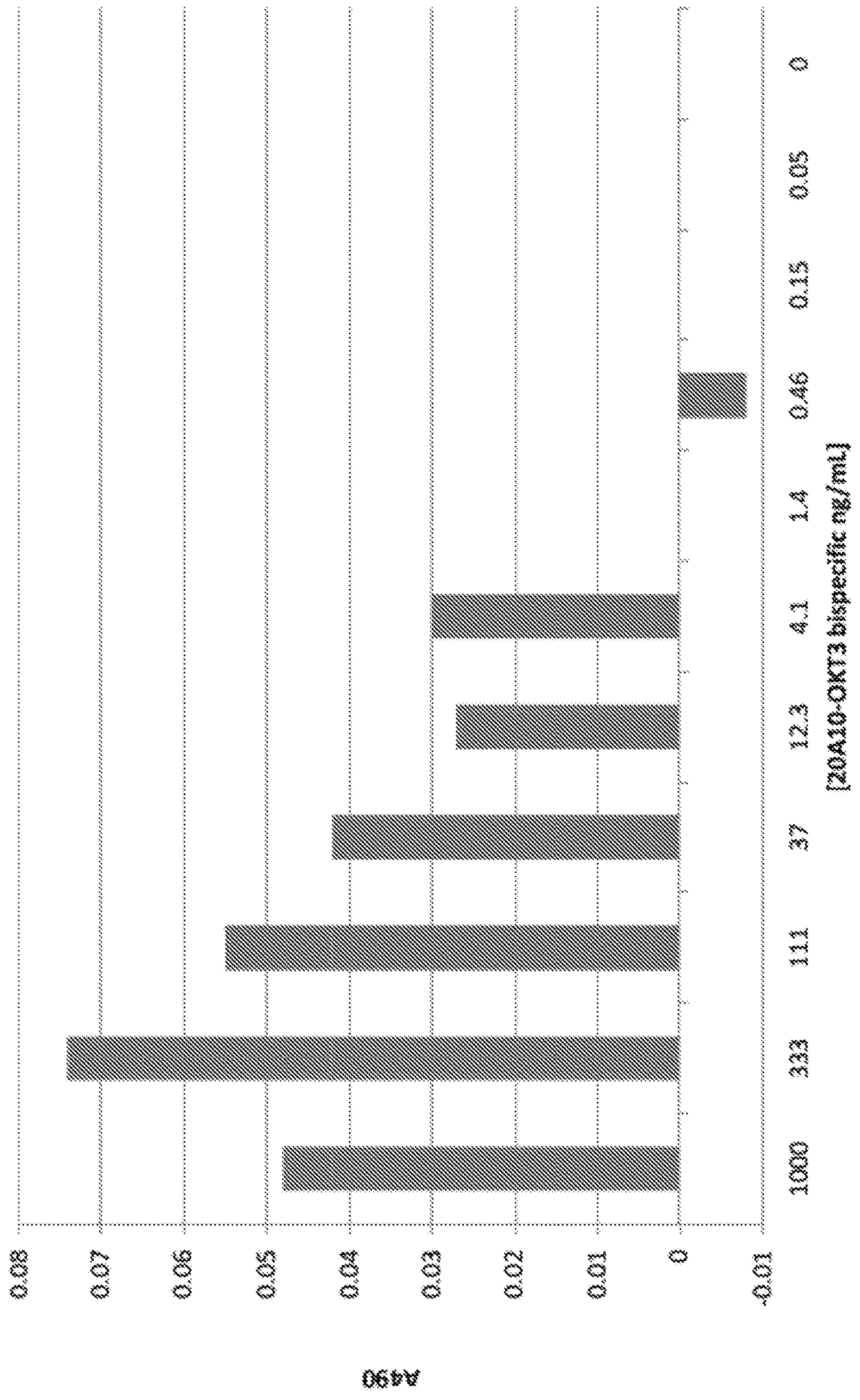
FIG. 1N shows the graph of cell killing as a function of the concentration of 20A10-OKT3, anti-MUC1*/anti-CD3 bispecific antibody.
Figure 1D:
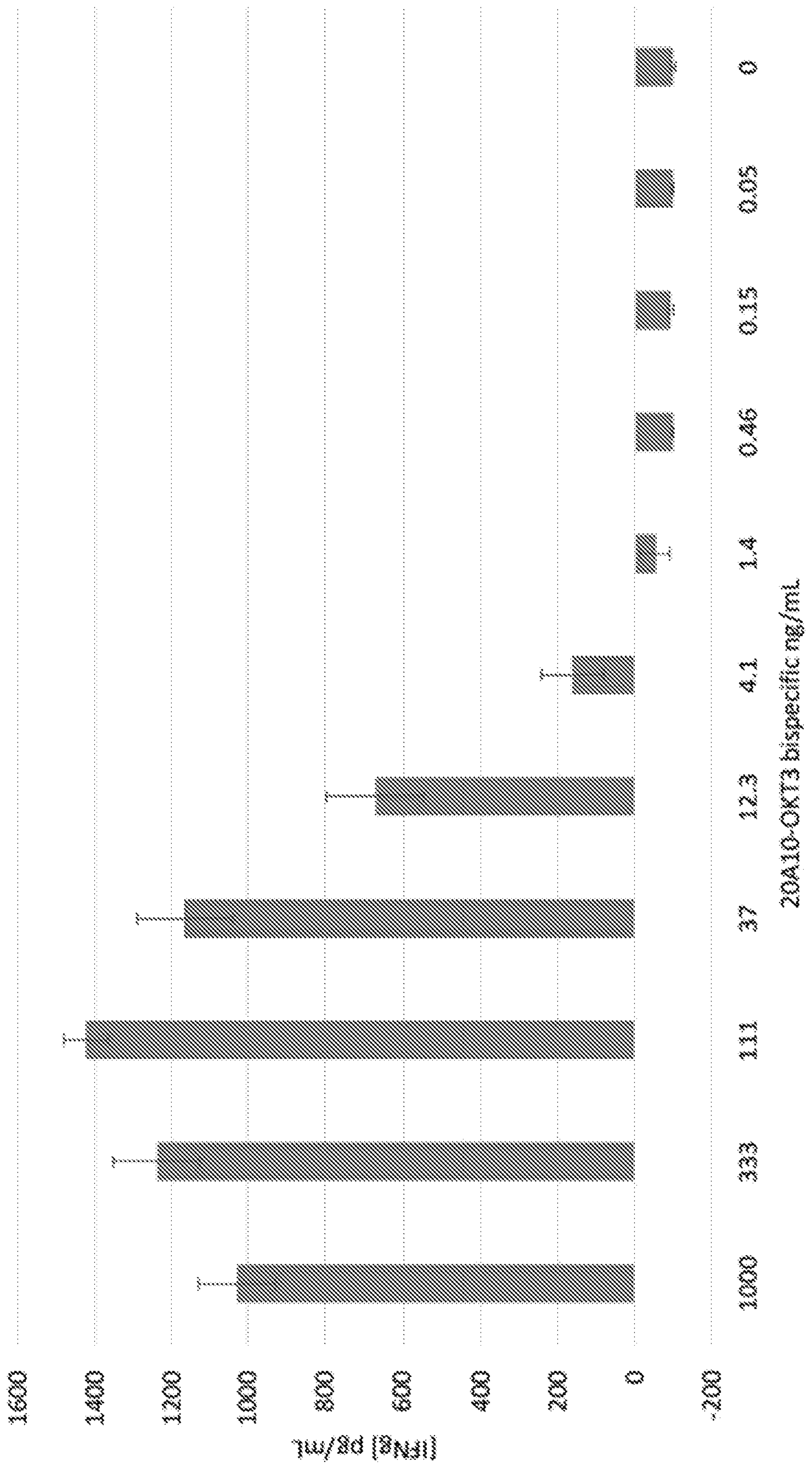
Figure 1P:
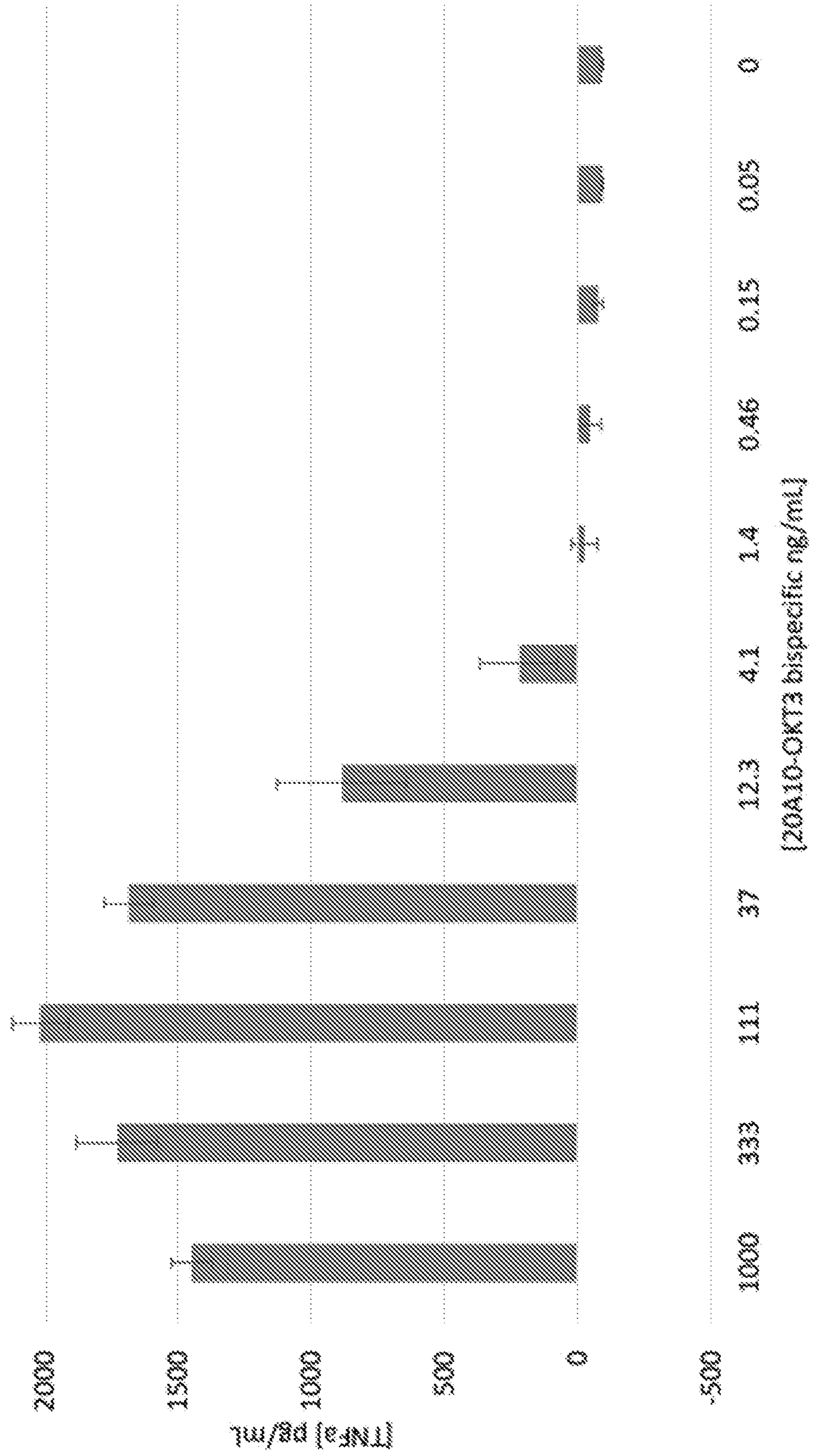

As an example of how antibodies of the invention can be incorporated into bispecific antibodies, a bispecific antibody using a knob-in-hole, also known as KIH (Spiess et al. Molecular Immunology 67, 95-106 (2015)), format was constructed. In this example, a first arm of the antibody is the humanized anti-MUC1* antibody 20A10, also known as hu20A10, with a 14616 human framework region; the second arm of the antibody is either the anti-CD3 antibody OKT3 or 12F6, which both bind to the same epitope on human T cells. The resultant bispecific antibodies are referred to here as 20A10-OKT3-BiTE and 20A10-12F6-BiTE. In a demonstration of function, the bispecific antibodies are added at various concentrations to cells in culture wherein both human T cells and MUC1* positive cancer cells are present. In one case the cancer cells are T47D breast cancer cells and in the other case a MUC1* negative line HCT-116 colon cancer cells have been transduced to express MUC1*, called HCT-MUC1*. As can be seen in the photographs shown in FIGS. 1A-IL, FIGS. 2A-2L, FIGS. 3A-3L and FIGS. 4A-4L, the addition of either bispecific antibody mediated the joining together of the T cells and the MUC1* positive cancer cells as evidenced by a bispecific dose-dependent cell clustering. Two control experiments were performed. In one control, no bispecific antibody is added. In another control, only MUC1* cancer cells are present. No clustering is observed. In another control, bispecific antibody is added to MUC1* positive cancer cells, but no T cells are present. In addition, cancer cell killing was quantified. Measurement of the cytotoxicity of the anti-MUC1* targeting bispecific antibody in which 20A10 binds to the extra cellular domain of MUC1* on the tumor cell surface and an anti-CD3 antibody called OKT3 was measured using an LDH cytotoxicity assay. A cartoon depicting how the LDH cytotoxicity assay works is shown (FIG. 1M), wherein a higher measurement at A490 indicates higher cell killing. FIG. 1N shows the graph of cell killing as a function of the concentration of 20A10-OKT3, anti-MUC1*/anti-CD3 bispecific antibody. As can be seen in the graph, 20A10 incorporated into a bispecific antibody, wherein the second arm is an antibody or antibody fragment that binds to CD3 or other surface molecule on a T cell, is a potent killer of MUC1* positive tumor cells. In addition to analyzing the target cancer cells, the T cells were also analyzed. As is well-known, activated CD8 positive cytotoxic T cells secrete interferon-gamma (IFN-g) when they are activated and primed to kill. Secretion of IFN-g from the T cells into the conditioned media was measured in an ELISA assay (FIG. 1O). As can be seen in the figure, half-maximal secretion of IFN-g is achieved at a low bispecific concentration of 12.3 ng/mL. Activated T cells also secrete TNF-alpha into the conditioned media. ELISA measure of TNF-α also shows half-maximal secretion at very low concentration of 12.3 ng/ml of the 20A10-CD3 bispecific antibody (FIG. 1P).

Figure 2I:
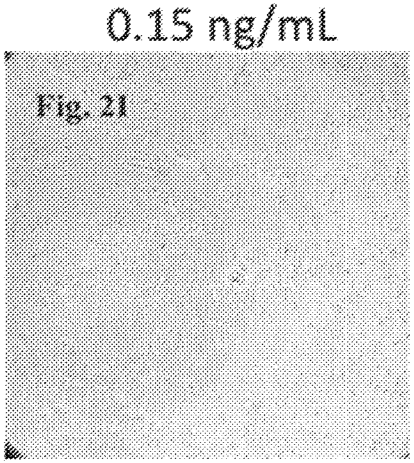
In FIG. 2I concentration is 0.15 ng/mL.
Figure 2J:
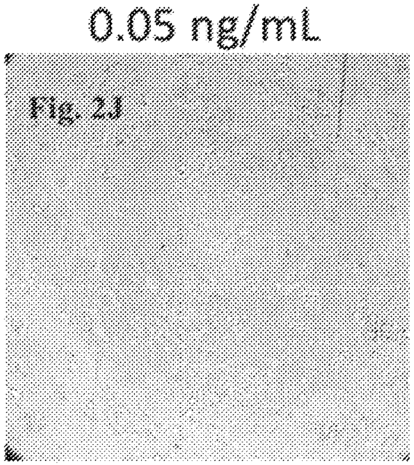
In FIG. 2J concentration is 0.05 ng/ml.
Figure 2K:
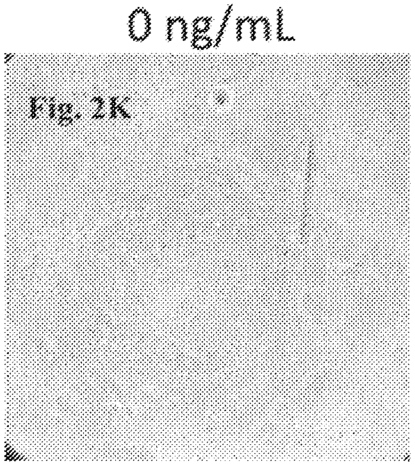
FIG. 2K is a control well in which both T cells and cancer cells are present, but no bispecific antibody has been added.
Figure 2L:
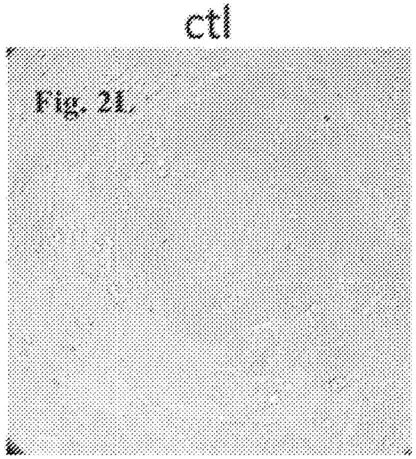
FIG. 2L is a control well in which only cancer cells are present.
Figure 2M:
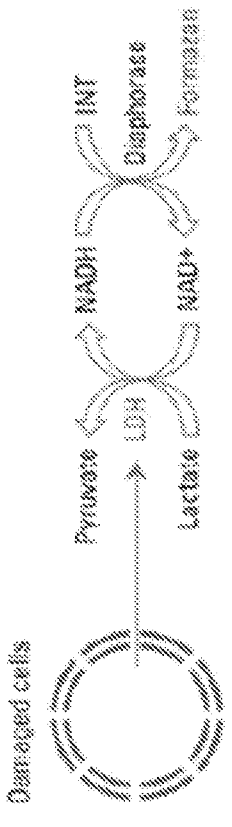
FIG. 2M shows a cartoon depicting how the LDH cytotoxicity assay works, wherein a higher measurement at A490 indicates higher cell killing.
Figure 2N:
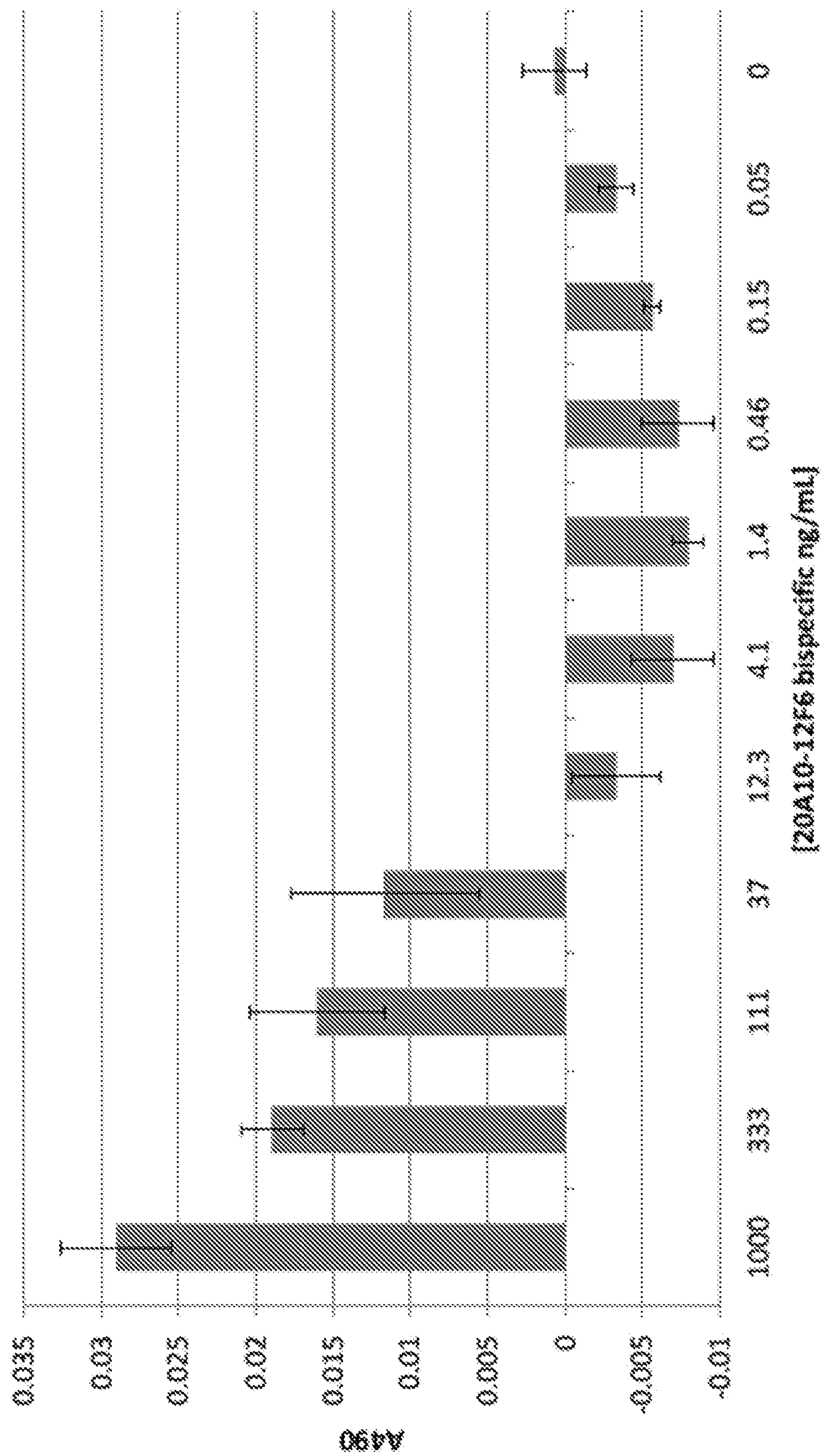
FIG. 2N shows the graph of cell killing as a function of the concentration of 20A10-OKT3, anti-MUC1*/anti-CD3 bispecific antibody.
Figure 20:
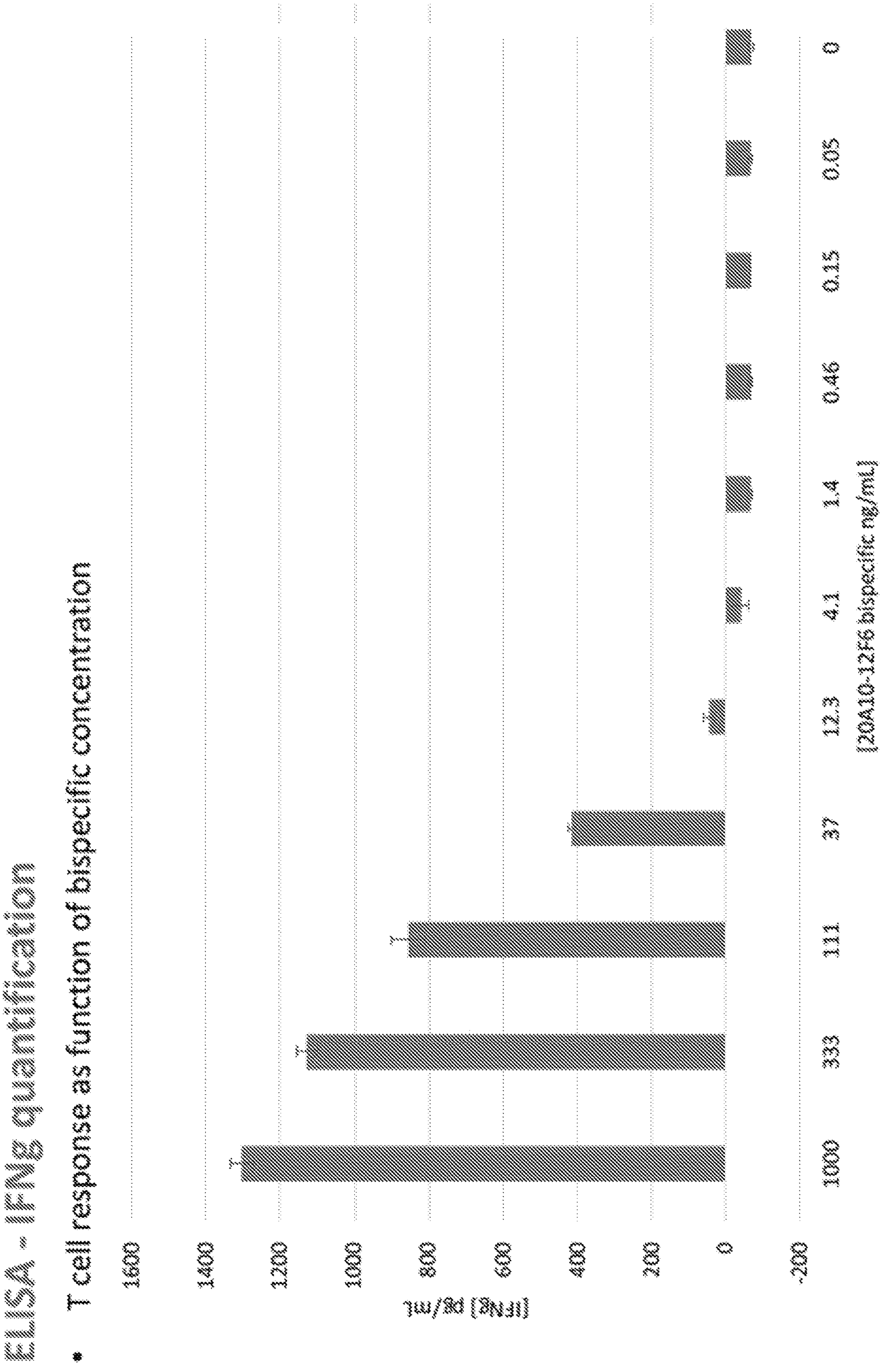
FIGS. 20A-20B shows a graph of fitted data to measure IC50 as well as the data in tabular form.
Figure 2P:
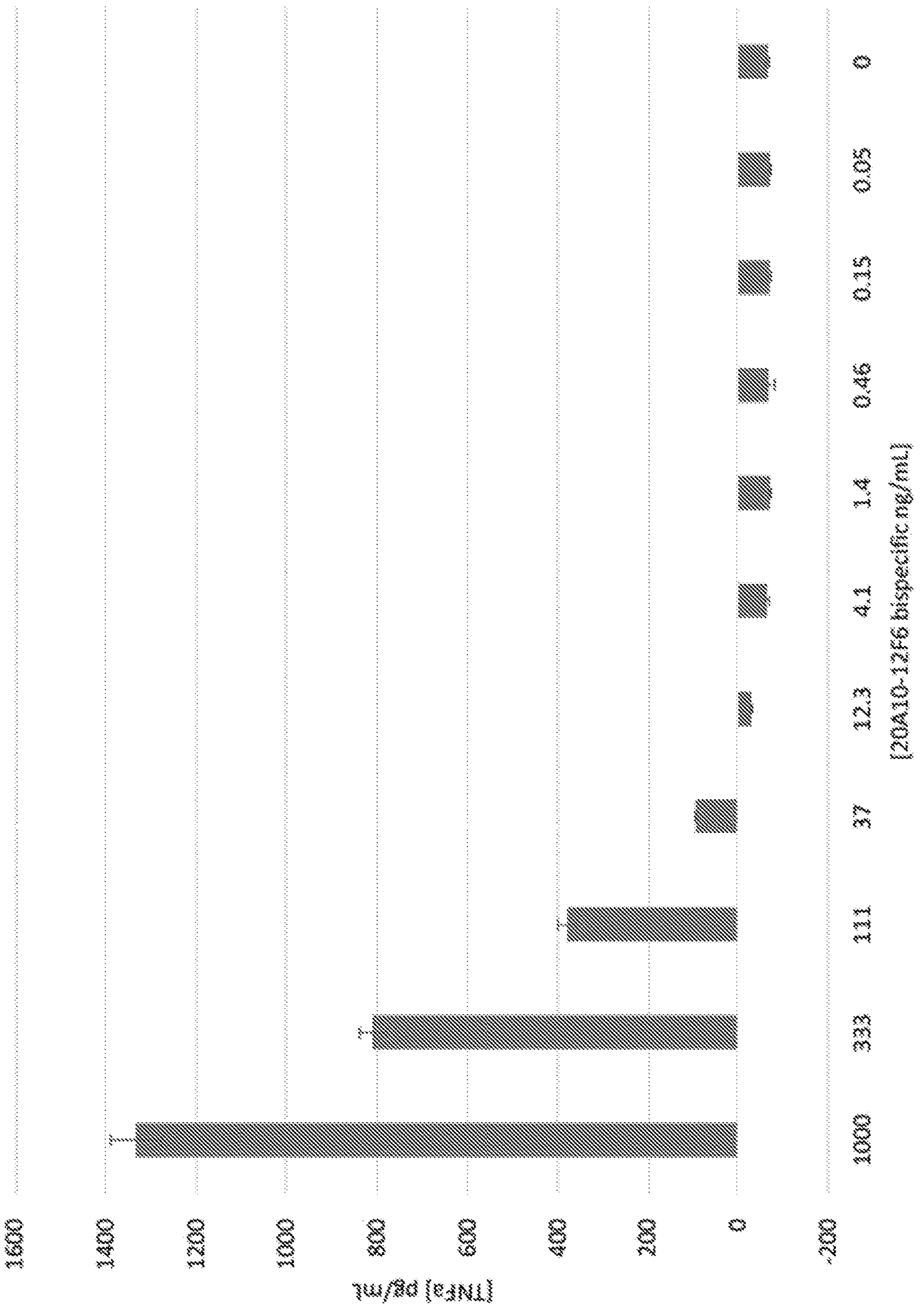
Figures 3A, 3B, 3C, 3D, 3E, 3F, 3G, 3H:
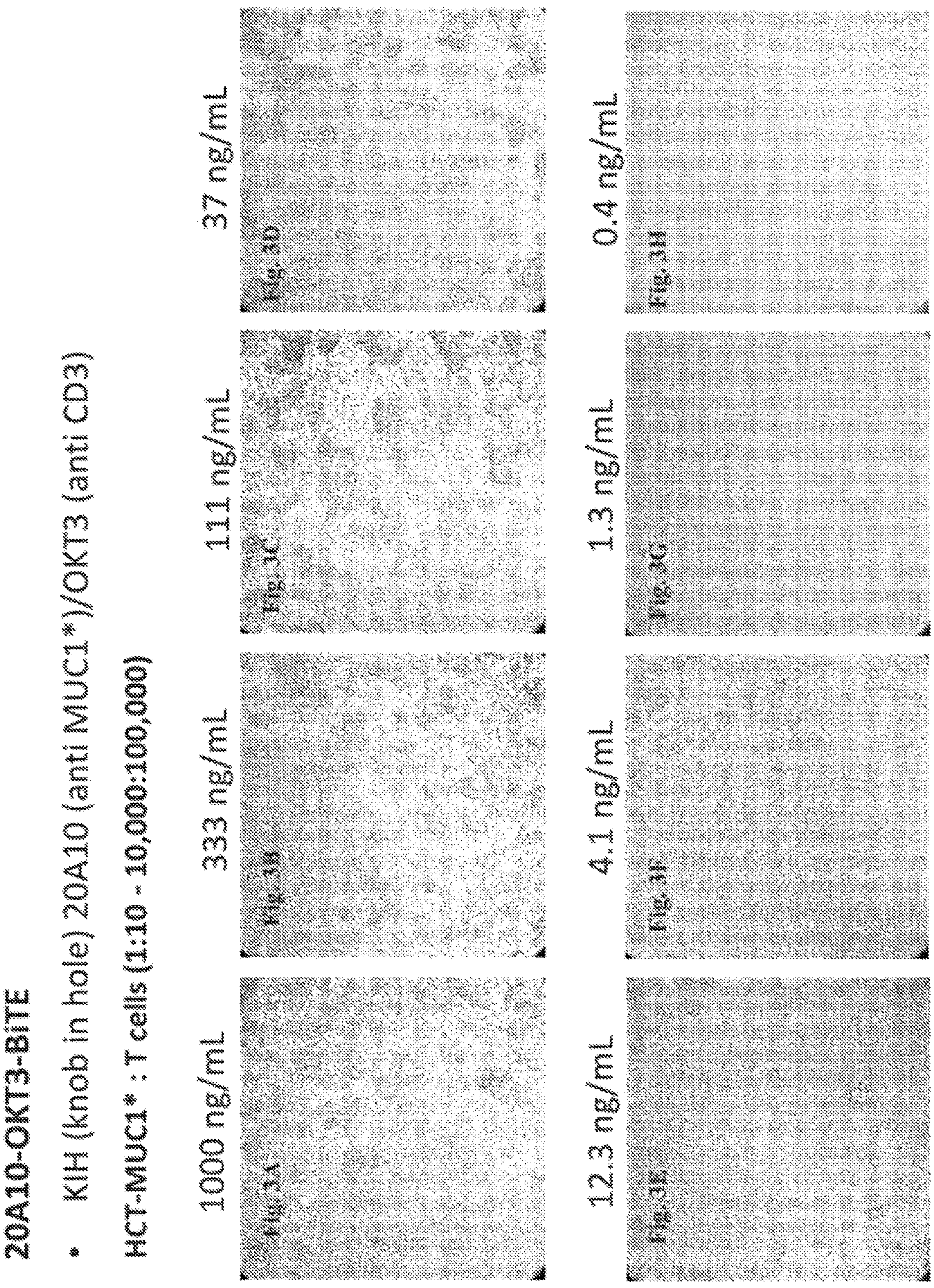
FIGS. 3A-3L show photographs of HCT-MUC1*-transduced cancer cells in culture with human T cells to which have been added various concentrations of bispecific antibody 20A10-OKT3-BiTE. 20A10 is a humanized anti-MUC1* antibody and OKT3 is an antibody that binds to CD3 that is present on human T cells. As can be seen in the figure, the addition of the bispecific antibody mediates the joining together of T cells and cancer cells, seen here as cell clustering.
Figure 3I:
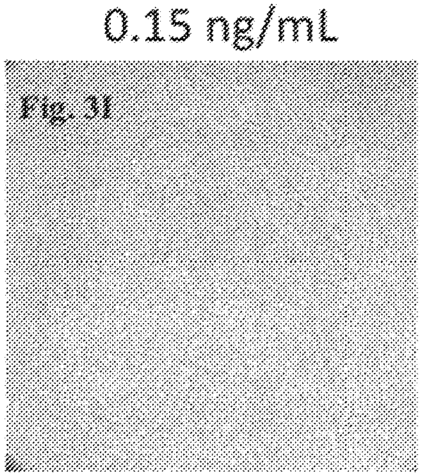
Figure 3J:
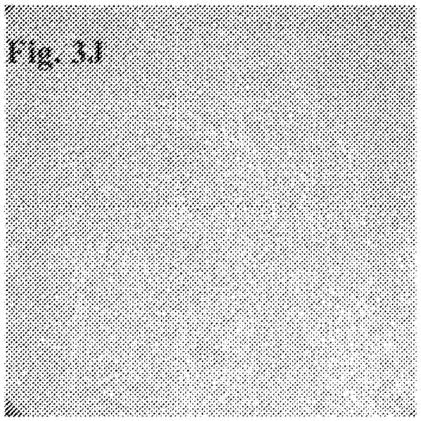
Figure 3K:
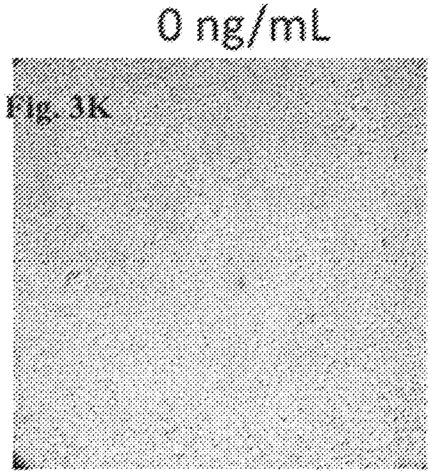
Figure 3L:
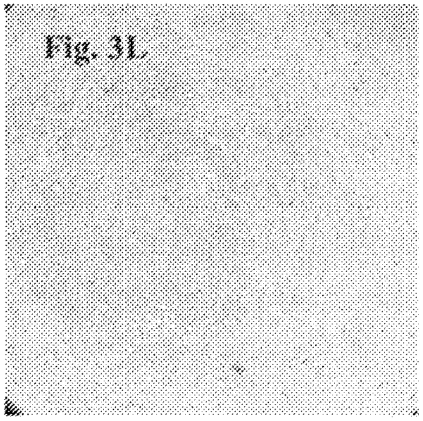
Figure 4I:
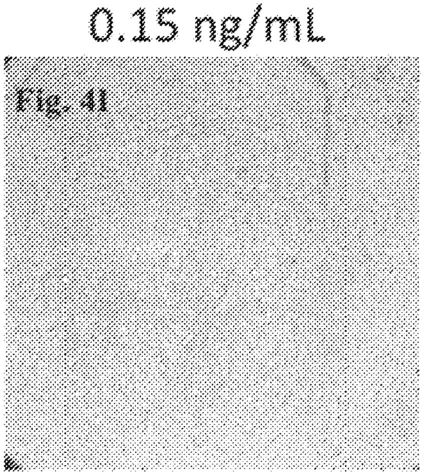
Figure 4J:
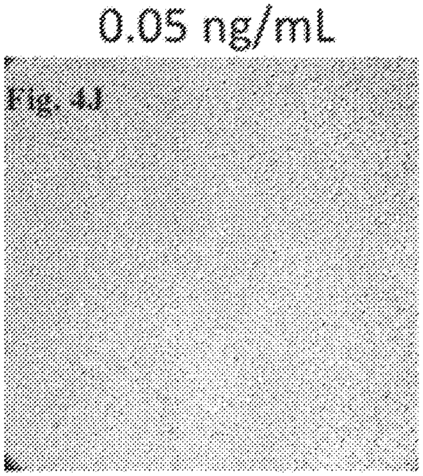
Figure 4K:
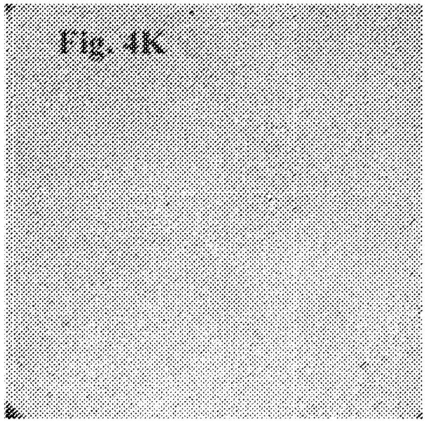
Figure 4L:
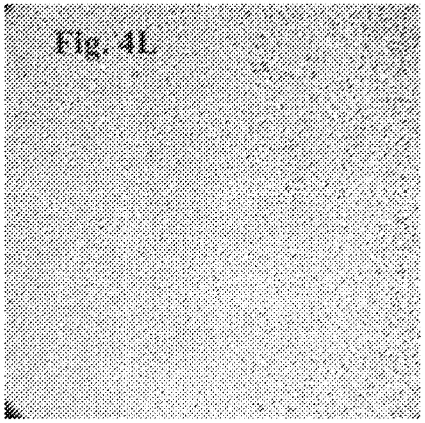
Figure 5A:
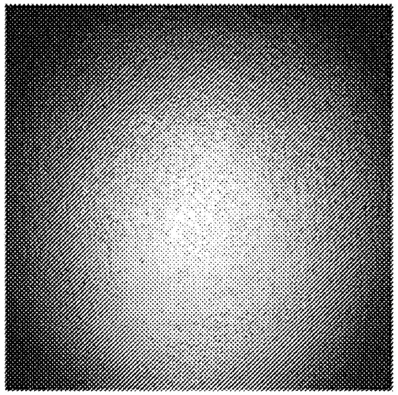
FIGS. 5A-5F show photographs of HCT-WT cancer cells, which are negative for MUC1 and MUC1*. The cancer cells have been incubated with MNC2-ADC for 72 hours. In this specific case, the toxic MMAE (monomethyl auristatin) was covalently coupled to a deglycosylated MNC2, which binds to MUC1*. As can be seen in the figure, the addition of the MNC2-ADC did not affect the viability of these HCT, MUC1-negative cells.
Figure 5B:
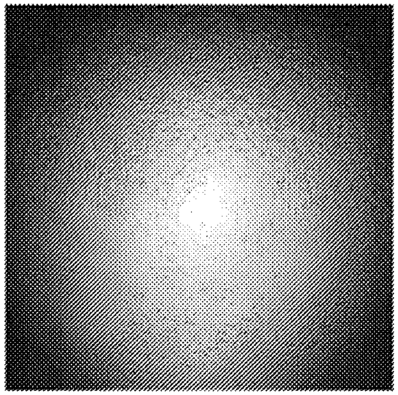
Figure 5C:
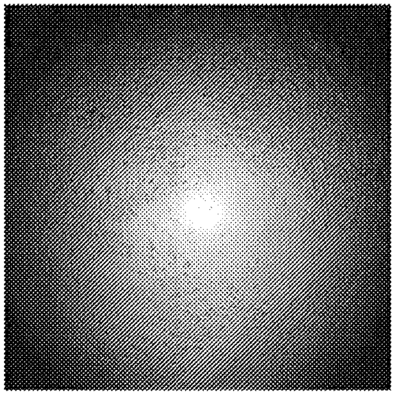
Figure 5D:
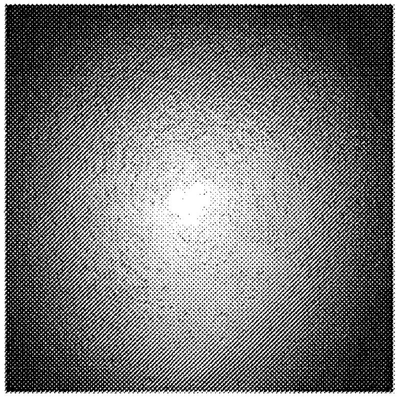
Figure 5E:
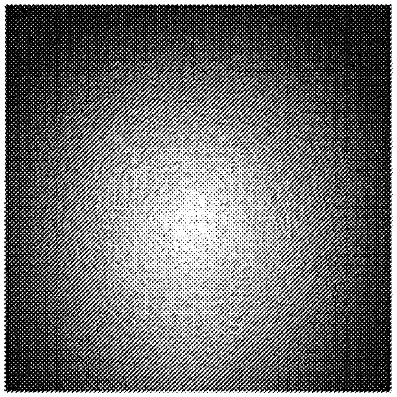
Figure 5F:
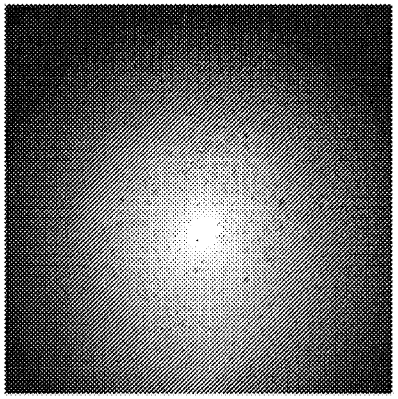
Figure 8A:
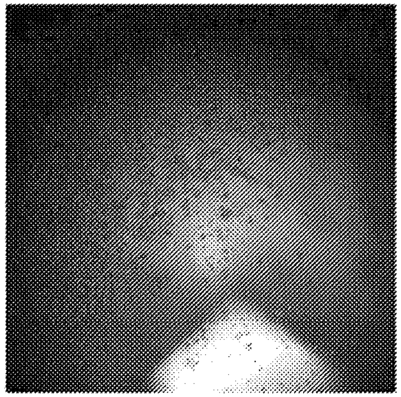
FIGS. 8A-8G show photographs of K562-MUC1* cells. These MUC1* negative cells were transduced to express MUC1*. The cells have been incubated with MNC2-ADC for 72 hours. In this specific case, the toxic MMAE (monomethyl auristatin) was covalently coupled to a deglycosylated MNC2, which binds to MUC1*. As can be seen in the figure, the addition of the MNC2-ADC at the higher concentrations tested here, 10 nM and 100 nM, induced cell clumping which is an indicator of cell death.
Figure 8B:
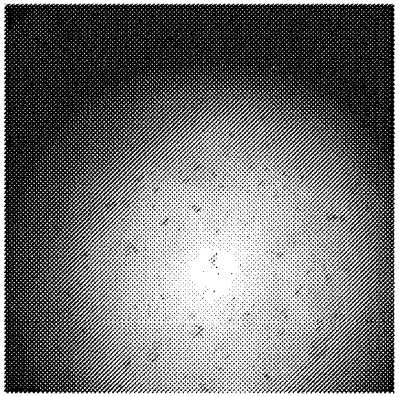
Figure 8C:
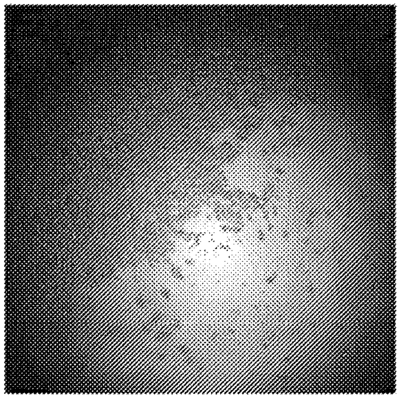
Figure 8D:
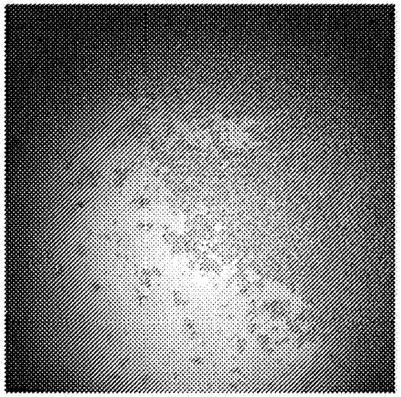
Figure 8E:
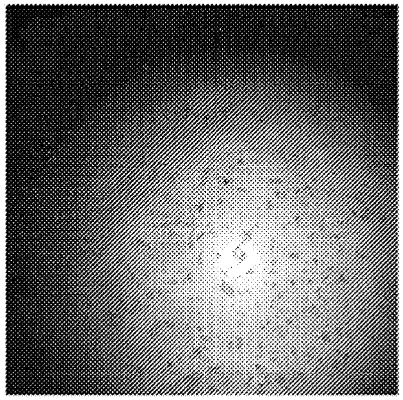
Figure 8F:
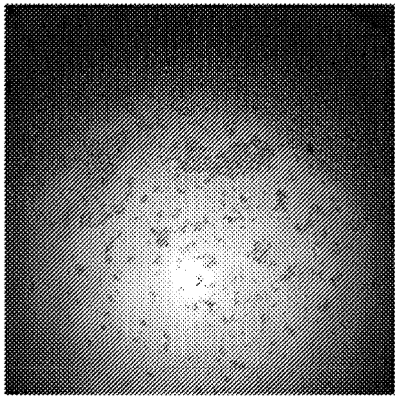
Figure 8G:
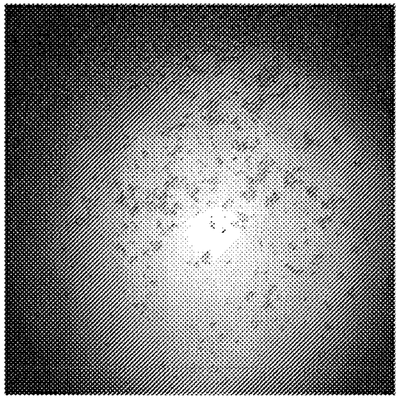

In yet another example, an anti-MUC1*/anti-CD3 bispecific antibody is constructed using 20A10 for binding to the extra cellular domain of MUC1* positive cancer cells and an anti-CD3 antibody 12F6 to bind to the T cells. As can be seen in the photographs shown in FIG. 2A-2L, the addition of either bispecific antibody mediated the joining together of the T cells and the MUC1* positive cancer cells as evidenced by a bispecific dose-dependent cell clustering. Two control experiments were performed. In one control, no bispecific antibody is added. In another control, only MUC1* cancer cells are present. No clustering is observed. In another control, bispecific antibody is added to MUC1* positive cancer cells, but no T cells are present. In addition, cancer cell killing was quantified. Measurement of the cytotoxicity of the anti-MUC1* targeting bispecific antibody in which 20A10 binds to the extra cellular domain of MUC1* on the tumor cell surface and an anti-CD3 antibody called 12F6 was measured using an LDH cytotoxicity assay. A cartoon depicting how the LDH cytotoxicity assay works is shown (FIG. 2M), wherein a higher measurement at A490 indicates higher cell killing. FIG. 2N shows the graph of cell killing as a function of the concentration of 20A10-12F6, anti-MUC1*/anti-CD3 bispecific antibody. As can be seen in the graph, 20A10 incorporated into a bispecific antibody, wherein the second arm is an antibody or antibody fragment that binds to CD3 or other surface molecule on a T cell, is a potent killer of MUC1* positive tumor cells. In addition to analyzing the target cancer cells, the T cells were also analyzed. As is well-known, activated CD8 positive cytotoxic T cells secrete interferon-gamma (IFN-g) when they are activated and primed to kill. Secretion of IFN-g from the T cells into the conditioned media was measured in an ELISA assay (FIG. 2O). As can be seen in the figure, half-maximal secretion of IFN-g is achieved at a low bispecific concentration of 50 ng/mL. Activated T cells also secrete TNF-alpha into the conditioned media. ELISA measure of TNF-α also shows half-maximal secretion at very low concentration of 200 ng/mL of the 20A10-CD3 bispecific antibody (FIG. 2P). The difference in efficacy between 20A10 paired with OKT3 compared to 12F6 demonstrates that the potency of an anti-MUC1*/anti-T cell is modulated by the affinity and specificity of each of the two antibodies.

In yet another example, an anti-MUC1* antibody 20A10 is paired with an anti-CD3 antibody fragment and tested for killing of a MUC1* negative line, HCT-116 colon cancer cells, that have been transduced to express MUC1*, called HCT-MUC1*. In one case the antibody fragment for binding to the T cell is OKT3. In another case, the anti-CD3 antibody is 12F6. As can be seen in the photographs of FIG. 3A-3L (OKT3) and FIG. 4A-4L (12F6), the addition of either bispecific antibody mediated the joining together of the T cells and the MUC1* positive cancer cells as evidenced by a bispecific dose-dependent cell clustering. Two control experiments were performed. In one control, no bispecific antibody is added, but both T cells and MUC1* cancer cells are present. No clustering is observed. In another control, bispecific antibody is added to MUC1* positive cancer cells, but no T cells are present.

Antibody-Drug Conjugates

An antibody-drug conjugate (ADC) allows the targeted delivery of therapeutic agent(s) to specific cells and/or tissues. In certain embodiments, the ADC comprises an agent (e.g., a therapeutic agent) capable of inhibiting topoisomerase (e.g., topoisomerase I (TopoI)) or inhibiting tubulin production.

In another aspect, provided herein are conjugates, e.g., antibody-drug conjugates. The ADC comprises a therapeutic agent (indicated as X); a linking moiety (indicated as L); a coupling moiety (indicated as R); and a conjugation moiety (indicated as Z) to an antibody (indicated as Ab)

by nucleophilic attack by a thiol group of a cysteine. In some embodiments, intracellular cleavage of the L linker allows the separation of the therapeutic agent X from the Ab, thereby promoting the uptake or retention therapeutic agent X into cells or tissue retention.

In certain embodiments, the ADC comprises Formula (I): $[Ab]-[Z-L-R-X]_y$, wherein: X is a moiety derived from a compound capable of inhibiting topoisomerase I or a compound capable of inhibiting tubulin formation; R is a coupling moiety; L is a di- or tri- or tetra-peptide linking moiety having Z bonded to N-terminus and R bonded to the C-terminus; [Ab] is an antibody comprising an anti-MUC1* binding domain comprising three heavy chain (HC) complementarity determining region (CDRs): MUC1* HC-CDR1, MUC1* HC-CDR2, and MUC1* HC-CDR3; wherein the MUC1* HC-CDR1, the MUC1* HC-CDR2, and the MUC1* HC-CDR3 of the MUC1* binding domain comprises amino acid sequences selected from those set forth in Table 1; wherein the MUC1* binding domain comprises three light chain (LC) complementarity determining region (CDRs): MUC1* LC-CDR1, MUC1* LC-CDR2, and MUC1* LC-CDR3; wherein the MUC1* LC-CDR1, the MUC1* LC-CDR2, and the MUC1* LC-CDR3 of the MUC1* binding domain comprises amino acid sequences selected from those set forth in Table 1; Z is a conjugation moiety capable of forming a covalent bond with a sulfur atom of a cysteine residue; and wherein y is an integer from 1 to 10.

The ADC can comprise the structure provided below wherein n is 1 to 10:

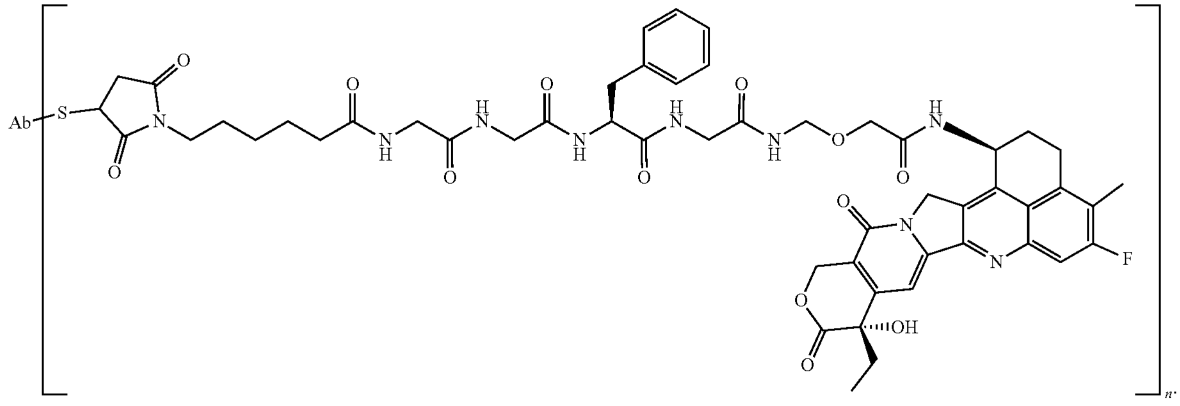

The ADC can comprise the structure provided below wherein n is 1 to 10:

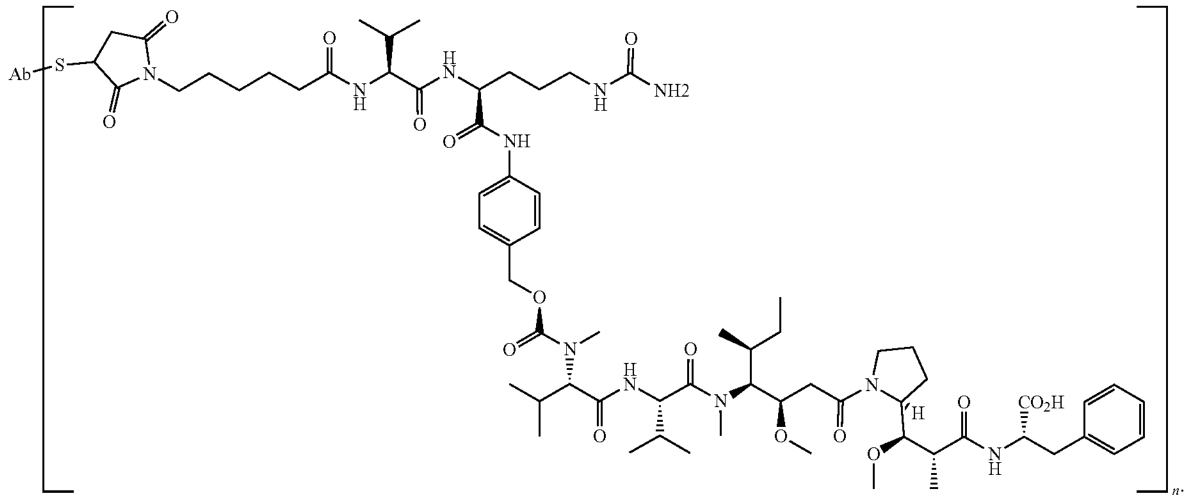

The efficacy of an ADC is governed, in part, by the drug to antibody ratio or the DAR. Basically, the more toxins you attach to your antibody, the more cell killing there is. However, attaching too many toxins to an antibody can destabilize the antibody or sterically hinder the interaction between the antibody and the target antigen. Hydrophobic interaction chromatography (HIC) is a bioanalytical technique that is used to determine the drug-antibody ratio (DAR) of antibody-drug-conjugates (ADC's). An HIC column on a high-pressure liquid chromatography (HPLC) system is used for the analysis and characterization of ADCs using a salt gradient buffer. HIC separates proteins according to differences in their surface hydrophobicity, the more drug that is bound to the antibody, the longer the retention time. FIGS. 30-35 show the HIC chromatograms for a batch of MNC2 and a batch of MN20A10 conjugated to several toxic payloads and the corresponding calculated DAR for each.

In certain embodiments, the DAR for a conjugate provided herein ranges from 1 to 20. In certain embodiments, the DAR for a conjugate provided herein ranges from 1 to 15. In certain embodiments, the DAR for a conjugate provided herein ranges from 1 to 10. In certain embodiments, the DAR for a conjugate provided herein ranges from 1 to 8. In certain embodiments, the DAR for a conjugate provided herein ranges from 1 to 7. In certain embodiments, the DAR for a conjugate provided herein ranges from 1 to 6. In certain embodiments, the DAR for a conjugate provided herein ranges from 1 to 5. In certain embodiments, the DAR for a conjugate provided herein ranges from 1 to 4.

In certain embodiments, the DAR for a conjugate provided herein is about 1, about 2, about 3, about 4, about 5, about 6, about 7, about 8, about 9, about 10, about 11, or about 12. In some embodiments, the DAR for a conjugate provided herein is about 3.1, about 3.2, about 3.3, about 3.4, about 3.5, about 3.6, about 3.7, about 3.8, or about 3.9. In some embodiments, the DAR for a conjugate provided herein is about 7.1, about 7.2, about 7.3, about 7.4, about 7.5, about 7.6, about 7.7, about 7.8, about 7.9, or about 8.0.

In some embodiments, the DAR for a conjugate provided herein is about 1. In some embodiments, the DAR for a conjugate provided herein is about 2. In some embodiments, the DAR for a conjugate provided herein is about 3. In some embodiments, the DAR for a conjugate provided herein is about 4. In some embodiments, the DAR for a conjugate provided herein is about 3.8. In some embodiments, the DAR for a conjugate provided herein is about 5. In some embodiments, the DAR for a conjugate provided herein is about 6. In some embodiments, the DAR for a conjugate provided herein is about 7. In some embodiments, the DAR for a conjugate provided herein is about 8.

In certain embodiments, fewer than the theoretical maximum of units are conjugated to the polypeptide, e.g., antibody, during a conjugation reaction.

In certain embodiments, the amino acid that attaches to a unit is in the heavy chain of an antibody. In certain embodiments, the amino acid that attaches to a unit is in the light chain of an antibody. In certain embodiments, the amino acid that attaches to a unit is in the hinge region of an antibody. In certain embodiments, the amino acid that attaches to a unit is in the Fc region of an antibody. In certain embodiments, the amino acid that attaches to a unit is in the constant region (e.g., CH1, CH2, or CH3 of a heavy chain, or CH1 of a light chain) of an antibody. In yet other embodiments, the amino acid that attaches to a unit or a drug unit is in the VH framework regions of an antibody. In yet other embodiments, the amino acid that attaches to unit is in the VL framework regions of an antibody.

It is to be understood that the preparation of the conjugates described herein may result in a mixture of conjugates with a distribution of one or more units attached to a polypeptide (i.e., heterogenous), for example, an antibody. Individual conjugate molecules may be identified in the mixture by mass spectroscopy and separated by HPLC, e.g. hydrophobic interaction chromatography, including such methods known in the art. In certain embodiments, a homogeneous conjugate with a single DAR (loading) value may be isolated from the conjugation mixture by electrophoresis or chromatography.

The present disclosure provides an antibody-drug conjugate (ADC) comprising a monoclonal antibody, or an antigen-binding fragment thereof, directed against MUC1* conjugated to a cytotoxin. The term "antibody-drug conjugate," as used herein, refers to a compound comprising a monoclonal antibody (mAb) attached to a cytotoxic agent (generally a small molecule drug with a high systemic toxicity) via chemical linkers. In some embodiments, an ADC may comprise a small molecule cytotoxin that has been chemically modified to contain a linker. The linker is then used to conjugate the cytotoxin to the antibody, or antigen-binding fragment thereof. Upon binding to the target antigen on the surface of a cell, the ADC is internalized and trafficked to the lysosome where the cytotoxin is released by either proteolysis of a cleavable linker (e.g., by cathepsin B found in the lysosome) or by proteolytic degradation of the antibody, if attached to the cytotoxin via a non-cleavable linker. The cytotoxin then translocates out of the lysosome and into the cytosol or nucleus, where it can then bind to its target, depending on its mechanism of action.

The antibody-drug conjugate described herein may comprise a whole antibody or an antibody fragment. The parent antibody may be murine, rabbit, human, humanized, camelid or other species.

The ADC may comprise an antigen-binding fragment of an antibody. The terms "antibody fragment," "antigen-binding fragment," "functional fragment of an antibody," and "antigen-binding portion" are used interchangeably herein and refer to one or more fragments or portions of an antibody that retain the ability to specifically bind to an antigen (see, generally, Holliger et al., Nat. Biotech., 23 (9): 1 126-1129 (2005)). The antibody fragment may comprise, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab') 2 fragment, which is a bivalent fragment comprising two Fab fragments linked by a disulfide bridge at the hinge region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242:423-426 (1988); Huston et al., Proc. Natl. Acad. Sci. USA, 85:5879-5883 (1988); and Osbourn et al., Nat. Biotechnol., 16:778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites.

The terms "cytotoxin" and "cytotoxic agent" refer to any molecule that inhibits or prevents the function of cells and/or causes destruction of cells (cell death), and/or exerts antiproliferative effects. It will be appreciated that a cytotoxin or cytotoxic agent of an ADC also is referred to in the art as the "payload" of the ADC. A number of classes of cytotoxic agents are known in the art to have potential utility in ADC molecules and can be used in the ADC described herein. Such classes of cytotoxic agents include, for example, anti-microtubule agents (e.g., auristatins and maytansinoids), pyrrolobenzodiazepines (PBDs), RNA polymerase II inhibitors (e.g., amatoxins), and DNA alkylating agents (e.g., indolinobenzodiazepine pseudodimers). Examples of specific cytotoxic agents that may be used in the ADC described herein include, but are not limited to, amanitins, auristatins, calicheamicin, daunomycins, doxorubicins, duocarmycins, dolastatins, enediynes, lexitropsins, taxanes, puromycins, maytansinoids, *vinca* alkaloids, tubulysins, and pyrrolobenzodiazepines (PBDs). More specifically, the cytotoxic agent may be, for example AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM1, DM4, vinblastine, methotrexate, netropsin, or derivatives or analogs thereof.

Auristatins represent a class of highly potent antimitotic agents that have shown substantial preclinical activity at well-tolerated doses. Examples of auristatins that may be used in connection with the ADC described herein include, but are not limited to, monomethyl auristatin E (MMAE) and the related molecule monomethyl auristatin F (MMAF).

In one embodiment, the cytotoxic agent may be a pyrrolobenzodiazepine (PBD) or a PBD derivative. PBD translocates to the nucleus where it crosslinks DNA, preventing replication during mitosis, damaging DNA by inducing single strand breaks, and subsequently leading to apoptosis. Some PBDs also have the ability to recognize and bind to specific sequences of DNA.

The anti-MUC1* monoclonal antibody described herein comprises at least one cytotoxin molecule conjugated thereto; however, the anti-MUC1* monoclonal antibody may comprise any suitable number of cytotoxin molecules conjugated thereto (e.g., 1, 2, 3, 4, or more cytotoxin molecules) to achieve a desired therapeutic effect.

The disclosure also provides a composition comprising the above-described antibody or antibody-drug conjugate and a pharmaceutically acceptable (e.g., physiologically acceptable) carrier. Any suitable carrier known in the art can be used within the context of the invention. The choice of carrier will be determined, in part, by the particular site to which the composition may be administered and the particular method used to administer the composition. The composition optionally may be sterile. The compositions can be generated in accordance with conventional techniques described in, e.g., Remington: The Science and Practice of Pharmacy, 21st Edition, Lippincott Williams & Wilkins, Philadelphia, Pa. (2001).

The composition desirably comprises the antibody or antibody-drug conjugate in an amount that is effective to treat or prevent MUC1* expressing cancer. Thus, the disclosure provides a method of killing MUC1* positive cells, which comprises contacting the cells that express MUC1* with the antibody or antibody-drug conjugate described herein, or a composition comprising the antibody or ADC described herein, whereby the antibody or antibody-drug conjugate binds to MUC1* on the cells and kills the cells.

The disclosure also provides use of the antibody or ADC described herein, or the composition comprising the antibody or ADC, in the manufacture of a medicament for treating MUC1* positive cancer.

As demonstrated herein, MUC1* is expressed on a variety of cancer types. As such, the disclosure provides a method of killing such cancer cells, which comprises contacting the cancer cells that express MUC1* with the antibody-drug conjugate described herein, or a composition comprising the ADC described herein, whereby the antibody-drug conjugate binds to MUC1* on the cells and kills the cells.

The antibody-drug conjugate described herein, or a composition comprising the antibody-drug conjugate, may be contacted with a population of cells that expresses MUC1* ex vivo, in vivo, or in vitro, preferably in vivo.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the antibody or ADC or the composition comprising the antibody or ADC and a pharmaceutically acceptable carrier. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the antibody or ADC to elicit a desired response in the individual. For example, a therapeutically effective amount of the ADC of the invention is an amount which binds to MUC1* on the MUC1* positive cells and destroys them.

Alternatively, the pharmacologic and/or physiologic effect may be prophylactic, i.e., the effect completely or partially prevents a disease or symptom thereof. In this respect, the inventive method comprises administering a "prophylactically effective amount" of the ADC or a composition comprising the ADC to a mammal that is predisposed to a cancer that expresses MUC1*. A "prophylactically effective amount" refers to an amount effective, at dosages and for periods of time necessary, to achieve a desired prophylactic result (e.g., prevention of disease onset).

Therapeutic or prophylactic efficacy can be monitored by periodic assessment of treated patients. In one embodiment, the ADC described herein inhibits or suppresses proliferation of MUC1*-expressing cells by at least about 10% (e.g., at least about 20%, at least about 30%, at least about 40%, at least about 50%, at least about 60%, at least about 70%, at least about 80%, at least about 90%, or at least about 100%). Cell proliferation can be measured using any suitable method known in the art, such as measuring incorporation of labeled nucleosides (e.g., 3H-thymidine or bromodeoxyuridine Brd (U)) into genomic DNA (see, e.g., Madhavan, H. N., J. Stem Cells Regen. Med., 3 (1): 12-14 (2007)).

The antibody or ADC described herein, or a composition comprising the antibody ADC, can be administered to a mammal (e.g., a human) using standard administration techniques, including, for example, intravenous, intraperitoneal, subcutaneous. More preferably, the antibody or ADC or composition containing the same is administered to a mammal by intravenous injection.

The antibody or ADC described herein, or the composition comprising the antibody or ADC, can be administered with one or more additional therapeutic agents, which can be coadministered to the mammal. The term "coadministering," as used herein, refers to administering one or more additional therapeutic agents and the antibody or ADC described herein, or the antibody or ADC-containing composition, sufficiently close in time such that the antibody or ADC can enhance the effect of one or more additional therapeutic agents, or vice versa. In this regard, the antibody or ADC or the composition containing the same may be administered first, and the one or more additional therapeutic agents may be administered second, or vice versa. For example, the antibody or ADC or composition containing the same may be administered in combination with other agents (e.g., as an adjuvant) for the treatment or prevention of MUC1* positive cancer. In this respect, the antibody or ADC or antibody or ADC-containing composition can be used in combination with at least one other anticancer agent including, for example, any suitable chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery.

Figure 9A:
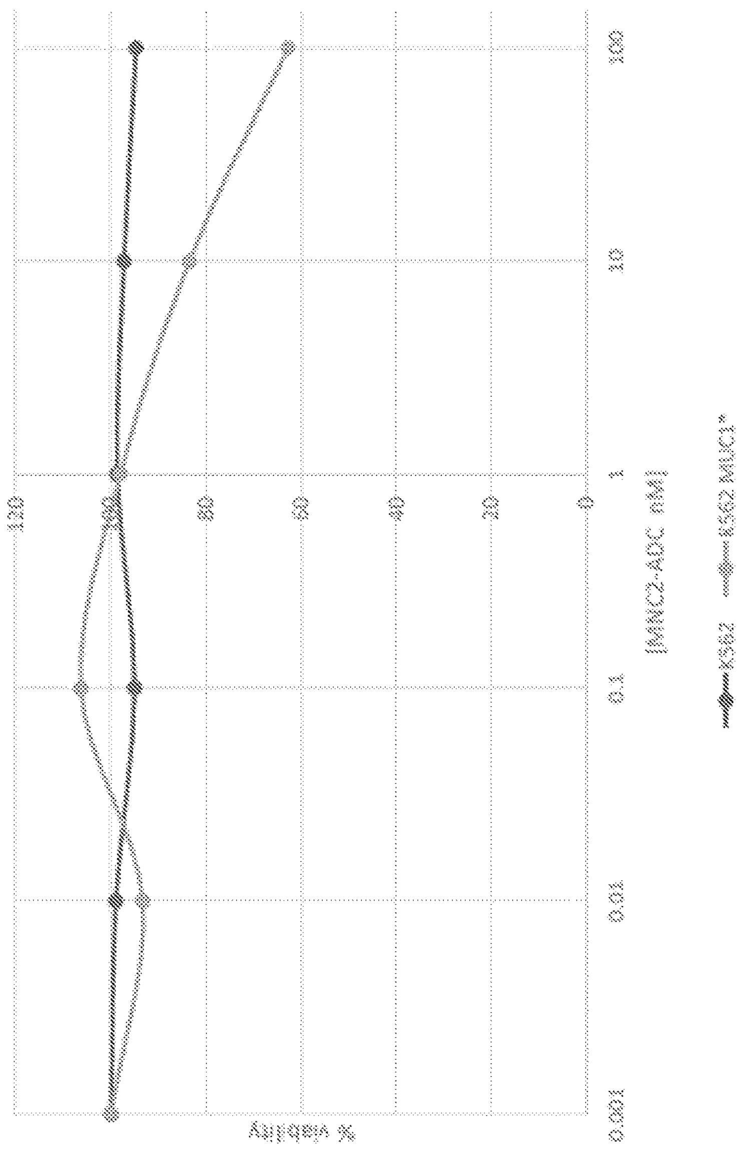
FIGS. 9A-9B show a graphs of cell viability assays, wherein PrestoBlue was used to measure cell death. The graph shows cell viability as a function of MNC2-ADC concentration, comparing the effect of MNC2-ADC on K562-WT cells versus K562-MUC1* cells. As can be seen, the MNC2-ADC antibody induced death only of the MUC1* expressing cells at concentrations of 10 nM and 100 nM.
Figure 9B:
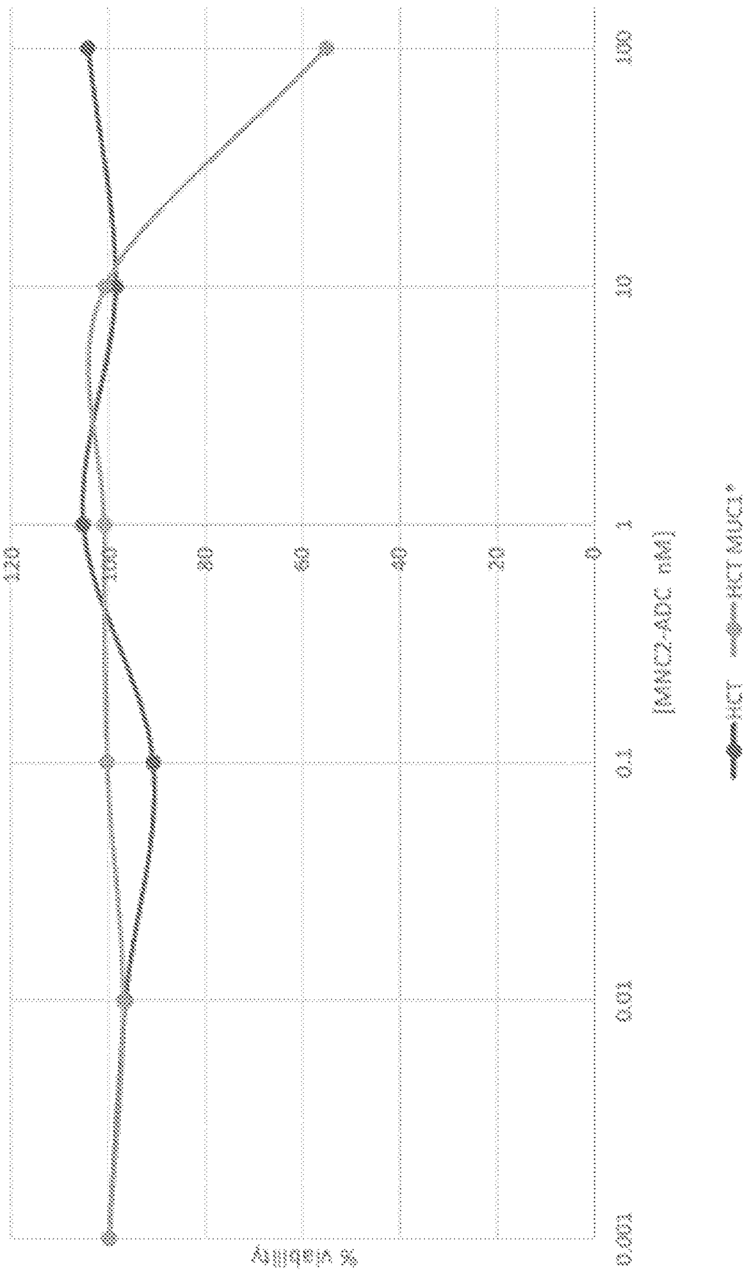
Figure 10A:
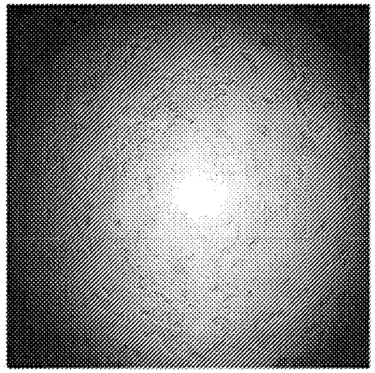
FIGS. 10A-10G show photographs of T47D-WT breast cancer cells, which express both full-length MUC1, which MNC2 does not bind, and MUC1* to which MNC2 does bind. The cells have been incubated with MNC2-ADC for 72 hours. In this specific case, the toxic MMAE (monomethyl auristatin) was covalently coupled to a deglycosylated MNC2, which binds to MUC1*.
Figure 10B:
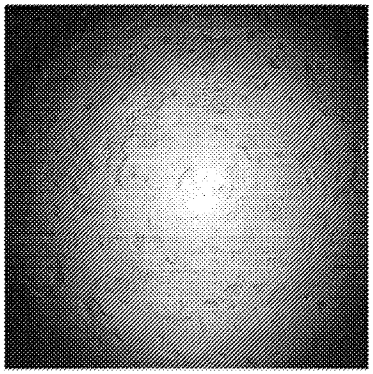
Figure 10C:
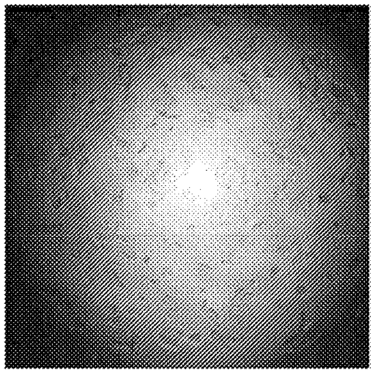
Figure 10D:
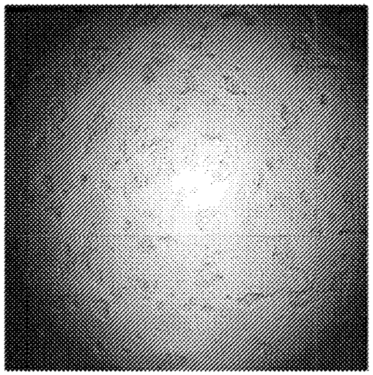
Figure 10E:
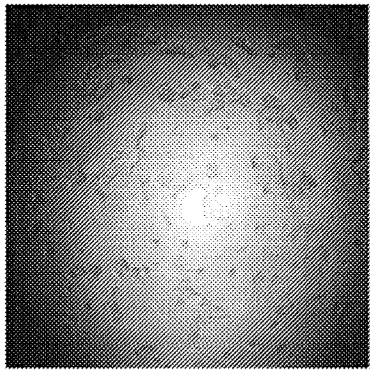
Figure 10F:
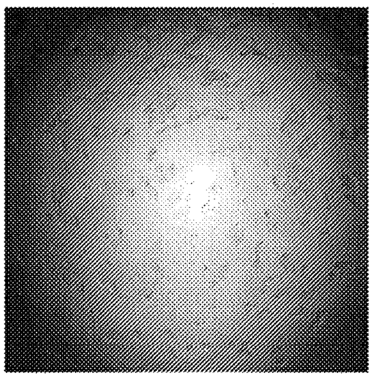
Figure 10G:
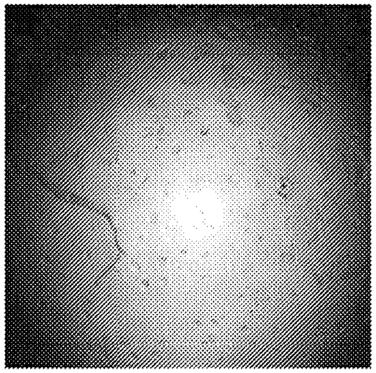

As one example of how antibodies of the invention can be incorporated into ADCs, antibody drug conjugates, for the treatment of MUC1* positive cancers, a toxin was attached to anti-MUC1* antibody MNC2. In this particular example, the toxin is MMAE, monomethyl auristatin, although there are a variety of toxins and functional linkers known to those skilled in the art that facilitate ADC-directed killing of target cells, especially cancer cells. In this example, MNC2 was deglycosylated, then reacted with a linker that facilitated the covalent attachment of the MMAE, referred to herein as MNC2-ADC. MNC2-ADC, at a range of concentrations, was incubated with target cells for various time periods. Cells were then photographed and cell viability was measured using a cell death indicator called PrestoBlue™ (Thermo Fisher Scientific, Waltham, MA). MNC2-ADC incubated with HCT, which is a MUC1 and MUC1* negative cell line, did not induce cell death at any concentration (FIG. 5A-5F). However, when HCT cells were transduced to express MUC1*, creating HCT-MUC1*, then MNC2-ADC did induce cell death in a dose dependent manner (FIG. 6A-6G). A graph of the measured loss of cell viability is shown in FIG. 9B. Similarly, MNC2-ADC did not induce cell death in K562 cells, which are MUC1* negative cells (FIG. 7A-7G). Again, when the cells were transduced to express MUC1*, creating K562-MUC1*, MNC2-ADC was able to induce cell death in a concentration dependent manner (FIG. 8A-8G). A graph of the measured loss of cell viability is shown in FIG. 9A.

Figure 12:
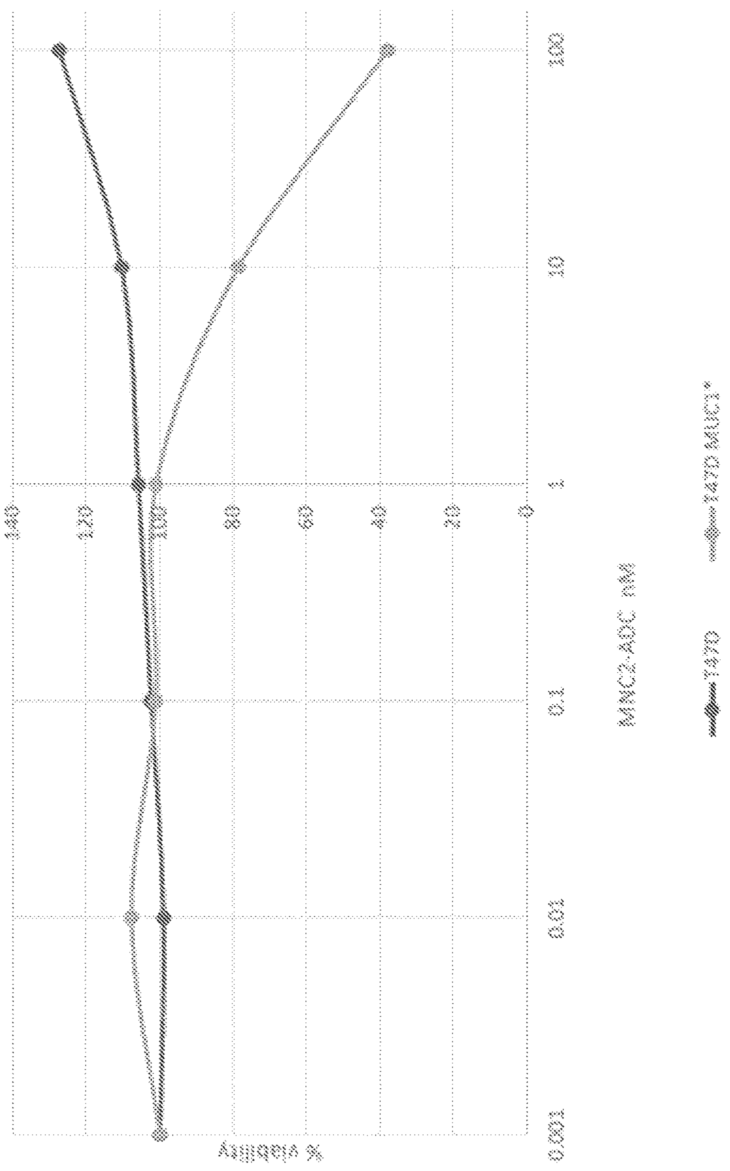
FIG. 12 shows a graph of a cell viability assay, wherein PrestoBlue was used to detect dead cells. The graph shows cell viability as a function of MNC2-ADC concentration, comparing the effect of MNC2-ADC on T47D-WT cells versus T47D-MUC1* cells. As can be seen, the MNC2-ADC antibody induced death of the MUC1* expressing cells at concentrations of 10 nM and 100 nM.
Figure 13A:
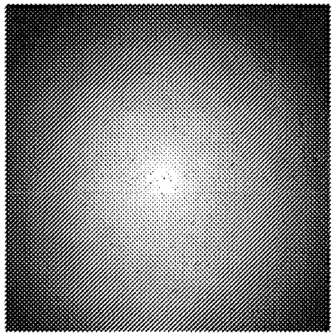
FIGS. 13A-13J show photographs of T47D-WT breast cancer cells, which express both full-length MUC1, which MNC2 does not bind, and MUC1* to which MNC2 does bind. The cells have been incubated with MNC2-ADC for 72 hours. In this specific case, the toxic MMAE (monomethyl auristatin) was covalently coupled to a deglycosylated MNC2, which binds to MUC1*. As can be seen, the MNC2-ADC antibody induced death of the T47D-WT cells at the highest concentration of 1000 nM of MNC2-ADC.
Figure 13B:
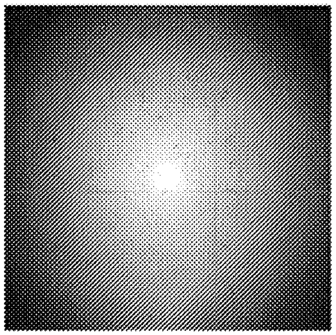
Figure 13C:
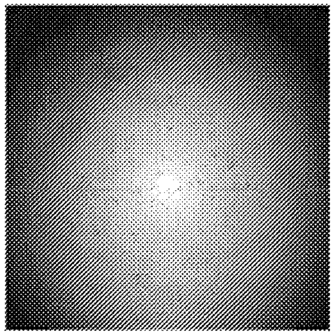
Figure 13D:
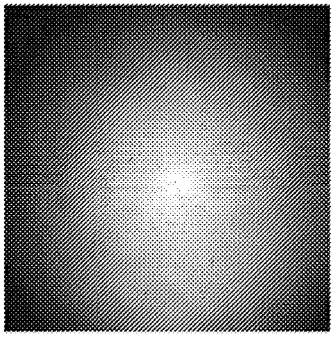
Figure 13E:
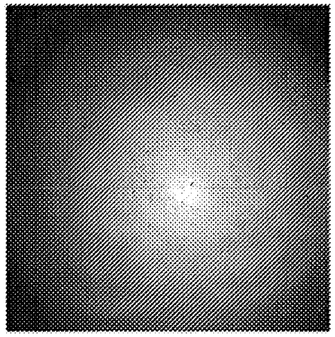
Figure 13F:
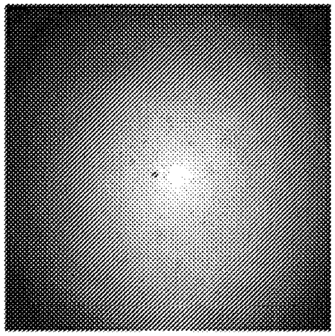
Figure 13G:
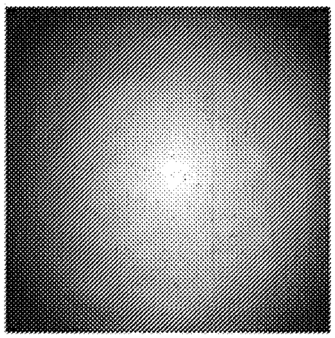
Figure 13H:
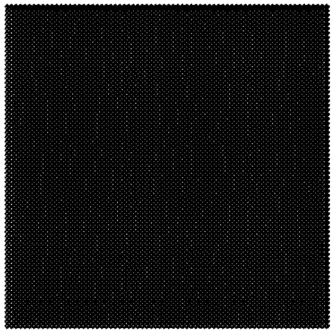
Figure 13I:
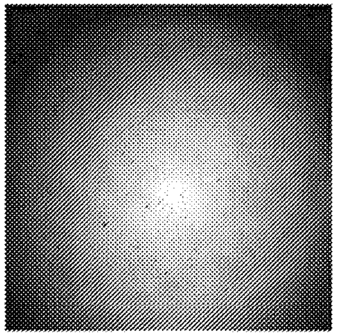
Figure 13J:
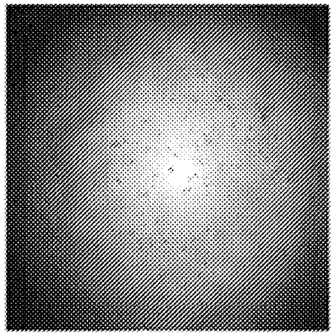
Figure 14A:
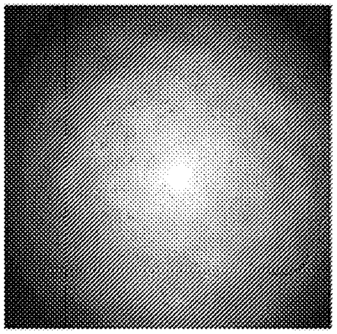
FIGS. 14A-14J show photographs of T47D-MUC1* cells that have been transduced to express even more MUC1*. The cells have been incubated with MNC2-ADC for 72 hours. In this specific case, the toxic MMAE (monomethyl auristatin) was covalently coupled to a deglycosylated MNC2, which binds to MUC1*. As can be seen in the figure, the addition of the MNC2-ADC at the higher concentrations tested here, 10 nM, 39 nM, 100 nM, 393 nM and 1000 nM induced cell clumping which is an indicator of cell death.
Figure 14B:
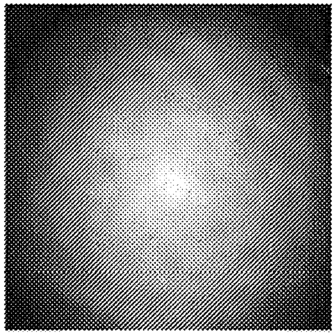
Figure 14C:
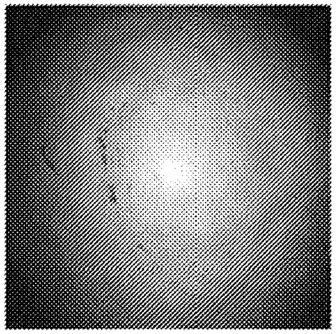
Figure 14D:
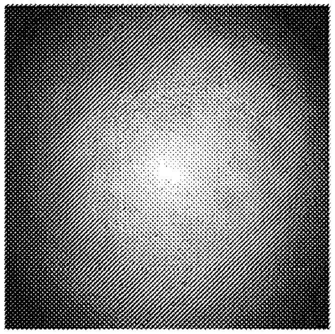
Figure 14E:
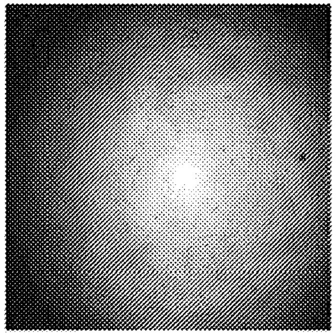
Figure 14F:
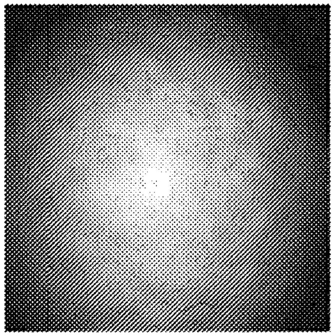
Figure 14G:
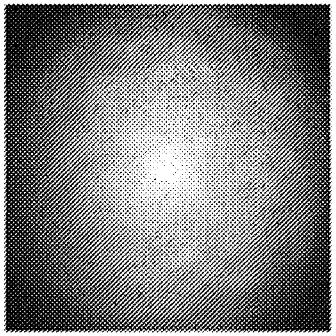
Figure 14H:
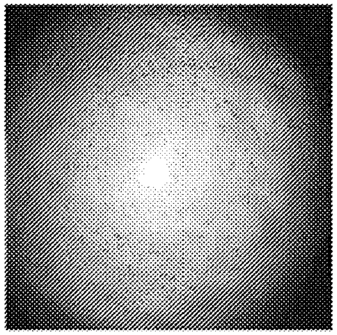
Figure 14I:
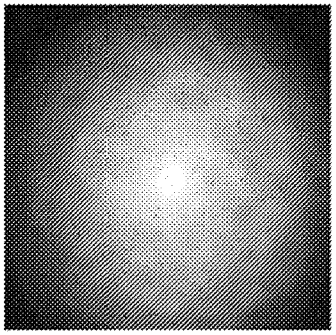
Figure 14J:
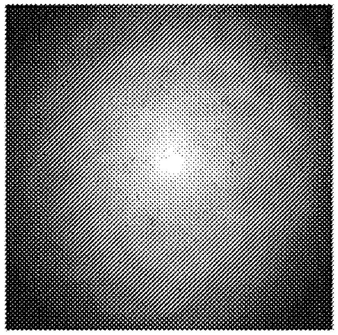
Figure 15A:
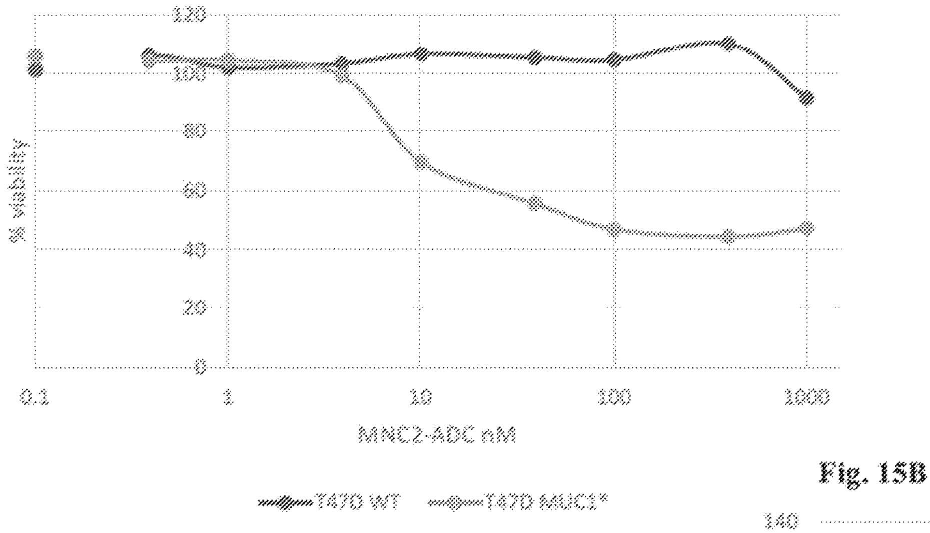
FIGS. 15A-15B shows a graph of a cell viability assay, wherein PrestoBlue was used to measure cell death. The graph shows cell viability as a function of MNC2-ADC concentration, comparing the effect of MNC2-ADC on T47D-WT cells versus T47D-MUC1* cells. As can be seen, the MNC2-ADC antibody induced death of the T47D-WT cells at the highest concentration of 1000 nM of MNC2-ADC, while the T47D-MUC1* cells were killed at concentrations of 10 nM, 39 nM, 100 nM, 393 nM and 1000 nM.
Figure 15B:
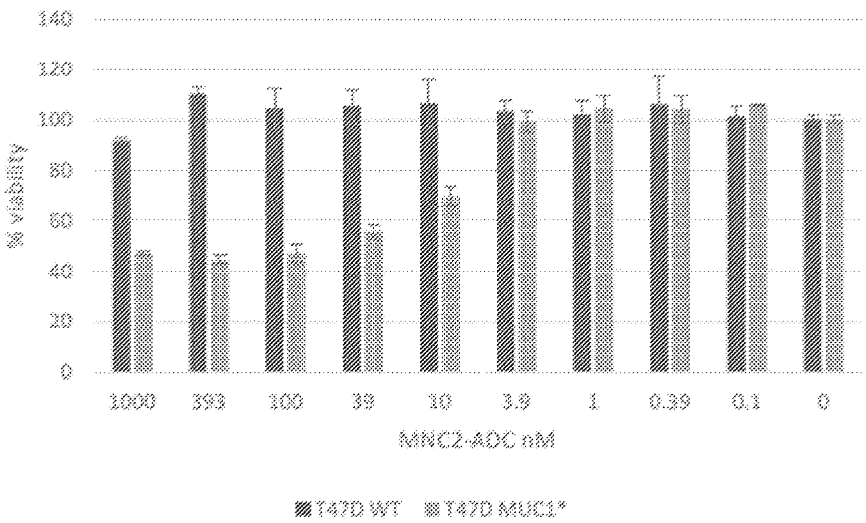

T47D cells are a naturally occurring breast cancer cell line that express both full-length MUC1, to which MNC2 does not bind, as well as MUC1*, to which MNC2 does bind. T47D-MUC1* is a cell line in which T47D cells have been transduced to express even more MUC1*. MNC2-ADC was incubated with T47D-WT cells (FIG. 10A-10G) or T47D-MUC1* cells (FIG. 11A-11G). As can be seen in the graph of measured cell viability (FIG. 12), only T47D-MUC1* cells were killed at the highest concentration tested. Another experiment was performed in which the concentration of added MNC2-ADC was greatly increased. In this case, T47D-WT cells were killed by MNC2-ADC at 1000 nM (FIGS. 13A-13J) and T47D-MUC1* cells were killed at 10 nM, 39 nM, 100 nM, 393 nM, and at 1000 nM (FIG. 14A-14J). A graph of the measured cell death induced by MNC2-ADC for T47D and T47D-MUC1* is shown in FIG. 15A. These experiments are shown as just one example. For an ADC to work, engagement of the ADC with the target cell must induce receptor internalization, which this set of examples demonstrates. The toxin that is attached to the anti-MUC1* antibody may be one of several known to those skilled in the art. Similarly, MNC2 may be human or humanized.

Figure 17:
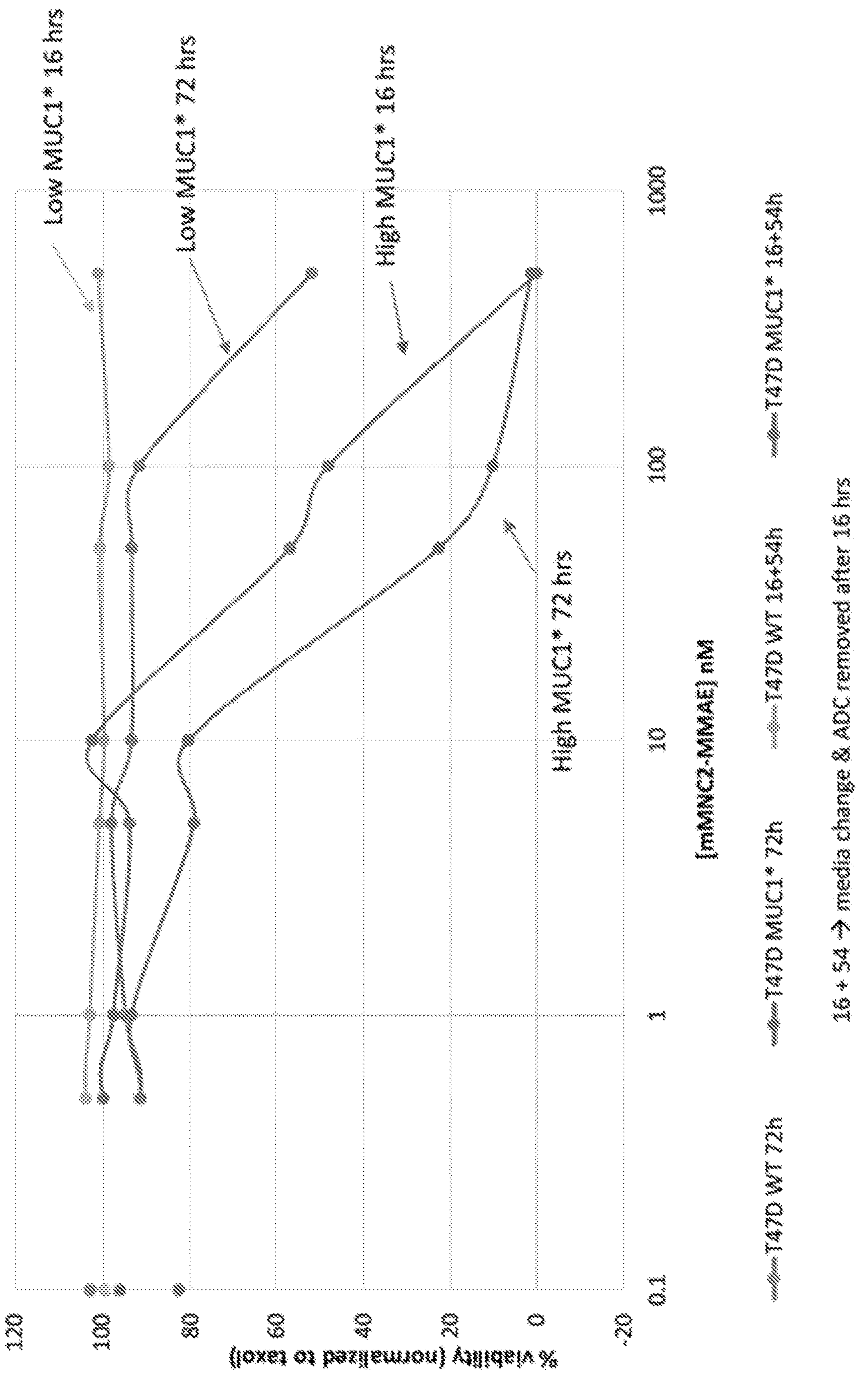
FIG. 17 shows the graph of cancer cell killing as a function of concentration of the MNC2-ADC MMAE added to cell culture media for either 72 hours or 16 hours. In the latter case, media is exchanged after 16 hours to a media that does not contain MNC2-ADC and experiment is allowed to continue until 72 hours after initial addition of MNC2-ADC to cancer cells. Cell viability is measured using Presto Blue. Cell death is normalized to Taxol added to a final concentration of 1 μM, whereas the percent viable cells at 72 hours is normalized to 0% viability.

However, optimization of the toxin coupling chemistry greatly improved the results for an MNC2-ADC. In this next experiment, a valine-citrulline p-aminobenzylcarbamate (VC-PAB) linker was used to connect the deglycosylated antibody and the toxin. The linker is separately coupled to the MMAE at one end, then the other end is reacted with maleimide, then coupled to the antibody after reduction through alkylation. MMAE inhibits cell division by blocking the polymerization of tubulin. The linker, which is stable outside of the cell gets cleaved by Cathepsin B the ADC is internalized, which activates the MMAE. This optimized MNC2-ADC, over concentrations ranging from 0.1 ng/mL to 500 ng/mL, was incubated with either T47D wild type (-WT) (FIGS. 16A and 16C) or T47D cells that were transduced to express even more MUC1*, (T47D-MUC1*) (FIGS. 16B and 16D). In one case, the MNC2-ADC was incubated with 5,000 target MUC1* positive cells per well of a 96-well plate for 72 hours (FIG. 16A-16B). Alternatively, the MNC2-ADC was only incubated with the target MUC1* positive cells for 16 hours, after which media was replaced and cells remained in culture for another 54 hours (FIG. 16C-16D). For comparison, the well-known cancer drug Taxol was added to T47D-wt or T47D-MUC1* cells for 72 hours (FIG. 16E-16F). The viability of the 72 hour co-cultures was measured using a cell death indicator called PrestoBlue™ (Thermo Fisher Scientific, Waltham, MA) (FIG. 17). As can be seen in the figure, higher antigen density cells are killed faster and at lower MNC2-ADC concentrations. 90% of the high MUC1* cells were killed at an MNC2-ADC concentration of 100 nM in a 72 hour incubation.

Figures 18A, 18B, 18C, 18D:
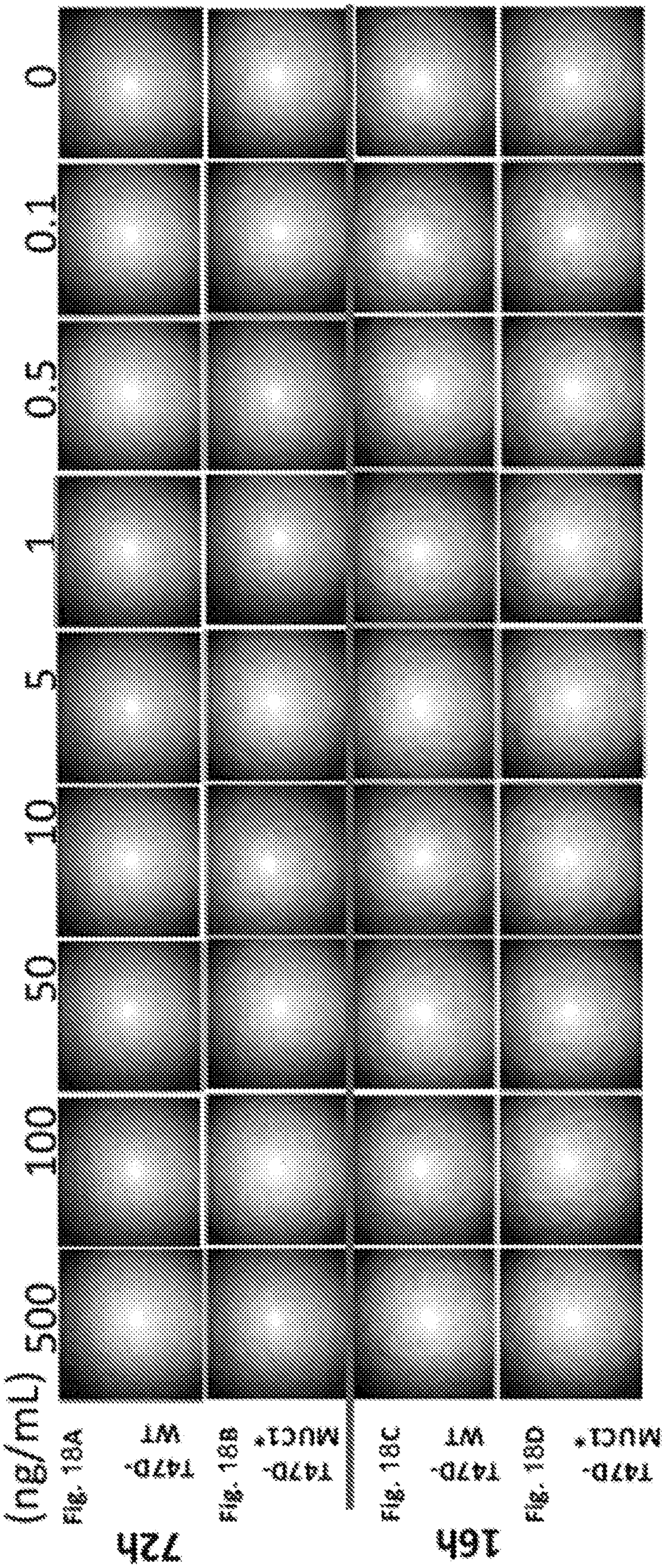
FIGS. 18A-18F shows magnified photographs of cancer cells to which was added an 20A10-ADC over a range of concentrations. Here, the toxin that is conjugated to the antibody is MMAE.
Figure 18E:
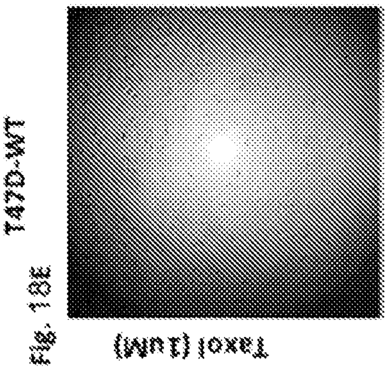
Figure 18F:
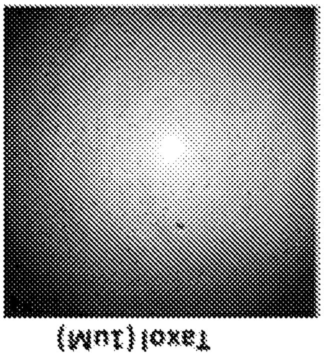
Figure 19:
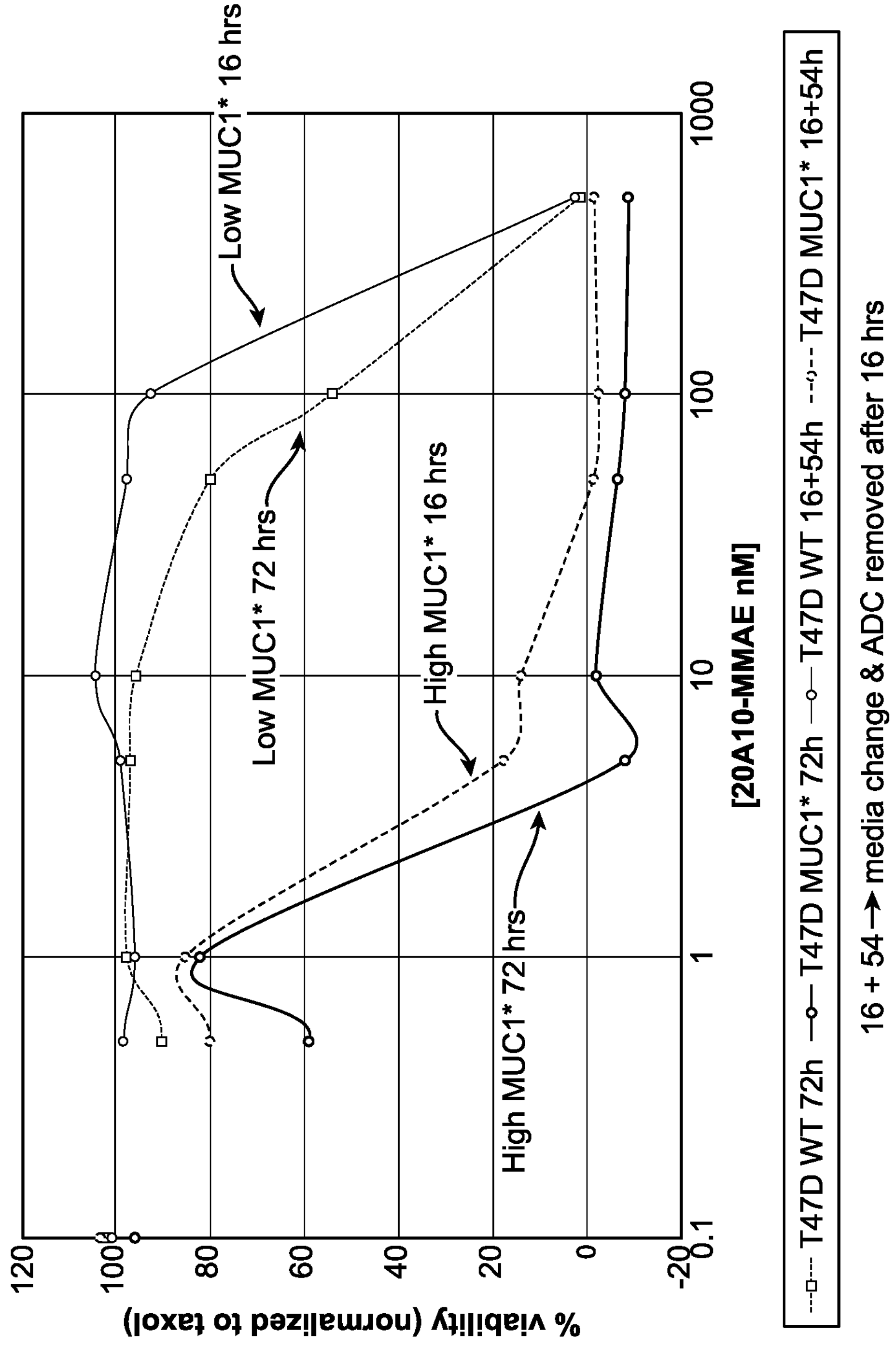
FIG. 19 shows the graph of cancer cell killing as a function of concentration of the 20A10-ADC MMAE added to cell culture media for either 72 hours or 16 hours. In the latter case, media is exchanged after 16 hours to a media that does not contain 20A10-ADC and experiment is allowed to continue until 72 hours after initial addition of 20A10-ADC to cancer cells. Cell viability is measured using Presto Blue. Cell death is normalized to Taxol added to a final concentration of 1 μM, whereas the percent viable cells at 72 hours is normalized to 0% viability.

As another example of how antibodies of the invention can be incorporated into ADCs, antibody drug conjugates, for the treatment of MUC1* positive cancers, a toxin was attached to another anti-MUC1* antibody, 20A10. Magnified photographs of the remaining cancer cells were taken after 72 hours in co-culture with the 20A10-ADC (FIG. 18A-18F) In this particular example, the toxin is MMAE, monomethyl auristatin, although there are a variety of toxins and functional linkers known to those skilled in the art that facilitate ADC-directed killing of target cells, especially cancer cells. 20A10 was deglycosylated, then reacted with a linker that facilitated the covalent attachment of the MMAE, referred to herein as 20A10-ADC or 20A10-MMAE. 20A10-ADC, over concentrations ranging from 0.1 ng/ml to 500 ng/mL, was incubated with either T47D wild type (-WT) (FIGS. 18A and 18C) or T47D cells that were transduced to express even more MUC1*, (T47D-MUC1*) (FIGS. 18B and 18D). In one case, the 20A10-ADC was incubated with the target MUC1* positive cells for the entire 72 hour assay (FIG. 18A-18B). Alternatively, the 20A10-ADC was only incubated with the target MUC1* positive cells for 16 hours, after which media was replaced and cells remained in culture for another 54 hours (FIG. 18C-18D). For comparison, the well-known cancer drug Taxol was added to T47D-wt or T47D-MUC1* cells for 72 hours (FIG. 18E-18F). The viability of the 72 hour co-cultures was measured using a cell death indicator called PrestoBlue™ (Thermo Fisher Scientific, Waltham, MA) (FIG. 19). As can be seen in the figure, the higher the antigen density, the more killing the cancer cells are killed. Even with a 16 hour incubation, more than 80% of the high MUC1* cells were killed, and with a 72 hour incubation 100% were killed at a concentration less than 10 nM. Cells expressing lower amounts of MUC1* required higher 20A10-ADC concentration and longer incubation periods to effect 100% cell killing.

Figures 20A, 20B:
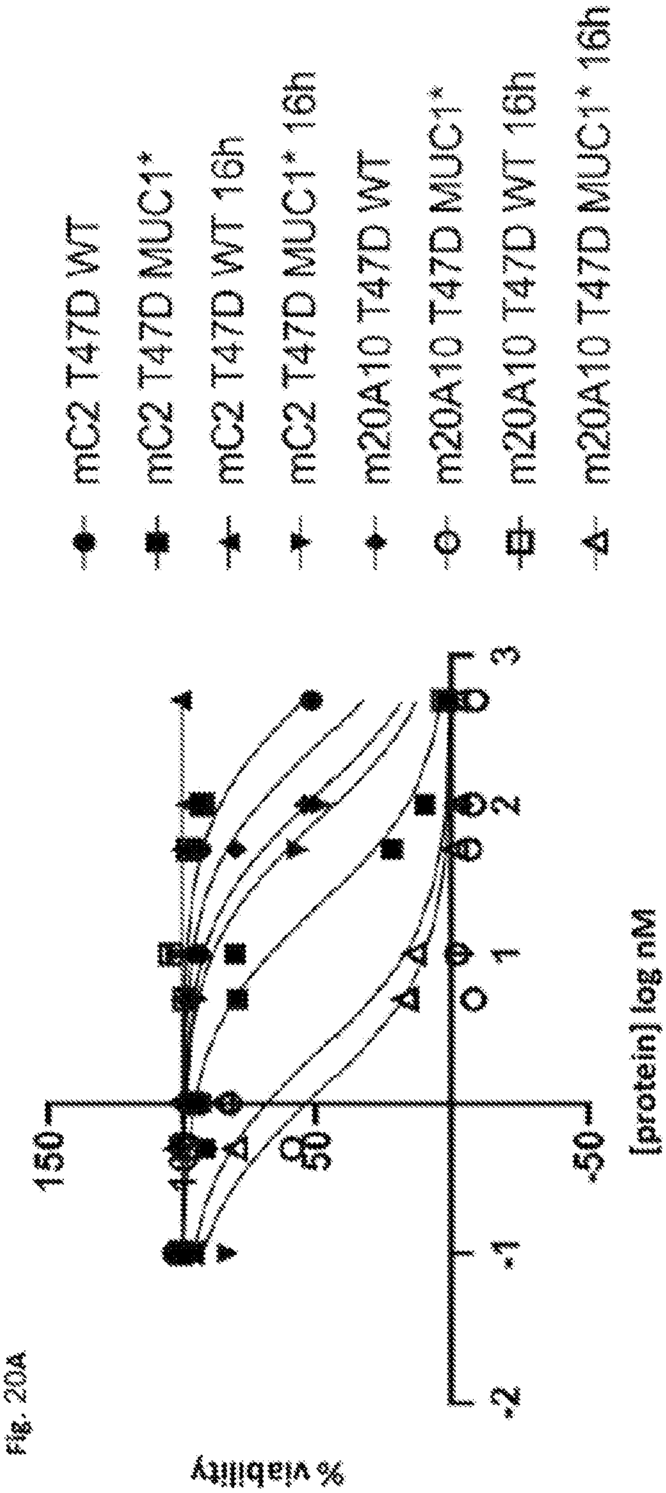
Figures 22A, 22B, 22C, 22D, 22E, 22F, 22G, 22H:
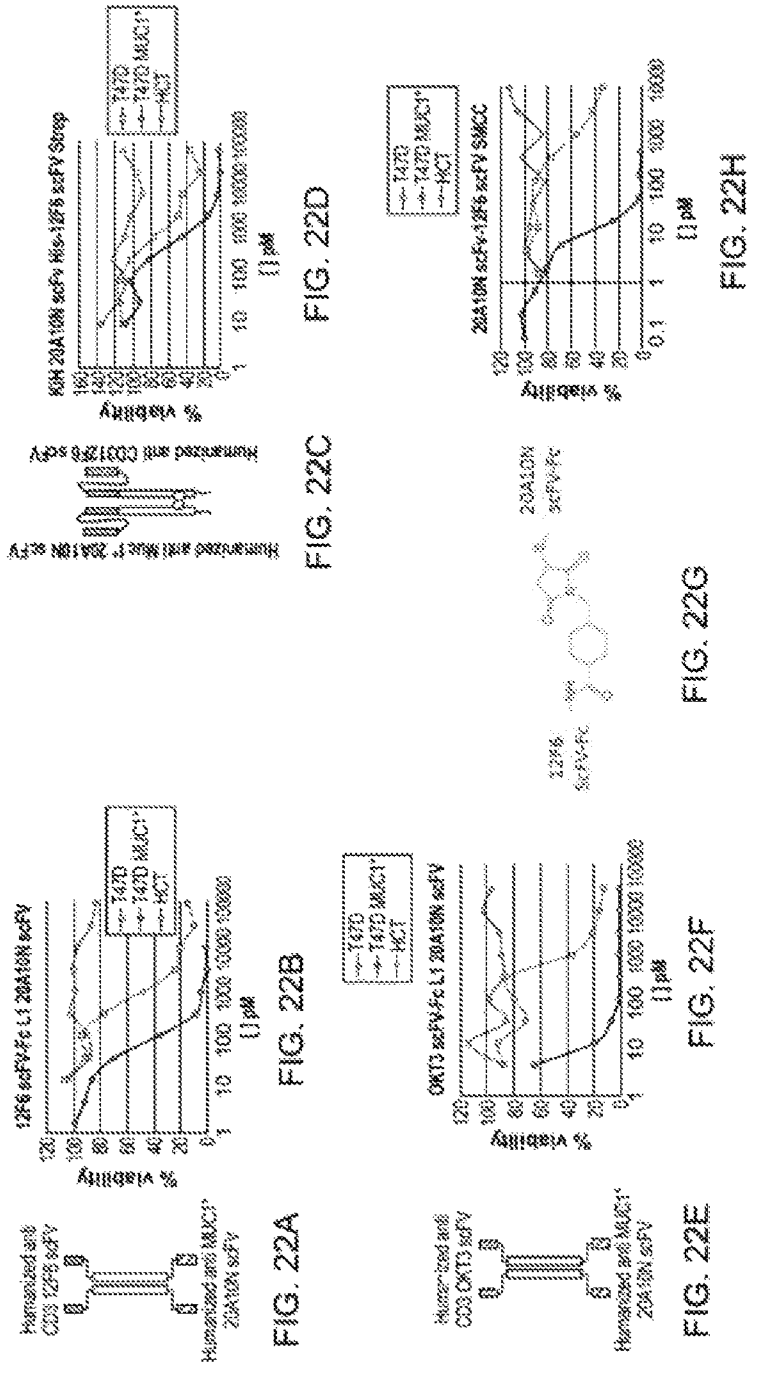
FIGS. 22A-22H show MN20A10-OKT3 or MN20A10-12F6 in various bispecific formats. The figure shows the killing curve of T47D-wt or T47D-MUC1* by different format of bispecific antibodies.
Figure 23:
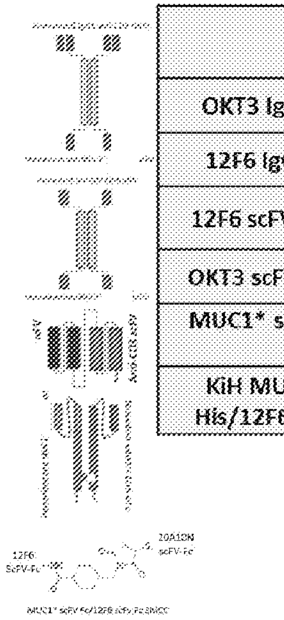
FIG. 23 shows IC50s MN20A10-OKT3 or MN20A10-12F6 in various bispecific formats

The graph of FIG. 20A plots IC50 for these experiments. The data are also shown in tabular form in FIG. 20B.

These experiments demonstrate that anti-MUC1* antibodies can be successfully incorporated into many ADC formats, using optimized coupling chemistry as well as new, improved toxins and linkers.

One of the in vitro methods for characterizing each ADC is to measure the ability of the antibody to bind the target antigen before as well as after the coupling of the toxin to the antibody. The specificity of the antibody can be compromised by the process of chemically conjugating a number toxins to the antibody. This phenomenon is due more to the intrinsic stability, or instability, of each antibody than being due to elements of the coupling process. In many cases, the payload is coupled to the antibody via binding to free thiols that are generated by breaking, or reducing, disulfide bonds. Disulfide bonding holds together the two heavy chains as well as supports the structure of the variable regions, which are the antibody recognition units. A significant challenge is reducing enough disulfide bonds to allow for the attachment of multiple toxins, without breaking the disulfide bonds that maintain critical antibody structure. Unexpectedly, MNC2 is a very stable, well-behaved antibody that allowed the attachment of many toxins without corrupting the structure of the antibody or altering its ability to recognize its target antigen. A challenge encountered when attaching payloads to antibody MN20A10 involved the timing of the disulfide reduction and the conjugation of the toxin. Most protocols for ADC coupling call for iterative disulfide reduction, then testing for the number of free thiols. If this is a prolonged process, the free thiols can re-oxidize, which may recreate the original structure or could create a new structure that results in loss of antibody target specificity. This situation occurred when attempting to conjugate toxins to antibody MN20A10, which is an IgG2b isotype. This problem was overcome by 1) empirically determining the number of molar equivalents required to reduce MN20A10; 2) adding that number of reducing equivalents all at once; 3) adding coupling reagents at elevated temperature where the time to reach desired temperature is decreased by performing reaction in a water bath, and further accelerating the reaction time by intermittent shaking during the reaction period. FIG. 36A-36D shows graphs of flow cytometry measuring the ability of MNC2 to recognize breast cancer cells and lung cancer cells before, then after coupling of MMAE. FIG. 37A-37D shows graphs of flow cytometry measuring the ability of MN20A10 to recognize breast cancer cells and lung cancer cells before then after coupling of MMAE. It appears that, in comparison to MN20A10, MNC2 appears less able to recognize cancer cells after coupling of MMAE. In light of the fact that, in this experiment, the drug-antibody-ratio (DAR) of MNC2-MMAE was higher than the DAR of 20A10-MMAE, combined with the greater ability of MNC2-MMAE to eradicate these same tumors in animals, the attachment of several toxins to the MNC2 antibody could sterically hindered the binding of the secondary antibody.

One of the key goals researchers are trying to achieve is the development of an anti-cancer therapeutic that can recognize and kill the early cancer cells that express low levels of the target antigen. Statistically, cancer patients have a greater chance of survival if their cancers are treated at a very early stage. To date, there are few if any targeted cancer therapeutics that are able to kill the early, low antigen expressing cancer cells. The more recent targeted therapies typically can only kill the cancer cell if the expression of the target antigen rises above a certain threshold. The breast cancer drug Herceptin, for example, can only be prescribed if the patient's expression of the target, HER2, is relatively high. Even then, about 20% of patients treated with Herceptin will develop resistance to Herceptin that often carries with it resistance to other anti-cancer therapeutics. It is now appreciated that tumor recurrence is frequently caused by the low antigen expressing cells that are not killed off by the therapeutic. In the case that the target antigen is a growth factor receptor, then later stage tumors express higher levels of the growth factor receptors, but those higher levels also drive tumor growth at a faster rate than the cells expressing lower levels of the growth factor receptor.

Therefore, although seldom done, it is critically important to test anti-cancer therapeutics against both the low antigen expressing early cancer cells and the later cancer cells that express high levels of the targeted antigen. In FIGS. 38A-45D, the ability of MNC2-ADCs and MN20A10-ADCs to kill multiple cancer sub-types was tested, where the tumors were either low-medium antigen expressing cancer cells or high antigen expressing cancer cells. Surprisingly, MNC2-ADCs and MN20A10-ADCs showed the remarkable ability to kill both low antigen expressing cancer cells and high antigen expressing cells. The low expressing cancer cells were killed by treatment with either MNC2-ADC or MN20A10-ADC in the high nanomolar range of ADC, which is considered druggable. The cancer cells that expressed high levels of MUC1* were killed with IC50s in the single digit nanomolar range. Sub-micromolar levels of antibody are considered druggable. Again, because MNC2 and MN20A10 have a high degree of cancer-specificity, this dosing range would be very tolerable. In vitro measurement of ADC killing often under-estimates the in vivo killing potential of the ADC. In vivo, killing due to a "bystander" effect is commonly observed. That is when the killing of cells within the tumor triggers host release of cytokines, macrophages and the like that greatly increase killing. These effects do not happen in vitro.

For example, MNC2-MMAE, MNC2-MMAF, MN20A10-MMAE and MN20A10-MMAF were tested for their ability to kill, in vitro, T47D wild-type breast cancer cells that express low levels of MUC1* and also T47D-MUC1* cells that were engineered to express more MUC1*. Similarly, the anti-MUC1*-ADCs were tested for their ability to kill HPAF II wild-type pancreatic cancer cells that express low levels of MUC1* as well as HPAF II-MUC1* cells that were engineered to express more MUC1* FIG. 38A-38F. In these experiments the DARs of MNC2-MMAE and MNC2-MMAF are comparable at 4.1 vs 3.7. There was a bit of a gap between DARs of MN20A10-MMAE and MN20A10-MMAF, being 5.8 and 3.8 respectively, which is reflected in their killing potency. As can be seen in the figure, both wild-type, low antigen expressing cells are killed when treated with the ADCs at sub-micro molar dose, which is considered druggable. Unexpectedly, although MUC1* is a growth factor receptor, the more MUC1* that is expressed, the greater is the ADC-mediated killing. Both breast and pancreatic cancer cells that were engineered to express more MUC1* were readily killed by MNC2-MMAE, MNC2-MMAF, MN20A10-MMAE and MN20A10-MMAF at very low nanomolar concentrations. The killing of target cells by MNC2-Deruxtecan or MN20A10-Deruxtecan was compared to MNC2-MMAE, MNC2-MMAF. MN20A10-MMAE and MN20A10-MMAF (FIG. 40A-40C). In this in vitro assay, all five anti-MUC1* ADCs appear to have comparable killing potency, although killing of bystander cells cannot be determined in this assay. The anti-MUC1*-ADCs were also shown to be potent killers of MUC1* positive prostate cancer cells (FIGS. 41A-41B) and non-small cell lung cancer cells (FIG. 42A-42B).

In a set of flow cytometry experiments, the specific killing effect of MNC2-MMAE or MN20A10-MMAE is determined by measuring the viability of target cancer cells after the addition of the MUC1*-ADCs. Here the target cells are T47D wild-type breast cancer cells or T47D breast cancer cells that were engineered to express more MUC1*, called T47D-MUC1*. As can be seen in FIG. 43 both MN20A10-MMAE and MNC2-MMAE effectively kill both the wild-type breast cancer cells and the cells that have been engineered to express more MUC1*. However, with both MUC1*-ADCs, killing potency if greater when the cells overexpress the target antigen. Cancer cells expressing low levels of MUC1* are consistent with early stage cancers whereas cells expressing high levels of MUC1* are consistent with late stage cancers.

To demonstrate that any cell expressing MUC1* would be killed by the MUC1*-ADCs described herein, we engineered a MUC1-negative colon cancer cell line, HCT-116, to express MUC1*, e.g. HCT-MUC1*. What can be seen in the cell viability assay of FIG. 44 is that only the MUC1* expressing cells are killed. The viability of MUC1* expressing cancer cells was measured after the addition of either MN20A10, unconjugated, or MN20A10-MMAE. As can be seen in FIG. 45 MN20A10-MMAE effectively killed non-small cell lung cancer cells, DU145 hormone refractory prostate cancer cells and pancreatic cancer cells.

FIG. 46-FIG. 48 show magnified photographs of the various types of cancer cells after treatment with either an MNC2-ADC or an MN20A10-ADC. The killing effect can be readily seen as the significant decrease in cell number, the change in cell morphology from the characteristic flat, spreading morphology to the rounded up morphology and lifting off of the cells. In contrast, the control wells show confluent monolayer of compact cells with the normal flat spreading morphology and without dead floating cells. FIGS. 46A-46C and FIGS. 46G-46F show T47D-MUC1* breast cancer cells treated with MNC2-MMAE. FIGS. 46D-46F and FIG. 46G-46J show T47D-MUC1* breast cancer cells treated with MNC2-Deruxtecan. FIGS. 47A-47B show DU145 hormone resistant prostate cancer cells treated with MNC2-MMAE. FIGS. 47C-47D show DU145 hormone resistant prostate cancer cells treated with MNC2-Deruxtecan. FIGS. 48A-48B and FIGS. 48G-48H show T47D-MUC1* breast cancer cells treated with MN20A10-MMAE. FIGS. 48C-48D and FIGS. 48I-48J show T47D-MUC1* breast cancer cells treated with MN20A10-Deruxtecan. FIG. 48K-48L show DU145 hormone resistant prostate cancer cells treated with MN20A10-MMAE. FIG. 48M-48N show DU145 hormone resistant prostate cancer cells treated with MN20A10-Deruxtecan. As is visually apparent, the killing effect of the anti-MUC1*-ADCs shown in FIGS. 46-48 is consistent with the killing that was measured by flow cytometry, shown in FIGS. 38-45.

MNC2-ADCs and MN20A10-ADCs were also assayed for their ability to kill both low and high MUC1* expressing cells by monitoring killing in real-time using an xCELLigence instrument (FIG. 53-56). In the xCelligence system, target cancer cells, which are adherent, are plated onto electrode array 96-well plates. Adherent cells insulate the electrode and increase the impedance. The number of adherent cancer cells is directly proportional to impedance. Antibodies and antibody-drug-conjugates are much smaller and do not significantly contribute to impedance. Therefore, increasing impedance reflects the growth of the cancer cells and decreasing impedance reflects the killing of the cancer cells.

Breast cancer cell line T47D-wt expresses MUC1* at low to low-medium levels.

Pancreatic cancer cell line HPAF II-wt expresses even lower levels of MUC1* and lung cancer cell line NCI-H1975 express still lower levels of MUC1*. Both MNC2 and MN20A10, conjugated to MMAE, MMAF, Deruxtecan, or exatecan efficiently kill low expressing T47D-wt breast cancer cells (FIG. 49 and FIG. 54), non-small cell lung cancer cells (FIG. 51 and FIG. 56), and pancreatic cancer cells (FIG. 52). Cancer cells that express low levels of MUC1* are consistent with early cancer cells and are effectively killed by MNC2-ADCs and MN20A10-ADCs when administered at mid-nanomolar dose. As can be clearly seen in FIG. 54 and FIG. 56, where MNC2-Exatecan (DAR 8.2) is compared to MNC2-deruxtecan (DAR 4.0) and MNC2-MMAE (DAR 4.1), MNC2-Exatecan shows more potent killing of the low MUC1* expressing cancer cells, which may be due to the higher number of toxins attached to it.

In the next set of experiments, MNC2-ADCs and MN20A10-ADCs are tested for their ability to kill cancer cells expressing high levels of MUC1*. The expectation is that the higher the levels of MUC1*, the more difficult it would be to kill the cells because MUC1* is the growth factor receptor driving the growth of these cells. Unexpectedly, the experiments show that the more MUC1* is expressed, the easier it is to kill the cells. xCELLigence real-time killing assay was also used to compare MNC2 and MN20A10, conjugated to MMAE, MMAF, Deruxtecan, or Exatecan for killing cancer cells that express higher levels of MUC1*. Breast cancer cell lines T47D-MUC1* and HPAF II-MUC1* have been engineered to express high levels of MUC1*, consistent with later stage cancers. As can be seen in FIG. 50, FIG. 53, and FIG. 55, cancer cells that express high levels of MUC1* are completely killed at very low nanomolar dose, 6 nM-19 nM. S In addition to the in vitro assays, in vivo experiment were also performed, wherein anti-MUC1* antibodies MNC2 and MN20A10, conjugated to MMAE, MMAF, Deruxtecan or Exatecan were administered to test mice that had been implanted with either high or low MUC1* expressing breast, lung, or pancreatic tumors. These experiments are more fully detailed in Experiment 18. In one example, NOD/SCID/GAMMA mice were implanted with T47D breast cancer cells that were either wild-type or that had been engineered to express more MUC1*. Animals were administered three injections of MNC2-MMAE, DAR 3.85, at an initial dose of 5 mg/kg, then increased to 10 mg/kg. As can be seen in FIG. 57, mice bearing tumors that expressed high levels of MUC1*, consistent with late stage cancers, were efficiently eliminated by Day 26. Mice implanted with tumors with low MUC1* expressing cells, consistent with early cancers, were not totally eliminated but tumor volume was slight in comparison with the control group. By comparison (FIG. 58), animals that were given the same dose of MN20A10-MMAE, DAR 2.96, did not have complete tumor elimination, likely due to the lesser number of toxins attached. The same dosages of either MNC2-MMAE (FIG. 59) or MN20A10-MMAE (FIG. 60) were given to animals implanted with non-small cell lung cancer tumors. MNC2-MMAE, DAR 4.1 was very effective at eliminating tumors in test mice implanted with pancreatic tumors that were either high or low MUC1* expressers FIG. 61. FIG. 62 shows an update of the experiment shown in FIG. 61. After 66 days, animals treated with MNC2-MMAE were tumor free since day 18, without tumor recurrence. MNC2-Deruxtecan was given to mice implanted with human breast cancer cells expressing low or high levels of MUC1* (FIG. 63 and FIG. 64). Tumors expressing high MUC1* were essentially eliminated by Day 26. Mice implanted with low MUC1* expressing cells were greatly reduced compared to the controls but may require a higher dose or repeat injections.

In an animal model, we showed that as tumors progress to late stage, their expression of MUC1* increases. FIGS. 65A-65D show images of tumor cells. Staining of the Day 0 cells shows the cells express more full-length MUC1 than MUC1* and the staining intensity is light, indicating low numbers of MUC1* receptors, which is indicative of early cancers. Sixty-two (62) days post tumor implantation, which equates to approximately 7 years in human time, one can readily see that MUC1* expression, in terms of extent of expression as well as intensity of expression, has dramatically shifted from low expression to high expression in the late stage tumor. In contrast, the staining of a serial section of the tumor shows full-length MUC1 is expressed, as expected because it is cleaved to MUC1* after surface expression. However, the intensity of the staining has not increased, indicating that the vast majority of the expressed MUC1 has been cleaved to the growth factor receptor form, MUC1*, in the late-stage tumor.

Antibodies

An antibody (Ab) that binds to a polypeptide of interest binds as "binding" in this context is understood by one skilled in the art. For example, an antibody, or a conjugate as described herein comprising such Ab, may bind to other polypeptides or proteins, generally with lower affinity as determined by, e.g., immunoassays or other assays known in the art. In a specific embodiment, Ab, or a conjugate as described herein comprising such Ab that specifically bind to a polypeptide of interest binds to the polypeptide of interest with an affinity that is at least 2 logs, 2.5 logs, 3 logs, 4 logs or greater than the affinity when Ab or the conjugate bind to another polypeptide. In another specific embodiment, Ab, or a conjugate as described herein comprising such Ab, does not specifically bind a polypeptide other than the polypeptide of interest. In a specific embodiment, Ab, or a conjugate as described herein comprising Ab, specifically binds to a polypeptide of interest with an affinity (Kd) less than or equal to 20 mM. In particular embodiments, such binding is with an affinity (Kd) less than or equal to about 20 mM, about 10 mM, about 1 mM, about 100 μM, about 10 μM, about 1 μM, about 100 nM, about 10 nM, or about 1 nM. Unless otherwise noted, “binds,” “binds to,” “specifically binds” or “specifically binds to” in this context are used interchangeably.

In some embodiments, the target cell is a cancer cell. In some embodiments the cancer is breast cancer, colon cancer, prostate cancer, pancreatic cancer, or lung cancer.

In some embodiments, the antibody binds to a cancer cell that expresses MUC1* on the surface.

In certain embodiments, the antibody comprises about 10, about 20, about 30, about 40, about 50, about 100, about 150, about 200, about 250, about 300, about 350, about 400, about 450, about 500, about 550, about 600, about 650, about 700, about 750, about 800, about 850, about 900, or about 950 amino acids.

In certain embodiments, the antibody comprises about 10-50, about 50-100, about 100-150, about 150-200, about 200-250, about 250-300, about 300-350, about 350-400, about 400-450, about 450-500, about 500-600, about 600-700, about 700-800, about 800-900, or about 900-1000 amino acids.

In certain embodiments, the conjugate comprises an antibody, Ab. In certain embodiments, the Ab is a monoclonal antibody. In certain embodiments, the Ab is a human antibody. In certain embodiments, the Ab is a humanized antibody. In certain embodiments, the Ab is a chimeric antibody. In certain embodiments, the Ab is a full-length antibody that comprises two heavy chains and two light chains. In particular embodiments, the Ab is an IgG antibody, e.g., is an IgG1, IgG2, IgG3 or IgG4 antibody. In certain embodiments, the Ab is a single chain antibody. In yet other embodiments, the Ab is an antigen-binding fragment of an antibody, e.g., a Fab fragment.

In particular embodiments, the Ab is an IgG1 antibody. In particular embodiments, the Ab is an IgG2b antibody.

In certain embodiments, the antibody specifically binds to a cell surface protein. In certain embodiments, the antibody specifically binds to a cell surface receptor. In certain embodiments, the antibody specifically binds to a cell surface receptor ligand.

In some embodiments, the antibody, or functional fragment or functional variant thereof binds specifically to MUC1*. In some embodiments, the antibody comprises an anti-MUC1* heavy chain and an anti-MUC1* light chain.

In some embodiments, the anti-MUC1* heavy chain comprises an anti-MUC1* heavy chain variable domain. In some embodiments, the anti-MUC1* heavy chain variable domain comprises a variable domain of an IgG1, IgG2, IgG3, or IgG4 heavy chain. In some embodiments, the anti-MUC1* light chain comprises an anti-MUC1* light chain variable domain. In some embodiments, the anti-MUC1* light chain variable domain comprises a variable domain of a Kappa or Lambda light chain.

In some embodiments, the anti-MUC1* heavy chain variable domain comprises the variable domain of an IgG1 heavy chain and the anti-MUC1* light chain variable domain comprises the variable domain of a Kappa or Lambda light chain. In some embodiments, the anti-MUC1* heavy chain variable domain comprises the variable domain of an IgG2 heavy chain and the anti-MUC1* light chain variable domain comprises the variable domain of a Kappa or Lambda light chain. In some embodiments, the anti-MUC1* heavy chain variable domain comprises the variable domain of an IgG3 heavy chain and the anti-MUC1* light chain variable domain comprises the variable domain of a Kappa or Lambda light chain. In some embodiments, the anti-MUC1* heavy chain variable domain comprises the variable domain of an IgG4 heavy chain and the anti-MUC1* light chain variable domain comprises the variable domain of a Kappa or Lambda light chain.

In some embodiments, the anti-MUC1* heavy chain variable domain comprises the variable domain of an IgG1 heavy chain and the anti-MUC1* light chain variable domain comprises the variable domain of a Kappa light chain. In some embodiments, the anti-MUC1* heavy chain variable domain comprises the variable domain of an IgG2 heavy chain and the anti-MUC1* light chain variable domain comprises the variable domain of a Kappa light chain. In some embodiments, the anti-MUC1* heavy chain variable domain comprises the variable domain of an IgG3 heavy chain and the anti-MUC1* light chain variable domain comprises the variable domain of a Kappa light chain. In some embodiments, the anti-MUC1* heavy chain variable domain comprises the variable domain of an IgG4 heavy chain and the anti-MUC1* light chain variable domain comprises the variable domain of a Kappa light chain.

In some embodiments, the anti-MUC1* heavy chain variable domain comprises the variable domain of an IgG1 heavy chain and the anti-MUC1* light chain variable domain comprises the variable domain of a Lambda light chain. In some embodiments, the anti-MUC1* heavy chain variable domain comprises the variable domain of an IgG2 heavy chain and the anti-MUC1* light chain variable domain comprises the variable domain of a Lambda light chain. In some embodiments, the anti-MUC1* heavy chain variable domain comprises the variable domain of an IgG3 heavy chain and the anti-MUC1* light chain variable domain comprises the variable domain of a Lambda light chain. In some embodiments, the anti-MUC1* heavy chain variable domain comprises the variable domain of an IgG4 heavy chain and the anti-MUC1* light chain variable domain comprises the variable domain of a Lambda light chain.

In some embodiments, the antibody, or functional fragment or functional variant thereof, that binds specifically to MUC1* comprises a single-chain variable fragment (scFv) or an antigen-binding fragment (Fab). In some embodiments, the antibody, or functional fragment or functional variant thereof, that binds specifically to MUC1* comprises a single-chain variable fragment. In some embodiments, the antibody, or functional fragment or functional variant thereof, that binds specifically to MUC1* comprises an antigen-binding fragment (Fab).

In some embodiments, the anti-MUC1* heavy chain variable domain comprises complementarity determining regions (CDRs): HC-CDR1, HC-CDR2, and HC-CDR3, and wherein the HC-CDR1, the HC-CDR2, and the HC-CDR3 of the anti-MUC1* heavy chain variable domain comprise amino acid sequences according to HC-CDR1: SEQ ID NO: 1 or 4; HC-CDR2: SEQ ID NO: 2 or 5; HC-CDR3: SEQ ID NO: 3 or 6; and wherein the CDRs comprise from 0-2 amino acid modification(s) (e.g., 0 or 1 amino acid modification(s)) in at least one of the HC-CDR1, HC-CDR2, or HC-CDR3.

In some embodiments, the anti-MUC1* light chain variable domain comprises complementarity determining regions (CDRs): LC-CDR1, LC-CDR2, and LC-CDR3, and wherein the LC-CDR1, the LC-CDR2, and the LC-CDR3 of the anti-MUC1* light chain variable domain comprises amino acid sequences according to LC-CDR1: SEQ ID NO: 13 or 16; LC-CDR2: SEQ ID NO: 14 or 17; LC-CDR3: SEQ ID NO: 15 or 18; and wherein the CDRs comprise from 0-2 amino acid modification(s) (e.g., 0 or 1 amino acid modification(s)) in at least one of the LC-CDR1, LC-CDR2, or LC-CDR3.

In some embodiments, the anti-MUC1* heavy chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOS: 38 or 44. In some embodiments, the anti-MUC1* light chain comprises an amino acid sequence with at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NOs: 41 or 47.

Antibody drug conjugates (ADCs) work when the variable regions of the antibody portion recognize a molecule expressed on the outside of the cancer cell. After the antibody binds to the target antigen, the entire ADC is internalized. Antibody internalization is a requirement for the function of ADC cell killing. Often, cell internalization of the ADC biochemically alters the toxin making it more potent in some cases, while in other cases the alteration traps the toxin inside the cell to reduce off-target toxicities. Not all receptors are internalized after ligand binding or specially after antibody binding which can dimerize the receptor, making internalization more difficult if not impossible. FIG. 25A-25D shows photographs taken on a confocal microscope documenting that anti-MUC1* antibodies, such as MNC2, are internalized after they bind to the extra cellular domain of the MUC1* receptor.

Payload

Antibody drug conjugates (ADCs) combine the target specificity of an antibody (e.g., a monoclonal antibody) with the potency of a small molecule drug (known as payload or cytotoxic group) by connecting them into a single ADC molecule that retain the properties of both. The improved selectivity and potency of ADCs leads to superior safety and efficacy resulting in broader therapeutic windows compared to conventional chemotherapeutic drugs. The term "payload" and "cytotoxic group" are used interchangeably herein.

In some embodiments, the payload is a topoisomerase inhibitor. In some embodiments, the topoisomerase inhibitor is a topoisomerase I inhibitor. In some embodiments, the topoisomerase inhibitor is Exatecan or a derivative thereof. In some embodiments, the topoisomerase inhibitor is deruxtecan or a derivative thereof.

In some embodiments, the payload is a tubulin formation inhibitor. In some embodiments, the tubulin formation inhibitor is monomethylauristatin E (MMAE) or monomethylauristatin F (MMAF).

Some of the more recent toxic payloads used in ADC format, such as Deruxtecan, belong to the exatecan family of topoisomerase I inhibitors. One such recent payload coupler configuration used in ADC format is Deruxtecan, shown in FIG. 28. Here, a maleimidocaproyl (MC) portion facilitates coupling to a Cysteine on the antibody. The maleimidocaproyl is connected to the toxic payload, Dxd, via a glycine phenylalanine linker, GGFG, a coupler HN-CH2-which connects to the Dxd. Dxd is a topoisomerase I inhibitor, which is the mechanism by which it inhibits cell division. In another example shown in FIG. 29, an Exatecan payload was attached to antibodies via a para-aminobenzyl (PAB) portion, connected to a valine-citrulline (VC) portion, that is in turn connected to a maleimidocaproyl (MC) portion that facilitates coupling to a Cysteine on the antibody.

Exatecans have a high level of bystander effect, meaning that they can kill neighboring cells. Clinical trials for a new ADC targeting HER2+ breast cancers, Enhertu, was plagued by severe and life-threatening side effects, such as pneumonitis. It has been reported that up to 16% of the Enhertu patients suffered from treatment induced pneumonitis. Enhertu did however receive FDA approval as it reportedly increased survival for metastatic breast cancer patients by nearly two years. It is not completely clear whether these side effects are due to the payload or to the target, HER2, which is also expressed on normal lung and normal heart. Recall that the first two patients treated with a HER2 targeting CAR T cell product died shortly after the infusion. Follow-on research indicated that the fatalities were due to the use of an antibody that had an extremely high affinity for HER2. More recently, yet another patient died after being treated with a different HER2-targeting ADC. These results underscore the importance of selecting an antibody with superior cancer selectivity to avoid these life-threatening toxicities. MNC2 and MN20A10 unexpectedly have an extremely high degree of cancer specificity and elicited no toxicities in animal studies, where each antibody was incorporated into several ADC formats.

Linkers

In certain embodiments, the linker-L-comprises one or more of carbon atoms, nitrogen atoms, sulfur atoms, oxygen atoms, and combinations thereof. In certain embodiments, the linker-L-comprises one or more amino acids. In certain embodiments, the linker-L-comprises one or more of an ether bond, thioether bond, amine bond, amide bond, carbon-carbon bond, carbon-nitrogen bond, carbon-oxygen bond, carbon-sulfur bond, and combinations thereof. In certain embodiments, the linker-L-comprises a linear structure. In certain embodiments, the linker-L-comprises a di-, tri-, or tetra-peptide linking moiety.

The linker can comprise at least one glycine. The linker can comprise at least one glycine

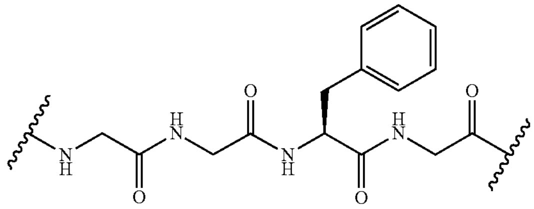

.

and a phenylalanine. The linker can comprise a structure of: The linker can comprise a valine. The linker can comprise a citrulline. The linker can comprise a valine and a citrulline. The linker can be a dipeptide linking moiety having the structure of:

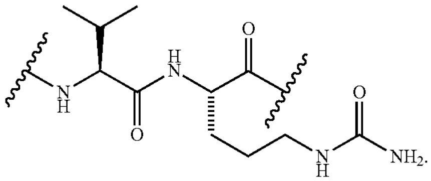 [SMILES: *N[C@H](C(=O)N[C@@H](CCCNC(N)=O)C(*)=O)C(C)C]

.

In certain embodiments, Z is a conjugation moiety capable of forming a covalent bond with an amino acid of a polypeptide. Z can bind to the N-terminus of the linker. Z can comprise a maleimide. In specific embodiments, the amino acid is a cysteine. In certain embodiments, Z is

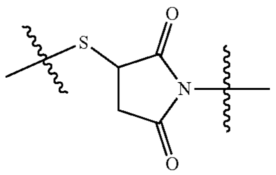

or

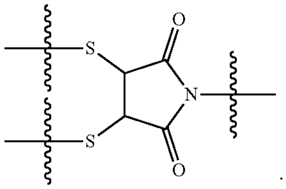

.

In certain embodiments, Z is

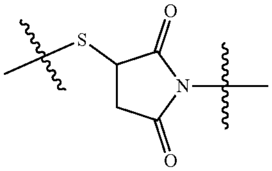

.

In certain embodiments, Z is

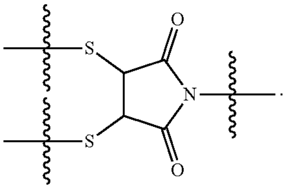 [SMILES: *SC1C(=O)N(*)C(=O)C1S*]

The linker can comprise a coupling moiety, R. In certain embodiments, R is a coupling moiety capable of binding a payload to a C-terminus of the linker. R can comprise a moiety having the structure of:

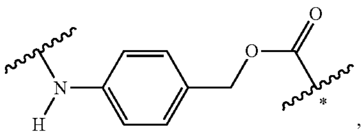 [SMILES: *Nc1ccc(COC(*)=O)cc1]

, wherein the * indicates the point of attachment for the payload. R can comprise a group of structure

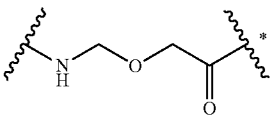

or

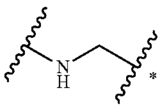

, wherein the * indicates the point of attachment for the payload. R can comprise a group having the structure of:

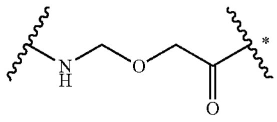

, wherein the * indicates the point of attachment for the payload (e.g., cytotoxic group). R can comprise a group having the structure of:

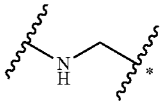

, wherein the * indicates the point of attachment for the payload.

Figure 26:
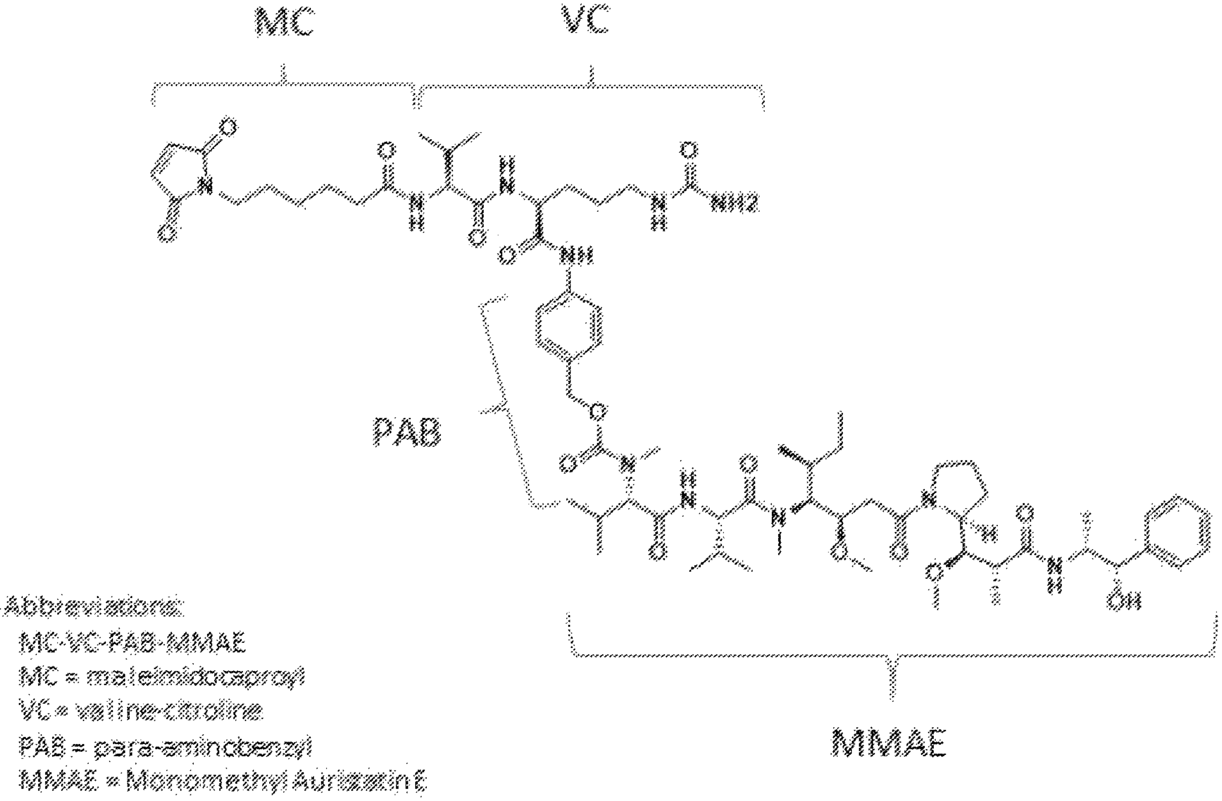
FIG. 26 shows the chemical structure of a chemical entity that includes the toxic payload MMAE, which can be conjugated to an antibody to form an antibody-drug-conjugate, also known as an ADC. MC indicates the maleimidocaproyl (MC) portion that facilitates coupling to a Cysteine on the antibody. VC indicates the valine-citrulline (VC) portion and PAB indicates the para-aminobenzyl (PAB) portion, both of which facilitate enzymatic cleavage inside the cancer cells by the lysosomal enzyme, cathepsin B. MMAE indicates the Monomethyl Auristatin E (MMAE) portion that is the toxic payload that inhibits cell division by blocking the polymerization of tubulin, the toxic payload after cellular internalization and/or cleavage of non-toxic portions.

FIG. 26 shows the chemical structure of payload monomethyl Auristatin E, MMAE, as well as convenient linker molecules and reactive molecules to facilitate chemical coupling of the payload to an antibody. In this instance, MMAE is connected to the antibody via an para-aminobenzyl (PAB) portion, connected to a valine-citrulline (VC) portion, that is in turn connected to a maleimidocaproyl (MC) portion that facilitates coupling to a Cysteine on the antibody. Once the ADC has been internalized, cathepsin B enzymatically cleaves the payload from the antibody, which is facilitated by both PAB and VC. The payload, Monomethyl Auristatin E (MMAE), inhibits cell division by blocking the polymerization of tubulin.

Monomethyl Auristatin F, called MMAF, is another example of a toxic payload that inhibits cell division by blocking the polymerization of tubulin. In the example shown in FIG. 27, the payload, MMAF, is connected to the antibody via a para-aminobenzyl (PAB) portion, connected to a valine-citrulline (VC) portion, that is in turn connected to a maleimidocaproyl (MC) portion that facilitates coupling to a Cysteine on the antibody. Once the ADC has been internalized, cathepsin B enzymatically cleaves the payload from the antibody. Unlike MMAE, MMAF contains a carboxylic acid, which makes it difficult for the payload to exit the cell after the payload has been cleaved from the antibody.

Some of the more recent toxic payloads used in ADC format, such as Deruxtecan, belong to the exatecan family of topoisomerase I inhibitors. One such recent payload coupler configuration used in ADC format is Deruxtecan, shown in FIG. 28A-28E. Here, a maleimidocaproyl (MC) portion facilitates coupling to a Cysteine on the antibody. The maleimidocaproyl is connected to the toxic payload, Dxd, via a glycine phenylalanine linker, GGFG, a coupler HN-CH2-which connects to the Dxd. Dxd is a topoisomerase I inhibitor, which is the mechanism by which it inhibits cell division. In another example shown in FIG. 29A-29E, we attached an Exatecan payload to our antibodies via a para-aminobenzyl (PAB) portion, connected to a valine-citroline (VC) portion, that is in turn connected to a maleimidocaproyl (MC) portion that facilitates coupling to a Cysteine on the antibody.

Pharmaceutical Compositions

In another aspect, provided herein are pharmaceutical compositions comprising the conjugates (e.g., ADCs) and multispecific antibodies as disclosed herein. In some embodiments, the pharmaceutical composition comprises the conjugate of Formula (I) and a pharmaceutically acceptable carrier. In some embodiments, the pharmaceutical composition comprises the multispecific antibody as disclosed herein and a pharmaceutically acceptable carrier.

Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen.

In certain embodiments, a pharmaceutical composition disclosed herein further comprises a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, peritumoral, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

EXAMPLES

Example 1: Anti-MUC1* Internalization Experiments

Figure 25B:
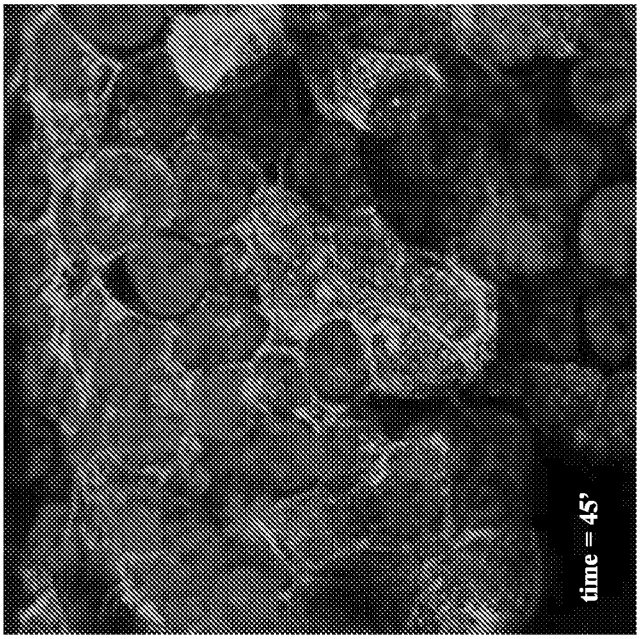
FIGS. 25A-25B shows magnified photographs of human cancer cells stained with anti-MUC1* antibody MNC2, where the nuclei of the cell are stained blue with DAPI and the MNC2 antibody fluoresces red.
Figure 25A:
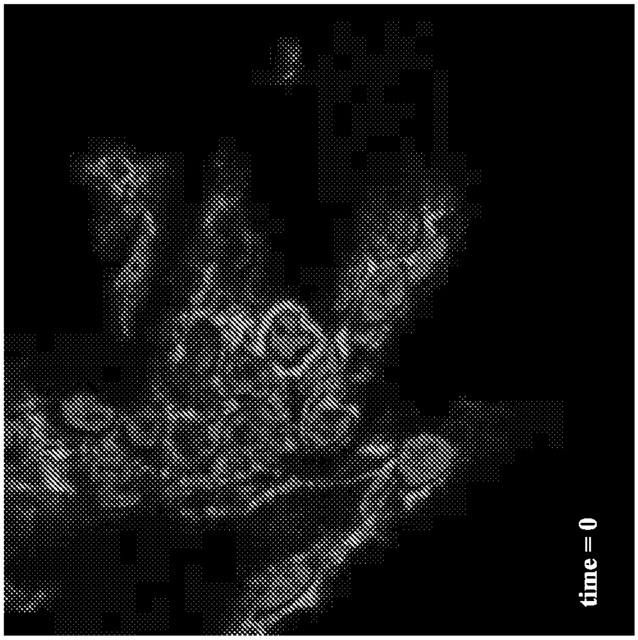

MNC2 internalization was demonstrated (FIG. 25A-25B).

8-well chamber slides (Nunc™ Lab-Tek™ II Chamber Slide™ System Thermo cat #154534PK or Ibidi™ 8-well μ-slide ibiTreat: #1.5 polymer coverslip, tissue culture treated, sterilized) were coated with Collagen (Sigma #C3867), wherein 300 μL of collagen per well were added and incubated overnight at 4° C., washed once with PBS, then once with water, then air-dried in a Biosafety hood. Dry wells under the hood.

T47D breast cancer cells were plated at 30,000-50,000 cells per well in 10% RPMI and cultured for 48 h or until ~70% confluent. Media was removed and cells were serum starved for 24 hours in 2% RPMI. Cells were washed with ice cold PBS.

Antibody was diluted in cold PBS plus 2% FBS to a final concentration of 300 μg/mL. 200 μl of the antibody solution was added to each well and incubated for 2 hours at 4° C. in dark on rocking platform shaker at speed 6. Cells were then washed three times with cold PBS.

An anti-mouse Alexa 488 antibody or an anti-human Alexa 555 antibody at 10 μg/mL was diluted 1:200 in PBS with 2% FBS and incubated for 1 hour at 4° C. in dark, shaking. Cells were washed three times with cold PBS.

For internalization, warm 10% RPMI+75 nM lysotracker deep red (1/13,333) was added and incubated at 37° C. in a $CO_2$ incubator for 2 hours. Cells were washed three times with cold PBS.

Cells were fixed with fresh 4% formaldehyde in PBS for 15 minutes at room temperature, then washed three times with cold PBS. Hoescht dye 33342 in PBS was added at 1 ug/mL and incubated for 10 minutes at room temperature, after which media was removed without a wash step. For Nunc™ Lab-Tek™, cover glass (#1.5) was mounted on chamber slides with mounting medium (Prolong Diamond antifade), avoiding bubbles. Slides were then stored for 24 hours on level surface at room temperature. Longer term storage was at 4° C. in dark. For Ibidi slides, add Ibidi mounting medium.

Photographs were taken on a confocal microscope.

Example 2: General Description for the Small Scale (3 mg) Preparation of MNC2-ADC or MN20A10-ADC (Antibody-Drug-Conjugates)

A solution of unconjugated MNC2, an IgG1 antibody, or MN20A10, an IgG2b antibody, was reduced with an excess of dithiothreitol (DTT) in a pH 8.0 borate buffer. After 2 hours of reducing at 37° C., an aliquot was tested for the amount of free thiol present using an Ellman's thiol test. Depending on the antibody isotype, the number of free thiols varies. If analysis of free thiols using Ellman's reagent indicated an insufficient number of free thiols, then more DTT was added and incubated for an additional time period at 37° C. The process of free thiol determination and adding more reducing agent was repeated until a sufficient number of free thiols was obtained. MN20A10 required more reducing agent than MNC2 and required longer reducing times than MNC2. The reduced antibody was then placed in a pH 6.0 2-(N-morpholino) ethanesulfonic acid (MES) buffer and the free cysteines were alkylated with 11 molar equivalents of a maleimide-linked-toxic agent for about 1 hour. The crude ADC was then purified through a desalting column to remove low molecular weight contaminants such as excess toxic agent, DMSO and other small molecular weight contaminants. The drug-antibody-ratio (DAR) was calculated from the ratio of toxin UV absorbance @ 248 nm (or 370 nm in the case of deruxtecan) to antibody absorbance @ 280 nm. Analysis of the conjugates to determine the drug-antibody-ratio (DAR), i.e, the [Drug: mAb] molar ratio, was accomplished by hydrophobic interaction chromatography-high-performance liquid chromatography following a literature method (Effects of drug loading on the antitumor activity of a monoclonal antibody drug conjugate. Hamblett, K. J., Senter, P. D., Chace, D. F., Sun, M. M. C., Lenox, J., Cerveny, C. G., Kissler, K. M., Bernhardt, S. X., Kopcha, A. K., Zabinski, R. F., Meyer, D. L., and Francisco, J. A. Clin Cancer Res. 2004 Oct. 15; 10 (20): 7063-70. DOI: 10.1158/1078-0432.CCR-04-0789)

This procedure was followed to generate small scale preparations of MNC2-MMAE, MNC2-MMAF, MNC2-deruxtecan, MNC2-exatecan, MN20A10-MMAE, MN20A10-MMAF, MN20A10-deruxtecan and MN20A10-exatecan.

Example 3: Detailed Example of Generation of Small-Scale (3 mg) Prep of MNC2-Deruxtecan IgG1 MNC2 antibody (3.00 mg, 1.578 mL, 1.9 mg/mL, 20 nM) was thawed from −80° C. in a 37° C. water bath for 1 minute. The protein concentration was determined by nanodrop using an extinction coefficient of 14,000 L/g-cm for mouse IgG1 antibodies. The antibody solution was concentrated using centrifuge filters (Amicon Ultra 0.5 mL 50,000 mw cut off (Catalog #UFC505024) (14,000×g at 4° C. for 8 min) to obtain a volume of equal to or less than 100 μL. Then the buffer was exchanged to pH 8.0 borate buffer (25 mM sodium tetraborate, 25 mM NaCl, 1 mM EDTA) by concentrating to <100 μL and resuspending in approximately 300 μL fresh buffer. This process was repeated for a total of 3 times. The concentrated antibody (~100 μL) was transferred to a 0.5 mL screw cap centrifuge tube and was brought up to 300 μL with pH 8.0 borate buffer (25 mM sodium tetraborate, 25 mM sodium chloride, 1 mM EDTA) to make a 10 mg/mL antibody solution.

A solution of dithiothreitol (DTT) (6.48 mM) was prepared by weighing DTT (5 mg, 32.4 mmol) and dissolving it in 5 mL of pH 8.0 borate buffer (25 mM sodium tetraborate, 25 mM sodium chloride, 1 mM EDTA). The DTT solution (6.48 mM, 30.9 uL, 200 nmol, 10 equivalents) was added to the antibody solution and the tube was heated in a 37° C. water bath for 2 hr. The warm reaction mixture was periodically vortexed every 15 minutes. After 2 hours an aliquot of the reaction mixture (6 μL) was taken out for Ellman's thiol analysis, which showed 7.68 free thiols per antibody out of a total possible 8 thiols for an IgG1.

The antibody reduction mixture was cooled in an ice bath to 4° C. and the solution was transferred to a centrifuge filter (Amicon Ultra 0.5 mL 50,000 mw cut off) and the buffer was switched 3 times to pH 6.0 MES buffer (50 mM). [14,000×g, at 4 C, for 8 min). The concentrated reduced antibody was diluted to 640 μL with pH 6.0 MES buffer (50 mM).

A stock solution of Deruxtecan (10 mg/mL, 9.7 mM) in DMSO was prepared by weighing 1.80 mg, 1.74 μMoles and dissolving it in DMSO (180 μL). A solution of deruxtecan (2 mM, 110.2 μL, 220 nmoles) in 50% DMSO/pH 6.0 MES buffer (50 mM) was prepared by diluting the deruxtecan solution (22.8 μL, 10 mg/mL in DMSO) with DMSO (32.3 μL) and then further diluted with 50 mM MES pH 6.0 (50 mM, 55.1 μL) to make a solution of 2 mM deruxtecan in 50% DMSO/50% pH 6.0 MES buffer (50 mM). Deruxtecan solution (110.1 μL, 50% DMSO/50% pH 6.0 MES buffer, 2 mM, 73.4 nmoles, 11 equiv) was added to the tube containing 640 μL of reduced antibody. The reaction was mixed slowly on a vertical rotator for 1 hour at room temperature and monitored by hydrophobic interaction chromatography (HIC) HPLC, which indicates whether or not there is unreacted antibody remaining. The retention time of a trace of unreacted antibody is compared to the reaction product to determine if unreacted antibody remains and if so, the reaction is allowed to continue. For small scale the time is typically 1-2 hours. Large scale preparations can require allowing the reaction to take place over 8-12 hours.

After ~1 hour the reaction was purified on a desalting column (Cytiva PD miditrap g-25 medium, Cat #28918008). The top of the column was uncapped and the packing buffer was discarded. The column bottom was uncapped and the column was conditioned with Gibco PBS pH 7.4 (Ref #10010-023) (3×5 mL) by gravity flowthrough. The antibody solution (750 μL) was loaded onto the column and allowed to enter the resin bed fully, followed by PBS (250 μL). The purified ADC was then eluted from the column with pH 7.4 PBS (1.25 mL). Nanodrop protein concentration determination showed 1.76 mg/mL of antibody in 1.25 mL of PBS, or 2.2 mg (73% yield) of conjugated antibody recovered from an initial 3.0 mg of unconjugated antibody. The purified ADC was analyzed by UV-VIS spectroscopy at 370 nm and 280 nm to give a drug-antibody-ratio (DAR) of 6.7.

Example 4: MN20A10-Deruxtecan

MN20A10-deruxtecan was prepared in a similar manner, but with 20 equivalents of DTT which gave 4.77 free thiols per antibody. After coupling with deruxtecan, the purified ADC had a DAR of 4.60 by UV-VIS spectroscopy at 370 nm and 280 nm.

Example 5: MNC2-MC-VC-PAB-MMAE

MNC2-MC-VC-PAB-MMAE was prepared in a similar manner, but with 5 equivalents of DTT which gave 6.12 free thiols per antibody. After coupling with MC-VC-PAB-MMAE the purified ADC had a DAR of 4.39 by HIC-HPLC and 5.12 by UV-VIS spectroscopy at 248 nm and 280 nm.

Example 6: MNC2-MC-VC-PAB-MMAF

MNC2-MC-VC-PAB-MMAF was prepared in a similar manner, but with 5 equivalents of DTT which gave 4.53 free thiols per antibody. After coupling with MC-VC-PAB-MMAF the purified ADC had a DAR of 3.65 by HIC-HPLC.

Example 7: MNC2-MC-VC-PAB-Exatecan

MNC2-MC-VC-PAB-Exatecan was prepared in a similar manner, but with 10 equivalents of DTT which gave 6.20 free thiols per antibody. After coupling with MC-VC-PAB- Exatecan the purified ADC had a DAR of 8.40 by UV-VIS spectroscopy at 370 and 280 nm.

Example 8: MN20A10-MC-VC-PAB-MMAE

MN20A10-MC-VC-PAB-MMAE was prepared in a similar manner, but with 7.5 equivalents of DTT which gave 4.08 free thiols per antibody. After coupling with MC-VC-PAB-MMAE the purified ADC had a DAR of 3.81 by HIC-HPLC, and a DAR of 4.11 by UV-VIS spectroscopy at 248 and 280 nm.

Example 9: MN20A10-MC-VC-PAB-MMAF

MN20A10-MC-VC-PAB-MMAF was prepared in a similar manner, but with 15 equivalents of DTT which gave 3.87 free thiols per antibody. After coupling with MC-VC-PAB-MMAF the purified ADC had a DAR of 3.79 by HIC-HPLC.

Example 10: Large Scale (30 mg) Preparation of MNC2-ADC or MN20A10-ADC Antibody-Drug-Conjugates In a similar manner to the small-scale ADC preparation, a solution of unconjugated antibody was reduced with an excess of dithiothreitol (DTT) in a pH 8.0 borate buffer. After 2 hours of reducing, an aliquot was tested for the amount of free thiol present using an Ellman's thiol test. The reduced antibody was then placed in a pH 6.0 MES buffer and the free cysteines were alkylated with 11 molar equivalents of a maleimide-linked-toxic agent overnight. The crude ADC was then purified through a desalting column.

Aliquots of IgG1 MNC2 antibody (15.7 mL of 1.92 mg/mL, 30.1 mg, 200 nmoles) were thawed from −80° C. in a 37° C. water bath for 1 minute. The volumes were consolidated and the concentration was determined by nanodrop using the mouse IgG1 antibody setting with the background subtraction turned off. 30 mg antibody in 16.17 mL at 1.9 mg/mL 200 nmol. The solution was concentrated using 3 centrifuge filters (Amicon Ultra 4 mL 30,000 mw cut off (Ref #UFC803024)) and the buffer was exchanged to pH 8.0 borate buffer (25 mM sodium tetraborate, 25 mM NaCl, 1 mM EDTA) 3 times spinning in an Eppendorf 5804R centrifuge with a swing bucket rotor at 4000 g for 15-25 minutes. The concentrated antibody was transferred to a 5 mL screw cap tube and was brought up to 3 mL with pH 8.0 borate buffer (25 mM sodium tetraborate, 25 mM sodium chloride, 1 mM EDTA) to make a 10 mg/mL antibody solution.

A solution of DTT (6.48 mM) was prepared by weighing DTT (5 mg) and dissolving it in pH 8.0 borate buffer (5 mL) (25 mM sodium tetraborate, 25 mM sodium chloride, 1 mM EDTA). The DTT solution (6.48 mM, 617 μL, 4000 nmoles, 20 equiv) was added to the antibody solutions and the tubes were heated in a 37° C. in a shaker incubator for 2 hr. After 2 hours, an aliquot of the reaction mixture (6 μL) was taken out for Ellman's thiol analysis. Analysis of these results showed 7.12 moles free thiols per mole of antibody.

In a similar manner MN20A10 was reduced with a total of 20 equivalents of DTT over a period of 3 hours with several iterations of free thiol testing.

The tube of reduced antibody was then cooled in an ice bath to 4 C, the solution was transferred equally to 3 centrifuge filters (Amicon Ultra 4 mL 30,000 to mw cut off (Ref #UFC803024)) and the buffer was exchanged to pH 6.0 MES (50 mM) buffer three times spinning in an Eppendorf 5804R centrifuge at 4000 g for 15-25 minutes. The concentrates were transferred to a 15 mL falcon tube and the concentrators were rinsed with buffer two times to bring the final volume to 6400 μL with pH 6.0 MES (50 mM) buffer.

A stock solution of deruxtecan (10 mg/mL, 9.67 mM) in DMSO was prepared by weighing deruxtecan (3.4 mg, 3.29 μMols) and dissolving it in DMSO (340 μL). A 1100 μL solution of 2 mM deruxtecan in 50% DMSO/pH 6.0 MES (50 mM) was prepared by diluting the DMSO stock deruxtecan solution (227.5 μL of 9.67 mM, 2.22 μMoles) with DMSO (322.5 μL) and then further diluted with pH 6.0 MES (50 mM, 550 μL) to make 1100 μL of 2.068 mg/mL (2 mM) deruxtecan in 50% DMSO/50% pH 6.0 MES (50 mM). The deruxtecan solution (2 mM, 1000 μL, 2200 nmoles, 11 equiv) was added to the tube containing 6400 μL of reduced antibody. The reaction was mixed on a vertical rotator for 18 hours at room temperature and monitored by HIC HPLC after 1 hour and the next day.

After 18 hour the reaction was purified on a desalting column (Cytiva Sephadex G-25 medium Cat #17003301). Sephadex g-25 medium grade gel (10.13 g) was swelled in Gibco PBS pH 7.4 (Gibco catalog #10010-023, 50 mL) in a round bottom flask for 3 hours at room temp. A 25 g Teledyne Isco Redi-Sep Sample Load Cartridge (Isco catalog #693873240) was attached to a ring stand and PBS was injected through the bottom to prime the cartridge. After 3 hours of swelling the resin, the flask was vacuum degassed with argon/vacuum 3 times. The swollen resin was then poured into the cartridge and the bottom was uncapped allowing the PBS to elute. The round bottom flask was washed with PBS to transfer all of the resin to the cartridge. A waste container was placed below the column. The column was conditioned with Gibco PBS pH 7.4 (Ref #10010-023) 3×50 mL by gravity flowthrough. A filter was placed on top of the cartridge and was pushed down the column packing tool being mindful to only slightly compress the gel. The column height was approximately 74 mm. Antibody solution (7500 μL) was loaded onto the column and allowed to enter the resin bed fully. PBS (2500 μL) was added to the column. A new 50 mL falcon tube was placed below the column and the purified ADC was eluted with PBS pH 7.4 (14 mL). For column efficiency 1 mL fractions were passed through the column until a total of 50 mL had passed through the column. The collected solution was analyzed by nanodrop to show 1 mg/mL antibody concentration in 17.5 mL PBS, or 17.5 mg of antibody, 58% yield from unconjugated MNC2.

Example 11: MNC2-MMAE

MNC2-MMAE was prepared in a similar manner, but with 10 equivalents of DTT which gave 6.32 free thiols per antibody. After coupling with MC-VC-PAB-MMAE the purified ADC had a DAR of 4.10 by HIC-HPLC and 5.20 by UV-VIS spectroscopy at 248 nm and 280 nm.

Example 12: MN20A10-MMAE

MN20A10-MMAE was prepared in a similar manner, but with 20 equivalents of DTT which gave 3.67 free thiols per antibody. After coupling with MC-VC-PAB-MMAE the purified ADC had a DAR of 2.96 by HIC-HPLC and 3.57 by UV-VIS spectroscopy at 248 nm and 280 nm.

TABLE 8

| ADC DARs | | | | | |
|---|---|---|---|---|---|
| Example | ADC | DAR by HIC HPLC | DAR by | Equiv DTT | Free Thiol |
| 2 | MNC2- | — | 6.7 (370/280 | 10 | 7.68 |
| 3 | MN20A10- | — | 4.6 (370/280 | 20 | 4.77 |
| 4 | MNC2-MC- | 4.39 | 5.12 (248/280 | 5 | 6.12 |
| 5 | MNC2-MC- | 3.65 | — | 5 | 4.53 |
| 6 | MNC2-MC- | — | 8.40 (370/280 | 10 | 6.2 |
| 7 | MN20A10- | 3.81 | 4.11 (370/280 | 7.5 | 4.08 |
| 8 | MN20A10- | 3.79 | — | 15 | 3.87 |
| 9 | MNC2- | — | 4.5 (370/280 | 20 | 7.12 |
| 10 | MNC2-MC- | 4.10 | 5.20 (248/280 | 10 | 6.32 |
| 11 | MN20A10- | 2.96 | 3.57 (248/280 | 20 | 3.67 |

In general, MN20A10 required an unexpectedly larger amount of reducing agent (DTT) to obtain the same number of free thiols as compared to the MNC2 antibody. MN20A10 required 20 equivalents of DTT to get 3.67-4.2 free thiols (Examples 11 and 3).

Scaling up MN20A10 with 20 equivalents of DTT resulted in fewer free thiols (3.67) then on a small scale (4.2).

Examples 7 and 8 demonstrate the challenges associated with reducing MN20A10.

In Example 7, 7.5 equivalents of DTT gave 4.08 free thiols, whereas in Example 8 even more (15 equivalents) was used resulting in similar or lower reduction (3.87 free thiols).

In contrast MNC2 required as few as 5 equivalents of DTT to get 4.5-6.1 free thiols (Examples 5 and 4).

20 equivalents of DTT were used on MNC2-deruxtecan (3 mg and 30 mg) to force the reaction to highest possible DAR. (Examples 2 and 9).

MNC2-MC-VC-PAB-Exactacan (Example 6) was reduced with 10 equivalents of DTT in order to directly compare the results with Example 2.

Example 13: Ellman's Thiol Test for the Determination of the Number of Free Thiols in an ADC Reduction Prepare 40 mL solution of a 2 mM Ellman's reagent, dissolve 31.7 mg of Ellman's reagent (5,5'-Dithiobis(2-nitrobenzoic acid, ThermoScientific Cat #22582) and 164 mg of sodium acetate in 40 mL of water. Keep stock Ellman's solution at 4 C.

Desalting reduced antibody aliquot: Take two of spin columns (Zeba spin desalting columns Ref #89882) and break the bottom off and loosen the cap. Place them in spin centrifuge tubes. Spin in a microcentrifuge (Spectrafuge 24D) at 1.5×g for 1 minute to remove buffer. Discard the eluted buffer. Condition the column by adding 400 μL of buffer (pH 8.0 Borate buffer composed of 25 mM sodium tetraborate, 25 mM NaCl, 1 mM EDTA) conditioning for 5 minutes followed by centrifuging for 1 minute at 1.5×g. Discard the eluent in-between spins. Repeat conditioning and centrifugation.

Prepare Ellman's reagent: To make 1 mL of Ellman's reagent pipette 850 μL of water into a tube. Add 100 μL of 1M Tris-HCl pH 8.0 followed by 50 μL of Ellman's stock prepared above. Add 70 μL to the bottom of two new centrifuge tubes (Protein LoBind Tube, Eppendorf Cat #022431102) labelling one Sample and the other Control. Once the columns have been conditioned, move them to clean new centrifuge tubes labelled Sample and Control.

Sample and Control prep: The final concentration of thiols after dilution should be in the 10-50 μM range. Antibody reduction reactions are run at 10 mg/mL or 66.7 μM. The dilution is a 5× dilution which brings the concentration to 13.3 μM. Based on past data a reading of ~0.24 mAu will correspond to ~4 thiols per antibody when the control is ~0.03. If more equivalents of reducing agent are added the new concentration should be reflected in the next thiol test.

Prepare a control solution immediately prior to running the test. The control should have the same concentration of DTT or TCEP as the reaction with no antibody present. Pipette 24 μL of Borate Buffer (or appropriate buffer) into two tubes labelled Sample prep and Control prep. Add 6 μL of reduced antibody solution and 6 μL of control solution to each respective tube. Slowly load the 30 μL from each tube to the respective tube with the desalting column. Try to dispense the liquid to the middle of the desalting resin without touching the sides. Spin the tubes at 1.5 g for 2 minutes and analyze the flowthrough in a 100 μL cuvette on a spectrophotometer at 412 nm.

The concentration of antibody in the thiol test is calculated by the using the using C1×V1=MNC2×V2. Where C1 is the initial concentration (66.7 μM), V1 is the 6 μL taken from the sample, and V2 is the 30 μL it was diluted to. Solving for MNC2 give the concentration of the antibody in the thiol assay, which is 13.34 μM. The absorbance at 412 nm is used to determine to the concentration of free thiol in the sample. First, the absorbance of the control is subtracted from the sample. The control subtracted absorbance is then put into beers law A=ebc where A is the absorbance, e if the molar absorptivity of the antibody, b is the path length of the cuvette, and c is the Molar concentration. The molar absorptivity of the Ellman's reagent is 14,150 L/mol-cm. The path length of the cuvette is 1 cm. Calculate the molar concentration of free thiol in the sample.

Once the concentration is determined there is a dilution factor of 3.333 from the 30 μL going through the column to into 70 μL of Ellman's reagent. Divide the dilution-factor-adjusted thiol concentration the concentration of the antibody to calculate the number of free thiols per antibody.

Example 14: Determination of Drug-Antibody Ratio (DAR) by UV

To estimate the DAR, the UV absorbance ratio (R) of the ADC is measured at 248 nm and 280 nm in a quartz cuvette. R=(Absorbance @248 nm)/(Absorbance @280 nm).

The value for R is put into the following equation, and the DAR is calculated: DAR=(21×R−9)/(1.615−0.1425×R)

Example 15: Determination of Drug-Antibody Ratio (DAR) by HIC-HPLC

Another method that can be used to estimate the DAR of ADC's is through the use of HIC-HPLC analysis. Briefly, samples of ADC and unconjugated antibody are injected into an HPLC. The peaks observed at differing retention times correspond to different drug-antibody-ratios. The HPLC retention time and peak area are analyzed in a spreadsheet in which the peaks are initially arbitrarily set to DAR's of 1-8 for IgG1 and 1-10 for IgG2. The time between peaks is used in combination with the analyst attempting to fit these peaks to integers corresponding to a specific number of drugs bound to the antibody. The process in confounded by the fact that several different ADC's exist for each DAR. For example, there are 8 possible ACD's (maleimide binding sites) for a DAR of 1. In general, the different in retention time between different DAR's is larger than the differences in retention time within a group of ACD's having the same DAR. After the analyst sets the DAR for each peak, the peaks areas are summed, and the contribution of from each DAR peak area is calculated. The average DAR is then determined for the sample based on all peaks.

Drug-to-antibody ratio (DAR) and drug load distribution by hydrophobic interaction chromatography and reversed phase high-performance liquid chromatography, Jun Ouyan, Methods Mol. Biol. 2013; 1045:275-83.

Example 16: Measuring Target Cell Killing by MNC2-ADC or MN20A10-ADC by xCELLigence Assay To assess real-time killing of target cancer cells including breast cancer cells (T47D), non-small cell lung cancer cells (NCI-H1975) and pancreatic cancer cells (HP AF II) assays were performed on an xCELLigence RTCA MP Instrument (Agilent). Target Cancer cells were seeded onto a multi-electrode well plate at a density of 5000 cells/well (100 μL of a 50,000 cells/mL stock) and incubated for 24 hr in a 37° C./5% $CO_2$ incubator. mAb MNC2 ADCs or mAb MN20A10-ADCs were prepared as a 2× solution in corresponding growth media and 100 μL of each concentration was added to target cells. As a positive control (100% cell killing) cells were treated with either 1% triton or 1 μM Taxol instead of ADC. After 40-120 hours incubation in a 37° C./5% $CO_2$ incubator cell killing was assessed. In this assay, impedance is measured in real-time. When the adherent cancer cells are killed and come off the electrode surface, impedance (insulation) decreases.

MNC2-ADCs and MN20A10-ADCs were also assayed for their ability to kill both low and high MUC1* expressing cells by monitoring killing in real-time using an xCELLigence instrument. In the xCelligence system, target cancer cells, which are adherent, are plated onto electrode array 96-well plates. Adherent cells insulate the electrode and increase the impedance. The number of adherent cancer cells is directly proportional to impedance. Antibodies and antibody-drug-conjugates are much smaller and do not significantly contribute to impedance. Therefore, increasing impedance reflects the growth of the cancer cells and decreasing impedance reflects the killing of the cancer cells.

Figure 27:
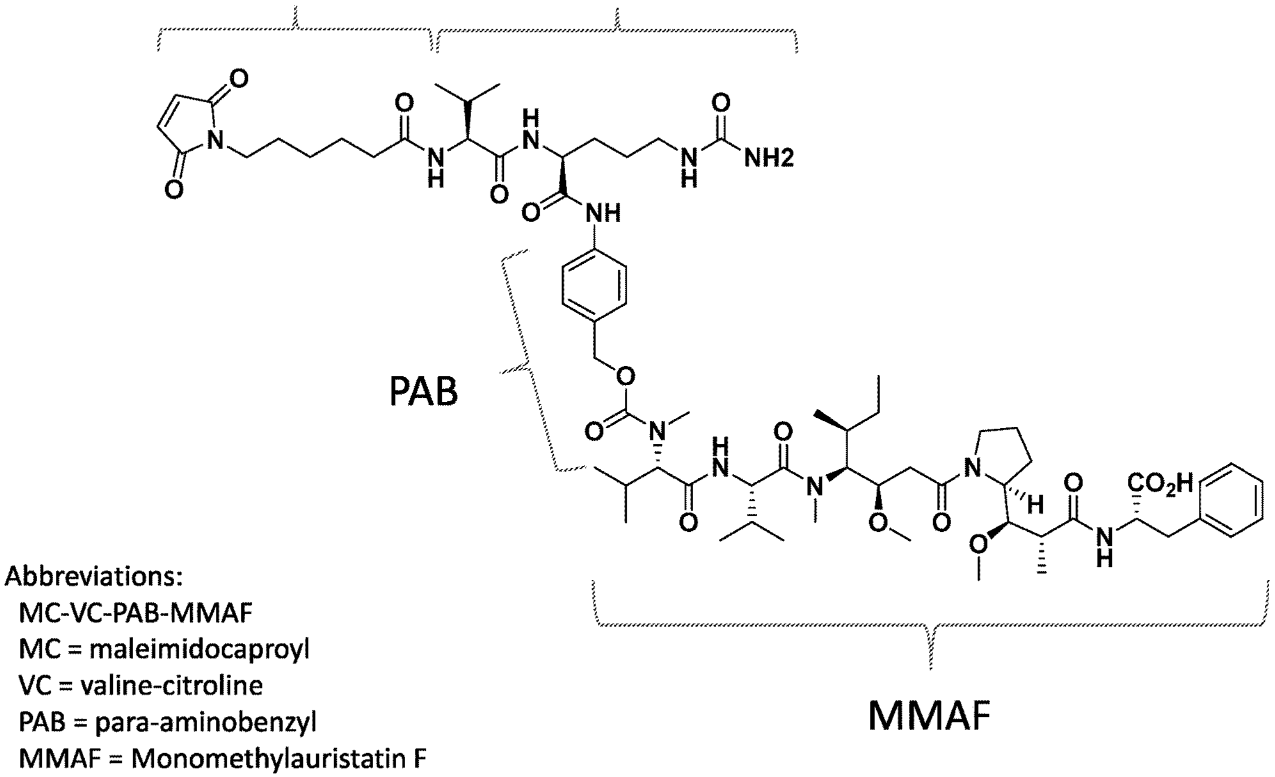
FIG. 27 shows the chemical structure of a chemical entity that includes the toxic payload MMAF, which can be conjugated to an antibody to form an antibody-drug-conjugate, also known as an ADC. MC indicates the maleimidocaproyl (MC) portion that facilitates coupling to a Cysteine on the antibody. indicates the valine-citrulline (VC) portion and PAB indicates the para-aminobenzyl (PAB), both of which facilitate enzymatic cleavage of the toxic payload inside the cancer cells by the lysosomal enzyme, cathepsin B. MMAF indicates the Monomethyl Auristatin E (MMAF) portion that is the toxic payload after cellular internalization and/or cleavage of non-toxic portions. The MMAF payload contains a carboxylic acid, making it difficult, if not impossible, to exit cell membranes after the payload has been cleaved from the antibody. Therefore, MMAF can only show potent tubulin inhibition after the payload has been internalized.

Breast cancer cell line T47D-wt expresses MUC1* at low to low-medium levels. Pancreatic cancer cell line HPAF II-wt expresses even lower levels of MUC1* and lung cancer cell line NCI-H1975 express still lower levels of MUC1*. As can be seen in FIG. 24, FIG. 26 and FIG. 27, these cancer cells that express low levels of MUC1*, consistent with early cancer cells, are effectively killed by MNC2-ADCs and MN20A10-ADCs when administered at mid-nanomolar dose. Breast cancer cell lines T47D-MUC1* and HPAF II-MUC1* have been engineered to express high levels of MUC1*, consistent with later stage cancers. As can be seen in FIG. 25 and FIG. 28, cancer cells that express high levels of MUC1* are completely killed at very low nanomolar dose. FIG. 49A-49D show the killing potency of MNC2-MMAE, MN20A10-MMAE, MNC2-MMAF and MN20A10-MMAF on T47D breast cancer cells that express low to medium levels of MUC1*. As can be seen in the figure, both anti-MUC1* antibodies MNC2 and MN20A10 effectively kill the target cells when dosed at a concentration of 500 nM within a 40 hour timeframe. As can be seen in FIG. 49E-49J, after 120 hours potent killing is seen at a concentration as low as 167 nM. In fact MN20A10-MMAE shows effective killing at 56 nM. Here the comparison to MNC2-Deruxtecan and MN20A10-Deruxtecan shows comparable killing at the same concentration, 167 nM, as MNC2-MMAE, MNC2-MMAF, MN20A10-MMAE and MN20A10-MMAF.

In the next set of experiments, MNC2-ADCs and MN20A10-ADCs are tested for their ability to kill cancer cells expressing high levels of MUC1*. The expectation is that the higher the levels of MUC1*, the more difficult it would be to kill the cells because MUC1* is the growth factor receptor driving the growth of these cells. Unexpectedly, the experiments show that the more MUC1* is expressed, the easier it is to kill the cells. FIG. 50A-50D show that T47D breast cancer cells that were engineered to express high levels of MUC1*, indicative of late stage cancers, are efficiently killed by MNC2-MMAE, MNC2-MMAF and MN20A10-MMAE at concentrations as low as 19 nM and even as low as 6 nM. As is demonstrated in Figure N25E-N25J, when the experiment is allowed to proceed for 120 hours, near total killing of cancer cells expressing high levels of MUC1* is seen at concentrations as low as 6 nM for MNC2-MMAE, MNC2-MMAF and MNC2-Deruxtecan. For MN20A10, where lower numbers of MMAF and Deruxtecan were able to attach, cancer cell killing was seen at higher concentrations between 19 nM and 167 nM.

Similar to breast cancer cells expressing low levels of MUC1*, NCI-H1975 non-small cell lung cancer cells that express even lower levels of MUC1*, undergo stasis at 40 hours, but killing at 120 hours when treated with MNC2-MMAE, MNC2-MMAF, MNC2-Deruxtecan, MN20A10-MMAE, or MN20A10-MMAF (FIG. 51A-FIG. 51I). HP AF II-wt pancreatic cancer cells that express MUC1* at low levels, but higher than the H1975 lung cancer cells, are killed by MNC2-MMAE, MNC2-MMAF, MN20A10-MMAE and MN20A10-MMAF at a concentration of 167 nM to 500 nM at 40 hours, which improves to killing at concentrations of 56 nM after 120 hours (FIG. 52A-FIG. 52I). However, if the pancreatic cells are engineered to express high levels of MUC1*, MNC2-ADCs and MN20A10-ADCs are far more potent at killing the cancer cells. After about 40 hours, near total killing of cancer cells is seen at concentration between 167 nM and 56 nM, while after 120 hours, near total killing is accomplished at concentrations between 19 nM and 56 nM (FIG. 53A-FIG. 53I).

The toxin Exatecan was then conjugated to MNC2 via a linker comprising maleimidocaproyl, valine-citrulline, and para-aminobenzyl, as shown in Figure N4E-N4H. Additionally, the conjugation was performed in a solution containing propylene glycol MES pH 6.0 buffer.

As demonstrated in FIGS. 65A-65D, tumor cells implanted in an animal greatly increase MUC1* expression as the tumor develops from early stage to late stage. The tumor cells that were implanted are T47D-wt breast cancer cells, which are a cell line derived from a breast cancer patient who died decades ago. The cell line, provided by the ATCC, has been expanded several thousand if not millions of times. Essentially all the T47D cells are identical. Staining of the Day 0 cells shows the cells express more full-length MUC1 than MUC1* and the staining intensity is light, indicating low numbers of MUC1* receptors, which is indicative of early cancers. Sixty-two (62) days post tumor implantation, which equates to approximately 7 years in human time, one can readily see that MUC1* expression, in terms of extent of expression as well as intensity of expression, has dramatically shifted from low expression to high expression in the late stage tumor. In contrast, the staining of a serial section of the tumor shows full-length MUC1 is expressed, as expected because it is cleaved to MUC1* after surface expression. However, the intensity of the staining has not increased, indicating that the vast majority of the expressed MUC1 has been cleaved to the growth factor receptor form, MUC1*, in the late-stage tumor.

As is known to cancer clinicians and pathologists, tumors that develop in patients are not homogeneous populations of a single clone, as cell lines are. Actual tumors are somewhat heterogeneous in that they are comprised of low antigen expressing cells as well as high antigen expressing cells. However it is also known that early cancers are characterized by a majority of cells that are low expressers, while later stage cancers are characterized by a majority of cells that are high expressers.

Example 17: Measuring Target Cell Killing by MNC2-ADC or MN20A10-ADC by PrestoBlue Live/Dead Cell Assay Another method of measuring the killing activity of mAb MNC2-ADCs and mAb MN20A10-ADCs against target cancer cells including T47D breast cancer cells NCI-H1975 non-small cell lung cancer cells and HPAFII pancreatic cancer cells is to use the PrestoBlue live/dead cell assay (ThermoFisher). Target cancer cells were seeded in a black-walled, clear-bottom 96-well tissue culture plate at a density of 5000 cells/well (100 μL of a 50,000 cells/mL stock) and incubated overnight in a 37° C./5% $CO_2$ incubator. MNC2 ADCs and MN20A10 ADCs were prepared as a 2× solution in corresponding cancer cell growth media and 100 μL of each concentration was added to target cancer cells. As a positive control (100% killing) cancer cells were treated with 1 μM Taxol instead of ADC. After 72 hour-120 hour incubation in a 37° C./5% $CO_2$ incubator, cell viability was measure by fluorescence using the PrestoBlue HS assay (ThermoFisher). Briefly, after the incubation period, 20 μL of PrestoBlue HS solution was added. Fluorescence (Ex 560 nm/Em 590 nm) was recorded after 30-90 min. incubation using a Tecan plate reader. Percentage viability was determined by PrestoBlue HS staining and normalized to 1 μM taxol treated cells.

The normalized fluorescence values were imported into the graph program, Sigma Plot, data plotted as MNC2-ADC or MN20A10-ADC concentration versus normalized fluorescence signal and curve fitted using a four-parameter Hill equation: f=y0+a*x^b/(c^b+x^b)

IC50 values were calculated from the fitted data for the killing ability of MNC2-ADCs and MN20A10-ADCs for target cancer cells and are reported in nM.

To visually assess target cell killing or changes in cancer cell morphology, brightfield images of target cancer cells, including T47D breast cancer cells, NCI-H1975 non-small cell lung cancer cells and HPAFII pancreatic cancer cells were taken on an Olympus IX-71 microscope at 4× or 20× magnification after 120 hours incubation at the indicated MNC2-ADC or MN20A10-ADC concentration.

FIG. 46A-FIG. 48N show magnified photographs of the various types of cancer cells after treatment with either an MNC2-ADC or an MN20A10-ADC. The killing effect can be readily seen as the significant decrease in cell number, the change in cell morphology from the characteristic flat, spreading morphology to the rounded up morphology and lifting off of the cells. In contrast, the control wells show confluent monolayer of compact cells with the normal flat spreading morphology and without dead floating cells. FIGS. 46A-46C and FIGS. 46G-46F show T47D-MUC1* breast cancer cells treated with MNC2-MMAE. FIGS. 46D-46F and FIGS. 46G-46J show T47D-MUC1* breast cancer cells treated with MNC2-Deruxtecan. FIGS. 47A-47B show DU145 hormone resistant prostate cancer cells treated with MNC2-MMAE. FIGS. 47C-47D show DU145 hormone resistant prostate cancer cells treated with MNC2-Deruxtecan. FIGS. 48A-48B and FIG. 48G-48H show T47D-MUC1* breast cancer cells treated with MN20A10-MMAE. FIGS. 48C-48D and FIG. 48I-48J show T47D-MUC1* breast cancer cells treated with MN20A10-Deruxtecan. FIG. 48K-48L show DU145 hormone resistant prostate cancer cells treated with MN20A10-MMAE. FIG. 48M-48N show DU145 hormone resistant prostate cancer cells treated with MN20A10-Deruxtecan. As is visually apparent, the killing effect of the anti-MUC1*-ADCs shown in FIGS. 46A-48N is consistent with the killing that was measured by flow cytometry, shown in FIGS. 38A-45D.

Example 18: Animal Studies: In Vivo Measuring Target Cell Killing by MNC2-ADC or MN20A10-ADC In vivo experiments were performed to measure xenograft target cancer cell killing by MNC2-ADC or MN20A10-ADC.

For breast cancer xenografts, female NOD/SCID mice (weight 18-22 g, 6-8 weeks old, Charles River Laboratories) previously implanted with a 90-day release estrogen pellet (Innovative Research Laboratories) were subcutaneously injected under isoflurane anesthesia (ISOTHESIA, 250 ml (HENRY SCHEN, NDC: 11695-6776-2) with one million luciferase-mCherry positive T47D breast cancer cells expressing medium to high levels of MUC1* (ATCC) using a BD 26G Insulin Syringes with Detachable Needle (Fisher cat: 329652) or BD 28G Lo-Dose U-100 Insulin Syringes (Fisher cat: 329461).

For lung cancer xenografts or pancreatic cancer xenografts, female NU/NU mice (weight 18-22 g, 6-8 weeks old, Charles River Laboratories) were subcutaneously injected under isoflurane anesthesia (ISOTHESIA, 250 ml (HENRY SCHEN, NDC: 11695-6776-2) with one million luciferase-mCherry positive NCI-H1975 non-small cell lung cancer cells (ATCC) or with one million luciferase-mCherry positive HPAFII pancreatic cancer cells (ATCC) expressing low to medium levels of MUC1*.

After 4-6 days post-xenograft, mice were injected intraperitoneal into the scruff of the neck with 150 μl, 30 mg/mL, D-Luciferin (XenoLight™ D-Luciferin Potassium Salt; PerkinElmer P/N 122799) before being placed under isoflurane anesthesia prior to bioluminescence image acquisition using the Xenogen IVIS-Spectrum system (Perkin Elmer). Group selection was performed to evenly distribute xenografted mice to ensure mock-treated groups and ADC-treated groups had equivalent initial tumor sizes.

At Day 5-7 post-xenograft, mice were injected intraperitoneal with phosphate-buffered saline (PBS) or with 5-10 mg/kg MNC2-ADC or 5-10 mg/kg MN20A10-ADC. Mice were injected once per week thereafter for a total of four injections of MNC2-ADC or MN20A10-ADC.

Bioluminescent imaging was performed once per week to measure tumor growth non-invasively in real time. Data was expressed graphically as Radiance (photons/sec) as a function of days post-tumor implantation.

In some measurements of tumor growth, caliper measurements of the tumors in mice were taken. The two longest perpendicular axes in the x/y plane of each xenograft tumor were measured to the nearest 0.1 mm by two independent observers. The depth was assumed to be equivalent to the shortest of the perpendicular axes, defined as y. Measurements were made using a digital vernier caliper while mice were conscious and were calculated according to the following equation: Xenograft volume=$xy^2/2$ Humane criteria for euthanasia was followed where: tumor burden reached or exceeded 20 mm in diameter (in line with the IACUC policy), tumors became ulcerated, or tumor position interfered with normal ambulation, feeding/drink/or elimination; body condition score of 2 or weight loss >15% from pre-xenograft weight.

In vivo experiments were also performed in order to assess the killing potency of MNC2-ADCs and MN20A10-ADCs in immune-compromised mice implanted with several different types of human cancers wherein some expressed low levels of MUC1* and others expressed high levels of MUC1*. In all cases, the human cancer cell lines had been engineered to express mCherry and also Luciferase to enable measurement of the tumors by bioluminescence. In order to optically measure tumor volume, the Luciferase substrate, Luciferin is injected into the animals and bioluminescence is photographed on an IVIS instrument within 10 minutes of the Leciferin injection. Expression levels of Luciferase varied, in some cases by a lot, making it challenging to compare tumor size across different cell lines. In those instances, caliper measurements of the tumors were also taken to allow for comparisons of tumor size between cell lines. Additionally, in those cases photographs of the animals were taken so that visual comparison of tumor size between cell lines can be made.

In one experiment MNC2-MMAE was administered to female NOD/SCID/GAMMA (NSG) mice, bearing 90-day estrogen release pellets, then implanted with either 1M T47D-wt breast cancer cells that express low to medium levels of MUC1*, indicative of early-stage cancers, or 1M T47D-MUC1* cells that were engineered to express high levels MUC1*, indicative of late-stage cancers. Tumors were allowed to engraft for seven (7) days before the first injection of MNC2-MMAE at a dose of 5 mg/kg. On Day 14 and Day 20, the dose was increased to 10 mg/kg. First, mice implanted with T47D-wt tumors, which express low levels of MUC1*. Comparing at FIG. 57A, control mice, to FIG. 57B, MNC2-MMAE treated mice, it can be readily seen that the treated mice survived with very little tumor burden until Day 56, when the experiment was ended. In contrast, tumors in the untreated control mice continued to grow until due to excess tumor burden they had to be sacrificed at Day 56. Next, mice implanted with T47D-MUC1* tumors that express high levels of MUC1* were reviewed. Comparing the bioluminescence of the control animals implanted with T47D-wt (FIG. 57A and FIG. 57E) versus animals implanted with T47D-MUC1* (FIG. 57C and FIG. 57F), the T47D-MUC1* lines express slightly less Luciferase than the T47D-wt cell line. However, visual inspection of the tumors showed that tumor size was comparable between the two cell lines. Animals bearing T47D-MUC1* tumors were dosed with MNC2-MMAE according to the same schedule as animals bearing T47D-wt tumors. However, looking at FIG. 57D it is clear that the MNC2-MMAE treated animals are tumor-free from Day 34 until Day 56 when the experiment was ended because the control mice had excessive tumor burden and had to be sacrificed. This same experiment was performed in parallel, but animals were dosed with MN20A10-MMAE (FIG. 58A-58F). The MN20A10-MMAE results follow the same trend as the MNC2-MMAE results with the caveat that MNC2-MMAE is more effective here than MN20A10. One possible explanation for this disparity is the difference in the number of toxins that were attached to the MNC2 antibody (DAR 3.85) versus MN20A10 (DAR 2.96).

In another experiment, female nu/nu mice were implanted with 1M human NCI-H1975 non-small cell lung cancer cells that express low to medium levels of MUC1*, indicative of early-stage cancers. On Day 7 and Day 14 post tumor implantation, the animals were injected with MNC2-MMAE at 5 mg/kg. On Day 19, the dose was increased to 10 mg/kg. The bioluminescent photographs clearly show that increasing the dose of MNC2-MMAE to 10 mg/kg on Day 19 and Day 27 increased the killing of the tumor cells (FIG. 59A-59C). The efficacy of the MNC2-MMAE treatment can be appreciated by comparing the tumor weights of sacrificed animals in the control group versus those of the treated group. Control animals had to be sacrificed at Day 20 post implantation because of life-threatening tumor size, where the tumors weighed 0.82, 0.3, 0.49, 0.41 and 0.5 grams. In contrast, animals that needed to be sacrificed in the treated group at Day 54 weighed 0.28 and 0.4 grams. Two mice in the treated group remained tumor free at Day 67 when the experiment was arbitrarily ended. The results of an experiment performed in parallel, where animals were treated with MN20A10-MMAE (FIG. 60A-60D), show the same trend, albeit that the MN20A10-MMAE had a less profound effect than the MNC2-MMAE, possibly because of the lower DAR of MN20A10-MMAE. Still the treatment suppressed tumor growth as can be seen in the bioluminescent photographs, as well as the weights of the tumors excised from the control animals that had to be sacrificed at Day 26. Tumor weights ranged from 2.2 grams to 0.65 grams. The graph of FIG. 60D shows that tumor volume dramatically tracked downward after dose was increased to 10 mg/kg at Day 19. The data suggest that if the dose had been higher at the onset, the tumor growth would have been more dramatically reduced.

In yet another experiment MNC2-MMAE was administered to female nu/nu (NSG) mice, implanted with either 0.5M HP AF II-wt pancreatic cancer cells that express low to medium levels of MUC1*, indicative of early-stage cancers, or 0.5M HPAF II-MUC1* pancreatic cancer cells that were engineered to express high levels MUC1*, indicative of late-stage cancers. Tumors were allowed to engraft for five (5) days before three (3) injections of MNC2-MMAE at a dose of 10 mg/kg on Day 5, Day 12, and Day 19. First, mice implanted with HPAF II-wt tumors, which express low levels of MUC1* were tested. Comparing at FIG. 61A, control mice, to FIG. 61B, MNC2-MMAE treated mice, it can be readily seen at Day 18 that the treated mice have smaller tumors than the control mice. The IVIS instrument malfunctioned on Day 25, leading to artificially lower readings in the control animals. For this reason, caliper measurements were also taken on Day 25. As can be seen in FIG. 61H, the average tumor volume measured by caliper is drastically different between the control animals and the treated animals that had been implanted with HPAF II-wt tumors.

Next, mice implanted with T47D-MUC1* tumors that express high levels of MUC1* were tested. Comparing the bioluminescence of the control animals implanted with T47D-wt (FIG. 57A and FIG. 57E) versus animals implanted with T47D-MUC1* (FIG. 57C and FIG. 57F), the T47D-MUC1* lines express slightly less Luciferase than the T47D-wt cell line. However, visual inspection of the tumors showed that tumor size was comparable between the two cell lines. Animals bearing T47D-MUC1* tumors were dosed with MNC2-MMAE according to the same schedule as animals bearing T47D-wt tumors. However, looking at FIG. 57D it is clear that the MNC2-MMAE treated animals are tumor-free from Day 34 until Day 56 when the experiment was ended because the control mice had excessive tumor burden and had to be sacrificed.

EMBODIMENTS

Embodiment 1. A conjugate for Formula (I): [Ab]-[Z-L-R-X]$_y$ Formula (I), wherein: X is a moiety derived from a compound capable of inhibiting topoisomerase I or a compound capable of inhibiting tubulin formation; R is a coupling moiety; L is a di- or tri- or tetra-peptide linking moiety having Z bonded to N-terminus and R bonded to the C-terminus; [Ab] is an antibody comprising an anti-MUC1* binding domain comprising three heavy chain (HC) complementarity determining region (CDRs): MUC1* HC-CDR1, MUC1* HC-CDR2, and MUC1* HC-CDR3; wherein the MUC1* HC-CDR1, the MUC1* HC-CDR2, and the MUC1* HC-CDR3 of the MUC1* binding domain comprises amino acid sequences selected from those set forth in Table 1; wherein the MUC1* binding domain comprises three light chain (LC) complementarity determining region (CDRs): MUC1* LC-CDR1, MUC1* LC-CDR2, and MUC1* LC-CDR3; wherein the MUC1* LC-CDR1, the MUC1* LC-CDR2, and the MUC1* LC-CDR3 of the MUC1* binding domain comprises amino acid sequences selected from those set forth in Table 1; Z is a conjugation moiety capable of forming a covalent bond with a sulfur atom of a cysteine residue; and wherein y is an integer from 1 to 10.

Embodiment 2. The conjugate of Embodiment 1, wherein L comprises a valine and a citrulline.

Embodiment 3. The conjugate of Embodiment 1, wherein L comprises a glycine and a phenylalanine.

Embodiment 4. The conjugate of Embodiment 1, wherein R comprises a para-aminobenzyl.

Embodiment 5. The conjugate of Embodiment 1, wherein R comprises a moiety comprising the structure of:

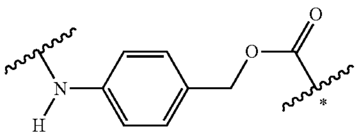

, wherein the * indicates the point of attachment for the X group.

Embodiment 6. The conjugate of Embodiment 1, wherein R comprises a moiety comprising the structure of:

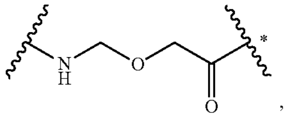 [SMILES: *NCOCC(*)=O]

, wherein the * indicates the point of attachment for the X group.

Embodiment 7. The conjugate of Embodiment 1, wherein R comprises a moiety comprising the structure of:

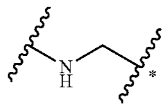

, wherein the * indicates the point of attachment for the X group

Embodiment 8. The conjugate of Embodiment 1, wherein L is a dipeptide linking moiety comprising the structure of:

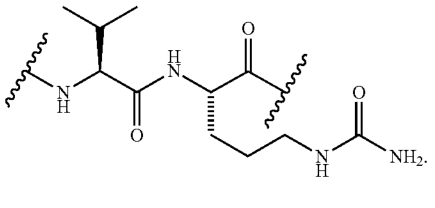 [SMILES: *N[C@H](C(=O)N[C@@H](CCCNC(N)=O)C(*)=O)C(C)C]

Embodiment 9. The conjugate of Embodiment 1, wherein L is a tetra-peptide linking moiety comprising the structure of:

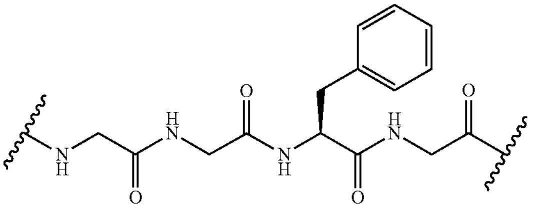

.

Embodiment 10. The conjugate of Embodiment 1, wherein X is MMAE or MMAF.

Embodiment 11. The conjugate of Embodiment 1, wherein X is exatecan or Dxd

Embodiment 12. The conjugate of Embodiment 1, wherein R comprises a moiety comprising the structure of:

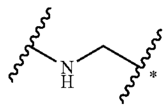

, wherein the * indicates the point of attachment for the X group, and wherein X is Dxd.

Embodiment 13. The conjugate of Embodiment 1, wherein R comprises a moiety comprising the structure of:

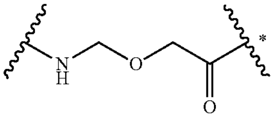

, wherein the * indicates the point of attachment for the X group, and wherein X is exatecan.

Embodiment 14. The conjugate of Embodiment 1, wherein the antibody is isotype IgG1 or IgG2.

Embodiment 15. The conjugate of Embodiment 1, wherein the antibody is isotype IgG2b.

Embodiment 16. The conjugate of Embodiment 1, wherein the anti-MUC1* binding domain comprises a heavy chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 38 or 44.

Embodiment 17. The conjugate of Embodiment 1, wherein the anti-MUC1* binding domain comprises a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 39 or 45.

Embodiment 18. The conjugate of Embodiment 1, wherein the anti-MUC1* binding domain comprises a light chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 41 or 47.

Embodiment 19. The conjugate of Embodiment 1, wherein the anti-MUC1* binding domain comprises a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 42 or 48.

Embodiment 20. The conjugate of Embodiment 1, wherein the anti-MUC1* binding domain comprises a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 129 or 130

Embodiment 21. An antibody conjugate comprising an antibody comprising an anti-MUC1* binding domain, wherein the antibody is conjugated to a payload via a maleimide-cysteine bond, wherein the payload comprises a linker and a cytotoxic compound, wherein the cytotoxic compound comprises a tubulin inhibitor or a topoisomerase I inhibitor.

Embodiment 22. The antibody conjugate of Embodiment 21, wherein the linker comprises a valine.

Embodiment 23. The antibody conjugate of Embodiment 21, wherein the linker comprises a citrulline.

Embodiment 24. The antibody conjugate of Embodiment 21, wherein the linker comprises a valine and a citrulline.

Embodiment 25. The antibody conjugate of Embodiment 21, wherein the linker is a dipeptide linking moiety comprising the structure of:

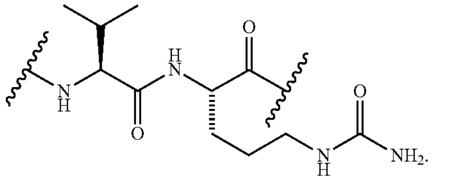 [SMILES: *N[C@H](C(=O)N[C@@H](CCCNC(N)=O)C(*)=O)C(C)C]

Embodiment 26. The antibody conjugate of Embodiment 21, wherein the linker comprises at least one glycine.

Embodiment 27. The antibody conjugate of Embodiment 21, wherein the linker comprises at least one glycine and a phenylalanine.

Embodiment 28. The antibody conjugate of Embodiment 21, wherein the linker comprises a structure of:

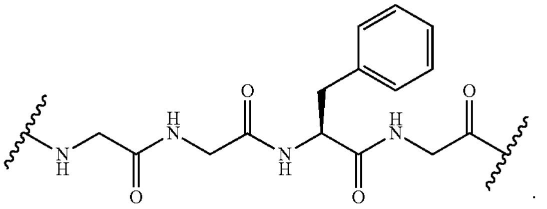 [SMILES: *NCC(=O)NCC(=O)N[C@@H](Cc1ccccc1)C(=O)NCC(*)=O]

Embodiment 29. The antibody conjugate of Embodiment 21, wherein the linker comprises a para-aminobenzyl.

Embodiment 30. The antibody conjugate of Embodiment 21, wherein the linker comprises a group of structure

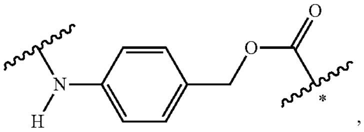 [SMILES: *Nc1ccc(COC(*)=O)cc1]

wherein the * indicates the point of attachment for the cytotoxic group.

Embodiment 31. The antibody conjugate of Embodiment 21, wherein the linker comprises a group of structure

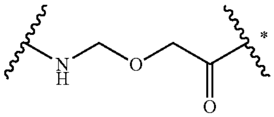

or

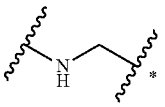

wherein the * indicates the point of attachment for the cytotoxic group.

Embodiment 32. The antibody conjugate of Embodiment 21, wherein the tubulin inhibitor is MMAE or MMAF.

Embodiment 33. The antibody conjugate of Embodiment 21, wherein the topoisomerase I inhibitor is exatecan or deruxtecan, or a derivative thereof.

Embodiment 34. The antibody conjugate of Embodiment 21, wherein the linker comprises a group comprising the structure of:

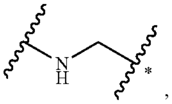 [SMILES: *CN*]

wherein the * indicates the point of attachment for the cytotoxic group, and wherein the topoisomerase I inhibitor is Dxd.

Embodiment 35. The antibody conjugate of Embodiment 21, wherein the linker comprises a group comprising the structure of:

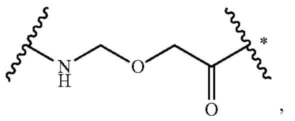 [SMILES: *NCOCC(*)=O]

wherein the * indicates the point of attachment for the cytotoxic group, and wherein the topoisomerase I inhibitor is exatecan.

Embodiment 36. The antibody conjugate of Embodiment 21 comprising the structure provided below wherein n is 1 to 10:

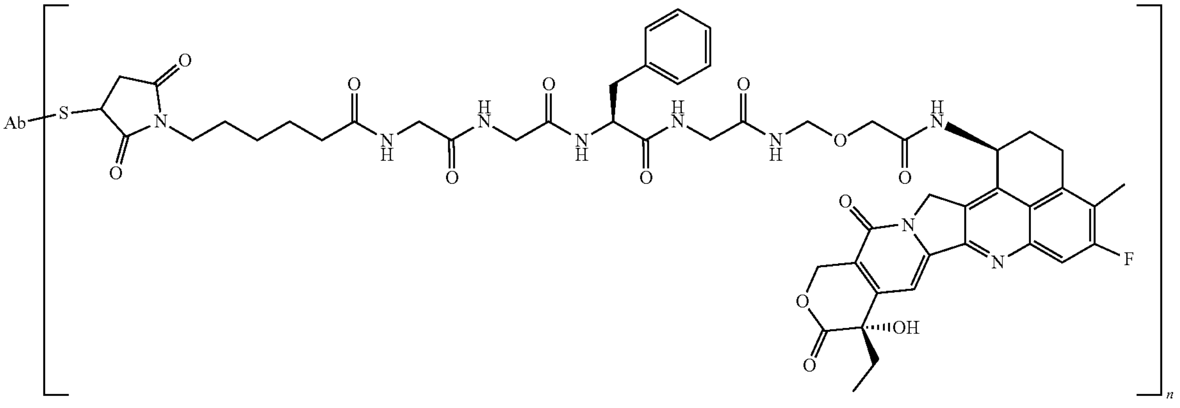

Embodiment 37. The antibody conjugate of Embodiment 21 comprising the structure provided below wherein n is 1 to 10:

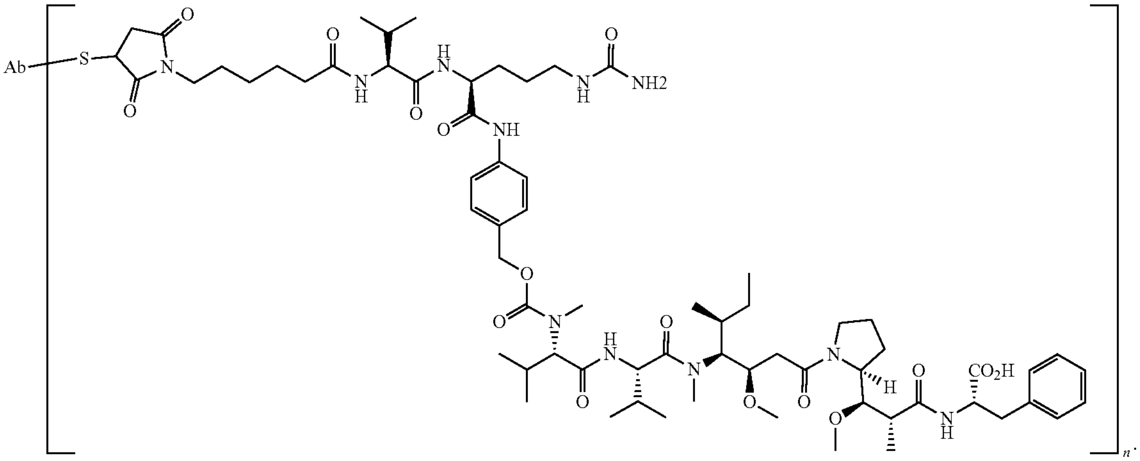

Embodiment 38. The antibody conjugate of Embodiment 21, wherein the antibody isotype is IgG1 or IgG2.

Embodiment 39. The antibody conjugate of Embodiment 21, wherein the antibody isotype is IgG2b.

Embodiment 40. The antibody conjugate of Embodiment 21, wherein the antibody is conjugated to at least two payloads.

Embodiment 41. The antibody conjugate of Embodiment 21, wherein the antibody is conjugated to at least three payloads.

Embodiment 42. The antibody conjugate of Embodiment 21, wherein the antibody is conjugated to at least four payloads.

Embodiment 43. The antibody conjugate of Embodiment 21, wherein the antibody is conjugated to at least five payloads.

Embodiment 44. The antibody conjugate of Embodiment 21, wherein the antibody is conjugated to at least six payloads.

Embodiment 45. The antibody conjugate of Embodiment 21, wherein the antibody is conjugated to at least seven payloads.

Embodiment 46. The antibody conjugate of Embodiment 21, wherein the antibody is conjugated to at least eight payloads.

Embodiment 47. The antibody conjugate of Embodiment 21, wherein the anti-MUC1* binding domain comprises three light chain (LC) complementarity determining region (CDRs): LC-CDR1, LC-CDR2, and LC-CDR3; wherein the LC-CDR1, the LC-CDR2, and the LC-CDR3 of the MUC1* binding domain comprises amino acid sequences selected from those set forth in Table 1; and wherein at least one of the LC-CDR1, LC-CDR2 and LC-CDR3 comprises from 0-2 amino acid modification(s).

Embodiment 48. The antibody conjugate of Embodiment 21, wherein the anti-MUC1* binding domain comprises three heavy chain (HC) complementarity determining region (CDRs): HC-CDR1, HC-CDR2, and HC-CDR3; wherein the HC-CDR1, the HC-CDR2, and the HC-CDR3 of the MUC1* binding domain comprises amino acid sequences selected from those set forth in Table 1; and wherein at least one of the HC-CDR1, HC-CDR2 and HC-CDR3 comprises from 0-2 amino acid modification(s).

Embodiment 49. The antibody conjugate of Embodiment 21, wherein the anti-MUC1* binding domain comprises a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 2.

Embodiment 50. The antibody conjugate of Embodiment 21, wherein the anti-MUC1* binding domain comprises a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 2.

Embodiment 51. The antibody conjugate of Embodiment 21, wherein the anti-MUC1* binding domain comprises a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to a sequence set forth in Table 3.

Embodiment 52. An antibody comprising a MUC1* binding domain and a CD3 binding domain, wherein the MUC1* binding domain comprises three heavy chain (HC) complementarity determining region (CDRs): MUC1* HC-CDR1, MUC1* HC-CDR2, and MUC1* HC-CDR3; wherein the MUC1* HC-CDR1 comprises an amino acid sequence of SEQ ID NO: 1, the MUC1* HC-CDR2 comprises an amino acid sequence of SEQ ID NO: 2, and the MUC1* HC-CDR3 comprises an amino acid sequence of SEQ ID NO: 3; wherein the MUC1* binding domain comprises three light chain (LC) complementarity determining region (CDRs): MUC1* LC-CDR1, MUC1* LC-CDR2, and MUC1* LC-CDR3; wherein the MUC1* LC-CDR1 comprises an amino acid sequence of SEQ ID NO: 13, the MUC1* LC-CDR2 comprises an amino acid sequence of SEQ ID NO: 14, and the MUC1* LC-CDR3 comprises an amino acid sequence of SEQ ID NO: 15; wherein the CD3 binding domain comprises three heavy chain (HC) complementarity determining region (CDRs): CD3 HC-CDR1, CD3 HC-CDR2, and CD3 HC-CDR3; wherein the CD3 HC-CDR1, the CD3 HC-CDR2, and the CD3 HC-CDR3 of the CD3 binding domain comprises amino acid sequences selected from those set forth in Table 2; and wherein the CD3 binding domain comprises three light chain (LC) complementarity determining region (CDRs): CD3 LC-CDR1, CD3 LC-CDR2, and CD3 LC-CDR3; wherein the CD3 LC-CDR1, the CD3 LC-CDR2, and the CD3 LC-CDR3 of the CD3 binding domain comprises amino acid sequences selected from those set forth in Table 4.

Embodiment 53. The antibody of Embodiment 52, wherein the antibody comprises an Fc domain.

Embodiment 54. The antibody of Embodiment 52, wherein the Fc domain is a heterodimeric Fc domain.

Embodiment 55. The antibody of Embodiment 52, wherein the heterodimeric Fc domain comprises a knob chain and a hole chain, forming a knob-into-hole (KiH) structure.

Embodiment 56. The antibody of Embodiment 55, wherein the knob chain comprises a sequence having at least about 95% identity to a sequence selected from SEQ ID NOs: 121, 122, 123 or 124.

Embodiment 57. The antibody of Embodiment 55, wherein the hole chain comprises a sequence having at least about 95% identity to a sequence selected from SEQ ID NOs: 125, 126, 127, or 128.

Embodiment 58. The antibody of Embodiment 52, wherein the MUC1* binding domain comprises a heavy chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 2.

Embodiment 59. The antibody of Embodiment 52, wherein the MUC1* binding domain a light chain variable domain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 2.

Embodiment 60. The antibody of Embodiment 52, wherein the MUC1* binding domain comprises a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from Table 3.

Embodiment 61. The antibody of Embodiment 52, wherein the CD3 binding domain comprises a heavy chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 26 or 31.

Embodiment 62. The antibody of Embodiment 52, wherein the CD3 binding domain a light chain comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 29 or 35.

Embodiment 63. The antibody of Embodiment 52, wherein the CD3 binding domain comprises a single-chain variable fragment (scFv) comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 131 or 132.

Embodiment 64. The antibody of Embodiment 52, comprising a sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from SEQ ID NOs: 50, 52, 54, 58, 62, 66, 70, 74, 78, 82, 86, 90, 94, 98, 102, 106, 110, or 114.

Embodiment 65. A method of treating cancer comprising administering an antibody or antibody conjugate of any one of Embodiments 1-64 to a subject in need thereof.

Embodiment 66. The method of Embodiment 65, wherein the cancer expresses MUC1*.

Embodiment 67. The method of Embodiment 65, wherein the cancer is breast cancer, colon cancer, prostate cancer, pancreatic cancer, or lung cancer.

The invention claimed is:

1. A conjugate of Formula (I):

[Ab]-[Z-L-R-X]$_y$,    Formula (I), wherein:

[Ab] is an antibody comprising an anti-MUC1* binding domain comprising three heavy chain (HC) complementarity determining regions (CDRs): MUC1* HC-CDR1, MUC1* HC-CDR2, and MUC1* HC-CDR3; and three light chain (LC) complementarity determining regions (CDRs): MUC1* LC-CDR1, MUC1* LC-CDR2, and MUC1* LC-CDR3;

wherein:

(a) the MUC1* HC-CDR1 comprises the amino acid sequence of SEQ ID NO: 1, the MUC1* HC-CDR2 comprises the amino acid sequence of SEQ ID NO: 2, the MUC1* HC-CDR3 comprises the amino acid sequence of SEQ ID NO: 3, the MUC1* LC-CDR1 comprises the amino acid sequence of SEQ ID NO: 13, the MUC1* LC-CDR2 comprises the amino acid sequence of SEQ ID NO: 14, and the MUC1* LC-CDR3 comprises the amino acid sequence of SEQ ID NO: 15; or (b) the MUC1* HC-CDR1 comprises the amino acid sequence of SEQ ID NO: 4, the MUC1* HC-CDR2 comprises the amino acid sequence of SEQ ID NO: 5, the MUC1* HC-CDR3 comprises the amino acid sequence of SEQ ID NO: 6, the MUC1* LC-CDR1 comprises the amino acid sequence of SEQ ID NO: 16, the MUC1* LC-CDR2 comprises the amino acid sequence of SEQ ID NO: 17, and the MUC1* LC-CDR3 comprises the amino acid sequence of SEQ ID NO: 18;

Z is a conjugation moiety that forms a covalent bond with a sulfur atom of a cysteine residue of the antibody;

L is a di- or tri- or tetra-peptide linking moiety, wherein Z is bonded to the N-terminus of L and R is bonded to the C-terminus of L;

R is a coupling moiety;

X is selected from exatecan, Dxd, monomethyl auristatin E (MMAE), and monomethyl auristatin F (MMAF), wherein Dxd is —O—CH2CO-Exatecan;

and y is an integer from 1 to 8.

2. The conjugate of claim 1, wherein the antibody comprises:

a. a heavy chain comprising a sequence having at least 90% identity to the amino acid sequence of SEQ ID NO: 39, and a light chain comprising a sequence having at least 90% identity to the amino acid sequence of SEQ ID NO: 42; or b. a heavy chain comprising a sequence having at least 90% identity to the amino acid sequence of SEQ ID NO: 45, and a light chain comprising a sequence having at least 90% identity to the amino acid sequence of SEQ ID NO: 48.

3. The conjugate of claim 1, wherein y is at least 3.

4. The conjugate of claim 1, wherein L comprises two, three, or four amino acids selected from a group comprising valine, citrulline, glycine, alanine, isoleucine, methionine, tryptophan, serine, threonine, asparagine, glutamine, cysteine, tyrosine, leucine, tryptophan, proline, lysine, arginine, histidine aspartate, glutamate and phenylalanine.

5. The conjugate of claim 4, wherein L is a. a dipeptide linking moiety comprising:

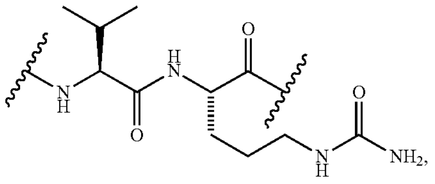 [SMILES: *N[C@H](C(=O)N[C@@H](CCCNC(N)=O)C(*)=O)C(C)C]

or b. a tetra-peptide linking moiety comprising:

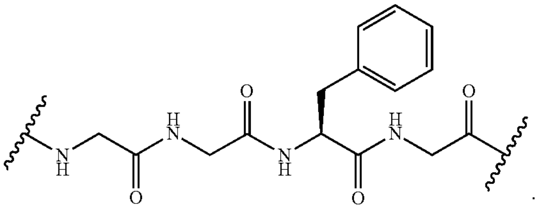 [SMILES: *NCC(=O)NCC(=O)N[C@@H](Cc1ccccc1)C(=O)NCC(*)=O]

6. The conjugate of claim 1, wherein R comprises:

a.

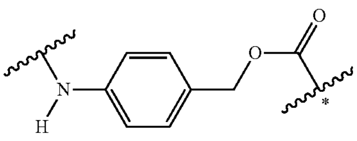

, b.

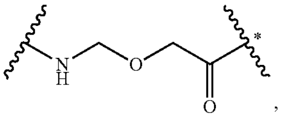

, or

-continued c.

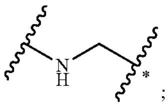

;

wherein the * indicates the point of attachment for X.

7. The conjugate of claim 1, wherein X is exatecan or Dxd.

8. The conjugate of claim 1, wherein X is monomethyl auristatin E (MMAE) or monomethyl auristatin F (MMAF).

9. The conjugate of claim 1, comprising:

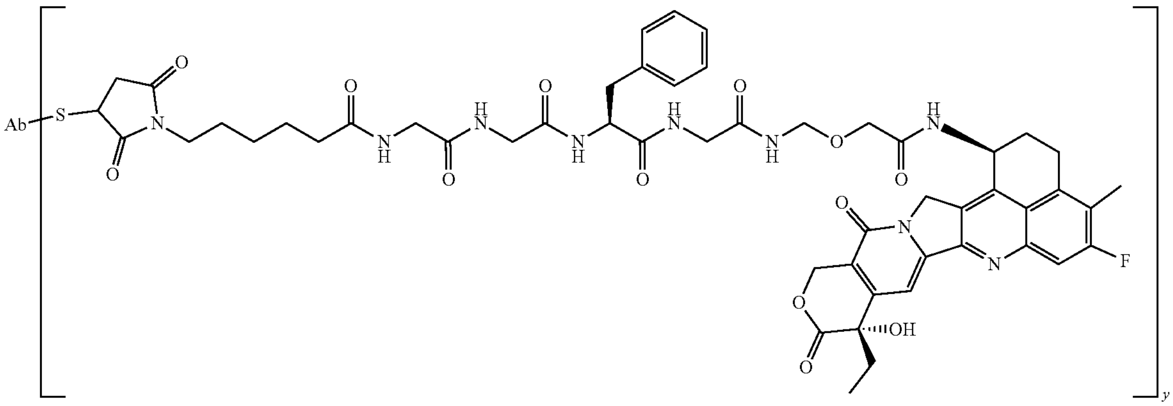

.

10. The conjugate of claim 9, wherein:

the MUC1* HC-CDR1 comprises the amino acid sequence of SEQ ID NO: 4, the MUC1* HC-CDR2 comprises the amino acid sequence of SEQ ID NO: 5, the MUC1* HC-CDR3 comprises the amino acid sequence of SEQ ID NO: 6,

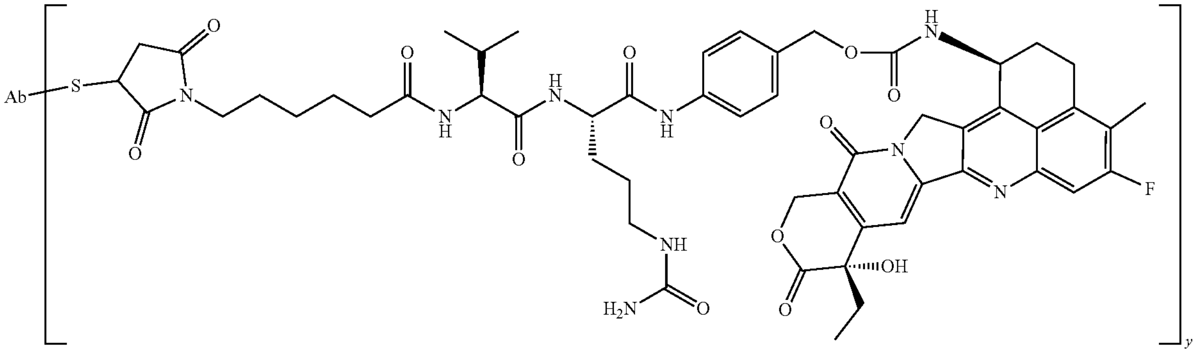

the MUC1* LC-CDR1 comprises the amino acid sequence of SEQ ID NO: 16, the MUC1* LC-CDR2 comprises the amino acid sequence of SEQ ID NO: 17, and the MUC1* LC-CDR3 comprises the amino acid sequence of SEQ ID NO: 18.

11. The conjugate of claim 9, wherein Ab comprises a heavy chain consisting of the amino acid sequence of SEQ ID NO: 38 and a light chain consisting of the amino acid sequence of SEQ ID NO: 41.

12. The conjugate of claim 9, wherein Ab comprises a heavy chain consisting of the amino acid sequence of SEQ ID NO: 44 and a light chain consisting of the amino acid sequence of SEQ ID NO: 47.

13. The conjugate of claim 12, wherein y is at least 3.

14. The conjugate of claim 1, comprising:

wherein Ab comprises a heavy chain consisting of the amino acid sequence of SEQ ID NO: 38 and a light chain consisting of the amino acid sequence of SEQ ID NO: 41.

15. The conjugate of claim 1, comprising:

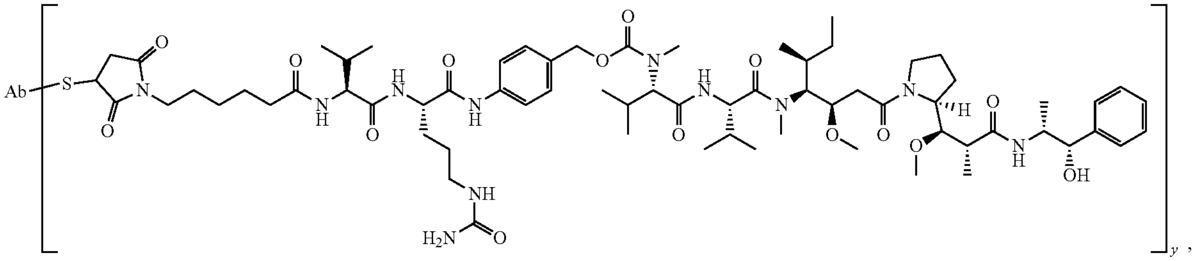

wherein Ab comprises:

a heavy chain consisting of the amino acid sequence of SEQ ID NO: 38 and a light chain consisting of the amino acid sequence of SEQ ID NO: 41, or a heavy chain consisting of the amino acid sequence of SEQ ID NO: 44 and a light chain consisting of the amino acid sequence of SEQ ID NO: 47.

16. The conjugate of claim 1, comprising:

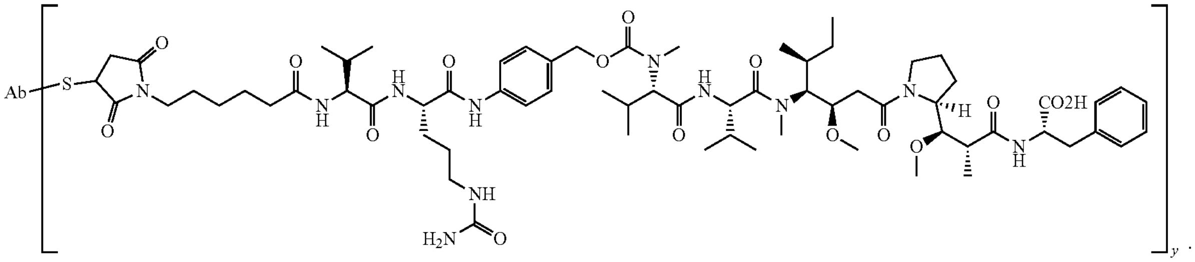

17. The conjugate of claim 1, wherein the antibody comprises:

a. a heavy chain comprising the amino acid sequence of SEQ ID NO: 39, and a light chain comprising the amino acid sequence of SEQ ID NO: 42; or b. a heavy chain comprising the amino acid sequence of SEQ ID NO: 45, and a light chain comprising the amino acid sequence of SEQ ID NO: 48.

18. A method of treating cancer comprising administering the conjugate of claim 1 to a subject.

19. The method of claim 18, wherein the cancer expresses MUC1*.

20. The method of claim 19, wherein the cancer comprises breast cancer, colon cancer, prostate cancer, pancreatic cancer, or lung cancer.

* * * * *

SEQUENCE LISTING

```
Sequence total quantity: 133
SEQ ID NO: 1            moltype = AA  length = 5
FEATURE                 Location/Qualifiers
source                  1..5
                        mol_type = protein
                        organism = synthetic construct
SEQUENCE: 1
TYAMS                                                                   5

SEQ ID NO: 2            moltype = AA  length = 16
FEATURE                 Location/Qualifiers
source                  1..16
                        mol_type = protein
                        organism = synthetic construct
SEQUENCE: 2
SIGRAGSTYY SDSVKG                                                       16

SEQ ID NO: 3            moltype = AA  length = 12
FEATURE                 Location/Qualifiers
source                  1..12
                        mol_type = protein
                        organism = synthetic construct
SEQUENCE: 3
GPIYNDYDEF AY                                                           12

SEQ ID NO: 4            moltype = AA  length = 5
FEATURE                 Location/Qualifiers
source                  1..5
                        mol_type = protein
                        organism = synthetic construct
SEQUENCE: 4
GYAMS                                                                   5

SEQ ID NO: 5            moltype = AA  length = 17
FEATURE                 Location/Qualifiers
source                  1..17
                        mol_type = protein
                        organism = synthetic construct
SEQUENCE: 5
TISSGGTYIY YPDSVKG                                                      17

SEQ ID NO: 6            moltype = AA  length = 12
FEATURE                 Location/Qualifiers
source                  1..12
                        mol_type = protein
                        organism = synthetic construct
SEQUENCE: 6
LGGDNYYEYF DV                                                           12

SEQ ID NO: 7            moltype = AA  length = 5
FEATURE                 Location/Qualifiers
source                  1..5
                        mol_type = protein
                        organism = synthetic construct
SEQUENCE: 7
RYTMH                                                                   5

SEQ ID NO: 8            moltype = AA  length = 17
FEATURE                 Location/Qualifiers
source                  1..17
                        mol_type = protein
                        organism = synthetic construct
SEQUENCE: 8
YINPSRGYTN YNQKVKD                                                      17

SEQ ID NO: 9            moltype = AA  length = 6
FEATURE                 Location/Qualifiers
source                  1..6
                        mol_type = protein
                        organism = synthetic construct
SEQUENCE: 9
YYDDHY                                                                  6

SEQ ID NO: 10           moltype = AA  length = 5
FEATURE                 Location/Qualifiers
source                  1..5
                        mol_type = protein
                        organism = synthetic construct
```

-continued

```
SEQUENCE: 10
SYTMH                                                               5

SEQ ID NO: 11           moltype = AA  length = 17
FEATURE                 Location/Qualifiers
source                  1..17
                        mol_type = protein
                        organism = synthetic construct
SEQUENCE: 11
YINPSSGYTK YNQKFKD                                                  17

SEQ ID NO: 12           moltype = AA  length = 10
FEATURE                 Location/Qualifiers
source                  1..10
                        mol_type = protein
                        organism = synthetic construct
SEQUENCE: 12
WQDYDVYFDY                                                          10

SEQ ID NO: 13           moltype = AA  length = 17
FEATURE                 Location/Qualifiers
source                  1..17
                        mol_type = protein
                        organism = synthetic construct
SEQUENCE: 13
KSSQSVLYSS NQKNYLA                                                  17

SEQ ID NO: 14           moltype = AA  length = 7
FEATURE                 Location/Qualifiers
source                  1..7
                        mol_type = protein
                        organism = synthetic construct
SEQUENCE: 14
WASTRES                                                             7

SEQ ID NO: 15           moltype = AA  length = 8
FEATURE                 Location/Qualifiers
source                  1..8
                        mol_type = protein
                        organism = synthetic construct
SEQUENCE: 15
HQYLSSLT                                                            8

SEQ ID NO: 16           moltype = AA  length = 15
FEATURE                 Location/Qualifiers
source                  1..15
                        mol_type = protein
                        organism = synthetic construct
SEQUENCE: 16
RASKSVSTSG YSYMH                                                    15

SEQ ID NO: 17           moltype = AA  length = 7
FEATURE                 Location/Qualifiers
source                  1..7
                        mol_type = protein
                        organism = synthetic construct
SEQUENCE: 17
LASNLES                                                             7

SEQ ID NO: 18           moltype = AA  length = 9
FEATURE                 Location/Qualifiers
source                  1..9
                        mol_type = protein
                        organism = synthetic construct
SEQUENCE: 18
QHSRELPFT                                                           9

SEQ ID NO: 19           moltype = AA  length = 10
FEATURE                 Location/Qualifiers
source                  1..10
                        mol_type = protein
                        organism = synthetic construct
SEQUENCE: 19
SASSSVSYMN                                                          10

SEQ ID NO: 20           moltype = AA  length = 7
FEATURE                 Location/Qualifiers
source                  1..7
                        mol_type = protein
```

```
                         organism = synthetic construct
SEQUENCE: 20
DTSKLAS                                                          7

SEQ ID NO: 21            moltype = AA  length = 9
FEATURE                  Location/Qualifiers
source                   1..9
                         mol_type = protein
                         organism = synthetic construct
SEQUENCE: 21
QQWSSNPFT                                                        9

SEQ ID NO: 22            moltype = AA  length = 10
FEATURE                  Location/Qualifiers
source                   1..10
                         mol_type = protein
                         organism = synthetic construct
SEQUENCE: 22
RASSSVSYMH                                                       10

SEQ ID NO: 23            moltype = AA  length = 8
FEATURE                  Location/Qualifiers
source                   1..8
                         mol_type = protein
                         organism = synthetic construct
SEQUENCE: 23
YATSNLAS                                                         8

SEQ ID NO: 24            moltype = AA  length = 9
FEATURE                  Location/Qualifiers
source                   1..9
                         mol_type = protein
                         organism = synthetic construct
SEQUENCE: 24
QQWSSNPPT                                                        9

SEQ ID NO: 25            moltype = DNA  length = 1350
FEATURE                  Location/Qualifiers
source                   1..1350
                         mol_type = other DNA
                         organism = synthetic construct
SEQUENCE: 25
caggttcaac tggttcagag cggtggaggt gtggttcagc ctggtcgtag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccatt actgtctgga ttactggggt cagggaacca ccctgaccgt tagcagtgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggacgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                 1350

SEQ ID NO: 26            moltype = AA  length = 449
FEATURE                  Location/Qualifiers
source                   1..449
                         mol_type = protein
                         organism = synthetic construct
SEQUENCE: 26
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
```

```
QGNVFSCSVM HEALHNHYTQ KSLSLSPGK                                449

SEQ ID NO: 27          moltype = AA  length = 119
FEATURE                Location/Qualifiers
source                 1..119
                       mol_type = protein
                       organism = synthetic construct
SEQUENCE: 27
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSS   119

SEQ ID NO: 28          moltype = DNA  length = 639
FEATURE                Location/Qualifiers
source                 1..639
                       mol_type = other DNA
                       organism = synthetic construct
SEQUENCE: 28
cagatgaccc agagcccttc ttccttatct gccagcgtgg gcgatagagt gaccatcaca  60
tgcagcgcca gctcttctgt tagctacatg aactggtacc agcaaacacc tggaaaggcc  120
cctaaaagat ggatctacga caccagcaag ctggcctctg gcgtgccctc tagattcagc  180
ggctctggct ccggcaccga ctacaccttt acaattagct ccctgcagcc cgaggatatc  240
gccacctact actgccagca gtggagcagc aaccccttca cattcggcca gggcacaaag  300
ctgcaaatca ccagacgtac ggtggctgca ccatctgtct tcatcttccc gccatctgat  360
gagcagttga aatctggaac tgcctctgtt gtgtgcctgc tgaataactt ctatcccaga  420
gaggccaaag tacagtggtg cgtggataac gccctccaat cgggtaactc ccaggagagt  480
gtcacagagc aggacagcaa ggacagcacc tacagcctca gcagcaccct gacgctgagc  540
aaagcagact acgagaaaca caaagtctac gcctgcgaag tcacccatca gggcctgagc  600
tcgcccgtca caaagagctt caacagggga gagtgttag                         639

SEQ ID NO: 29          moltype = AA  length = 212
FEATURE                Location/Qualifiers
source                 1..212
                       mol_type = protein
                       organism = synthetic construct
SEQUENCE: 29
QMTQSPSSLS ASVGDRVTIT CSASSSVSYM NWYQQTPGKA PKRWIYDTSK LASGVPSRFS  60
GSGSGTDYTF TISSLQPEDI ATYYCQQWSS NPFTFGQGTK LQITRRTVAA PSVFIFPPSD  120
EQLKSGTASV VCLLNNFYPR EAKVQWCVDN ALQSGNSQES VTEQDSKDST YSLSSTLTLS  180
KADYEKHKVY ACEVTHQGLS SPVTKSFNRG EC                                212

SEQ ID NO: 30          moltype = AA  length = 106
FEATURE                Location/Qualifiers
source                 1..106
                       mol_type = protein
                       organism = synthetic construct
SEQUENCE: 30
QMTQSPSSLS ASVGDRVTIT CSASSSVSYM NWYQQTPGKA PKRWIYDTSK LASGVPSRFS  60
GSGSGTDYTF TISSLQPEDI ATYYCQQWSS NPFTFGQGTK LQITRR                 106

SEQ ID NO: 31          moltype = DNA  length = 1350
FEATURE                Location/Qualifiers
source                 1..1350
                       mol_type = other DNA
                       organism = synthetic construct
SEQUENCE: 31
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagcccccca tcgagaaaac catctccaaa  1020
gccaaagggc agccccgaga accacaggtg tacaccctgc ccccatcccg ggacgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                   1350
```

-continued

```
SEQ ID NO: 32          moltype = AA  length = 449
FEATURE                Location/Qualifiers
source                 1..449
                       mol_type = protein
                       organism = synthetic construct
SEQUENCE: 32
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 33          moltype = AA  length = 119
FEATURE                Location/Qualifiers
source                 1..119
                       mol_type = protein
                       organism = synthetic construct
SEQUENCE: 33
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSS   119

SEQ ID NO: 34          moltype = DNA  length = 645
FEATURE                Location/Qualifiers
source                 1..645
                       mol_type = other DNA
                       organism = synthetic construct
SEQUENCE: 34
gatatccaga tgacacagag ccccagctct ctgtctgctt ctgtgggcga cagagtgacc  60
atgacctgta gagcctcctc aagcgtgtcc tacatgcact ggtaccagca aaacacctggc  120
aaggccccaa agccttggat ctacgccacc tctaatctgg ccagcggcgt gccttctaga  180
ttcagcggca gcggatctgg caccgattac accctgacca tcagcagcct gcagcccgag  240
gatatcgcca catactactg ccagcagtgg agctccaatc ctcctacctt cggccagggc  300
accaagctgc agatcacaag acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggtgcgtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 35          moltype = AA  length = 214
FEATURE                Location/Qualifiers
source                 1..214
                       mol_type = protein
                       organism = synthetic construct
SEQUENCE: 35
DIQMTQSPSS LSASVGDRVT MTCRASSSVS YMHWYQQTPG KAPKPWIYAT SNLASGVPSR  60
FSGSGSGTDY TLTISSLQPE DIATYYCQQW SSNPPTFGQG TKLQITRRTV AAPSVFIFPP  120
SDEQLKSGTA SVVCLLNNFY PREAKVQWCV DNALQSGNSQ ESVTEQDSKD STYSLSSTLT  180
LSKADYEKHK VYACEVTHQG LSSPVTKSFN RGEC                             214

SEQ ID NO: 36          moltype = AA  length = 108
FEATURE                Location/Qualifiers
source                 1..108
                       mol_type = protein
                       organism = synthetic construct
SEQUENCE: 36
DIQMTQSPSS LSASVGDRVT MTCRASSSVS YMHWYQQTPG KAPKPWIYAT SNLASGVPSR  60
FSGSGSGTDY TLTISSLQPE DIATYYCQQW SSNPPTFGQG TKLQITRR              108

SEQ ID NO: 37          moltype = DNA  length = 1347
FEATURE                Location/Qualifiers
source                 1..1347
                       mol_type = other DNA
                       organism = synthetic construct
SEQUENCE: 37
gaggtgcagc tggtggagtc tggggggaggc ctggtcaagc ctgggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgctct gaccagcggc gtgcacacct tcccagctgt cctacagtcc  540
tcaggactct actccctcag cagcgtggtg accgtgccct ccagcaactt cggcacccag  600
acctacacct gcaacgtaga tcacaagccc agcaacacca aggtggacaa gacagttgag  660
```

```
cgcaaatgtt gtgtcgagtg cccaccgtgc ccagcaccac ctgtggcagg accgtcagtc  720
ttcctcttcc ccccaaaacc caaggacacc ctcatgatct cccggacccc tgaggtcacg  780
tgcgtggtgg tggacgtgag ccacgaagac cccgaggtcc agttcaactg gtacgtggac  840
ggcgtggagg tgcataatgc caagacaaag ccacgggagg agcagttcaa cagcacgttc  900
cgtgtggtca gcgtcctcac cgttgtgcac caggactggc tgaacggcaa ggagtacaag  960
tgcaaggtct ccaacaaagg cctcccagcc cccatcgaga aaaccatctc caaaaccaaa  1020
gggcagcccc gagaaccaca ggtgtacacc ctgcccccat cccgggagga gatgaccaag  1080
aaccaggtca gcctgacctg cctggtcaaa ggcttctacc ccagcgacat cgccgtggag  1140
tgggagagca atgggcagcc ggagaacaac tacaagacca cacctcccat gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa atagtaa                                     1347

SEQ ID NO: 38           moltype = AA  length = 451
FEATURE                 Location/Qualifiers
source                  1..451
                        mol_type = protein
                        organism = synthetic construct
SEQUENCE: 38
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 39           moltype = AA  length = 121
FEATURE                 Location/Qualifiers
source                  1..121
                        mol_type = protein
                        organism = synthetic construct
SEQUENCE: 39
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
S                                                                 121

SEQ ID NO: 40           moltype = DNA  length = 663
FEATURE                 Location/Qualifiers
source                  1..663
                        mol_type = other DNA
                        organism = synthetic construct
SEQUENCE: 40
gacattgtgc tgacccagtc tccagcctcc ttggccgtgt ctccaggaca gagggccacc  60
atcacctgca gagccagtaa gagtgtcagt accagcggat actcctacat gcactggtat  120
cagcagaaac caggacaacc tcctaaactc ctgatttacc tggcatccaa tctggagagc  180
ggggtcccag ccaggttcag cggcagtggg tctgggaccg atttcaccct cacaattaat  240
cctgtggaag ctaatgatac tgcaaattat tactgtcagc acagtaggga gctgcctttc  300
acattcggcg gagggaccaa ggtggagatc aaacgaactc gtacggtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggtgcgtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tag                                                               663

SEQ ID NO: 41           moltype = AA  length = 220
FEATURE                 Location/Qualifiers
source                  1..220
                        mol_type = protein
                        organism = synthetic construct
SEQUENCE: 41
DIVLTQSPAS LAVSPGQRAT ITCRASKSVS TSGYSYMHWY QQKPGQPPKL LIYLASNLES  60
GVPARFSGSG SGTDFTLTIN PVEANDTANY YCQHSRELPF TFGGGTKVEI KRTRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 42           moltype = AA  length = 113
FEATURE                 Location/Qualifiers
source                  1..113
                        mol_type = protein
                        organism = synthetic construct
SEQUENCE: 42
DIVLTQSPAS LAVSPGQRAT ITCRASKSVS TSGYSYMHWY QQKPGQPPKL LIYLASNLES  60
GVPARFSGSG SGTDFTLTIN PVEANDTANY YCQHSRELPF TFGGGTKVEI KRT        113

SEQ ID NO: 43           moltype = DNA  length = 1350
FEATURE                 Location/Qualifiers
```

-continued

```
source                  1..1350
                        mol_type = other DNA
                        organism = synthetic construct
SEQUENCE: 43
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
gctagcacca agggcccatc ggtcttcccc ctggcaccct cctccaagag cacctctggg  420
ggcacagcgg ccctgggctg cctggtcaag gactacttcc ccgagccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                 1350

SEQ ID NO: 44           moltype = AA  length = 450
FEATURE                 Location/Qualifiers
source                  1..450
                        mol_type = protein
                        organism = synthetic construct
SEQUENCE: 44
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 45           moltype = AA  length = 120
FEATURE                 Location/Qualifiers
source                  1..120
                        mol_type = protein
                        organism = synthetic construct
SEQUENCE: 45
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120

SEQ ID NO: 46           moltype = DNA  length = 663
FEATURE                 Location/Qualifiers
source                  1..663
                        mol_type = other DNA
                        organism = synthetic construct
SEQUENCE: 46
gaaattgtgc tgacacagag ccccgccaca ctgtcacttt ctccaggcga aagagccaca  60
ctgagctgca agagcagcca gagcgtgctg tactccagca accagaagaa ctacctggcc  120
tggtatcagc agaagcccgg ccaagctcct cggctgctga tctattgggc cagcacaaga  180
gagagcggca tccctgccag attttctggc agcggctctg gcaccgattt caccctgacc  240
ataagcagcc tggaacctga ggacttcgcc gtgtattact gccaccagta cctgagcagc  300
ctgacctttg gcggaggcac caaggtggaa atcaagcggc gtacggtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggtgcgtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tag                                                              663

SEQ ID NO: 47           moltype = AA  length = 220
FEATURE                 Location/Qualifiers
source                  1..220
                        mol_type = protein
                        organism = synthetic construct
SEQUENCE: 47
EIVLTQSPAT LSLSPGERAT LSCKSSQSVL YSSNQKNYLA WYQQKPGQAP RLLIYWASTR  60
ESGIPARFSG SGSGTDFTLT ISSLEPEDFA VYYCHQYLSS LTFGGGTKVE IKRRTVAAPS  120
```

```
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 48           moltype = AA  length = 113
FEATURE                 Location/Qualifiers
source                  1..113
                        mol_type = protein
                        organism = synthetic construct
SEQUENCE: 48
EIVLTQSPAT LSLSPGERAT LSCKSSQSVL YSSNQKNYLA WYQQKPGQAP RLLIYWASTR  60
ESGIPARFSG SGSGTDFTLT ISSLEPEDFA VYYCHQYLSS LTFGGGTKVE IKR         113

SEQ ID NO: 49           moltype = DNA  length = 1419
FEATURE                 Location/Qualifiers
source                  1..1419
                        mol_type = other DNA
                        organism = synthetic construct
SEQUENCE: 49
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcggc  360
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaa                        1419

SEQ ID NO: 50           moltype = AA  length = 473
FEATURE                 Location/Qualifiers
source                  1..473
                        mol_type = protein
                        organism = synthetic construct
SEQUENCE: 50
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 51           moltype = DNA  length = 1419
FEATURE                 Location/Qualifiers
source                  1..1419
                        mol_type = other DNA
                        organism = synthetic construct
SEQUENCE: 51
caggtgcaac tggtgcagtc cggcggaggc gtggtgcagc ctggccggag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccact actgtctgga ctactgggga cagggaacca ccctgaccgt cagctctggc  360
ggcggaggct ccggcggagg tggcagcggc ggcggcggct ctgatatcca gatgacccag  420
agcccttctt ccttatctgc cagcgtgggc gatagagtga ccatcacatg cagcgccagc  480
tcttctgtta gctacatgaa ctggtaccag caaacacctg gaaaggcccc taaaagatgg  540
atctacgaca ccagcaagct ggcctctggc gtgccctcta gattcagcgg ctctggctcc  600
ggcaccgact acacctttac aattagctcc ctgcagcccg aggatatcgc cacctactac  660
tgccagcagt ggagcagcaa ccccttcaca ttcggccagg gcacaaagct gcaaatcacc  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
```

-continued

```
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaa                        1419

SEQ ID NO: 52          moltype = AA  length = 473
FEATURE                Location/Qualifiers
source                 1..473
                       mol_type = protein
                       organism = synthetic construct
SEQUENCE: 52
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 53          moltype = DNA  length = 2217
FEATURE                Location/Qualifiers
source                 1..2217
                       mol_type = other DNA
                       organism = synthetic construct
SEQUENCE: 53
caggtgcaac tggtgcagtc cggcggaggc gtggtgcagc ctggccggag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccact actgtctgga ctactgggga cagggaacca ccctgaccgt cagctctggc  360
ggcggaggct ccggcggagg tggcagcggc ggcggcggct ctgatatcca gatgacccag  420
agcccttctt ccttatctgc cagcgtgggc gatagagtga ccatcacatg cagcgccagc  480
tcttctgtta gctacatgaa ctggtaccag caaacacctg gaaaggcccc taaaagatgg  540
atctacgaca ccagcaagct ggcctctggc gtgccctcta gattcagcgg ctctggctcc  600
ggcaccgact acacctttac aattagctcc ctgcagcccg aggatatcgc cacctactac  660
tgccagcagt ggagcagcaa ccccttcaca ttcggccagg gcacaaagct gcaaatcacc  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcgggggtgg cggttctggt  1440
ggtggtggct ctggaggagg aaccggtcag gtgcagctgg ttgaatctgg cggcggactt  1500
gtgaagcctg gcggatctct gagactgagc tgtgccgcca gcggcttcac ctttagcaca  1560
tacgccatga gctggatcag acaggcccct ggcaaaggcc tggaatgggt ggcgtctatt  1620
ggcagagccg gcagcaccta ctacagcgac tctgtgaagg gcagattcac catcagccgg  1680
gacaacgcca agaacagcct gtacctgcag atgaactccc tgagagccga ggacaccgcc  1740
gtgtactatt gtgccagagg acccatctac aacgactacg acgagttcgc ctattggggc  1800
cagggcacac tggtcacagt ttctagcggc ggtggcggaa gcggaggcgg tggctccggt  1860
ggcggaggca gcgaaattgt gctgacacag agccccgcca cactgtcact ttctccaggc  1920
gaaagagcca cactgagctg caagagcagc cagagcgtgc tgtactccag caaccagaag  1980
aactacctgg cctggtatca gcagaagccc ggccaagctc ctcggctgct gatctattgg  2040
gccagcacaa gagagagcgg catccctgcc agattttctg gcagcggctc tggcaccgat  2100
ttcaccctga ccataagcag cctggaacct gaggacttcg ccgtgtatta ctgccaccag  2160
tacctgagca gcctgacctt tggcggaggc accaaggtgg aaatcaagcg gtgataa     2217

SEQ ID NO: 54          moltype = AA  length = 737
FEATURE                Location/Qualifiers
source                 1..737
                       mol_type = protein
                       organism = synthetic construct
SEQUENCE: 54
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
```

-continued

```
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGGSG  480
GGGSGGGTGQ VQLVESGGGL VKPGGSLRLS CAASGFTFST YAMSWIRQAP GKGLEWVASI  540
GRAGSTYYSD SVKGRFTISR DNAKNSLYLQ MNSLRAEDTA VYYCARGPIY NDYDEFAYWG  600
QGTLVTVSSG GGGSGGGGSG GGGSEIVLTQ SPATLSLSPG ERATLSCKSS QSVLYSSNQK  660
NYLAWYQQKP GQAPRLLIYW ASTRESGIPA RFSGSGSGTD FTLTISSLEP EDFAVYYCHQ  720
YLSSLTFGGG TKVEIKR                                                 737

SEQ ID NO: 55          moltype = DNA  length = 2220
FEATURE                Location/Qualifiers
source                 1..2220
                       mol_type = other DNA
                       organism = synthetic construct
SEQUENCE: 55
caggtgcaac tggtgcagtc cggcggaggc gtggtgcagc ctggccggag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccact actgtctgga ctactgggga cagggaacca ccctgaccgt cagctctggc  360
ggcggaggct ccggcggagg tggcagcggc ggcggcggct ctgatatcca gatgacccag  420
agcccttctt ccttatctgc cagcgtgggc gatagagtga ccatcacatg cagcgccagc  480
tcttctgtta gctacatgaa ctggtaccag caaacacctg gaaaggcccc taaaagatgg  540
atctacgaca ccagcaagct ggcctctggc gtgccctcta gattcagcgg ctctggctcc  600
ggcaccgact acacctttac aattagctcc ctgcagcccg aggatatcgc cacctactac  660
tgccagcagt ggagcagcaa ccccttcaca ttcggccagg gcacaaagct gcaaatcacc  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcgggggtgg cggttctggt  1440
ggtggtggct ctggaggagg aaccggtgag gtgcagctgg tggagtctgg gggaggcctg  1500
gtcaagcctg gggggtccct gagactctcc tgtgcagcct ctggattcac cttcagtggc  1560
tatgccatga gctgggtccg ccaggctcca gggaaggggc tggagtgggt ctcaaccatt  1620
agtagtggcg gaacctacat atactacccc gactcagtga agggccgatt caccatctcc  1680
agagacaacg ccaagaactc actgtatctg caaatgaaca gcctgagagc cgaggacacg  1740
gccgtgtatt actgtgcgag acttgggggg gataattact acgaatactt cgatgtctgg  1800
ggcaaaggga ccacggtcac cgtctcctcc ggcggtggcg gatccggcgg tggcggatcc  1860
ggcggtggcg gatccgacat tgtgctgacc cagtctccag cctccttggc cgtgtctcca  1920
ggacagaggg ccaccatcac ctgcagagcc agtaagagtg tcagtaccag cggatactcc  1980
tacatgcact ggtatcagca gaaaccagga caacctccta aactcctgat ttacctggca  2040
tccaatctgg agagcggggt cccagccagg ttcagcggca gtgggtctgg gaccgatttc  2100
accctcacaa ttaatcctgt ggaagctaat gatactgcaa attattactg tcagcacagt  2160
agggagctgc ctttcacatt cggcggaggg accaaggtgg agatcaaacg aacttgataa  2220

SEQ ID NO: 56          moltype = AA  length = 738
FEATURE                Location/Qualifiers
source                 1..738
                       mol_type = protein
                       organism = synthetic construct
SEQUENCE: 56
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGGSG  480
GGGSGGGTGE VQLVESGGGL VKPGGSLRLS CAASGFTFSG YAMSWVRQAP GKGLEWVSTI  540
SSGGTYIYYP DSVKGRFTIS RDNAKNSLYL QMNSLRAEDT AVYYCARLGG DNYYEYFDVW  600
GKGTTVTVSS GGGGSGGGGS GGGGSDIVLT QSPASLAVSP GQRATITCRA SKSVSTSGYS  660
YMHWYQQKPG QPPKLLIYLA SNLESGVPAR FSGSGSGTDF TLTINPVEAN DTANYYCQHS  720
RELPFTFGGG TKVEIKRT                                                738

SEQ ID NO: 57          moltype = DNA  length = 2205
FEATURE                Location/Qualifiers
source                 1..2205
                       mol_type = other DNA
                       organism = synthetic construct
```

SEQUENCE: 57
caggtgcaac tggtgcagtc cggcggaggc gtggtgcagc ctggccggag cctgagactg 60
agctgcaagg cctccggcta cacctttaca agatacacta tgcactgggt cagacaggcc 120
cctggcaagg gcctggaatg gattggctac atcaacccta gccggggata taccaactac 180
aaccagaaag tgaaggacag attcaccatc agcacagata agtccaagtc caccgctttc 240
ctgcagatgg actccctgcg tccagaggac acagctgtgt actactgcgc ccggtactac 300
gacgaccact actgtctgga ctactgggga cagggaacca ccctgaccgt cagctctggc 360
ggcggaggct ccggcggagg tggcagcggc ggcggcggct ctgatatcca gatgacccag 420
agcccttctt ccttatctgc cagcgtgggc gatagagtga ccatcacatg cagcgccagc 480
tcttctgtta gctacatgaa ctggtaccag caaacacctg gaaaggcccc taaaagatgg 540
atctacgaca ccagcaagct ggcctctggc gtgccctcta gattcagcgg ctctggctcc 600
ggcaccgact acacctttac aattagctcc ctgcagcccg aggatatcgc cacctactac 660
tgccagcagt ggagcagcaa ccccttcaca ttcggccagg gcacaaagct gcaaatcacc 720
agagagccca aatcttgtga caaaactcac acatgcccac cgtgcccagc acctgaactc 780
ctggggggac cgtcagtctt cctcttcccc ccaaaaccca aggacaccct catgatctcc 840
cggacccctg aggtcacatg cgtggtggtg gacgtgagcc acgaagaccc tgaggtcaag 900
ttcaactggt acgtggacgg cgtggaggtg cataatgcca agacaaagcc gcgggaggag 960
cagtacaaca gcacgtaccg tgtggtcagc gtcctcaccg tcctgcacca ggactggctg 1020
aatggcaagg agtacaagtg caaggtctcc aacaaagccc tcccagcccc catcgagaaa 1080
accatctcca aagccaaagg gcagccccga gaaccacagg tgtacaccct gcccccatcc 1140
cgggaggaga tgaccaagaa ccaggtcagc ctgacctgcc tggtcaaagg cttctatccc 1200
agcgacatcg ccgtggagtg ggagagcaat gggcagccgg agaacaacta caagaccacg 1260
cctcccgtgc tggactccga cggctccttc ttcctctaca gcaagctcac cgtggacaag 1320
agcaggtggc agcaggggaa cgtcttctca tgctccgtga tgcatgaggc tctgcacaac 1380
cactacacgc agaagagcct ctccctgtct ccgggtaaag gcggcggggg gagcggtggt 1440
ggcggtagca ccggtcaggt gcagctggtt gaatctggcg gcggacttgt gaagcctggc 1500
ggatctctga gactgagctg tgccgccagc ggcttcacct ttagcacata cgccatgagc 1560
tggatcagac aggcccctgg caaaggcctg gaatgggtgg cgtctattgg cagagccggc 1620
agcacctact acagcgactc tgtgaagggc agattcacca tcagccggga caacgccaag 1680
aacagcctgt acctgcagat gaactccctg agagccgagg acaccgccgt gtactattgt 1740
gccagaggac ccatctacaa cgactacgac gagttcgcct attggggcca gggcacactg 1800
gtcacagttt ctagcggcgg tggcggaagc ggaggcggtg gctccggtgg cggaggcagc 1860
gaaattgtgc tgacacagag ccccgccaca ctgtcacttt ctccaggcga aagagccaca 1920
ctgagctgca agagcagcca gagcgtgctg tactccagca accagaagaa ctacctggcc 1980
tggtatcagc agaagcccgg ccaagctcct cggctgctga tctattgggc cagcacaaga 2040
gagagcggca tccctgccag atttctggc agcggctctg gcaccgattt caccctgacc 2100
ataagcagcc tggaacctga ggacttcgcc gtgtattact gccaccagta cctgagcagc 2160
ctgacctttg gcggaggcac caaggtggaa atcaagcggt gataa 2205

SEQ ID NO: 58 moltype = AA length = 733
FEATURE Location/Qualifiers
source 1..733
mol_type = protein
organism = synthetic construct
SEQUENCE: 58
QVQLVQSGGG VVQPGRSLRL SCKASGYTFT RYTMHWVRQA PGKGLEWIGY INPSRGYTNY 60
NQKVKDRFTI STDKSKSTAF LQMDSLRPED TAVYYCARYY DDHYCLDYWG QGTTLTVSSG 120
GGGSGGGGSG GGGSDIQMTQ SPSSLSASVG DRVTITCSAS SSVSYMNWYQ QTPGKAPKRW 180
IYDTSKLASG VPSRFSGSGS GTDYTFTISS LQPEDIATYY CQQWSSNPFT FGQGTKLQIT 240
REPKSCDKTH TCPPCPAPEL LGGPSVFLFP PKPKDTLMIS RTPEVTCVVV DVSHEDPEVK 300
FNWYVDGVEV HNAKTKPREE QYNSTYRVVS VLTVLHQDWL NGKEYKCKVS NKALPAPIEK 360
TISKAKGQPR EPQVYTLPPS REEMTKNQVS LTCLVKGFYP SDIAVEWESN GQPENNYKTT 420
PPVLDSDGSF FLYSKLTVDK SRWQQGNVFS CSVMHEALHN HYTQKSLSLS PGKGGGGSGG 480
GGSTGQVQLV ESGGGLVKPG GSLRLSCAAS GFTFSTYAMS WIRQAPGKGL EWVASIGRAG 540
STYYSDSVKG RFTISRDNAK NSLYLQMNSL RAEDTAVYYC ARGPIYNDYD EFAYWGQGTL 600
VTVSSGGGGS GGGGSGGGGS EIVLTQSPAT LSLSPGERAT LSCKSSQSVL YSSNQKNYLA 660
WYQQKPGQAP RLLIYWASTR ESGIPARFSG SGSGTDFTLT ISSLEPEDFA VYYCHQYLSS 720
LTFGGGTKVE IKR 733

SEQ ID NO: 59 moltype = DNA length = 2208
FEATURE Location/Qualifiers
source 1..2208
mol_type = other DNA
organism = synthetic construct
SEQUENCE: 59
caggtgcaac tggtgcagtc cggcggaggc gtggtgcagc ctggccggag cctgagactg 60
agctgcaagg cctccggcta cacctttaca agatacacta tgcactgggt cagacaggcc 120
cctggcaagg gcctggaatg gattggctac atcaacccta gccggggata taccaactac 180
aaccagaaag tgaaggacag attcaccatc agcacagata agtccaagtc caccgctttc 240
ctgcagatgg actccctgcg tccagaggac acagctgtgt actactgcgc ccggtactac 300
gacgaccact actgtctgga ctactgggga cagggaacca ccctgaccgt cagctctggc 360
ggcggaggct ccggcggagg tggcagcggc ggcggcggct ctgatatcca gatgacccag 420
agcccttctt ccttatctgc cagcgtgggc gatagagtga ccatcacatg cagcgccagc 480
tcttctgtta gctacatgaa ctggtaccag caaacacctg gaaaggcccc taaaagatgg 540
atctacgaca ccagcaagct ggcctctggc gtgccctcta gattcagcgg ctctggctcc 600
ggcaccgact acacctttac aattagctcc ctgcagcccg aggatatcgc cacctactac 660
tgccagcagt ggagcagcaa ccccttcaca ttcggccagg gcacaaagct gcaaatcacc 720
agagagccca aatcttgtga caaaactcac acatgcccac cgtgcccagc acctgaactc 780
ctggggggac cgtcagtctt cctcttcccc ccaaaaccca aggacaccct catgatctcc 840

-continued

```
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcggcggggg gagcggtggt  1440
ggcggtagca ccggtgaggt gcagctggtg gagtctgggg gaggcctggt caagcctggg  1500
gggtccctga gactctcctg tgcagcctct ggattcacct tcagtggcta tgccatgagc  1560
tgggtccgcc aggctccagg gaaggggctg gagtgggtct caaccattag tagtggcgga  1620
acctacatat actaccccga ctcagtgaag ggccgattca ccatctccag agacaacgcc  1680
aagaactcac tgtatctgca aatgaacagc ctgagagccg aggacacggc cgtgtattac  1740
tgtgcgagac ttgggggggga taattactac gaatacttcg atgtctgggg caaagggacc  1800
acggtcaccg tctcctccgg cggtggcgga tccggcggtg gcggatccgg cggtggcgga  1860
tccgacattg tgctgaccca gtctccagcc tccttggccg tgtctccagg acagagggcc  1920
accatcacct gcagagccag taagagtgtc agtaccagcg gatactccta catgcactgg  1980
tatcagcaga aaccaggaca acctcctaaa ctcctgattt acctggcatc caatctggag  2040
agcggggtcc cagccaggtt cagcggcagt gggtctggga ccgatttcac cctcacaatt  2100
aatcctgtgg aagctaatga tactgcaaat tattactgtc agcacagtag ggagctgcct  2160
ttcacattcg gcggagggac caaggtggag atcaaacgaa cttgataa              2208

SEQ ID NO: 60           moltype = AA  length = 734
FEATURE                 Location/Qualifiers
source                  1..734
                        mol_type = protein
                        organism = synthetic construct
SEQUENCE: 60
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGSGG  480
GGSTGEVQLV ESGGGLVKPG GSLRLSCAAS GFTFSGYAMS WVRQAPGKGL EWVSTISSGG  540
TYIYYPDSVK GRFTISRDNA KNSLYLQMNS LRAEDTAVYY CARLGGDNYY EYFDVWGKGT  600
TVTVSSGGGG SGGGGSGGGG SDIVLTQSPA SLAVSPGQRA TITCRASKSV STSGYSYMHW  660
YQQKPGQPPK LLIYLASNLE SGVPARFSGS GSGTDFTLTI NPVEANDTAN YYCQHSRELP  720
FTFGGGTKVE IKRT                                                   734

SEQ ID NO: 61           moltype = DNA  length = 2217
FEATURE                 Location/Qualifiers
source                  1..2217
                        mol_type = other DNA
                        organism = synthetic construct
SEQUENCE: 61
caggtgcagc tggttgaatc tggcggcgga cttgtgaagc ctggcggatc tctgagactg  60
agctgtgccg ccagcggctt caccttttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
gccagatttt ctggcagcgg ctctggcacc gatttcaccc tgaccataag cagcctggaa  660
cctgaggact tcgccgtgta ttactgccac cagtacctga gcagcctgac ctttggcgga  720
ggcaccaagg tggaaatcaa gcgggagccc aaatcttgtg acaaaactca cacatgccca  780
ccgtgcccag cacctgaact cctgggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc  1020
gtcctgcacc aggactggct gaatggcaag gagtacaagt gcaaggtctc caacaaagcc  1080
ctcccagccc ccatcgagaa aaccatctcc aaagccaaag ggcagccccg agaaccacag  1140
gtgtacaccc tgcccccatc ccgggaggag atgaccaaga accaggtcag cctgacctgc  1200
ctggtcaaag gcttctatcc cagcgacatc gccgtggagt gggagagcaa tgggcagccg  1260
gagaacaact acaagaccac gcctcccgtg ctggactccg acggctcctt cttcctctac  1320
agcaagctca ccgtggacaa gagcaggtgg cagcagggga acgtcttctc atgctccgtg  1380
atgcatgagg ctctgcacaa ccactacacg cagaagagcc tctccctgtc tccgggtaaa  1440
ggcgggggtg gcggttctgg tggtggtggc tctggaggag gaaccggtca ggtgcaactg  1500
gtgcagtccg gcggaggcgt ggtgcagcct ggccggagcc tgagactgag ctgcaaggcc  1560
tccggctaca cctttacaag atacactatg cactgggtca gacaggcccc tggcaagggc  1620
ctggaatgga ttggctacat caaccctagc cggggatata ccaactacaa ccagaaagtg  1680
aaggacagat tcaccatcag cacagataag tccaagtcca ccgctttcct gcagatggac  1740
```

-continued

```
tccctgcgtc cagaggacac agctgtgtac tactgcgccc ggtactacga cgaccactac  1800
tgtctggact actggggaca gggaaccacc ctgaccgtca gctctggcgg cggaggctcc  1860
ggcggaggtg gcagcggcgg cggcggctct gatatccaga tgacccagag cccttcttcc  1920
ttatctgcca gcgtgggcga tagagtgacc atcacatgca gcgccagctc ttctgttagc  1980
tacatgaact ggtaccagca aacacctgga aaggccccta aaagatggat ctacgacacc  2040
agcaagctgg cctctggcgt gccctctaga ttcagcggct ctggctccgg caccgactac  2100
acctttacaa ttagctccct gcagcccgag gatatcgcca cctactactg ccagcagtgg  2160
agcagcaacc ccttcacatt cggccagggc acaaagctgc aaatcaccag atgataa     2217

SEQ ID NO: 62          moltype = AA  length = 737
FEATURE                Location/Qualifiers
source                 1..737
                       mol_type = protein
                       organism = synthetic construct
SEQUENCE: 62
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKREP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLTC LVKGFYPSDI AVEWESNGQP  420
ENNYKTTPPV LDSDGSFFLY SKLTVDKSRW QQGNVFSCSV MHEALHNHYT QKSLSLSPGK  480
GGGGSGGGG SGGGTGQVQL VQSGGGVVQP GRSLRLSCKA SGYTFTRYTM HWVRQAPGKG  540
LEWIGYINPS RGYTNYNQKV KDRFTISTDK SKSTAFLQMD SLRPEDTAVY YCARYYDDHY  600
CLDYWGQGTT LTVSSGGGGS GGGGSGGGGS DIQMTQSPSS LSASVGDRVT ITCSASSSVS  660
YMNWYQQTPG KAPKRWIYDT SKLASGVPSR FSGSGSGTDY TFTISSLQPE DIATYYCQQW  720
SSNPFTFGQG TKLQITR                                                 737

SEQ ID NO: 63          moltype = DNA  length = 2220
FEATURE                Location/Qualifiers
source                 1..2220
                       mol_type = other DNA
                       organism = synthetic construct
SEQUENCE: 63
gaggtgcagc tggtggagtc tgggggaggc ctggtcaagc ctgggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg gcatccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgcctttcac attcggcgga  720
gggaccaagg tggagatcaa acgaactgag cccaaatctt gtgacaaaac tcacacatgc  780
ccaccgtgcc cagcacctga actcctgggg ggaccgtcag tcttcctctt ccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaaggcgggg gtggcggttc tggtggtggt ggctctggag gaggaaccgg tcaggtgcaa  1500
ctggtgcagt ccggcggagg cgtggtgcag cctggccgga gcctgagact gagctgcaag  1560
gcctccggct acacctttac aagatacact atgcactggg tcagacaggc ccctggcaag  1620
ggcctggaat ggattggcta catcaaccct agccggggat ataccaacta caaccagaaa  1680
gtgaaggaca gattcaccat cagcacagat aagtccaagt ccaccgcttt cctgcagatg  1740
gactccctgc gtccagagga cacagctgtg tactactgcg cccggtacta cgacgaccac  1800
tactgtctgg actactgggg acagggaacc accctgaccg tcagctctgg cggcggaggc  1860
tccggcggag gtggcagcgg cggcggcggc tctgatatcc agatgaccca gagcccttct  1920
tccttatctg ccagcgtggg cgatagagtg accatcacat gcagcgccag ctcttctgtt  1980
agctacatga actggtacca gcaaacacct ggaaaggccc ctaaaagatg gatctacgac  2040
accagcaagc tggcctctgg cgtgccctct agattcagcg gctctggctc cggcaccgac  2100
tacaccttta caattagctc cctgcagccc gaggatatcg ccacctacta ctgccagcag  2160
tggagcagca accccttcac attcggccag ggcacaaagc tgcaaatcac cagatgataa  2220

SEQ ID NO: 64          moltype = AA  length = 738
FEATURE                Location/Qualifiers
source                 1..738
                       mol_type = protein
                       organism = synthetic construct
SEQUENCE: 64
```

-continued

```
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
KGGGGGSGGG GSGGGTGQVQ LVQSGGGVVQ PGRSLRLSCK ASGYTFTRYT MHWVRQAPGK  540
GLEWIGYINP SRGYTNYNQK VKDRFTISTD KSKSTAFLQM DSLRPEDTAV YYCARYYDDH  600
YCLDYWGQGT TLTVSSGGGG SGGGGSGGGG SDIQMTQSPS SLSASVGDRV TITCSASSSV  660
SYMNWYQQTP GKAPKRWIYD TSKLASGVPS RFSGSGSGTD YTFTISSLQP EDIATYYCQQ  720
WSSNPFTFGQ GTKLQITR                                               738

SEQ ID NO: 65          moltype = DNA  length = 2205
FEATURE                Location/Qualifiers
source                 1..2205
                       mol_type = other DNA
                       organism = synthetic construct
SEQUENCE: 65
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
gccagatttt ctggcagcgg ctctggcacc gatttcaccc tgaccataag cagcctggaa  660
cctgaggact tcgccgtgta ttactgccac cagtacctga gcagcctgac ctttggcgga  720
ggcaccaagg tggaaatcaa gcgggagccc aaatcttgtg acaaaactca cacatgccca  780
ccgtgcccag cacctgaact cctgggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc  1020
gtcctgcacc aggactggct gaatggcaag gagtacaagt gcaaggtctc caacaaagcc  1080
ctcccagccc ccatcgagaa aaccatctcc aaagccaaag ggcagccccg agaaccacag  1140
gtgtacaccc tgcccccatc ccgggaggag atgaccaaga accaggtcag cctgacctgc  1200
ctggtcaaag gcttctatcc cagcgacatc gccgtggagt gggagagcaa tgggcagccg  1260
gagaacaact acaagaccac gcctcccgtg ctggactccg acggctcctt cttcctctac  1320
agcaagctca ccgtggacaa gagcaggtgg cagcagggga acgtcttctc atgctccgtg  1380
atgcatgagg ctctgcacaa ccactacacg cagaagagcc tctccctgtc tccgggtaaa  1440
ggcggcgggg ggagcggtgg tggcggtagc accggtcagg tgcaactggt gcagtccggc  1500
ggaggcgtgg tgcagcctgg ccggagcctg agactgagct gcaaggcctc cggctacacc  1560
tttacaagat acactatgca ctgggtcaga caggcccctg gcaagggcct ggaatggatt  1620
ggctacatca accctagccg gggatatacc aactacaacc agaaagtgaa ggacagattc  1680
accatcagca cagataagtc caagtccacc gctttcctgc agatggactc cctgcgtcca  1740
gaggacacag ctgtgtacta ctgcgcccgg tactacgacg accactactg tctggactac  1800
tggggacagg gaaccaccct gaccgtcagc tctggcggcg gaggctccgg cggaggtggc  1860
agcggcggcg gcggctctga tatccagatg acccagagcc cttcttcctt atctgccagc  1920
gtgggcgata gagtgaccat cacatgcagc gccagctctt ctgttagcta catgaactgg  1980
taccagcaaa cacctggaaa ggcccctaaa agatggatct acgacaccag caagctggcc  2040
tctggcgtgc cctctagatt cagcggctct ggctccggca ccgactacac ctttacaatt  2100
agctccctgc agcccgagga tatcgccacc tactactgcc agcagtggag cagcaacccc  2160
ttcacattcg gccagggcac aaagctgcaa atcaccagat gataa                  2205

SEQ ID NO: 66          moltype = AA  length = 733
FEATURE                Location/Qualifiers
source                 1..733
                       mol_type = protein
                       organism = synthetic construct
SEQUENCE: 66
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKREP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLTC LVKGFYPSDI AVEWESNGQP  420
ENNYKTTPPV LDSDGSFFLY SKLTVDKSRW QQGNVFSCSV MHEALHNHYT QKSLSLSPGK  480
GGGGSGGGGS TGQVQLVQSG GGVVQPGRSL RLSCKASGYT FTRYTMHWVR QAPGKGLEWI  540
GYINPSRGYT NYNQKVKDRF TISTDKSKST AFLQMDSLRP EDTAVYYCAR YYDDHYCLDY  600
WGQGTTLTVS SGGGGSGGGG SGGGGSDIQM TQSPSSLSAS VGDRVTITCS ASSSVSYMNW  660
YQQTPGKAPK RWIYDTSKLA SGVPSRFSGS GSGTDYTFTI SSLQPEDIAT YYCQQWSSNP  720
FTFGQGTKLQ ITR                                                    733

SEQ ID NO: 67          moltype = DNA  length = 2208
```

-continued

```
FEATURE               Location/Qualifiers
source                1..2208
                      mol_type = other DNA
                      organism = synthetic construct
SEQUENCE: 67
gaggtgcagc tggtggagtc tgggggaggc ctggtcaagc ctgggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg gcatccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgcctttcac attcggcgga  720
gggaccaagg tggagatcaa acgaactgag cccaaatctt gtgacaaaac tcacacatgc  780
ccaccgtgcc cagcacctga actcctgggg ggaccgtcag tcttcctctt ccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaaggcggcg gggggagcgg tggtggcggt agcaccggtc aggtgcaact ggtgcagtcc  1500
ggcggaggcg tggtgcagcc tggccggagc ctgagactga gctgcaaggc ctccggctac  1560
acctttacaa gatacactat gcactgggtc agacaggccc ctggcaaggg cctggaatgg  1620
attggctaca tcaaccctag ccggggatat accaactaca accagaaagt gaaggacaga  1680
ttcaccatca gcacagataa gtccaagtcc accgctttcc tgcagatgga ctccctgcgt  1740
ccagaggaca cagctgtgta ctactgcgcc cggtactacg acgaccacta ctgtctggac  1800
tactggggac agggaaccac cctgaccgtc agctctggcg gcggaggctc cggcggaggt  1860
ggcagcggcg gcggcggctc tgatatccag atgacccaga gcccttcttc cttatctgcc  1920
agcgtgggcg atagagtgac catcacatgc agcgccagct cttctgttag ctacatgaac  1980
tggtaccagc aaacacctgg aaaggcccct aaaagatgga tctacgacac cagcaagctg  2040
gcctctggcg tgccctctag attcagcggc tctggctccg gcaccgacta cacctttaca  2100
attagctccc tgcagcccga ggatatcgcc acctactact gccagcagtg gagcagcaac  2160
cccttcacat tcggccaggg cacaaagctg caaatcacca gatgataa              2208

SEQ ID NO: 68         moltype = AA  length = 734
FEATURE               Location/Qualifiers
source                1..734
                      mol_type = protein
                      organism = synthetic construct
SEQUENCE: 68
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
KGGGGSGGGG STGQVQLVQS GGGVVQPGRS LRLSCKASGY TFTRYTMHWV RQAPGKGLEW  540
IGYINPSRGY TNYNQKVKDR FTISTDKSKS TAFLQMDSLR PEDTAVYYCA RYYDDHYCLD  600
YWGQGTTLTV SSGGGGSGGG GSGGGGSDIQ MTQSPSSLSA SVGDRVTITC SASSSVSYMN  660
WYQQTPGKAP KRWIYDTSKL ASGVPSRFSG SGSGTDYTFT ISSLQPEDIA TYYCQQWSSN  720
PFTFGQGTKL QITR                                                   734

SEQ ID NO: 69         moltype = DNA  length = 2217
FEATURE               Location/Qualifiers
source                1..2217
                      mol_type = other DNA
                      organism = synthetic construct
SEQUENCE: 69
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
```

-continued gccagatttt ctggcagcgg ctctggcacc gatttcaccc tgaccataag cagcctggaa 660
cctgaggact tcgccgtgta ttactgccac cagtacctga gcagcctgac ctttggcgga 720
ggcaccaagg tggaaatcaa gcgggagccc aaatcttgtg acaaaactca cacatgccca 780
ccgtgcccag cacctgaact cctgggggga ccgtcagtct tcctcttccc cccaaaaccc 840
aaggacaccc tcatgatctc ccggacccct gaggtcacat gcgtggtggt ggacgtgagc 900
cacgaagacc ctgaggtcaa gttcaactgg tacgtggacg gcgtggaggt gcataatgcc 960
aagacaaagc cgcgggagga gcagtacaac agcacgtacc gtgtggtcag cgtcctcacc 1020
gtcctgcacc aggactggct gaatggcaag gagtacaagt gcaaggtctc caacaaagcc 1080
ctcccagccc ccatcgagaa aaccatctcc aaagccaaag ggcagccccg agaaccacag 1140
gtgtacaccc tgcccccatc ccgggaggag atgaccaaga accaggtcag cctgacctgc 1200
ctggtcaaag gcttctatcc cagcgacatc gccgtggagt gggagagcaa tgggcagccg 1260
gagaacaact acaagaccac gcctcccgtg ctggactccg acggctcctt cttcctctac 1320
agcaagctca ccgtggacaa gagcaggtgg cagcagggga acgtcttctc atgctccgtg 1380
atgcatgagg ctctgcacaa ccactacacg cagaagagcc tctccctgtc tccgggtaaa 1440
ggcgggggtg gcggttctgg tggtggtggc tctggaggag gaaccggtca agtgcagctg 1500
gtgcagtccg gaggaggcgt cgtgcagcct ggaagaagcc tccggctgag ctgcaaggcc 1560
agcggctata cattcaccag ctacaccatg cactgggtgc ggcaggcccc tggcaaaggc 1620
ctggaatgga tcggctacat caacccttcc agcggctaca ccaagtacaa ccagaaattc 1680
aaggaccggt ttaccattag cgccgataag agcaagagca cagcctttct gcagatggac 1740
agcctgagac cagaggacac cggcgtgtac ttctgcgccc gctggcagga ctacgacgtt 1800
tatttcgact actggggcca gggcacccct gtgacagtga gcagcggcgg cggaggctcc 1860
ggcggaggtg gcagcggcgg cggcggctct gatatccaga tgacacagag ccccagctct 1920
ctgtctgctt ctgtgggcga cagagtgacc atgacctgta gagcctcctc aagcgtgtcc 1980
tacatgcact ggtaccagca aacacctggc aaggccccaa agccttggat ctacgccacc 2040
tctaatctgg ccagcggcgt gccttctaga ttcagcggca gcggatctgg caccgattac 2100
accctgacca tcagcagcct gcagcccgag gatatcgcca catactactg ccagcagtgg 2160
agctccaatc ctcctacctt cggccagggc accaagctgc agatcacaag atgataa 2217

SEQ ID NO: 70 moltype = AA length = 737
FEATURE Location/Qualifiers
source 1..737
mol_type = protein
organism = synthetic construct
SEQUENCE: 70
QVQLVESGGG LVKPGGSLRL SCAASGFTFS TYAMSWIRQA PGKGLEWVAS IGRAGSTYYS 60
DSVKGRFTIS RDNAKNSLYL QMNSLRAEDT AVYYCARGPI YNDYDEFAYW GQGTLVTVSS 120
GGGGSGGGGS GGGGSEIVLT QSPATLSLSP GERATLSCKS SQSVLYSSNQ KNYLAWYQQK 180
PGQAPRLLIY WASTRESGIP ARFSGSGSGT DFTLTISSLE PEDFAVYYCH QYLSSLTFGG 240
GTKVEIKREP KSCDKTHTCP PCPAPELLGG PSVFLFPPKP KDTLMISRTP EVTCVVVDVS 300
HEDPEVKFNW YVDGVEVHNA KTKPREEQYN STYRVVSVLT VLHQDWLNGK EYKCKVSNKA 360
LPAPIEKTIS KAKGQPREPQ VYTLPPSREE MTKNQVSLTC LVKGFYPSDI AVEWESNGQP 420
ENNYKTTPPV LDSDGSFFLY SKLTVDKSRW QQGNVFSCSV MHEALHNHYT QKSLSLSPGK 480
GGGGSGGGG SGGGTGQVQL VQSGGGVVQP GRSLRLSCKA SGYTFTSYTM HWVRQAPGKG 540
LEWIGYINPS SGYTKYNQKF KDRFTISADK SKSTAFLQMD SLRPEDTGVY FCARWQDYDV 600
YFDYWGQGTP VTVSSGGGGS GGGGSGGGGS DIQMTQSPSS LSASVGDRVT MTCRASSSVS 660
YMHWYQQTPG KAPKPWIYAT SNLASGVPSR FSGSGSGTDY TLTISSLQPE DIATYYCQQW 720
SSNPPTFGQG TKLQITR 737

SEQ ID NO: 71 moltype = DNA length = 2220
FEATURE Location/Qualifiers
source 1..2220
mol_type = other DNA
organism = synthetic construct
SEQUENCE: 71
gaggtgcagc tggtggagtc tggggagggc ctggtcaagc ctggggggtc cctgagactc 60
tcctgtgcag cctctggatt caccttcagt ggctatgcca tgagctgggt ccgccaggct 120
ccagggaagg ggctggagtg ggtctcaacc attagtagtg gcggaaccta catatactac 180
cccgactcag tgaagggccg attcaccatc tccagagaca acgccaagaa ctcactgtat 240
ctgcaaatga acagcctgag agccgaggac acggccgtgt attactgtgc gagacttggg 300
ggggataatt actacgaata cttcgatgtc tggggcaaag ggaccacggt caccgtctcc 360
tccggcggtg gcggatccgg cggtggcgga tccggcggtg gcggatccga cattgtgctg 420
acccagtctc cagcctcctt ggccgtgtct ccaggacaga gggccaccat cacctgcaga 480
gccagtaaga gtgtcagtac cagcggatac tcctacatgc actggtatca gcagaaacca 540
ggacaacctc ctaaactcct gatttacctg gcatccaatc tggagagcgg ggtcccagcc 600
aggttcagcg gcagtgggtc tgggaccgat ttcaccctca caattaatcc tgtggaagct 660
aatgatactg caaattatta ctgtcagcac agtagggagc tgcctttcac attcggcgga 720
gggaccaagg tggagatcaa acgaactgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggag gagatgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgatgcatg aggctctgca caaccactac acgcagaaga gcctctccct gtctccgggt 1440
aaaggcgggg gtggcggttc tggtggtggt ggctctggag gaggaaccgg tcaagtgcag 1500

-continued

```
ctggtgcagt ccggaggagg cgtcgtgcag cctggaagaa gcctccggct gagctgcaag  1560
gccagcggct atacattcac cagctacacc atgcactggg tgcggcaggc ccctggcaaa  1620
ggcctggaat ggatcggcta catcaaccct tccagcggct acaccaagta caaccagaaa  1680
ttcaaggacc ggtttaccat tagcgccgat aagagcaaga gcacagcctt tctgcagatg  1740
gacagcctga gaccagagga caccggcgtg tacttctgcg cccgctggca ggactacgac  1800
gtttatttcg actactgggg ccagggcacc cctgtgacag tgagcagcgg cggcggaggc  1860
tccggcggag gtggcagcgg cggcggcggc tctgatatcc agatgacaca gagccccagc  1920
tctctgtctg cttctgtggg cgacagagtg accatgacct gtagagcctc ctcaagcgtg  1980
tcctacatgc actggtacca gcaaacacct ggcaaggccc caaagccttg gatctacgcc  2040
acctctaatc tggccagcgg cgtgccttct agattcagcg gcagcggatc tggcaccgat  2100
tacaccctga ccatcagcag cctgcagccc gaggatatcg ccacatacta ctgccagcag  2160
tggagctcca atcctcctac cttcggccag ggcaccaagc tgcagatcac aagatgataa  2220

SEQ ID NO: 72          moltype = AA  length = 738
FEATURE                Location/Qualifiers
source                 1..738
                       mol_type = protein
                       organism = synthetic construct
SEQUENCE: 72
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
KGGGGGSGGG GSGGGTGQVQ LVQSGGGVVQ PGRSLRLSCK ASGYTFTSYT MHWVRQAPGK  540
GLEWIGYINP SSGYTKYNQK FKDRFTISAD KSKSTAFLQM DSLRPEDTGV YFCARWQDYD  600
VYFDYWGQGT PVTVSSGGGG SGGGGSGGGG SDIQMTQSPS SLSASVGDRV TMTCRASSSV  660
SYMHWYQQTP GKAPKPWIYA TSNLASGVPS RFSGSGSGTD YTLTISSLQP EDIATYYCQQ  720
WSSNPPTFGQ GTKLQITR                                                738

SEQ ID NO: 73          moltype = DNA  length = 2205
FEATURE                Location/Qualifiers
source                 1..2205
                       mol_type = other DNA
                       organism = synthetic construct
SEQUENCE: 73
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
gccagatttt ctggcagcgg ctctggcacc gatttcaccc tgaccataag cagcctggaa  660
cctgaggact tcgccgtgta ttactgccac cagtacctga gcagcctgac ctttggcgga  720
ggcaccaagg tggaaatcaa gcgggagccc aaatcttgtg acaaaactca cacatgccca  780
ccgtgcccag cacctgaact cctgggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc  1020
gtcctgcacc aggactggct gaatggcaag gagtacaagt gcaaggtctc caacaaagcc  1080
ctcccagccc ccatcgagaa aaccatctcc aaagccaaag ggcagccccg agaaccacag  1140
gtgtacaccc tgcccccatc ccgggaggag atgaccaaga accaggtcag cctgacctgc  1200
ctggtcaaag gcttctatcc cagcgacatc gccgtggagt gggagagcaa tgggcagccg  1260
gagaacaact acaagaccac gcctcccgtg ctggactccg acggctcctt cttcctctac  1320
agcaagctca ccgtggacaa gagcaggtgg cagcagggga acgtcttctc atgctccgtg  1380
atgcatgagg ctctgcacaa ccactacacg cagaagagcc tctccctgtc tccgggtaaa  1440
ggcggcgggg ggagcggtgg tggcggtagc accggtcaag tgcagctggt gcagtccgga  1500
ggaggcgtcg tgcagcctgg aagaagcctc cggctgagct gcaaggccag cggctataca  1560
ttcaccagct acaccatgca ctgggtgcgg caggcccctg gcaaaggcct ggaatggatc  1620
ggctacatca acccttccag cggctacacc aagtacaacc agaaattcaa ggaccggttt  1680
accattagcg ccgataagag caagagcaca gcctttctgc agatggacag cctgagacca  1740
gaggacaccg gcgtgtactt ctgcgcccgc tggcaggact acgacgttta tttcgactac  1800
tggggccagg gcacccctgt gacagtgagc agcggcggcg gaggctccgg cggaggtggc  1860
agcggcggcg gcggctctga tatccagatg acacagagcc ccagctctct gtctgcttct  1920
gtgggcgaca gagtgaccat gacctgtaga gcctcctcaa gcgtgtccta catgcactgg  1980
taccagcaaa cacctggcaa ggccccaaag ccttggatct acgccacctc taatctggcc  2040
agcggcgtgc cttctagatt cagcggcagc ggatctggca ccgattacac cctgaccatc  2100
agcagcctgc agcccgagga tatcgccaca tactactgcc agcagtggag ctccaatcct  2160
cctaccttcg gccagggcac caagctgcag atcacaagat gataa                  2205

SEQ ID NO: 74          moltype = AA  length = 733
FEATURE                Location/Qualifiers
```

```
source                  1..733
                        mol_type = protein
                        organism = synthetic construct
SEQUENCE: 74
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKREP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLTC LVKGFYPSDI AVEWESNGQP  420
ENNYKTTPPV LDSDGSFFLY SKLTVDKSRW QQGNVFSCSV MHEALHNHYT QKSLSLSPGK  480
GGGGSGGGGS TGQVQLVQSG GGVVQPGRSL RLSCKASGYT FTSYTMHWVR QAPGKGLEWI  540
GYINPSSGYT KYNQKFKDRF TISADKSKST AFLQMDSLRP EDTGVYFCAR WQDYDVYFDY  600
WGQGTPVTVS SGGGGSGGGG SGGGGSDIQM TQSPSSLSAS VGDRVTMTCR ASSSVSYMHW  660
YQQTPGKAPK PWIYATSNLA SGVPSRFSGS GSGTDYTLTI SSLQPEDIAT YYCQQWSSNP  720
PTFGQGTKLQ ITR                                                     733

SEQ ID NO: 75           moltype = DNA  length = 2208
FEATURE                 Location/Qualifiers
source                  1..2208
                        mol_type = other DNA
                        organism = synthetic construct
SEQUENCE: 75
gaggtgcagc tggtggagtc tgggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg gcatccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgcctttcac attcggcgga  720
gggaccaagg tggagatcaa acgaactgag cccaaatctt gtgacaaaac tcacacatgc  780
ccaccgtgcc cagcacctga actcctgggg ggaccgtcag tcttcctctt ccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaaggcggcg gggggagcgg tggtggcggt agcaccggtc aagtgcagct ggtgcagtcc  1500
ggaggaggcg tcgtgcagcc tggaagaagc ctccggctga gctgcaaggc cagcggctat  1560
acattcacca gctacaccat gcactgggtg cggcaggccc ctggcaaagg cctggaatgg  1620
atcggctaca tcaacccttc cagcggctac accaagtaca accagaaatt caaggaccgg  1680
tttaccatta gcgccgataa gagcaagagc acagcctttc tgcagatgga cagcctgaga  1740
ccagaggaca ccggcgtgta cttctgcgcc cgctggcagg actacgacgt ttatttcgac  1800
tactggggcc agggcacccc tgtgacagtg agcagcggcg gcggaggctc cggcggaggt  1860
ggcagcggcg gcggcggctc tgatatccag atgacacaga gccccagctc tctgtctgct  1920
tctgtgggcg acagagtgac catgacctgt agagcctcct caagcgtgtc ctacatgcac  1980
tggtaccagc aaacacctgg caaggcccca aagccttgga tctacgccac ctctaatctg  2040
gccagcggcg tgccttctag attcagcggc agcggatctg gcaccgatta caccctgacc  2100
atcagcagcc tgcagcccga ggatatcgcc acatactact gccagcagtg gagctccaat  2160
cctcctacct tcggccaggg caccaagctg cagatcacaa gatgataa               2208

SEQ ID NO: 76           moltype = AA  length = 734
FEATURE                 Location/Qualifiers
source                  1..734
                        mol_type = protein
                        organism = synthetic construct
SEQUENCE: 76
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
KGGGGSGGGG STGQVQLVQS GGGVVQPGRS LRLSCKASGY TFTSYTMHWV RQAPGKGLEW  540
IGYINPSSGY TKYNQKFKDR FTISADKSKS TAFLQMDSLR PEDTGVYFCA RWQDYDVYFD  600
YWGQGTPVTV SSGGGGSGGG GSGGGGSDIQ MTQSPSSLSA SVGDRVTMTC RASSSVSYMH  660
```

-continued

```
WYQQTPGKAP KPWIYATSNL ASGVPSRFSG SGSGTDYTLT ISSLQPEDIA TYYCQQWSSN  720
PPTFGQGTKL QITR                                                    734

SEQ ID NO: 77          moltype = DNA  length = 2217
FEATURE                Location/Qualifiers
source                 1..2217
                       mol_type = other DNA
                       organism = synthetic construct
SEQUENCE: 77
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcggc  360
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcgggggtgg cggttctggt  1440
ggtggtggct ctggaggagg aaccggtcag gtgcagctgg ttgaatctgg cggcggactt  1500
gtgaagcctg gcggatctct gagactgagc tgtgccgcca gcggcttcac ctttagcaca  1560
tacgccatga gctggatcag acaggcccct ggcaaaggcc tggaatgggt ggcgtctatt  1620
ggcagagccg gcagcaccta ctacagcgac tctgtgaagg gcagattcac catcagccgg  1680
gacaacgcca agaacagcct gtacctgcag atgaactccc tgagagccga ggacaccgcc  1740
gtgtactatt gtgccagagg acccatctac aacgactacg acgagttcgc ctattggggc  1800
cagggcacac tggtcacagt ttctagcggc ggtggcggaa gcggaggcgg tggctccggt  1860
ggcggaggca gcgaaattgt gctgacacag agccccgcca cactgtcact ttctccaggc  1920
gaaagagcca cactgagctg caagagcagc cagagcgtgc tgtactccag caaccagaag  1980
aactacctgg cctggtatca gcagaagccc ggccaagctc ctcggctgct gatctattgg  2040
gccagcacaa gagagagcgg catccctgcc agattttctg gcagcggctc tggcaccgat  2100
ttcaccctga ccataagcag cctggaacct gaggacttcg ccgtgtatta ctgccaccag  2160
tacctgagca gcctgacctt tggcggaggc accaaggtgg aaatcaagcg gtgataa     2217

SEQ ID NO: 78          moltype = AA  length = 737
FEATURE                Location/Qualifiers
source                 1..737
                       mol_type = protein
                       organism = synthetic construct
SEQUENCE: 78
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGGSG  480
GGGSGGGTGQ VQLVESGGGL VKPGGSLRLS CAASGFTFST YAMSWIRQAP GKGLEWVASI  540
GRAGSTYYSD SVKGRFTISR DNAKNSLYLQ MNSLRAEDTA VYYCARGPIY NDYDEFAYWG  600
QGTLVTVSSG GGGSGGGGSG GGGSEIVLTQ SPATLSLSPG ERATLSCKSS QSVLYSSNQK  660
NYLAWYQQKP GQAPRLLIYW ASTRESGIPA RFSGSGSGTD FTLTISSLEP EDFAVYYCHQ  720
YLSSLTFGGG TKVEIKR                                                 737

SEQ ID NO: 79          moltype = DNA  length = 2220
FEATURE                Location/Qualifiers
source                 1..2220
                       mol_type = other DNA
                       organism = synthetic construct
SEQUENCE: 79
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcggc  360
```

-continued

```
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcgggggtgg cggttctggt  1440
ggtggtggct ctggaggagg aaccggtgag gtgcagctgg tggagtctgg gggaggcctg  1500
gtcaagcctg gggggtccct gagactctcc tgtgcagcct ctggattcac cttcagtggc  1560
tatgccatga gctgggtccg ccaggctcca gggaaggggc tggagtgggt ctcaaccatt  1620
agtagtggcg gaacctacat atactacccc gactcagtga agggccgatt caccatctcc  1680
agagacaacg ccaagaactc actgtatctg caaatgaaca gcctgagagc cgaggacacg  1740
gccgtgtatt actgtgcgag acttgggggg gataattact acgaatactt cgatgtctgg  1800
ggcaaaggga ccacggtcac cgtctcctcc ggcggtggcg gatccggcgg tggcggatcc  1860
ggcggtggcg gatccgacat tgtgctgacc cagtctccag cctccttggc cgtgtctcca  1920
ggacagaggg ccaccatcac ctgcagagcc agtaagagtg tcagtaccag cggatactcc  1980
tacatgcact ggtatcagca gaaaccagga caacctccta aactcctgat ttacctggca  2040
tccaatctgg agagcggggt cccagccagg ttcagcggca gtgggtctgg gaccgatttc  2100
accctcacaa ttaatcctgt ggaagctaat gatactgcaa attattactg tcagcacagt  2160
agggagctgc ctttcacatt cggcggaggg accaaggtgg agatcaaacg aacttgataa  2220

SEQ ID NO: 80          moltype = AA  length = 738
FEATURE                Location/Qualifiers
source                 1..738
                       mol_type = protein
                       organism = synthetic construct
SEQUENCE: 80
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGGSG  480
GGGSGGGTGE VQLVESGGGL VKPGGSLRLS CAASGFTFSG YAMSWVRQAP GKGLEWVSTI  540
SSGGTYIYYP DSVKGRFTIS RDNAKNSLYL QMNSLRAEDT AVYYCARLGG DNYYEYFDVW  600
GKGTTVTVSS GGGGSGGGGS GGGGSDIVLT QSPASLAVSP GQRATITCRA SKSVSTSGYS  660
YMHWYQQKPG QPPKLLIYLA SNLESGVPAR FSGSGSGTDF TLTINPVEAN DTANYYCQHS  720
RELPFTFGGG TKVEIKRT                                                738

SEQ ID NO: 81          moltype = DNA  length = 2205
FEATURE                Location/Qualifiers
source                 1..2205
                       mol_type = other DNA
                       organism = synthetic construct
SEQUENCE: 81
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcggc  360
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
```

-continued

```
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcggcggggg gagcggtggt  1440
ggcggtagca ccggtcaggt gcagctggtt gaatctggcg gcggacttgt gaagcctggc  1500
ggatctctga gactgagctg tgccgccagc ggcttcacct ttagcacata cgccatgagc  1560
tggatcagac aggcccctgg caaaggcctg gaatgggtgg cgtctattgg cagagccggc  1620
agcacctact acagcgactc tgtgaagggc agattcacca tcagccggga caacgccaag  1680
aacagcctgt acctgcagat gaactccctg agagccgagg acaccgccgt gtactattgt  1740
gccagaggac ccatctacaa cgactacgac gagttcgcct attggggcca gggcacactg  1800
gtcacagttt ctagcggcgg tggcggaagc ggaggcggtg gctccggtgg cggaggcagc  1860
gaaattgtgc tgacacagag ccccgccaca ctgtcacttt ctccaggcga aagagccaca  1920
ctgagctgca agagcagcca gagcgtgctg tactccagca accagaagaa ctacctggcc  1980
tggtatcagc agaagcccgg ccaagctcct cggctgctga tctattgggc cagcacaaga  2040
gagagcggca tccctgccag atttctggc agcggctctg gcaccgattt caccctgacc  2100
ataagcagcc tggaacctga ggacttcgcc gtgtattact gccaccagta cctgagcagc  2160
ctgacctttg gcggaggcac caaggtggaa atcaagcggt gataa                2205

SEQ ID NO: 82           moltype = AA  length = 733
FEATURE                 Location/Qualifiers
source                  1..733
                        mol_type = protein
                        organism = synthetic construct
SEQUENCE: 82
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGSGG  480
GGSTGQVQLV ESGGGLVKPG GSLRLSCAAS GFTFSTYAMS WIRQAPGKGL EWVASIGRAG  540
STYYSDSVKG RFTISRDNAK NSLYLQMNSL RAEDTAVYYC ARGPIYNDYD EFAYWGQGTL  600
VTVSSGGGGS GGGGSGGGGS EIVLTQSPAT LSLSPGERAT LSCKSSQSVL YSSNQKNYLA  660
WYQQKPGQAP RLLIYWASTR ESGIPARFSG SGSGTDFTLT ISSLEPEDFA VYYCHQYLSS  720
LTFGGGTKVE IKR                                                     733

SEQ ID NO: 83           moltype = DNA  length = 2208
FEATURE                 Location/Qualifiers
source                  1..2208
                        mol_type = other DNA
                        organism = synthetic construct
SEQUENCE: 83
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcggc  360
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaag gcggcggggg gagcggtggt  1440
ggcggtagca ccggtgaggt gcagctggtg gagtctgggg gaggcctggt caagcctggg  1500
gggtccctga gactctcctg tgcagcctct ggattcacct tcagtggcta tgccatgagc  1560
tgggtccgcc aggctccagg gaaggggctg gagtgggtct caaccattag tagtggcgga  1620
acctacatat actaccccga ctcagtgaag ggccgattca ccatctccag agacaacgcc  1680
aagaactcac tgtatctgca aatgaacagc ctgagagccg aggacacggc cgtgtattac  1740
tgtgcgagac ttgggggga taattactac gaatacttcg atgtctgggg caaagggacc  1800
acggtcaccg tctcctccgg cggtggcgga tccggcggtg gcggatccgg cggtggcgga  1860
tccgacattg tgctgaccca gtctccagcc tccttggccg tgtctccagg acagagggcc  1920
accatcacct gcagagccag taagagtgtc agtaccagcg gatactccta catgcactgg  1980
tatcagcaga aaccaggaca acctcctaaa ctcctgattt acctggcatc caatctggag  2040
agcggggtcc cagccaggtt cagcggcagt gggtctggga ccgatttcac cctcacaatt  2100
aatcctgtgg aagctaatga tactgcaaat tattactgtc agcacagtag ggagctgcct  2160
```

-continued

```
ttcacattcg gcggagggac caaggtggag atcaaacgaa cttgataa              2208

SEQ ID NO: 84          moltype = AA  length = 734
FEATURE                Location/Qualifiers
source                 1..734
                       mol_type = protein
                       organism = synthetic construct
SEQUENCE: 84
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGKGGGGSGG  480
GGSTGEVQLV ESGGGLVKPG GSLRLSCAAS GFTFSGYAMS WVRQAPGKGL EWVSTISSGG  540
TYIYYPDSVK GRFTISRDNA KNSLYLQMNS LRAEDTAVYY CARLGGDNYY EYFDVWGKGT  600
TVTVSSGGGG SGGGGSGGGG SDIVLTQSPA SLAVSPGQRA TITCRASKSV STSGYSYMHW  660
YQQKPGQPPK LLIYLASNLE SGVPARFSGS GSGTDFTLTI NPVEANDTAN YYCQHSRELP  720
FTFGGGTKVE IKRT                                                   734

SEQ ID NO: 85          moltype = DNA  length = 2145
FEATURE                Location/Qualifiers
source                 1..2145
                       mol_type = other DNA
                       organism = synthetic construct
SEQUENCE: 85
caggttcaac tggttcagag cggtggaggt gtggttcagc ctggtcgtag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccatt actgtctgga ttactggggt cagggaacca ccctgaccgt tagcagtgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc gggggtggcg gttctggtgg tggtggctct  1380
ggaggaggaa ccggtcaggt gcagctggtt gaatctggcg gcggacttgt gaagcctggc  1440
ggatctctga gactgagctg tgccgccagc ggcttcacct ttagcacata cgccatgagc  1500
tggatcagac aggcccctgg caaaggcctg gaatgggtgg cgtctattgg cagagccggc  1560
agcacctact acagcgactc tgtgaagggc agattcacca tcagccggga caacgccaag  1620
aacagcctgt acctgcagat gaactccctg agagccgagg acaccgccgt gtactattgt  1680
gccagaggac ccatctacaa cgactacgac gagttcgcct attggggcca gggcacactg  1740
gtcacagttt ctagcggcgg tggcggaagc ggaggcggtg gctccggtgg cggaggcagc  1800
gaaattgtgc tgacacagag ccccgccaca ctgtcacttt ctccaggcga aagagccaca  1860
ctgagctgca agagcagcca gagcgtgctg tactccagca accagaagaa ctacctggcc  1920
tggtatcagc agaagcccgg ccaagctcct cggctgctga tctattgggc cagcacaaga  1980
gagagcggca tccctgccag atttctggc agcggctctg gcaccgattt caccctgacc  2040
ataagcagcc tggaacctga ggacttcgcc gtgtattact gccaccagta cctgagcagc  2100
ctgacctttg gcggaggcac caaggtggaa atcaagcggt gataa                 2145

SEQ ID NO: 86          moltype = AA  length = 713
FEATURE                Location/Qualifiers
source                 1..713
                       mol_type = protein
                       organism = synthetic construct
SEQUENCE: 86
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGS GGGTGQVQLV ESGGGLVKPG  480
```

```
GSLRLSCAAS GFTFSTYAMS WIRQAPGKGL EWVASIGRAG STYYSDSVKG RFTISRDNAK  540
NSLYLQMNSL RAEDTAVYYC ARGPIYNDYD EFAYWGQGTL VTVSSGGGGS GGGGSGGGGS  600
EIVLTQSPAT LSLSPGERAT LSCKSSQSVL YSSNQKNYLA WYQQKPGQAP RLLIYWASTR  660
ESGIPARFSG SGSGTDFTLT ISSLEPEDFA VYYCHQYLSS LTFGGGTKVE IKR         713

SEQ ID NO: 87           moltype = DNA  length = 2148
FEATURE                 Location/Qualifiers
source                  1..2148
                        mol_type = other DNA
                        organism = synthetic construct
SEQUENCE: 87
caggttcaac tggttcagag cggtggaggt gtggttcagc ctggtcgtag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccatt actgtctgga ttactggggt cagggaacca ccctgaccgt tagcagtgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc gggggtggcg gttctggtgg tggtggctct  1380
ggaggaggaa ccggtgaggt gcagctggtg gagtctgggg gaggcctggt caagcctggg  1440
gggtccctga gactctcctg tgcagcctct ggattcacct tcagtggcta tgccatgagc  1500
tgggtccgcc aggctccagg gaaggggctg gagtgggtct caaccattag tagtggcgga  1560
acctacatat actaccccga ctcagtgaag ggccgattca ccatctccag agacaacgcc  1620
aagaactcac tgtatctgca aatgaacagc ctgagagccg aggacacggc cgtgtattac  1680
tgtgcgagac ttggggggga taattactac gaatacttcg atgtctgggg caaagggacc  1740
acggtcaccg tctcctccgg cggtggcgga tccggcggtg gcggatccgg cggtggcgga  1800
tccgacattg tgctgaccca gtctccagcc tccttggccg tgtctccagg acagagggcc  1860
accatcacct gcagagccag taagagtgtc agtaccagcg gatactccta catgcactgg  1920
tatcagcaga aaccaggaca acctcctaaa ctcctgattt acctggcatc caatctggag  1980
agcggggtcc cagccaggtt cagcggcagt gggtctggga ccgatttcac cctcacaatt  2040
aatcctgtgg aagctaatga tactgcaaat tattactgtc agcacagtag ggagctgcct  2100
ttcacattcg gcggagggac caaggtggag atcaaacgaa cttgataa              2148

SEQ ID NO: 88           moltype = AA  length = 714
FEATURE                 Location/Qualifiers
source                  1..714
                        mol_type = protein
                        organism = synthetic construct
SEQUENCE: 88
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGGSGGGGS GGGTGEVQLV ESGGGLVKPG  480
GSLRLSCAAS GFTFSGYAMS WVRQAPGKGL EWVSTISSGG TYIYYPDSVK GRFTISRDNA  540
KNSLYLQMNS LRAEDTAVYY CARLGGDNYY EYFDVWGKGT TVTVSSGGGG SGGGGSGGGG  600
SDIVLTQSPA SLAVSPGQRA TITCRASKSV STSGYSYMHW YQQKPGQPPK LLIYLASNLE  660
SGVPARFSGS GSGTDFTLTI NPVEANDTAN YYCQHSRELP FTFGGGTKVE IKRT        714

SEQ ID NO: 89           moltype = DNA  length = 2133
FEATURE                 Location/Qualifiers
source                  1..2133
                        mol_type = other DNA
                        organism = synthetic construct
SEQUENCE: 89
caggttcaac tggttcagag cggtggaggt gtggttcagc ctggtcgtag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccatt actgtctgga ttactggggt cagggaacca ccctgaccgt tagcagtgct  360
```

```
agcaccaagg gcccatcggt cttcccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc ggcgggggga gcggtggtgg cggtagcacc  1380
ggtcaggtgc agctggttga atctggcggc ggacttgtga agcctggcgg atctctgaga  1440
ctgagctgtg ccgccagcgg cttcaccttt agcacatacg ccatgagctg gatcagacag  1500
gcccctggca aaggcctgga atgggtggcg tctattggca gagccggcag cacctactac  1560
agcgactctg tgaagggcag attcaccatc agccgggaca acgccaagaa cagcctgtac  1620
ctgcagatga actccctgag agccgaggac accgccgtgt actattgtgc cagaggaccc  1680
atctacaacg actacgacga gttcgcctat tggggccagg gcacactggt cacagtttct  1740
agcggcggtg gcggaagcgg aggcggtggc tccggtggcg gaggcagcga aattgtgctg  1800
acacagagcc ccgccacact gtcactttct ccaggcgaaa gagccacact gagctgcaag  1860
agcagccaga gcgtgctgta ctccagcaac cagaagaact acctggcctg gtatcagcag  1920
aagcccggcc aagctcctcg gctgctgatc tattgggcca gcacaagaga gagcggcatc  1980
cctgccagat tttctggcag cggctctggc accgatttca ccctgaccat aagcagcctg  2040
gaacctgagg acttcgccgt gtattactgc caccagtacc tgagcagcct gacctttggc  2100
ggaggcacca aggtggaaat caagcggtga taa                              2133

SEQ ID NO: 90           moltype = AA  length = 709
FEATURE                 Location/Qualifiers
source                  1..709
                        mol_type = protein
                        organism = synthetic construct
SEQUENCE: 90
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGST GQVQLVESGG GLVKPGGSLR  480
LSCAASGFTF STYAMSWIRQ APGKGLEWVA SIGRAGSTYY SDSVKGRFTI SRDNAKNSLY  540
LQMNSLRAED TAVYYCARGP IYNDYDEFAY WGQGTLVTVS SGGGGSGGGG SGGGGSEIVL  600
TQSPATLSLS PGERATLSCK SSQSVLYSSN QKNYLAWYQQ KPGQAPRLLI YWASTRESGI  660
PARFSGSGSG TDFTLTISSL EPEDFAVYYC HQYLSSLTFG GGTKVEIKR             709

SEQ ID NO: 91           moltype = DNA  length = 2136
FEATURE                 Location/Qualifiers
source                  1..2136
                        mol_type = other DNA
                        organism = synthetic construct
SEQUENCE: 91
caggttcaac tggttcagag cggtggaggt gtggttcagc ctggtcgtag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccatt actgtctgga ttactggggt cagggaacca ccctgaccgt tagcagtgct  360
agcaccaagg gcccatcggt cttcccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc ggcgggggga gcggtggtgg cggtagcacc  1380
```

-continued

```
ggtgaggtgc agctggtgga gtctgggggga ggcctggtca agcctggggg gtccctgaga  1440
ctctcctgtg cagcctctgg attcaccttc agtggctatg ccatgagctg ggtccgccag  1500
gctccaggga aggggctgga gtgggtctca accattagta gtggcggaac ctacatatac  1560
taccccgact cagtgaaggg ccgattcacc atctccagag acaacgccaa gaactcactg  1620
tatctgcaaa tgaacagcct gagagccgag gacacggccg tgtattactg tgcgagactt  1680
gggggggata attactacga atacttcgat gtctggggca aagggaccac ggtcaccgtc  1740
tcctccggcg gtggcggatc cggcggtggc ggatccggcg gtggcggatc cgacattgtg  1800
ctgacccagt ctccagcctc cttggccgtg tctccaggac agagggccac catcacctgc  1860
agagccagta agagtgtcag taccagcgga tactcctaca tgcactggta tcagcagaaa  1920
ccaggacaac ctcctaaact cctgatttac ctggcatcca atctggagag cggggtccca  1980
gccaggttca gcggcagtgg gtctgggacc gatttcaccc tcacaattaa tcctgtggaa  2040
gctaatgata ctgcaaatta ttactgtcag cacagtaggg agctgccttt cacattcggc  2100
ggagggacca aggtggagat caaacgaact tgataa                          2136

SEQ ID NO: 92          moltype = AA  length = 710
FEATURE                Location/Qualifiers
source                 1..710
                       mol_type = protein
                       organism = synthetic construct
SEQUENCE: 92
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGST GEVQLVESGG GLVKPGGSLR  480
LSCAASGFTF SGYAMSWVRQ APGKGLEWVS TISSGGTYIY YPDSVKGRFT ISRDNAKNSL  540
YLQMNSLRAE DTAVYYCARL GGDNYYEYFD VWGKGTTVTV SSGGGGSGGG GSGGGGSDIV  600
LTQSPASLAV SPGQRATITC RASKSVSTSG YSYMHWYQQK PGQPPKLLIY LASNLESGVP  660
ARFSGSGSGT DFTLTINPVE ANDTANYYCQ HSRELPFTFG GGTKVEIKRT             710

SEQ ID NO: 93          moltype = DNA  length = 2145
FEATURE                Location/Qualifiers
source                 1..2145
                       mol_type = other DNA
                       organism = synthetic construct
SEQUENCE: 93
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc gggggtggcg gttctggtgg tggtggctct  1380
ggaggaggaa ccggtcaggt gcagctggtt gaatctggcg gcggacttgt gaagcctggc  1440
ggatctctga gactgagctg tgccgccagc ggcttcacct ttagcacata cgccatgagc  1500
tggatcagac aggcccctgg caaaggcctg gaatgggtgg cgtctattgg cagagccggc  1560
agcacctact acagcgactc tgtgaagggc agattcacca tcagccggga caacgccaag  1620
aacagcctgt acctgcagat gaactccctg agagccgagg acaccgccgt gtactattgt  1680
gccagaggac ccatctacaa cgactacgac gagttcgcct attggggcca gggcacactg  1740
gtcacagttt ctagcggcgg tggcggaagc ggaggcggtg gctccggtgg cggaggcagc  1800
gaaattgtgc tgacacagag ccccgccaca ctgtcacttt ctccaggcga aagagccaca  1860
ctgagctgca agagcagcca gagcgtgctg tactccagca accagaagaa ctacctggcc  1920
tggtatcagc agaagcccgg ccaagctcct cggctgctga tctattgggc cagcacaaga  1980
gagagcggca tccctgccag atttctggc agcggctctg gcaccgattt caccctgacc  2040
ataagcagcc tggaacctga ggacttcgcc gtgtattact gccaccagta cctgagcagc  2100
ctgacctttg gcggaggcac caaggtggaa atcaagcggt gataa                 2145

SEQ ID NO: 94          moltype = AA  length = 713
FEATURE                Location/Qualifiers
source                 1..713
```

```
                        mol_type = protein
                        organism = synthetic construct
SEQUENCE: 94
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGGSGGGGS GGGTGQVQLV ESGGGLVKPG  480
GSLRLSCAAS GFTFSTYAMS WIRQAPGKGL EWVASIGRAG STYYSDSVKG RFTISRDNAK  540
NSLYLQMNSL RAEDTAVYYC ARGPIYNDYD EFAYWGQGTL VTVSSGGGGS GGGGSGGGGS  600
EIVLTQSPAT LSLSPGERAT LSCKSSQSVL YSSNQKNYLA WYQQKPGQAP RLLIYWASTR  660
ESGIPARFSG SGSGTDFTLT ISSLEPEDFA VYYCHQYLSS LTFGGGTKVE IKR         713

SEQ ID NO: 95           moltype = DNA  length = 2148
FEATURE                 Location/Qualifiers
source                  1..2148
                        mol_type = other DNA
                        organism = synthetic construct
SEQUENCE: 95
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc gggggtggcg gttctggtgg tggtggctct  1380
ggaggaggaa ccggtgaggt gcagctggtg gagtctgggg gaggcctggt caagcctggg  1440
gggtccctga gactctcctg tgcagcctct ggattcacct tcagtggcta tgccatgagc  1500
tgggtccgcc aggctccagg gaaggggctg gagtgggtct caaccattag tagtggcgga  1560
acctacatat actaccccga ctcagtgaag ggccgattca ccatctccag agacaacgcc  1620
aagaactcac tgtatctgca aatgaacagc ctgagagccg aggacacggc cgtgtattac  1680
tgtgcgagac ttggggggga taattactac gaatacttcg atgtctgggg caaagggacc  1740
acggtcaccg tctcctccgg cggtggagga tctggcggag gtggatccgg cggtggcgga  1800
tctgacattg tgctgaccca gtctccagcc tccttggccg tgtctccagg acagagggcc  1860
accatcacct gcagagccag taagagtgtc agtaccagcg gatactccta catgcactgg  1920
tatcagcaga aaccaggaca acctcctaaa ctcctgattt acctggcatc caatctggag  1980
agcggggtcc cagccaggtt cagcggcagt gggtctggga ccgatttcac cctcacaatt  2040
aatcctgtgg aagctaatga tactgcaaat tattactgtc agcacagtag ggagctgcct  2100
ttcacattcg gcggagggac caaggtggag atcaaacgaa cttgataa               2148

SEQ ID NO: 96           moltype = AA  length = 714
FEATURE                 Location/Qualifiers
source                  1..714
                        mol_type = protein
                        organism = synthetic construct
SEQUENCE: 96
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGGSGGGGS GGGTGEVQLV ESGGGLVKPG  480
GSLRLSCAAS GFTFSGYAMS WVRQAPGKGL EWVSTISSGG TYIYYPDSVK GRFTISRDNA  540
KNSLYLQMNS LRAEDTAVYY CARLGGDNYY EYFDVWGKGT TVTVSSGGGG SGGGGSGGGG  600
SDIVLTQSPA SLAVSPGQRA TITCRASKSV STSGYSYMHW YQQKPGQPPK LLIYLASNLE  660
SGVPARFSGS GSGTDFTLTI NPVEANDTAN YYCQHSRELP FTFGGGTKVE IKRT        714

SEQ ID NO: 97           moltype = DNA  length = 2133
```

```
FEATURE                Location/Qualifiers
source                 1..2133
                       mol_type = other DNA
                       organism = synthetic construct
SEQUENCE: 97
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc ggcgggggga gcggtggtgg cggtagcacc  1380
ggtcaggtgc agctggttga atctggcggc ggacttgtga agcctggcgg atctctgaga  1440
ctgagctgtg ccgccagcgg cttcaccttt agcacatacg ccatgagctg gatcagacag  1500
gcccctggca aaggcctgga atgggtggcg tctattggca gagccggcag cacctactac  1560
agcgactctg tgaagggcag attcaccatc agccgggaca acgccaagaa cagcctgtac  1620
ctgcagatga actccctgag agccgaggac accgccgtgt actattgtgc cagaggaccc  1680
atctacaacg actacgacga gttcgcctat tggggccagg gcacactggt cacagtttct  1740
agcggcggtg gcggaagcgg aggcggtggc tccggtggcg gaggcagcga aattgtgctg  1800
acacagagcc ccgccacact gtcactttct ccaggcgaaa gagccacact gagctgcaag  1860
agcagccaga gcgtgctgta ctccagcaac cagaagaact acctggcctg gtatcagcag  1920
aagcccggcc aagctcctcg gctgctgatc tattgggcca gcacaagaga gagcggcatc  1980
cctgccagat tttctggcag cggctctggc accgatttca ccctgaccat aagcagcctg  2040
gaacctgagg acttcgccgt gtattactgc caccagtacc tgagcagcct gacctttggc  2100
ggaggcacca aggtggaaat caagcggtga taa                               2133

SEQ ID NO: 98          moltype = AA  length = 709
FEATURE                Location/Qualifiers
source                 1..709
                       mol_type = protein
                       organism = synthetic construct
SEQUENCE: 98
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGST GQVQLVESGG GLVKPGGSLR  480
LSCAASGFTF STYAMSWIRQ APGKGLEWVA SIGRAGSTYY SDSVKGRFTI SRDNAKNSLY  540
LQMNSLRAED TAVYYCARGP IYNDYDEFAY WGQGTLVTVS SGGGGSGGGG SGGGGSEIVL  600
TQSPATLSLS PGERATLSCK SSQSVLYSSN QKNYLAWYQQ KPGQAPRLLI YWASTRESGI  660
PARFSGSGSG TDFTLTISSL EPEDFAVYYC HQYLSSLTFG GGTKVEIKR             709

SEQ ID NO: 99          moltype = DNA  length = 2136
FEATURE                Location/Qualifiers
source                 1..2136
                       mol_type = other DNA
                       organism = synthetic construct
SEQUENCE: 99
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
gactacgacg tttatttcga ctactggggc cagggcaccc ctgtgacagt gagcagcgct  360
agcaccaagg gcccatcggt cttccccctg gcaccctcct ccaagagcac ctctgggggc  420
acagcggccc tgggctgcct ggtcaaggac tacttccccg agccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
```

```
tcagtcttcc tcttccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaaggc ggcgggggga gcggtggtgg cggtagcacc  1380
ggtgaggtgc agctggtgga gtctggggga ggcctggtca agcctggggg gtccctgaga  1440
ctctcctgtg cagcctctgg attcaccttc agtggctatg ccatgagctg ggtccgccag  1500
gctccaggga aggggctgga gtgggtctca accattagta gtggcggaac ctacatatac  1560
taccccgact cagtgaaggg ccgattcacc atctccagag acaacgccaa gaactcactg  1620
tatctgcaaa tgaacagcct gagagccgag gacacggccg tgtattactg tgcgagactt  1680
ggggggggata attactacga atacttcgat gtctggggca aagggaccac ggtcaccgtc  1740
tcctccggcg gtggaggatc tggcggaggt ggatccggcg gtggcggatc tgacattgtg  1800
ctgacccagt ctccagcctc cttggccgtg tctccaggac agagggccac catcacctgc  1860
agagccagta agagtgtcag taccagcgga tactcctaca tgcactggta tcagcagaaa  1920
ccaggacaac ctcctaaact cctgatttac ctggcatcca atctggagag cggggtccca  1980
gccaggttca gcggcagtgg gtctgggacc gatttcaccc tcacaattaa tcctgtggaa  2040
gctaatgata ctgcaaatta ttactgtcag cacagtaggg agctgccttt cacattcggc  2100
ggagggacca aggtggagat caaacgaact tgataa                          2136
```

```
SEQ ID NO: 100         moltype = AA  length = 710
FEATURE                Location/Qualifiers
source                 1..710
                       mol_type = protein
                       organism = synthetic construct
SEQUENCE: 100
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGST GEVQLVESGG GLVKPGGSLR  480
LSCAASGFTF SGYAMSWVRQ APGKGLEWVS TISSGGTYIY YPDSVKGRFT ISRDNAKNSL  540
YLQMNSLRAE DTAVYYCARL GGDNYYEYFD VWGKGTTVTV SSGGGGSGGG GSGGGGSDIV  600
LTQSPASLAV SPGQRATITC RASKSVSTSG YSYMHWYQQK PGQPPKLLIY LASNLESGVP  660
ARFSGSGSGT DFTLTINPVE ANDTANYYCQ HSRELPFTFG GGTKVEIKRT            710
```

```
SEQ ID NO: 101         moltype = DNA  length = 2127
FEATURE                Location/Qualifiers
source                 1..2127
                       mol_type = other DNA
                       organism = synthetic construct
SEQUENCE: 101
caggtgcagc tggttgaatc tggcggcgga cttgtgaagc ctggcggatc tctgagactg  60
agctgtgccg ccagcggctt caccttttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
gctagcacca agggcccatc ggtcttcccc ctggcaccct cctccaagag cacctctggg  420
ggcacagcgg ccctgggctg cctggtcaag gactacttcc ccgagccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa ggcgggggtg gcggttctgg tggtggtggc  1380
tctggaggag gaaccggtca ggtgcaactg gtgcagtccg gcggaggcgt ggtgcagcct  1440
ggccggagcc tgagactgag ctgcaaggcc tccggctaca cctttacaag atacactatg  1500
cactgggtca gacaggcccc tggcaagggc ctggaatgga ttggctacat caaccctagc  1560
cggggatata ccaactacaa ccagaaagtg aaggacagat tcaccatcag cacagataag  1620
tccaagtcca ccgctttcct gcagatggac tccctgcgtc cagaggacac agctgtgtac  1680
tactgcgccc ggtactacga cgaccactac tgtctggact actggggaca gggaaccacc  1740
```

-continued

```
ctgaccgtca gctctggcgg cggaggctcc ggcggaggtg gcagcggcgg cggcggctct  1800
gatatccaga tgacccagag cccttcttcc ttatctgcca gcgtgggcga tagagtgacc  1860
atcacatgca gcgccagctc ttctgttagc tacatgaact ggtaccagca aacacctgga  1920
aaggccccta aaagatggat ctacgacacc agcaagctgg cctctggcgt gccctctaga  1980
ttcagcggct ctggctccgg caccgactac acctttacaa ttagctccct gcagcccgag  2040
gatatcgcca cctactactg ccagcagtgg agcagcaacc ccttcacatt cggccagggc  2100
acaaagctgc aaatcaccag atgataa                                       2127

SEQ ID NO: 102         moltype = AA  length = 707
FEATURE                Location/Qualifiers
source                 1..707
                       mol_type = protein
                       organism = synthetic construct
SEQUENCE: 102
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGGSGGGG SGGGTGQVQL VQSGGGVVQP  480
GRSLRLSCKA SGYTFTRYTM HWVRQAPGKG LEWIGYINPS RGYTNYNQKV KDRFTISTDK  540
SKSTAFLQMD SLRPEDTAVY YCARYYDDHY CLDYWGQGTT LTVSSGGGGS GGGGSGGGGS  600
DIQMTQSPSS LSASVGDRVT ITCSASSSVS YMNWYQQTPG KAPKRWIYDT SKLASGVPSR  660
FSGSGSGTDY TFTISSLQPE DIATYYCQQW SSNPFTFGQG TKLQITR                 707

SEQ ID NO: 103         moltype = DNA  length = 2130
FEATURE                Location/Qualifiers
source                 1..2130
                       mol_type = other DNA
                       organism = synthetic construct
SEQUENCE: 103
gaggtgcagc tggtggagtc tgggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgctagca ccaagggccc atcggtcttc cccctggcac cctcctccaa gagcacctct  420
gggggcacag cggccctggg ctgcctggtc aaggactact tccccgagcc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaaggcgggg gtggcggttc tggtggtggt  1380
ggctctggag gaggaaccgg tcaggtgcaa ctggtgcagt ccggcggagg cgtggtgcag  1440
cctggccgga gcctgagact gagctgcaag gcctccggct acacctttac aagatacact  1500
atgcactggg tcagacaggc ccctggcaag ggcctggaat ggattggcta catcaaccct  1560
agccggggat ataccaacta caaccagaaa gtgaaggaca gattcaccat cagcacagat  1620
aagtccaagt ccaccgcttt cctgcagatg gactccctgc gtccagagga cacagctgtg  1680
tactactgcg cccggtacta cgacgaccac tactgtctgg actactgggg acagggaacc  1740
accctgaccg tcagctctgg cggcggaggc tccggcggag gtggcagcgg cggcggcggc  1800
tctgatatcc agatgaccca gagcccttct tccttatctg ccagcgtggg cgatagagtg  1860
accatcacat gcagcgccag ctcttctgtt agctacatga actggtacca gcaaacacct  1920
ggaaaggccc ctaaaagatg gatctacgac accagcaagc tggcctctgg cgtgccctct  1980
agattcagcg gctctggctc cggcaccgac tacaccttta caattagctc cctgcagccc  2040
gaggatatcg ccacctacta ctgccagcag tggagcagca accccttcac attcggccag  2100
ggcacaaagc tgcaaatcac cagatgataa                                    2130

SEQ ID NO: 104         moltype = AA  length = 708
FEATURE                Location/Qualifiers
source                 1..708
                       mol_type = protein
                       organism = synthetic construct
SEQUENCE: 104
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
```

-continued

```
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGGSGGG GSGGGTGQVQ LVQSGGGVVQ  480
PGRSLRLSCK ASGYTFTRYT MHWVRQAPGK GLEWIGYINP SRGYTNYNQK VKDRFTISTD  540
KSKSTAFLQM DSLRPEDTAV YYCARYYDDH YCLDYWGQGT TLTVSSGGGG SGGGGSGGGG  600
SDIQMTQSPS SLSASVGDRV TITCSASSSV SYMNWYQQTP GKAPKRWIYD TSKLASGVPS  660
RFSGSGSGTD YTFTISSLQP EDIATYYCQQ WSSNPFTFGQ GTKLQITR              708

SEQ ID NO: 105         moltype = DNA  length = 2115
FEATURE                Location/Qualifiers
source                 1..2115
                       mol_type = other DNA
                       organism = synthetic construct
SEQUENCE: 105
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
gctagcacca agggcccatc ggtcttcccc ctggcaccct cctccaagag cacctctggg  420
ggcacagcgg ccctgggctg cctggtcaag gactacttcc ccgagccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa ggcggcgggg ggagcggtgg tggcggtagc  1380
accggtcagg tgcaactggt gcagtccggc ggaggcgtgg tgcagcctgg ccggagcctg  1440
agactgagct gcaaggcctc cggctacacc tttacaagat acactatgca ctgggtcaga  1500
caggccccctg gcaagggcct ggaatggatt ggctacatca accctagccg gggatatacc  1560
aactacaacc agaaagtgaa ggacagattc accatcagca cagataagtc caagtccacc  1620
gctttcctgc agatggactc cctgcgtcca gaggacacag ctgtgtacta ctgcgcccgg  1680
tactacgacg accactactg tctggactac tggggacagg gaaccaccct gaccgtcagc  1740
tctggcggcg gaggctccgg cggaggtggc agcggcggcg gcggctctga tatccagatg  1800
acccagagcc cttcttcctt atctgccagc gtgggcgata gagtgaccat cacatgcagc  1860
gccagctctt ctgttagcta catgaactgg taccagcaaa cacctggaaa ggcccctaaa  1920
agatggatct acgacaccag caagctggcc tctggcgtgc cctctagatt cagcggctct  1980
ggctccggca ccgactacac ctttacaatt agctccctgc agcccgagga tatcgccacc  2040
tactactgcc agcagtggag cagcaacccc ttcacattcg gccagggcac aaagctgcaa  2100
atcaccagat gataa                                                   2115

SEQ ID NO: 106         moltype = AA  length = 703
FEATURE                Location/Qualifiers
source                 1..703
                       mol_type = protein
                       organism = synthetic construct
SEQUENCE: 106
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS TGQVQLVQSG GGVVQPGRSL  480
RLSCKASGYT FTRYTMHWVR QAPGKGLEWI GYINPSRGYT NYNQKVKDRF TISTDKSKST  540
AFLQMDSLRP EDTAVYYCAR YYDDHYCLDY WGQGTTLTVS SGGGGSGGGG SGGGGSDIQM  600
TQSPSSLSAS VGDRVTITCS ASSSVSYMNW YQQTPGKAPK RWIYDTSKLA SGVPSRFSGS  660
GSGTDYTFTI SSLQPEDIAT YYCQQWSSNP FTFGQGTKLQ ITR                   703

SEQ ID NO: 107         moltype = DNA  length = 2118
FEATURE                Location/Qualifiers
source                 1..2118
                       mol_type = other DNA
                       organism = synthetic construct
SEQUENCE: 107
gaggtgcagc tggtggagtc tgggggaggc ctggtcaagc ctgggggggtc cctgagactc  60
```

-continued

```
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgctagca ccaagggccc atcggtcttc cccctggcac cctcctccaa gagcacctct  420
gggggcacag cggccctggg ctgcctggtc aaggactact tccccgagcc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaaggcggcg gggggagcgg tggtggcggt  1380
agcaccggtc aggtgcaact ggtgcagtcc ggcggaggcg tggtgcagcc tggccggagc  1440
ctgagactga gctgcaaggc ctccggctac acctttacaa gatacactat gcactgggtc  1500
agacaggccc ctggcaaggg cctggaatgg attggctaca tcaaccctag ccggggatat  1560
accaactaca accagaaagt gaaggacaga ttcaccatca gcacagataa gtccaagtcc  1620
accgctttcc tgcagatgga ctccctgcgt ccagaggaca cagctgtgta ctactgcgcc  1680
cggtactacg acgaccacta ctgtctggac tactggggac agggaaccac cctgaccgtc  1740
agctctggcg gcggaggctc cggcggaggt ggcagcggcg gcggcggctc tgatatccag  1800
atgacccaga gcccttcttc cttatctgcc agcgtgggcg atagagtgac catcacatgc  1860
agcgccagct cttctgttag ctacatgaac tggtaccagc aaacacctgg aaaggcccct  1920
aaaagatgga tctacgacac cagcaagctg gcctctggcg tgccctctag attcagcggc  1980
tctggctccg gcaccgacta cacctttaca attagctccc tgcagcccga ggatatcgcc  2040
acctactact gccagcagtg gagcagcaac cccttcacat tcggccaggg cacaaagctg  2100
caaatcacca gatgataa                                                2118
```

```
SEQ ID NO: 108          moltype = AA  length = 704
FEATURE                 Location/Qualifiers
source                  1..704
                        mol_type = protein
                        organism = synthetic construct
SEQUENCE: 108
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG STGQVQLVQS GGGVVQPGRS  480
LRLSCKASGY TFTRYTMHWV RQAPGKGLEW IGYINPSRGY TNYNQKVKDR FTISTDKSKS  540
TAFLQMDSLR PEDTAVYYCA RYYDDHYCLD YWGQGTTLTV SSGGGGSGGG GSGGGGSDIQ  600
MTQSPSSLSA SVGDRVTITC SASSSVSYMN WYQQTPGKAP KRWIYDTSKL ASGVPSRFSG  660
SGSGTDYTFT ISSLQPEDIA TYYCQQWSSN PFTFGQGTKL QITR                  704
```

```
SEQ ID NO: 109          moltype = DNA  length = 2127
FEATURE                 Location/Qualifiers
source                  1..2127
                        mol_type = other DNA
                        organism = synthetic construct
SEQUENCE: 109
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
gctagcacca agggcccatc ggtcttcccc ctggcaccct cctccaagag cacctctggg  420
ggcacagcgg ccctgggctg cctggtcaag gactacttcc ccgagccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
```

-continued

```
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa ggcgggggtg gcggttctgg tggtggtggc  1380
tctggaggag gaaccggtca agtgcagctg gtgcagtccg gaggaggcgt cgtgcagcct  1440
ggaagaagcc tccggctgag ctgcaaggcc agcggctata cattcaccag ctacaccatg  1500
cactgggtgc ggcaggcccc tggcaaaggc ctggaatgga tcggctacat caacccttcc  1560
agcggctaca ccaagtacaa ccagaaattc aaggaccggt ttaccattag cgccgataag  1620
agcaagagca cagcctttct gcagatggac agcctgagac cagaggacac cggcgtgtac  1680
ttctgcgccc gctggcagga ctacgacgtt tatttcgact actggggcca gggcacccct  1740
gtgacagtga gcagcggcgg cggaggctcc ggcggaggtg gcagcggcgg cggcggctct  1800
gatatccaga tgacacagag ccccagctct ctgtctgctt ctgtgggcga cagagtgacc  1860
atgacctgta gagcctcctc aagcgtgtcc tacatgcact ggtaccagca aaacacctggc  1920
aaggccccaa agccttggat ctacgccacc tctaatctgg ccagcggcgt gccttctaga  1980
ttcagcggca gcggatctgg caccgattac accctgacca tcagcagcct gcagcccgag  2040
gatatcgcca catactactg ccagcagtgg agctccaatc ctcctacctt cggccagggc  2100
accaagctgc agatcacaag atgataa                                      2127

SEQ ID NO: 110         moltype = AA  length = 707
FEATURE                Location/Qualifiers
source                 1..707
                       mol_type = protein
                       organism = synthetic construct
SEQUENCE: 110
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGGSGGGG SGGGTGQVQL VQSGGGVVQP  480
GRSLRLSCKA SGYTFTSYTM HWVRQAPGKG LEWIGYINPS SGYTKYNQKF KDRFTISADK  540
SKSTAFLQMD SLRPEDTGVY FCARWQDYDV YFDYWGQGTP VTVSSGGGGS GGGGSGGGGS  600
DIQMTQSPSS LSASVGDRVT MTCRASSSVS YMHWYQQTPG KAPKPWIYAT SNLASGVPSR  660
FSGSGSGTDY TLTISSLQPE DIATYYCQQW SSNPPTFGQG TKLQITR                 707

SEQ ID NO: 111         moltype = DNA  length = 2130
FEATURE                Location/Qualifiers
source                 1..2130
                       mol_type = other DNA
                       organism = synthetic construct
SEQUENCE: 111
gaggtgcagc tggtggagtc tggggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgctagca ccaagggccc atcggtcttc cccctggcac cctcctccaa gagcacctct  420
gggggcacag cggccctggg ctgcctggtc aaggactact tccccgagcc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaaggcgggg gtggcggttc tggtggtggt  1380
ggctctggag gaggaaccgg tcaagtgcag ctggtgcagt ccggaggagg cgtcgtgcag  1440
cctggaagaa gcctccggct gagctgcaag gccagcggct atacattcac cagctacacc  1500
atgcactggg tgcggcaggc ccctggcaaa ggcctggaat ggatcggcta catcaaccct  1560
tccagcggct acaccaagta caaccagaaa ttcaaggacc ggtttaccat tagcgccgat  1620
aagagcaaga gcacagcctt tctgcagatg gacagcctga gaccagagga caccggcgtg  1680
tacttctgcg cccgctggca ggactacgac gtttatttcg actactgggg ccagggcacc  1740
cctgtgacag tgagcagcgg cggcggaggc tccggcggag gtggcagcgg cggcggcggc  1800
tctgatatcc agatgacaca gagccccagc tctctgtctg cttctgtggg cgacagagtg  1860
accatgacct gtagagcctc ctcaagcgtg tcctacatgc actggtacca gcaaacacct  1920
ggcaaggccc caaagccttg gatctacgcc acctctaatc tggccagcgg cgtgccttct  1980
agattcagcg gcagcggatc tggcaccgat tacaccctga ccatcagcag cctgcagccc  2040
gaggatatcg ccacatacta ctgccagcag tggagctcca atcctcctac cttcggccag  2100
```

```
ggcaccaagc tgcagatcac aagatgataa                                  2130

SEQ ID NO: 112          moltype = AA  length = 708
FEATURE                 Location/Qualifiers
source                  1..708
                        mol_type = protein
                        organism = synthetic construct
SEQUENCE: 112
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGGSGGG GSGGGTGQVQ LVQSGGGVVQ  480
PGRSLRLSCK ASGYTFTSYT MHWVRQAPGK GLEWIGYINP SSGYTKYNQK FKDRFTISAD  540
KSKSTAFLQM DSLRPEDTGV YFCARWQDYD VYFDYWGQGT PVTVSSGGGG SGGGGSGGGG  600
SDIQMTQSPS SLSASVGDRV TMTCRASSSV SYMHWYQQTP GKAPKPWIYA TSNLASGVPS  660
RFSGSGSGTD YTLTISSLQP EDIATYYCQQ WSSNPPTFGQ GTKLQITR               708

SEQ ID NO: 113          moltype = DNA  length = 2115
FEATURE                 Location/Qualifiers
source                  1..2115
                        mol_type = other DNA
                        organism = synthetic construct
SEQUENCE: 113
caggtgcagc tggttgaatc tggcggcgga cttgtgaagc ctggcggatc tctgagactg  60
agctgtgccg ccagcggctt caccttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
gctagcacca agggcccatc ggtcttcccc ctggcaccct cctccaagag cacctctggg  420
ggcacagcgg ccctgggctg cctggtcaag gactacttcc ccgagccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa ggcggcgggg ggagcggtgg tggcggtagc  1380
accggtcaag tgcagctggt gcagtccgga ggaggcgtcg tgcagcctgg aagaagcctc  1440
cggctgagct gcaaggccag cggctataca ttcaccagct acaccatgca ctgggtgcgg  1500
caggcccctg gcaaaggcct ggaatggatc ggctacatca acccttccag cggctacacc  1560
aagtacaacc agaaattcaa ggaccggttt accattagcg ccgataagag caagagcaca  1620
gcctttctgc agatggacag cctgagacca gaggacaccg gcgtgtactt ctgcgcccgc  1680
tggcaggact acgacgttta tttcgactac tggggccagg gcacccctgt gacagtgagc  1740
agcggcggcg gaggctccgg cggaggtggc agcggcggcg gcggctctga tatccagatg  1800
acacagagcc ccagctctct gtctgcttct gtgggcgaca gagtgaccat gacctgtaga  1860
gcctcctcaa gcgtgtccta catgcactgg taccagcaaa cacctggcaa ggccccaaag  1920
ccttggatct acgccacctc taatctggcc agcggcgtgc cttctagatt cagcggcagc  1980
ggatctggca ccgattacac cctgaccatc agcagcctgc agcccgagga tatcgccaca  2040
tactactgcc agcagtggag ctccaatcct cctaccttcg gccagggcac caagctgcag  2100
atcacaagat gataa                                                  2115

SEQ ID NO: 114          moltype = AA  length = 703
FEATURE                 Location/Qualifiers
source                  1..703
                        mol_type = protein
                        organism = synthetic construct
SEQUENCE: 114
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS TGQVQLVQSG GGVVQPGRSL  480
RLSCKASGYT FTSYTMHWVR QAPGKGLEWI GYINPSSGYT KYNQKFKDRF TISADKSKST  540
```

-continued

```
AFLQMDSLRP EDTGVYFCAR WQDYDVYFDY WGQGTPVTVS SGGGGSGGGG SGGGGSDIQM  600
TQSPSSLSAS VGDRVTMTCR ASSSVSYMHW YQQTPGKAPK PWIYATSNLA SGVPSRFSGS  660
GSGTDYTLTI SSLQPEDIAT YYCQQWSSNP PTFGQGTKLQ ITR                    703

SEQ ID NO: 115         moltype = DNA  length = 2118
FEATURE                Location/Qualifiers
source                 1..2118
                       mol_type = other DNA
                       organism = synthetic construct
SEQUENCE: 115
gaggtgcagc tggtggagtc tgggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgctagca ccaagggccc atcggtcttc cccctggcac cctcctccaa gagcacctct  420
gggggcacag cggccctggg ctgcctggtc aaggactact tccccgagcc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaaggcggcg gggggagcgg tggtggcggt  1380
agcaccggtc aagtgcagct ggtgcagtcc ggaggaggcg tcgtgcagcc tggaagaagc  1440
ctccggctga gctgcaaggc cagcggctat acattcacca gctacaccat gcactgggtg  1500
cggcaggccc ctggcaaagg cctggaatgg atcggctaca tcaacccttc cagcggctac  1560
accaagtaca accagaaatt caaggaccgg tttaccatta gcgccgataa gagcaagagc  1620
acagcctttc tgcagatgga cagcctgaga ccagaggaca ccggcgtgta cttctgcgcc  1680
cgctggcagg actacgacgt ttatttcgac tactggggcc agggcacccc tgtgacagtg  1740
agcagcggcg gcggaggctc cggcggaggt ggcagcggcg gcggcggctc tgatatccag  1800
atgacacaga gccccagctc tctgtctgct tctgtgggcg acagagtgac catgacctgt  1860
agagcctcct caagcgtgtc ctacatgcac tggtaccagc aaacacctgg caaggcccca  1920
aagccttgga tctacgccac ctctaatctg gccagcggcg tgccttctag attcagcggc  1980
agcggatctg gcaccgatta caccctgacc atcagcagcc tgcagcccga ggatatcgcc  2040
acatactact gccagcagtg gagctccaat cctcctacct tcggccaggg caccaagctg  2100
cagatcacaa gatgataa                                                2118

SEQ ID NO: 116         moltype = AA  length = 704
FEATURE                Location/Qualifiers
source                 1..704
                       mol_type = protein
                       organism = synthetic construct
SEQUENCE: 116
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG STGQVQLVQS GGGVVQPGRS  480
LRLSCKASGY TFTSYTMHWV RQAPGKGLEW IGYINPSSGY TKYNQKFKDR FTISADKSKS  540
TAFLQMDSLR PEDTGVYFCA RWQDYDVYFD YWGQGTPVTV SSGGGGSGGG GSGGGGSDIQ  600
MTQSPSSLSA SVGDRVTMTC RASSSVSYMH WYQQTPGKAP KPWIYATSNL ASGVPSRFSG  660
SGSGTDYTLT ISSLQPEDIA TYYCQQWSSN PPTFGQGTKL QITR                   704

SEQ ID NO: 117         moltype = DNA  length = 1449
FEATURE                Location/Qualifiers
source                 1..1449
                       mol_type = other DNA
                       organism = synthetic construct
SEQUENCE: 117
gaggtgcagc tggtggagtc tgggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
```

-continued

```
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg gcatccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgcctttcac attcggcgga  720
gggaccaagg tggagatcaa acgaactgag cccaaatctt gtgacaaaac tcacacatgc  780
ccaccgtgcc cagcacctga actcctgggg ggaccgtcag tcttcctctt ccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgtgg  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaatgataa                                                          1449
```

```
SEQ ID NO: 118          moltype = AA  length = 481
FEATURE                 Location/Qualifiers
source                  1..481
                        mol_type = protein
                        organism = synthetic construct
SEQUENCE: 118
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLW CLVKGFYPSD IAVEWESNGQ  420
PENNYKTTPP VLDSDGSFFL YSKLTVDKSR WQQGNVFSCS VMHEALHNHY TQKSLSLSPG  480
K                                                                  481
```

```
SEQ ID NO: 119          moltype = DNA  length = 1473
FEATURE                 Location/Qualifiers
source                  1..1473
                        mol_type = other DNA
                        organism = synthetic construct
SEQUENCE: 119
gaggtgcagc tggtggagtc tgggggaggc ctggtcaagc ctggggggtc cctgagactc  60
tcctgtgcag cctctggatt caccttcagt ggctatgcca tgagctgggt ccgccaggct  120
ccagggaagg ggctggagtg ggtctcaacc attagtagtg gcggaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg gcatccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgcctttcac attcggcgga  720
gggaccaagg tggagatcaa acgaactgag cccaaatctt gtgacaaaac tcacacatgc  780
ccaccgtgcc cagcacctga actcctgggg ggaccgtcag tcttcctctt ccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgtgg  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaaaccggtc atcatcacca tcaccattga taa                              1473
```

```
SEQ ID NO: 120          moltype = AA  length = 489
FEATURE                 Location/Qualifiers
source                  1..489
                        mol_type = protein
                        organism = synthetic construct
SEQUENCE: 120
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRTE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
```

-continued

```
ALPAPIEKTI SKAKGQPREP QVYTLPPSRE EMTKNQVSLW CLVKGFYPSD IAVEWESNGQ  420
PENNYKTTPP VLDSDGSFFL YSKLTVDKSR WQQGNVFSCS VMHEALHNHY TQKSLSLSPG  480
KTGHHHHHH                                                         489

SEQ ID NO: 121         moltype = DNA  length = 1446
FEATURE                Location/Qualifiers
source                 1..1446
                       mol_type = other DNA
                       organism = synthetic construct
SEQUENCE: 121
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
gccagatttt ctggcagcgg ctctggcacc gatttcaccc tgaccataag cagcctggaa  660
cctgaggact tcgccgtgta ttactgccac cagtacctga gcagcctgac ctttggcgga  720
ggcaccaagg tggaaatcaa gcgggagccc aaatcttgtg acaaaactca cacatgccca  780
ccgtgcccag cacctgaact cctgggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc  1020
gtcctgcacc aggactggct gaatggcaag gagtacaagt gcaaggtctc caacaaagcc  1080
ctcccagccc ccatcgagaa aaccatctcc aaagccaaag ggcagccccg agaaccacag  1140
gtgtacaccc tgcccccatc ccgggaggag atgaccaaga accaggtcag cctgtggtgc  1200
ctggtcaaag gcttctatcc cagcgacatc gccgtggagt gggagagcaa tgggcagccg  1260
gagaacaact acaagaccac gcctcccgtg ctggactccg acggctcctt cttcctctac  1320
agcaagctca ccgtggacaa gagcaggtgg cagcagggga acgtcttctc atgctccgtg  1380
atgcatgagg ctctgcacaa ccactacacg cagaagagcc tctccctgtc tccgggtaaa  1440
tgataa                                                            1446

SEQ ID NO: 122         moltype = AA  length = 480
FEATURE                Location/Qualifiers
source                 1..480
                       mol_type = protein
                       organism = synthetic construct
SEQUENCE: 122
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKREP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480

SEQ ID NO: 123         moltype = DNA  length = 1470
FEATURE                Location/Qualifiers
source                 1..1470
                       mol_type = other DNA
                       organism = synthetic construct
SEQUENCE: 123
caggtgcagc tggttgaatc tggcggcgga cttgtgaagc ctggcggatc tctgagactg  60
agctgtgccg ccagcggctt cacctttagc acatacgcca tgagctggat cagacaggcc  120
cctggcaaag gcctggaatg ggtggcgtct attggcagag ccggcagcac ctactacagc  180
gactctgtga agggcagatt caccatcagc cgggacaacg ccaagaacag cctgtacctg  240
cagatgaact ccctgagagc cgaggacacc gccgtgtact attgtgccag aggacccatc  300
tacaacgact acgacgagtt cgcctattgg ggccagggca cactggtcac agtttctagc  360
ggcggtggcg gaagcggagg cggtggctcc ggtggcggag gcagcgaaat tgtgctgaca  420
cagagccccg ccacactgtc actttctcca ggcgaaagag ccacactgag ctgcaagagc  480
agccagagcg tgctgtactc cagcaaccag aagaactacc tggcctggta tcagcagaag  540
cccggccaag ctcctcggct gctgatctat tgggccagca caagagagag cggcatccct  600
gccagatttt ctggcagcgg ctctggcacc gatttcaccc tgaccataag cagcctggaa  660
cctgaggact tcgccgtgta ttactgccac cagtacctga gcagcctgac ctttggcgga  720
ggcaccaagg tggaaatcaa gcgggagccc aaatcttgtg acaaaactca cacatgccca  780
ccgtgcccag cacctgaact cctgggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc  1020
gtcctgcacc aggactggct gaatggcaag gagtacaagt gcaaggtctc caacaaagcc  1080
ctcccagccc ccatcgagaa aaccatctcc aaagccaaag ggcagccccg agaaccacag  1140
gtgtacaccc tgcccccatc ccgggaggag atgaccaaga accaggtcag cctgtggtgc  1200
ctggtcaaag gcttctatcc cagcgacatc gccgtggagt gggagagcaa tgggcagccg  1260
gagaacaact acaagaccac gcctcccgtg ctggactccg acggctcctt cttcctctac  1320
```

-continued

```
agcaagctca ccgtggacaa gagcaggtgg cagcagggga acgtcttctc atgctccgtg  1380
atgcatgagg ctctgcacaa ccactacacg cagaagagcc tctccctgtc tccgggtaaa  1440
accggtcatc atcaccatca ccattgataa                                   1470

SEQ ID NO: 124         moltype = AA  length = 488
FEATURE                Location/Qualifiers
source                 1..488
                       mol_type = protein
                       organism = synthetic construct
SEQUENCE: 124
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKREP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480
TGHHHHHH                                                           488

SEQ ID NO: 125         moltype = DNA  length = 1455
FEATURE                Location/Qualifiers
source                 1..1455
                       mol_type = other DNA
                       organism = synthetic construct
SEQUENCE: 125
caggtgcaac tggtgcagtc cggcggaggc gtggtgcagc ctggccggag cctgagactg  60
agctgcaagg cctccggcta cacctttaca agatacacta tgcactgggt cagacaggcc  120
cctggcaagg gcctggaatg gattggctac atcaacccta gccggggata taccaactac  180
aaccagaaag tgaaggacag attcaccatc agcacagata agtccaagtc caccgctttc  240
ctgcagatgg actccctgcg tccagaggac acagctgtgt actactgcgc ccggtactac  300
gacgaccact actgtctgga ctactgggga cagggaacca ccctgaccgt cagctctggc  360
ggcggaggct ccggcggagg tggcagcggc ggcggcggct ctgatatcca gatgacccag  420
agcccttctt ccttatctgc cagcgtgggc gatagagtga ccatcacatg cagcgccagc  480
tcttctgtta gctacatgaa ctggtaccag caaacacctg gaaaggcccc taaaagatgg  540
atctacgaca ccagcaagct ggcctctggc gtgccctcta gattcagcgg ctctggctcc  600
ggcaccgact acacctttac aattagctcc ctgcagcccg aggatatcgc cacctactac  660
tgccagcagt ggagcagcaa ccccttcaca ttcggccagg gcacaaagct gcaaatcacc  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgagctgcg ccgtcaaagg cttctatccc  1200
agcgacatcg ccgtggagtg ggagagcaat gggcagccgg agaacaacta caagaccacg  1260
cctcccgtgc tggactccga cggctccttc ttcctcgtga gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaaa ccggttggag ccatcctcag  1440
ttcgaaaagt gataa                                                   1455

SEQ ID NO: 126         moltype = AA  length = 483
FEATURE                Location/Qualifiers
source                 1..483
                       mol_type = protein
                       organism = synthetic construct
SEQUENCE: 126
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LSCAVKGFYP SDIAVEWESN GQPENNYKTT  420
PPVLDSDGSF FLVSKLTVDK SRWQQGNVFS CSVMHEALHN HYTQKSLSLS PGKTGWSHPQ  480
FEK                                                                483

SEQ ID NO: 127         moltype = DNA  length = 1455
FEATURE                Location/Qualifiers
source                 1..1455
                       mol_type = other DNA
                       organism = synthetic construct
SEQUENCE: 127
caagtgcagc tggtgcagtc cggaggaggc gtcgtgcagc ctggaagaag cctccggctg  60
agctgcaagg ccagcggcta tacattcacc agctacacca tgcactgggt gcggcaggcc  120
cctggcaaag gcctggaatg gatcggctac atcaaccctt ccagcggcta caccaagtac  180
aaccagaaat tcaaggaccg gtttaccatt agcgccgata agagcaagag cacagccttt  240
ctgcagatgg acagcctgag accagaggac accggcgtgt acttctgcgc ccgctggcag  300
```

```
gactacgacg tttatttcga ctactggggc cagggcaccc ctgtgacagt gagcagcggc  360
ggcggaggct ccggcggagg tggcagcggc ggcggcggct ctgatatcca gatgacacag  420
agccccagct ctctgtctgc ttctgtgggc gacagagtga ccatgacctg tagagcctcc  480
tcaagcgtgt cctacatgca ctggtaccag caaacacctg gcaaggcccc aaagccttgg  540
atctacgcca cctctaatct ggccagcggc gtgccttcta gattcagcgg cagcggatct  600
ggcaccgatt acaccctgac catcagcagc ctgcagcccg aggatatcgc cacatactac  660
tgccagcagt ggagctccaa tcctcctacc ttcggccagg gcaccaagct gcagatcaca  720
agagagccca aatcttgtga caaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgagctgcg ccgtcaaagg cttctatccc  1200
agcgacatcg ccgtggagtg ggagagcaat gggcagccgg agaacaacta caagaccacg  1260
cctcccgtgc tggactccga cggctccttc ttcctcgtga gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaaa ccggttggag ccatcctcag  1440
ttcgaaaagt gataa                                                   1455

SEQ ID NO: 128          moltype = AA  length = 483
FEATURE                 Location/Qualifiers
source                  1..483
                        mol_type = protein
                        organism = synthetic construct
SEQUENCE: 128
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
REPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LSCAVKGFYP SDIAVEWESN GQPENNYKTT  420
PPVLDSDGSF FLVSKLTVDK SRWQQGNVFS CSVMHEALHN HYTQKSLSLS PGKTGWSHPQ  480
FEK                                                                483

SEQ ID NO: 129          moltype = AA  length = 248
FEATURE                 Location/Qualifiers
source                  1..248
                        mol_type = protein
                        organism = synthetic construct
SEQUENCE: 129
QVQLVESGGG LVKPGGSLRL SCAASGFTFS TYAMSWIRQA PGKGLEWVAS IGRAGSTYYS  60
DSVKGRFTIS RDNAKNSLYL QMNSLRAEDT AVYYCARGPI YNDYDEFAYW GQGTLVTVSS  120
GGGGSGGGGS GGGGSEIVLT QSPATLSLSP GERATLSCKS SQSVLYSSNQ KNYLAWYQQK  180
PGQAPRLLIY WASTRESGIP ARFSGSGSGT DFTLTISSLE PEDFAVYYCH QYLSSLTFGG  240
GTKVEIKR                                                           248

SEQ ID NO: 130          moltype = AA  length = 249
FEATURE                 Location/Qualifiers
source                  1..249
                        mol_type = protein
                        organism = synthetic construct
SEQUENCE: 130
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRT                                                          249

SEQ ID NO: 131          moltype = AA  length = 241
FEATURE                 Location/Qualifiers
source                  1..241
                        mol_type = protein
                        organism = synthetic construct
SEQUENCE: 131
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
R                                                                  241

SEQ ID NO: 132          moltype = AA  length = 241
FEATURE                 Location/Qualifiers
source                  1..241
                        mol_type = protein
                        organism = synthetic construct
SEQUENCE: 132
```

-continued

```
QVQLVQSGGG VVQPGRSLRL SCKASGYTFT RYTMHWVRQA PGKGLEWIGY INPSRGYTNY  60
NQKVKDRFTI STDKSKSTAF LQMDSLRPED TAVYYCARYY DDHYCLDYWG QGTTLTVSSG  120
GGGSGGGGSG GGGSDIQMTQ SPSSLSASVG DRVTITCSAS SSVSYMNWYQ QTPGKAPKRW  180
IYDTSKLASG VPSRFSGSGS GTDYTFTISS LQPEDIATYY CQQWSSNPFT FGQGTKLQIT  240
R                                                                  241

SEQ ID NO: 133          moltype = AA  length = 45
FEATURE                 Location/Qualifiers
source                  1..45
                        mol_type = protein
                        organism = synthetic construct
SEQUENCE: 133
GTINVHDVET QFNQYKTEAA SRYNLTISDV SVSDVPFPFS AQSGA                  45
```